US012649699B2

(12) United States Patent
Kukolj et al.

(10) Patent No.: US 12,649,699 B2
(45) Date of Patent: Jun. 9, 2026

(54) PHOSPHATE SENSING MICROBIAL GENE SWITCH

(71) Applicant: SWITCH BIOWORKS, INC., San Carlos, CA (US)

(72) Inventors: Caroline Kukolj, Redwood City, CA (US); Tim Schnabel, Menlo Park, CA (US); Timothy Lyndon Haskett, Menlo Park, CA (US); Gregory Alexander Knauf, San Mateo, CA (US); Tomasz Zajkowski, Warsaw (PL); Elizabeth Leigh Ordeman, Palo Alto, CA (US); Niklaus Hoyt Evitt, New Haven, CT (US); James Pearce, La Jolla, CA (US); Sandipan Samaddar, Redwood City, CA (US); Daniel Torres Naylor, San Mateo, CA (US); Hsiao-Han Lin, San Carlos, CA (US); Alexis Makena Chun, San Bruno, CA (US)

(73) Assignee: SWITCH BIOWORKS, INC., San Carlos, CA (US)

( * ) Notice: Subject to any disclaimer, the term of this patent is extended or adjusted under 35 U.S.C. 154(b) by 0 days.

(21) Appl. No.: 19/042,264

(22) Filed: Jan. 31, 2025

(65) Prior Publication Data

US 2025/0243130 A1    Jul. 31, 2025

Related U.S. Application Data

(60) Provisional application No. 63/627,673, filed on Jan. 31, 2024.

(51) Int. Cl.
| | |
|---|---|
| *C12N 1/21* | (2006.01) |
| *A01C 21/00* | (2006.01) |
| *C05F 11/08* | (2006.01) |
| *C05G 1/00* | (2006.01) |
| *C05G 3/60* | (2020.01) |
| *C12N 9/00* | (2006.01) |
| *C12N 15/74* | (2006.01) |

(52) U.S. Cl.
CPC ............ *C05F 11/08* (2013.01); *A01C 21/007* (2013.01); *C05G 1/00* (2013.01); *C05G 3/60* (2020.02); *C12N 9/93* (2013.01); *C12N 15/74* (2013.01); *C12Y 603/01002* (2013.01); *C12N 2830/003* (2013.01); *C12N 2830/005* (2013.01); *C12N 2830/48* (2013.01)

(58) Field of Classification Search
None
See application file for complete search history.

(56) References Cited

U.S. PATENT DOCUMENTS

| | | | |
|---|---|---|---|
| 8,415,120 | B2 | 4/2013 | Collier et al. |
| 11,565,979 | B2 | 1/2023 | Temme et al. |
| 2011/0212508 | A1 | 9/2011 | Rao et al. |
| 2020/0299637 | A1 | 9/2020 | Voigt et al. |
| 2020/0331820 | A1 | 10/2020 | Tamsir et al. |
| 2022/0127624 | A1 | 4/2022 | Schnabel et al. |
| 2023/0383341 | A1* | 11/2023 | Liu ........................ C12N 15/74 |

FOREIGN PATENT DOCUMENTS

| | | | | |
|---|---|---|---|---|
| WO | 2017011602 A1 | 1/2017 | | |
| WO | WO-2021146209 A1 * | 7/2021 | .............. | C05F 11/08 |
| WO | 2021221690 A1 | 11/2021 | | |
| WO | WO-2024108099 A1 * | 5/2024 | .............. | A01H 3/00 |
| WO | 2024123814 A1 | 6/2024 | | |
| WO | 2024145279 A1 | 7/2024 | | |
| WO | 2024192029 A1 | 9/2024 | | |

OTHER PUBLICATIONS

Yokobayashi et al (PNAS, 2002, vol. 99, No. 26, pp. 16587-16591) (Year: 2002).*
Bertram (Microbial Biotechnology 2008, 1 (1), 2-16). (Year: 2008).*
BMQ95821, Zheng Y et al. 2023 (Year: 2023).*
ADR22390, Hegedus, D et al. 2004 (Year: 2004).*
Ghenov (Brazilian Journal of Biology, 2022, vol. 82, pp. 1-8). (Year: 2022).*
Harrison et al. "Employing site-specific recombination for conditional genetic analysis in Sinorhizobium meliloti." Applied and environmental microbiology 77.12 (2011): 3916-3922.
International Search Report and Written Opinion in PCT/US2025/013983, mailed Jun. 5, 2025, 20 pages.
International Search Report and Written Opinion in PCT/US2025/014079, mailed May 13, 2025, 15 pages.
Sheets et al. "Light-inducible recombinases for bacterial optogenetics." ACS Synthetic Biology 9.2 (2020): 227-235.
Ambrosio et al. "Metabolic engineering of a diazotrophic bacterium improves ammonium release and biofertilization of plants and microalgae." Metabolic engineering 40 (2017): 59-68.
Haskett et al. "Control of nitrogen fixation and ammonia excretion in Azorhizobium caulinodans." PLoS Genetics 18.6 (2022): e1010276, 1-20.
Haskett, Timothy L. Discovery and characterisation of tripartite Integrative & Conjugative Elements. Diss. Murdoch University, (2018): 212 pages.
International Search Report and Written Opinion in PCT/IB2024/053106, mailed Nov. 15, 2024, 17 pages.
Martin et al. "The master regulator PhoP coordinates phosphate and nitrogen metabolism, respiration, cell differentiation and antibiotic biosynthesis: comparison in *Streptomyces coelicolor* and *Streptomyces avermitilis*." The Journal of antibiotics 70.5 (2017): 534-541.
Mutalik et al. "Precise and reliable gene expression via standard transcription and translation initiation elements." Nature methods 10.4 (2013): 354-360.

(Continued)

*Primary Examiner* — Celine X Qian
(74) *Attorney, Agent, or Firm* — McKee, Voorhees & Sease, PLC

(57) ABSTRACT

Genetically engineered bacteria which express RNAs or proteins that produce ammonia upon decreases in phosphate concentrations are disclosed.

16 Claims, 23 Drawing Sheets

Specification includes a Sequence Listing.

(56)           References Cited

OTHER PUBLICATIONS

Mutalik et al. "Supplementary Information: Precise and reliable gene expression via standard transcription and translation initiation elements." Nature methods 10.4 (2013): 1-42.

Ryu et al. "Control of nitrogen fixation in bacteria that associate with cereals." Nature Microbiology 5.2 (2020): 314-330.

Schnabel et al. "Engineering posttranslational regulation of glutamine synthetase for controllable ammonia production in the plant symbiont Azospirillum brasilense." Applied and Environmental Microbiology 87.14 (2021): e00582-21, 1-16.

Schnabel et al. "Improved stability of engineered ammonia production in the plant-symbiont Azospirillum brasilense." ACS synthetic biology 10.11 (2021): 2982-2996.

Schnabel, Tim. Engineering Ammonia Production in Free-Living Diazotrophs for Plant Fertilization. Stanford University, (2021): 284 pages.

Shulse et al. "Engineered root bacteria release plant-available phosphate from phytate." Applied and environmental microbiology 85.18 (2019): e01210-19, 1-11.

Tiwari et al. "Regulation of organophosphate metabolism in cyanobacteria. A review." Microbiology 84 (2015): 291-302.

Torres-Bacete et al. "A portable library of phosphate-depletion based synthetic promoters for customable and automata control of gene expression in bacteria." Microbial Biotechnology 14.6 (2021): 2643-2658.

Trung et al. "An auto-inducible phosphate-controlled expression system of Bacillus licheniformis." BMC biotechnology 19 (2019): 1-8.

Wen et al. "The diversity of Shine-Dalgarno sequences sheds light on the evolution of translation initiation." RNA biology 18.11 (2021): 1489-1500.

\* cited by examiner

*K. radicincitans* DF-PpstS.Kr and P depletion

*K. radicincitans* DF-Pliar and P depletion

*P. stutzeri* DF-PpstS.Ps and P depletion

*P. stutzeri* DF-Pliar and P depletion

*H. seropedicae* DF-PpstS.Hs and P depletion

*H. seropedicae* DF-Pliar and P depletion

A. brasilense DF-PpstS.Ab and P depletion in media

A. brasilense DF-Pliar and P depletion in media

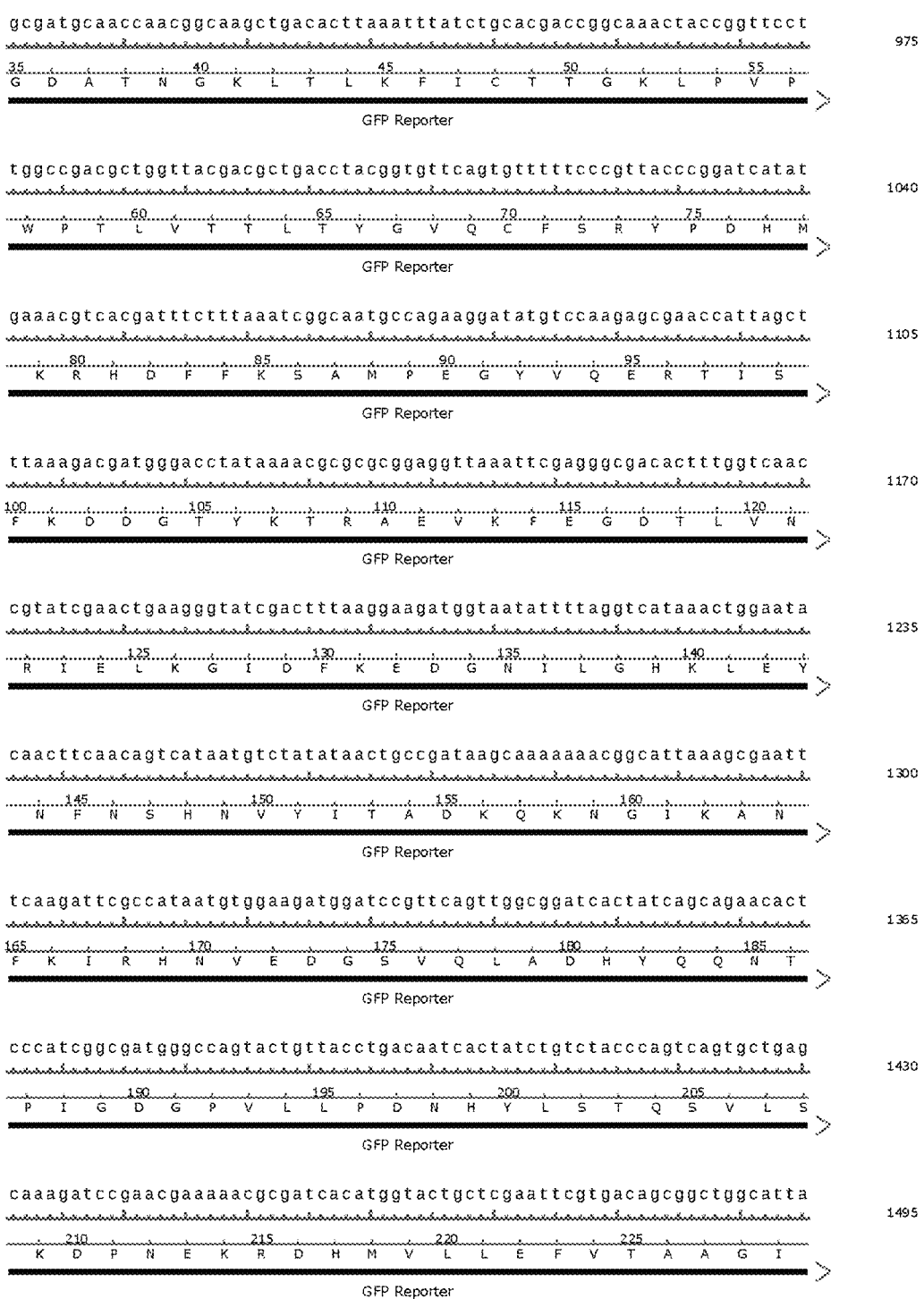

```
gcgatgcaaccaacggcaagctgacacttaaatttatctgcacgaccggcaaactaccggttcct          975

35        40              45              50              55
 G  D  A  T  N  G  K  L  T  L  K  F  I  C  T  T  G  K  L  P  V  P
                            GFP Reporter tggccgacgctggttacgacgctgacctacggtgttcagtgttttttcccgttacccggatcatat         1040

60              65              70              75
 W  P  T  L  V  T  T  L  T  Y  G  V  Q  C  F  S  R  Y  P  D  H  M
                            GFP Reporter gaaacgtcacgatttctttaaatcggcaatgccagaaggatatgtccaagagcgaaccattagct         1105

80              85              90              95
 K  R  H  D  F  F  K  S  A  M  P  E  G  Y  V  Q  E  R  T  I  S
                            GFP Reporter ttaaagacgatgggacctataaaacgcgcgcggaggttaaattcgagggcgacactttggtcaac         1170

100              105             110             115             120
 F  K  D  D  G  T  Y  K  T  R  A  E  V  K  F  E  G  D  T  L  V  N
                            GFP Reporter cgtatcgaactgaagggtatcgactttaaggaagatggtaatattttaggtcataaactggaata         1235

125             130             135             140
 R  I  E  L  K  G  I  D  F  K  E  D  G  N  I  L  G  H  K  L  E  Y
                            GFP Reporter caacttcaacagtcataatgtctatataactgccgataagcaaaaaaacggcattaaagcgaatt         1300

145             150             155             160
 N  F  N  S  H  N  V  Y  I  T  A  D  K  Q  K  N  G  I  K  A  N
                            GFP Reporter tcaagattcgccataatgtggaagatggatccgttcagttggcggatcactatcagcagaacact         1365

165             170             175             180             185
 F  K  I  R  H  N  V  E  D  G  S  V  Q  L  A  D  H  Y  Q  Q  N  T
                            GFP Reporter cccatcggcgatgggccagtactgttacctgacaatcactatctgtctacccagtcagtgctgag         1430

190             195     200             205
 P  I  G  D  G  P  V  L  L  P  D  N  H  Y  L  S  T  Q  S  V  L  S
                            GFP Reporter caaagatccgaacgaaaaacgcgatcacatggtactgctcgaattcgtgacagcggctggcatta         1495

210             215             220             225
 K  D  P  N  E  K  R  D  H  M  V  L  L  E  F  V  T  A  A  G  I
                            GFP Reporter
```

Fig. 18B

SEQUENCE LISTING

```
Sequence total quantity: 533
SEQ ID NO: 1            moltype = DNA  length = 1578
FEATURE                 Location/Qualifiers
source                  1..1578
                        mol_type = other DNA
                        organism = synthetic construct
SEQUENCE: 1
atggcacata tgaccaatgt gcgccgggtg tttaatgaat tgattggcga cgatgaaagt   60
gaaactcagg aagagtcgct gtcggaacag tggcgtgagc tgtggcagga tgcgttgcag   120
gaagatgaca ctacgccagt gctggcgcat cttagcgagg atgatcgcaa acaggtgcta   180
acgctgattg ccgatttccg caaagagctg gataagcgca ccatcgggcc gcgaggacgt   240
caggtgctcg accatctgat gccgcatctg ctaagtgatg tctgtgcgcg tgaagacgct   300
gccgttacgc tgtcgcgcat taccgccttg ctggtgggca ttgttacccg caccacctat   360
ttagaattgc tcagtgaatt ccccgcggcg cttaaacatt tgatttctct gtgtgccgcg   420
tcgccgatga ttgccagcca gctggcgcgt tatccattat tgctggatga attgctcgat   480
ccaaacaccc tttaccagcc gacggcgacc gatgcctacc gcgatgagtt gcgccagtat   540
ttgctgcgcg tgccggaaga tgacgaagag caacagcttg aggcgctgcg tcagttcaaa   600
caggcgcagc tgttacgcat cgccgcagcg gatatcgccg gtacgctacc ggtgatgaaa   660
gtgagcgatc acttaacctg gctggcggaa gccatgatag atgccgtcgt tcagcaggcg   720
tgggttcaaa tggttgcccg ctacggtaag ccgaatcacc tgaacgaacg cgaagggcgt   780
ggttttgcgg tggtcggcta cggcaagctg ggcggctggg agttaggcta cagttccgat   840
cttgacctta tcttcctcca tgattgccca atggatgcga tgactgacgg tgagcgggaa   900
atcgacgggc ggcagtttta tctgcgctct gcgcaacgca ttatgcatct gttcagtacg   960
cgtacctctt ccggcatttt gtatgaagtg gatgctcgac tgcgtccgtc cggggcggcg   1020
ggaatgctgg tgacatccgc agaagcattt gccgattatc agaaaaacga ggcctggacg   1080
tgggaacatc aggcgctggt gcgtgcgcgt gtagtgtacg gcgatccgca gctcaccgcg   1140
cactttgacg cagtgcgtcg cgagattatg acgctgccgc gtgaaggtaa aactctgcaa   1200
acggaagtgc gggaaatgcg cgagaaaatg cgcgctcatc tcggcaataa acatcgcgat   1260
cgctttgata tcaaagctga tgaaggggga attaccgata tcgaatttat tacccaatat   1320
ctggtgttgc gctacgctca tgaaaaaccg aagttaaccg gctggtcaga caacgtgcgt   1380
attctggaac tactggcgca aaacgacatt atggaagagc aggaagcgat ggcgctgacc   1440
cgtgcttaca ctacgcttcg cgatgaactt catcatctgg cattacagga attgccgggc   1500
catgtgtcgg aggattgctt caccgcagag cgtgaactgg tgcgggcaag ctggcagaag   1560
tggctggtgg aagaatga                                                 1578

SEQ ID NO: 2            moltype = DNA  length = 1578
FEATURE                 Location/Qualifiers
source                  1..1578
                        mol_type = other DNA
                        organism = synthetic construct
SEQUENCE: 2
atggctcata tgaccaatgt gcgacgtgtt ttcaacgaac tcatcgggga cgacgaatcg   60
gaaacgcagg aagagagcct ctctgaacag tggcgtgagc tgtggcagga tgcactgcaa   120
gaggatgata cgaccccggt gcttgcccat ctgagtgaag acgataggaa gcaggttctg   180
accctgatcg cggacttccg aaaggaactt gataaacgca ccattggacc gcggggtcgt   240
caagtgctgg atcatctgat gccccatctt ctgtcggatg tgtgcgcacg agaggatgct   300
gccgtcaccc tctcgcgcat taccgccctt ctggtcggta tcgtgacccg cactacgtac   360
ctcgagcttc tctcggagtt ccccgcagcc ctcaagcatc tgatctcctt gtgcgcggcc   420
tcgccaatga tcgcgtcgca attggcccgt tacccgctgt tgcttgatga gcttctggat   480
ccaaatacct tgtaccagcc aacggcgacc gatgcctaca gggatgaact ccgccagtat   540
ctccttcggg ttcccgaaga cgacgaagaa caacagctcg aagcgcttcg gcaatttaag   600
caggcccaat tgcttcgcat cgcggcagcg gacattgctg gcacccttcc ggtgatgaaa   660
gtttcggacc atctgacatg gctggcggag gccatgattg acgccgtcgt ccagcaagcg   720
tgggtgcaga tggtcgctcg ttatggaaag cccaaccacc tgaatgagcg cgagggccgc   780
ggattcgcgg tggttggcta tggcaagctg ggtggttggg aattggggta ttcctccgac   840
ctggatctga tcttcttaca tgactgccct atggacgcca tgacagatgg cgagcgggag   900
atcgacggta gacaatttta ccttcgcctg gcccaacgca taatgcattt attctcgacg   960
cgcacgtcga gtggtatcct ttacgaagtg gacgcgagac tgcggccttc cggcgccgca   1020
ggcatgctgg tgacctcggc cgaagcgttc gccgattacc aaaaaaacga agcctggacg   1080
tgggaacatc aagctcttgt ccgcgcgcgc gtggtctatg gagatccgca gctcaccgcc   1140
catttcgacg cggtgcggcg cgaaattatg acgctcccac gcgaaggcaa gacgctgcag   1200
accgaggtgc gcgaaatgcg ggagaaaatg cgcgcccatt tgggtaataa gcaccgcgac   1260
aggttcgata tcaaggcgga cgaaggcgga atcacggaca tcgaatttat tactcaatat   1320
ttggtcctgc gatatgcaca cgaaaagccc aaactaacac gctggtccga taacgtcagg   1380
atcttagagc ttcttgctca gaacgatatc atggaagagc aagaggctat ggcgcttacc   1440
```

```
cgtgcctaca cgacgctgcg ggatgaactt catcatcttg cgctgcagga actgccgggt  1500
catgtctcag aagattgctt taccgctgaa cgcgaactgg tccgggcaag ctggcagaag  1560
tggctggtcg aagagtga                                                 1578
```

```
SEQ ID NO: 3              moltype = DNA  length = 1578
FEATURE                   Location/Qualifiers
source                    1..1578
                          mol_type = other DNA
                          organism = synthetic construct
SEQUENCE: 3
atggcgcaca tgacgaacgt caggagagtc ttcaacgagc tcatcgggga tgacgagtcg  60
gagacgcaag aggaaagctt aagcgagcaa tggagggaat tatggcaaga cgcactccaa  120
gaggacgata ccacccccgt cttagcccac ttgtcggaag acgacaggaa gcaagttttg  180
accttaatcg cggactttag gaaggaatta gacaaaagga cgattggccc caggggcagg  240
caagtcttgg atcacttaat gccccactta ttgtccgacg tgtgcgccag ggaggatgcc  300
gcagtgacct taagcagaat cacggcgctc ttagtcggca tcgtcacgag gacgacgtac  360
ctggagctct tgtcggagtt tccggccgcc ttgaagcacc tcatcagctt atgcgcggcc  420
agccccatga tcgcgtcgca attagccaga tacccgctgc ttttagacga gctcttggac  480
ccgaatacgt tgtatcaacc caccgccaca gacgcgtata gggacgaact cagacaaatc  540
cttttaagag tccccgagga cgatgaggaa cagcaattgg aagccttaag gcaatttaag  600
caagcccaat tactgagaat tgcagccgca gacattgcgg gcaccttgcc cgttatgaag  660
gtttcggacc atctgacgtg gttagccgag gcgatgatcg acgcggtggt ccaacaagcc  720
tgggtccaga tggtcgcgag gtatggcaaa ccaaaccatt taaatgagag agagggcaga  780
ggcttcgcag tcgtgggata tgggaaatta gggggtgggg aactgggta ttccagtgac  840
ttggatttga tatttttgca cgactgtccc atggacgcca tgacggatgg cgaaagagag  900
attgatggaa gacaattcta cttaaggtta gcccagagga tcatgcactt attttccacc  960
aggacgagca gtgggatcct ctacgaggtc gacgccaggt taagacctag tggcgccgc  1020
ggcatgttag tcaccagtgc tgaggcgttc gcggactacc aaaagaatga agcatggacc  1080
tgggagcacc aagccttagt tagggccagg gtggtctatg gagaccccca attgacggcc  1140
catttcgatg cggtcagaag ggaaatcatg accttaccca ggagggcaa gaccttacag  1200
accgaggtca gagagatgag agaaaagatg agggcccact tgggagacaa gcacagagac  1260
aggttcgaca taaaggcgga cgagggcggc atcacggaca ttgagttcat cactcagtac  1320
ttagtcctca gatatgccca cgagaagccc aaactgacca gatggagtga taatgtcaga  1380
atcttagagt tgttagctca gaatgatatc atggaggaac aagaggccat ggccttaacg  1440
agggcctata cgaccttgag ggacgagttg caccacttag cgctgcaaga gctccccggg  1500
cacgtcagcg aagactgttt tacggccgaa agagagttag ttagagcgtc ttggcaaaaa  1560
tggttagtcg aggagtga                                                 1578
```

```
SEQ ID NO: 4              moltype = DNA  length = 1578
FEATURE                   Location/Qualifiers
source                    1..1578
                          mol_type = other DNA
                          organism = synthetic construct
SEQUENCE: 4
atggcccaca tgactaacgt acgacgcgtt ttcaacgagc ttataggtga cgacgaaagc  60
gaaacccagg aggagtctct cagtgaacag tggcgcgaac tctggcagga cgcccttcag  120
gaagacgaca cgactcctgt tcttgcacat ctctcagagg acgatcgtaa gcaggtcctc  180
actctcatag ctgacttccg taaggaactc gacaagcgta ctataggacc acgcgggcgc  240
caggtacttg accatcttat gcctcatctc ctctcggacg tatgtgctcg cgaagacgcg  300
gcggtcacac tctcacgtat aactgcactt ctcgtaggta tagtgactag aacaacttac  360
ctcgagcttc taagcgagtt ccctgctgct ctcaagcacc ttatatcgct ctgcgctgca  420
tctccaatga tagcttctca gctcgctcgc tacccctcc tcctcgatga acttctagac  480
cccaacactc tctaccagcc tactgcaacg gacgcatacc gtgatgaact acggcagtac  540
ctcctccggt tcctgaaga cgatgaagaa caacagctcg aagctctccg ccagttcaaa  600
caggctcagc tcctccggat agcggcggcc gacatagcag ggacactccc agtcatgaaa  660
gtctcagacc acctcacatg gctcgctgag gcaatgattg acgctgttgt caacaagcca  720
tgggtgcaga tggtggctcg ttacggaaag cccaaccatc tcaacgaacg ggaaggacgg  780
gggttcgccg ttgttgggta cggtaagctc ggaggatggg aactcggtta ctcgtcggac  840
ctcgacctca ttttccttca tgactgcccg atggacgcta tgaccgatgg agaacgtgaa  900
atagacggcc gccagttcta tctccgcctc gcacagcgaa taatgcacct cttctcgaca  960
cgcacttcgt cgggtatact atatgaagtt gacgcgcgcc tccggccctc gggtgctgca  1020
gggatgctcg ttacgtcggc ggaagccttc gctgactatc agaagaatga agcgtggact  1080
tgggaacatc aggcactcgt ccgcgctcgc gtcgtttacg gggacccaca gcttactgct  1140
cacttcgacg ccgttcgccg agaaataatg actcttccac gcgaagggaa gacgcttcag  1200
actgaggttc gcgaaatgcg ggaaaagatg cgtgcgcacc ttggtaacaa gcaccgggac  1260
cgattcgata ttaaggccga tgaaggtggg ataacagata tagaattcat aacgcagtac  1320
ctcgttcttc ggtacgcgca cgaaaagcct aagctcacac ggtggtcgga caacgttcgg  1380
atactcgaac ttcttgccca gaacgatata atggaagaac aggaagctat ggctctcact  1440
cgcgcgtaca ccactctccg tgacgagctc catcatctcg cccttcagga acttcctggt  1500
cacgtttctg aagactgctt cacagcggaa cgcgaactcg tccgcgcctc gtggcagaag  1560
tggcttgtag aggaatga                                                 1578
```

```
SEQ ID NO: 5              moltype = DNA  length = 1578
FEATURE                   Location/Qualifiers
source                    1..1578
                          mol_type = other DNA
                          organism = synthetic construct
```

```
SEQUENCE: 5
atggctcaca tgacaaacgt tcgtcgtgta ttcaacgaac taatcggaga cgacgaatca   60
gaaacacagg aagaatcact ttcagaacag tggcgagaac tttggcagga cgctctacag  120
gaagatgata caacaccggt actcgctcac ttaagtgaag acgaccgaaa gcaggtactt  180
acacttatcg cagacttccg aaaggaactt gacaagcgaa caattggtcc tcgtggtcga  240
caggttctag atcatctcat gccacacctt ctttcagacg tttgcgcacg agaagacgca  300
gctgtaactc tttctcggat cacagctcta cttgttggaa tcgtaacacg tactacatac  360
cttgaactac tttcagaatt cccagcagca ctaaagcacc taatctcact ttgcgcagct  420
tcacctatga tcgcatcaca acttgcacgg tatcctcttc tacttgacga gctacttgac  480
cctaacacac tatatcagcc aacagctact gacgcttacc gagacgagct tcgtcagtat  540
ctacttcgtg taccagagga cgacgaggag cagcagctag aagcacttag acagttcaag  600
caggcacagc ttcttcgtat tgctgctgct gacatcgctg gaactcttcc tgtaatgaag  660
gtaagtgacc accttacttg gcttgcagaa gctatgatcg acgcagtagt acagcaggct  720
tgggtacaaa tggtagcacg atatgggaaa cctaaccacc ttaacgaacg tgaaggtcgc  780
ggattcgctg tagtaggtta cggaaagctt ggtggttggg aacttggata ctcatcagac  840
ttagacctaa ttttcctaca cgattgccct atggacgcaa tgacagacgg ggaacgcgag  900
atcgatggtc gtcagttcta ccttcgactt gctcagcgta tcatgcatct tttctcaact  960
cgaacatcat caggaatcct ttacgaagta gacgcacgtc ttcgcccatc aggagcagct 1020
ggtatgcttg taacttcagc cgaagctttc gcagattacc agaagaacga agcttggaca 1080
tgggaacacc aggctcttgt acgagcaaga gttgtatatg gtgaccctca gttaacagca 1140
cacttcgacg ctgtacggcg tgagatcatg acactccctc gagagggaaa gacactccag 1200
acagaagtac gtgaaatgcg tgaaaagatg cgagcacacc taggaaacaa gcatcgtgac 1260
cgtttcgaca tcaaggcaga cgaaggaggt atcactgaca tcgagttcat cacacagtac 1320
cttgtactac gttacgcaca cgaaaagcca aagcttactc gttggtccga caacgtacgc 1380
atccttgaac tcctcgcaca gaacgacatc atggaagaac aagaagcaat ggcacttaca 1440
cgagcatata caacactacg agacgaacta caccaccttg ctctccagga gctaccagga 1500
cacgtatcag aggactgctt cactgctgaa cgggagcttg tacgtgcttc atggcagaag 1560
tggctcgttg aagaatga                                                1578

SEQ ID NO: 6            moltype = DNA   length = 1020
FEATURE                 Location/Qualifiers
source                  1..1020
                        mol_type = other DNA
                        organism = synthetic construct
SEQUENCE: 6
atggacgaag agcaacagct tgaggcgctg cgtcagttca aacaggcgca gctgttacgc   60
atcgccgcag cggatatcgc cggtacgcta ccggtgatga aagtgagcga tcacttaacc  120
tggctggcgg aagccatgat agatgccgtc gttcagcagg cgtgggttca aatggttgcc  180
cgctacggta agccgaatca cctgaacgaa cgcgaagggc gtggttttgc ggtggtcgac  240
tacggcaagc tgggcggctg ggagttaggc tacagttccg atcttgacct tatcttcctc  300
catgattgcc caatggatgc gatgactgac ggtgagcggg aaatcgacgg gcggcagttt  360
tatctgcgtc tggcgcaacg cattatgcat ctgttcagta cgcgtacctc ttccggcatt  420
ttgtatgaag tggatgctcg actgcgtccg tccggggcgg tgggaatgct ggtgacatcc  480
gcagaagcat ttgccgatta tcagaaaaac gaggcctgga cgtgggaaca tcaggcgctg  540
gtgcgtgcgc gtgtagtgta cggcgatccg cagctcaccg cgcactttga cgcagtgcgt  600
cgcgagatta tgacgctgcc gcgtgaaggt aaaactctgc aaacggaagt gcgggaaatg  660
cgcgagaaaa tgcgcgctca tctcgagcaat aaacatcggc atcgctttga tatcaaagct  720
gatgaagggg gaattaccga tatcgaattt attacccaat atctggtgtt gcgctacgct  780
catgaaaaac cgaagttaac gcgctggtca gacaacgtgc gtattctgga actactggcg  840
caaaacgaca ttatggaaga gcaggaagcg atggcgctga cccgtgctta cactacgctt  900
cgcgatgaac ttcatcatct ggcattacag gaattgccgg gccatgtgtc ggaggattgc  960
ttcaccgcag agcgtgaact ggtgcgggca agctggcaga agtggctggt ggaagaatga 1020

SEQ ID NO: 7            moltype = DNA   length = 1671
FEATURE                 Location/Qualifiers
source                  1..1671
                        mol_type = other DNA
                        organism = synthetic construct
SEQUENCE: 7
atgctcggcc gggtggagga ccgctacgcc gagctgttcg aggaggcgcc gtcgctgtcc   60
ggccccggca acctcgtctt caccggcacc gacgacgacc ccggcacggt gaagacgctg  120
gccggcatgg gctaccgcga ccccagccgg gtcatcgccg tggtctccac ctggcaccgc  180
gggcgctacc gctccacccg ctcgggccgc gcgcgggagc tgctgaccga gctggtgccg  240
gccatgacga acgagctggc gaagaccccc gccccgaccg acgcgctggt taagttcgac  300
agcttcctgg agcggcttcc ggcgggggtc gggctgttct cgctgttcat cgccaacccc  360
tggctgctcg ccctggtcgc ggagatcatg ggcacggcgc cgcagctggc cgagacgttg  420
tcgcgcaacc cgtcgctgct cgacgccgtg ctgtcgcccg acttcttcga cccgctgccc  480
gacgcggcgg ggctgacgcc ggagtaccag cgcttcatcg ccggggcgca caacttcgag  540
gatgtgtcag ccctgtcgcg gcgctggacc aacgaccagc gcttccgcgc cgggggcgca  600
atcctgcgcg gcatcaccga cggcgaccgc tgcggccccct tcctcgccga tctggccgac  660
gtggtggtgc cggagctggc cgcccgcgtg gaggaggagt tcgccgcccg ccacggccgc  720
atccccggcg gcgcctgggt ggtggtggcg atgggcaagc taggcagccg gcagctcacc  780
atcacctccg acatcgacct gatcgtggtc tacgaggtgc gccggggcac ccgccagtcg  840
gacggagcca agccgcctggc cccaacgag tattacatca agcgaggca gcgcctgacc  900
aacgccatca ccgccccgat ggccgacggg cggctgtacg aggtggacat gcggctgcgc  960
ccgtcgggca acgccggtcc gctcgccacc gcgctgacg ccttcaccgc ctatcaggcc 1020
aaggatgcct ggacgtggga gcacatggcc ctgacccgcg cccgcgtcat cggcagtgat 1080
tccggcggcg cgatccggc gctgggtcat aaggtcgagt cggcgatccg cggtgtgctg 1140
accggcccgc gcgaccccgg caaggtgctg cgggacgtcc ccgacatgcg ccgccgcatc 1200
```

-continued

```
gacaaggagt tcggcaccac caacccgtgg aacgtcaaat acgcccgcgg cggcctgatc  1260
gacatcgagt tcacggccca gtatctccag ctccgtcacg gccacgcgca tccggacatc  1320
ctgtccatcg ccaccagccg cgccctgctc aacgccgctg cggccgggct gctggcgccg  1380
gaggtggcgg aggagctggt ggcgacgctg aagctgtggc ggcggggtgca gggcttcctg  1440
cgcctgacca ccgacggcgt gctcgatccg cggcaggttt cgcccaccct gcgggagggc  1500
ctctcgcgcg ccgccttccc ggacgaggag ccggcggttg acttcgccgc gctcgacagc  1560
agaatccggg acatcgccgc ccgcgcccac cgccatttcg tggcgctggt cgaggagccg  1620
gcgtcaaggc tgcctccccc agagaccaac gaagaagcca aactcccatg a            1671
```

```
SEQ ID NO: 8              moltype = DNA  length = 1575
FEATURE                   Location/Qualifiers
source                    1..1575
                          mol_type = other DNA
                          organism = synthetic construct
SEQUENCE: 8
atgcccggca cggtgaagac gctggccggc atgggctacc gcgaccccag ccgggtcatc  60
gccgtggtct ccacctggca ccgcgggcgc taccgctcca cccgctcggg ccgcgcgcgg  120
gagctgctga ccgagctggt gccggccatg ctgaacgagc tggcgaagac ccccgccccg  180
gacgacgcgc tggttaagtt cgacagcttc ctggagcggc ttccggcggg ggtcgggctg  240
ttctcgctgt tcatcgccaa cccctggctg ctcgccctgg tcgcggagat catgggcacg  300
gcgccgcagc tggccgagac gttgtcgcgc aacccgtcgc tgctcgacgc cgtgctgtcg  360
cccgacttct tcgacccgct gcccgacgcg gcggggctga ccagcgcttc  420
atcgccgggg cgcacaactt cgaggatgtg ctgaccctgt cgcggcgctg gaccaacgac  480
cagcgcttcc gcgccggggc gcacatcctg cgcggcatca ccgacggcga ccgctgcggc  540
cccttcctcg ccgatctggc cgacgtggtg gtgccggagc tggccgcccg cgtggaggag  600
gagttcgccg cccgccacgg ccgcatcccc ggcgcgcct gggtggtggt ggcgatgggc  660
aagctaggca gccggcagct caccatcacc tccgacatcg acctgatcgt ggtctacgag  720
gtgccgccgg gcacccgcca gtcggacgga gccaagccgc tggcccccaa cgagtattac  780
atcaagctga cgcagcgcct gaccaacgcc atcaccgccc cgatggccga cgggcggctg  840
tacgaggtgg acatgcggct gcgcccgtcg ggcaacgccg gtccgctcgc caccgcgctg  900
gacgccttca ccgcctatca ggccaaggat gcctggacgt gggagcacat ggccctgacc  960
cgcgcccgcg tcatcggcag tgattccggc ggcggcgatc cggcgctggg tcataaggtc  1020
gagtcggcga tccgcggtgt gctgaccggc ccgcgcgacc cggccaaggt gctgcggacc  1080
gtcgccgaca tgcgccgccg catcgacaag gagttcggca ccaccaaccc gtggaacgtc  1140
aaatacgccc gcggcggcct gatcgacatc gagttcacgg cccagtatct ccagctccgt  1200
cacggccacg cgcatccgga catcctgtcc atcgccacca gccgcgccct gctcaacgcc  1260
gctgcggccg ggctgctggc cggggtc gcggaggagc tggtggcgac gctgaagctg  1320
tggcggcggg tgcagggctt cctgcgcctg accaccgacg gcgtgctcga tccgcggcag  1380
gtttcgccca ccctgcggga gggcctctcg cgcgccgcct cccggacga ggagccggcg  1440
gttgacttcg ccgcgctcga cagcagaatc cgggacatcg ccgcccgcgc ccaccgccat  1500
ttcgtggcgc tggtcgagga gccggcgtca aggctgcctc cccagagac caacgaagaa  1560
gccaaactcc catga                                                   1575
```

```
SEQ ID NO: 9              moltype = DNA  length = 1500
FEATURE                   Location/Qualifiers
source                    1..1500
                          mol_type = other DNA
                          organism = synthetic construct
SEQUENCE: 9
atgcaccgcg ggcgctaccg ctccacccgc tcgggccgcg cgcgggagct gctgaccgag  60
ctggtgccgg ccatgctgaa cgagctggcg aagacccccg ccccgacga cgcgctggtt  120
aagttcgaca gcttcctgga gcggcttccg gcgggggtcg ggctgttctc gctgttcatc  180
gccaacccct ggctgctcgc cctggtcgcg gagatcatgg gcacggcagc tggccgagac  240
gagacgttgt cgcgcaaccc gtcgctgctc gacgccgtgc tgtcgcccga cttcttcgac  300
ccgctgcccg acgcggcggg gctgacgccg gagtaccagc gcttcatcgc cggggcgcac  360
aacttcgagg atgtgctgac cctgtcgcgg cgctggacca cgaccagcg cttccgcgcc  420
ggggcgcaca tcctgcgcgg catcaccgac ggcgaccgct gcggcccctt cctcgccgat  480
ctggccgacg tggtggtgcc ggagctggcc gcccgcgtgg aggaggagtt cgccgcccgc  540
cacggccgca tccccggcgg cgcctgggtg gtggtggcga tgggcaagct aggcagccgg  600
cagctcacca tcacctccga catcgacctg atcgtggtct acgaggtgcc gccgggcacc  660
cgccagtcgg acggagccaa gccgctggcc cccaacgagt attacatcaa gctgacgcag  720
cgcctgacca acgccatcac cgccccgatg gccgatgggc ggctgtacga ggtggacatg  780
cggctgcgcc cgtcgggcaa cgccggtccg ctcgccaccg cgctggacgc cttcaccgcc  840
tatcaggcca aggatgcctg gacgtgggag cacatggccc tgacccgcgc cgcgtcatc  900
ggcagtgatt ccggcggcgg cgatccggcg ctgggtcata aggtcgagtc ggcgatccgc  960
ggtgtgctga ccggccgcg cgaccgcgcc aaggtgctgc gggacgtcgc cgacatgcgc  1020
cgccgcatcg acaaggagtt cggcaccacc aacccgtgga acgtcaaata cgcccgcggc  1080
ggcctgatcg acatcgagtt cacgcccag tatctccagc tccgtcacgg ccacgcgcat  1140
ccggacatcc tgtccatcgc caccagccgc gccctgctca acgccgctgc ggccgggctg  1200
ctggcgccgg aggtggcgga ggagctggtg gcgacgctga agctgtggcg gcgggtgcag  1260
ggcttcctgc gcctgaccac cgacggcgtg ctcgatccgc ggcaggtttc gcccaccctg  1320
cgggagggc tctcgcgcgc cgccttcccg gacgaggagc cggcggttga cttcgccgcg  1380
ctcgacagca gaatccggga catcgccgcc cgcgcccacc gccatttcgt ggcgctggtc  1440
gaggagccgg cgtcaaggct gcctccccca gagaccaacg aagaagccaa actcccatga  1500
```

-continued

```
SEQ ID NO: 10            moltype = DNA  length = 1428
FEATURE                  Location/Qualifiers
source                   1..1428
                         mol_type = other DNA
                         organism = synthetic construct
SEQUENCE: 10
atgctgaacg agctggcgaa gaccccccgcc ccggacgacg cgctggttaa gttcgacagc  60
ttcctggagc ggcttccggc gggggtcggg ctgttctcgc tgttcatcgc caaccctgg   120
ctgctcgccc tggtcgcgga gatcatgggc acggcgccgc agctggccga gacgttgtcg   180
cgcaacccgt cgctgctcga cgccgtgctg tcgcccgact tcttcgaccc gctgcccgac   240
gcggcggggc tgacgccgga gtaccagcgc ttcatcgccg gggcgcacaa cttcgaggat   300
gtgctgaccc tgtcgcggcg ctggaccaac gaccagcgct tccgcgccgg ggcgcacatc   360
ctgcgcggca tcaccgacgg cgaccgctgc ggccccttcc tcgccgatct ggccgacgtg   420
gtggtgccgg agctggccgc ccgcgtggag gaggagttcg ccgcccgcca cggccgcatc   480
cccggcggcg cctgggtggt ggtggcgatg ggcaagctag gcagccggca gctcaccatc   540
acctccgaca tcgacctgat cgtggtctac gaggtgccgc cgggcacccg ccagtcggac   600
ggagccaagc cgctggcccc caacgagtat tacatcaagc tgacgcagcg cctgaccaac   660
gccatcaccg ccccgatggc cgacgggcgg ctgtacgagg tggacatgcg gctgcgcccg   720
tcgggcaacg ccggtccgct cgccaccgcg ctggacgcct tcaccgccta tcaggccaag   780
gatgcctgga cgtgggagca catggccctg acccgcgccc gcgtcatcgg cagtgattcc   840
ggcggcggcg atccggcgct gggtcataag gtcgagtcgg cgatccgcgg tgtgctgacc   900
ggcccgcgcg accggccaa ggtgctgcgg gacgtcgccg acatgcgccg ccgcatcgac   960
aaggagttcg gcaccaccaa cccgtggaac gtcaaatacg cccgcggcgg cctgatcgac  1020
atcgagttca cggcccagta tctccagctc cgtcacggcc acgcgcatcc ggacatcctg  1080
tccatcgcca ccagccgcgc cctgctcaac gccgctgacg ccgggctgct ggcgccggag  1140
gtggcggagg agctggtggc gacgctgaag ctgtggcggc gggtgcaggg cttcctgcgc  1200
ctgaccaccg acggcgtgct cgatccgcgg caggtttcgc ccaccctgcg ggagggcctc  1260
tcgcgcgccg ccttcccgga cgaggagccg gcggttgact tcgccgcgct cgacagcaga  1320
atccgggaca tcgcgcgccg cgccaccgc catttcgtgg cgctggtcga ggagccggcg  1380
tcaaggctgc ctccccaga gaccaacgaa gaagccaaac tcccatga              1428

SEQ ID NO: 11            moltype = DNA  length = 1143
FEATURE                  Location/Qualifiers
source                   1..1143
                         mol_type = other DNA
                         organism = synthetic construct
SEQUENCE: 11
atgaacttcg aggatgtgct gaccctgtcg cggcgctgga ccaacgacca gcgcttccgc   60
gccggggcgc acatcctgcg cggcatcacc gacggcgacc gctgcggccc cttcctcgcc   120
gatctggccg acgtggtggt gccggagctg gccgcccgcg tggaggagga gttcgccgcc   180
cgccacggcc gcatccccgg cggcgcctgg gtggtggtgg cgatgggcaa gctaggcagc   240
cggcagctca ccatcaccc cgacatcgac ctgatcgtgg tctacgaggt gccgccgcgtc   300
acccgccagt cggacggagc caagccgctg gcccccaacg agtattacat caagctgacg   360
cagcgcctga ccaacgccat caccgccccg atggccgacg ggcggctgta cgaggtggac   420
atgcggctgc gcccgtcggg caacgccggt ccgctcgcca ccgcgctgga cgccttcacc   480
gcctatcagg ccaaggatgc ctggacgtgg gagcacatgg cctgcaccg cgcccgcgtc   540
atcggcagtg attccggcgg cggcgatccg gcgctgggtc ataaggtcga gtcggcgatc   600
cgcggtgtgc tgaccggccc gcgcgacccg gccaaggtgc tgcgggacgt cgccgacatg   660
cgccgccgca tcgacaagga gttcggcacc accaacccgt ggaacgtcaa atacgcccgc   720
ggcggcctga tcgacatcga gttcacggcc cagtatctcc agctccgtca cggccacggc   780
catccggaca tcctgtccat cgccaccagc cgcgccctgc tcaacgccgc tgcggccggg   840
ctgctggcgc cggaggtggc ggaggagctg gtggcgacgc tgaagctgtg gcggcgggtg   900
cagggcttcc tgcgcctgac caccgacggc gtgctcgatc cgcggcaggt ttcgcccacc   960
ctgcgggagg gcctctcgcg cgcgccttc ccggacgagg agccggcggt tgacttcgcc  1020
gcgctcgaca gcagaatccg ggacatcgcc gcccgcgccc accgccattt cgtggcgctg  1080
gtcgaggagc cggcgtcaag gctgcctccc cagagacca acgaagaagc caaactccca  1140
tga                                                               1143

SEQ ID NO: 12            moltype = DNA  length = 1500
FEATURE                  Location/Qualifiers
source                   1..1500
                         mol_type = other DNA
                         organism = synthetic construct
SEQUENCE: 12
atgcatagag gcagatatag aagtacgagg agcggaaggg ccagagaatt attaacggaa   60
ttagtccccg caatgttaaa tgaattagcc aaaacgcctg cgcccgatga tgccttagtg   120
aaatttgatt cgtttttaga aagattgccc gccggcgtgg gcttatttag cttatttatt   180
gcgaatccat ggttattggc gttagtgcgc gaaattatgg gtaccgcccc ccaattagcg   240
gaaactctaa gtaggaatcc tagttttatt agatgctgtct taagcccgga ttttttttgat   300
cccttaccgg atgccgccgg cttaaccccc gaatatcaaa ggtttattgc gggcgcccat   360
aattttgaag acgtttttaac tttaagcaga aggtggacga atgatcaaag atttaggcg    420
ggcgcccata tttttaagag gtattacgggat ggagataggt gtgggccgtt tttggctgac   480
ttagcggatg tcgttgtccc agaattagca gcgagggtcg aagaagaatt tgccggcagg   540
catggtagaa ttccgggagg tgcgtgggtc gtcgtcgcca tgggaaaatt gggttcgaga   600
caattgacga ttacgagtga tattgattta attgtcgtgt atgaagttcc ccctggtacg   660
aggcaaagcg atgcgctaa accccttagcg ccgaatgaat actatattaa attaacccaa   720
aggttaacga atgcgattac ggcgcccatg gcagacggca gattatatga agtcgatatg   780
agattaaggc ccagcgggaa tgcggggcccc ttggcgacgg cctagatgc gtttacggcg    840
```

```
taccaagcga aagacgcttg gacctgggaa catatggcgt taacgagagc tagagtgata  900
ggttcggaca gtggtggggg tgaccccgcc ttaggccaca aagtggaaag cgccattagg  960
ggcgtcttaa cggggcccag ggatcccgcg aaagtcttaa gagatgtggc ggatatgagg  1020
aggaggattg ataaagaatt tgggacgacg aatccctgga atgtaaagta tgcgaggggg  1080
gggttaattg atatagaatt taccgcgcaa tacttgcaat tgaggcatgg gcatgcccac  1140
cctgatattt taagtattgc gacgtcgaga gcgttattga atgcggccgc cgcgggatta  1200
ttagcccccg aagtcgccga agaattagtc gccaccttaa aattatggag aagagtccaa  1260
ggatttttaa gattaacgac agatggggtc ttagacccta gacaagtgag cccgacgtta  1320
agagaagggt tgagcagggc ggcgtttccc gatgaagaac ccgccgtcga ttttgcggcc  1380
ttggattcgc ggattagaga tattgcggcg agagcgcata ggcactttgt cgccttagtg  1440
gaagaacccg ccagccgctt accgccgccg gaaacaaatg aggaggcgaa gttgccctga  1500
```

```
SEQ ID NO: 13          moltype = DNA   length = 1413
FEATURE                Location/Qualifiers
source                 1..1413
                       mol_type = other DNA
                       organism = synthetic construct
SEQUENCE: 13
atgcgtgcgc tgcgcacgga cgcggcgcgt gagcatctcg cccgcatcgt ggcccttctc  60
atcgagcaac tgtcccatgg cggcgacccg gacggcgcac tcaatgccat ggacagcttc  120
ctgcgcgacc tgcccggtcc gcacctgctg gcggcgctgg agcacaatcc ggacctcgtg  180
cgcctcatcg ccaccatcgt cagcgccgcc ccgcgcctcg gcgagacgct ggcccggccg  240
ccctcgctcg ccgatgcgct gctcgatccc gccttcttcg acgtgctgcc cgacgagccg  300
gccctcgccg cccatctcga agccttgctc gatgcggcgc cgaatgagga agaacagttc  360
gaccgcgccc gccgcttccg gcaggaacag cacgttctga tcggcgtgcg catcgtctcc  420
ggcacgctgc cggcggcgcc ggcgggcgag gcctatgccc gcgtggcgga ggtcatcatc  480
cgcgccctgc acgcccgcgt ctgggcgcgc ttcgtggagg cgcacggcag cattcccggc  540
gcggatacgg cagtgctctc catgggcaag ctcggcagcc gcgagatgac cgccggctcc  600
gacctcgatc tcatcgtgct ctacgatttc gatccggcct cggacggcac gtcggatggc  660
ccgcgcccgc tggtcggagc gcagtatttc gcccgcttca cccagcgcct cgtcaccgcg  720
ctgaccagcc tcaccaatgc cggcaagctc tatgacgtgg acctgcgcct gcgcccgtcc  780
ggccggtcag gcccggtggc gacgcgcatc ggctccttcg agaattacca gcgcaccgag  840
gcctggacct gggagcacat ggcgctgacc cgggcgcgga tcatctccgc cagccccgcc  900
tttgcccggc gggtggagca ggtgatcctg caggtgctcg cccatccgcg tgatccccgc  960
cgcatcgccg gcgacattct cgacatgcgc cgggccatcg cggcggagaa gggcgaaagc  1020
gaccgctgga atctcaagca cgcggccggc ggacaggtgg acgcggagtt cctcgcccag  1080
ttcctcgtgc tcatccatgc cgaacggcat ccggagatcg tcgataccgc gacggcgcgc  1140
atcctcaccg tggcgggctg gcttcagctc ctgagtcccg aggattgcca gaccctctcc  1200
aacgcctgcc ggctctatca ggatctcacg caggtgctcc gcctcgccat cgaccggcca  1260
ttcgtgccgg cgcaggcgag cccggcgctg aaagcgctgc tggcgcgggc gggcgagatg  1320
ccggacttct cctccctcga cgcccatctc accgacacgg aagcgcgcgt gcgggccatc  1380
ttcgagcgca ttctggaagc cgcttccgcc tga                                 1413
```

```
SEQ ID NO: 14          moltype = DNA   length = 1383
FEATURE                Location/Qualifiers
source                 1..1383
                       mol_type = other DNA
                       organism = synthetic construct
SEQUENCE: 14
atgcatctcg cccgcatcgt ggcccttctc atcgagcaac tgtcccatgg cggcgacccg  60
gacggcgcac tcaatgccat ggacagcttc ctgcgcgacc tgcccggtcc gcacctgctg  120
gcggcgctgg agcacaatcc ggacctcgtg cgcctcatcg ccaccatcgt cagcgccgcc  180
ccgcgcctcg gcgagacgct ggcccggccg ccctcgctcg ccgatgcgct gctcgatccc  240
gccttcttcg acgtgctgcc cgacgagccg gccctcgccg cccatctcga agccttgctc  300
gatgcggcgc cgaatgagga agaacagttc gaccgcgccc gccgcttccg gcaggaacag  360
cacgttctga tcggcgtgcg catcgtctcc ggcacgctgc cggcggcgcc ggcgggcgag  420
gcctatgccc gcgtggcgga ggtcatcatc cgcgccctgc acgcccgcgt ctgggcgcgc  480
ttcgtggagg cgcacggcag cattcccggc gcggatacgg cagtgctctc catgggcaag  540
ctcggcagcc gcgagatgac cgccggctcc gacctcgatc tcatcgtgct ctacgatttc  600
gatccggcct cggacggcac gtcggatggc ccgcgcccgc tggtcggagc gcagtatttc  660
gcccgcttca cccagcgcct cgtcaccgcg ctgaccagcc tcaccaatgc cggcaagctc  720
tatgacgtgg acctgcgcct gcgcccgtcc ggccggtcag gcccggtggc gacgcgcatc  780
ggctccttcg agaattacca gcgcaccgag gcctggacct gggagcacat ggcgctgacc  840
cgggcgcgga tcatctccgc cagccccgcc tttgcccggc gggtggagca ggtgatcctg  900
caggtgctcg cccatccgcg tgatccccgc cgcatcgccg gcgacattct cgacatgcgc  960
cgggccatcg cggcggagaa gggcgaaagc gaccgctgga atctcaagca cgcggccggc  1020
ggacaggtgg acgcggagtt cctcgcccag ttcctcgtgc tcatccatgc cgaacggcat  1080
ccggagatcg tcgataccgc gacggcgcgc atcctcaccg tggcgggctg gcttcagctc  1140
ctgagtcccg aggattgcca gaccctctcc aacgcctgcc ggctctatca ggatctcacg  1200
caggtgctcc gcctcgccat cgaccggcca ttcgtgccgg cgcaggcgag cccggcgctg  1260
aaagcgctgc tggcgcgggc gggcgagatg ccggacttct cctccctcga cgcccatctc  1320
accgacacgg aagcgcgcgt gcgggccatc ttcgagcgca ttctggaagc cgcttccgcc  1380
tga                                                                  1383
```

```
SEQ ID NO: 15          moltype = DNA   length = 1353
FEATURE                Location/Qualifiers
source                 1..1353
                       mol_type = other DNA
                       organism = synthetic construct
```

```
SEQUENCE: 15
atggagcaac tgtcccatgg cggcgacccg gacggcgcac tcaatgccat ggacagcttc   60
ctgcgcgacc tgcccggtcc gcacctgctg gcggcgctgg agcacaatcc ggacctcgtg  120
cgcctcatcg ccaccatcgt cagcgccgcc ccgcgcctcg gcgagacgct ggcccggcgc  180
ccctcgctcg ccgatgcgct gctcgatccc gccttcttcg acgtgctgcc cgacgagccg  240
gccctcgccg cccatctcga agccttgctc gatgcggcgc cgaatgagga agaacagttc  300
gaccgcgccc gccgcttccg gcaggaacag cacgttctga tcggcgtgcg catcgtctcc  360
ggcacgctgc cggcggcgcg ggcgggcgag gcctatgccc cgcgtggcgga ggtcatcatc  420
cgcgccctgc acgcccgcgt ctgggcgcgc ttcgtggagg cgcacggcag cattcccggc  480
gcggatacgg cagtgctctc catgggcaag ctcggcagcc gcgagatgac cgccggctcc  540
gacctcgatc tcatcgtgct ctacgatttc gatccggcct cggacggcac gtcggatggc  600
ccgcgccgc tggtcggagc gcagtatttc gcccgcttca cccagcgcct cgtcaccgcg  660
ctgaccagcc tcaccaatgc cggcaagctc tatgacgtgg acctgcgcct gcgcccgtcc  720
ggccggtcag gcccggtggc gacggcatc ggctccttcg agaattacca gcgcaccgag  780
gcctggacct gggagcacat ggcgctgacc cgggcgcgga tcatctccgc cagccccgcc  840
tttgcccggc gggtggagca ggtgatcctg caggtgctcg cccatccgcg tgatccccgc  900
cgcatcgccg gcgacattct cgacatgcgc cgggccatcg cggcggagaa gggcgaaagc  960
gaccgctgga atctcaagca gcggccggc ggacaggtgg acgcgggagt cctcgcccaa 1020
ttcctcgtgc tcatccatgc cgaacggcat ccggagatcg tcgataccgc gacggcgcgc 1080
atcctcaccg tggcgggctg gcttcagctc ctgagtcccg aggattgcca gaccctctcc 1140
aacgcctgcc ggctctatca ggatctcacg caggtgctcc gcctcgccat cgaccggcca 1200
ttcgtgccgg cgcaggcgag cccggcgctg aaagcgctgc tggcgcgggc gggcgagatg 1260
ccggacttct cctccctcga cgcccatctc accgacacgg aagcgcgcgt gcgggccatc 1320
ttcgagcgca ttctggaagc cgcttccgcc tga                             1353

SEQ ID NO: 16          moltype = AA  length = 525
FEATURE                Location/Qualifiers
source                 1..525
                       mol_type = protein
                       organism = synthetic construct
SEQUENCE: 16
MAHMTNVRRV FNELIGDDES ETQEESLSEQ WRELWQDALQ EDDTTPVLAH LSEDDRKQVL   60
TLIADFRKEL DKRTIGPRGR QVLDHLMPHL LSDVCAREDA AVTLSRITAL LVGIVTRTTY  120
LELLSEFPAA LKHLISLCAA SPMIASQLAR YPLLLDELLD PNTLYQPTAT DAYRDELRQY  180
LLRVPEDDEE QQLEALRQFK QAQLLRIAAA DIAGTLPVMK VSDHLTWLAE AMIDAVVQQA  240
WVQMVARYGK PNHLNEREGR GFAVVGYGKL GGWELGYSSD LDLIFLHDCP MDAMTDGERE  300
IDGRQFYLRL AQRIMHLFST RTSSGILYEV DARLRPSGAA GMLVTSAEAF ADYQKNEAWT  360
WEHQALVRAR VVYGDPQLTA HFDAVRREIM TLPREGKTLQ TEVREMREKM RAHLGNKHRD  420
RFDIKADEGG ITDIEFITQY LVLRYAHEKP KLTRWSDNVR ILELLAQNDI MEEQEAMALT  480
RAYTTLRDEL HHLALQELPG HVSEDCFTAE RELVRASWQK WLVEE                  525

SEQ ID NO: 17          moltype = AA  length = 339
FEATURE                Location/Qualifiers
source                 1..339
                       mol_type = protein
                       organism = synthetic construct
SEQUENCE: 17
MDEEQQLEAL RQFKQAQLLR IAAADIAGTL PVMKVSDHLT WLAEAMIDAV VQQAWVQMVA   60
RYGKPNHLNE REGRGFAVVG YGKLGGWELG YSSDLDLIFL HDCPMDAMTD GEREIDGRQF  120
YLRLAQRIMH LFSTRTSSGI LYEVDARLRP SGAAGMLVTS AEAFADYQKN EAWTWEHQAL  180
VRARVVYGDP QLTAHFDAVR REIMTLPREG KTLQTEVREM REKMRAHLGN KHRDRFDIKA  240
DEGGITDIEF ITQYLVLRYA HEKPKLTRWS DNVRILELLA QNDIMEEQEA MALTRAYTTL  300
RDELHHLALQ ELPGHVSEDC FTAERELVRA SWQKWLVEE                         339

SEQ ID NO: 18          moltype = AA  length = 556
FEATURE                Location/Qualifiers
source                 1..556
                       mol_type = protein
                       organism = synthetic construct
SEQUENCE: 18
MLGRVEDRYA ELFEEAPSLS GPGNLVFTGT DDDPGTVKTL AGMGYRDPSR VIAVVSTWHR   60
GRYRSTRSGR ARELLTELVP AMLNELAKTP APDDALVKFD SFLERLPAGV GLFSLFIANP  120
WLLALVAEIM GTAPQLAETL SRNPSLLDAV LSPDFFDPLP DAAGLTPEYQ RFIAGAHNFE  180
DVLTLSRRWT NDQRFRAGAH ILRGITDGDR CGPFLADLAD VVVPELAARV EEEFAARHGR  240
IPGGAWVVVA MGKLGSRQLT ITSDIDLIVV YEVPPGTRQS DGAKPLAPNE YYIKLTQRLT  300
NAITAPMADG RLYEVDMRLR PSGNAGPLAT ALDAFTAYQA KDAWTWEHMA LTRARVIGSD  360
SGGGDPALGH KVESAIRGVL TGPRDPAKVL RDVADMRRRI DKEFGTTNPW NVKYARGGLI  420
DIEFTAQYLQ LRHGHAHPDI LSIATSRALL NAAAAGLLAP EVAEELVATL KLWRRVQGFL  480
RLTTDGVLDP RQVSPTLREG LSRAAFPDEE PAVDFAALDS RIRDIAARAH RHFVALVEEP  540
ASRLPPPETN EEAKLP                                                  556

SEQ ID NO: 19          moltype = AA  length = 524
FEATURE                Location/Qualifiers
source                 1..524
                       mol_type = protein
                       organism = synthetic construct
SEQUENCE: 19
MPGTVKTLAG MGYRDPSRVI AVVSTWHRGR YRSTRSGRAR ELLTELVPAM LNELAKTPAP   60
DDALVKFDSF LERLPAGVGL FSLFIANPWL LALVAEIMGT APQLAETLSR NPSLLDAVLS  120
```

```
PDFFDPLPDA AGLTPEYQRF IAGAHNFEDV LTLSRRWTND QRFRAGAHIL RGITDGDRCG   180
PFLADLADVV VPELAARVEE EFAARHGRIP GGAWVVVAMG KLGSRQLTIT SDIDLIVVYE   240
VPPGTRQSDG AKPLAPNEYY IKLTQRLTNA ITAPMADGRL YEVDMRLRPS GNAGPLATAL   300
DAFTAYQAKD AWTWEHMALT RARVIGSDSG GGDPALGHKV ESAIRGVLTG PRDPAKVLRD   360
VADMRRRIDK EFGTTNPWNV KYARGGLIDI EFTAQYLQLR HGHAHPDILS IATSRALLNA   420
AAAGLLAPEV AEELVATLKL WRRVQGFLRL TTDGVLDPRQ VSPTLREGLS RAAFPDEEPA   480
VDFAALDSRI RDIAARAHRH FVALVEEPAS RLPPPETNEE AKLP                    524

SEQ ID NO: 20            moltype = AA  length = 499
FEATURE                  Location/Qualifiers
source                   1..499
                         mol_type = protein
                         organism = synthetic construct
SEQUENCE: 20
MHRGRYRSTR SGRARELLTE LVPAMLNELA KTPAPDDALV KFDSFLERLP AGVGLFSLFI   60
ANPWLLALVA EIMGTAPQLA ETLSRNPSLL DAVLSPDFFD PLPDAAGLTP EYQRFIAGAH   120
NFEDVLTLSR RWTNDQRFRA GAHILRGITD GDRCGPFLAD LADVVVPELA ARVEEEFAAR   180
HGRIPGGAWV VVAMGKLGSR QLTITSDIDL IVVYEVPPGT RQSDGAKPLA PNEYYIKLTQ   240
RLTNAITAPM ADGRLYEVDM RLRPSGNAGP LATALDAFTA YQAKDAWTWE HMALTRARVI   300
GSDSGGGDPA LGHKVESAIR GVLTGPRDPA KVLRDVADMR RRIDKEFGTT NPWNVKYARG   360
GLIDIEFTAQ YLQLRHGHAH PDILSIATSR ALLNAAAAGL LAPEVAEELV ATLKLWRRVQ   420
GFLRLTTDGV LDPRQVSPTL REGLSRAAFP DEEPAVDFAA LDSRIRDIAA RAHRHFVALV   480
EEPASRLPPP ETNEEAKLP                                               499

SEQ ID NO: 21            moltype = AA  length = 475
FEATURE                  Location/Qualifiers
source                   1..475
                         mol_type = protein
                         organism = synthetic construct
SEQUENCE: 21
MLNELAKTPA PDDALVKFDS FLERLPAGVG LFSLFIANPW LLALVAEIMG TAPQLAETLS   60
RNPSLLDAVL SPDFFDPLPD AAGLTPEYQR FIAGAHNFED VLTLSRRWTN DQRFRAGAHI   120
LRGITDGDRC GPFLADLADV VVPELAARVE EEFAARHGRI PGGAWVVVAM GKLGSRQLTI   180
TSDIDLIVVY EVPPGTRQSD GAKPLAPNEY YIKLTQRLTN AITAPMADGR LYEVDMRLRP   240
SGNAGPLATA LDAFTAYQAK DAWTWEHMAL TRARVIGSDS GGGDPALGHK VESAIRGVLT   300
GPRDPAKVLR DVADMRRRID KEFGTTNPWN VKYARGGLID IEFTAQYLQL RHGHAHPDIL   360
SIATSRALLN AAAAGLLAPE VAEELVATLK LWRRVQGFLR LTTDGVLDPR QVSPTLREGL   420
SRAAFPDEEP AVDFAALDSR IRDIAARAHR HFVALVEEPA SRLPPPETNE EAKLP        475

SEQ ID NO: 22            moltype = AA  length = 380
FEATURE                  Location/Qualifiers
source                   1..380
                         mol_type = protein
                         organism = synthetic construct
SEQUENCE: 22
MNFEDVLTLS RRWTNDQRFR AGAHILRGIT DGDRCGPFLA DLADVVVPEL AARVEEEFAA   60
RHGRIPGGAW VVVAMGKLGS RQLTITSDID LIVVYEVPPG TRQSDGAKPL APNEYYIKLT   120
QRLTNAITAP MADGRLYEVD MRLRPSGNAG PLATALDAFT AYQAKDAWTW EHMALTRARV   180
IGSDSGGGDP ALGHKVESAI RGVLTGPRDP AKVLRDVADM RRRIDKEFGT TNPWNVKYAR   240
GGLIDIEFTA QYLQLRHGHA HPDILSIATS RALLNAAAAG LLAPEVAEEL VATLKLWRRV   300
QGFLRLTTDG VLDPRQVSPT LREGLSRAAF PDEEPAVDFA ALDSRIRDIA ARAHRHFVAL   360
VEEPASRLPP PETNEEAKLP                                              380

SEQ ID NO: 23            moltype = AA  length = 470
FEATURE                  Location/Qualifiers
source                   1..470
                         mol_type = protein
                         organism = synthetic construct
SEQUENCE: 23
MRALRTDAAR EHLARIVALL IEQLSHGGDP DGALNAMDSF LRDLPGPHLL AALEHNPDLV   60
RLIATIVSAA PRLGETLARR PSLADALLDP AFFDVLPDEP ALAAHLEALL DAAPNEEEQF   120
DRARRFRQEQ HVLIGVRIVS GTLPAARAGE AYARVAEVII RALHARVWAR FVEAHGSIPG   180
ADTAVLSMGK LGSREMTAGS DLDLIVLYDF DPASDGTSDG PRPLVGAQYF ARFTQRLVTA   240
LTSLTNAGKL YDVDLRLRPS GRSGPVATRI GSFENYQRTE AWTWEHMALT RARIISASPA   300
FARRVEQVIL QVLAHPRDPR RIAGDILDMR RAIAAEKGES DRWNLKHAAG GQVDAEFLAQ   360
FLVLIHAERH PEIVDTATAR ILTVAGWLQL LSPEDCQTLS NACRLYQDLT QVLRLAIDRP   420
FVPAQASPAL KALLARAGEM PDFSSLDAHL TDTEARVRAI FERILEAASA             470

SEQ ID NO: 24            moltype = AA  length = 460
FEATURE                  Location/Qualifiers
source                   1..460
                         mol_type = protein
                         organism = synthetic construct
SEQUENCE: 24
MHLARIVALL IEQLSHGGDP DGALNAMDSF LRDLPGPHLL AALEHNPDLV RLIATIVSAA   60
PRLGETLARR PSLADALLDP AFFDVLPDEP ALAAHLEALL DAAPNEEEQF DRARRFRQEQ   120
HVLIGVRIVS GTLPAARAGE AYARVAEVII RALHARVWAR FVEAHGSIPG ADTAVLSMGK   180
LGSREMTAGS DLDLIVLYDF DPASDGTSDG PRPLVGAQYF ARFTQRLVTA LTSLTNAGKL   240
YDVDLRLRPS GRSGPVATRI GSFENYQRTE AWTWEHMALT RARIISASPA FARRVEQVIL   300
```

```
QVLAHPRDPR RIAGDILDMR RAIAAEKGES DRWNLKHAAG GQVDAEFLAQ FLVLIHAERH   360
PEIVDTATAR ILTVAGWLQL LSPEDCQTLS NACRLYQDLT QVLRLAIDRP FVPAQASPAL   420
KALLARAGEM PDFSSLDAHL TDTEARVRAI FERILEAASA                        460

SEQ ID NO: 25            moltype = AA  length = 450
FEATURE                  Location/Qualifiers
source                   1..450
                         mol_type = protein
                         organism = synthetic construct
SEQUENCE: 25
MEQLSHGGDP DGALNAMDSF LRDLPGPHLL AALEHNPDLV RLIATIVSAA PRLGETLARR   60
PSLADALLDP AFFDVLPDEP ALAAHLEALL DAAPNEEEQF DRARRFRQEQ HVLIGVRIVS   120
GTLPAARAGE AYARVAEVII RALHARVWAR FVEAHGSIPG ADTAVLSMGK LGSREMTAGS   180
DLDLIVLYDF DPASDGTSDG PRPLVGAQYF ARFTQRLVTA LTSLTNAGKL YDVDLRLRPS   240
GRSGPVATRI GSFENYQRTE AWTWEHMALT RARIISASPA FARRVEQVIL QVLAHPRDPR   300
RIAGDILDMR RAIAAEKGES DRWNLKHAAG GQVDAEFLAQ FLVLIHAERH PEIVDTATAR   360
ILTVAGWLQL LSPEDCQTLS NACRLYQDLT QVLRLAIDRP FVPAQASPAL KALLARAGEM   420
PDFSSLDAHL TDTEARVRAI FERILEAASA                                   450

SEQ ID NO: 26            moltype = AA  length = 237
FEATURE                  Location/Qualifiers
source                   1..237
                         mol_type = protein
                         organism = synthetic construct
SEQUENCE: 26
MSTKKKPLTQ EQLEDARRLK AIYEKKKNEL GLSQESVADK MGMGQSGVGA LFNGINALNA   60
YNAALLAKIL KVSVEEFSPS IAREIYEMYE AVSMQPSLRS EYEYPVFSHV QAGMFSPELR   120
TFTKGDAERW VSTTKKASDS AFWLEVEGNS MTAPTGSKPS FPDGMLILVD PEQAVEPGDF   180
CIARLGGDEF TFKKLIRDSG QVFLQPLNPQ YPMIPCNESC SVVGKVIASQ WPEETFG     237

SEQ ID NO: 27            moltype = AA  length = 218
FEATURE                  Location/Qualifiers
source                   1..218
                         mol_type = protein
                         organism = synthetic construct
SEQUENCE: 27
MARLNRESVI DAALELLNET GIDGLTTRKL AQKLGIEQPT LYWHVKNKRA LLDALAVEIL   60
ARHHDYSLPA AGESWQSFLR NNAMSFRRAL LRYRDGAKVH LGTRPDEKQY DTVETQLRFM   120
TENGFSLRDG LYAISAVSHF TLGAVLEQQE HTAALTDRPA APDENLPPLL REALQIMDSD   180
DGEQAFLHGL ESLIRGFEVQ LTALLQIVGG DKLIIPFC                          218

SEQ ID NO: 28            moltype = AA  length = 207
FEATURE                  Location/Qualifiers
source                   1..207
                         mol_type = protein
                         organism = synthetic construct
SEQUENCE: 28
MSRLDKSKII NGALELLNGV GIEGLTTRKL AQKLGVEQPT LYWHVKNKRA LLDALPIEML   60
DRHHTHSCPL EPESWQDFLR NNAKSYRCAL LSHRDGAKVH LGTRPTEKQY ETLENQLAFL   120
CQQGFSLENA LYALSAVGHF TLGCVLEEQE HQVAKEERET PTTDSMPPLL KQAIELFDRQ   180
GAEPAFLFGL ELIICGLEKQ LKCESGS                                      207

SEQ ID NO: 29            moltype = AA  length = 360
FEATURE                  Location/Qualifiers
source                   1..360
                         mol_type = protein
                         organism = synthetic construct
SEQUENCE: 29
MKPVTLYDVA EYAGVSYQTV SRVVNQASHV SAKTREKVEA AMAELNYIPN RVAQQLAGKQ   60
SLLIGVATSS LALHAPSQIV AAIKSRADQL GASVVVSMVE RSGVEACKAA VHNLLAQRVS   120
GLIINYPLDD QDAIAVEAAC TNVPALFLDV SDQTPINSII FSHEDGTRLG VEHLVALGHQ   180
QIALLAGPLS SVSARLRLAG WHKYLTRNQI QPIAEREGDW SAMSGFQQTM QMLNEGIVPT   240
AMLVANDQMA LGAMRAITES GLRVGADISV VGYDDTEDSS CYIPPLTTIK QDFRLLGQTS   300
VDRLLQLSQG QAVKGNQLLP VSLVKRKTTL APNTQTASPR ALADSLMQLA RQVSRLESGQ   360

SEQ ID NO: 30            moltype = AA  length = 200
FEATURE                  Location/Qualifiers
source                   1..200
                         mol_type = protein
                         organism = synthetic construct
SEQUENCE: 30
MARTPSRSSI GSLRSPHTHK AILTSTIEIL KECGYSGLSI ESVARRAGAS KPTIYRWWTN   60
KAALIAEVYE NESEQVRKFP DLGSFKADLD FLLRNLWKVW RETICGEAFR CVIAEAQLDP   120
ATLTQLKDQF MERRREMPKK LVENAISNGE LPKDTNRELL LDMIFGFCWY RLLTEQLTVE   180
QDIEEFTSLL INGVCPGTQR                                              200
```

```
SEQ ID NO: 31              moltype = DNA   length = 70
FEATURE                    Location/Qualifiers
source                     1..70
                           mol_type = other DNA
                           organism = synthetic construct
SEQUENCE: 31
attatcaccg ccagaggtaa aatagtcaac acgcacggtg ttagatattt ataaatagtg   60
gtgatagatt                                                          70

SEQ ID NO: 32              moltype = DNA   length = 55
FEATURE                    Location/Qualifiers
source                     1..55
                           mol_type = other DNA
                           organism = synthetic construct
SEQUENCE: 32
tccctatcag tgatagagat tgacatccct atcagtgata gagatactga gcaca         55

SEQ ID NO: 33              moltype = DNA   length = 67
FEATURE                    Location/Qualifiers
source                     1..67
                           mol_type = other DNA
                           organism = synthetic construct
SEQUENCE: 33
taatgtgagt tagctcactc attaggcacc ccaggcttta cactttatgc ttccggctcg   60
tatgttg                                                             67

SEQ ID NO: 34              moltype = DNA   length = 56
FEATURE                    Location/Qualifiers
source                     1..56
                           mol_type = other DNA
                           organism = synthetic construct
SEQUENCE: 34
gattcgttac caattgacat gatacgaaac gtaccgtatc gttaaggtta ctagag       56

SEQ ID NO: 35              moltype = AA    length = 605
FEATURE                    Location/Qualifiers
source                     1..605
                           mol_type = protein
                           organism = synthetic construct
SEQUENCE: 35
MDTYAGAYDR QSRERENSSA ASPATQRSAN EDKAADLQRE VERDGGRFRF VGHFSEAPGT   60
SAFGTAERPE FERILNECRA GRLNMIIVYD VSRFSRLKVM DAIPIVSELL ALGVTIVSTQ  120
EGVFRQGNVM DLIHLIMRLD ASHKESSLKS AKILDTKNLQ RELGGYVGGK APYGFELVSE  180
TKEITRNGRM VNVVINKLAH STTPLTGPFE FEPDVIRWWW REIKTHKHLP FKPGSQAAIH  240
PGSITGLCKR MDADAVPTRG ETIGKKTASS AWDPATVMRI LRDPRIAGFA AEVIYKKKPD  300
GTPTTKIEGY RIQRDPITLR PVELDCGPII EPAEWYELQA WLDGRGRGKG LSRGQAILSA  360
MDKLYCECGA VMTSKRGEES IKDSYRCRRR KVVDPSAPGQ HEGTCNVSMA ALDKFVAERI  420
FNKIRHAEGD EETLALLWEA ARRFGKLTEA PEKSGERANL VAERADALNA LEELYEDRAA  480
GAYDGPVGRK HFRKQQAALT LRQQGAEERL AELEAAEAPK LPLDQWFPED ADADPTGPKS  540
WWGRASVDDK RVFVGLFVDK IVVTKSTTGR GQGTPIEKRA SITWAKPPTD DDEDDAQDGT  600
EDVAA                                                              605

SEQ ID NO: 36              moltype = AA    length = 246
FEATURE                    Location/Qualifiers
source                     1..246
                           mol_type = protein
                           organism = synthetic construct
SEQUENCE: 36
MNNVIPLQNS PERVSLLPIA PGVDFATALS LRRMATSTGA TPAYLLAPEV SALLFYMPDQ   60
RHHMLFATLW NTGMRIGEAR MLTPESFDLD GVRPFVRILS EKVRARRGRP PKDEVRLVPL  120
TDISYVRQME SWMITTRPRR REPLWAVTDE TMRNWLKQAV RRAEADGVHF SIPVTPHTFR  180
HSYIMHMLYH RQPRKVIQAL AGHRDPRSME VYTRVFALDM AATLAVPFTG DGRDAAEILR  240
TLPPLK                                                             246

SEQ ID NO: 37              moltype = AA    length = 385
FEATURE                    Location/Qualifiers
source                     1..385
                           mol_type = protein
                           organism = synthetic construct
SEQUENCE: 37
MLTVKQIEAA KPKEKPYRLL DGNGLYLYVP VSGKKVWQLR YKIDGKEKIL TVGKYPLMTL   60
QEARDKAWTA RKDISVGIDP VKAKKASSNN NSFSAIYKEW YEHKKQVWSV GYATELAKMF  120
DDDILPIIGG LEIQDIEPMQ LLEVIRRFED RGAMERANKA RRRCGEVFRY AIVTGRAKYN  180
PAPDLADAMK GYRKKNFPFL PADQIPAFNK ALATFSGSIV SLIATKVLRY TALRTKELRS  240
MLWKNVDFEN RIITIDASVM KGRKIHVVPM SDQVVELLTT LSSITKPVSE FVFAGRNDKK  300
KPICENAVLL VIKQIGYEGL ESGHGFRHEF STIMNEHEWP ADAIEVQLAH ANGGSVRGIY  360
NHAQYLDKRR EMMQWWADWL DEKVE                                        385
```

```
SEQ ID NO: 38               moltype = AA    length = 92
FEATURE                     Location/Qualifiers
source                      1..92
                            mol_type = protein
                            organism = synthetic construct
SEQUENCE: 38
MVVTTSDVVM CQMRRSDVQG GYRVYGSWMA ENVQDQVSIL NQKLSEFAPS MPHAVRSDVI   60
NNRLQNLHLH AHHFLIRRHQ LITHLNPHLH RN                                 92

SEQ ID NO: 39               moltype = AA    length = 368
FEATURE                     Location/Qualifiers
source                      1..368
                            mol_type = protein
                            organism = synthetic construct
SEQUENCE: 39
MSVKKLENGQ YQVDVSFGFD PITGERIRTR PVASTRKEAL ELEAKLRREF QEERARKSRS   60
VSFPTLISIY LASCEIDSKP NYYQNQKYII NKHISDYFLK SDIQKITHRE ITDFRKHLME  120
TGLSNKSVNN IMTSLSKIFD TAVHEEILKR NPCDNVKRLP LTRKKMKFWR PEEFKKFISL  180
IPQDQLLFKT FYTVAFLTGL RCGEMLALQW KDIDKILLEI DVHKSCTWLD GQFVVTTPKT  240
KNSIRRVSIN KKLLKLLERW KEAQEELFNE LGIRHSHDTY IFQYKDTPSR KDIFSRKIKY  300
FCKDSDLTPI RLHDFRHSHV ALLIHQGEDY ITIKERLGHG SVKTTIDVYG HLYPNKQKEM  360
ADKLDDLL                                                           368

SEQ ID NO: 40               moltype = AA    length = 197
FEATURE                     Location/Qualifiers
source                      1..197
                            mol_type = protein
                            organism = synthetic construct
SEQUENCE: 40
LDRLRAVLDQ GRNPKLYLQQ ERAKYSANQS FESIFRDWID SAGKQGLKEK TWHYQKRSSE   60
IYLLPRLGKY PLTDITELSL RNCLREVSES SPSNTERLVS VLHKFYDWLI DEQILEINAA  120
AGITAKKVGG KKGKRTRVLN DNEIRILWRY LHESKITEKN RIYIKLLLLL GGRKGELIQA  180
EKHHFDLQSA MWTVPIE                                                  197

SEQ ID NO: 41               moltype = DNA    length = 1818
FEATURE                     Location/Qualifiers
source                      1..1818
                            mol_type = other DNA
                            organism = synthetic construct
SEQUENCE: 41
atggacacgt atgcgggcgc atacgatcga cagagccgtg agcgtgaaaa tagctcagcc   60
gctagcccag caacccaacg atctgccaac gaggataaag cagctgatct gcaacgggag  120
gtggagcgtg atggcggacg gttccgcttt gtgggtcact tctcggaagc tccggggtaca  180
tccgcctttg gtactgctga acgcccggaa tttgaacgta ttctgaatga atgtcgcgcg  240
ggccgcttaa acatgattat tgtatatgat gtcagccggt ttagccgctt gaaggtgatg  300
gatgctatac ctattgtcag tgagctgcta gcattaggcg taacaattgt ctcgacccag  360
gaaggcgttt ttcgccaagg taacgttatg gatctgatcc acttaattat gaggttagat  420
gcatcgcata aggaaagttc gctcaaatcc gctaagattt tagataccaa aaacctccag  480
cgtgagctgg gtggctatgt gggcgggaaa gcgccgtatg gctttgaatt ggtcagcgaa  540
actaaagaga tcaccagaaa tggtcgtatg gtcaacgtgg ttattaataa acttgcacat  600
tcaaccacgc cactgacagg tccgtttgag tttgaaccgg atgttattcg ttggtggtgg  660
cgcgaaatca aaactcacaa acatctgccg tttaaaccgg gatcacaggc tgccatccat  720
ccgggctcca tcacgggtct gtgcaaacgt atggacgcag acgcggtgcc tacccgcggc  780
gagacgatcg gcaagaaaac cgcgagcagt gcgtgggacc cggccactgt tatgcggatt  840
ctgcgggacc cgagaattgc cggcttcgcg gccgaagtga tatacaaaaa aaaacccgat  900
ggcactccca cgaccaaaat agaaggttat cgcatccagc gagatccgat caccccttcgt  960
ccagtagagc ttgattgtgg gcctattatt gaaccggctg agtggtacga attacaggcg  1020
tggctggacg gtcgtgggag aggcaaaggc ctctctcgtg gtcaggccat tttgtctgca  1080
atggataaac tctattgcga atgcggtgca gttatgacga gtaagcgtgg tgaggaaagc  1140
atcaaagatt cctatcgctg ccggcgccgc aaagtggtgg accgtcggc ccctgggcag  1200
catgaaggaa catgtaacgt atccatggcg gcgcttgaca agttcgttgc gagcgcatt  1260
tttaataaaa ttcgtcacgc ggaaggcgac gaagaaacac tggcgctgtt gtgggaagcg  1320
gcccgccgct tcggtaaact gacagaagct ccagaaaaga gtggagagcg cgcgaatctg  1380
gtggcagaac gtgcagatgc cctgaacgcg ctggaagaac tttacgaaga tcgtgccgcc  1440
ggtgcgtacg atgggccggt tggtcgcaag catttccgca aacagcaggc agccctgact  1500
ctgcgtcagc aaggcgcgga ggaacgcctg gcggaactgg aagccgcgga ggctccgaag  1560
ctgccgttgg atcaatggtt cccagaagat gcggacgcg acccaacggg gcctaaaagc  1620
tggtggggac gtgcctctgt cgatgataaa cgagtgttcg ttgggctatt tgtagacaaa  1680
atcgtggtca ccaaatctac caccggccgt ggccagggca cgcctatcga aaaacgtgca  1740
tcaatcacct gggcgaaacc ccccacggac gatgacgagg atgacgccca agatggaacc  1800
gaagatgtgg cggcctaa                                                1818

SEQ ID NO: 42               moltype = DNA    length = 50
FEATURE                     Location/Qualifiers
source                      1..50
                            mol_type = other DNA
                            organism = synthetic construct
```

-continued

```
SEQUENCE: 42
ctacgccccc aactgagaga actcaaaggt taccccagtt ggggcactac                  50

SEQ ID NO: 43                moltype = DNA   length = 53
FEATURE                      Location/Qualifiers
source                       1..53
                             mol_type = other DNA
                             organism = synthetic construct
SEQUENCE: 43
ccgcggtgcg ggtgccaggg cgtgcccttg ggctccccgg gcgcgtactc cac             53

SEQ ID NO: 44                moltype = DNA   length = 35
FEATURE                      Location/Qualifiers
source                       1..35
                             mol_type = other DNA
                             organism = synthetic construct
SEQUENCE: 44
gctagcacaa tacctaggac tgagctagct gtcaa                                  35

SEQ ID NO: 45                moltype = AA   length = 242
FEATURE                      Location/Qualifiers
source                       1..242
                             mol_type = protein
                             organism = synthetic construct
SEQUENCE: 45
GESLFKGPRD YNPISSTICH LTNESDGHTT SLYGIGFGPF IITNKHLFRR NNGTLLVQSL      60
HGVFKVKNTT TLQQHLIDGR DMIIIRMPKD FPPFPQKLKF REPQREERIC LVTTNFQTKS     120
MSSMVSDTSC TFPSSDGIFW KHWIQTKDGQ CGSPLVSTRD GFIVGIHSAS NFTNTNNYFT     180
SVPKNFMELL TNQEAQQWVS GWRLNADSVL WGGHKVFMSK PEEPFQPVKE ATQLMNELVY     240
SQ                                                                    242

SEQ ID NO: 46                moltype = AA   length = 241
FEATURE                      Location/Qualifiers
source                       1..241
                             mol_type = protein
                             organism = synthetic construct
SEQUENCE: 46
SKALLKGVRD FNPISACVCL LENSSDGHSE RLFGIGFGPY IIANQHLFRR NNGELTIKTM      60
HGEFAVANST QLQMKPVEGR DIIVIKMAKD FPPFPQKLKF RQPTIKDRVC MVSTNFQQKS     120
VSSLVSESSH IVHKEDTSFW QHWITTKDGQ AGSPLVSIID GNILGIHSLT HTTNGSNYFV     180
EFPEKFVATY LDAADGWCKN WKFNADKISW GSFTLVEDAP EDDFMAKKTV AAIMDDLVRT     240
Q                                                                     241

SEQ ID NO: 47                moltype = AA   length = 242
FEATURE                      Location/Qualifiers
source                       1..242
                             mol_type = protein
                             organism = synthetic construct
SEQUENCE: 47
MGVSLSRGVR DYNAISSMVC RVTNDSGSSS TTMYGIGYGC YIITNKHLFR ENNGRLLITS      60
HHGEYICKNS ASLKLSLVPG RDMLLIRLPK DCPPFPSKLK FREPTSEEKA VLVVTNFQEK     120
HLSSMVSESS CVVQREDSPI WRHWISTKDG HCGAPIVSIR DGYIIGSHCG ENPMTSNFFT     180
SIPKDFQNLL NGKEANEWVS GWKYNIDAVC WGGLSVVNDA PSEPFITAKV VSALDTEGIK     240
VQ                                                                    242

SEQ ID NO: 48                moltype = AA   length = 219
FEATURE                      Location/Qualifiers
source                       1..219
                             mol_type = protein
                             organism = synthetic construct
SEQUENCE: 48
SNSMFRGLRD YNPISNNICH LTNVSDGASN SLYGVGFGPL ILTNRHLFER NNGELIIKSR      60
HGEFVIKNTT QLHLLPIPDR DLLLIRLPKD VPPFPQKLGF RQPEKGERIC MVGSNFQTKS     120
ITSIVSETST IMPVENSQFW KHWISTKDGQ CGSPMVSTKD GKILGLHSLA NFQNSINYFA     180
AFPDDFTEKY LHTIEAHEWV KHWKYNTSAI SWGSLNIQA                            219

SEQ ID NO: 49                moltype = AA   length = 219
FEATURE                      Location/Qualifiers
source                       1..219
                             mol_type = protein
                             organism = synthetic construct
SEQUENCE: 49
SKSVYKGLRD YSGISTLICQ LTNSSDGHKE TMFGVGYGSF IITNGHLFRR NNGMLTVKTW      60
HGEFVIHNTT QLKIHFIQGR DVILIRMPKD FPPFGKRNLF RQPKREERVC MVGTNFQEKS     120
LRATVSESSM ILPEGKGSFW IHWITTQDGF CGLPLVSVND GHIVGIHGLT SNDSEKNFFV     180
PLTDGFEKEY LENADNLSWD KHWFWEPSKI AWGSLNLVE                            219
```

```
SEQ ID NO: 50              moltype = AA   length = 219
FEATURE                    Location/Qualifiers
source                     1..219
                           mol_type = protein
                           organism = synthetic construct
SEQUENCE: 50
SKSLFRGLRD YNPIASSICQ LNNSSGARQS VMFGLGFGGL IVTNQHLFKR NDGELTIRSH    60
HGEFVVKDTK TLKLLPCKGR DIVIIRLPKD FPPFPKRLQF RTPTTEDRVC LIGSNFQTKS   120
ISSTMSETSA TYPVDNSHFW KHWISTKDGH CGLPIVSTRD GSILGLHSLA NSTNTQNFYA   180
AFPDNFETTY LSNQDNDNWI KQWRYNPDEV CWGSLQLKR                          219

SEQ ID NO: 51              moltype = AA   length = 182
FEATURE                    Location/Qualifiers
source                     1..182
                           mol_type = protein
                           organism = synthetic construct
SEQUENCE: 51
APITAYAQQT RGLLGCIITS LTGRDKNQVE GEVQIVSTAT QTFLATCING VCWTVYHGAG    60
TRTIASPKGP VIQTYTNVDQ DLVGWPAPQG SRSLTPCTCG SSDLYLVTRH ADVIPVRRRG   120
DSRGSLLSPR PISYLKGSSG GPLLCPTGHA VGLFRAAVCT RGVAKAVDFI PVENLETTMR   180
SP                                                                  182

SEQ ID NO: 52              moltype = AA   length = 233
FEATURE                    Location/Qualifiers
source                     1..233
                           mol_type = protein
                           organism = Homo sapiens
SEQUENCE: 52
IVGGQECKDG ECPWQALLIN EENEGFCGGT ILSEFYILTA AHCLYQAKRF KVRVGDRNTE    60
QEEGGEAVHE VEVVIKHNRF TKETYDFDIA VLRLKTPITF RMNVAPACLP ERDWAESTLM   120
TQKTGIVSGF GRTHEKGRQS TRLKMLEVPY VDRNSCKLSS SFIITQNMFC AGYDTKQEDA   180
CQGDSGGPHV TRFKDTYFVT GIVSWGEGCA RKGKYGIYTK VTAFLKWIDR SMK          233

SEQ ID NO: 53              moltype = AA   length = 315
FEATURE                    Location/Qualifiers
source                     1..315
                           mol_type = protein
                           organism = Homo sapiens
SEQUENCE: 53
QWYLSGVTQR DLNVKAAWAQ GYTGHGIVVS ILDDGIEKNH PDLAGNYDPG ASFDVNDQDP    60
DPQPRYTQMN DNRHGTRCAG EVAAVANNGV CGVGVAYNAR IGGVRMLDGE VTDAVEARSL   120
GLNPNHIHIY SASWGPEDDG KTVDGPARLA EEAFFRGVSQ GRGGLGSIFV WASGNGGREH   180
DSCNCDGYTN SIYTLSISSA TQFGNVPWYS EACSSTLATT YSSGNQNEKQ IVTTDLRQKC   240
TESHTGTSAS APLAAGIIAL TLEANKNLTW RDMQHLVVQT SKPAHLNAND WATNGVGRKV   300
SHSYGYGLLD AGAMV                                                    315

SEQ ID NO: 54              moltype = DNA   length = 714
FEATURE                    Location/Qualifiers
source                     1..714
                           mol_type = other DNA
                           organism = synthetic construct
SEQUENCE: 54
atgggtgaat ccctgttcaa aggcccgcgc gattataacc cgatctcctc aacgatctgt    60
catctcacga atgagtccga cggccacact acgtctcttt acggtatcgg attcggcccg   120
ttcatcatta cgaacaagca cttgttccgc cgtaacaacg gtaccctgct tgtacaatcc   180
ctgcacggtg tgttcaaggt gaagaacacg accaccctgc aacaacatct gatcgacggc   240
cgcgacatga tcatcatcag gatgcctaaa gatttccctc cattcccgca gaaactcaaa   300
tttcgcgaac cgcagcgcga agaacgcatc tgcctggtca ccactaattt ccaaaccaag   360
tccatgtcgt ccatggtctc tgacacctca tgtacattcc cgtcgtcaga tggaatcttc   420
tggaagcatt ggattcagac taaggacggc cagtgcggtt ccccgcttgt cagcaccagg   480
gatggtttca ttgtgggtat ccacagcgcc tcgaattta cgaataccaa caattacttc    540
acctcggtcc cgaagaactt tatggaactt ctaacaaacc aagaggccca caatgggttt   600
tcgggatggc gcctgaacgc ggattcggtg ttatggggcg gccacaaagt gttcatggtc   660
aagcccgagg aaccctttca gccggtgaag gaggccacac agctgatgaa ctaa         714

SEQ ID NO: 55              moltype = DNA   length = 657
FEATURE                    Location/Qualifiers
source                     1..657
                           mol_type = other DNA
                           organism = synthetic construct
SEQUENCE: 55
atgagtaagg cattgctgaa gggagtccgc gacttcaacc cgatctcggc ttgtgtctgc    60
ctgttggaga actcctcgga tggccacagc gaacgcctgt tcgggatcgg cttcggccg    120
tatatcatcg ccaatcagca ccttttccgc cgaaacaacg gcgagctgac gatcaagaca   180
atgcacggtg aattcaaagt taagaactcg acccagctgc aaatgaagcc ggttgaagga   240
cgcgacatca tcgttatcaa gatggctaaa gacttcccgc cgttccccca gaagctgaag   300
ttccggcaac cgacgatcaa ggaccgcgtt tgcatggtgt ccaccaattt ccagcaaaag   360
agcgtgagta gcctcgtttc cgaatcgagc catatcgtgc acaaagagga tacttcgttc   420
```

```
tggcaacatt ggatcactac taaagacggt caatgcggaa gtccgcttgt gagcatcatt   480
gacgggaaca tcctgggaat ccacagcttg acacacacca ctaacggttc caactatttt   540
gtggaattcc cggaaaagtt tgtggcaacc tacctggatg ccgccgatgg ctggtgtaaa   600
aactggaaat tcaacgcgga taagatcagt tggggatctt tcacattggt cgagtaa      657
```

SEQ ID NO: 56            moltype = DNA  length = 729
FEATURE                  Location/Qualifiers
source                   1..729
                         mol_type = other DNA
                         organism = synthetic construct
SEQUENCE: 56
```
atgggcgttt cgctgagtcg gggcgtccgc gactacaacg ccatctcttc gatggtgtgc   60
cgggtgacaa atgattccgg ctcgtcgtct accacaatgt atggtattgg ttacggctgc   120
tacatcatca ccaataagca tctgttcagg gagaacaacg gccgactgct gattacatcc   180
catcacgggg agtatatttg caagaattcg gcgagtctga agctgagcct tgttccaggt   240
cgtgatatgc tgctgatccg gctcccaaag gactgccccc cgtttccgag caaactgaag   300
ttccgggagc aacctcgga agagaaggcg gtgctggtcg tcaccaactt ccaggaaaaa   360
cacctgtcgt ccatggtgag cgaaagcagt tgcgtcgtac aacgggaaga ctccccgatt   420
tggcgccact ggatctccac caaggacggc cattgcggcg ctccgattgt gtcgatccgg   480
gatgggtata tcatcggtag ccattgcggc gaaaacccta tgacgagcaa cttttttcacg   540
tcgatcccaa aggattttca aaacctgctg aacgggaagg aggcgaacga gtgggtgtcc   600
ggctggaagt ataacatcga tgcggtctgc tggggtggcc ttagcgtggt caatgacgcc   660
ccgtccgaac ctttttattac cgctaaggtt gtttccgccc tggatacgga aggaatcaag   720
gtccagtaa                                                           729
```

SEQ ID NO: 57            moltype = AA  length = 382
FEATURE                  Location/Qualifiers
source                   1..382
                         mol_type = protein
                         organism = Bacillus subtilis
SEQUENCE: 57
```
MKVPKTMLLS TAAGLLLSLT ATSVSAHYVN EEHLFKVTAH TETDPVASGD DAADDPAIWV   60
HEKHPEKSKL ITTNKKSGLV VYDLDGKQLH SYEFGKLNNV DLRYDFPLNG EKIDIAAASN   120
RSEGKNTIEV YAIDGDKGKL KSITDPKHPI STNISEVYGF SLYHSQKTGA FYALVTGKQG   180
EFEQYEIVDG GKGYVTGKKV REFKLNSQTE GLVADDEYGN LYIAEEDEAI WKFNAEPGGG   240
SKGQVVDRAT GDHLTADIEG LTIYYAPNGK GYLMASSQGN NSYAMYERQG ENRYVANFEI   300
TDGEKIDGTS DTDGIDVLGF GLGPKYPYGI FVAQDGENID NGQAVNQNFK IVSWEQIAQH   360
LGEMPDLHKQ VNPRKLKDRS DG                                             382
```

SEQ ID NO: 58            moltype = AA  length = 103
FEATURE                  Location/Qualifiers
source                   1..103
                         mol_type = protein
                         organism = unidentified
SEQUENCE: 58
```
MKFFNYILFL IIINISYSQI LFVFQHIRHG AREPIYYDRT RKDKNVDYYG YQWTGKAVLT   60
PIGKRMNYLL GIRNRNKYKN LLNEIYDSRE IFVSSTGFDR TIN                      103
```

SEQ ID NO: 59            moltype = AA  length = 114
FEATURE                  Location/Qualifiers
source                   1..114
                         mol_type = protein
                         organism = unidentified
SEQUENCE: 59
```
MKLGTQSEGC VVDDRTGILY VAEEDVGLWR IDPGSTVPVR IAAADGRQIV ADAEGVALAP   60
VGERGGYVVV SSQGDNAYTL YSLPDERYAG RFRVVDGPRS ADRRRPGRHR TDAR          114
```

SEQ ID NO: 60            moltype = AA  length = 162
FEATURE                  Location/Qualifiers
source                   1..162
                         mol_type = protein
                         organism = Clostridium colicanis
SEQUENCE: 60
```
MGLNYSQVIA RNNAQLSSIK IGEPLTIKNT TIVPKEVYSE ETLIKENNNQ YIRIPVTDTK   60
LPTPEMVDLF VSSVTNLPKN SWLHFHCKEG IGRTTTFMTM FDMMKNAKTV PLNDIVLRQI   120
KLANLENKEK GLESTTRMAF YNKFYAYAKN GDFTKKFSEF NN                       162
```

SEQ ID NO: 61            moltype = AA  length = 164
FEATURE                  Location/Qualifiers
source                   1..164
                         mol_type = protein
                         organism = Chlorobaculum limnaeum
SEQUENCE: 61
```
MATKVRAFGA WRGVKEIEAV AVDDGNATVY YSDERFGIRK YSADPAAVDA GKELAVFGQS   60
GFAADREGIA VTRNAEGGTL VLVSDQSGGA LRIYSSTKVD ENRYRFITSV PYRATETDGL   120
DLSTEIRTPE FPEGVLVAMS DDRTFQFYSL GEVLKRLGER VDGE                     164
```

SEQ ID NO: 62            moltype = AA  length = 175
FEATURE                  Location/Qualifiers

```
source                  1..175
                        mol_type = protein
                        organism = Bacillus amyloliquefaciens
SEQUENCE: 62
MNHSKTLLLT AAAGLMLTCG AVSSQAKHKL SDPYHFTVNA AAETEPVDTA GDAADDPAIW   60
LDPKNPQNSK LITTNKKSGL VVYSLEGKML HSYHTGKLNN VDIRYDFPLN GKKSILRRHP  120
IGLKERIPLR FTPLTGKTAH YKALRIQTAR LHQQLMKYTV SACTTVKKQE NITRW       175

SEQ ID NO: 63           moltype = AA  length = 235
FEATURE                 Location/Qualifiers
source                  1..235
                        mol_type = protein
                        organism = Cystobacter fuscus
SEQUENCE: 63
MGGAALRALA ANTPGPLVVV DLREESHGFL GDLPVSWYAP RNVGNRGRTR EATLAEELRL   60
LDSLRRHESL AFDGQGKDRG PPEPVRPIAA FGTVCTEESI CTEAGAGYAR LLVTDHHGPD  120
AGELDRFVAF LERLPDGAWV HYHCRGGRGR TSTFLLLHDL LRNAHRLPFS VIAHRQRVLS  180
DGYDLLAHGE PADWKTPLRR ARAEIVPAFA EFARERAVGG SQRFTEWLGA RQEMR       235

SEQ ID NO: 64           moltype = AA  length = 260
FEATURE                 Location/Qualifiers
source                  1..260
                        mol_type = protein
                        organism = Acinetobacter baumannii
SEQUENCE: 64
MNILFKMTVL AASLLLVACN DNDDQEAQTA PSTNQSKYYQ TKTPYQPQQE IKNYEQTPNG   60
FQPVFTELVA RHGSRGLSSL KYDLALYNLW KQAKAENALT PLGEQLGADL EAMMKANILL  120
GYGVEGIRQY GYGNETMTGI LEHRGIADRL LQRLPTLLNS QASILVQSSG VDRAVDSAKF  180
FTAELIKQRP PLKDKIVPLS YTNLSSESVP SVEDGGVDRF KLYFHSLNAD EDLVQPLSAS  240
QQKFMMLARP IKILKKIIKI                                             260

SEQ ID NO: 65           moltype = AA  length = 268
FEATURE                 Location/Qualifiers
source                  1..268
                        mol_type = protein
                        organism = unidentified
SEQUENCE: 65
MRWVKAVLTF GLLGCLLKGK PLVPKPPCFV KDPTSAKRFQ TRLRVLSPRN PTLTKNLQRL   60
RVIGSPQPSF KQLKMLLQEN PQLYGIVDLR KETHFFMKGQ SISWGTKGNC VNHRTIQEHL  120
SEHAWTELQG LKYLRLHVPD HYPPTIEQIN TFLQFYKSLP PGAVLLIHCR GGRGRTTTFL  180
TLVDIIENAK CDSFDTILAR QWRLGGADLR KPRTGVKKRP AETRLKLLKL FYARVRKDAE  240
GSLRPFQRQR RKTQLPEALS LPPPSVLI                                    268

SEQ ID NO: 66           moltype = AA  length = 280
FEATURE                 Location/Qualifiers
source                  1..280
                        mol_type = protein
                        organism = Clostridium ihumii
SEQUENCE: 66
MSYFKKLLLV LLLIFSFAFN SFSVLGYDEA SNIYTVLDNE NSNSLPNLFR KDASLNISGS   60
AQFTAAQVEN IINNIDSNKL YIVDLRQESH GLLNENIAFM FWNPNVDLND GLSSSEVLRV  120
ESKEISKIPI SSVMHIYNKK LDLLKTVKVQ SVLSEKNLVT SKNINYIRFA VKDNYIPSDD  180
IVDEFVDFVK SEGTSSHLHF HCEAGEGRTT TFMAMYQMMN NKDNLSLDEI LQYQIKLGGI  240
SLIDIPIRKD FLNTFYNYTK ANIDSNFEVP YSKWVERKVI                        280

SEQ ID NO: 67           moltype = AA  length = 283
FEATURE                 Location/Qualifiers
source                  1..283
                        mol_type = protein
                        organism = Desulfovibrio fructosovorans
SEQUENCE: 67
MESDPTLIFD SIREQGLPSH FRSLAGPWAV PITTTPPSRQ GLAELRASGS EQPSSSEMAT   60
TIKGLAPEVT VVDLRQESHA LLGEHPVSWY GLRNWANDGK SLQAVECDEE TRIGDLPPCG  120
EAAVSRVISK DPDGALAEVR VEEVAYDRAR SEQEALCGLG LGTFRIAVRD HSRPSDADVD  180
RFIRFVRELP PGTWLHFHCH AGDGRTTTFL LLYDMLRNAA VLGLEELAAR QHMIGGIDLL  240
HTPHTGWKGA LYNERAAFVG RFHHYAGTRD FRRVLWTQYL ASA                    283

SEQ ID NO: 68           moltype = AA  length = 285
FEATURE                 Location/Qualifiers
source                  1..285
                        mol_type = protein
                        organism = Clostridium novyi
SEQUENCE: 68
MKKTNFSFTL FILLFLISIP VNGKLISTDA PVPPKPLVVL DSNSTSPLPS FFRIIPELNI   60
SGSKQFTPAQ LKNIQNKINS KNLYIVDLRE ESHGFINDNT AISFYLPRKY INDNFNTHEI  120
LKKEKLDLDS IKNVENLNIY DQLGTLKETL KPDKTLSEKE LTKHNKIHYV RLPVIDNYIP  180
SPEIVDKFIE LIKSKPSNSH LHFHCKEGQG RTTMFMAMYE MMHNKDNLSL DEILKHQQDI  240
GGIILTGNPA RGTFLKNFYN YTIDNKKNNF DTSYSQWLKN ISSMK                 285
```

-continued

```
SEQ ID NO: 69            moltype = AA   length = 291
FEATURE                  Location/Qualifiers
source                   1..291
                         mol_type = protein
                         organism = Clostridium bornimense
SEQUENCE: 69
MAKKIHFNFI KIFIVLIIFS LALPNLLVNG KSPSSDIHIV LDTLNNTEIP RNFRSTNNIN     60
VSNSINTKGM ENLNISGSSQ FSKTNLPLLI KSINTNLPII DIDLRQESHG FVNEMPISFK    120
NDKNNANLGL SSEEVLLKEI KDLNTINLNS TLTFYNDKNN PVLVKSVENE SLVISKNSIG    180
YLRIAVTDSM LPNKDEVNKF VTFVKNQPKN THLHFHCKEG IGRTTIFMIL YDMMKNYNDI    240
PMEDIISRQI ALAKLDEKDY MAFYDKNHTE FFTSFYNYCR SSKDLFLSPW Q            291

SEQ ID NO: 70            moltype = AA   length = 297
FEATURE                  Location/Qualifiers
source                   1..297
                         mol_type = protein
                         organism = Bacteroides stercorirosoris
SEQUENCE: 70
MFCPVSILWG QDRIQQYAGT AMPYPIVKDS FVFFQDSMVP FYVNHLGRHG ARFPTSGKAL     60
NRVKEILELA RRENRLTSGG VTLLSTIQNL SDTFDGQWGK LSVVGEEEQR GIARRMIERY    120
PQLFSDSVKV QAIATYVPRC IHSMDAFLAC MVEFNSSLHI QRNEGKQYND ILRFFDLNQS    180
YVDYKENGDW RPIYETFVRR KISPASVMEN FFLESGQETD KEAEEFVMAL FSIAAILPDT    240
GTPINLDGLF TIGEWDNYWQ TQNLRQYMSK SSSPVGRMLP VAIAWLCYQN LFIQLMK      297

SEQ ID NO: 71            moltype = AA   length = 303
FEATURE                  Location/Qualifiers
source                   1..303
                         mol_type = protein
                         organism = Clostridium paraputrificum
SEQUENCE: 71
MKKYLKIISS ILIFSLLSPL SISAKEVEQV YLSLDYENTD SLPHNFRKTT DLSNVIKGGG     60
NTTGLENLNI SGSSQFTSLS FLNLKKNINT KNEFWDIDLR QESHGFINGN AVSWYGPGDK    120
ANAGLNYKEV IAKEAKQLSE IPFGKSITLD NGKHTLIPTV VENESKLVSS NNVKYLRIAV    180
TDGDRPTDES VDQFVKFVTH LPNNYWLHFH CKEGIGRTTT FMSLFDMMKN SKNVSLDDII    240
KRQFLLGGFN LFKPGDENKR VLFLRNFYKY TKENNDNFKT TWSDWIKQNN ITPYTSTTEL    300
PKN                                                                 303

SEQ ID NO: 72            moltype = AA   length = 304
FEATURE                  Location/Qualifiers
source                   1..304
                         mol_type = protein
                         organism = Clostridium pasteurianum
SEQUENCE: 72
MRKRIKLFWI TFFIAIFSLS FIFENVNAVS FAPKELRLTL NANNTVTLPK NFRKTTDSDK     60
IKDIDKSVNL EGMNKLNISG SGQFSEKGLE MAKENIGEKV PITVVDLREE SHGFLNGNAI    120
SWTDGHNKAN KGLIEAQVIK DENERLKKLS EEKTVEIKNR TLNVEKVENE ENLTKKHGIS    180
YTRITVTDKE APSKEAVDEF VNFAKSVPNS GWLHFHCKAG KGRTTTFMAM YDMMKNAKNV    240
SFEDIIKRQF LLGGENLLKR TTVENIKGTR AKFLKNFYDY CRTNNDNFNT TWEQWLKNNP    300
DNSR                                                               304

SEQ ID NO: 73            moltype = AA   length = 308
FEATURE                  Location/Qualifiers
source                   1..308
                         mol_type = protein
                         organism = Clostridium perfringens
SEQUENCE: 73
MFKYFKKNAL IIFLVLSIFT SFFINNTSIV LAEDNNVHLV LDTKNINNLP NNFRTTSDLE     60
RLKNLSNINT KGLDTLNISG SQQFSPNNLS LLVTSIKTNL PITVVDLRQE SHGFINEYPV    120
SWKGTKNAAN LGLTREEVID TERNLLNSIT LGTPIQFFNN PKLTVIPEKV LSENQLIKAN    180
SMDYIRIPVT DGKLPTYEMV DFFVQYINSM PKDSWLHFHC KEGIGRTTTF MIMYDIMKNY    240
NNATLDEIIY RQLVLFGLTE KNFNSFLSKE RLDFFTKFYQ YVQEENTDFK TSWSQWLNKN    300
NFPLVTIR                                                           308

SEQ ID NO: 74            moltype = AA   length = 308
FEATURE                  Location/Qualifiers
source                   1..308
                         mol_type = protein
                         organism = Clostridium botulinum
SEQUENCE: 74
MYKKAKLKLY IPMLLLITIF SSFFLNFNIA LAFNEPNNKS DVHIIVDNLR TNKIPSNFRT     60
TSNLTNIKNN SSLNLKGLET LNTSGSQQFS KDNLDILTKS IDSTLPILVI DLRQESHGFV    120
NEFPISFANE KNDANLGLSK SAVTFTEKKD LKSIKLNTPL TFYKHPEINV VPKEVLSEKQ    180
LTKSYSLNYS RVPVTDTKLP TNEMVDCFIN IVKECSKENW LHFHCKAGFG RTTTFMIMYD    240
MIKNYNNATY DEIIKRQFAL ANFDEKEIIE LSSSDRINFL NQFYNYCKDV NGNFDTTWSS    300
WLNDSQKH                                                           308
```

```
SEQ ID NO: 75              moltype = AA   length = 311
FEATURE                    Location/Qualifiers
source                     1..311
                           mol_type = protein
                           organism = unidentified
SEQUENCE: 75
MKNIYILLFL FSLGVVAQSF LYQHQPTLFP IVDAPLNSEN HLPKKWRSTK QISQLVGNYA    60
NLKGLTQLHL SGSGQFSQED LKNMSQEIKG KAFVLDLREE SHGFIDGTPI SWTDGLNYGN   120
VGKTLRQIEL DEQKRLKLTA QKGSIIVDLS KDLGENFQKF FVREVKTEKE LVESFGYTYI   180
RLPITDHHRP VDSVVDQFIE IVLSLPADSW IHLHCKGGKG RTTTFMTLYD IMHNAQTVGL   240
NDILSRQTLL GGADLVQAEK NETYKQKPAK DRIEFIRAFY TYCREVPNFE MTWSDWVHQK   300
QLVAYQTSSS N                                                        311

SEQ ID NO: 76              moltype = AA   length = 314
FEATURE                    Location/Qualifiers
source                     1..314
                           mol_type = protein
                           organism = Acidovorax avenae
SEQUENCE: 76
MPHVSLACRH HAGTRPDRSA GRTALQLRQP EAETRLELVY DTEPPHPAGT MAFFRHSTQA    60
SELPPGIDTR GLESLQLSGS ERITSVEQVR AIRQACGDAP LVVVDLRQES HAVADGHSLT   120
WRGPMDWGNV GLGTAAATAR EAEQLEELRR QGNAVATHAD HVKGKSDEPA LRRLDTTLAR   180
SEQEIVEAAG ADYRRIAVTD HLRPSRGEVD QFIDLVRGLP DGAGLHVHCN GGRGRTTTFM   240
VLYDMPRNAR EAGADAIMAR QSRLGMDYNR CAYRPPDACG FQVKFSERTL AVVRTSWRSP   300
INPLIPRVSP IDCS                                                     314

SEQ ID NO: 77              moltype = AA   length = 314
FEATURE                    Location/Qualifiers
source                     1..314
                           mol_type = protein
                           organism = Clostridium sp.
SEQUENCE: 77
MKKSTAVFFA FILVFISLSS TTLSLDTAAV AASDEVQLAL DSLNESTPRN FRKTSTPIYL    60
TKNEKFSLKG LDKLNISGSQ QFSEKNLPIL LEEIGTSKPI TIVDLRQESH GFINGLPVSW   120
KNLNNDVNKG LTRDEVIEKE ANQLSSIPLN SPVTVYRAPN NIKIPTEVFN EDALVTSKNL   180
SYIRVPVTDL GLPTDDMVDY FIEVFKNLPK DSWVHFHCKA GVGRTTTFMI MYDMLINYNQ   240
VSATDIIDRQ LKLANFDEVT IREFYTPERY KFLLNFYNYC KENGGSFKMS WSTWSKEYDG   300
FISLNKDTGY LKVS                                                     314

SEQ ID NO: 78              moltype = AA   length = 325
FEATURE                    Location/Qualifiers
source                     1..325
                           mol_type = protein
                           organism = Clostridium sp.
SEQUENCE: 78
MKQNEITLNN STNYNTIEDN FRHGHHGWYS YRHPFLYEYC YHINDEMIQE PYYKSRSNKL    60
HLVINSDNAK KLPDNFRNTI DLANFKDNKV INLNGLANLN ASASSQFSES GLAFVKQSIG   120
HAMPIIIVDL RQESHGFING VAISWADNHN KANKGLTKEA VLTDENTRLH GILLNKPIYI   180
GDITLIPKKL ENEKSLVQSY DMSYMRIPVT DNEMPNNGMV DYFIKFVNSL LPNTWLHFHC   240
KAGLGRTTTF IVMYDMMKNA KNVSLQDIMN RQVLLGGKNL LRDEQLLMNR SEQRVKLIKR   300
FYRYCVENND NFKTTWSQWI RQHRN                                         325

SEQ ID NO: 79              moltype = AA   length = 332
FEATURE                    Location/Qualifiers
source                     1..332
                           mol_type = protein
                           organism = Acidaminococcus sp.
SEQUENCE: 79
MLRVGGLFFI GGKMLKKVPF LLMLSASLIA FSAPLPCVRA KEAPKSVPLE APFSYEGALW    60
RLDAENAPGL PRNYRTCDDA YRAIPPRYAK EASSRIPSCK GLSELHISGS SQYSEKGLDA   120
ILADLRNRTQ GPIVLVDLRQ ESHGFVNGMP VSWYGKRNWA NREKGHFAVL ADEAQRIHAL   180
QGQDVTLVRL KTDKRSASTM TVEAGQVLTE AELAAQKGVM YVRFTATDHL WPDAGEIERF   240
RRFVKTLPKD AWLHFHCVAG EGRTTAFMTM YDMLKNPDVP YEDIVLRQLR IGGVYTPFLG   300
KGLSTWKKPY YRAKKRGLEA FYRKLHKTQV TD                                 332

SEQ ID NO: 80              moltype = AA   length = 332
FEATURE                    Location/Qualifiers
source                     1..332
                           mol_type = protein
                           organism = Anaerovibrio lipolyticus
SEQUENCE: 80
MLMKKNRIEK SACSIFAVVC SLLIMLMATA QAAEKQEAPI WRLDSKPGAV LPRSLRFMTD    60
EFPQDLNSVP SRKGMDTLRC SASAEFSGFG LSMIRDKIYE HAGKNAVIYM VDLRKESHGF   120
VNGEFAVSHY FKKNLGNRNL ASAAVPQAEE KALQSIMGQE ITFVPLGKTD TKLFTASTVK   180
VEQIETEEAI TARLGIHYKR IPIADQCAPS DEDIDEFMNF YKNLPSNSWL HPHCHAGHGR   240
TTTFMVFYDI LCNPDVALDD IVARQHALGG TNLFAPGKKN NWKGEEIRKR AQQVRNFYAY   300
VQANHRNKYA QPYSQWMKAQ NSRVDNAQKS KS                                 332
```

-continued

```
SEQ ID NO: 81                 moltype = AA   length = 339
FEATURE                       Location/Qualifiers
source                        1..339
                              mol_type = protein
                              organism = Cellulophaga sp.
SEQUENCE: 81
MNKYINYIGV MVVVLAFACK ENSLPAIAPN VITEKTKNDT DDPAIWVNLK NAEKSIVFGT   60
DKETDGGVYA FDLNGKIIKN KSITGVKRPN NVDVAYNFKI NDSTFTDVLV FTEREKQQIR  120
MFSVPDMMPL DNGGFSVFKN EKNLEYTLPM GVGLYTSSVD NTLYAIVGRK NGPKDGYLHQ  180
YKLSTDTTGV VQSTLVRKFG VFSGKKEIEA IAVDSELGYV YYSDEQHGIR KYYAEPTKGD  240
KEISCFGGEL FLSDIEGIAI AKQAKGKGYI IVSDQQKGQF NIFSRDTNKF VKAVNLSTTE  300
TDGCEVVTVP LNNVFKNGLF VAMNDAKDFY FYDLAKLGL                         339

SEQ ID NO: 82                 moltype = AA   length = 339
FEATURE                       Location/Qualifiers
source                        1..339
                              mol_type = protein
                              organism = Bifidobacterium dentium
SEQUENCE: 82
MLMSTRMMKR IVGSVACVAA AAMLMPGTVC PALALESDGQ YYSSKQPYVA PSAATVASYS   60
KAPEGYEPIY TESMARHGSR GLSSYKYDAL LMKMAEAAER DGGFKSDAIK TEFMKNLNGI  120
TAANVENGYG MLTGQGADQH YGIGERAYQR NQSLFDQAAV DGGTISYQSS GEARATESGE  180
NFEKGFNAAS GGKLTDSVVK PTDPADSGDG KDFQKNPDTL YFHKVQNPDG TEKTPGTKAY  240
DIANDYQNFI SWPTMRSSPV PRRPSATMPT SSGPRMTCCR RSSPTNSLPN SRTANTRGTT  300
PPMAPRRVPR TARRAPTRPR TPMRAAKAPR RSRASTTPQ                         339

SEQ ID NO: 83                 moltype = AA   length = 344
FEATURE                       Location/Qualifiers
source                        1..344
                              mol_type = protein
                              organism = Chryseobacterium sp.
SEQUENCE: 83
MKNIHYILAL SVLPFVINCT GQKDLAEKLK PAVITETVVH DTDDPAIWIN PQDATKSIII   60
GTDKDTDGGL YAFDLNGKII NKVSGLKRPN NVDLEYGFML NGKKTDIAAV TERETNKVKL  120
YTLPELKEVG EISVFDGESE RGPMGISLYK NPQTEEIFAV VGRKSGPADG YLWQYKLIEK  180
DGIITGEVVR KFGKYSGLKE IESIAVDDEM GYIYYSDEQF GVHKYYADPA KGNEELSVFG  240
KGDFKSDVEG ISIYPTSQGK GYILVSNQQN DTFNVYLRED QSKGKIAEIP VSTLESDGSE  300
VTNVNLGPKF PKGVFVAMSN GRVFHFYDWR MVEKAITSAV KAVK                   344

SEQ ID NO: 84                 moltype = AA   length = 347
FEATURE                       Location/Qualifiers
source                        1..347
                              mol_type = protein
                              organism = Erythrobacter litoralis
SEQUENCE: 84
MLKPFHGFAL ISLGIAAACA SIHVTGDPAV TVTAVAETEP VGTANEDAAD DPAIWRNPAD   60
PAKSLIVGTD KKAGLHVYDL AGRELSFMPA PGLNNVDLVE LPDGRVLALS SDRSDLETAH  120
VSVARLDPDT AALTPIARIE VGPGEGYGIC MGEVDGDGSF TVFSAPKKGI VYRTALQFEG  180
EELIDKTETL TSVPSQPEGC IADPRTGTLY IGEEAAGIWA IDMQTGDKRL VAEVDNRLLV  240
ADVEGLAIAP EGRDGGYLVA SSQGDNAYAV FRLPGMEPVG RFRIGAGAFG STEETDGIEL  300
DPRAFGPAFP GGLFVAQDGM NGASAQNFKL VRWDAVLEAL EAVPPAP              347

SEQ ID NO: 85                 moltype = AA   length = 350
FEATURE                       Location/Qualifiers
source                        1..350
                              mol_type = protein
                              organism = unidentified
SEQUENCE: 85
MRLTFIVCAS ICLLGCSTTQ RGPAWAGGET PVAVAALAET RVDTDPAVDA DDPALWSDES   60
DPTRAVMFGT DKTDGLYVHD LDGSVRQFLA SGALNNVDLR TGFSAEGRDD FVLVAATNDE  120
RMGINLYLFD PRTLETRDYG FIETDIGEPY GFCMGRRSDG FYLIANNKQG DIKIWRLANG  180
AEPGAAEMVR QLKLPSQLEG CVVDDDRDVL YVGEENAAIW RFDFDPAASP TPTKVASVDR  240
QRITDDIEGL TIMRDGRQRY LIASSQGDDT FPVFRITEEG ETYLGRFTVV ARDDIDGVTH  300
TDGLDAWSGP IGRYPEGALA IHDDNEEPLE GQQNYKIVDW REVKAALDLP              350

SEQ ID NO: 86                 moltype = AA   length = 355
FEATURE                       Location/Qualifiers
source                        1..355
                              mol_type = protein
                              organism = Devosia riboflavina
SEQUENCE: 86
MIDLRPALAL LALSLCWTGT ALAQPEPIFA SVSATLETEN VDIDPDDPAI WINTADPAQS   60
RVIGTDKDVG LVVFDLDGKI VQRLSDGRLN NVDIRQDVTV GNETLSLVAA SRRNDDTIVF  120
YTVDETGTLT KATPFAFPGA PRKIDDDIYG IGLYHDAVAH RLFVIASFKT GEIMQWEVTS  180
NAGQLSLAFT RELAVPTQPE GVVADDELGF IYVGEEDGGL WRFAAAPDAD ASGHLVDKVG  240
SACLPEDDLE GLAVVKGADN SSYILASAQG VNRYVLYARQ PDADGNQPCY GAFNLVTGAT  300
DPVSETGLD VTTTALSDRF PKGLMVVQDD RNEGFNRNFK FVSWADVMQA MQLAD          355
```

```
SEQ ID NO: 87            moltype = AA  length = 360
FEATURE                  Location/Qualifiers
source                   1..360
                         mol_type = protein
                         organism = Bradyrhizobium sp.
SEQUENCE: 87
MRCGPGKPVG LSYQMPAPDS DLGARAPASS SVESRTPFRI PPTTIPKKIS DQNPPTLVYD   60
MIEPSTFRTT SDTSGMESCD LTGFDGLSLS GSEQFSERQL EELITLTRPK RIVIIDTRQE  120
FHGFANGEPI SWYAADNYNW GNVEKPAEII PAKETKKLAK LPTKFPFGLT IESGSVVKGK  180
ASSAPPKVLD FGKVKIETEE ELVKRKGVAY LRIPTPDHAR PTDAEIDKLV SELRNLARAG  240
DVHLHFHCRG GIGRTTLLMT LADMLHNSDK VQCAHIIERQ IKLRRRDEFP TSKALNKVLR  300
NEKSELMNTF FQYAKEQPLE KADAISWTEW LALKAHREHQ ILDTSSVGTP PTAPPGHRMP  360

SEQ ID NO: 88            moltype = AA  length = 362
FEATURE                  Location/Qualifiers
source                   1..362
                         mol_type = protein
                         organism = Algoriphagus marincola
SEQUENCE: 88
MHKKLNYFLS IFTLTGLASC QESSLQKGDL PDEKVELISP LHISDSVIHD TDDPAIWINK   60
SNPSQSLIIG TDKDSIGALY VFDLTGKTID SLVRRDIQRP NNVDIGYGLI HGKDTIDFAV  120
TGERLTSKIR FFSLPDMKEL NPGGLEVYQG ETGEDYRDLM GIALYQSPKS GKTYVIAGRK  180
NGPTDGTYLW QYEVKSQDGN LSLELVRKFG NFSGNKEIEA IAVDNELGYI YYSDEGTGVR  240
KYYAEPDMGN EELALFATEG FTDDHEGISI YKTSETEGYL LVSDQGANLF HVFPREGSQS  300
NPHQHSLITT LPLSTLSSDG NEVTSADLGG EFSEGLFVAM SDDKTFQIYS WKQLKKHINQ  360
NQ                                                                 362

SEQ ID NO: 89            moltype = AA  length = 369
FEATURE                  Location/Qualifiers
source                   1..369
                         mol_type = protein
                         organism = Bryobacter aggregatus
SEQUENCE: 89
MKKNQTFLSF FLLAAYGIAQ KESPQPKLQY AVILTRHGVR APLAPNRWLH FYSVGSWPSW   60
GVLPGHLTPH GRQMMKLMGA YYGETFRAEG LLARNGCEDS GRIYVWSDSD QRTTESARAL  120
LEGIIPGCRY AVHSGRPGIP DPLLSTQGTA RFRSEDRSGL QPALDKLHFV LKGARARSNL  180
SLRTAATLAE NLMLEYANGF EGNELGWGRL SQEDLQEILT LRAAQPRKAE YARNLWLRIQ  240
TSLCQAATGE SIDGSIGPKN TALLILSGHD KNLESLAALL GLNWQLASYP KNYASPGGAL  300
VFTLWRQDGR FRLRSQYIAQ SLEQLHNGSG GTPVVIDLGS SDFTPITRPP HGHFCVATSL  360
LVTSSKRRR                                                          369

SEQ ID NO: 90            moltype = AA  length = 371
FEATURE                  Location/Qualifiers
source                   1..371
                         mol_type = protein
                         organism = Asticcacaulis sp.
SEQUENCE: 90
MDLKRFYVGF TTASAVVITA TLLTGCASLH SELVSDSKLI AIGTGTPVLA SAETVAVGTA   60
GLDAADDPEI WVDPMDKSRS LILGTDKKAG LYAYNLDGSV RDFVAHGPLN NVDLRTIYGE  120
TGSFTLIAAS DRARNGAALF TLTDDLKLKV AGFLPMTTSE AYGLCMGTIE AGITIVIIGK  180
NGDVVQAIYS ETEAGPRGEI VRRFNVGTQS EGCVIDDRTG ALYIAEEAKG IWRYGVEPAT  240
GSTRVELQAA PSNILVPDVE GLALLVDEDS GLSYLIASSQ GDSAFAVWQV AGETSIYKGR  300
FSVFPGNGFD AVTGTDGVAA LGGQVGPYAE GVVVMQDDSD MEGETPTGAR ARQNFKIVPW  360
MDVKKALNIG S                                                       371

SEQ ID NO: 91            moltype = AA  length = 375
FEATURE                  Location/Qualifiers
source                   1..375
                         mol_type = protein
                         organism = unidentified
SEQUENCE: 91
MGSNYTIYKR FFNSRNVKRL LIVLLFIGIV HVSFTWYLFH SESTNTITPT MKLLAEGSID   60
QDDMCIWIHP TESSKSVIIT ADKKAEKVFV YDLEGSVLQV LSMPKPGNID VRYGFPLGGK  120
KIDIVAYLQR KKGHRIIVFA VEPKTHQLKR VDDNSILVGK GVGGTLYHSQ KTDKFYFIKT  180
AEKKGKGGIE QFELFDDGKS KITGRKVRQW DLAGCEGAVA DDESCALYIS QEDKGVWKVG  240
AEPGEPTPGE LIIKTWKNGL MFDVEGLTIY KSHTREGYLM VSNQSRNSVK VYQLGKEDKF  300
LGTFHIDGAI HTDGIDMTNV CLGIRFPKGL FVCHTDQEGS NRCPVLVTPW ESIARGLNFK  360
VDVSWNPRSE TFKHF                                                   375

SEQ ID NO: 92            moltype = AA  length = 375
FEATURE                  Location/Qualifiers
source                   1..375
                         mol_type = protein
                         organism = Bacillus licheniformis
SEQUENCE: 92
MNFYKTLALS TLAASLLSPS WSILPRAEAS AYKDFSVTAD AETEPVDTPD DAADDPAIWV   60
HPKQPEKSRL ITTNKKSGLI VYDLNGKQLA AYPFGKLNNV DLRYNFPLDG KKIDIAGASN  120
RSDGKNTVEI YAFDGEKNKL KNIVNPQKPI QTDIEEVYGF SLYHSQKTGK FYAMVTGKNG  180
```

```
EFEQYELFDN GKGQVEGKKV RSFKMSSQTE GLAADDEYGK MYIAEEDAAI WSFSAEPNGG  240
DKGKIVDRAG GPHLTADIEG LTIYYGEDGE GYLIASSQGD NRYAIYDRRG KNDYVADFSI  300
DDGKEIDGTS DTDGIDVIGF GLGKKYPYGI FVAQDAKIRK MDSQPIRTSK LSPGKKLLTR  360
WTTSLISMIR SIPEN                                                   375
```

SEQ ID NO: 93          moltype = AA   length = 381
FEATURE                Location/Qualifiers
source                 1..381
                       mol_type = protein
                       organism = Deinococcus proteolyticus
SEQUENCE: 93
```
MSRFIRPLLL VSLCAGVCAC APVATGPASP QAQTGAGALP VVEARAQTAP VGDPADSDDP  60
AIWVDAAEPA RSFVIATRKE GGLTVFDLKG QTIQDLNPGG VRYNNVDLVR GFRLGGETVD  120
LAVTSDRKGD RVAAFVIDPQ TRTLREVTSP ATPLLFSPGP GTDGKRTAYG LAAYRTAAGE  180
DRVLVSQNGF PVVGEFELYD DGQGVSVRPV RRLELPAALP GLTVDDPQFE GMVVDAEQGV  240
AFLGQEQIGV WRWDLDGRRS VLLDQVAPLA PRLHADVEGL TLVRGSGGRG YLLVSSQGSN  300
AYAVYSRDGK RYFGSFQVTA GSDLVQDSDG ADAVLTPLGS DYPGGLLVVQ DGEAGGAEGQ  360
TNFKLVSWAD VERALNLPDV R                                            381
```

SEQ ID NO: 94          moltype = AA   length = 387
FEATURE                Location/Qualifiers
source                 1..387
                       mol_type = protein
                       organism = unidentified
SEQUENCE: 94
```
MNNNQYQLDK VVILSRHGIR TPLENTIAFL EKSSPFKWPS WDHAYGYLTT RGGVLETFFG  60
HYLSQWLEQK NINIEPENPD IYVYANSLQR TVATAQFLVA GAFAGYDIPI HHKYTIEKMD  120
PIFDPSVKND SLEIKQKVLK EIEEADQKQS IFKNLAPAYK IVSDILDYPH SQLYAELKCD  180
FADIPYELHF VKNEEPELRG PLAIGICVVD AFLLQYYSAF PKEQIAWGRI TSQEQWQQLM  240
HIRNQYIDLV FHSRTIARHN SKLLINKIDD LLHNKTHKVN LLVGHDSTIA ALLGALDFAE  300
YQLPNQFENT PIGGMVILQR YRNKASEKYL FKAEYVYQSF EQLYTAQPLD INHPPQHYQL  360
QLKNAVANSD GFYQWQDIET RLKEFKK                                      387
```

SEQ ID NO: 95          moltype = AA   length = 388
FEATURE                Location/Qualifiers
source                 1..388
                       mol_type = protein
                       organism = Bacillus sp.
SEQUENCE: 95
```
MLKEISTAAL MTSVLFSTVN SAADLVGEFP SLSVQEKQRH SKFVKVEAKE ETAAVANAGD  60
AADDPAIWVH PHDSEKSKII GTNKEEGISV YDLKGKLLYS YNFGKLNNVD VRYGFPIGGK  120
KIDIAAASNR STNTIDIFAI NSKTGELENI TGSPIKSNMK EVYGFSLYHS QKTGVFYALV  180
VGKDGTFEQY ELFDNGKGKI EGKKVRELKL SSQSEGIVAD DEYGTMYIGE EDVAIWKFNA  240
EPDGGKQPIT KVDSADGNHL TADIEGLTIY YGKNGTGYLI ASSQGNNTYA VYDRKGNNEY  300
IGNFAIVDGK NTDGTSDTDG IDVMSFGLGK KYPNGIFLAQ DGENIERGKI VNQNFKMVDW  360
KKIAKGFDSK LQIENNVDPR KLKFRQNS                                     388
```

SEQ ID NO: 96          moltype = AA   length = 391
FEATURE                Location/Qualifiers
source                 1..391
                       mol_type = protein
                       organism = Saccharicrinis fermentans
SEQUENCE: 96
```
MQFINLTTLF IAAASILSSC QPKGNQNNNS EAERDNTAIL EKNKEARDDS LKLTEAYALQ  60
AQFSNIVSAD YETTPVKSNL GDDAADDPAI WINKIHPEKS MIIGTNKKAG LNVYDLQGNE  120
LQFIPIGKMN NADVSYNFAY KGGQQVDLLAG SNRTSQSIDV LLIDGANQKI IEKPLCSIPS  180
SVDDVYGLCM YFDAVANKHY VFVNGKNGKI EQWLLKNDND SIKGELARSF WVSSQPEGMV  240
VDHVTNTLFV GVEEDAIYKF KAQAQADTSS IRLTASCNAN NAHISYDIEG LTIYRISDTK  300
GYLLASIQGN FSYAIFDLSE KNNYITSFII KDGVFDGVEE TDGIDANASL MGPKFPKGML  360
VVQDGFNKDK KENQNQNFKI ISFERILQFL Q                                 391
```

SEQ ID NO: 97          moltype = AA   length = 403
FEATURE                Location/Qualifiers
source                 1..403
                       mol_type = protein
                       organism = Asticcacaulis benevestitus
SEQUENCE: 97
```
MTPSRILTFA TLFACLAVVT PCSTASAKEN TFTLERVVIL MRHGIKRPNN DPPLPKRFTD  60
QAWPVWSVPP AGLTPHGEQA IARIADFDRL TYAGLLGSDC PPAGAVRVIA DTDQRTIRTA  120
EVYASTVFKG CDVRVEHAGE GHADAHFSPF NEDVASPPLD RKAFMDEALT SGGMAAIDKA  180
HHVDYALLSE VLNLKDLPGC QIDKVCSLSD MPSVLDVSGR DPKVSGALKT ASSLSQILML  240
EYANGFPMDE VGWGKVSESQ ITALSALHAE EFRLIARPKA VATYASGGLL KDIEAALFGP  300
DASPYTLLVG HDGNIAYVGG ALGLHWQAQG FAADDPPPGG ALIFELWRDG AGEAFVRVRF  360
RSSSLEGMRN LTHLKRAAST RIPMPLCDVK AECSAATFKA LIP                    403
```

```
SEQ ID NO: 98               moltype = AA   length = 405
FEATURE                     Location/Qualifiers
source                      1..405
                            mol_type = protein
                            organism = Amycolatopsis orientalis
SEQUENCE: 98
MRIAALLPLL LAASLLTGVP AEASQNPSPV AQTRAFVDDA GADPANADAD DPAIWVHPEN  60
PSASVVLGTL KEGGLAAFDL KARQLQHLAV PAGGRFNNVD VVGDLAVVSD RGRDRVRVYR  120
IDPAGAAAGS RVLRDVTDPA AAPVFSASES EVDEQRTAYG LAAGRDPRTG TRWVAVTRRH  180
ETRVALLRLV DKPDGTVGTA PIGTIDLPAS FRLPNGRTWS PCGEPDERPQ LEGSVLDVGH  240
RVLYTAQEDV GIWRIPLGEE GFGRPALIDK VRSFGVPQRF DEATEECVAD GPDPGFGGKW  300
LTADAEGLTL ADGKLLASSQ GDSRFVVYDR AGTPRRDFRI VAGRGTDSVE HSDGAAITTR  360
SLGPLFPHGL LVVHDGERRP AATGPSGEEL ATTGFAFVRL EAVVR                 405

SEQ ID NO: 99               moltype = AA   length = 408
FEATURE                     Location/Qualifiers
source                      1..408
                            mol_type = protein
                            organism = Asticcacaulis benevestitus
SEQUENCE: 99
MTLKHWLRFA LTFSGACLLA IQASAQPTKV ERVVMLMRHG VRSPITGEAP LDTQTGAPWP  60
VWSVPPETIT PHGAEALKAL GNVDRAWLSA RGILPAKACP DLAKTIVWTN TSPRTIATGQ  120
AYVQGLAPGC ALHVGHLPED QIDPLFEPTR APPPWFDAQR AVTSINAYTG GMPVLVQRHD  180
ATLGQLEHVL DCGASPCSPQ RAPRLAVTAD NRGLVFEGPV RDASGTAEVL MLEYLEGFPL  240
KEVGWGRANP ATLKTVGEVH AALFDVFSRP PYMMAFQTEP TARRIIDDFS RPDAPDFDML  300
VGHDTNVAAL AALLGVTVEA PGFAVNDPSP GGALVLALIR DAQGRAFVRV YYRSQSADDI  360
RAARDHATWK SLTMNACKQG PQHMCPLPDF VALLKAGTAE ARAPLVAR              408

SEQ ID NO: 100              moltype = AA   length = 423
FEATURE                     Location/Qualifiers
source                      1..423
                            mol_type = protein
                            organism = unidentified
SEQUENCE: 100
MLFRFVLPAV LLLPAFCSFA QTPTDDVRAV VIVARHGVRA PIENETRSSV FNAQRWPAWP  60
SAPGDLTPHG IAALKRMGEF YRQRYATLLH DCNSVAVEST NTSRTIGSAK AVMSVVPDC   120
DVRVMADLTA DPPSIDKAKL ADATHGRMAD QPEWFTHAFA RPLEEMHDVL AKCAGCKQVP  180
DFRTSMLDPS AHSENMMQAQ GEKAGALVPR DPRKENAAAL GADFSENFLL QYAEGMPMDQ  240
VGWGRVDRAR LDDLMEMNTR YHDFILRTPY YAQQAAGAMA QKISDWLSMA AILNIPVRPG  300
RPDVPAGGRE SVLYLSVHDA NLTWLGGLLR IAWLVSDETL NATPPGSALV FELHHNRQSN  360
ADTVQVFFIA QTLDQIRNLT DLTRAEKPSI SPIYVPGCSG PGPGYACSME AFVRVTKEAT  420
KVP                                                               423

SEQ ID NO: 101              moltype = AA   length = 426
FEATURE                     Location/Qualifiers
source                      1..426
                            mol_type = protein
                            organism = Bacteroides sp.
SEQUENCE: 101
MAENPLDEIR RDPERAGGVY YVTDLSHPVT PAPKGYTPFY INGYFRHGAR QIDDEVTYPA  60
IYGVLEKAHA TNNLTDFGKA LYERLEPFKK NVFYKEGDLT QIGYRQTREI GRRMVQNYPE  120
VFEGHPYLKT NATNVLRVAA TMQSVNSGIL SLRPGLEWAE IDNSRSFLTT LNPYGNVCPG  180
RSPLDKYILG KENCWYKKYR SYIDEKLDVD AFFRRLFIDV TQVESEYDKY DLIHRFWLMA  240
SLMQCLDRQV PIWDIFTEEE ILVWAEIENY KYFAQKGPEP VSHGRSWGLA SRTLRHLLDE  300
SAEDLVRKRH GINLNFGHDG VLMAILTNLQ AGTWAREASN SKEALQSWKY WDIPMGANLQ  360
MIFYQSEGNP DVLVKFMLNE KDLRLPLEAV EASYYKWNEV YKFYIEHCDK VEKSLAETLK  420
LSYEDF                                                            426

SEQ ID NO: 102              moltype = AA   length = 432
FEATURE                     Location/Qualifiers
source                      1..432
                            mol_type = protein
                            organism = Barnesiella intestinihominis
SEQUENCE: 102
MKKRTLTAGT ILLCLSAISF GQNSIKDFLH QNPQFFGSTA SVYYCNDTTD TPAPKDFIPF  60
HIDHIARHGS RTHDSKSMVP NLYKLMNKAD SLNLLTREGK LLRNQIDTIY HLMNHRWGDL  120
TPLGAQHRD MARRMYHRFR PAFTPQDGKV TLVAQSTTVP RSMASMAAFV AEMRGYTPTA  180
EFSMDPSNGY DNTLRFFKGK EYQQYLSKGS WKKILRAYQE KHTPTRLIDR IFKKGWEQII  240
PDPITFMTHL YALTIILPNT DYDISLYPWF TEEEKFDLWS ANNLSQYLRK ANSIPGKGLP  300
VAIAKPLLKD MLATSQAAID GNGVEANLRF AHGENTIPLL ALLGIENAAV VEADPEKVTE  360
VWQDFKYNPM ATNIQWILYK NTDGKILVKV LFNEQETKLP IDSEYAPYYD WKLFQKYCEK  420
QMAKYPDTTP AL                                                     432

SEQ ID NO: 103              moltype = AA   length = 433
FEATURE                     Location/Qualifiers
source                      1..433
                            mol_type = protein
                            organism = Endozoicomonas elysicola
```

```
SEQUENCE: 103
MKLQTLLGHC LKKVMAFDYC NNSLKSYLMH GRTSGCFHIC SLPESGFKKL FLIFHTVFAM    60
CFLSVGVDAT GIGFEMETPA DYLISLVRHG DRSPRDLGDM AQYWPMGPGQ LTAGGLEQEY   120
LLGKKIRQHY FSESLPDSWS PKISQHYAKG LDRTIQSASA LLQGVYPGQP RNTGLPGGIQ   180
VPPVYASPLA SDDLFSAQRL CPGYLHRVQA LEKSADWLRK KEQYRDQLSS WFELSEGSGA   240
GDLYSLIPLI DQISIHRMHR RPMPKGITIQ EAIELEELLN WVVSRIIANY EIAQLIGAPL   300
AKAMIRDFKR VQQCLEDKGS CNSCQRWTLY SASDSNLLAI MTMLGAPSDR IVDYATHFGV   360
QLNWNEGRPE IALSLNHEPF SVPGCVGHCS LDQWLVLLEQ SLPDDWDYLC ARDRGGFAPY   420
PEPYVPSGSV ASR                                                     433

SEQ ID NO: 104               moltype = AA   length = 440
FEATURE                      Location/Qualifiers
source                       1..440
                             mol_type = protein
                             organism = Asaia astilbes
SEQUENCE: 104
MLMIGSPVNA LAALWGFALS SLLLCGVATP ARAVPLSAAP PSADAVLERV VLVARHGIRS    60
PTHDPAALAH ETGIAWPEWP VSPGQLTEHG RATLSVMMRD IGRHYDLGCS THKESCLTQT   120
RPVIWADSAD DRTRESGEIM AASLAPDLHL VSRSLGAKVK DPLFGGPPQD FFVREAKRLY   180
KDALTAQKDD MRSRPESVKA GLAAMQLLLA PQGCVKDDGP CLSGPITVTS KNGKPVLEGG   240
PVLGASLAEN LLLLHVQGLD HKKAGWTTAI DPAFLTRALA VHDYLSDLTR KRGKLVEEKS   300
RALAGVIDAF LQGRDAQLPN GDSIGPQTRF LAFAGHDTTL DALAARYGLS WSFKDQPTEQ   360
LRTRRWLSRD GESQAARSFI ALSFSTNPWL HCLKEGGSMK PMEGFRPWCR SRAERAGNSR   420
LSCRREGMMR CTQLSSWRSR                                               440

SEQ ID NO: 105               moltype = AA   length = 440
FEATURE                      Location/Qualifiers
source                       1..440
                             mol_type = protein
                             organism = Alistipes timonensis
SEQUENCE: 105
MKRPLLILSA CLCALAAAVS CSSGLRTADG ESVPDRVMGV YLPYPETVAP SPGAPEGYET    60
FYISHYGRHG SRYLLYDSQY AFVRDVLSRA AADGKLTPSG QKALADFLEA YPQFEGRAGM   120
LTRIGAAQHR AIARRMAERH PSAFAPEAAV RASTSATART QESMEAFCAA LQTCRPSLRI   180
TCAEDAALNP YSAGSGIPTE YDLRVKSPEA EWRPDFETFC RQQIDAERFA ARIFTDTDYA   240
AGLCDLTDLE RGAFYLAVHF RGCGIAADWL RLFTLDELCT LAACDAYTFY MEKGPAAETS   300
DRTWALSAHI LDKMLTDAEQ DIADGTAANL RFGHDGCIMA LLTLMGADGW TATAATQEEI   360
ARAWDVSQIP MACNLQWIFY RPVSGEGEPL VRTLLNERPL RLPVTDPEGM CAWSDLKRYL   420
AERCDTAFAV LNKDRTPNNL                                               440

SEQ ID NO: 106               moltype = AA   length = 442
FEATURE                      Location/Qualifiers
source                       1..442
                             mol_type = protein
                             organism = unidentified
SEQUENCE: 106
MKLLNKTTFL IGLGLVFQTM TISAQTLTDR VYEDPTTSAN IYHVYKQREG KLTPAPKGYQ    60
PFYISHYGRH GSRYLTGDYY FRPAMAMLEA EKEKGNLTEV GENLYSDIKK LAAAHEGMYG   120
ELSPRGAREH RAISGRMYNR FTKVFKSKTR NKVNCISSVV PRCIISMANF TTALNDNRPE   180
LEFSYTTGDK YFELLAHNYD TDEIYKTIGH ITDSLRKATC HYDKFYGKIF KNPTVAVDSM   240
KSPYSLIGSV YSSACICECL DFLNVDLFKY FDKDELAQQA VVRNNRVYGD LGNSIECGDV   300
VAASARFLLQ DFVDKADAAL QNGSDVAADL RFGHDSGIQP FFCILGIEGH DKQLHIADAD   360
KCWFSDLTVC MGTNLQMIFY KNKKGQVLVK LLYNEAEAMI PAVQAYSGPY YRWEDLRSYF   420
VDRIAAAKAF AATLPPPQPR EE                                            442

SEQ ID NO: 107               moltype = AA   length = 444
FEATURE                      Location/Qualifiers
source                       1..444
                             mol_type = protein
                             organism = unidentified
SEQUENCE: 107
MTLRKTLSAA VVTMLTAFAL TATAQTTADA DISAKEAISK DNNLAGCMYR AYPGPTKQLT    60
PAPEGKRPFY ISHYGRHGSR WLIGRDDYKY LVEVLQKADS AKTLTKYGQE LLKKLRVIND   120
HSRKRLGELT SLGAKQHREI GGRMADRFPE VFQGGVRIEA RSSTVVRCIL SMENELLEMM   180
RRYNNLRIWS DASDRDMWFM AGGRENLGDV KGKKAAQELE WKWEQTKMPL FKSMFTKIFN   240
DTAYVNKMVN KDKLVYRLYS IAVNMQSLDE RKEISLYDLF DNDQLYACYE KENAGWFINY   300
GSNLWTQGKM PYSQRFLLRD IITKADSCIA LPKPGATLRF GHDTMICPMV CLLGIGGRDK   360
MLDDTDFDNI AEKWRMYEFV PMAANIQFIF YRSSPSDGDV LVKVLLNEDE VAVTEDLKTD   420
IFPYYHWKDF KEYFLKKLDN FQLR                                          444

SEQ ID NO: 108               moltype = AA   length = 463
FEATURE                      Location/Qualifiers
source                       1..463
                             mol_type = protein
                             organism = Desulfovibrio piger
SEQUENCE: 108
MLPSRKEILM RTWTCLAGLL ALLLGLMPCP VSAAPSAYHL SKVVMLTRHG VAAPADDNQL    60
PRITGKAWPQ WPVGPGQISP RGAQLLTAQW ASLRALYLQA DLLPAQKTES RVFVRADNTP   120
RSRGTAEALL QGLTPGTLPA YAVVNLDPDP LFEPVQAGLA IFDPAETALA ILDHINGDFS   180
```

```
QFWESLGEPM SLLDQLAGPL SAEACNSINL PGGGCRLSDMV PTISIMDMGR RVEIRGGLGL   240
GSTLVDLLVQ EYAQWPQQEA AWGQANAAAL RKLLPIRSEI FNALHRTPLI AGIYGGPLLR   300
DMALALYSQH ADPRLNEAKC AVFVGNDNNL AAIGALLGID WQASGFPPNA LPPGTILAME   360
LWEGPGNDSE VRFRVFMQSL DFMHAPLSVT TASGYQTAPE SYGPALLEAH VTLDGQKDGP   420
VMSRELFEQR VRGALEGRGL PRITFLPEMV SPQAPAPSLP VQP                     463

SEQ ID NO: 109              moltype = AA   length = 488
FEATURE                    Location/Qualifiers
source                     1..488
                           mol_type = protein
                           organism = Chitinibacter sp.
SEQUENCE: 109
MRHLFCLSVL SALLTACGGD ITDPAATPAP TATPVATATP APTVQPYTVS AVSFDAETEN   60
VLSAAGDVDD PAIWVHPSQS AKSLVVTAIK DGGMRVYDLQ GQLVQSIGPG ALNNDSKGKS   120
RYNNVDIVYG FKLDDNSTVD LAIATDRGQD LIRVWKIDPN NSTTPLSDIT SATPLRLFPT   180
VPTEGSESDA SKDAAIAVSK QNTGYGITHF SDKASGKHFV LVNQRKQARI RQFELIAEAG   240
GTVNVVAVAG RDWRFPYSWR GQNLRETNDL DATRDWSPQF EGMVVDQRNG MLYAGQEDVG   300
IWRVDLKTGQ ADTQPVYETR GSSRETYTTG TPATVVKHSF FNPESKISRD LEGLSIYYGP   360
NGTGYLIASS QGGAHGGAPN VSDAPYDDSF AVFALNGNAK PVLKQGFRLS QGPNGNTEGV   420
QECDGADVVA LQLPGYPFGL LVTQDGYNDD LNNLDGVTAQ TNLKFTSWEK IATALKLEKY   480
NNFDPRKL                                                            488

SEQ ID NO: 110              moltype = AA   length = 510
FEATURE                    Location/Qualifiers
source                     1..510
                           mol_type = protein
                           organism = Caulobacter sp.
SEQUENCE: 110
MIHRRQRLAA ASALALTLGA VAGQTFAQAV APVGATVPTA EGGANAAALL YDRADPGKSV   60
IAATGELGGL EFHDLDGARK SALPGGETYG VDVRDDVLAV LDRKDGRIRL SRYDFATGQA   120
SAIDARPLML GYAGEGLCLH RSARDGSLYA FALGGDGQLD QWLLFPTADG KLDGRIVRRL   180
HLSSEAKYCV ADDASGMLYV AQQAVGVWRY DADPEAEAVA TVVDINRLGH IAGEVGGLAI   240
LNGGAQGDYL VAANADAGDY NVYDRNADDR FLGRFRIQAN GADAIEGPAG LFGVRAPLGA   300
DLPAGALLVT DDRKVGANTK LLSWRDVAVA LKVSPGQVTP PAAPSRLALV KPTMETRPVE   360
HGGDAADDPA IFVHPTDPAR SVIVATDKKA GLYVYDLAGK PLQFLPDGKM NNVDLRGGFK   420
LGGRTTTLVV ASDRTHKSIA LYTIDPDTRM LTNVADGVQA TGLSDPYGCA CTRAARVRPT   480
CSSAIPTAAC ASGNWSPPRP ARSAPRRSAT                                    510

SEQ ID NO: 111              moltype = AA   length = 540
FEATURE                    Location/Qualifiers
source                     1..540
                           mol_type = protein
                           organism = Butyrivibrio sp.
SEQUENCE: 111
MKKTVITACS LVLAAVIGST GCGKISLKNP NMKNSETNSE LKTEDNTEVK TETNTETNTE   60
TNTGATTEAK TEAKTEETTE AKTETTTEAK AETTAEDNTE ANSEATSEVN AESNTETETN   120
TGSTQNIDEE ANAGGRIIDY DGYKLDQVVI LSRHNIRSPL SGGDSLLGKI TPHEWFNWTS   180
APSELSLRGG VLETQMGQYF RQWAEEEELI PTNYHPDNGQ VRIYANSKQR TIATAQYFTA   240
GMFPTAGLPV EYHMEFDKMD PVFTPQLTFW TDEYEKDAKD QIYEYYADAM KSLNDNYELL   300
SDVIDLEESN GFKDQSITAF TAGDEEFSLK EGAEPGVSGS LKTACSVSDA LVLQYYEESD   360
TQKAGFGQEL TYEQWKSISE IKDVYGDVLF TAPMIAVNVA YPLVSEIYDE MNTDGRVFTF   420
LCGHDSNVGS VLAAIGAEDY ELPNAIEKKT PIGCKIVFTK WSKGSEVFWS ADLVYQTPSQ   480
LRNMPILDTD SNSPEIFHIS FKNIKQNEDG LYKADEFMKI FLDAMDSYES LYQEYVEKAA   540

SEQ ID NO: 112              moltype = AA   length = 549
FEATURE                    Location/Qualifiers
source                     1..549
                           mol_type = protein
                           organism = Desulfatirhabdium butyrativorans
SEQUENCE: 112
MKPKRCFLMT VCALLILISG PAMAQPQAPV LSVTTRGWVY LSWTEVSGAT GYTLSYAQIP   60
YTGSSAIGTV DMGTQTSLSG ALAADTAFYV AVQSRDNTGI SEYSNVVSIA GDSTTLKQII   120
IFGRHSIRSA TSDPASLAQY AVDAYPEFTG VPAGYLTPRG QQAATLLGSY FHEYLLLEGL   180
LTGEAQTDIS RSYFRANSIQ RSNVTAAKFG SGLIPGATIP VHSYKIADGA SSAEPDPVFD   240
PILTKVATVD PARALGEVQG IFNSGAAISS AYSGELSLIR SALYPKGTQP TPGAAHGSTD   300
PTSQTSHPIT LKASTSTLYT GGVIDLGGLN LTNSAADPFV MQYTDNFPLN DVAWGRLSLD   360
AVSQQSRIIN LIFNIQILPP YLNQVQSSNA AQHVLRTMEQ AVTGQNISGA FGDAQTRVHV   420
IVSSDGYVIG LAGLLHLHWL LPGYQPDFCP PGGALVFEVR QVNGTGEHVV RVYYTAQSFD   480
QLRNLTPLSL ANPPQTMNLL VPGCSRSATN LDVPFSAFQQ VLQNAIGMEY VQDPSKETPP   540
GVLTGVPLE                                                          549

SEQ ID NO: 113              moltype = AA   length = 556
FEATURE                    Location/Qualifiers
source                     1..556
                           mol_type = protein
                           organism = Cystobacter fuscus
SEQUENCE: 113
MFQGVLLTEL LLGARGCSST MRCPRRLGAA STLEEFMSAK RRVLGSASLA LVLVPLASLA   60
EPPVIPPRAE TPVLHRYDEA PRTPDSDDPA IWIHPSRPER GLVIGVLKEA GLQVYDLSGR   120
```

```
VVQTVLPANR PAISAGDPMA PGPRPEAATS ACPESESGET FGRFNNVDIQ YGFPLRGADG  180
RVRKVDLAVV TDRGCDRLRI YAIDPGRAGG PLFDVTARAA RRVFPERFVR PSPFQPTGEP  240
EGVRPNPLDD QNTAYGLALY RDPSNRFHAF VTQRSRAVVA WLELYEAGTE QVGYREVREF  300
RFDSRFSLPR PGGGGALAWS PCREEPAEDP QFEGLVVDQQ EGILYAAQEV VGLWKIPLSV  360
SLPRVVDVPR GRLIEPVKSF GAPYWAVPDD GEYACELEAP APAPEGTIAV PGNPAVGGKH  420
LEADAEGLAL YYAGDEKGYL IVSSQGDDTF HLYDREGGWT RERGNRHLGT FQVEGVGETD  480
GHDVVNVPMG AGFPRGLVVL QTGKAPPPPS TEPVNGYAYD GSTRFKLVRW DDIAEAVPPG  540
FKVDTDDYHP RDPHDD                                                  556

SEQ ID NO: 114           moltype = AA  length = 636
FEATURE                  Location/Qualifiers
source                   1..636
                         mol_type = protein
                         organism = unidentified
SEQUENCE: 114
MMIRVLSKLL LPCLLCGLLT ACATSPLKAT DKLALPPPSA AWKNISAITK KGQPLWLITS  60
ETTGLSLIDS SNNRLLALQG HFELLDVRPA HDNEFWALTV DSQSNAPQLL LMQTHPEIRL  120
RERHTLFNGD FQIDGLCLYK DAQSHLMAYF LDGNGSGELR WLVDGSSGKV VDTSITMLNL  180
PPNSEHCVTH DASNSLFISE AEIGIWRYPA NPEIENSRIL VDRTFDGGKI DGEVMHLTTT  240
RNALYAATEQ RLNIYSPAQW QLQSSVPFPP GVTVEGIAAS QSQLAVLDEA QQALTLMPLS  300
QPTSYRSSEK HILPVVKANA QTTAMDRRGD AADDPAIWIH PQEPEKSLIL GTNKKWGLLV  360
YNLQGEAVRS IATGHINNVD VRQNLLFANE PIDIAVASNR SNNAIALYKI HPETGDVNSW  420
ASLPTDLNDV YGICLFTPTP SDIYIIINDK SGRVNQYKLG SRNRKPHATL THSVQLKSQP  480
EGCVADDTRR ELFIGEEDKG VWRFNLTNDK LVEPELIATT NGHLVADVEG IDIVKNEFGN  540
YLVVSSQGDH SYAVFENKAP YEFLGKFRIA PNATLKIDGT SETDGLAVTG MPLGNNYPAG  600
LMVVQDGHNL MPNAPQNFKL ISWKDVLNAL KIPTVE                            636

SEQ ID NO: 115           moltype = AA  length = 644
FEATURE                  Location/Qualifiers
source                   1..644
                         mol_type = protein
                         organism = Microbulbifer agarilyticus
SEQUENCE: 115
MALKTLPKLF SILAVAALCS ACGPQIGNDA AKPKGIASEH QLALTDVVSS QLAPLALGGV  60
EYLLLASEKR GLVLVDKEGS EKLALDGGTV ERFALHPLEQ DRWLIAVYDE DNGELQLRLL  120
DVEEGSPRIR YLAAMPTNAP QVAMCFSSQA GRTHLFAIDE TGLGHEYVVH PREQAWTFTG  180
LRPLYFGEQV SSCVVDDRRG KLLVAQPPLG IWSLNADAET DEARQVFIAA SALPDGEFGG  240
LWLDEVNGNL WLTAAEKVMA FDINDPAKGP LFVEALADIE PVSAAVQGEA LLALEEEGDQ  300
VHRFAVSLPQ PPAEVQAFRG PVEIPRVRAS GQTAPVASGG DAADDPAIWV NPAKPSASLI  360
FGTDKKSGLS VYDLNGKLVE HFEVGRVNNV DLRPMQHGKF VAIAAATNRT DPGVSLFGIT  420
AAGAVEYLGL RNLDMEDPYG LCVYRKGADL MTWVSDKEGA VQLLQIVPGT GNVDWSLRKL  480
ATLEVASQVE GCVVDDEMQM LFFGEEDGGI WRLDIAAYLA GEAKPQLIAP VDGERLAADV  540
EGMGFYHAAD KSYLVVSSQG NNSYALFNRD GSEFVGHFKV DINLDKGLDG SSETDGLEVS  600
SAALGAQYPQ GLLVVQDGRN RMPSASQNFK LVSWADIAET LQLP                  644

SEQ ID NO: 116           moltype = AA  length = 655
FEATURE                  Location/Qualifiers
source                   1..655
                         mol_type = protein
                         organism = Acinetobacter nectaris
SEQUENCE: 116
MNIIFLKKTC FVSIVLLGLM GCGQKTMPVP EKSVISKDGT IQFESISING TKDVFKVQSA  60
KLLSIPYWSE AHLIQTSKTQ GLQILNRQNH VLQSIDGAFG DIDYRIKDNL LFIQSVDLKQ  120
QRPTLLIFDM KSKQWQPSIL LEKTKFKIAV CLYQDQSQQL YSFVIGGQGS AQQWAVNTTP  180
NAKQPMQLVR NLNIPIGSKS CVVEDQQERL LINEEGIGIW EYLTDAEQPF KRKIVDMVKP  240
YGHIEGSPGA FTQVDNMLFV VDTQQPFIYK YIHDGKNWQI SDQLNTAELK KPEQLSAKRE  300
GEKVQLLLND NHKLKIASLP YTTAHQDKKK DEHFQFVQAK VQTTPVPNVG DAADDPAIWY  360
NEEIPTASRI LGTDKQGGLQ VYSLDGNEQQ YLAVGRLNNV DIRPNFNWDG QRVDLAVATN  420
RDHNSLHLFA IEKKTGHVSE IGQAQTSLKD IYGLCLYQNK QGDIYAIPND KDGTFIQYHL  480
SALKNKVNAK EIQKFSVKTQ PEGCVVDDKN DQIFLGEEDR AVWQKSLLQN NSNLQEEVATV  540
GKNQIQDDIE GMGLYHGKKQ SYLVVSSQGN NSYAVMEAHA PYRYRGSFKI VMNSVEQIDA  600
VSETDGLDVT SHNLGGVWEK GMLVVQDGHK VMPEDHQNFK YVPWSEISEK LNLEE       655

SEQ ID NO: 117           moltype = AA  length = 669
FEATURE                  Location/Qualifiers
source                   1..669
                         mol_type = protein
                         organism = Catenovulum agarivorans
SEQUENCE: 117
MQYFHQLTHN KLAKVSVVIT AAVFALAACQ SSIETTAHSA VQALAKAPQQ IFQHDKLNGQ  60
KVIQLNQDTW VANSENFGLM LINQQGKMVQ NYAGNFESLD IRQLDNKTWF VSSVDKEAGQ  120
FLLFKVVLAA NAQTHKITLL NTIKPEASVI DNQCLAYQNG QLSSFWLTAQ QQVEQRIVYL  180
NQPNAQPSNV LVRSFSAPPG ASACVVDDVK QQVYVAEESA GVWAYPTNPE KELSRTPIAL  240
VAPFGQIDGE IKDISLLIDG SLLVALPEAE QIQHYQTDNS SHLAQVYSVA GFTIESIDAQ  300
QTADNKWLAN FYDDESGAYY SIELPLMVAD KSIAKQGASQ LTADMQTAPV ARFGDAADDP  360
EVWLNPNNGA DSLILTTDKR YGLNVYNLAG ELVETIASGR INNIDISYGA EFNGDKFDFA  420
TASNRTYNSI TMYKISHTGV ISELANLPTS LPDVYGLCQY QSPITGDYFV FINDESGIYH  480
QYQLDFSTNQ VTGKLVREFK VASQPEGCVA DAQTQTLYLG EEDWGIWTIG AEPDAGTRLA  540
PFYQVDGDVL VDDVEGLSLY LPNKSAAKNR SEKYLVASSQ GDDSYVVFDL AKNASRGHVV  600
```

```
AKFNIVADVQ KGIDGASETD GLAVIAAPLG DLYPLGALVV QDGRNIMPVQ PQNFKLVDWR  660
KISGLIIKQ                                                           669

SEQ ID NO: 118        moltype = AA  length = 736
FEATURE               Location/Qualifiers
source                1..736
                      mol_type = protein
                      organism = Corynebacterium timonense
SEQUENCE: 118
MRKFSGAFVI SLAAAVIAQN ASVSSAQVAD YSAEFSARTT PSFTGSNTSY ANSNEASKLS  60
TELQEAPDGF EPSYSALFAR HGSRTSSDSG YYDRLINGLE AAGRVDFFGG APTRTELGKE  120
IEDHLRQLRQ LHDQIGGGNL TGLGREESRE LADSFAERNR ELLSDSEAKL RLEASTKGRS  180
IETGEIFAQQ LIAHRFVVAQ IPDRATQNKE VLQNQDVPES PAQQRREAYL QTDPGYQAVK  240
GIPENWTAEV QPYANAVFEQ LQGSRKPSFY GYCGGRARDL FEARAFSELM SVEREAAGVG  300
PFPAIPGAED MYRSVQQCTA IDEFYKRGVG LEGQDHSNAN GLPLLNQIFA GIDASENNEE  360
VGQLLFSHNE ILTPFNAVLA IPEIGANQKF RPGELFNYET YPVLNQAQSD PMMGNIEWNV  420
FKHENGTRLV RMQHNERAVH FGRSCKPINE EFDYFLYED LKACLPDAGQ SIPSEDELSK   480
ARKLLQEALS EEELIQIVSV IENEDGSTTL KLSNGQVVTV PPNRQIVGTE ETGSAVIIKL  540
SDGSVIEIAK GPKGEPGEQG PKGEPGEQGP KGEPGEQGPK GEPGEQGPKG EPGEQGPKGE  600
PGEQGPKGEQ GEPSRIVAQG VDGEGNTVLT FSDGTVVTIP SGALSIERQY LDSEGNTVVE  660
FSNGQKIVIA SPAPSKSSSG SSWSDSSSLT AVGSSAFAAG GVVVAFVLAI AAVVGGLLGI  720
IPLAPPIQSL IDLVQR                                                  736

SEQ ID NO: 119        moltype = AA  length = 738
FEATURE               Location/Qualifiers
source                1..738
                      mol_type = protein
                      organism = Alteromonas macleodii
SEQUENCE: 119
MDKQKITRIY PTMGKTFFLT GMLATLFSCA TAGKASHQPQ ADIQEPVLKL KQLANGFSQT  60
LYYRSDNQQT AYKDTHANEQ ETPKALNKSY KDTHANDNEK LAPALNAQTN DDTHTIELQL  120
NEHQGISISN SQGKARFIAG SFVLASAEIA EFENKQWVSM VVFNNNTQHI EAYRLAPDTL  180
DIQQQLTQSA KGSEAICAAV TAQGAPHIVN IDATGTLNQF EIHDNQFLPL RNFAIGPGMK  240
SCSLDMLTHS IYLADEFAGV WKVNADIESE LEKELFFHNA NIAIEGVSTL SSNTSLFKGS  300
LLGWVSPNKS GVWLQSQCQT EFITLQYDLA GVPQTIEPEF IHLAFYEYEK GPRISVIVDD  360
DASGNFFSAE LSSELSAAYF NHGCLSKDEE PIANAGSRSP KYALARVLPS AETQPVKNYG  420
DAADDPAIWV NAQSPSQSRI LGTDKKGALN TYDLLGHQQQ SLAVGRVNNV DVGYNVAIAN  480
INNSGETTFT DIAIASNRSH NSLSVFEIDE FGVLAHLGEI DTTLTDIYGM CLFVENGVTQ  540
VFANDTSGLF ERYEVSFNKN KKAKGTLTQS FSLPSQPEGC VVDLTHTNTAY FGEEGAGIWS  600
MDINSTKHEP AFVSAIAPPV EADVEGLALF TVDAQTYLIA SSQGNNSYAI YNINSKNADK  660
LTLMGLIRIT ADMNNSIDGV SETDGLEATN ANLGGVYSEG LWVVQDGRNV MPSETQNFKL  720
VSGARLKEAI RNLVSTKH                                                738

SEQ ID NO: 120        moltype = AA  length = 791
FEATURE               Location/Qualifiers
source                1..791
                      mol_type = protein
                      organism = Clostridium sp.
SEQUENCE: 120
MKKLFKILFS IFIAIILSFN FITYYPKASN NLELVQDSTN ITKIPKNFRK STDVLNLDEG  60
EKINLTGLKE LNISGSAQFS KEGLSLIKKS IGDKYNITVV DLREESHGFI NGIPISFKNK  120
NNNANEGLSL NEILNDEAKR LNSIKINEPI TFSNTNISVI PKEVYSEETL TKNNNLNYIR  180
IPVTDGGLPS TDMVNRFKET VINNKGNNNW FHFHCKAGIG RTTTFMIMYD IVKNCNEVSL  240
EDIITRQVKL FEMSENDSKG FYSGDRYKFL SDFYNECKGN SKNIFNKNNN KNDYYIKNNI  300
MPKTLYVIKD NEMTKEEQTM VATLQGNVAT KSKEQIYILN NYEPSYETWL NDLKENYNVK  360
YKFIKDPYEL LSKFKDYIKG YILYNNSNKY SINNGCSLAS LENGIVIDEL IEEKVKEIGV  420
KNLIKDCRDT DKYWAFNNLW NKGLNHSTVI QLSPDKTMAL RDYAIVSKSL VFYEEEINNK  480
EFREKIFSSM DDVSRVFGWG PDEHTNVSIA SKFGVDIVAS DWSYNLSVLS SYPTRDQKQN  540
LSKESVKDNA HYVTFIMSDG DNQQWFLGSN FNSNNWYGSK YRGKFNLGWS ISPSIYYLAP  600
TVFNKYYESA SNIRYKDYYL APPSGNGYMY PSKFPEEKLN NYTKRLSNYM KKVDQNYVLI  660
LDDESFYRTD LWDKYTCHNN IDGLIYLDYK KNNNYNGEIV WSNNKPVVSC RDLMWKGLEE  720
EDTLIENINS RVKEGYTDIK NPKSYTCVYV HVWSKNMDDL NLVIEELNKN SKVEVVTPYT  780
FMKLIKENIK K                                                       791

SEQ ID NO: 121        moltype = AA  length = 821
FEATURE               Location/Qualifiers
source                1..821
                      mol_type = protein
                      organism = Clostridium beijerinckii
SEQUENCE: 121
MNKNFKRITI LTLLIVSIFS FAVNNNAIAQ VPSDKDNGVH LILDSVNYNS VLPKHFRKTT  60
DLAVVKDNKD LDLKGLDKLN ISGSQQFSGN NIDLLTKAID TSLPMTVIDL RQECHGFING  120
FAVSWADARN NANVGLTRDQ VIAKEKEDLK SIKLNEPITF YNNSKQTMDV KTVQSEEELT  180
KSKKLGYERV TVRDGGIPTD DMVDYFMEFI KNKPKDSWLH FHCKEGIGRT STFMIMYDMI  240
NNYKDVNADG IIKRQLALAN FEDTTLKSFY NNERMGFLNK FYDYCKANGD SFDTKWSEWN  300
SKASSIDETD KSNAIQVSNV NSVYMKNNIV PKSLYAISLD SMTPGERTMI TSLQGLVNNH  360
CSFQIYTLNS SQPDYKIWLE DLKSNHNVPY EMISDPWELL KIYKDYIKGY VLYNGETKDP  420
SINNACSLAG VKDAIVIDEK LEPKIKELGI ESKGDCRSTD ENWAYDNLWN KGLNHSMVME  480
LSPDRIDALR DYAIMTKSLI FYEGSVDKTA LRDKIFSSVD DNATCLGWGP DEFINVSTAS  540
```

-continued

```
KYGVSMVAAD WSYNLTTLSA FKEPHINKNS SLKVPKEENV HYVTFIMSDG DNQQWNLGTN  600
YGSSKWFGYE NRDKLSLGWS MTPALYYLSP TVFDLYNKSI SNEDPRNNFI VAPSGNGYIY  660
PSKFPRNKLG SYVDLLNNYM KRVNENCVSI IDDSAFHDIE LWNEFTKKSN IKGLFYIDYH  720
RHDNYKGEIL WSNNKPLVSC RDLLWNSLED EEELVKRIND RVSLGQTNIH SPEAYSFVYV  780
HVWTKETSNV EKVTKMLKEN KSVRVVPPET FMELISKNVK H                     821

SEQ ID NO: 122            moltype = AA   length = 293
FEATURE                   Location/Qualifiers
source                    1..293
                          mol_type = protein
                          organism = Bdellovibrio bacteriovorus
SEQUENCE: 122
MKKLLLLPVL FAVAACAEKT VSLTPDKPVS TKIPFFMTRP QPTTPVELVF DNDHATAKPM  60
NYRKNDSLRM SGSATFSPKA LKEVSKPVKK NKASLYVFDL RQESHGLIND IPVTWYADRD  120
WANADLNHEE AVRRERRLLG DLRVGEKIGT TTIQSIETEE SMIRTGGHQY VRLTVTDHVR  180
PVDSEVDRFI ESVRALPENA WVHFHCRAGK GRTTTFMVLY DMLKNAKADS FEAIIKHNTE  240
LSNDYDVLTV PADEKDWKYP YQKERAAFVT EFYNYAKAHP NGEGMLWGEW VLR          293

SEQ ID NO: 123            moltype = AA   length = 301
FEATURE                   Location/Qualifiers
source                    1..301
                          mol_type = protein
                          organism = Clostridium tyrobutyricum
SEQUENCE: 123
MKKNRVRIGI FLLFFIFLLG ASNVNVLALQ KNTADNKLEL TVDSHKKAEM PKRFRKTSDK  60
IKTEGKMPNL TGLAELNASG SQQFTPGNIN LVKDAIGKDK KISIVDLRQE SHGFINHLAV  120
SWKLPDSNKA NKGLTREQVI KEEKKLLKSI KLNEPLKIKN KTVIPVKVQS EKQLVKDTGM  180
DYIRVTVTDT ERPEDDMVDY FVKKVRKLPE DTWLHFHCKA GMGRTTTFMA MYDMMKNSKK  240
VSLEDIMERQ ELLGGVKLLK PVGGKESESQ KRSDFLRQFY QYTKENNDNF KTSWSQWLNS  300
K                                                                 301

SEQ ID NO: 124            moltype = AA   length = 302
FEATURE                   Location/Qualifiers
source                    1..302
                          mol_type = protein
                          organism = Acidaminococcus fermentans
SEQUENCE: 124
MKFWKITTGI LLMSQLSLGL AWADAPSIAA IVKPSKGYVW RLDTKNKLQL PRNYRADVEN  60
CMSGSAQPSI LGLSSLVQEL AQQGVKPQQI ILVDLRQESH GFVNGQAVSW YGDNNWANVG  120
KADAAIRKDE ANRLAKTLGK ETSYYKLDKN KQPHFKGKEN VAAALTERQA AASFGLGYAR  180
FASTDHIWPE PEEVDAFLAW QKTLPKDAWL HFHCQAGKGR TTAYMIMRDI WLNGQKDSLE  240
TICARQHALG GQDVLHMTHK EAWRQTIDDN KVYRLKQFYT YVKGLQQGTI TGTWTEYLKQ  300
NP                                                                302

SEQ ID NO: 125            moltype = AA   length = 307
FEATURE                   Location/Qualifiers
source                    1..307
                          mol_type = protein
                          organism = Desulfovibrio alcoholivorans
SEQUENCE: 125
MTPLCSARFL PRLLACALFL AILGAAKPGP GADGPVLIYD YPPGQALPIH FRLADGGPKG  60
DPASAKLRLS GSSEFDAAGL DNLARTLPGP LTIVDLRQES HGFLNDRPVS WFAPKDEANM  120
GKTPEEAARD EAQRLAALSK AGTAAVTVIE AKSKSGGIKK ARTLRVDVVG VASEAQLTAA  180
RAVGYLRLFV TDDMAPDAAQ VDRFVEYCRS MAPNTWLHVH CHAGDGRTTT FMVLYALLHN  240
PAGRSLEEIA ADQAAAGGVD LIGQPRKGWK KPLYMARVAF LERFAAYAAA NPGGAPMTFS  300
AWTATHK                                                           307

SEQ ID NO: 126            moltype = AA   length = 317
FEATURE                   Location/Qualifiers
source                    1..317
                          mol_type = protein
                          organism = Desulfovibrio frigidus
SEQUENCE: 126
MSAKIFFPIK TRILDDIFKL ILASFVILLI FNSNSFADDS VLILDAPAVE NLPRNFRTSA  60
FPFKNSTDSP SRTGLDTLKI SGSGQFSADQ FDVMRSNLPA TVTVVDLRQE FHGNLNGAAV  120
CWFSYRDSGN KGLDSAQVTS GEQEALSLLG AQKEIQLGMN IIKNDDGGFK VDKKYQLKPH  180
TVYSEHELMG ARGVGYIRIA CTDHLRPPDV AVERFVKFVR NLKSDVWLHF HCRAGKGRTT  240
TFMLMYDMLR NANKLDLGTL AARQKMIGGS GLLGKVSTDK EWKIEIGHER QNFIRKFYDY  300
AKANPNGLPM TWLEWQK                                                317

SEQ ID NO: 127            moltype = AA   length = 319
FEATURE                   Location/Qualifiers
source                    1..319
                          mol_type = protein
                          organism = Clostridium acetobutylicum
SEQUENCE: 127
MHKKTKLICI GILATAIVTI SIYNFDFFKR TPLKEHKVKL VIDAENKNTL PPKFRTTSDT  60
ISLHKKGSLN LSGLSDLNAS GSGAFSEDEL KSIKNKIGNK PIVDIDLRQE SHIFVNGIGI  120
SWYGKNDDAN LNLTSSEVLK DENNKLMRIS KDKKVTFDKL SKKKSISNIS QLNDVKSVET  180
```

```
EEQLAKALGI NYSRITVPDH KTPDDAQINS FVSFVKNLPK GTWLHFHCRG GKGRTTTFMA  240
MYDMMINSKK VSFYDIMKRQ KLIGGADLLS GQDSLGKSDA EKRVQLLKKF YNYCQNNNDN  300
FKTSWTNYNN KYRIKNLQR                                               319

SEQ ID NO: 128           moltype = AA  length = 324
FEATURE                  Location/Qualifiers
source                   1..324
                         mol_type = protein
                         organism = Allisonella histaminiformans
SEQUENCE: 128
MKLQWMTTLL LTSCISLAGY CGSGAAEMHS PIPLQQEIPP APGYFNGRLW RLDASASSPF  60
PSHFRTSASA FDLSLPHKLP LPSRKGLDRL RISGSAQPSG MAIPALARHL KYLASGGPVF  120
LIDLRQESHG FFNGNAVSWY GNRNWANRNK TTEAVCQDEK ERIQSACGTQ VTVYSLNEEK  180
EPADAEKITV QSASTEEALA ARAGLHYVRF PITDHTTPSE ATIRQFISFM RSLPPDAWVH  240
FHCEAGMGRT TTMMILWDIY NNPELPLETI VERQHLIGGA QISLYPQEER KGPWKFNESQ  300
SRARIIHMFY DTMHSQSASH ADRA                                         324

SEQ ID NO: 129           moltype = AA  length = 328
FEATURE                  Location/Qualifiers
source                   1..328
                         mol_type = protein
                         organism = Centipeda periodontii
SEQUENCE: 129
MHAFKHLLTA LLLCTLCIIP YTASATDTNA DYRGYVWRID TAAGNEAELP HNFRTAGSPF  60
QTRTDTAKFG VDPNYTPSRE GLDALPLSGS AEFSVPAFHA LLKDLHTRAK GSICIVDLRQ  120
ESHGFMNGNA VSWYGKHDWG NIGRTKYEAL CDENMRIRSA QGKDVVLAHL DKKKQPKNPQ  180
TIRVITAMTE RELVEDAGVR YVRLAVTDHK WADPQTIDNF VDLVKKMPAD TWMHFHCQAG  240
KGRTTSFMAM YDMMKNPSVP LKDILYRQYL LGGAYLAYDP TTLHAPTGWE DADYHHKAEM  300
IAKFYDVQQ NHKNDYAIPW SMWLKKNP                                      328

SEQ ID NO: 130           moltype = AA  length = 331
FEATURE                  Location/Qualifiers
source                   1..331
                         mol_type = protein
                         organism = Desulfovibrio magneticus
SEQUENCE: 130
MPTLPPPCRR LRRSHRTRLA APWPLAGLLA VALALFLTGP IAVAWAEPEP DVGVLTLDAA  60
AASALPHRFR TCFFPLARPD GATTPSQEGL NGLRISGSSQ FSLAGLAIMR EQFPPRAVIV  120
DLRRESHGFL GDAAVSWRLP DNQGNPGREA AFVAAAEAGL LAAIDERPDI VVAREAKRGG  180
PTPLTLGPLA AVNEAQAAAS LGLGYLRLAV SDHTRPDDAV VERFVRFYRS LPPDVWLHFH  240
CRGGAGRTTT FMTLVDMLRN APAVAFEDII ARQKALGGSD LAKTTGGSAP GRDALARERL  300
DFLRRFYDYA RANPSGAPLG WRAWLAGGAK P                                 331

SEQ ID NO: 131           moltype = AA  length = 397
FEATURE                  Location/Qualifiers
source                   1..397
                         mol_type = protein
                         organism = unidentified
SEQUENCE: 131
MKAKICGSLC LLSAAVLLSN AHAETPSDVL QAIPHTEELL NVVVVSRHGV RSPTQSAEKL  60
HGWSDKKWSA WPVAPGLLTS RGFYLVKATW KLNRSRAPFT YGVCPKPEDV QIIADVDERT  120
RKTAEALNEG LYPTCGYKVK VTSSEHSAIF SPLKAKVCRI DYPKELEEKL TQKVVGINEK  180
FAAQMAEISK LTGHEFTGPM RAKVSKYKVG FKGAPYDCSS ITEIFALEWG QNPEKKVAWD  240
QLDWNGILHL MPIRVSVFSA LNRDMEVARY KGSALANKII ESLDHGPKYT YLIGHDTNLA  300
NLGEIFDLNW KLPGRDQNEN TPGGYLTFEK WSVNGQPEIR VFYSALSPEQ IHAERVTQPT  360
DDFEILPRGT KFDEWKTTYG RRLQSNCIAD DKYENRK                           397

SEQ ID NO: 132           moltype = AA  length = 424
FEATURE                  Location/Qualifiers
source                   1..424
                         mol_type = protein
                         organism = Acinetobacter nectaris
SEQUENCE: 132
MIKNKLICAI LTSITALTGT TVYAATNDYQ LEQVVTLVRH GIRPQTNLQE LNDATGKDWP  60
KWSVPDGYLT QRGYDGILNQ SQYQLKTWQE AGLPISLNQE NCSNQNQVFI WAAPDQRTRK  120
TADAIAESIS QTCHPEVGVS GYKHDPLFDA LKMGSATDQF DEIKKEFKAR IVSQDDIQAK  180
YAQSNQHLKA TVCAPNGCDF LDKDWKLKLN KNGQPKLNGP ADEGSNIGET IRLQYSENFP  240
LSQVAFGHVK NANDVKKLMV LHDAKYKYLN EIPLFAQRGG SILYQQILDA LDNSKATEAP  300
LHRPLVVFVG HDTNISEIKT LLQFNWQLPQ YLANDIPPGG TLSFEKYKEK STGQYFVKIG  360
FSARTLDQWR HLTPLSKAQP LHEDVLKYSY CKTTSVGVLC PLNQFLQNAQ KQIVRLNIDQ  420
PLYK                                                              424

SEQ ID NO: 133           moltype = AA  length = 431
FEATURE                  Location/Qualifiers
source                   1..431
                         mol_type = protein
                         organism = Dyella marensis
```

```
SEQUENCE: 133
MRPPGRFARA ALLGAALLAP VLAQADDATL RLRVVVLRHG VRAPTKAPDA LAPYASRPWE  60
TWPVAPGQLT PHGIEGMRAL GANYRRTLAA DGLWSGACDR MDQLVVIADS TPRNHASGAA  120
LVQGLAPACD GTYLALPTDQ NNPLFHFGGK DDDKDEDDKP ALPVTWPPAV LAQLQRVLLG  180
CEGQACLAKA HADGRKTLLD AADDAARAKA LKTAGSLSEN LMLEYAQGFP SAQVAWGQGD  240
EATIGRLVTL HNLQFALSKK AMPAAARGGS NLLAHVLATL QQADGEKPDA AALAPASARA  300
VLVVGHDTNL AQLAGLLDVD WHDAAHPDDY PPGGALVFDL WQTHDTYSVT VSTAMPTLDA  360
LRRADVARPT ALTRKTLRLT PCPVTDHCPL DKLSSWLRGR LDATRIDPAL PDMRAWSASS  420
QEAPHEPAVS K                                                       431

SEQ ID NO: 134          moltype = AA   length = 432
FEATURE                 Location/Qualifiers
source                  1..432
                        mol_type = protein
                        organism = Escherichia coli
SEQUENCE: 134
MKAILIPFLS LLIPLTPQSA FAQSEPELKL ESVVIVSRHG VRAPTKATQL MQDVTPDAWP  60
TWPVKLGWLT PRGGELIAYL GHYQRQRLVA DGLLAKKGCP QSGQVAIIAD VDERTRKTGE  120
AFAAGLAPDC AITVHTQADT SSPDPLFNPL KTGVCQLDNA NVTDAILSRA GGSIADFTGH  180
RQTAFRELER VLNFPQSNLC LKREKQDESC SLTQALPSEL KVSADNVSLT GAVSLASMLT  240
EIFLLQQAQG MPEPGWGRIT DSHQWNTLLS LHNAQFYLLQ RTPEVARSRA TPLLDLIKTA  300
LTPHPPQKQA YGVTLPTSVL FIAGHDTNLA NLGGALELNW TLPGQPDNTP PGGELVFERW  360
RRLSDNSQWI QVSLVFQTLQ QMRDKTPLSL NTPPGEVKLT LAGCEERNAQ GMCSLAGFTQ  420
IVNEARIPAC SL                                                      432

SEQ ID NO: 135          moltype = AA   length = 436
FEATURE                 Location/Qualifiers
source                  1..436
                        mol_type = protein
                        organism = Anaerovibrio sp.
SEQUENCE: 135
MQPLNYTIKK CLGLLGPAAI SALLLLSWST WTEAASELTD KGYQLDQIVM FSRHNLRTSI  60
TSEDSSAATM MTHPMPKWQV PRGNLTMKGG VNETILGQYF QLYLMDEGFM ADSWQPGYGQ  120
VDFYANSYER TIATARYFAT GLLPTANITI KHTKAVGGSD AVFNKPFAMD TPKLMELAME  180
YHNEYFQSYK DVFSKCYDSF ARVTDFPNSP YAKKHGIDHI NTDDLALTFS GKEKNVINYD  240
GTARKAYKLL DPIIMNYYQE ADNSKADFGT GLTRKDWENL GAVKTKSIEM VVGNPAVALS  300
HSHDILNIME SDLKNDTLKF AFICGHDTNI FTILTALETE DYSLPETILT KAPLGVKIVF  360
EKRRNPQGDL FIYPYIAYMS DDQQRNSRQL SLHEPPMIYP LNFRGLAKNG DGLYRYEDIL  420
TLMDRVNAKY EEYCLH                                                  436

SEQ ID NO: 136          moltype = AA   length = 436
FEATURE                 Location/Qualifiers
source                  1..436
                        mol_type = protein
                        organism = Avibacterium paragallinarum
SEQUENCE: 136
MKKLTLSLNL VSLLSGSLFY PTNLSAAPNV PDNHQAQALQ LKKIVIFSRH GIRTPLVGKE  60
SILSQATPYR WVKWQDKTGY LTAKGARLEK LFAAYWSEWL QQTGILSSQC PKDDLFIYTN  120
ARPRTIDTGV SFAKGAYSHC AIRVNYLGEY NTMDNTFNPV IRSKVDKAFE QKARKAVDEL  180
VGEGGFAQLN RHLQSNFNAL SQALNQGQSP LCQEKQLCNL DQEANTLTFT QGKEPKTTGA  240
LRDGTGAADS FLLQYYEGFP AKDVAWGRID NQESWKKIVD IKERYNQLLF GTQVMAKEAA  300
TPLLTFIQNS FKDYGYQHPY IEKARNAKVV LLVGHDSNVG SLLPLLKVKP YYLPDQLETT  360
PISGKVAFEK WVNAKGEAFM KVEYVYQTID QLRNGTKLSL TNPPNRITLQ LEDCPTNAQG  420
LCKMDDFYNA VKNALK                                                  436

SEQ ID NO: 137          moltype = AA   length = 438
FEATURE                 Location/Qualifiers
source                  1..438
                        mol_type = protein
                        organism = Cronobacter sakazakii
SEQUENCE: 137
MKTLFLHLFL FIFIFMPGVF PLHAQGADKM KLERVVIVSR HGVRAPTKFT PLMQEITPYP  60
WPQWDVPLGW LTTRGGELAS ELGRYQKRVL LDKGILESHG CPSPEQVAVI ADTDQRTRKT  120
GEAFLAGFAP GCQNKVHYQK ELDKKDPLFN PVKMGVCSFN VSKTREAILT RAEGNIERYT  180
QRYDSAFRTL EQVLNFSQSA ACKSPRQPGC TLTGVLPSEL SVSQDNVSLF GAWSLSSTLT  240
EIFLLQEAQG MAEVAWGRIH GEKQWTELLR LHNAQFDLLQ RTPDVARTRA TPLLDLISRA  300
LISNGSTESH YGIKLPVSLL FIAGHDTNIA NLSGVFALNW SLPGQPDNTP PGGELVFERW  360
KRVSDNTDWI QISFVYQTLQ QMREFKSSSS SSLPHKIVLP LPSCQEKNAE GMCSLKRFND  420
IVQTIRVPQC AVMAEKDQ                                                438

SEQ ID NO: 138          moltype = AA   length = 451
FEATURE                 Location/Qualifiers
source                  1..451
                        mol_type = protein
                        organism = unidentified
SEQUENCE: 138
MLGSRNLLTV FLFTFTSLSF AQTNVIAGSK TAYQYNSNQT LTLAPTGYQA FYIDHVGRHG  60
SRYISKSKYE DLAYHILLLA DSQHQLTDSG KDLLRQVTIL KQLNQNHYGQ LTNLGRKDIS  120
LISNRMLENN PTVFKGQKIE VISSSSPRAK ETAEIFIDSF KAKYPNIHVI QQPDNEQTLL  180
```

```
RFFEYSPAYS EYKKSKAVKD AVKSIEYASQ TKQMSKQVAK GIFKKSFLIK LKKGLDESED 240
TLVKTSDFVI AIYQLYQELQ AFSPQVLTDN HLDLGRYFST EQKIWLNTVV TAKNYLQIGP 300
AFDATGIQIK IAAPLLWDMI HSADKAIVDN NVDANLRFAH AETVSPLATL LEIEGSANVT 360
KTLFNYPTIW RADKIIPMGA NIQWIFYKSK QTHQPILIKV LLNEREVHLP IKTDSYPYYR 420
WNNVKQFYVN KLNKLGLDEN QSAIEMLKNL K                                451

SEQ ID NO: 139              moltype = AA   length = 544
FEATURE                    Location/Qualifiers
source                     1..544
                           mol_type = protein
                           organism = Corynebacterium singulare
SEQUENCE: 139
MRIRTLALAT AIACTLTPVQ ALAADDTTYY STKQHYEPQG SNYSTAPTGF HQIYTSTVNR 60
HGSRGLSGFK YDDLAQQMLE YAKEHDQLTE LGEKLIPQVE AMITVNKELA GGPGQEAGYG 120
NLTVVGREEL QGIGQRNAQR NAALMESIEE DNLKVKYMSS GADRANDSGW SFGEAWLSHN 180
SKLSDNLVDG MEDGHVAIET RTDLLHAHKD KKSPSYERYS KWKDSETLDS KVQEAYAKPA 240
SQTAARSLLN KIFTEDFIAG LEDGTITFVG RDNKGKSVEG IVEAALQFYN LYIIAPALAH 300
EEQTPSEGWI FDQYMDNASS PTFAYLLDVE DYYQKGPAIE GQTVAYDNYE PLLEEMIQGV 360
KDRAEGGDVA AEYRFGHAET IIPLAALLKL PGSEKGTPAD ELYTWENSEW RGDKVAPMGA 420
NIQWDAFQNE RGETLVRMLY NEKEIAFHDG CEPIETGSTF YTIDELSDCL PLGATSDHSK 480
ARLQEDKTHE TAQPSPSDAV SSKAKVWGIV AAVLGALAIA VGAATANAQQ IKDILNKFGI 540
HVPF                                                             544

SEQ ID NO: 140              moltype = DNA   length = 1149
FEATURE                    Location/Qualifiers
source                     1..1149
                           mol_type = genomic DNA
                           organism = Bacillus subtilis
SEQUENCE: 140
atgaaggttc caaaaacaat gctgctaagc actgccgcgg gtttattgct tagcctgaca 60
gcaacctcgg tgtcggctca ttatgtgaat gaggaacatc ttttcaaagt gactgcacac 120
acggagacag atccggtcgc atctggcgat gacgcagcag atgacccggc catttgggtt 180
catgaaaaac acccggaaaa aagcaagctg attacaacaa ataagaagtc agggctcgtt 240
gtgtatgatt tagacggaaa acagcttcat tcttatgagt ttggcaagct caataatgtc 300
gatctgcgct atgattttcc attgaacggc gaaaaaattg atattgctgc cgcatccaat 360
cggtccgaag gaaaaaatac aattgaagta tatgcaatag acggggataa aggaaaattg 420
aaaagcatta cagatccgaa acatcctatt tctaccaata tttctgaggt ttatggattc 480
agcttgtatc acagccagaa aacaggagca ttttacgcat tagtgacagg caaacaaggg 540
gaatttgagc agtatgaaat tgttgatggt ggaaagggtt atgtaacagg gaaaaaagtg 600
cgtgaattta agttgaattc tcagaccgaa ggccttgttg cggatgatga gtacggaaac 660
ctatacatag cagaggaaga tgaggccatc tggaaattta acgctgagcc cggcggagga 720
tcaaaggggc aggttgttga ccgtgcgaca ggagatcatt tgacagctga tattgaagga 780
ctgacaatct attatgcacc aaatgacaaa ggatatctca ttcagttcaag tcaaggaaat 840
aacagctatg caatgtatga acggcagggg gaaaatcgct atgtagccaa ctttgagatt 900
acagatggcg agaagataga cggtactagt gacacggatg gtattgatgt tctcggtttc 960
ggacttggcc caaaatatcc gtacgggatt tttgtggcgc aggatggcga aaatatcgat 1020
aacggacaag ccgtcaatca aaatttcaaa attgtatcgt gggaacaaat tgcacagcat 1080
ctcggcgaaa tgcctgatct tcataaacag gtgaacccga ggaagctgaa agaccgttct 1140
gacggctag                                                        1149

SEQ ID NO: 141              moltype = DNA   length = 312
FEATURE                    Location/Qualifiers
source                     1..312
                           mol_type = genomic DNA
                           organism = unidentified
SEQUENCE: 141
atgaaatttt tcaattacat tctgtttctg atcatcatta atatcagcta tagccaaatc 60
ctgttcgttt ttcagcacat ccgtcacggc gcgcgtgaac cgatttatta cgaccgcacg 120
cgcaaggaca agaacgtgga ttattatggt taccaatgga cgggtaaagc cgttctgacg 180
ccgatcggta aacgcatgaa ttatctgctg ggtattcgta tcgcaacaa gtataagaat 240
ctgctgaatg agatttacga cagtcgtgaa atctttgtta gtagtacggg tttcgaccgc 300
accattaatt ga                                                    312

SEQ ID NO: 142              moltype = DNA   length = 345
FEATURE                    Location/Qualifiers
source                     1..345
                           mol_type = genomic DNA
                           organism = unidentified
SEQUENCE: 142
atgaaactgg gtacgcaaag cgaggggttgc gtggtggatg accgcaccgg tatcctgtac 60
gttgccgaag aggatgttgg cctgtggcgt attgacccag gcagtacggt tccggttcgc 120
attgccgcgg ccgacggtcg ccagatcgtt gcggacgccg aaggtgttgc cctggcgccg 180
gtgggcgaac gtggtggtta tgtggttgtt agtagccaag cgacaacgc ctacacgctg 240
tatagtctgc cagatgagcg ttatgccggt cgctttcgcg tggttgacgg tccacgcagt 300
gcggaccgtc gccgtccggg ccgccatcgt acggatgccc gctga               345
```

-continued

```
SEQ ID NO: 143          moltype = DNA  length = 489
FEATURE                 Location/Qualifiers
source                  1..489
                        mol_type = genomic DNA
                        organism = Clostridium colicanis
SEQUENCE: 143
atgggtctga actacagcca agtgatcgcc cgcaacaatg cccaactgag tagtatcaaa   60
atcgcgcgaac cactgacgat caagaatacc accattgttc cgaaagaagt gtatagtgag  120
gagacgctga tcaaggagaa taataaccaa tacattcgca tcccggttac ggacacgaaa  180
ctgccaaccc cggaaatggt ggatctgttc gtgagcagtg ttaccaatct gccaaagaat  240
agctggctgc attttcactg taaagaaggt atcggccgca cgaccacctt catgacgatg  300
tttgacatga tgaagaacgc gaaaacggtg ccactgaatg acatcgttct gcgtcaaatc  360
aagctggcga atctggagaa taaagaaaag ggcctggaga gtacgacccg tatggccttc  420
tataacaagt tttacgccta tgccaagaat ggtgatttca cgaaaaaatt cagtgaattt  480
aacaattaa                                                           489

SEQ ID NO: 144          moltype = DNA  length = 495
FEATURE                 Location/Qualifiers
source                  1..495
                        mol_type = genomic DNA
                        organism = Chlorobaculum limnaeum
SEQUENCE: 144
atggcgacga aggtgcgtgc ctttggtgcc tggcgcggcg ttaaggaaat tgaggccgtt   60
gcggtggacg atggtaatgc gacggtgtac tacagtgacg agcgctttgg catccgtaag  120
tatagtgcgg atccagccgc cgtggacgcc ggtaaggaac tggccgtgtt cggtcagagt  180
ggtttcgccg ccgatcgtga gggtatcgcc gttacccgca acgcggaagg tggcaccctg  240
gtgctggtta gtgatcaaag cggtggcgcg ctgcgtatct atagtagcac caaggtggac  300
gagaatcgct atcgttttat cacgagtgtg ccatatcgcg ccacggaaac cgatggtctg  360
gatctgagca cggaaatccg caccccggaa ttcccggaag gtgttctggt tgccatgagt  420
gatgaccgta cgttccaatt ttacagtctg ggtgaggtgc tgaagcgtct gggtgaacgt  480
gtggacggcg aataa                                                    495

SEQ ID NO: 145          moltype = DNA  length = 528
FEATURE                 Location/Qualifiers
source                  1..528
                        mol_type = genomic DNA
                        organism = Bacillus amyloliquefaciens
SEQUENCE: 145
atgaaccata gtaaaaccct gctgctgacg gccgccgcgg gtctgatgct gacctgtggc   60
gccgttagta gtcaggcgaa gcataaactg agcgatccgt atcattttac ggtgaatgcc  120
gcggccgaaa ccgaaccggt ggatacggcg ggtgatgccc cgatgatcc agcgatctgg  180
ctggacccga aaaatccgca aaatagtaag ctgatcacga cgaacaaaaa gagtggcctg  240
gtggtgtata gtctggaggg taagatgctg catagttatc ataccggtaa actgaataac  300
gtggatatcc gttacgactt tccgctgaat ggtaagaaaa gtatcctgcg ccgccaccca  360
atcggcctga aagaacgtat tccgctgcgc ttcacccccac tgacgggcaa aacggcccac  420
tataaggccc tgcgtatcca aacggcccgc ctgcatcagc agctgatgaa gtataccgtg  480
agcgcctgca ccacggtgaa aaagcaagaa aatattaccc gctggtaa               528

SEQ ID NO: 146          moltype = DNA  length = 708
FEATURE                 Location/Qualifiers
source                  1..708
                        mol_type = genomic DNA
                        organism = Cystobacter fuscus
SEQUENCE: 146
atgggtggtg ccgccctgcg tgcgctggcg gccaatacgc cgggtccgct ggttgtggtt   60
gatctgcgtg aggaaagcca cggtttcctg ggtgatctgc cagtgagttg gtatgcgccg  120
cgcaacgtgg gcaatcgtgg tcgcacgcgt gaagccacgc tggccgagga actgcgcctg  180
ctggacagtc tgcgtcgtca tgagagtctg gcgtttgatg gtcaaggcaa agatcgtggt  240
ccaccggaac cagttcgtcc aatcgcgggcc ttcggtaccg tgtgtacgga agaaagtatt  300
tgtacggaag ccggtgccgg ctatgcccgc ctgctggtta ccgaccatca tggtccggat  360
gcgggtgagc tggaccgttt cgttgccttt ctggagcgcc tgccggatgg tgcgtggggtg  420
cattaccact gtcgtggtgg ccgcggtcgt acgagtacgt ttctgctgct gcatgacctg  480
ctgcgcaatg cccaccgtct gccgttcagc gttattgccc accgtcagcg cgttctgagt  540
gacggctatg atctgctggc ccacggtgaa ccagcagatt ggaaaacacc attgcgtcgt  600
gcacgtgcag aaattgttcc agcatttgcg gagttcgcgc gtgagcgcgc ggttggtggc  660
agccaacgtt ttaccgagtg gctgggtgcc cgtcaagaaa tgcgttga               708

SEQ ID NO: 147          moltype = DNA  length = 783
FEATURE                 Location/Qualifiers
source                  1..783
                        mol_type = genomic DNA
                        organism = Acinetobacter baumannii
SEQUENCE: 147
atgaatattc tgttcaagat gacggttctg gccgcgagtc tgctgctggt ggcctgtaat   60
gacaatgatg accaggaggc gcaaaccgcc ccgagtacca accaaagcaa atactatcaa  120
accaaaacgc catatcagcc gcaacaagag attaagaatt atgagcaaac cccaaacggc  180
tttcagccgt ttttaccga actggttgcc cgccatggta gccgcggtct gagtagcctg  240
aaatatgatc tggccctgta taacctgtgg aagcaagcca aagcggagaa tgcgctgacc  300
```

```
ccactgggtg agcaactggg tgccgacctg gaagcgatga tgaaggcgaa tattctgctg    360
ggttatggcg tggagggtat tcgccaatat ggttacggca atgagacgat gacgggcatc    420
ctggagcatc gtggcatcgc cgatcgcctg ctgcaacgcc tgccgaccct gctgaacagt    480
caagccagta tcctggttca aagtagtggt gtggaccgtg ccgttgacag tgccaaattc    540
tttacggccg agctgatcaa acaacgcccg ccgctgaaag ataaaattgt gccgctgagc    600
tacaccaatc tgagtagtga gagcgtgccg agtgttgaag acggcggcgt ggaccgcttc    660
aagctgtatt tccacagcct gaatgcggat gaggacctgg ttcagccgct gagtgccagt    720
cagcaaaagt ttatgatgct ggcgcgtccg attaagatcc tgaagaaaat cattaaaatt    780
tga                                                                 783

SEQ ID NO: 148        moltype = DNA   length = 807
FEATURE               Location/Qualifiers
source                1..807
                      mol_type = genomic DNA
                      organism = unidentified
SEQUENCE: 148
atgcgttggg ttaaagcggt gctgacgttc ggtctgctgg gctgtctgct gaagggcaaa    60
ccactggttc ccaagccacc gtgtttcgtg aaagacccga ccagcgccaa gcgtttccag    120
acgcgtctgc gcgtgctgag tccacgcaat ccaaccctga cgaagaacct gcaacgcctg    180
cgtgttattg gtagtccgca accgagtttt aaacagctga aaatgctgct gcaagaaaat    240
ccgcaactgt acggtatcgt tgacctgcgt aaagagaccc atttcttcat gaaaggtcag    300
agtattagct ggggcacgaa gggtaattgc gttaatcatc gtacgattca agaacatctg    360
agtgaacatg cctggacgga gctgcaaggt ctgaaatatc tgcgtctgca cgttccggac    420
cattacccgc cgacgatcga acaaattaac acctttctgc aattctataa gagtctgcca    480
ccaggcgcgg ttctgctgat tcattgtcgc ggtggccgtg gccgcacgac gaccttcctg    540
acgctggtgg acatcattga aaatgccaag tgtgacagtt tcgataccat cctggcccgc    600
caatggcgtc tgggtggcgc cgacctgcgc aagccacgta cgggtgttaa aaaacgccca    660
gccgaaacgc gtctgaaact gctgaagctg ttttatgcgc gcgtgcgtaa agatgccgag    720
ggcagtctgc gcccatttca gcgccaacgc cgcaagacgc agctgccaga agccctgagc    780
ctgccgccac cgagtgtgct gatctga                                       807

SEQ ID NO: 149        moltype = DNA   length = 843
FEATURE               Location/Qualifiers
source                1..843
                      mol_type = genomic DNA
                      organism = Clostridium ihumii
SEQUENCE: 149
atgagttact ttaagaagct gctgctggtg ctgctgctga tttttcagctt tgccttcaat   60
agttttagtg tgctgggcta cgatgaagcc agtaatatct acacggttct ggataatgag    120
aacagtaata gcctgccgaa tctgtttcgt aaggacgcga gtctgaatat tagtggtagc    180
gcccagttca cggccgcgca agtggagaat atcatcaata atattgatag taataaaactg   240
tacatcgttg atctgcgcca agaaagtcat ggtctgctga cgaaaatat tgcctttatg     300
ttttggaatc caaatgtgga cctgaatgac ggcctgagta gtacgcgaggt gctgcgcgtg   360
gagagtaagg agattagcaa aatcccgatc agtagtgtga tgcacatcta taataagaag    420
ctggatctgc tgaaaaccgt gaaagttcag agcgtgctga gtgagaagaa tctggttacc    480
agcaaaaata tcaattatat tcgctttgcg gtgaaagaca actacattcc aagtgatgac    540
atcgttgatg agttcgtgga ctttgttaag agcgagggta cgagtagtca tctgcacttc    600
cattgtgaag ccggcgaggg tcgtacgacg acctttatgg ccatgtacca aatgatgaat    660
aataaagata acctgagtct ggacgagatt ctgcaatacc aaaatcaaact gggcggtatt    720
agtctgattg acatcccaat ccgcaaggat ttcctgaata cgttctataa ctacaccaaa    780
gcgaacattg acagtaattt tgaggtgccg tatagtaaat gggttgaacg taaagttatc    840
taa                                                                 843

SEQ ID NO: 150        moltype = DNA   length = 852
FEATURE               Location/Qualifiers
source                1..852
                      mol_type = genomic DNA
                      organism = Desulfovibrio fructosovorans
SEQUENCE: 150
atggagagtg atccgacgct gatcttcgac agtatccgcg aacaaggtct gccaagtcat    60
tttcgtagtc tggcgggccc gtgggccgtt ccaattacca caacaccacc aagtcgtcaa    120
ggtttggcag aattgcgtgc aagtggcagt gaacagccga gtagtagtga aatggccacg    180
acgatcaagg gtctggcccc ggaagtgacc gtggtggatc tgcgtcaaga aagtcacgcc    240
ctgctgggtg agcacccggt tagttggtac ggcctgcgca actgggcgaa tgacggtaaa    300
agtctgcagg cggtggaatg tgatgaggaa acgcgcattg gtgacctgcc gccatgtggc    360
gaggccgcg tgagtcgtgt gattagcaag gatccagacg gtgccctggc cgaagttcgc     420
gtggaagagg ttgcgtatga tcgcgcccgt agcgaacaag aggccctgtg cggcctgggt    480
ctgggcacct tccgtattgc cgtgcgcgac catagccgtc caagtgatgc ggacgttgat    540
cgcttcatcc gctttgtgcg cgaactgcca ccgggtacgt ggctgcactt ccattgtcac    600
gccggcgacg gtcgcaccac gacctttctg ctgctgtacg acatgctgcg taacgccgcc    660
gttctgggtc tggaggagct ggccgcccgc cagcatatga tcggcggtat cgacctgctg    720
cacacgccgc ataccggttg gaaaggtgcc ctgtataatg aacgtgcggc ctttgtgggt    780
cgtttccacc attacgcggg cacgcgcgat ttccgtcgcg tgctgtggac ccagtatctg    840
gccagcgcct ga                                                       852
```

```
SEQ ID NO: 151          moltype = DNA  length = 858
FEATURE                 Location/Qualifiers
source                  1..858
                        mol_type = genomic DNA
                        organism = Clostridium novyi
SEQUENCE: 151
atgaagaaaa cgaactttag ctttacgctg ttcatcctgc tgtttctgat tagtatcccg   60
gttaacggca agctgattag tacggatgcg ccggttccgc caaaaccgct ggttgtgctg  120
gacagcaata gtacgagtcc actgccgagc tttttccgta ttatcccaga actgaatatt  180
agtggtagta agcaattcac cccggcccag ctgaagaaca tccagaataa aattaacagc  240
aaaaatctgt atatcgtgga cctgcgcgaa gagagtcacg gttttattaa tgataatacg  300
gcgattagtt tctatctgcc gcgtaagtac attaatgata attttaatac ccatgagatc  360
ctgaaaaaag agaagctgga cctggatagc attaaaaatg ttgaaaatct gaacatttat  420
gaccagctgg gtacgctgaa ggaaaccctg aaaccagata aaacgctgag tgagaaggag  480
ctgaccaaac acaataagat ccattatgtg cgcctgccag ttattgataa ctacatcccg  540
agcccagaaa ttgttgacaa gtttatcgaa ctgattaaaa gtaaaccaag caatagtcac  600
ctgcactttc attgcaagga aggccaaggt cgtacgacca tgtttatggc catgtatgag  660
atgatgcaca acaaagataa tctgagcctg gacgaaatcc tgaaacatca acaggatatt  720
ggcggtatta ttctgacggg caacccagcg cgcggtacgt tcctgaagaa ttttttacaat  780
tatacgattg acaataaaaa gaacaatttc gataccagtt atagccaatg gctgaagaac  840
atcagtagca tgaaataa                                                 858
```

```
SEQ ID NO: 152          moltype = DNA  length = 876
FEATURE                 Location/Qualifiers
source                  1..876
                        mol_type = genomic DNA
                        organism = Clostridium bornimense
SEQUENCE: 152
atggccaaaa aaatccattt caactttatc aaaattttta tcgttctgat cattttcagc   60
ctggccctgc caaatctgct ggtgaacggt aagagtccaa gcagcgacat tcacattgtg  120
ctggatacgc tgaataatac ggaaatccca cgcaatttc gtagtacgaa taatattaac   180
gttagtaata gcatcaatac gaaaggcatg gagaacctga atatcagtgg tagcagtcag  240
tttagtaaga cgaacctgcc gctgctgatc aaaagcatta atacgaatct gccgatcatc  300
gacattgatc tgcgccaaga gagtcatggc tttgtgaacg aaatgccgat cagtttcaag  360
aacgataaga ataacgcgaa tctgggcctg agcagtgagg aggttctgct gaaagagatt  420
aaagacctga acaccatcaa tctgaacagc accctgacgt tctataacga caagaataat  480
ccggttctgg tgaaaagtgt tgaaaatgaa agcctggtga ttagtaaaaa cagcatcggt  540
tatctgcgta tcgccgtgac ggacagcatg ctgccgaata aggatgaggt taataaattt  600
gttacgtttg tgaagaacca accgaagaat acccatctgc acttccactg taaagagggt  660
attggccgca cgaccatctt tatgatcctg tatgacatga tgaagaatta caacgacatt  720
ccaatggaag acatcattag ccgtcagatc gcgctggcca aactggacga aaaagattat  780
atggcctttt acgacaaaaa tcatacggaa ttctttacca gtttctataa ctattgccgt  840
agcagcaagg atctgttcct gagcccgtgg caatga                             876
```

```
SEQ ID NO: 153          moltype = DNA  length = 894
FEATURE                 Location/Qualifiers
source                  1..894
                        mol_type = genomic DNA
                        organism = Bacteroides stercorirosoris
SEQUENCE: 153
atgttttgcc cggtgagcat tctgtggggc caggatcgta ttcaacaata cgcgggtacg   60
gccatgccat atccgatcgt gaaggatagt ttcgtgttct tccaagacag tatggtgccg  120
ttctacgtga accacctggg tcgccatggc gcccgtttcc caaccagcgg taaggcgctg  180
aatcgtgtga aagagatcct ggaactggcc cgccgtgaga atcgcctgac gagtggtggc  240
gttaccctgc tgagtacgat ccagaatctg agcgatacgt ttgacggtca atggggcaaa  300
ctgagtgtgg ttggtgagga ggaacagcgc ggcattgcgc gccgcatgat cgaacgttat  360
ccgcaactgt tcagcgatag tgtgaaggtt caagcgattg ccacctatgt gccacgctgt  420
atccacagta tggacgcctt cctggcgtgt atggtggagt ttaatagtag tctgcacatt  480
cagcgcaacg aaggtaagca gtataatgat atcctgcgtt tctttgacct gaatcaaagt  540
tatgttgact acaaagaaaa tggcgactgg cgcccgatct atgagacgtt tgtgcgtcgc  600
aagattagtc cagccagcgt tatggaaaac ttctttctgg agagtggtca ggaaaccgat  660
aaagaggcgg aggagttcgt gatggccctg tttagcattg ccgcgatcct gccggatacg  720
ggcaccccga ttaatctgga cggtctgttc acgatcggcg aatgggaata ttattggcag  780
acccaaaatc tgcgccaata tatgagtaaa agtagcagcc cagtgggtcg tatgctgccg  840
gttgccatcg cgtggctgtg ctaccaaaac ctgtttattc aactgatgaa gtaa          894
```

```
SEQ ID NO: 154          moltype = DNA  length = 912
FEATURE                 Location/Qualifiers
source                  1..912
                        mol_type = genomic DNA
                        organism = Clostridium paraputrificum
SEQUENCE: 154
atgaagaagt acctgaaaat cattagtagt attctgatct ttagtctgct gagtccactg   60
agcatcagtg ccaaagaggt tgaacaagtg tatctgagtc tggactatga aaatacggac  120
agcctgccgc acaactttcg taaaaccacg gatctgagta tgttattaa gggcggtggc   180
aataccacgg gtctggaaaa tctgaatatc agtggcagta gccaattcac gagtctgagc  240
tttctgaacc tgaaaaaaaa tatcaatacc aaaaatgaat ctgggacat tgatctcgc    300
caagagagcc atggtttcat caatggtaat gccgtgagct ggtatggtcc aggcgacaag  360
```

-continued

```
gcgaacgccg gtctgaatta taaggaagtt atcgccaaag aggccaagca actgagtgaa    420
atcccattcg gtaaaagcat tacgctggat aacggtaaac acacgctgat cccaaccgtg    480
gtggagaatg agagtaagct ggtgagtagt aataacgtta aatatctgcg tattgccgtg    540
acggacggtg accgcccgac cgacgaaagt gttgaccagt tcgtgaagtt tgttacgcat    600
ctgccgaaca attactggct gcacttccac tgtaaggagg gcatcggtcg caccacgacg    660
tttatgagtc tgtttgatat gatgaaaaac agtaagaatg ttagtctgga cgatatcatc    720
aagcgccaat tcctgctggg cggctttaat ctgttcaaac cgggtgacga gaacaagcgt    780
gtgctgttcc tgcgcaattt ctacaaatat acgaaagaga ataacgacaa tttcaagacc    840
acgtggagtg attggattaa gcaaaataac atcaccccat ataccagcac gaccgagctg    900
ccgaaaaatt aa                                                         912
```

```
SEQ ID NO: 155          moltype = DNA   length = 915
FEATURE                 Location/Qualifiers
source                  1..915
                        mol_type = genomic DNA
                        organism = Clostridium pasteurianum
SEQUENCE: 155
atgcgcaagc gtatcaagct gttttggatt acgttcttca ttgcgatttt tagtctgagt     60
tttatctttg agaatgtgaa cgcggttagt tttgccccga aagaactgcg tctgaccctg    120
aatgcgaata cacggttac cctgccgaaa aattttcgca aaacgacgga cagtgacaag     180
attaaagaca tcgataagag tgtgaacctg gagggtatga ataaactgaa catcagtggc    240
agcggtcagt ttagtgagaa gggcctggag atggccaagt atctgggtgc tgagaaagtt    300
ccaatcacgg tggtggatct gcgcgaggaa agtcatggtt tcctgaacgg taatgccatt    360
agttggaccg acgccacaa taaagccaat aaaggtctga tcgaagccca ggtgattaag    420
gacgagaacg aacgtctgaa aaagctgagc gaggagaaga cggtggagat caagaatcgc    480
accctgaacg ttgaaaaggt ggaaaatgaa gaaaatctga cgaaaaagca tggtattagt    540
tacacccgca ttacggtgac ggacaaggaa gcgccaagta aggaggccgt tgacgaattt    600
gttaactttg ccaagagtgt gccaaatagt ggttggctgc actttcactg taaggccggt    660
aaaggtcgca ccacgacgtt catggcgatg tatgacatga tgaaaaatgc gaagaacgtt    720
agcttcgagg atattatcaa acgtcaattt ctgctgggcg gaaaacct gctgaaacgt    780
accacggtgg agaacattaa gggcacccgc gcgaagttcc tgaaaaattt ttacgactat    840
tgtcgtacga acaatgataa ttttaacacg acctgggagc aatggctgaa gaacaacccg    900
gacaatagtc gctaa                                                     915
```

```
SEQ ID NO: 156          moltype = DNA   length = 927
FEATURE                 Location/Qualifiers
source                  1..927
                        mol_type = genomic DNA
                        organism = Clostridium perfringens
SEQUENCE: 156
atgtttaaat acttcaagaa aaatgcgctg attatttttc tggttctgag tattttcacg     60
agtttttca tcaacaatac gagtatcgtg ctggccgagg acaataatgt gcacctggtg    120
ctggatacga agaacattaa taatctgcca aataactttc gtaccacgag tgacctggag    180
cgcctgaaaa atctgagtaa cattaatacg aagggcctgg atacgctgaa tattagcggt    240
agccagcaat tcagtccgaa taacctgagc ctgctggtga ccagcatcaa aaccaatctg    300
ccaattaccg tggttgacct gcgccaagaa agtcatggtt ttatcaacga gtacccggtg    360
agttggaagg gtacgaaaaa tgcggccaat ctgggcctga cccgtgagga agttatcgac    420
acggaacgca acctgctgaa tagtattacc ctgggtacgc cgattcagtt cttcaacaat    480
ccgaagctga ccgtgatccc agaaaaggtg ctgagtgaga accagctgat taaggcgaat    540
agtatgggatt atattcgtat cccggttacg gacggtaaac tgccgacgta tgagatggtg    600
gatttttcg ttcaatacat caatagcatg ccaaaggaca gttggctgca cttttcactgt    660
aaggaaggca tcggccgtac gacgacgttc atgattatgt atgatatcat gaaaaattat    720
aacaacgcca ccctggatga aatcatttac cgtcaactgg tgctgtttgg tctgacggaa    780
aagaatttca atagctttct gagtaaggaa cgtctggatt ttttcacgaa gttctaccaa    840
tatgttcaag aggaaaatac ggacttcaaa accagctgga gccaatggct gaacaagaac    900
aatttcccgc tggtgacgat tcgttga                                         927
```

```
SEQ ID NO: 157          moltype = DNA   length = 927
FEATURE                 Location/Qualifiers
source                  1..927
                        mol_type = genomic DNA
                        organism = Clostridium botulinum
SEQUENCE: 157
atgtgtataaa aagcgaagct gaagctgtac atcccaatgc tgctgctgat taccatcttt     60
agcagtttct tcctgaattt caacattgcg ctggccttta cgagccgaa caataagagt    120
gatgttcata tcattgtgga caatctgcgt acgaataaaa tcccgagtaa tttccgtacc    180
acgagtaatc tgacgaacat caaaaacaat agcagtctga tctgaaagg cctggaaacc    240
ctgaacacga gcggtagtca acaatttagc aaggacaatc tggatattct gaccaaaagt    300
atcgatagca cgctgccaat tctggttatt gatctgcgcc aggagagtca cggcttcgtg    360
aatgaatttc caattagctt cgcgaatgag aagaacgacg cgaatctggg tctgagcaag    420
agtgccgtta ccttcacgga gaaaaaggat ctgaaaagta tcaagctgaa taccccgctg    480
acgttctata agcacccaga aatcaatgtg gttccgaaag aggtgctgag tgaaaagcaa    540
ctgacgaaga gttatagcct gaattacagt cgcgttccgg tgacggacac gaaactgcca    600
accaacgaga tggttgactg cttcattaat atcgtgaagg agtgtagcaa agaaaactgg    660
ctgcattttc actgcaaagc gggtttcggc cgcacgacga cgtttatgat tatgtatgat    720
atgatcaaga attacaataa tgccacgtat gacgagatta tcaagcgtca attcgccctg    780
gccaatttcg acgaaaaaga gattatcgaa ctgagtagta gtgatcgcat caactttctg    840
aatcaattct caactattg taaagacgtg aatggtaatt ttgatacgac gtggagcagt    900
tggctgaatg acagtcagaa gcactga                                         927
```

-continued

```
SEQ ID NO: 158          moltype = DNA   length = 936
FEATURE                 Location/Qualifiers
source                  1..936
                        mol_type = genomic DNA
                        organism = unidentified
SEQUENCE: 158
atgaagaaca tttacattct gctgtttctg ttcagtctgg gtgttgtggc ccaaagcttc   60
ctgtatcaac atcaaccaac gctgttccca atcgttgatg ccccactgaa cagtgagaat  120
catctgccga agaagtggcg tagcaccaaa cagattagtc aactggttgg taattacgcc  180
aatctgaagg gcctgacgca actgcatctg agtggcagtg gtcaatttag ccaggaggac  240
ctgaaaaaca tgagccagga aattaaaggc aaggccttcg tgctggatct gcgcgaggaa  300
agtcacggtt tcatcgatgg taccccgatt agctggacga acggcctgaa ttatggtaac  360
gttggcaaaa ccctgcgcca aatcgaactg gatgagcaaa agcgcctgaa actgacggcc  420
caaaagggta gtattattgt ggacctgagc aaggatctgg gtgaaaattt tcaaaagttc  480
tttgtgcgtg aggtgaaaac ggagaaggaa ctggtggaga gttttggtta tacgtacatc  540
cgtctgccga ttacggatca tcaccgcccg gttgacagcg tggtggatca gttcatcgag  600
attgttctga gcctgccagc ggacagctgg atccacctgc attgcaaagg tggtaagggt  660
cgcaccacca cgtttatgac cctgtatgac atcatgcaca acgcgcaaac ggtgggtctg  720
aatgatatcc tgagtcgtca aaccctgctg ggcggtgccg acctggtgca ggccgaaaaa  780
aacgagacct ataagcaaaa gccggccaaa gaccgcatcg aattcattcg tgcgttctac  840
acgtattgtc gcgaggtgcc aaactttgaa atgacgtgga gcgactgggt gcatcaaaag  900
caactggttg cctatcaaac gagtagtagc aattga                            936

SEQ ID NO: 159          moltype = DNA   length = 945
FEATURE                 Location/Qualifiers
source                  1..945
                        mol_type = genomic DNA
                        organism = Acidovorax avenae
SEQUENCE: 159
atgccacatg tgagcctggc ctgtcgtcat catgcaggta cacgtccaga tagaagtgca   60
ggtcgtacag cattgcaatt gcgtcaacca gaagcagaaa cgcgcctgga gctggtttac  120
gacacggagc cgccgcaccc agcgggtacg atggccttct ttcgccatag cacccaagcg  180
agtgaactgc cgccgggcat cgacacgcgc ggtctggaga gtctgcaact gagcggtagc  240
gaacgtatta cgagtgtgga gcaggtgcgc gccattcgtc aagcctgtgg cgacgccccg  300
ctggttgtgg ttgatctgcg tcaagaaagt catgcggtgg ccgatggtca cagtctgacc  360
tggcgcggcc cgatggactg gggtaatgtt ggtttgggta cagcagcagc aacagcaaga  420
gaagcagaac aactggagga actgcgccgt cagggtaatg ccgtggccac gcacgcggac  480
cacgttaaag gtaagagtga tgagccggcg ctgcgtccgc tggacacgac gctggcccgt  540
agtgagcaag agattgttga ggcggccggt gcggactatc gccgtatcgc cgttaccgat  600
catctgcgtc caagtcgcgg tgaggttgac cagttcattg atctggtgcg tggtctgccg  660
gatggtgcgg cctgcacgt gcattgtaat ggtggccgcg gccgtaccac gaccttcatg  720
gtgctgtacg atatgccgcg taatgcccgc gaagccggtg atcatgcgct catgcgcgac  780
caaagtcgcc tgggcatgga ctataaccgt tgcgcctatc gcccaccaga tgcctgtggt  840
ttccaggtta agttcagcga acgtacgctg cggtggttc gcaccagttg gcgcagtcca  900
atcaatccgc tgattccgcg tgtgagtccg atcgactgta gttaa                  945

SEQ ID NO: 160          moltype = DNA   length = 945
FEATURE                 Location/Qualifiers
source                  1..945
                        mol_type = genomic DNA
                        organism = Clostridium sp.
SEQUENCE: 160
atgaaaaaaa gcacggcggt tttcttcgcg ttcattctgg tgttcatcag cctgagtagc   60
acgacggtca gtctggatac cgccgccgtg gccgcgagtg acgaagttca gctggccctg  120
gatagcctga atgagagtac gccacgcaac tttcgcaaga cgagtacccc gatttatctg  180
acgaaaaatg agaaattcag tctgaaaggt ctggataagc tgaatatcag tggtagtcaa  240
cagttcagcg aaaaaaacct gccaatcctg ctggaggaaa ttggtaccag taaaccgatt  300
acgattgttg acctgcgtca ggagagccat ggttttatca atggcctgcc ggtgagttgg  360
aagaacctga ataatgatgt gaataaaggt ctgacgcgcg atgaggtgat tgaaaaggag  420
gccaatcaac tgagtagtat cccgctgaat agtccggtga cggtgtatcg cgcccccaaat  480
aatatcaaga ttccgacgga agttttaat gaagacgccc tggtgaccag taagaatctg  540
agctatatcc gtgtgccggt tacggatctg ggtctgccaa ccgacgatat ggtggactat  600
tttatcgaag ttttcaaaaa cctgccgaaa gatagttgtg acttttca ctgcaaagcc  660
ggcgttggtc gcacgacgac gttcatgatc atgtacgaca tgctgatcaa ttataaccaa  720
gttagtgcga ccgacattat cgaccgtcag ctgaagctgg ccaacttcga tgaggtgacg  780
atccgcgaat tctacacccc ggagcgctac aaattcctgc tgaacttcta taattattgt  840
aaggagaacg gtggcagttt caagatgagt tggagcacgt ggagtaagga gtacgacggc  900
ttcattagtc tgaataaaga cacgggttat ctgaaggtga gttaa                  945

SEQ ID NO: 161          moltype = DNA   length = 978
FEATURE                 Location/Qualifiers
source                  1..978
                        mol_type = genomic DNA
                        organism = Clostridium sp.
SEQUENCE: 161
atgaaacaga tgaaattac gctgaataat agtacgaact ataataccat cgaggataat   60
tttcgccatg gtcatcacgg ctggtatagt tatcgccacc cattcctgta tgaatattgt  120
taccatatca acgatgagat gattcaagaa ccatactata agagccgcag taataaactg  180
```

```
cacctggtga tcaacagcga caacgccaaa aaactgccag acaatttccg taacaccatc  240
gacctggcca acttcaagga taataaggtg atcaatctga acggtctggc gaatctgaac  300
gccagtgcga gcagtcagtt cagtgaaagt ggtctggcct tcgtgaaaca aagtattggt  360
cacgccatgc caatcattat cgtggacctg cgccaggaga gccacggctt cattaatggt  420
gttgcgatta gctgggcgga caaccataat aaggcgaata aaggtctgac gaaagaagcc  480
gtgctgaccg atgagaatac gcgtctgcac ggtatcctgc tgaataaacc gatttacatc  540
ggtgatatca ccctgattcc gaagaaactg gagaatgaga aaagcctggt gcagagttat  600
gatatgagct acatgcgcat tccagtgacg gacaacgaaa tgccgaataa cggcatggtg  660
gattattta tcaaattcgt gaatagcctg ctgccgaata cctggctgca ttttcactgt  720
aaggccggtc tgggtcgtac caccacgttc attgtgatgt atgatatgat gaaaaatgcc  780
aagaacgtga gtctgcaaga tatcatgaat cgtcaagttc tgctgggcgg taaaaatctg  840
ctgcgtgacg aacagctgct gatgaatcgc agtgagcaac gcgttaagct gattaaacgc  900
ttttaccgtt attgtgtgga gaataacgat aactttaaga ccacgtggag tcagtggatc  960
cgtcagcatc gcaattga                                                 978

SEQ ID NO: 162        moltype = DNA   length = 999
FEATURE               Location/Qualifiers
source                1..999
                      mol_type = genomic DNA
                      organism = Acidaminococcus sp.
SEQUENCE: 162
atgctgcgcg tgggcggtct gttttttcatt ggtggcaaaa tgctgaagaa ggtgccgttt  60
ctgctgatgc tgagtgcgag tctgatcgcc tttagtgcgc cactgccatg cgtgcgtgcg  120
aaagaagccc cgaagagtgt gccactggag gcgccattta gctacgaggg tgccctgtgg  180
cgcctggatg ccgagaacgc gccaggcctg ccacgcaatt atcgtacgtg tgatgacgcc  240
tatcgtgcca ttccaccgcg ctacgcgaaa gaagcgagta gtcgtatccc aagctgtaag  300
ggtctgagtg agctgcacat cagtggtagc agtcaatata gtgaaaaagg tctggacgcc  360
atcctggcca acctgcgcaa ccgcacccag ggcccgattg ttctggtgga tctgcgccaa  420
gagagccatg gtttgtgaa tggcatgcca gttagctggt atggtaagcg taattgggcc  480
aaccgcgaga agggtcactt cgccgtgctg gccgacgaag cccaacgtat ccatgcgctg  540
caaggccaag atgttacgct ggtgcgcctg aagacggata aacgtagtgc gagtaccatg  600
accgttgagg ccggccaggt tctgacggaa gcggagctgg ccgcccagaa aggtgttatg  660
tacgtgcgct ttaccgccac ggatcacctg tggccggacg ccggtgaaat tgaacgcttc  720
cgccgtttcg tgaagaccct gccaaaagac gcctggctgc atttccactg tgtggcgggt  780
gaaggtcgca cgacggcctt catgacgatg tatgacatgc tgaagaatcc ggacgtgccg  840
tatgaagaca ttgttctgcg ccaactgcgt atcggtggcg tttacacccc gtttctgggc  900
aaaggtctga gtacctggaa gaagccgtat taccgcgcca aaaaacgcgg cctggaggcc  960
ttctatcgta agctgcataa aacgcaagtg accgactga                          999

SEQ ID NO: 163        moltype = DNA   length = 999
FEATURE               Location/Qualifiers
source                1..999
                      mol_type = genomic DNA
                      organism = Anaerovibrio lipolyticus
SEQUENCE: 163
atgctgatga aaaaaaatcg tatcgagaag agtgcctgta gcatctttgc cgtggtttgt  60
agtctgctga ttatgctgat ggcgaccgcc caagccgccg aaaaacaaga agcgccgatc  120
tggcgcctgg atagcaagcc aggtgccgtt ctgccacgta gtctgcgctt catgacggac  180
gagttcccgc aagacctgaa tagcgtgcca agtcgcaagg gcatggacac gctgcgctgc  240
agtgcgagcc cgaatttag tggttttggc ctgagcatga ttcgcgataa aatctatgag  300
catgccggta aaaatgcggt tatctatatg gtggacctgc gtaaggaaag tcacggcttc  360
gtgaatggtg aattcgccgt tagtcattac tttaagaaaa atctgggcaa ccgcaatctg  420
gccagtgcgg ccgttccaca agccgaggaa aaagccctgc agagtattat gggtcaagag  480
atcacctttg tgccgctggg caagaccgac acgaaactgt tcacggccag cacggtgaag  540
gtggaacaaa ttgaaaccga ggaagcgatc acggcccgtc tgggtattca ctataagcgc  600
attccgattg ccgatcaatg tgcgccaagt gacgaagata tcgatgaatt tatgaacttc  660
tacaaaaatc tgccaagcaa tagttggctg cactttcact gccacgccgg ccacggtcgt  720
accaccacgt tcatggtgtt ttacgatatt ctgtgtaacc cagatgttgc cctggacgat  780
attgtggcgc gccaacatgc cctgggtggc acgaatctgt tcgccccggg taaaaagaac  840
aattggaagg gcgaggaaat ccgtaagcgc gcccagcaag tcgtaattt ttacgcgtac  900
gttcaagcca atcatcgcaa caagtatgcc caaccatata gccaatggat gaaagcccaa  960
aatagtcgcg tggacaatgc ccagaagagc aaaagttaa                          999

SEQ ID NO: 164        moltype = DNA   length = 1020
FEATURE               Location/Qualifiers
source                1..1020
                      mol_type = genomic DNA
                      organism = Cellulophaga sp.
SEQUENCE: 164
atgaacaagt acattaacta catcggcgtt atggtggtgg ttctggcctt tgcctgcaaa  60
gagaacagtc tgccagcgat tgcgccgaac gtgattacgg aaaagaccaa aaatgatacc  120
gacgatccgg cgatctgggt gaatctgaag aacgccgaga aagtatcgt gttcggtacc  180
gataaggaaa cggacggcgg tgtgtacgcg tttgacctga cggtaaaat tatcaagaat  240
aaaagtatta ccggtgttaa acgcccaaac aacgtgacgta ttgcctataa ttttcaaaatt  300
aacgacagca cgttcacgga tgttctggtg tttacggaac gcgaaaaaca acaaatccgt  360
atgttcagtg ttccggacat gatgccgctg acaatggcg gctttagcgt gttcaagaac  420
gaaaaaaatc tggagtacac cctgccgatg ggtgttggcc tgtataccag tagcgttgac  480
aacaccctgt atgccatcgt gggtcgcaag aatggtccga agacggcta tctgcatcag  540
tacaagctga gtacggacac gacgggcgtg gttcagagca ccctggtgcg caagttcggt  600
```

-continued

```
gttttttagtg gtaagaaaga aattgaggcc attgccgtgg atagtgaact gggctatgtg   660
tactatagcg acgagcagca tggtatccga aagtactatg cggaaccaac gaaaggcgat   720
aaggaaatca gttgtttcgg tggtgagctg tttctgagcg acatcgaagg tattgccatc   780
gcgaagcaag cgaagggtaa aggttatatt attgttagtg accaacaaaa gggtcaattt   840
aacatcttca gtcgcgacac gaataaattc gtgaaagccg tgaacctgag caccaccgag   900
acggatggct gtgaggtggt tacggttccg ctgaataacg tgtttaaaaa tggcctgttc   960
gtggccatga acgacgcgaa ggatttctac ttttatgatc tggccaaact gggtctgtga  1020
```

SEQ ID NO: 165          moltype = DNA  length = 1020
FEATURE                 Location/Qualifiers
source                  1..1020
                        mol_type = genomic DNA
                        organism = Bifidobacterium dentium
SEQUENCE: 165
```
atgctgatga gtacgcgcat gatgaaacgc attgttggta gtgtggcgtg tgtggcggcc   60
gcggccatgc tgatgccagg caccgtttgc ccagccctgg cgctggagag cgacggtcag  120
tactatagta gcaagcaacc atatgtggcg ccgagtgccg ccacggtggc cagttatagc  180
aaggccccag aaggttacga gccgatctat acggaaagta tggcccgtca tggcagtcgc  240
ggtctgagca gttacaaata tgacgcgctg ctgatgaaaa tggccgaagc cgcggagcgc  300
gacggtggtt tcaagagtga tgccattaaa accgagttca tgaagaacct gaatggtatc  360
acggcggcca atgtggaaaa tggctatggt atgctgaccg gccagggcgc ggatcaacat  420
tacggcattg gtgagcgcgc ctatcagcgc aaccaaagcc tgtttgacca agcggccgtg  480
gatggtggta cgatcagtta tcaaagtagt ggtgaggccc gtgccaccga aagtggtgaa  540
aatttcgaga agggtttcaa cgcggccagc ggcggtaagc tgacggacag tgtggttaaa  600
ccaacggatc cggcggacag cggcgatggc aaggactttc aaaagaatcc agacacgctg  660
tatttccaca aagtgcaaaa tccagacggt acggagaaaa tggccgggtac caaagcctat  720
gatattgcga atgattatca aaatttcatc agctggccaa cgatgcgcag tagtccggtg  780
ccgcgtcgcc caagtgccac gatgccgacg agcagtggtc cgcgtatgac gtgttgccgc  840
cgtagtagtc cgaccaatag tctgccgaac agtcgcaccg ccaatacgcg cggtaccacg  900
ccgccaatgg caccacgtag agttccacgt acagcaagac gtgcaccaac acgtccacgt  960
acaccaatgc gtgcagcaaa agcaccaaga cgtagtcgtg ccagtacgac gccacaatga  1020
```

SEQ ID NO: 166          moltype = DNA  length = 1035
FEATURE                 Location/Qualifiers
source                  1..1035
                        mol_type = genomic DNA
                        organism = Chryseobacterium sp.
SEQUENCE: 166
```
atgaagaaca ttcactacat cctggccctg agtgtgctgc cattcgttat caattgtacg   60
ggccaaaaag acctggccga gaagctgaaa ccggcggtga tcacggaaac cgttgtgcat  120
gacacggacg acccagccat ttggatcaac ccccaagacg cgacgaaaag cattatcatt  180
ggtaccgata aggataccga tggcggtctg tatgccttcg atctgaatgg caaaatcatc  240
aacaaggtta gtggcttgaa gcgtccgaac aatgttgatc tggagtatgg tttttatgctg  300
aacggtaaaa agacggacat cgcggccgtt acggagcgtg aaacgaataa agtgaagctg  360
tacaccctgc cggaactgaa agaggttggc gagattagcg tgttcgatgg tgaaagtgaa  420
cgcggcccga tgggtattag tctgtacaag aacccacaaa ccgaagagat tttcgccgtg  480
gttggtcgca aaagcggtcc agccgacggc tatctgtcgc aatatagct gattgaaaaa  540
gacggtatca ttacgggcga ggtggttcgt aaatttggca agtacagcgg tctgaaggag  600
atcgaaagca tcgcggttga cgacgaaatg ggctatattt attacagtga tgagcagttc  660
ggtgtgcaca agtattacgc cgacccggcg aagggtaatg aagaactgag tgttttttggt  720
aaaggtgatt tcaaaagcga cgtggaaggc atcagtattt atccgacgag tcaaggtaaa  780
ggctatatcc tggtgagtaa tcaacaaaat gacacgttta acgtttatct gcgtgaggat  840
caaagtaagg gtaaaatcgc cgaaatcccg gttagcaccc tggagagtga cggtagcgaa  900
gttaccaatg tgaatctggg tccaaagttc ccgaaaggtg tttttgtggc catgagtaat  960
ggccgcgtgt ttcattttta tgattggcgt atggtggaaa aggccatcac gagtgccgtg  1020
aaagccgtga agtga                                                   1035
```

SEQ ID NO: 167          moltype = DNA  length = 1044
FEATURE                 Location/Qualifiers
source                  1..1044
                        mol_type = genomic DNA
                        organism = Erythrobacter litoralis
SEQUENCE: 167
```
atgctgaaac cgtttcacgg tttcgcgctg attagtctgg gtatcgccgc ggcgtgcgcc   60
agtattcatg ttacgggtga tccagccgtg acggttaccg ccgtggcgga aaccgagccg  120
gtgggtacgg cgaacgagga cgccgccgat gacccggcga tctggcgcaa tccggccgat  180
ccggcgaaga gcctgatcgt tggtacggac aaaaaaggcc gtctgcacgt gtatgacctg  240
gccggccgcg agctgagttt tatgccggcg ccgggcctga ataatgtgga cctggttgaa  300
ctgccggatg gccgtgtgct ggccctgagc agtgaccagg gcgatctgga gaccgcgcat  360
gttagtgtgg cccgtctgga cccggacacc gccgccctga cgccgattgc gcgtatcgag  420
gtgggtccag gcgaaggtta cggtatttgt atgggcgagg ttgatggtga cggcagcttc  480
acggtgttca gtgcccgaa aaagggtatt gtttaccgca cggccctgca gtttgagggt  540
gaggaactga ttgacaagac ggagaccctg acgagtgtgc cgagtcaacc ggaaggttgc  600
atcgccgacc cacgtacggg cacgctgtat attggcgagg aggcggccgg tatctgggcc  660
atcgacatgc agaccggcga caaacgtctg gtgcgcgaag tggataaccg cctgctggtg  720
gccgacgtga aagtctggc gatcgcccca gaaggccgtg atggtggcta cctggttgcg  780
agtagtcagg gtgataacgc ctatgccgtt ttccgcctgc cgggtatgga gccagtgggt  840
cgctttcgta ttggtgcggg tgcgttcggc agtacggaag agacggacgg tatcgagctg  900
gatccgcgcg cctttggccc agcctttcca ggtggccctg tcgttgcgca agacggtatg  960
```

-continued

```
aatggtgcca gtgcccagaa cttcaaactg gtgcgctggg atgccgttct ggaggccctg   1020
gaagccgttc caccggcgcc gtaa                                          1044

SEQ ID NO: 168        moltype = DNA  length = 1053
FEATURE               Location/Qualifiers
source                1..1053
                      mol_type = genomic DNA
                      organism = unidentified
SEQUENCE: 168
atgcgcctga ccttcattgt ttgtgccagc atctgtctgc tgggctgcag tacaacacaa   60
cgtggtccag catgggcagg tggtgaaaca ccagttgcag ttgcagcatt ggcagaaacg   120
cgcgttgaca ccgatccagc ggtggacgcc gatgatccag cgctgtggag tgacgagagc   180
gatccaacgc gcgccgttat gtttggtacc gataagacgg acggtctgta cgttcatgac   240
ctggatggta gcgtgcgtca attcctggcg agtggcgcct tgaacaacgt ggatctgcgt   300
accggtttca gtgcggaagg tcgcgatgac tttgtgctgg tggccgcgac caacgatgag   360
cgtatgggca ttaatctgta tctgttcgat ccgcgcacgc tggagacccg cgactatggt   420
ttcatcgaaa cggacattgg tgagccatac ggtttctgta tgggtcgccg cagtgacggc   480
ttctatctga tcgccaacaa taagcaaggt gatattaaga tttggcgcct ggccaacggt   540
gcggagccgg gtgccgcgga aatggttcgt cagctgaagc tgccgagcca actggagggc   600
tgtgttgtgg acgatgaccg cgacgttctg tatgtgggcg aagaaaatgc cgccatctgg   660
cgcttcgatt ttgatccggc ggccagtcca accccaacca aagtggcgag cgttgatcgt   720
cagcgcatta cggacgatat cgagggtctg acgattatcg tgacggtcg ccaacgctat    780
ctgatcgcga gtagccaagg cgatgacacg ttcccggtgt tccgcattac cgaggaaggt   840
gagacgtacc tgggccgctt taccgttgtt gcccgcgatg acatcgatgg tgtgacgcac   900
acggacggtc tggacgcgtg gagtggccca attggccgct atccggaagg tgcgctggcc   960
atccatgatg ataacgagga gccgctggaa ggtcagcaaa actacaagat tgtggactgg   1020
cgcgaagtta aagccgcgct ggatctgcca taa                               1053

SEQ ID NO: 169        moltype = DNA  length = 1068
FEATURE               Location/Qualifiers
source                1..1068
                      mol_type = genomic DNA
                      organism = Devosia riboflavina
SEQUENCE: 169
atgatcgacc tgcgcccggc cctggccctg ctggccctga gtctgtgctg gacgggcacg   60
gccctggccc agccggaacc aatcttcgcg agtgtgagcg cgaccctgga gaccgagaat   120
gtggacatcg atccggacga cccggccatc tggatcaata cggccgatcc agcgcagagt   180
cgtgtgatcg gcacggacaa agatgttggt ctggtggttt ttgatctgga cggtaagatt   240
gtgcagcgcc tgagtgacgg tcgcctgaat aatgttgata tccgccaaga cgttaccgtg   300
ggcaacgaga cgctgagcct ggtggccgcg agtcgccgca atgatgacac cattgtttt    360
tacaccgtgg acgaaacggg taccctgacg aaagccacgc cgttcgcgtt tccaggtgcg   420
ccgcgcaaaa ttgacgacga tatctatggt attggcctgt atcatgacgc cgttgcccat   480
cgcctgtttg tgattgccag cttcaaaacg ggcgagatca tggtgggatc agtgacgagt   540
aacgccggtc aactgagcct ggcctttacg cgtgagctgg cggttccaac ccaaccagag   600
ggcgttgtgg ccgatgacga actgggcttc atttatgtgg gtgaggaaga tggtggtctg   660
tggcgttttg cggccgcgcc ggatgccgac gccagtggtc acctggtgga caaagtgggt   720
agtgcgtgtc tgccagagga cgacctggaa ggcctgaccg tggtgaaggg tgcggataat   780
agcagttaca ttctggccag cgcccagggc gtgaatcgtt atgtgctgta cgcgcgccaa   840
ccggatgccg acggtaatca gccatgttat ggcgcgttca acctggtgac gggtgccacc   900
gacccggtga gtgagacgga cggcctggat gttacgacca cggccctgag tgaccgtttt   960
ccgaaaggtc tgatggttgt gcaagatgac cgcaatgaag gttttaaccg taatttcaag   1020
ttcgttagtt gggccgacgt tatgcaggcc atgcaactga cggattga              1068

SEQ ID NO: 170        moltype = DNA  length = 1083
FEATURE               Location/Qualifiers
source                1..1083
                      mol_type = genomic DNA
                      organism = Bradyrhizobium sp.
SEQUENCE: 170
atgcgctgtg gcccaggtaa gccggttggt ctgagttatc agatgccagc cccggacagt   60
gacctgggtg cgcgtgcccc agccagcagt agcgtggaga gtcgcacgcc gttccgcatc   120
ccgccaacca cgatcccgaa aaaaatcagt gaccaaaacc cgccaaccct ggtgtatgat   180
atgatcgagc cgagcacgtt tcgtaccacg agtgacacca gcggcatgga gagttgtgat   240
ctgaccggtt ttgacggtct gagcctgagt ggcagtgaac aattcagtga acgtcaactg   300
gaggaactga ttaccctgac gcgcccgaaa cgtatcgtga tcattgacac ccgtcaggaa   360
tttcatggtt tcgcgaacgg cgagccgatt agctggtatg ccgccgacaa ttataattgg   420
ggtaacgttg aaaaaccagc cgagatcatt ccagcgaagg aaacgaaaaa gctggccaaa   480
ctgccgacca aattcccgtt tggtctgacg atcgaaagtg gtagcgtggt gaaaggtaag   540
gccagtagtg ccccgccaaa ggttctggat ttcggtaaag tgaagattga aaccgaggaa   600
gagctggtga aacgcaaggg cgtggcgtat ctgcgtatcc cgacccgga ccatgcccgc    660
ccaacggatg ccgaaatcga taagctggtt agtgaactgc gcaatctggc ccgcgcgggt   720
gacgtgcacc tgcattttca ctgtcgtggc ggtatcggcc gcacgaccct gctgatgacc   780
ctggccgata tgctgcataa tagtgacaag gtgcaatgcg cccacatcat tgaacgtcag   840
atcaaactga gccgtcagcga cgagttccca acgagcaaag cgctgaacaa ggttctgcgt   900
aatgagaaga gtgagctgat gaataccttt ttccaatacg ccaaagaaca gccgctggag   960
aaagccgatg cgatcagctg gaccgagtgg ctggccctga aggcgcatcg cgagcatcaa   1020
attctggaca cgagtagtgt tggtacacca ccaacagcac caccaggtca tcgtatgcca   1080
taa                                                                1083
```

-continued

```
SEQ ID NO: 171          moltype = DNA  length = 1089
FEATURE                 Location/Qualifiers
source                  1..1089
                        mol_type = genomic DNA
                        organism = Algoriphagus marincola
SEQUENCE: 171
atgcacaaaa agctgaatta ctttctgagt attttcacgc tgaccggtct ggccagttgt    60
caagagagta gcctgcagaa gggcgacctg ccagacgaaa aagttgagct gatcagccca   120
ctgcatatta gtgacagtgt gatccacgat acggacgacc cggcgatttg gatcaataaa   180
agtaatccaa gtcaaagtct gatcatcggt acggataaag atagcattgg cgccctgtat   240
gttttcgacc tgacgggtaa aaccatcgat agtctggtgc gtcgtgacat tcaacgtccg   300
aacaatgttg acatcggtta cggtctgatt cacggcaagg acaccattga tttcgcggtg   360
acgggtgagc gcctgacgag caaaattcgt tttttcagtc tgccagatat gaaggagctg   420
aacccaggtg gcctggaagt gtatcaaggt gaaacgggcg aggactatcg cgacctgatg   480
ggtatcgccc tgtatcagag tccgaaaagt ggcaaaacct atgtgatcgc gggtcgtaaa   540
aatggtccga cggatggcac ctacctgtgg caatatgagg ttaaaagcca agatggtaat   600
ctgagtctgg aactggtgcg taagtttggc aattttagtg gcaataaaga gattgaggcc   660
atcgcggtgg ataacgagct gggttatatt tattatagcg acgaaggcac cggtgttcgc   720
aagtactacg ccgagccaga catgggcaac gaagagctgg ccctgttcgc caccgagggt   780
tttacggatg accatgaggg tattagtatt tataaaacga gtgaaaccga aggttatctg   840
ctggttagcg accaaggtgc caatctgttc cacgtttttc cgcgcgaggg cagccaaagt   900
aatccacatc aaacacagtct gatcaccacg ctgccgctga gtggtgacgg tagcgacggt   960
aatgaagtta ccagcgccga tctgggcggt gagttcagtg aaggcctgtt cgtggccatg  1020
agcgacgaca aaacgttcca gatctacagc tggaaacagc tgaaaaaaca tatcaatcag  1080
aatcaatga                                                          1089

SEQ ID NO: 172          moltype = DNA  length = 1110
FEATURE                 Location/Qualifiers
source                  1..1110
                        mol_type = genomic DNA
                        organism = Bryobacter aggregatus
SEQUENCE: 172
atgaaaaaga accaaacctt tctgagtttc ttcctgctgg cggcctatgg tatcgcgcaa    60
aaagagagtc cacaaccgaa gctgcaatat gccgttatgc tgacgcgcca cggcgtgcgt   120
gccccactgg ccccgaatcg ttggctgcac ttctatagcg tgggtagttg gccgagctgg   180
ggcgttctgc caggccatct gacgccgcac ggtcgtcaaa tgatgaaact gatgggtgcg   240
tactatggcg aaaccttccg cgccgaaggt ctgctggccc gtaacggttg tgaagacagt   300
ggtcgcatct acgtgtggag tgatagtgac cagcgcacga cggaaagtgc gcgtgccctg   360
ctggagggca ttatcccagg ttgccgctat gcggttcaca gtggtcgtcc gggcatccca   420
gatccgctgc tgagtacgca aggtacggcc cgctttcgta gcgaggatcg tagtggcctg   480
cagccggcgc tggacaaaact gcatttcgtg ctgaagggtg cccgcgcgcg tagtaatctg   540
agtctgcgca cggccgccac gctggcggaa aacctgatgc tggagtacgc caatggcttt   600
gaaggtaatg agctgggctg gggtcgcctg agccaagaag tcgcaaga gatcctgacg   660
ctgcgcgccg cccaaccgcg caaagcggaa tatgcgcgta atctgtggct gcgcatccaa   720
accagtctgt gccaagccgc cacgggtgag agtattgacg gtagtattgg tccaaagaat   780
accgccctgc tgatcctgag cggtcacgac aaaaacctgg aaagcctggc cgcgctgctg   840
ggtctgaatt ggcaactggc cagctacccg aaaaactatg ccatccgggg cggtgcgctg   900
gtgttcacgc tgtggcgtca agacggtcgc ttccgtctgc gtagtcagta catcgcccaa   960
agcctggagc aactgcacaa tggcagtggt ggcaccccag tggtgattga cctgggtagc  1020
agtgacttca ccccaatcac gcgcccaccg catggtcatt tctgtgttgc cacgagtctg  1080
ctggttacga gtagtaaacg tcgtcgttga                                    1110

SEQ ID NO: 173          moltype = DNA  length = 1116
FEATURE                 Location/Qualifiers
source                  1..1116
                        mol_type = genomic DNA
                        organism = Asticcacaulis sp.
SEQUENCE: 173
atggacctga gcgtttttta tgtgggtttc acgaccgcga gtgccgtggt gatcaccgcc    60
accctgctga cgggctgtgc gagtctgcac agtgagctgg ttagtgatag taaactgatc   120
gccatcggta ccggtacgcc agtgctggca agtgcggaaa cggttgcggt gggcaccgcc   180
ggcctggacg cggccgatga tccggagatc tgggtggacc caatggataa gagtcgcagt   240
ctgattctgg cacggacaa aaaggccggc ctgtatgcct ataatctgga tggcagcgtg   300
cgtgattttg tggcgcacgg tccgctgaac aatgttgacc tgcgtacgat ctatggtgaa   360
accggcagtt tcaccctgat tgccgccagc gaccgtgcgc gcaatggtgc cgccctgttt   420
acgctgacgg acgatctgaa actgaaagtg gcgggcttcc tgccaatgac cacgagcgaa   480
gcctacggtc tgtgcatggg caccattgag gcgggtatta cgatcgtgat cattggtaaa   540
aacggtgatg ttgtgcaagc catctatagt gaaacggagg ccggtccgcg tggtgaaatt   600
gttcgtcgct ttaatgtggg tacccagagt gaggggttgtg ttatcgacga tcgcacgggc   660
gcgctgtaca tcgccgaaga ggcgaaaggt atttggcgct atggtgtgga accggcgacg   720
ggcagcaccc gtgtggagct gcaagccgcg ccgagtaata tcctggttcc agacgtggag   780
ggtctggcgc tgctggtgga tgaagacagt ggtctgagtt atctgattgc gagcagccag   840
ggcgatagtg ccttcgccgt ttggcaagtg gccggtgaga ccagtatcta caagggtcgt   900
ttcagcgttt tcccaggcaa tggtttcgac gcggtgaacg gtacggatgg tgttgcccgc   960
ctgggtggtc aagtgggccc gtatgccgaa ggtgtggttg tgatgcagga cgacagtgat  1020
atggagggca aaacgccaac cggtgcgcgc gcccgccaaa acttcaaaat tgttccgtgg  1080
atggatgtga aaaaggcgct gaatatcggc agttaa                            1116

SEQ ID NO: 174          moltype = DNA  length = 1128
```

```
FEATURE             Location/Qualifiers
source              1..1128
                    mol_type = genomic DNA
                    organism = unidentified
SEQUENCE: 174
atgggtagca attacacgat ttataagcgt ttcttcaata gtcgtaatgt taagcgtctg   60
ctgattgtgc tgctgtttat cggtattgtg catgtgagct tcacgtggta tctgtttcat  120
agtgagagta ccaatacgat caccccaacg atgaaactgc tggccgaagg tagcatcgac  180
caagacgata tgtgtatctg gattcacccg acggagagca gtaagagcgt gatcattacc  240
gcggacaaaa aggccgaaaa agtgttcgtg tacgatctgg agggcagtgt tctgcaagtg  300
ctgagcatgc caaagccagg caatatcgac gtgcgctatg gtttcccgct gggtggtaaa  360
aagattgaca tcgtggccta cctgcaacgc aaaaagggcc atcgtatcat tgtttttgcg  420
gtggagccga aaacgcacca gctgaagcgc gtggatgaca atagtatcct ggtgggtaaa  480
ggtgttggtg gtacgctgta tcatagccaa aaaaccgaca agttttactt catcaagacc  540
gccgagaaga agggtaaggg cggtatcgaa cagtttgagc tgttcgacga tggcaaaagt  600
aagattaccg gtcgtaaggt gcgccaatgg gatctggccg gttgcgaagg tgccgtggcc  660
gacgacgaga gttgtgcgct gtatatcagt caagaagata aaggtgtttg gaaagtgggt  720
gccgaaccag gcgagccaac gccgggtgaa ctgatcatta aaacctggaa gaatggcctg  780
atgtttgacg tggaaggcct gaccatctat aagagccaca cgcgcgaggg ttatctgatg  840
gtgagtaatc aaagtcgcaa tagcgtgaag gtgtatcaac tgggcaaaga ggacaagttc  900
ctgggtacct ttcatattga cggtgcgatc cacacggacg gcattgatat gaccaatgtg  960
tgcctgggta ttcgcttccc aaagggtctg ttcgtttgtc atacggacca agaaggcagt 1020
aatcgttgtc cggttctggt taccccgtgg gagagtatcc cccgtggtct gaacttcaag 1080
gtggatgtga gttggaatcc acgcagtgag acgtttaaac atttctga             1128

SEQ ID NO: 175          moltype = DNA  length = 1128
FEATURE             Location/Qualifiers
source              1..1128
                    mol_type = genomic DNA
                    organism = Bacillus licheniformis
SEQUENCE: 175
atgaattttt ataaaacgct ggccctgagc acgctggccg ccagtctgct gagtccaagc   60
tggagcattc tgccgcgcgc ggaagccagt gcctacaagg atttcagtgt taccgccgat  120
gccgagaccg aaccagtgga cacgccggat gacgccgacg atgacccggc gatttgggtg  180
catccgaaac agccagagaa aagtcgtctg atcacgacga acaagaaaag cggtctgatt  240
gtgtatgacc tgaatggcaa gcagctggcc gcctatccgt tcggtaagct gaacaatgtt  300
gacctgcgtt acaattttcc gctggatggt aaaaagattg acatcgccgg tgccagtaac  360
cgtagcgacg gtaaaaatac cgtggagatt tatgcctttg atggtgaaaa aaacaagctg  420
aagaatatcg tgaacccaca aaagccgatt cagaccgaca ttgaagaagt ttacggcttc  480
agcctgtatc atagtcaaaa aacgggtaaa ttttatgcca tggtgacggg taagaatggt  540
gagttcgagc aatatgaact gtttgacaat ggcaagggtc aagttgaagg caaaaaggtg  600
cgtagcttca agatgagtag ccaaaccgag ggtctggcgg ccgacgacga atacggcaaa  660
atgtacatcg ccgaggagga tgcggccatt tggagtttta gcgccgaacc gaatggtggt  720
gacaaaggta agattgttga tcgcgccggt ggcccacatc tgacggcgga cattgaaggt  780
ctgaccatct actatggcga ggacggtgag ggttacctga tcgcgagcag tcagggtgac  840
aaccgttacg ccatttatga tcgccgcggt aaaaatgact atgtggcgga ttttagtatc  900
gacgacggca agaaattga tggtaccagc gacacggatg gcattgacgt gattggcttc  960
ggtctgggta agaaatatcc gtatggtatc tttgtggccc aggatgcgaa gatccgcaag 1020
atggacagcc aaccaatccg tacgagtaag ctgagcccgg gcaagaaact gctgacccgt 1080
tggacgacga gtctgattag catgatccgc agtattccag agaactga             1128

SEQ ID NO: 176          moltype = DNA  length = 1146
FEATURE             Location/Qualifiers
source              1..1146
                    mol_type = genomic DNA
                    organism = Deinococcus proteolyticus
SEQUENCE: 176
atgagccgtt tcattcgccc gctgctgctg gttagtctgt gtgccggcgt gtgtgcctgt   60
gccccggttg ccacgggtcc agcgagtccg caagcccaga ccggtgccgg cgcgctgccg  120
gtggttgaag cccgtgccca aacggcgccg gtgggtgacc cggccgatag cacgatcca  180
gcgatctggg tggacgccgc cgagccagcg cgcagtttcg ttatcgccac ccgcaaggaa  240
ggtggtctga cggtgtttga tctgaaaggt caaacgattc aggacctgaa cccgggcggc  300
gttcgttaca ataacgtgga tctggtgcgc ggtttccgtc tgggtggcga aacggtggac  360
ctggcggtta ccagtgaccg caagggcgac cgcgtgagcg ccttcgttat cgaccacacg  420
acgcgcaccc tgcgcgaggt gaccagcccg gccacccac tgctgttcag tccgggtcca  480
ggtacggacg gtaagcgtac ggcctacggc ctggccgcct atcgtaccgc cgcgggtgag  540
gatcgcgtgc tggtgagtca aaatggcttc ccggtggtgg gtgaattcga actgtacgac  600
gatggtcaag gtgtgagtgt tcgtccggtt cgccgtctgg agctgccagc cgcgctgccg  660
ggtctgaccg tggacgatcc acaatttgag ggcatggtgg ttgacgccga acagggtgg  720
gcgttcctgg gtcaagaaca aattggcgtt tggcgctggg atctggatgg tcgtcgcagt  780
gtgttggttgg atcaagttgc accattggca ccacgtttgc atgcagatgt ggaaggtctg  840
acgctggtgc gtggcagtgg tggccgcggt tatctgctgg tgagcagtca gggcagtaat  900
gcctatgccg tttacagccg cgatggtaaa cgctatttcg gtagctttca ggtgacggcc  960
ggtagtgatc tggtgcaaga cagtgatggt gccgacggtg ttctgacccc actggtgac 1020
gattatccgg gcggtctgct ggtggtgcaa gatggtgagg ccggtgccgc cgaaggtcag 1080
acgaacttta aactggttag ttgggcggac gtggagcgtg ccctgaacct gccagatgtg 1140
cgttga                                                          1146

SEQ ID NO: 177          moltype = DNA  length = 1164
```

-continued

```
FEATURE            Location/Qualifiers
source             1..1164
                   mol_type = genomic DNA
                   organism = unidentified
SEQUENCE: 177
atgaacaaca atcaatacca actggataaa gttgtgatcc tgagtcgtca cggtattcgt    60
accccactgg agaacaccat tgccttcctg gagaagagca gtccgttcaa atggccgagc   120
tgggaccacg cgtatggtta tctgacgacc cgcggtggcg ttctggaaac gttttttcggc  180
cattatctga gtcaatggct ggaacagaag aatatcaaca ttgaaccgga gaatccggat   240
atctatgttt atgccaatag cctgcaacgc accgttgcca ccgcccagtt cctggtggcc   300
ggtgcgtttg ccggttacga cattccaatc caccataagt ataccattga aaaaatggat   360
ccgatcttcg acccaagtgt gaagaatgat agcctggaga tcaaacaaaa ggtgctgaaa   420
gagattgaag aggccgacca aaagcaaagt attttcaaaa acctggcccc ggcgtacaag   480
atcgtgagcg acattctgga ttatccacac agtcaactgt atgccgaact gaaatgcgac   540
ttcgcggaca tcccgtatga gctgcatttt gttaagaatg aagaaccaga gctgcgtggt   600
ccgctggcca tcggtatttg tgtggtggat gcgttcctgc tgcagtatta cagcgccttc   660
ccgaaggagc aaatcgcctg gggtcgcatc acgagtcagg aacaatggca caactgatg    720
cacattcgca accagtacat cgacctggtt ttccacagcc gcaccatcgc ccgccacaat   780
agtaaactgc tgatcaataa aattgacgac ctgctgcata acaaaacgca taaagttaat   840
ctgctggtgg gtcatgatag caccatcgcc gcgctgctgg gcgccctgga ctttgcggaa   900
tatcaactgc cgaatcaatt cgaaaatacc ccgattggtg gtatggttat tctgcaacgc   960
tatcgtaata aagccagtga aaagtacctg ttcaaagccg agtatgtgta ccaaagtttc  1020
gagcaactgt atacggcgca accactggac atcaatcatc caccgcagca ttaccagctg  1080
caactgaaga atgccgtggc gaacagtgac ggctttttatc agtggcagga catcgagacg  1140
cgtctgaagg aattcaaaaa atga                                          1164

SEQ ID NO: 178          moltype = DNA  length = 1167
FEATURE            Location/Qualifiers
source             1..1167
                   mol_type = genomic DNA
                   organism = Bacillus sp.
SEQUENCE: 178
atgctgaagg aaaattagcac ggccgcgctg atgacgagtg ttctgttcag tacggtgaac   60
agcgccgcgg atctggtggg tgagtttccg agtctgagtg ttcaagagaa acaacgccat   120
agtaagtttg tgaaagttga agccaaagag gaaaccgacg cggtggccaa tgcgggtgac   180
gccgcggatg acccagccat ttgggtgcac ccgcatgaca gtgaaaagag taaaatcatc   240
ggtaccaaca aggaagaagg tattagtgtg tatgacctga aaggtaagct gctgtacagc   300
tataattttg gcaagctgaa caacgttgac gttcgttatg gtttccccat tggcggtaag   360
aaaattgaca tcgcggccgc gagtaatcgt agcacgaacc ccattgatat cttcgcgatc   420
aatagtaaga cgggcgagct ggaaaatatt acgggtagcc cgatcaaaag taatatgaaa   480
gaggtgtatg gttttagtct gtatcacagt caaaaaacgg gcgtgtttta cgccctggtt   540
gtgggtaaag acggtacgtt cgaacaatac gagctgttcg acaacggtaa gggcaagatt   600
gagggtaaga aagttcgcga gctgaaactg agcagccaaa gcgaaggtat cgtggcggac   660
gacgagtatg gcacgatgta tattggtgag gaggatgttg ccatctggaa gttcaatgcc   720
gaaccagatg gtggtaagca accgatcacc aaggtggaca gtgcggacgg caatcatctg   780
acggccgaca ttgagggcct gacgatctac tacggcaaaa atggtacggg ttacctgatc   840
gcgagtagcc aaggcaacaa tacctatgcc gtgtacgacc gtaaaggtaa taatgaatat   900
atcggtaact tgcgatcgt tgacggtaaa aacaccgacg gcaccagtga taccgacggc    960
attgacgtga tgagcttcgg tctgggtaag aaatatccaa atggtatttt cctggcgcag  1020
gatggcgaga acatcgagcg cggcaagatc gtgaatcaga actttaagat ggtggactgg  1080
aaaaagattg ccaaaggttt tgatagtaag ctgcaaattg aaaataatgt ggatccacgt  1140
aaactgaaat tccgccagaa tagttga                                      1167

SEQ ID NO: 179          moltype = DNA  length = 1176
FEATURE            Location/Qualifiers
source             1..1176
                   mol_type = genomic DNA
                   organism = Saccharicrinis fermentans
SEQUENCE: 179
atgcagttta ttaatctgac cacgctgtttt atcgcggcgg ccagtatcct gagtagctgt   60
cagccaaagg gtaaccagaa taataatagt gaagcggaac gcgataatac ggccattctg   120
gagaaaaaca aagaggcccg cgatgatagc ctgaaactga ccgaggcgta tgccctgcag  180
gcgcagttca gtaacattgt tagcgccgac tatgaaacga cgccagtgaa gagtaatctg   240
ggtgatgacg cggccgatga tccggcgatc tggattaaca aaatccatcc agaaaaaagt  300
atgatcattg gcacgaataa aaaagccggc ctgaacgttt atgacctgca aggcaatgag   360
ctgcagttta tcccgatcgg taagatgaat aatgccgatg tgagctataa cttcgcctac   420
aaaggccaac aggtggatct gctggcgggt agtaaccgta ccagtcaaag cattgacgtt   480
ctgctgatcg atggcgccaa tcaaaagatt atcgagaaac cactgtgtag tatcccaagt   540
agtgtggatg acgtgtatgg tctgtgcatg tacttcgatg ccgtggccaa taagcactat   600
gtgttcgtga atggcaaaaa tggtaagatt gaacagtggc tgctgaaaaa tgacaacgat   660
agtatcaagg gtgagctggc ccgcagcttt tgggttagta gccaaccaga gggtatggtg   720
gttgaccatg tgacgaatac gctgttcgtt ggcgttgagg aagatgcgat ttataagttc   780
aaagcccaag cccaggccga cacgagcagt attcgtctga ccgccagttg taacgcgaat   840
aacgcccaca ttagctacga tattgaaggt ctgacgatcc atcgcatcg tgatacgaaa    900
ggttatctgc tggcgagcat tcaaggtaat tttagttatg cgattttcga cctgagtgaa   960
aagaataatt atatcaccag ttttattatt aaagacggtg tgtttgacgg tgtggaggag  1020
accgacggca ttgacgccaa tgccagcctg atgggcccga gtcccaaa aggtatgctg    1080
gtggttcaag acggtttaa caaggacaaa aaggagaatc agaatcagaa cttcaagatc  1140
attagttttg aacgcatcct gcagtttctg cagtaa                            1176
```

-continued

```
SEQ ID NO: 180          moltype = DNA  length = 1212
FEATURE                 Location/Qualifiers
source                  1..1212
                        mol_type = genomic DNA
                        organism = Asticcacaulis benevestitus
SEQUENCE: 180
atgacgccga gtcgcattct gaccttcgcg accctgtttg cgtgcctggc cgttgtgacg    60
ccatgtagta cggcgagtgc caaagaaaat acgttcacgc tggaacgtgt ggttattctg    120
atgcgccacg gtattaaacg tccgaataat gacccgccgc tgccgaagcg cttcacggat    180
caggcgtggc cagtttggag cgtgccgcca gccggtctga cgccgcatgg cgaacaagcg    240
attgcccgca tcgccgactt cgatcgcctg acgtacgcgg gcctgctggg tagtgactgt    300
ccgccagccg gcgcggttcg cgtgatcgcc gacaccgacc aacgcacgat ccgcacggcc    360
gaagtgtatg cgagcacggt tttcaagggc tgtgacgtgc gtgttgaaca tgcgggtgaa    420
ggccatgccg acgcccattt tagtccgttc aacgaggatg tggccagtcc gccactggac    480
cgcaaagcct ttatggatga ggccctgacg agtggtggta tggccgccat cgacaaagcc    540
caccatgtgg attatgccct gctgagtgaa gtgctgaatc tgaaggacct gccgggttgt    600
cagatcgata aggtgtgcag tctgagcgac atgccaagtg ttctggatgt tagtggccgc    660
gatccgaagg tgagtggtgc gctgaaaacg gccagcagtc tgagtcaaat cctgatgctg    720
gagtacgcca acggtttccc gatggatgag gttggctggg gcaaagtgag cgagagccag    780
attaccgccc tgagtgccct gcacgcggag gaattccgtc tgatcgcgcg tccaaaagcc    840
gttgccacgt acgcgagcgg tggtctgctg aaggacattg aggcggccct gttcggtccg    900
gacgcgagtc catataccct gctggtgggt catgacggca atatcgccta tgttggtggt    960
gcgctgggcc tgcactggca agcccaaggt ttcgcggccg acgacccgcc accgggtggt    1020
gccctgattt ttgaactgtg gcgtgatggt gccggcgagg cctttgttcg cgtgcgtttt    1080
cgtagcagta gcctggaggg tatgcgtaac ctgacgcacc tgaaacgcgc cgccagtacg    1140
cgcattccaa tgccgctgtg tgacgtgaag gccgaatgta gcgccgcgac cttcaaagcc    1200
ctgatcccgt ga                                                       1212

SEQ ID NO: 181          moltype = DNA  length = 1218
FEATURE                 Location/Qualifiers
source                  1..1218
                        mol_type = genomic DNA
                        organism = Amycolatopsis orientalis
SEQUENCE: 181
atgcgtatcg ccgcgctgct gccactgctg ctggccgcca gcctgctgac gggcgttccg    60
gcggaagcca gtcaaaatcc gagcccagtg cccaaaccc gtgccttcgt tgacgacgcc    120
ggcgcggacc cagcgaatgc cgatgccgat gacccggcga tttgggtgca tccagagaat    180
ccgagtgcca gtgtggtgct gggtacgctg aaagaggtg gcctggccgc gtttgatctg    240
aaggcccgcc agctgcagca tctggccggtg ccagccggtg gccgtttta ataacgtggac    300
gttgtgggtg acctggcggt tgtgagtgac cgtggtcgcg accgcgtgcg tgtgtatcgc    360
attgatccgc ccggtgccgc cgccggtagt cgcgtgctgc gtgatgttac ggatccagcc    420
gcggccccgg tgttcagcgc cagtgagagt gaggtggacg agcaacgcac ggcctatggc    480
ctggccgccg tcgtgatccg cgcaccggt acgcgttggg tggccgttac gcgtcgtcat    540
gagaccgtg tggccctgct gcgcctggtg gacaaaccgg acggcacggt tggtaccgcc    600
ccgatcggta ccatcgatct gccggcgagc ttccgcctgc caaacggccg tacgtggagt    660
ccatggcggtg aaccagatga gcgcccgcag ctggagggta gtgttctgga cgtggggtcac    720
cgtgtgctgt atacggccca agaagatgtg ggtatctggc gtattccgct gggcgaggag    780
ggttttggtc gcccagcgct gattgataaa gtgcgtagtt tcggtgtgcc gcaacgcttc    840
gacgaagcca cggaggagtg cgttgcggac ggtccagacc cgggtttgg cggtaaatgg    900
ctgacggcgg atgccgaggg tctgacgctg gcggacggca agctgctggc cagtagtcaa    960
ggcgatagtc gcttcgtggt gtacgatcgc gcgggtaccc cgcgtcgtga cttccgcatc    1020
gtggccggtc gtggtaccga tagcgttgag catagtgacg gcgcggccat cacgacccgc    1080
agcctgggtc cgctgtttcc acatggtctg ctggtggttc acgacggcga acgtcgcccg    1140
gccgccacgg gtccaagtgg tgaggagctg gccacgaccg gtttcgcgtt cgtgcgcctg    1200
gaggcggtgg tgcgttaa                                                 1218

SEQ ID NO: 182          moltype = DNA  length = 1227
FEATURE                 Location/Qualifiers
source                  1..1227
                        mol_type = genomic DNA
                        organism = Asticcacaulis benevestitus
SEQUENCE: 182
atgacgctga acattggct gcgcttcgcc ctgacgttca gcggtgcgtg cctgctggcc    60
atccaggcga gtgcccaacc aaccaaagtt gaacgtgtgg ttatgctgat gcgccacggc    120
gtgcgcagtc cgattacggg tgaagcgccg ctggataccc aaaccggtgc cccgtggccg    180
gtttggagtg tgccaccgga gacgattacg ccgcacggcg cggaggccct gaaggccctg    240
ggcaatgtgg atcgcgcgtg gctgagcgcc cgtggtatcc tgccagccaa agcgtgtccg    300
gacctggcca agaccattgt gtggacgaat accagtccac gtacgatcgc cacgggtcag    360
gcgtatgttc aaggtctggc gccgggttgt gccctgcatg tgggccacct gccagaagac    420
caaattgacc cgctgttcga gccgacccgc gcgccaccgc catggttcga cgcccagcgt    480
gccgttacga gtatcaatgc ctacacgggc ggtatgccag ttctggtgca gcgccatgac    540
gccacgctgg ccaactgga acacgtgctg gactgtggtg ccagtccctg tagtccacaa    600
cgtgcccagc gcctggcggt gacggccgat aatcgtgccg tggtgtttga gggtccagtg    660
cgtgacgcga gtggtaccgc cgaagttctg atgctggagt acctggaagg cttcccactg    720
aaggaggttg gttggggtcg cgccaacccg gcgacgctga agaccgtggg tgaagttcat    780
gccgcgctgt ttgacgtgtt cagccgtccg ccgtatatga tggcctttca gacggaaccg    840
accgcccgtc gcattatcga cgattttagt cgcccagacg ccccagattt cgacatgctg    900
gttggtcacg atacgaatgt ggcgggccct gccgcgctgc tgggcgttac cgtggaagcg    960
```

```
ccgggttttg ccgttaatga cccgagcccg ggtggtgccc tggtgctggc gctgattcgt 1020
gatgcccaag gtcgtgcgtt cgtgcgcgtg tattaccgta gtcaaagcgc ggacgatatc 1080
cgtgccgcgc gcgatcatgc gacgtggaag agtctgacga tgaacgcctg taagcaaggc 1140
ccacaacaca tgtgtccgct gccggatttc gttgccctgc tgaaagcagg tacagcagaa 1200
gcacgtgcac cattggttgc aagataa                                     1227
```

SEQ ID NO: 183          moltype = DNA  length = 1272
FEATURE                 Location/Qualifiers
source                  1..1272
                        mol_type = genomic DNA
                        organism = unidentified
SEQUENCE: 183

```
atgctgttcc gctttgtgct gccggcggtt ctgctgctgc cggcgttctg cagctttgcg 60
cagacgccga ccgatgatgt gcgcgccgtt gtgattgtgg cggcgccatg cgttcgtgcc 120
ccaattgaaa atgaaacgcg cagtagcgtg ttcaacgccc aacgttggcc ggcctggccg 180
agtgccccag gtgacctgac cccgcatggc atcgccgccc tgaaacgcat gggtgagttc 240
tatcgtcaac gctacgccac cctgctgcat gactgcaata gcgttgccgt ggaaagtacg 300
aataccagtc gcacgatcgg cagtgccaaa gcggtgatga gcgttgttgt gccagactgt 360
gacgttcgcg ttatggccga tctgaccgcc gacccgccga gtatcgataa ggccaagctg 420
gccgacgcca cgcacggtcg catggcggat caaccagagt ggttcaccca tgcgttcgcc 480
cgcccgctgg aagaaatgca cgacgtgctg gcgaagtgcg ccggttgtaa acaggttcca 540
gactttcgca cgagtatgct ggacccaagt gcccacagtg aaaatatgat gcaagcccaa 600
ggcgagaagg ccggtgcgct ggtgccgcgt gacccacgca aagaaaatgc cgccgccctg 660
ggcgccgatt ttagcgagaa cttcctgctg caatatgcgg aaggtatgcc gatggaccaa 720
gtgggttggg gtcgtgtgga tcgtgcccgc ctggacgatc tgatggaaat gaatacccgt 780
tatcacgact ttattctgcg cacgccgtac tacgcgcaac aagccgccgg tgcgatggcc 840
cagaagatta gtgactggct gagtatggcc gccattctga atatcccagt gcgtccaggc 900
cgcccggatg ttccggccgg tggtcgtgag agtgtgctgt atctgagcgt gcacgacgcg 960
aacctgacct ggctgggtgg tctgctgcgc atcgcctggc tggttagcga cgaaacgctg 1020
aatgccaccc cgccggggcag tgcgctggtg ttcgagccgg atcataatcg ccaaagtaat 1080
gccgatacgg ttcaagtgtt ctttattgcc cagacgctgg accagatccg taacctgacc 1140
gatctgaccc gtgcggagaa gccaagtatc agcccaatct atgtgccagg ttgtagtggc 1200
ccgggtccgg gctacgcctg tagtatggaa gccttcgttc gtgtgaccaa ggaggcgacg 1260
aaggtgccgt ga                                                     1272
```

SEQ ID NO: 184          moltype = DNA  length = 1281
FEATURE                 Location/Qualifiers
source                  1..1281
                        mol_type = genomic DNA
                        organism = Bacteroides sp.
SEQUENCE: 184

```
atggccgaaa acccactgga tgagattcgt cgcgacccgg aacgcgcggg cggtgtttac 60
tacgtgacgg atctgagcca tccggtgacc ccagcgccaa aaggttatac gccattctac 120
atcaatggtt atttccgtca cggcgcgcgt cagatcgacg atgaggtgac ctatccagcc 180
atctatggcg tgctggagaa agcccatgcg acgaacaatc tgaccgactt tggtaaagcc 240
ctgtacgaac gtctggaacc gtttaaaaaa aatgtgttct acaaggaggg tgatctgacg 300
cagattggtt atcgccagac ccgtgaaatc ggccgccgta tggtgcagaa ttatccagag 360
gtgtttgaag gccatccata tctgaaaacg aatgcgacga atgttctgcg tgtggccgcc 420
acgatgcaaa gtgttaacag tggtatcctg agtctgcgtc caggtctgga atgggcggaa 480
atcgacaata gccgcagttt cctgacgacc ctgaatccgt atggcaatgt gtgtccgggt 540
cgtagtccgc tggacaagta tatcctgggt aaggagaact gctggtacaa gaaataccgt 600
agctatatcg acgaaaaact ggatgttgat gcgtttttcc gccgtctgtt cattgatgtg 660
acgcaggttg agagcgagta tgacaagtac gatctgatcc accgcttttg gctgatggcc 720
agtctgatgc aatgtctgga ccgccaggtt ccaatttggg atatcttcac ggaagaagag 780
atcctggtgt gggcggagat cgagaattat aaatacttcg cccaaaaggg tccggagcca 840
gttagtcatg gccgtagctg gggcctggcg agtcgcacgc tgcgtcacct gctggacgaa 900
agtgcggagg acctggttcg caaacgccat ggtattaacc tgaattttgg tcacgacggt 960
gtgctgatgg ccatcctgac gaacctgcag gcgggtacct gggcccgcga agcgagcaat 1020
agtaaggaag ccctgcaaag ctggaaatac tgggacatcc caatgggcgc caatctgcaa 1080
atgatcttct atcaaagtga gggtaatcca gatgttctgg tgaagttcat gctgaatgag 1140
aaagatctgc gtctgccgct ggaggccgtt gaggcgagct attacaaatg gaatgaggtg 1200
tacaagttct acatcgagca ctgcgacaaa gtggagaaaa gtctggccga aacgctgaaa 1260
ctgagttatg aggatttttg a                                           1281
```

SEQ ID NO: 185          moltype = DNA  length = 1299
FEATURE                 Location/Qualifiers
source                  1..1299
                        mol_type = genomic DNA
                        organism = Barnesiella intestinihominis
SEQUENCE: 185

```
atgaagaagc gtacgctgac cgccggtacg attctgctgt gcctgagtgc gatcagcttt 60
ggtcagaaca gtattaaaga cttcctgcac caaaatccac agttttttcgg tagtacggcc 120
agtgtgtact attgtaatga tacgacggac accccggccc caaaggattt tatcccgttt 180
cacatcgacc acattgcccg ccacggtagt cgtacgcacg atagtaaaag tatggtgcca 240
aacctgtata aactgatgaa caaagccgac agcctgaatc tgctgacgcg cgaaggcaag 300
ctgctgcgta accaaattga caccatctac catctgatga tcaccgctg gggtgacctg 360
acgccgctgg gcgcccgcca acaccgcgat atggcccgtc gcatgtacca tcgtttccgt 420
ccagccttta ccccgcagga cggtaaagtt acgctggtgg cgcaaagtac gacggttcca 480
cgcagcatgg ccagtatggc ggcgtttgtt gccgagatgc gtggctatac cccgacggcg 540
```

```
gaattcagca tggacccaag taacggctat gataataccc tgcgcttttt caaaggtaaa   600
gagtaccaac aatatctgag caagggcagc tggaaaaaga tcctgcgtgc ctatcaagag   660
aaacacacgc caacccgcct gatcgaccgt atcttcaaaa aaggttggga acaaatcatc   720
ccagatccga tcacctttat gacgcacctg tatgcgctga cgattatcct gccgaatacg   780
gactatgaca ttagtctgta tccgtggttt acggaggagg aaaagtttga tctgtggagc   840
gccaacaatc tgagtcagta tctgcgcaaa gcgaatagca tcccgggtaa gggtctgcca   900
gtggccattg cgaagccact gctgaaagat atgctggcca ccagtcaagc ggccattgac   960
ggtaacggtg ttgaggccaa tctgcgcttc gcgcacggcg aaaatacgat cccgctgctg   1020
gccctgctgg gtattgagaa cgccgccgtt gtggaagccg acccggagaa ggttacggaa   1080
gtgtggcaag actttaaata caatccgatg gccacgaata tccaatggat tctgtataag   1140
aacacggacg gcaagatcct ggtgaaagtt ctgtttaatg agcaggaaac caagctgcca   1200
attgatagtg agtatgcccc gtattacgat tggaagctgt tccaaaaata ttgcgaaaaa   1260
cagatggcca agtatccaga cacgacccca gccctgtga                         1299
```

```
SEQ ID NO: 186          moltype = DNA  length = 1302
FEATURE                 Location/Qualifiers
source                  1..1302
                        mol_type = genomic DNA
                        organism = Endozoicomonas elysicola
```

```
SEQUENCE: 186
atgaaactgc aaacgctgct gggtcattgt ctgaagaagg ttatggcctt cgactactgt   60
aataacagcc tgaaaagtta tctgatgcac ggccgtacca gtggttgctt tcatatttgt   120
agtctgccag aaagtggttt taaaaagctg ttcctgatct ttcacaccgt gttcgccatg   180
tgcttcctga gtgtgggcgt tgacgcgacc ggtattggtt tcgagatgga aacgccggcc   240
gattatctga tcagtctggt gcgccatggc gaccgcagtc cgcgtgacct gggtgatatg   300
gcgcagtact ggccgatggg tccaggccaa ctgaccgccg gtggtctgga gcaggagtat   360
ctgctgggta aaaagatccg tcaacattac tttagcgaga gtctgccaga cagttggagt   420
ccgaaaatta gtcaacacta tgccaagggt ctggatcgca cgatccaaag tgccagtgcc   480
ctgctgcaag gtgtttaccc aggtcagccg cgtaacacgg cctgccggg tggcatccaa   540
gtgccaccgg tttatgcgag tccgctggcc agtgacgacc tgttcagtgc ccaacgcctg   600
tgtccgggtt acctgcatcg tgtgcaagcg ctggagaaga gtgccgactg gctgcgcaaa   660
aaagaacagt atcgcgatca actgagcagt tggtttgagc tgagtgaggg tagtggcgcg   720
ggtgatctgt atagcctgat tccgctgatc gaccagatca gtattcatcg tatgcatcgc   780
cgtccgatgc caaaaggtat cacgattcaa gaagccatcg aactggagga actgctgaat   840
tgggttgtga gtcgtatcat tgccaattat gaaattgccc agctgattgg cgcccactg   900
gcgaaagcca tgattcgcga tttcaagcgt gttcagcagt gtctggagga taaaggcagc   960
tgcaatagtt gtcaacgttg gacgctgtat agtgccagtg acagtaatct gctggccatc   1020
atgacgatgc tgggtgcccc gagtgaccgt attgtggatt atgccaccca ctttggtgtg   1080
caactgaatt ggaatgaagg ccgcccagag attgcgctga gtctgaacca tgagccgttc   1140
agtgtgccgg gttgtgttgg tcactgtagt ctggaccagt ggctggtgct gctggaacaa   1200
agtctgccgg acgactggga ttatctgtgc gcccgcgacc gtggcggttt tgccccatat   1260
ccggagccgt atgttccaag cggcagtgtg gccagccgct aa                     1302
```

```
SEQ ID NO: 187          moltype = DNA  length = 1323
FEATURE                 Location/Qualifiers
source                  1..1323
                        mol_type = genomic DNA
                        organism = Asaia astilbes
```

```
SEQUENCE: 187
atgctgatga ttggtagccc agtgaatgcc ctggccgccc tgtggggctt tgcgctgagt   60
agtttgttgt tgtgtggtgt tgcaacacca gcacgtgcag ttccattgag tgcagcacca   120
ccaagtgcag atgcagttct ggagcgcgtt gtgctggttg cccgccacgg catccgtagt   180
ccgacgcacg acccagccggc cctggcgcat gaaaccggta tcgcctggcc ggaatgggccg   240
gttagtccag tcaactgac ggagcatggt cgcgccacgc tgagtgttat gatgcgcgat   300
attggtcgtc actatgatct gggttgtagt acccacaaag agagttgtct gacgcaaacg   360
cgcccggtga tctgggccga cagtgccgac gaccgcacgc gcgaaagtgg tgagattatg   420
gccgcgagtc tggccccaga cctgcacctg gtgagtcgca gtctgggtgc caaagtgaag   480
gacccgctgt tcggcggtcc gccacaagat tttttcgttc gtgaagccaa gcgtctgtat   540
aaagacgccc tgacgcgcca gaaagatgac atgcgcagtc gtccggaaag tgttaaggcc   600
ggtctggcgg ccatgcaact gctgctggcc ccacaaggct gtgtgaaaga tgacggtcca   660
tgcctgagtg gtccgatcac cgttacgagc aagaatggca aaccggtgct ggagggcggt   720
ccagtgctgg gtgccagcct ggccgagaac ctgctgctgc tgcatgttca aggtctggat   780
cacaaaaaag ccggctggac cacggccgatc gaccccggcgt ttctgacgcg cgccctggcc   840
gtgcacgact acctgagtga cctgacgcgt aaacgcggta agctggtgga agaaaagagt   900
cgtgcgctgg ccggcgttat cgacgccttc ctgcagggtc gcgatgcgca actgccaaat   960
ggcgatagca tcggtccgca aacccgtttt ctggcgtttg cgggtcacga cacgacgctg   1020
gacgccctgg ccgcgcgtta tggtctgagc tggagtttca aagatcagcc gaccgaacaa   1080
ctgcgcacgc gcgttggct gagccgtgac ggcgagagtc aagccgcccg tagttttatc   1140
gcgctgagtt ttagtaccaa tccgtggctg cactgtctga aggaaggtgg tagtatgaag   1200
ccgatggaag gtttccgccc atggtgccgc agtcgcgccg agcgtgcggg taatagccgc   1260
ctgagttgtc gtcgcgaggg catgatgcgc tgcacgcaac tgagtagttg gcgcagtcgc   1320
tga                                                                1323
```

```
SEQ ID NO: 188          moltype = DNA  length = 1323
FEATURE                 Location/Qualifiers
source                  1..1323
                        mol_type = genomic DNA
                        organism = Alistipes timonensis
```

```
SEQUENCE: 188
atgaaacgcc cactgctgat tctgagtgcg tgtctgtgtg cgctggccgc ggccgttagc    60
tgcagcagtg gcctgcgcac cgccgacggt gagagcgtgc cggatcgtgt tatgggtgtg   120
tatttgccgt atccggagac cgtggcgcca agtccgggtg ccccagaggg ttacgagacc   180
ttttatatca gtcactatgg tcgccatggc agtcgctatc tgtctgatga cagccaatat   240
gcgttcgtgc gtgacgttct gagtcgtgcc gccgcggatg gtaaactgac gccaagcggc   300
cagaaagccc tggcggactt tctggaggcc tatccgcagt ttgagggtcg cgccggtatg   360
ctgacccgca ttggtgcggc ccaacaccgt gccatcgccc gccgtatggc cgaacgccat   420
ccaagtgcct tcgccccgga agcggccgtg cgtgccagta cgagtgccac ggcccgcacg   480
caggagagca tggaggcctt ctgtgcggcc ctgcaaacgt gtcgtccaag tctgcgtatt   540
acgtgcgccg aagacgccgc cctgaacccg tacagtgcgg gcagcggtat tccgacggag   600
tacgacctgc gtgtgaaaag tccagaagcc gagtggcgtc cagacttcga aacgttctgt   660
cgccagcaaa tcgatgccga gcgttttgcc gcccgcatct ttacggacac ggattatgcc   720
gcgggcctgt gtgacctgac ggatctggaa cgtggtgcct tctacctggc ggttcatttt   780
cgcggttgcg gtattgcggc cgattggctg cgtctgttca cgctggacga gctgtgtacg   840
ctggcggcct gtgacgccta tacgtttttac atggaaaaag gtccagccgc ggaaacgagc   900
gatcgtacct gggccctgag tgcccacatc ctggacaaaa tgctgaccga cgccgagcaa   960
gatattgcgg acggtacggc cgccaacctg cgcttcggtc atgacggctg tatcatggcg  1020
ctgctgaccc tgatgggcgc ggatggttgg accgccacgg cggccaccca agaggaaatt  1080
gcgcgcgcct gggacgttag tcaaattccg atggcctgca atctgcagtg gatcttttat  1140
cgtccggtga gcggtgaggg tgagccactg gttcgcacgc tgctgaatga gcgtccactg  1200
cgtctgccgg tgaccgaccc ggaaggtatg tgtgcgtgga gtgatctgaa acgctatctg  1260
gcggaacgct gcgacacggc cttcgccgtg ctgaacaagg accgcacgcc aaataacctg  1320
tga                                                                1323

SEQ ID NO: 189            moltype = DNA  length = 1329
FEATURE                   Location/Qualifiers
source                    1..1329
                          mol_type = genomic DNA
                          organism = unidentified
SEQUENCE: 189
atgaaactgc tgaacaaaac gaccttcctg atcggcctgg gtctggtttt ccagacgatg    60
acgattagtg cccaaaccct gacggaccgc gtgtatgaag acccgacgac cagcgcgaat   120
atctaccatg tgtataaaca acgtgaaggc aaactgacgc cagccccaaa aggttaccag   180
ccgtttttata ttagtcacta cggccgccac ggtagccgtt atctgacggg tgattactac   240
ttccgcccgg ccatggccat gctggaggcg gagaaagaga aaggcaatct gacggaggtg   300
ggtgagaacc tgtatagtga cattaagaag ctggccgccg cgcatgaagg catgtacggt   360
gagctgagtc cgcgtggtgc ccgcgagcac cgcgccatta tgtgccgtat gtataatcgc   420
ttcacgaagg ttttcaaaag taaaacgcgc aacaaagtga attgtatcag tagcgttgtt   480
ccacgctgca tcattagtat ggccaatttt accacggccc tgaacgataa tcgtccggaa   540
ctggagttca gttacaccac gggtgacaag tactttgagc tgctggccca caactacgat   600
acggacgaga tctacaaaac gattggccat attaccgata gcctgcgcaa ggccacgtgt   660
cactatgaca aattctatgg taagattttt aagaatccaa gcccggccgt ggatagtatg   720
aaaagtccgt acagcctgat cggtagtgtt tatagtagcg cgtgtatctg cgagtgcctg   780
gacttcctga acgtggatct gttcaaatat ttcgacaagg acgaactggc ccaacaggcc   840
gtggttcgta taaccgcgt ttacggtgat ctgggtaata gcattgaatg cggtgatgtg    900
gttgccgcca gtgcccgctt tctgctgcaa gatttcgtgg acaaggccga tgcggccctg   960
caaaatggca gcgacgtggc ggccgatctg cgttttggcc atgacagtgg tattcaacca  1020
ttcttctgta tcctgggcat tgagggccac gacaaacaat tgcatattgc ggacgccgat  1080
aagtgttggt ttagcgatct gaccgtgtgt atgggtacca atctgcaaat gatcttctac  1140
aaaaacaaaa agggccaagt gctggttaaa ctgctgtata atgaagccga ggccatgatc  1200
ccggcggtgc aggcctacag cggtccgtac tatcgctgtg aagacctgcg tagctacttt  1260
gtggatcgta ttgccgccgc caaagccttc gccgccacgc tgccaccgcc gcaaccgcgt  1320
gaagaatga                                                          1329

SEQ ID NO: 190            moltype = DNA  length = 1335
FEATURE                   Location/Qualifiers
source                    1..1335
                          mol_type = genomic DNA
                          organism = unidentified
SEQUENCE: 190
atgacgctgc gcaagacgct gagtgccgcc gtggtgacga tgctgacggc gtttgccctg    60
acggcgacgg cccaaaccac ggccgatgcg gatatcagtg ccaaagaggc gattagtaaa   120
gacaacaatc tggcgggttg catgtatcgc gcctatccgg gcccaaccaa acagctgacg   180
ccagcgccgg agggtaaacg tccattctat atcagtcatt acggccgcca cggcagtcgt   240
tggctgattg tcgcgcgacga ctataagtat ctggtggagg ttctgcaaaa ggccgatagt   300
gcgaaaaccc tgacgaaata tggtcaggaa ctgctgaaga agctgcgtgt gatcaacgac   360
cacagccgta agcgcctggg cgagctgacg agtctgggtg cgaaacaaca tcgtgaaatt   420
ggcggtcgca tggccgatcg tttcccagaa gttttccagg gcggtgttcg tatcgaggcg   480
cgcagtagta cggtggtgcg ctgtattctg agtatggaga atgagctgct ggaaatgatg   540
cgtcgttaca ataacctgcg catctggagt gacgccagcg accgcgatat gtggtttatg   600
gccggtggtc gtgagaatct gggcgacgtg aaaggtaaaa aagcggccca gaactggag   660
tggaagtggg agcagaccaa aatgccactg ttcaaaagta tgttcacgaa gatcttcaat   720
gacacggcct atgtgaacaa aatggttaat aaggataagc tggttatcg cctgtacagc   780
atcgccgtga atatgcagag tctggacgaa cgcaaagaga tcagcctgta tgatctgttc   840
gacaatgatc aactgtatgc gtgttatgag aaggaaaatg ccggctggtt tatcaattat   900
ggcagtaatc tgtggacgca aggtaagatg ccgtacagcc aacgttttct gctgcgtgac   960
atcattacga aagcggacag ttgtatcgcc ctgccaaaac cggcgccac gctgcgcttt  1020
ggtcatgata ccatgatctg tccaatggtg tgtctgctgg gcattggtgg tcgcgacaaa  1080
```

```
atgctggacg acaccgactt cgataatatc gccgagaaat ggcgtatgta tgaatttgtt  1140
ccgatggccg cgaatattca attcatcttt tatcgcagca gtccgagtga cggtgacgtg  1200
ctggtgaagg tgctgctgaa cgaagatgag gtggccgtga cggaagacct gaaaacggac  1260
atctttccgt actatcactg gaaggatttc aaggagtact ttctgaagaa actggacaat  1320
ttccaactgc gttga                                                    1335

SEQ ID NO: 191          moltype = DNA  length = 1392
FEATURE                 Location/Qualifiers
source                  1..1392
                        mol_type = genomic DNA
                        organism = Desulfovibrio piger
SEQUENCE: 191
atgctgccaa gtcgtaagga aatcctgatg cgtacgtgga cgtgtctggc cggtctgctg  60
gccctgctgc tgggcctgat gccgtgcccg gttagtgccg cgccaagcgc gtatcacctg  120
agtaaagtgg ttatgctgac gcgccatggt gtggccgccc cggccgatga caatcaactg  180
ccgcgtatta cgggcaaggc gtggccacag tggccggtgg gcccgggtca aatcagtcca  240
cgcggtgccc agctgctgac ggcgcaatgg gcgagcctgc gtgccctgta tctgcaagcc  300
gatctgctgc cggcgcaaaa gaccgaaagt cgcgttttcg tgccgccga taacacgcca  360
cgcagtcgtg gtacagcaga agcattgttg caaggtttga caccaggtac cctgccagcc  420
tatcggtgg ttaatctgga cccgatcca ctgtttgagc cagtgcaagc cggcctggcc  480
atcttcgacc cagcggaaac ggcgctggcc attctggacc acattaatgg tgatttcagc  540
cagtttgggg agagtctggg tgagccgatg agtctgctgg accaactggc ggttccgctg  600
agcgccgaag cctgtaatag tattaacctg ccgggcggtt gtcgcctgag tgatatggtt  660
ccaacgatca gtattatgga catgggccgt cgtgtggaga tccgcggtgg cctgggtctg  720
ggtagtaccc tggtggatct gctggtgcaa gaatacgcgc aatggccgca acaagaagca  780
gcatggggtc aagcaaatgc agcagcattg cgtaaactgc tgccgatccg cagtgagatt  840
ttcaacgcgc tgcatcgtac cccactgatc gccggtattt atggtggccc actgctgcgc  900
gacatggccc tggccctgta tagccaacac gcggacccac gtctgaatga agccaagtgc  960
gcggtgttcg tgggcaacga taataatctg gccgcgatcg gcgccctgct gggcatcgac  1020
tggcaggcca gtgctttcc accaaacgcg ctgccgccag gtacgattct ggcgatggaa  1080
ctgtgggagg gtccgggtaa tgatagtgaa gttcgcttcc gtgtgtttat gcagagtctg  1140
gacttcatgc acgccccgct gagtgttacg acggcgagcg gctatcaaac cgccccagaa  1200
agttatggcc cagcgctgct ggaggcccac gtgacgctgg atggtcaaaa agacggcccg  1260
gttatgagtc gtgaactgtt cgaacaacgt gttcgtggtg cattggaagg tcgtggtttg  1320
ccaagaatca ccttcctgcc agaaatggtg agcccacaag ccccagcgcc aagtctgccg  1380
gttcaaccat aa                                                       1392

SEQ ID NO: 192          moltype = DNA  length = 1467
FEATURE                 Location/Qualifiers
source                  1..1467
                        mol_type = genomic DNA
                        organism = Chitinibacter sp.
SEQUENCE: 192
atgcgtcacc tgttttgcct gagtgtgctg agtgcgctgc tgacggcctg tggtggtgac  60
attacagatc cggcggcgac acctgcgcca acggcaacac cagttgctac tgcgactccg  120
gctccaacgg tccaaccgta taccgtgagc gccgttagct ttgatgccga aacggagaac  180
gtgctgagtc cggcgggtga cgtggacgac ccagcgatct gggttcatcc gagccaaagt  240
gccaaaagtc tggtggttac cgccattaag gacggtggca tgcgcgttta cgatctgcag  300
ggccaactgg ttcaaagtat tggtccaggt gccctgaaca atgacagcaa gggtaaaagc  360
cgctataata atgtggacat tgtttatggt tttaagctgg atgacaatag tacggtggac  420
ctggccattg ccacggaccg cggtcaagac ctgatccgtg tgtggaaaat tgacccaaat  480
aacagtacca ccccgctgag tgacatcacc agtgccacgc cactgcgcct gttcccaacg  540
gtgccgaccg aaggtagcga gagtgatgcc agtaaggacg ccgcgattgc cgttagcaaa  600
caaaatacgg gctatggtat tacgcacttc agtgacaagg ccagcggcaa acacttcgtt  660
ctggtgaacc agcgcaaaca agcgcgcatc cgtcaatttg agctgattgc cgaggcgggc  720
ggtaccgtta atgtggttgc ggtggcgggc cgcgactggc gcttcccata tagctggcgt  780
ggtcagaacc tgcgcgaaac gaatgacctg gacgcgacgc gtgattggag tccgcaattt  840
gaaggtatgt ggtggacca acgcaatggc atgctgtacg ccggtcaaga ggacgttggt  900
atctggccga ctggacctgaa gaccggtcag gccgacaccc aaccggttta tgagacgcgt  960
ggtagtagcc gcgaaacgta cacgacgggt accccggcca cggttgtgaa gcatagtttc  1020
tttaacccag agagcaagat tagtcgcgac ctggaaggcc tgagtatttta ctatggtccg  1080
aatggtacgg gctatctgat tgcgagtagt caaggcggtg cgcatggcgg tgccccgaac  1140
gtgagtgacg cgccgtatga cgatagcttc gccgtgtttg ccctgaatgg caacgcgaaa  1200
ccagtgctga agcaaggttt tcgcctgagt caaggtccaa atggcaacac cgagggcgtt  1260
caagaatgtg acggtgccga tgtggtggcc ctgcaactgc cgggttaccc gttcggtctg  1320
ctggttacgc aggacggcta taatgatgac ctgaataatc tggatggtgt gacggcgcaa  1380
accaatctga agttcacgag ttgggagaaa atcgccaccg ccctgaaact ggagaaatac  1440
aataattttg atccacgtaa gctgtga                                       1467

SEQ ID NO: 193          moltype = DNA  length = 1533
FEATURE                 Location/Qualifiers
source                  1..1533
                        mol_type = genomic DNA
                        organism = Caulobacter sp.
SEQUENCE: 193
atgattcatc gtcgccaacg tttggcagca gcaagtgcat tggcattgac attgggtgca  60
gttgcaggtc aaacctttgc gcaggccgtt gccccagtgg tgccaccgt tccgaccgcg  120
gaaggtggtc ccaatgcggc cgccctgctg tatgatcgcg cggacccagg taaaagcgtt  180
atcgccgcca ccggtgagct gggcggtctg gaattccatg atctggacgg tgcccgcaaa  240
```

-continued

```
agcgcgctgc caggtggcga aacctatggc gttgatgtgc gcgacgacgt gctggccgtt    300
ctggatcgca aggacggtcg tattcgcctg agtcgttatg actttgcgac cggtcaagcc    360
agtgccattg atgcccgtcc gctgatgctg ggttatgccg gtgagggtct gtgtctgcat    420
cgtagtgccc gtgacggtag tctgtacgcc ttcgccctgg gtggcgacgg ccagctggat    480
caatggctgc tgtttccgac cgccgacggt aaactggcag gtcgcattgt gcgtcgcctg    540
cacctgagta gtgaggcgaa atattgcgtt gcggacgatg ccagtggcat gctgtatgtg    600
gcgcagcaag ccgttggtgt ttggcgttat gacgcggatc cggaggccga agcggtggcc    660
acggttgttg acatcaaccg cctgggccac attgcgggtg aagtgggcgg cctggccatt    720
ctgaatggtg gcgcgcaggg tgattatctg gttgcggcga acgccgacgc cggtgactat    780
aatgtttacg atcgtaatgc ggacgaccgt tttctgggtc gcttccgtat tcaagccaat    840
ggcgcggacg cgatcgaggg tccagccggt ctgtttggtg ttcgtgcacc attgggtgca    900
gatttgccag caggtgcatt gttggttaca gatgatcgta aggttggcgc caatacgaaa    960
ctgctgagct ggcgcgatgt ggccgttgcc ctgaaggtta gtccaggtca agttacacca   1020
ccagcagcac caagtcgttt ggcattggtt aagccgacga tggaaacgcg tccggtggaa   1080
cacggtggcg acgccgcgga cgacccggcc attttgtgc  acccgacgga tccggcgcgt   1140
agtgttatcg tggccacgga caaaaaggcg ggtctgtatg tttatgacct ggccggtaaa   1200
ccactgcaat tcctgccgga tggcaaaatg aacaatgtgg aacctgcgtgg cggtttttaaa   1260
ctgggtggcc gcaccaccac gctggttgtg gccagtgatc gcacgcataa gagcatcgcc   1320
ctgtatacga ttgacccaga tacgcgcatg ctgaccaatg ttgccgacgg tgtgcaagcg   1380
acgggtctga gtgacccata cggttgtgcc tgtacgcgcg cggcccgtgt gcgcccgacg   1440
tgtagtagtg cgatcccaac ggccgcgtgt gccagcggta attggagccc accgcgtccg   1500
gcccgtagtg ccccacgccg tagtgccacg taa                                 1533
```

```
SEQ ID NO: 194          moltype = DNA  length = 1623
FEATURE                 Location/Qualifiers
source                  1..1623
                        mol_type = genomic DNA
                        organism = Butyrivibrio sp.
SEQUENCE: 194
atgaaaaaga ccgttattac ggcctgcagt ctggtgctgg cggccgttat cggtagtacc     60
ggctgtggta aaattagtct gaagaatcca aatatgaaaa acagtgaaac gaatagcgag    120
ctgaagacgg aggacaatac cgaagttaag acggaaacta acaccgagac gaataccgaa    180
accaacacag gggccacgac ggaagcgaaa acggaggcca agacggagga gacgaccgaa    240
gcgaagacgg agacgacgac cgaagccaaa gcggaagcga cggccgaaga taacacggag    300
gcgaatagcg aagcgacgag tgaagttaat gccgagacag acaccgagac ggaaaccaat    360
acggacgtagta cccagaatat cgatgaggaa gcgaacgccg gtggccgtat tatcgactac    420
gacggttata agctggatca agtggtgatt ctgagtcgtc ataacatccg tagtccgctg    480
agcggtggcg acagtctgct gggtaaaatt accccgcacg aatggtttaa ttggacgagt    540
gccccgacgg aactgagtct gcgcggtggc gtgctgaaaa cgcaaatggg tcaatatttc    600
cgtcaatggg cggaagagga ggaactgatt ccaacgaact accacccgga taatggccag    660
gttcgtatct atgccaacag caagcaacgc acgattgcga cggcgcagta ttttaccgcc    720
ggtatgttcc aacggccgg tctgccggtg gagtatcata tggaattcga caaaatggat    780
ccggtgttta cgccgcaact gacgtttttgg acggatgagt acgagaaaga cgccaaggat    840
cagatctatg aatattatgc ggatgccatg aaaagcctga atgataatta cgagctgctg    900
agcgatgtta ttgacctgga agaaagtaat ggtttcaaag atcaaagcat tacggccttc    960
accgcggtgt atgaggaatt cagtctgaaa gagggcgccg aaccaggtgt gagcggtagc   1020
ctgaagacgg cgtgcagtgt tagcgatgcc ctggtgctgc aatactacga ggaaagtgat   1080
acgcaaaagg ccggttttgg tcaagagctg acgtacgaac aatggaagag tatcagcgaa   1140
atcaaagatg tgtatggtga cgtgctgttc acggccccga tgattgcggt gaatgtggcc   1200
taccccgctgg tgagtgagat ctacgatgag atgaacaccg acggtcgcgt gtttacgttc   1260
ctgtgtggtc atgatagtaa tgtgggcagt gtgctggccg cgatcggtgc cgaagactat   1320
gaactgccga acgccattga gaaaaagacc ccgattggct gtaaaattgt ttttacgaag   1380
tggagtaaag gtagtgaggt gttctggagt gccgatctgg tttaccagac cccaagccaa   1440
ctgcgcaata tgccaattct ggacaccgat agtaacagtc cggagatctt ccacattagc   1500
ttcaagaata tcaaacaaaa cgaagacggt ctgtataagg cggacgagtt tatgaaaatc   1560
tttctggacg ccatggatag ttacgaaagt ctgtaccagg aatatgttga aaaggcggcg   1620
tga                                                                 1623
```

```
SEQ ID NO: 195          moltype = DNA  length = 1650
FEATURE                 Location/Qualifiers
source                  1..1650
                        mol_type = genomic DNA
                        organism = Desulfatirhabdium butyrativorans
SEQUENCE: 195
atgaaaccga gcgttgctt  cctgatgacg gtttgtgccc tgctgattct gatcagtggt     60
ccagcgatgg cgcagccgca ggccccagtg ctgagtgtga ccacgcgcgg ctgggtgtac    120
ctgagttgga ccgaggttag tggtgcgacg ggctataccc tgagttatgc ccagattccg    180
tacacgggta gtagtgccat cggtaccgtt gatatgggta cgcagaccag tctgagtggt    240
gccctggccg cggataccgc cttctacgtt gccgttcaaa gtcgtgacaa caccggtatt    300
agtgagtata gtaatgtggt gagtatcgcc ggtgacagca ccacgctgaa gcaaattatc    360
attttttggcc gccacagtat tcgtagtgcg accagcgacc cggccagtct ggcccaatac    420
gccgtggacg cgtatccgga attcacgggc gtgccggccg gttacctgac cccgcgcggc    480
caacaggcgg ccacgctgct gggcagttat ttccacgagt atctgctgct ggaaggtctg    540
ctgaccggtg aggcccaaac ggatattagt cgtagtcact tccgtgccaa cagtattcag    600
cgtagcaacg tgacggccgc caaatttggc agtggtctga ttccgggcgc gacgatccca    660
gtgcacagtt acaaaattgc ggatggtgcc agtagtgccg aaccggatcc agtgttcgac    720
ccgatcttga caaaagttgc aacagttgat ccagcacgtg cattgggtga gttcaaggt     780
atctttaata gcggtgcggc catcagcagt gcctacagtg cgagctgag  tctgattcgt     840
agcgccctgt atcccaaggg tacgcaacca acgccaggtg cggcccacgg cagtaccgac    900
```

```
ccgacgagtc aaacgagcca cccgattacc ctgaaagcca gcacgagtac cctgtacacg  960
ggtggtgtga ttgatctggg cggtctgaat ctgaccaaca gcgcggccga cccgttcgtt  1020
atgcagtaca cggataactt tccgctgaat gacgtggcgt ggggccgcct gagtctggat  1080
gccgttagtc aacaaagccg catcatcaat ctgatcttca atatccaaat cctgccaccg  1140
tatctgaatc aagtgcagag tagcaatgcc gcccagcatg tgctgcgtac gatggagcaa  1200
gccgtgacgg gtcaaaatat cagtggcgcc tttggtgacg cgcagacgcg cgtgcatgtg  1260
attgtgagta gtgacggtta tgttatcggt ctggccggtc tgctgcacct gcattggctg  1320
ctgccaggct accaaccgga cttttgccca ccaggtggtg ccctggtgtt cgaggttcgt  1380
caagtgaatg gtacgggtga acatgtggtg cgcgtttatt acaccgccca aagcttcgac  1440
caactgcgta acctgacgcc gctgagcctg gccaatccac cgcagaccat gaacctgctg  1500
gtgccaggtt gtagtcgcag tgccacgaat ctggatgtgc cattcagcgc gttccaacaa  1560
gtgctgcaga atgccattgg tatggagtac gttcaagatc caagtaaaga gaccccacca  1620
ggtgtgctga cgggcgttcc actggagtga                                   1650
```

SEQ ID NO: 196            moltype = DNA   length = 1671
FEATURE                   Location/Qualifiers
source                    1..1671
                          mol_type = genomic DNA
                          organism = Cystobacter fuscus
SEQUENCE: 196
```
atgtttcagg gtgttctgct gaccgagctg ctgctgggtg cgcgcggttg cagtagtacg  60
atgcgctgtc cgcgccgtct gggtgccgcc agcaccctgg aagaattcat gagtgccaaa  120
cgccgtgttc tgggtagtgc cagcctggcg ctggttctgg tgccactggc cagcctggcg  180
gaaccgccag tgattccgcc acgcgccgag accccggttc tgcaccgcta tgacgaggcc  240
ccgcgcacgc cggatagcga cgaccccgcg atctggatcc acccaagtcg tccggaacgc  300
ggtctggtga tcggcgttct gaaggaggcc ggtctgcaag tgtacgacct gagtggccgc  360
gttgtgcaga cggttctgcc agccaaccgt ccggccatca gtgccggcga cccgatggcg  420
ccaggtccgc gtccagaagc cgcgacgagc gcctgcccgg aaagtgaaag cggcgagacg  480
tttggtcgct tcaataacgt ggatattcaa tacggctttc cgctgcgtgg tgcggacggc  540
cgtgttcgca aggtggatct ggccgtggtg accgatcgtg gttgtgatcg cctgcgcatt  600
tacgccattg acccgggccg cgcgggtggt ccactgttcg acgttaccgc ccgcgccgcc  660
cgtcgtgttt tcccagagcg ctttgtgcgt ccgagtccgt tccaaccgac gggtgaaccg  720
gagggtgtgc gtccgaatcc actggatgac cagaacacgg cgtatggcct ggccctgtat  780
cgtgacccaa gtaatcgctt ccacgccttc gtgacgcagc gtagccgcgc cgtggtggcg  840
tggctggagc tgtacgaagc cggtaccgag caagttggtt atcgtgaagt gcgcgaattt  900
cgtttcgaca gtcgttttag tttgccacgt ccaggtggtg gtggtgcatt ggcatggagt  960
ccatgtcgtg aagaaccagc agaagatcca caattcgaag gtctggtggt tgatcagcag  1020
gagggtattc tgtatgccgc ccaagaggtg gtgggtctgt ggaagatccc actgagtgtg  1080
agtctgccgc gtgtggttga cgtgccacgt ggccgtctga ttgagccggt gaaaagtttt  1140
ggtgcgccgt actgggccgt tccggacgat ggtgagtatg cctgtgagct ggaagcccca  1200
gccccggcgc cagagggtac gattgccgtt ccgggtaacc cggccgtggg cggtaaacat  1260
ctggaagccg acgcggaggg cctggccctg tactatgcgg gtgatgagaa gggctatctg  1320
attgttagca gtcaaggtga tgacaccttc cacctgtacg accgcgaagg cggttggacg  1380
cgtgaacgcg gtaatcgcca tctgggcacc ttccaagtgg aaggtgtggg cgagacggat  1440
ggtcatgacg ttgtgaatgt gccaatgggt gccggcttcc cacgcggtct ggttgttctg  1500
caaaccggca aagccccgcc accaccgagt accgaaccag tgaatggcta tgcctatgat  1560
ggtagtacgc gctttaagct ggttcgctgg gacgacatcg ccgaagccgt gccgccgggc  1620
tttaaagttg ataccgacga ttaccacccg cgtgatccgc atgacgatta a           1671
```

SEQ ID NO: 197            moltype = DNA   length = 1911
FEATURE                   Location/Qualifiers
source                    1..1911
                          mol_type = genomic DNA
                          organism = unidentified
SEQUENCE: 197
```
atgatgatcc gtgtgctgag caagctgctg ctgccgtgcc tgctgtgtgg cctgctgacc  60
gcctgtgcca ccagcccact gaaagcgacg gataagctgg ccctgccgcc gccaagtgcc  120
gcgtggaaaa atattagtgc catcacgaaa aaaggtcaac cgctgtgtt gatcaccagt  180
gagacgacgg gcctgagcct gatcgacagt agcaataatc gcctgctggc gctgcaggt  240
cactttgagc tgctggatgt tcgtccggcc cacgacaacg aattctggcg gctgaccgtg  300
gatagccaaa gtaatgcccc gcaactgctg ctgatgcaaa cgcatccaga gattcgtctg  360
cgcgagcgtc acaccctgtt caatggtgat ttccagatcg acggtctgtg cctgtataag  420
gacgcccaaa gtcacctgat ggcctatttt ctggatggca atggtagcgg tgagctgcgc  480
tggctggtgg atggcagtag tggtaaggtt gtggatacga gtatcaccat gctggaacctg  540
ccaccgaata gcgaacattg tacggttcac gacgccagta cagtctgtt cattagcgag  600
gcggaaatcg gtatttggcg ctacccagcg aatccggaaa tcgaaaatag tcgtattctg  660
gttgatcgca cgttcgacgg cggtaagatc gatggtgagg tgatgcacct gacgacgacg  720
cgcaatgcgc tgtatgccgc gacggaacag cgtctgaata tctatagtcc agcccaatgg  780
caactgcaaa gcagtgtgcc gtttccgcca ggtgtgaccg ttgagggcat tgcggccagt  840
caaagccaac tggccgtgct ggacgaagcc cagcaagccc tgacgctgat gccgctgagt  900
caaccaacga gttatcgcag cagtgaaaaa catatcctgc cggttgtgaa ggccaatgcg  960
caaacaacag caatggatcg tcgtggtgat gcagcagatg atccagcaat ttggattcat  1020
ccacaagaac cagaaaaaag cctgattctg ggtacgaata agaagtgggg cctgctggtt  1080
tataacctgc aaggtgaggc cgttcgtagt attgcgacgg gtcacattaa taatgttgat  1140
gtgcgccaaa atctgctgtt cgccaacgag ccaatcgaca tcgccgtggc cagtaatcgt  1200
agtaataacg ccattgccct gtataaaatc cacccagaaa ccggtgacgt aacagttgg  1260
gccagcctgc cgacggatct gaatgatgtt tatggcattt gtctgttcac gccgaccca  1320
agtgacattt atattattat taacgataag agtggtcgcg tgaatcaata taaactgggc  1380
agccgcaatc gcaagccgca cgccacgctg acccacagcg tgcaactgaa gagtcagcca  1440
```

-continued

```
gagggttgcg tggccgacga tacgcgccgt gaactgttca tcggtgagga ggataaaggt   1500
gtgtggcgct tcaacctgac gaatgacaaa ctggttgagc cggagctgat tgcgaccacg   1560
aacggtcatc tggtggccga cgtggagggt atcgatatcg tgaaaaatga attcggcaac   1620
tacctggttg tgagtagcca gggtgatcac agttacgcgg tgttcgaaaa taaagccccg   1680
tatgaattcc tgggtaagtt tcgtattgcc ccgaatgcga ccctgaaaat cgacggtacc   1740
agtgaaacgg atggtctggc ggtgacgggc atgccactgg gtaataacta cccggccggt   1800
ctgatggtg ttcaagacgg tcacaatctg atgccaaatg ccccgcagaa tttcaagctg   1860
atcagttgga aggacgtgct gaacgcgctg aagattccaa ccgtggaata a           1911
```

SEQ ID NO: 198       moltype = DNA  length = 1935
FEATURE             Location/Qualifiers
source              1..1935
                    mol_type = genomic DNA
                    organism = Microbulbifer agarilyticus
SEQUENCE: 198

```
atggcgctga aaaccctgcc gaagctgttt agtattctgg ccgttgcggc cctgtgtagt   60
gcctgtggcc cacaaatcgg taacgatgcc gccaaaccga agggcattgc cagcgagcac   120
caactggccc tgacggatgt ggttagtagt caactggccc cactggccct gggtggcgtg   180
gaatatctgc tgctggccag tgaaaagcgt ggtctggttc tggtggacaa ggagggtagt   240
gagaaactgg cgctggacgg cggtaccgtt gaacgcttcg ccctgcatcc gctggagcaa   300
gaccgctggt tgattgcggt gtatgatgaa gacaatggtg agctgcagct gcgtctgctg   360
gatgtggaag agggtagccc gcgcatccgt tacctggccg cgatgccgac gaacgccccg   420
caagttgcca tgtgtttcag tagtcaagcg ggtcgcaccc acctgtttgc gatcgacgaa   480
acgggtctgg ccacgagta tgtggtgcac ccacgcgagc aggcctggac cttcacgggg   540
ctgcgtccgc tgtactttgg cgagcaggtg agcagttgtg ttgtggatga tcgccgcggt   600
aaactgctgg tggcccaacc gccgctgggt atctggactc tgaacgccga cgccgaaacc   660
gatgaggccc gtcaggtgtt cattgcggcc agcgcgctgc cggacggcga atttggtggt   720
ctgtggctgg atgaggtgaa cggtaatctg tggctgaccg cggccgaaaa ggttatggcc   780
ttcgacatta acgatccggc caaaggccca ctgtttgtgg aggccctggc cgacattgaa   840
ccagttagtg ccgccgtgca aggcgaagcc ctgctggccg tggaggaaga gggtgaccaa   900
gttcatcgct tcgccgtgag tctgccgcag ccgccagccg aagttcaagc gttccgtggc   960
ccggttgaga tcccacgcgt gcgtgccagt ggtcagacgg ccccagttgc gagcggcggc   1020
gacgccgcgg atgatccagc catctgggtt aatccggcca gccgagcgc cagtctgatc   1080
tttggtacgg acaaaaagag cggtctgagt gtttatgatc tgaacggcaa actggtggag   1140
cacttcgagg ttggtcgtgt gaataacgtg gatctgcgtc cgatgcaaca cggcaaattc   1200
gtggccattg ccgccgccac gaatcgcacc gacccaggtg ttagcctgtt cggcattacc   1260
gccgcgggcg ccgtggaata cctgggtctg cgtaatctgg atatggagga tccgtatggt   1320
ctgtgtgtgt atcgtaaagg tgccgacctg atgacgtggg tgagtgataa ggaaggtgcc   1380
gttcaactgc tgcaaattgt tccaggcacg ggtaatgtgg attggagtct gcgtaagctg   1440
gcgaccctgg aagtggcgag tcaagtggag ggttgtgtgg tggacgatga aatgcaaatg   1500
ctgttcttcg gcgaggaaga cggtggcatc tggcgcctgg acattgcggc ctatctggcg   1560
ggcgaggcca agccgcaact gatcgcgcca gtggatggca aacgtctggc cgcggacgtg   1620
gaaggtatgg gttttacca tgccgcggat aaaagctatc tggttgtgag cagtcagggt   1680
aacaatagtt atgccctgtt taaccgcgac ggcagtgagt tcgttggtca cttcaaggtg   1740
gatattaatc tggacaaagg tctggacggt agcagtgaaa cggatggcct ggaagtgagt   1800
agtgccgccc tgggtgcgca ataccacaa ggtctgctgg ttgttcaaga cggccgtaac   1860
cgcatgccga gtgccagcca gaacttcaag ctggttagct gggccgacat cgccgagacg   1920
ctgcaactgc catga                                                    1935
```

SEQ ID NO: 199       moltype = DNA  length = 1968
FEATURE             Location/Qualifiers
source              1..1968
                    mol_type = genomic DNA
                    organism = Acinetobacter nectaris
SEQUENCE: 199

```
atgaacatta tctttctgaa aaaaacctgt ttcgtgagca ttgtgctgct gggtctgatg   60
ggttgtggtc aaaagacgat gccagtgcca gaaaagagtg ttatcagtaa agacggcacg   120
attcaatttg aaagtattag tattaatggc accaaagatg tgttcaaggt tcaaagtgcg   180
aagctggctga gcatcccgta ttggagtgaa gcgcatccga ttcagacgag taaaacgcag   240
ggtctgcaaa tcctgaaccg tcagaatcac gtgctgcaaa gtattgatgg cgcctttggt   300
gacattgact accgtatcaa ggataatctg ctgttcattc agagtgtgga cctgaaacaa   360
cagcgcccaa ccctgctgat cttcgatatg aagagtaagc aatggcagcc aagtatcctg   420
ctggaaaaaa ccaagttcaa gattgcggtg tgcctgtatc aagaccagag tcagcagctg   480
tacagtttttg ttatcggtgg ccaaggtagt gcccaacaat gggccgtgaa caccacgcca   540
aatgccaaac agccgatgca actggttcgt aatctgaaca tcccaattgg tagtaagagc   600
tgcgtggtgg aggaccaaca agaacgcctg ctgattaatg aggagggcat cggtatctgg   660
gagtatctga cggatgccga gcaaccgttt aaacgtaaga tcgttgacat ggtgaaaccg   720
tatggtcata ttgagggcag tccaggtgcg ttcacgcagg ttgataatat gctgttcgtt   780
gtggacaccc aacagccgtt catctacaaa tatatccaca acggcaagaa ttggcaaatc   840
agcgatcaac tgaacaccgc cgagctgaaa aagccggaac aactgagtgc gaaacgcgag   900
ggcgagaaag ttcaactgct gctgaatgat aatcacaaac tgaaaatcgc cagtctgcca   960
tatacgaccc cccaccagga caagaaaaag gacgaacact ttcaattcgt gcaagcgaaa   1020
gtgcagacga ccccggttcc aaacgtgggt gacgccgcg atgacccagc catttggtac   1080
aatgaagaaa tcccgaccgg gagtcgtatc ctgggcacg ataagcaggg tggtctgcaa   1140
gtttacagtc tggatggcaa tgagcagcaa tatctggccg ttggtcgtct gaataacgtt   1200
gacatccgtc caaattttaa ttgggatggc caacgcgtgg atctggccgt tgcgacgaac   1260
cgcgatcata tagtctgca tctgttcgcg atcgaaaaga aacgggtca cgtgagtgaa   1320
attgccagg cccagacgag tctgaaggat atctatggtc tgtgtctgta tcaaaacaaa   1380
cagggtgaca tttatgccat cccaaatgat aaggacggta ccttcattca ataccatctg   1440
```

-continued

```
agtgccctga agaacaaagt taatgccaag gaaatccaaa aattcagtgt gaaaacccaa    1500
ccggagggtt gcgttgttga tgacaagaat gaccagatct tcctgggtga ggaagatcgt    1560
gcggtgtggc aaaagagcct gctgcagaat aatagtaacc tgcaagaggt tgccacggtt    1620
ggcaaaaatc aaattcagga cgacattgaa ggtatgggtc tgtatcatgg taaaaagcaa    1680
agttacctgg tggtgagcag tcaaggtaac aatagttatg cggttatgga agcccatgcc    1740
ccatatcgtt accgcggtag tttttaagatt gttatgaaca gtgtggaaca aatcgacgcc    1800
gttagcgaga ccgacggcct ggacgtgacg agccataatc tgggtggtgt ttgggaaaag    1860
ggtatgctgg ttgtgcaaga tggtcacaag gtgatgccag aggaccacca gaatttcaaa    1920
tacgtgccat ggagtgagat cagcgaaaaa ctgaatctgg aagagtga                1968
```

```
SEQ ID NO: 200          moltype = DNA   length = 2010
FEATURE                 Location/Qualifiers
source                  1..2010
                        mol_type = genomic DNA
                        organism = Catenovulum agarivorans
SEQUENCE: 200
atgcaatatt ttcaccaact gacgcacaac aagctggcga aagtgagtgt tgtgattacc    60
gcggccgttt tcgccctggc ggcctgccag agcagtattg agacgaccgc ccatagcgcc    120
gtgcaggcgc tggccaaagc cccgcaacaa atctttcaac atgacaagct gaacggccaa    180
aaggttatcc aactgaacca agacacctgg gtggcgaata gtgaaaattt cggtctgatg    240
ctgattaacc aacaaggtaa aatggtgcag aattatgccg gtaatttcga gagcctggat    300
atccgccaac tggacaataa gacgtggttt gttagtagtg tggacaaaga ggcgggccag    360
tttctgctgt tcaaggtggt gctggccgcg aatgcccaaa cccataaaat cacgctgctg    420
aacacgatta agccagaggc cagcgtgatt gataatcaat gtctggccta tcagaacggc    480
caactgagca gtttctggct gacggcccag caacaagtgg aacaacgtat cgtttatctg    540
aatcaaccga atgcgcagcc aagtaatgtg ctggtgcgca gttttagcgc cccgcgtgat    600
gcgagtgcgt gtgtggttga tgacgtgaaa caacaggttt acgtggccga ggaaagcgcc    660
ggcgtgtggg cgtatccaac gaatccggag aaagaactga gtcgtacgcc gattgccctg    720
gtggcgccat tcggtcagat tgacggtgaa atcaaggaca tcagcctgct gatcgacggc    780
agcctgctgg tggccctgcc ggaagcggaa caaattcaac actatcagac ggataatagc    840
agccacctgg cccaagtgta tagtgtggcg ggtttcacca ttgaaagcat cgacgcccaa    900
cagaccgccg ataacaagtg gctggccaac ttttacgatg atgaaagtgg cgcgtattat    960
agtattgagc tgccgctgat ggtggccgat aaaagtatcg ccaaacaagg tgccagccag    1020
ctgacggccg acatgcagac ggcgccagtt gcccgcttcg gcgatgcggc cgacgatccg    1080
gaagtggtgc tgaatccgaa caacggtgcc gatagtctga tcctgaccac cgacacaacgt    1140
tatggtctga atgtgtacaa tctggccggc gaactggtgg agacgattgc cagtggccgc    1200
atcaacaata ttgatatcag ttatggtgcg gaattcaatg gtgacaaatt tgatttcgcc    1260
accgccagca atcgtacgta taatagtatc acgatgtaca agatcagcca taccggcgtt    1320
atcagtgagc tggccaatct gccgacgagc ctgccaaacg tgtatgacgt gtgccaaatac    1380
caaagtccga ttacgggtga ctatttttgtt ttcatcaacg acgaaagtgg tatctaccac    1440
cagtaccaac tggactttag taccaatcaa gttaccggca agctggtgcg tgagttcaaa    1500
gtggccagcc aaccggaagg ttgcgttgcc gatgcgcaaa cgcaaacgct gtatctgggc    1560
gaggaggatt ggggtatttg gaccattggc gccgagccag acgccggtac ggcgcctggc    1620
ccgtttttacc aagttgacgg tgacgtgctg gttgatgatg tggagggcct gagtctgtat    1680
ctgccaaaca agagtgccgc caaaaatcgt agtgagaaat atctggttgc cagtagtcaa    1740
ggtgatgaca gctacgtggt gtttgatctg gccaagaatg cgagtcgtgg ccatgttgtg    1800
gccaaattca acatcgttgc cgacgttcaa aaaggtattg acggcgcgag tgagaccgac    1860
ggcctggccg tgatcgcggc cccgctgggg gatctgtatc cactgggtgc gctggtggtg    1920
caagacggtc gtaatattat gccggttcaa ccacaaaact tcaagctggt tgattggcgc    1980
aaaattagtg gcctgattat caaacagtga                                      2010
```

```
SEQ ID NO: 201          moltype = DNA   length = 2211
FEATURE                 Location/Qualifiers
source                  1..2211
                        mol_type = genomic DNA
                        organism = Corynebacterium timonense
SEQUENCE: 201
atgcgtaaat ttagtggtgc cttcgtgatc agcctggcgg ccgccgttat tgcccaaaat    60
gccagtgtga gcagtgcgca agttgccgac tacagtgcgg aatttagcgc gcgtacgacg    120
ccaagtttta cgggtagtaa caccagttat gccaatagca atgaggcgag taagctgagc    180
acggagctgc aggaagcccc ggatggcttc gagccaagtt atagcgcgct gttcgcgcgc    240
cacggtagtc gtacgagtag cgacagcggt tattacgacc gcctgattaa tggcctggaa    300
gccgccggtc gtgtggattt tttcggcggt gcgccgaccc gcaccgagct gggcaaagaa    360
attgaagatc acctgcgcca gctgcgtcaa ctgcatgatc aaattggcgg tggtaacctg    420
acgggtctgg gccgtgagga aagtcgcgaa ctgcgcggata gttttgcgga gcgtaatcgc    480
gagctgctga gcgatagtga ggccaaactg cgtctggagg ccagtaccaa aggtcgcagt    540
attgaaaccg gcgagatttt cgcgcagcaa ctgatcgccc atcgcttcgt tgtggcccag    600
attccagacc gcgcgacgca aaacaaagaa gttctgcaaa accaagatgt gccggagagc    660
ccagcgcagc aacgtgcgga agcctacctg caaacggacc caggttatca ggccgtgaag    720
ggtatcccag agaattggac ggccgaagtt cagccgtacg cgaacgccgt gtttgaacag    780
ctgcaaggta gtcgtaaacc aagtttctat ggttactgtg gtggtcgcgc ccgtgatctg    840
ttcgaagccc gcgcgtttag tgagctgatg agcgttgaac gcgaagccgc gggcgttggc    900
ccgtttccag ccattccggg tgccgaagac atgtatcgca gtgtgcaaca atgtacggcc    960
atcgacgagt tctataaagcg cggcgtgggt ctggagggcc aagatcacag caagtcgcgaat    1020
ggtctgccac tgctgaacca aattttttgcc ggtattgacg cgagtgagaa caacgaggaa    1080
gttggtcagc tgctgttcag ccacaatgaa atcctgacgc cgttcaatgc ggtgctggcc    1140
attccggaga ttggtgccaa tcaaaaaattt cgcccaggtg aactgtttaa ctatgagacg    1200
tatccggtgc tgaaccaagc gcaaagcgac ccaatgatgg gcaacatcga atggaacgtt    1260
tttaagcatg aaaaatggcac ccgcctggtg cgcatgcagc acaatgagcg agccgtgcac    1320
```

-continued

```
ttcggtcgca gctgcaaacc gatcaacgaa gagttcgact attttttatct gtacgaagat   1380
ctgaaggcct gtctgccgga cgccggtcaa agtatcccga gtgaggacga actgagtaag   1440
gcccgtaaac tgctgcaaga ggcgctgagc gaggaagagc tgatccaaat tgttagtgtg   1500
atcgaaaatg aagatggtag cacgaccctg aaactgagta acggtcaggt tgtgacggtg   1560
ccaccgaatc gccagattgt gggtacggaa gagaccggta gcgccgttat cattaagctg   1620
agtgatggta gtgtgatcga gatcgcgaaa gggccaaagg gggaacccgg ggagcagggt   1680
cctaagggtg aaccaggtga acaaggcccg aagggagagc caggggagca aggcccaaag   1740
ggtgagcctg gagagcaggg tccgaaagga gaaccaggcg agcagggccc gaagggagaa   1800
ccgggcgaac agggccgaa aggcgaacaa ggagaaccga gccgcatcgt tgcgcaaggt   1860
gtggacggtg aaggcaatac cgttctgacg ttcagtgatg gtacggttgt gacgattccg   1920
agtggtcgc tgagtattga acgccagtat ctggacagtg agggcaacac cgtggtggag   1980
ttcagcaatg gtcagaagat cgtgattgcc agtccagccc cgagtaaaag tagtagtggc   2040
agcagttgga gcgacagtag cagtctgacg gcggttggta gcagtgcctt cgccgcgggc   2100
ggtgtggtgg ttgcctttgt gctggccatt gcggccgtgg ttggcggtct gctgggcatc   2160
atcccgctgg cgccgccaat tcaaagtctg atcgacctgg tgcaacgcta a            2211
```

SEQ ID NO: 202        moltype = DNA  length = 2217
FEATURE               Location/Qualifiers
source                1..2217
                      mol_type = genomic DNA
                      organism = Alteromonas macleodii
SEQUENCE: 202

```
atggacaaac aaaaaattac gcgtatctat ccaaccatgg gcaagacctt ttttctgacc   60
ggtatgctgg cgaccctgtt tagttgcgcc accgcgggca aagccagtca tcaaccgcaa   120
gccgatatcc aagaaccggt tctgaagctg aagcagctgg cgaacggttt cagtcaaacg   180
ctgtattatc gcagcgacaa tcagcaaacc gcctacaaag atacgcatgc caatgagcaa   240
gagacgccaa aagccctgaa caagagttat aaggacacgc acgccaacga taatgaaaaa   300
ctggcccccgg cgctgaatgc ccaaaccaat gacgacacgc acacgattga actgcagctg   360
aatgagcacc aaggtatcag tatcagtaat agccaaggta aggcgcgttt tattgcgggt   420
agtttcgttc tggccagcgc ggagattgcc gaattcgaga ataaacaatg ggtgagcatg   480
gtggtgttca ataataatac ccaacacatc gaagcctacc gtctggcccc ggacacgctg   540
gatatccaac aacaactgac gcaaagtgcc aaagtagtg aggcgatttg tgccgcggtt   600
accgcccagg gcgcgccaca tatcgttaat atcgatgcca ccggtacgct gaatcaattc   660
gagattcacg ataaccaatt tctgccgctg cgcaatttcg ccatcggccc gggtatgaaa   720
agctgtagtc tggacatgct gacccacagt atctatctgg ccgatgaatt cgccggtctg   780
tggaaggtga acgccgatat tgaaagtgaa ctggaaaaag aactgttctt ccataatgcg   840
aacatcgcca tcgaaggtgt tagcacgctg agcagtaata cgagcctgtt taagggtagt   900
ctgctggtt gggtgagccc aaacaaaagt ggtgtttggc tgcagagtca atgtcagacg   960
gaatttatca cgctgcaata tgacctggcg ggcgtgccgc aaaccattga accagagttc   1020
attcacctgg ccttctatga atacgaaaag ggtccgcgca ttagcgtgat cgtggacgat   1080
gacgcgagtg gtaacttctt cagtgccgag ctgagtagcg aactgagcgc cgcctatttc   1140
aatcatggtt gtctgagtaa agatgaagaa ccaatcgcga acgccggtag ccgcagtccg   1200
aagtatgccc tggcgcgtgt tctgccaagt gccgaaacgc aaccggtgaa gaattatggt   1260
gacgcggcgg atgacccagc catctcggtt aacgcgcaga gcccgagtca aagccgtatt   1320
ctgggcaccg ataagaaagg tgccctgaat acgtatgacc tgctgggcca ccagcaacag   1380
agtctggcgg tgggtcgtgt taataacgtg gacgtggggt acaatgttgc catcgcgaac   1440
atcaataaca gtggcgagac gaccttcacg gacatcgcca gtgagtaa tcgtagtcat   1500
aatagtctga gtgtgtttga aattgacgag ttcggtgtgc tggcccacct gggtgaaatt   1560
gacacgacgc tgaccgatat ctacggcatg tgcctgtttg ttgaaaacgg tgtgacccaa   1620
gttttcgcca atgacacgag tggcctgttc gagcgctatg aagtgagctt taataagaat   1680
aaaaaggcca agggcacgct gacgcagagt tttagcctgc cgagtcagcc agaaggctgt   1740
gttgtggaca cccacacgaa cacggcctac ttcggtgagg aaggtgccgg tatttgggagc   1800
atggacatca acagcacgaa acacgaacca gcgttcgtta gtgcgatcgc cccgccagtg   1860
gaagcggatg ttgaaggcct ggccctgttt accgtggatg cgcaaacgta tctgattgcc   1920
agtagtcagg gtaacaatag ttatgccatc tataacatca atagtaaaaa cgccgacaaa   1980
ctgaccctga tgggtctgat tcgcatcacg gccgacatga ataacagtat tgatggtgtg   2040
agtgagaccg acggtctgga ggccacgaat gccaacctgg gcggtgtgta cagtgaaggt   2100
ctgtgggttg tgcaagatgg tcgcaatgtg atgccgagtg aaacccaaaa tttcaagctg   2160
gttagtggc gcgtctgaa ggaggccatc cgcaacctgg tgagcaccaa gcactga      2217
```

SEQ ID NO: 203        moltype = DNA  length = 2376
FEATURE               Location/Qualifiers
source                1..2376
                      mol_type = genomic DNA
                      organism = Clostridium sp.
SEQUENCE: 203

```
atgaaaaagc tgttcaaaat tctgttcagc attttattg ccatcattct gagtttcaat   60
ttcattacct attatccaaa ggccagtaat aacctggagc tggtcaagga tagcacgaat   120
atcacgaaga ttccgaaaaa ctttcgtaag agcacggacg tgctgaatct ggacgaaggc   180
gagaaaatca acctgaccgg tctgaaggaa ctgaatatta gtggtagcgc ccaattcagt   240
aaagaaggcc tgagcctgat taagaagagt atcggtgaca aatacaacat cacggttgtg   300
gacctgcgta aggagagtca cggctttatc aacggtatcc cgattagttt caagaataag   360
aataacaatg ccaatgaagg tctgagcctg aatgagatct tgaatgatga gcgaagcgt   420
ctgaacagta ttaagatcaa tgagccaatc accttttagta acacgaatat tagtgtgatc   480
ccgaaggaag tttatagcga ggaaaccctg accaaaaata taacctgaa ttacatccgt   540
attccggtga cggacggtgg tctgccaagt accgacatgg tgaaccgctt caaggagacc   600
gttatcaata acaaaggcaa taataattgg ttccactttc attgtaaggc cggtattggc   660
cgtacgacca cgttcatgat catgtatgat atcgtgaaa actgtaatga agttagtctg   720
gaggacatta tcacgcgtca ggtgaagctg tttgagatga gtgagaatga tagcaaggggt   780
```

-continued

```
ttctatagtg gtgatcgcta taaattcctg agtgactttt ataatgagtg taagggtaac   840
agcaagaata tttttaacaa gaataacaat aagaatgact attacatcaa gaacaatatt   900
atgccaaaga ccctgtatgt tattaaagat aacgaaatga cgaaggagga gcaaacgatg   960
gttgccaccc tgcagggcaa cgtggccacg aaaagcaaag aacagattta catcctgagt   1020
aattatgaac cgagttatga gacctggctg aatgatctga aagagaatta taatgttaaa   1080
tacaagttca ttaaagaccc atatgagctg ctgagtaaat ttaaagatta catcaagggt   1140
tacattctgt ataataatag taacaaatat agtattaaca atggctgtag cctggcgagt   1200
ctggaaaacg gtatcgttat cgatgagctg atcgaagaaa aggtgaaaga aattggcgtg   1260
aagaacctga tcaaagactg tcgtgacacc gacaagtatt gggccttcaa taacctgtgg   1320
aataaaggtc tgaatcacag tacggttatt cagctgagcc cggacaaaac catggccctg   1380
cgcgactacg ccatcgtgag taaaagtctg gttttttatg aggaagagat taacaacaag   1440
gaattccgcg agaaaatttt tagtagcatg gatgacgtta gtcgtgtttt tggttggggt   1500
ccagacgaac atacgaatgt gagtattgcg agtaagttcg gcgttgatat cgtggccagt   1560
gactggagtt acaacctgag tgtgctgagt agctatccga cgcgcgatca aaagcagaat   1620
ctgagtaaag agagcgttaa ggacaatgcg cactacgtga cgtttatcat gagtgacggt   1680
gataatcaac aatggttcct gggcagtaac ttcaatagca ataactggta tggtagcaaa   1740
tatcgcggta agttcaatct gggttggagt atcagtccga gtatttatta tctggccccg   1800
acggtttca acaagtacta tgaaagtgcc agtaatattc gctacaaaga ttattatctg   1860
gcgccgccaa gcggtaacgg ttatatgtat ccgagtaagt ttccagagga aaaaattgaat   1920
aactatacga aacgtctgag taattacatg aagaaagtgg accaaaacta tgtgctgatt   1980
ctggatgacg agagtttcta tcgtaccgat ctgtgggaca aatatacgtg ccataataat   2040
attgacggcc tgatttatct ggactataag aaaaataata actataagtg tgaaatcgtt   2100
tggagtaata ataaaccggt tgtgagttgt cgtgacctga tgtggaaggg cctgaggaa    2160
gaggacaccc tgatcgaaaa cattaatagc cgcgttaaag aaggttatac ggacattaag   2220
aatccgaaga gttacacgtg cgtgtatgtg cacgtttgga gtaaaaatat ggatgacctg   2280
aacctggtga tcgaagaact gaataagaac agcaaggtgg aagtggtgac cccgtacacg   2340
tttatgaagc tgattaaaga gaatatcaag aaatga                              2376
```

SEQ ID NO: 204      moltype = DNA  length = 2466
FEATURE             Location/Qualifiers
source              1..2466
                    mol_type = genomic DNA
                    organism = Clostridium beijerinckii
SEQUENCE: 204

```
atgaacaaga atttcaagcg tattaccatc ctgaccctgc tgattgttag tatttttcagt   60
tttgccgtta acaataatgc catcgcccaa gttccaagtg ataaagacaa cggcgtgcat   120
ctgattctgg acagtgttaa ttataacagt gtgctgccga aacacttccg caagacgacc   180
gatctggccg ttgttaaaga caacaaggac ctggatctga agggtctgga taaactgaat   240
attagcggca gtcaacaatt tagcgcgaac aatatcgacc tgctgacgaa ggcgattgat   300
acgagtctgc cgatgacggt gatcgacctg cgtcaggaat gtcatggttt catcaacggt   360
tttgccgtga gttgggcgga cgcccgcaat aatgccaacg tgggtctgac ccgcgaccaa   420
gttattgcga agaaaagga agacctgaag agtatcaagc tgaatgagcc aatcacgttt    480
tacaataaca gcaaacagac gatggatgtt aagacggttc aaagtgaaga ggagctgaac   540
aagagtaaga aactgggtta tgaacgcgtt acggttcgtg acggtggtat tccgacggat   600
gacatggtgg attacttcat ggagtttatt aaaaataagc caaaagacag ttggctgcac   660
ttccactgta aggagggcat cggtcgcacg agcacgtttt tgattatgta tgatatgatc   720
aacaactaca aagacgtgaa tgccgacggt atcatcaagc gtcaactggc gctggccaaa   780
ttcgaagaca ccacgctgaa aagttttttat aataatgaac gcatgggctt cctgaataag   840
ttttatgatt actgcaaagc gaatggcgat agcttcgaca ccaaatggag tgagtggaat   900
agcaaggcca gtagtattga cgaaacggat aaaagcaatg cgatccaagt gagtaacgtg   960
aatagcgtgt atatgaagaa caatattgtt ccgaagagtc tgtatgccat tagtctggac   1020
agcatgaccc caggtgagcg cacgatgatc accagtctgc aaggcctggt gaacaatcac   1080
tgtagtttcc aaatctatac cctgaatagc agtcagccag attataagat ttggctggaa   1140
gatctgaaaa gcaatcacaa cgtgccgtat gagatgatca gtgacccgtg ggaactgctg   1200
aagatttata aagattacat taaggggttac gttctgtata acggcgaaac gaaagatcca   1260
agtattaata acgcgtgtag cctggccggt gtgaaggacg cgattgttat cgatgagaaa   1320
ctggagccga agattaaaga actgggcatt gagagcaaag gtgactgtcg cagtaccgac   1380
gagaattggg cctatgataa tctgtggaac aagggtctga atcatagtat ggtgatggaa   1440
ctgagtccgg accgcattga tgccctgcgt gactatgcca tcatgacgaa aagtctgatt   1500
ttttacgaag gcagtgttga taagacggcc ctgcgcgaca aaatcttcag cagtgttgat   1560
gacaacgcca cctgtctggg ttggggccca gatgaattta tcaacgtgag tacggccagc   1620
aaatatggtt gagcatggt ggcggccgac tggagctata acctgacgac gctgagtgcg   1680
ttcaaagaac cgcacattaa taaaaacagc agtctgaagg ttccgaagga ggagaatgtg   1740
cattacgtga cgttcatcat gagtgacggt gacaaccaac aatggaacct gggcacgaac   1800
tatggtagca gtaaatggtt cggttacgag aaccgtgata aactgagtct gggctggagc   1860
atgacgccag ccctgtatta cctgagtccg accgtgttcg acctgtataa taagagtatt   1920
agtaacgaag atccacgcaa taatttttatt gtggccccaa gtggtaatgg ttacatctat   1980
ccgagcaaat ccccacgtaa caagctgggc agctatgttg acctgctgaa taattatatg   2040
aaacgcgtga atgagaactg tgtgagtatc attgacgaca gtgcctttca cgatatcgag   2100
ctgtggaatg aattcacgaa gaaaagcaat attaaaggtc tgttttacat cgactaccat   2160
cgtcatgaca attataaggg tgagattctg tggagcaata acaaaccact ggtgagttgc   2220
cgcgacctgc tgtggaatag tctggaagat gaagaggagc tggtgaagcg tatcaacgac   2280
cgcgtgagtc tgggccagac gaatatccat agcccggagg cctacagctt cgtttatgtg   2340
catgtgtgga cgaaagaaac cagcaacgtt gagaaagtga ccaagatgct gaaagagaat   2400
aaaagtgtgc gtgtggtgcc accggagacg tttatggaac tgatcagtaa aaatgtgaag   2460
cattaa                                                               2466
```

SEQ ID NO: 205      moltype = DNA  length = 882
FEATURE             Location/Qualifiers

```
source                    1..882
                          mol_type = genomic DNA
                          organism = Bdellovibrio bacteriovorus
SEQUENCE: 205
atgaaaaagc tgctgctgct gccagttctg ttcgccgtgg ccgcgtgtgc cgaaaaaacg   60
gttagtctga ccccagataa gccggttagt accaagatcc cgtttttcat gacgcgtcca   120
cagccgacca cgccggtgga actgtttttt gacaatgatc acgcgacggc caagccgatg   180
aactaccgta agaatgatag cctgcgtatg agtggtagtg ccaccttcag cccgaaagcg   240
ctgaaggagg tgagtaagcc agttaagaaa aataaagcca gcctgtacgt ttttgacctg   300
cgccaagaga gtcatggcct gattaatgac attccggtga cgtggtacgc ggatcgtgac   360
tgggcgaacg ccgacctgaa tcatgaagag gcggtgcgcc gtgagcgtcg cctgctgggt   420
gacctgcgtg ttggtgagaa aatcggcacg accacgatcc aaagcattga aaccgaggag   480
agtatgattc gtacgggtgg ccaccaatat gtgcgcctga ccgttacgga ccacgtgcgt   540
ccagttgaca gtgaggtgga tcgctttatc gagagtgtgc gtgccctgcc ggaaaatgcg   600
tgggtgcatt tccattgtcg cgcgggtaaa ggccgtacca cgaccttcat ggtgctgtat   660
gacatgctga aaaacgccaa agccgacagt tttgaggcga ttatcaaaca caatacggaa   720
ctgagtaatg attatgacgt tctgaccgtt ccggcggacg agaaggattg gaaatatccg   780
tatcaaaagg aacgtgccgc ctttgtgacg gaattctaca attatgcgaa ggcgcaccca   840
aatggcgagg gtatgctgtg gggtgaatgg gttctgcgct aa                       882

SEQ ID NO: 206          moltype = DNA   length = 906
FEATURE                 Location/Qualifiers
source                  1..906
                        mol_type = genomic DNA
                        organism = Clostridium tyrobutyricum
SEQUENCE: 206
atgaagaaga atcgtgtgcg catcggcatt tttctgctgt tttttatttt cctgctgggt   60
gcgagtaacg tgaatgttct ggccctgcag aaaaacaccg cggacaacaa gctggagctg   120
acggttgata gccacaagaa agcggaaatg ccaaagcgct tccgtaagac cagcgataaa   180
attaagaccg agggtaaaat gccgaatctg acgggtctgg cggaactgaa tgccagtgat   240
agccaacagt ttaccccggg taacatcaac ctggtgaagg acgcgattgg caaggacaaa   300
aaaattagta ttgttgatct gcgccaagag agtcatggtt ttatcaatca cctggccgtg   360
agctggaagc tgccagacag taacaaagcc aataagggcc tgacgcgcga acaggttatt   420
aaagaagaaa agaaactgct gaaaagtatt aagctgaatg aaccgctgaa gatcaagaat   480
aaaaccgtta tcccagtgaa ggttcaaagt gagaagcaac tggtgaagga cacgggtatg   540
gattatattc gcgttaccgt gaccgacacg gagcgcccgg aagatgacat ggttgattat   600
tttgtgaaga aagtgcgcaa actgccggag gacacgtggc tgcatttcca ctgtaaggcg   660
ggtatgggcc gtaccacgac cttcatggcg atgtacgata tgatgaaaaa tagcaaaaag   720
gtgagtctgg aagacatcat ggagcgccag gaactgtcgg gcggtgttaa gctgctgaag   780
ccggttggtg gtaaagagag tgagagtcag aagcgcagtg acttcctgcg tcaattttat   840
cagtacacga aggaaaataa tgataacttc aaaaccagtt ggagccaatg gctgaatagt   900
aaatga                                                               906

SEQ ID NO: 207          moltype = DNA   length = 909
FEATURE                 Location/Qualifiers
source                  1..909
                        mol_type = genomic DNA
                        organism = Acidaminococcus fermentans
SEQUENCE: 207
atgaagtttt ggaaaattac gacgggcatc ctgctgatga gccaactgag tctgggtctg   60
gcctggcaag acgcgccgag tattgccgcc atcgttaagc caagtaaagg ctatgtgtgg   120
cgtctggaca cgaaaaataa gctgcaactg ccccgcaact accgcgccga tgttgagaat   180
tgtatgagcg gtagtgcgca accgagtatt ctgggtctga gtagtctggt tcaagaactg   240
gcccagcaag gcgttaagcc gcaacaaatc atcctggtgg atctgcgcca agaaagtcat   300
ggcttcgtga acggccaggc ggttagctgg tatggcgaca ataactgggc caatgtgggt   360
aaagccgacg cggcgattcg taaagacgag gccaatcgcc tggcgaaaac cctgggtaag   420
gaaacgagtt attacaagct ggataaaaac aagcaaccgc actttaaagg taaggagaat   480
gttgccgccg cgctgacgga gcgacaagcc gccgcgagtt cggtctgggt ttatgcccgc   540
tttgcgagta ccgaccatat ttggccggag ccagaagagg tggatgcgtt tctggcgtgg   600
caaaaaaccc tgccaaagga cgcctggctg cacttccact gccaagccgg taagggtcgt   660
acgacggcgt atatgatcat gcgcgatatt tggctgaatg gccaaaaaga cagtctggaa   720
accatttgcg cccgtcaaca cgcgctgggt ggccaagacg ttctgcatat gacccataag   780
gaagcgtggc gccaaacgat cgatgacaat aaggtttacc gtctgaaaca attctatacg   840
tatgtgaagg gtctgcaaca gggtaccatt acgggtacct ggacggaata tctgaaacaa   900
aatccgtga                                                            909

SEQ ID NO: 208          moltype = DNA   length = 924
FEATURE                 Location/Qualifiers
source                  1..924
                        mol_type = genomic DNA
                        organism = Desulfovibrio alcoholivorans
SEQUENCE: 208
atgaccccac tgtgtagtgc ccgcttcctg ccgcgcctgc tggcgtgtgc cctgtttctg   60
gccatcctgg gcgccgcgaa accaggtccg ggtgccgatg gccagttct gatttatgac   120
tatccaccgg gtcaagcgct gccgatccat ttccgtctgg ccgatggtgg tccaaagggc   180
gatccggcga gcgccaagct gcgtctgagc ggcagtagcg agtttgacgc cgcgggtctg   240
gacaatctgg cccgcaccct gccgggccca ctgacgattg tggatctgcg ccaagaaagt   300
catggcttcc tgaatgaccg cccggttagt tggtttgcgc caaaggatga ggccaatatg   360
ggtaaaaccc cggaagaggc ggcccgcgat gaagcccagc gcctggcggc cctgagtaaa   420
```

```
gccggcacgg ccgcggtgac cgttatcgag gcgaaaagta agagcggtgg tattaaaaag  480
gcgcgtacgc tgcgcgtgga cgttgttggt gttgcaagtg aagcacaatt gacagcagca  540
agagcagttg gttacctgcg cctgttcgtg acggatgaca tggccccaga tgcggcgcaa  600
gttgaccgtt ttgtggaata ttgccgtagt atggccccga atacgtggct gcacgttcac  660
tgtcacgggc gcgatggtcg tacgacgacg tttatggtgc tgtatgccct gctgcataat  720
ccggccggtc gcagtctgga ggagatcgcg gccgatcagg cggccgcggg tggtgttgat  780
ctgattggtc aaccgcgcaa gggttggaaa aagccactgt acatggcccg tgttgccttt  840
ctggaaagat ttgcagcata tgcagcagca aatccaggtg gtgcaccaat gaccttcagc  900
gcctggaccg cgacgcacaa atga                                         924
```

SEQ ID NO: 209          moltype = DNA   length = 954
FEATURE                  Location/Qualifiers
source                   1..954
                           mol_type = genomic DNA
                           organism = Desulfovibrio frigidus
SEQUENCE: 209

```
atgagcgcca aaattttctt cccgatcaag acccgtatcc tggacgatat cttcaaactg  60
atcctggcca gtttcgttat tctgctgatt tttaacagta atagcttcgc cgacgatagt  120
gtgctgattc tggacgcgcc ggccgttgaa aatctgccgc gcaacttccg caccagtgcg  180
tttccattta agaatagtac ggatagccca agtcgtacgg gtctggacac cctgaaaatc  240
agcggtagtg gtcaattcag tgccgaccag tttgacgtga tgcgtagcaa cctgccggcc  300
acggtgaccg ttgtggacct gcgccaagaa tttcatggta atctgaatgg cgcggccgtt  360
tgctggttca gttaccgcga tagcggtaac aaaggcctgg atagtgccca agtgaccagt  420
ggtgagcaag aagccctgag tctgctgggt gcgcagaagg agattcaact gggtatgaat  480
atcatcaaaa atgacgatgg tggctttaag gttgacaaaa agtaccagct gaaaccgcac  540
acggtgtata gcgaacacga gctgatgggt gcccgtgcgg ttggttacat ccgcattgcg  600
tgtaccgatc acctgcgtcc gccggacgtt gccgtggagc gcttcgtgaa gtttgtgcgt  660
aatctgaaaa gcgatgtgtg gctgcacttc cattgtcgcg ccggcaaggg tcgtacgacc  720
acgtttatgc tgatgtatga catgctgcgt aatgccaaca aactggacct gggtaccctg  780
gccgcgcgcc aaaagatgat tggcggtagt ggtctgctgg gcaaagttag cacggataag  840
gagtggaaaa ttgagatcgg tcatgaacgt caaaatttca tccgtaagtt ctatgactac  900
gcgaaagcca acccaaatgg cctgccaatg acctggctgg agtggcaaaa gtga          954
```

SEQ ID NO: 210          moltype = DNA   length = 960
FEATURE                  Location/Qualifiers
source                   1..960
                           mol_type = genomic DNA
                           organism = Clostridium acetobutylicum
SEQUENCE: 210

```
atgcacaaga aaaccaagct gatctgtatc ggcattctgg cgaccgccat cgtgacgatt  60
agcatttata acttcgattt ctttaaacgc accccactga aggagcataa agtgaaactg  120
gtgatcgacg ccgaaaataa gaatacgctg ccaccaaaat tccgtacgac cagtgacacg  180
attagtctgc ataagaaggg tagcctgaat ctgagtggcc tgagcgacct gaacgccagt  240
ggtagtggcg ccttcagtga ggatgaactg aaaagcatca agaataagat tggtaacaaa  300
ccaatcgtgg acattgacct gcgccaagag agtcatattt ttgttaatgg catcggtatc  360
agttggtatg gtaaaaacga cgatgccaat ctgaatctga ccagcagtga agtgctgaag  420
gacgaaaata ataaactgat gcgtattagt aaggataaaa aggtgacctt tgacaaactg  480
agcaaaaaga agagtatcag caacatcagt caactgaatg acgtgaagag tgtggagacc  540
gaagaacagc tggccaaggc gctgggcatc aattacagcc gcatcacggt gccggaccac  600
aagacgccag acgatgccca aattaacagt ttcgttagct ttgttaaaaa tctgccgaag  660
ggtacctggc tgcacttcca ttgtcgcggt ggcaaagtgc aaccgacgac ctttatggcg  720
atgtatgaca tgatgattaa tagcaagaaa gttagtttct acgatattat gaagcgtcaa  780
aaactgattg tgggtgcgga cctgctgagt ggtcaggata gcctgggtaa aagtgacgcc  840
gagaaacgcg tgcagctgct gaaaaagttt tacaattatt gtcaaaataa caacgataat  900
ttcaaaacga gttggaccaa ctataataat aagtaccgca tcaaaaatct gcagcgttga  960
```

SEQ ID NO: 211          moltype = DNA   length = 975
FEATURE                  Location/Qualifiers
source                   1..975
                           mol_type = genomic DNA
                           organism = Allisonella histaminiformans
SEQUENCE: 211

```
atgaagctgc aatggatgac caccctgctg ctgacgagtt gtattagtct ggcgggctat  60
tgcggtagcg gtgcggccga aatgcacagt ccaattccac tgcagcaaga aattccgcca  120
gcgccgggct actttaatgg tcgtctgtgg cgcctggatg ccagcgccag tagcccattt  180
ccaagccatt ttcgcaccag tgcgagtgcc tttgacctga gtctgccgca caaactgccg  240
ctgccgagcg gcaagggtct ggatcgcctg cgtattagtg gcagcgccca gccaagtggt  300
atggccatcc cggccctggc gcgccacctg aaatacctgg ccagtggtgg cccagttttc  360
ctgatcgatc tgcgccaaga aagccacggt ttctttaacg gtaacgcggt tagttggtat  420
ggcaatcgta attgggccaa ccgcaataag acgacggagg cggtttgtca agacgagaag  480
gaacgtattc agagcgcctg tggcacgcag gtgacggttt atagcctgaa tgaagaaaaa  540
gaaccggccg acgcggagaa gatcaccgtg caaagtgcca gtaccgaaga ggccctggcg  600
gcccgcgccg gtctgcatta tgtgcgtttc ccgattacgg atcacaccac gccgagcgaa  660
ggcgacgatc gccagttcat cagtttcatg cgtagtctgc cgccggacgc ctgggtgcac  720
tttcactgtg aggccggtat gggccgcacc acgaccatga tgattctgtg ggacatttat  780
aacaatccgg aactgccact ggaaaccatt gttgagcgcc agcatctgat tggtggtgcc  840
caaatcagtc tgtatcccca agaagagcgc aaaggtccgt ggaagtttaa cgagagtcag  900
agccgcgcgc gcattattca tatgttctat gatacgatgc acagtcagag tgccagtcac  960
gccgatcgtg cctga                                                   975
```

```
SEQ ID NO: 212            moltype = DNA  length = 987
FEATURE                   Location/Qualifiers
source                    1..987
                          mol_type = genomic DNA
                          organism = Centipeda periodontii
SEQUENCE: 212
atgcacgcct ttaaacatct gctgacggcc ctgctgctgt gtaccctgtg tatcattcca    60
tataccgcca gcgcgacgga cacgaacgcg gactaccgtg gttatgtgtg gcgcattgat   120
acggccgcgg gtaatgaagc cgagctgcca cacaactttc gcaccgccgg cagcccgttc   180
cagacccgta ccgacacggc gaagttcggt gtggatccga attataccCC aagtcgtgaa   240
ggcctggatg ccctgccact gagcggtagc gcggaattca atgttccggc cttccatgcg   300
ctgctgaaag atctgcacac gcgcgccaag ggtagcattt gcattgttga cctgcgccaa   360
gagagtcacg gtttcatgaa cggtaatgcg gttagttggt acggtaaaca tgattggggc   420
aatatcggtc gtacgaagta tgaagccctg tgtgacgaga atatgcgcat cgtagcgcc    480
cagggcaagg atgtggtgct ggcgcacctg gataagaaaa agcaaccgaa aaatccacag   540
accatccgcg tgattacggc catgacggag cgcgaactgg tggaggatgc cggtgttcgc   600
tacgtgcgtc tggccgttac cgaccacaaa tgggccgacc cgcaaacgat tgataatttt   660
gtggacctgg tgaagaagat gccagcggat acgtggatgc actttcattg tcaggccggc   720
aaaggtcgta cgacgagttt catggcgatg tatgacatga tgaagaaccc gagcgtgcca   780
ctgaaggata tcctgtatcg ccaatacctg ctgggtggtg cctatctggc ctatgaccca   840
accacgctgc atgccccgac cggctgggag gatgccgact atcatcataa ggccgagatg   900
attgcgaaat tttatgatta tgttcagcaa aatcacaaaa atgactatgc catcccatgg   960
agtatgtggc tgaaaaagaa cccgtga                                       987

SEQ ID NO: 213            moltype = DNA  length = 996
FEATURE                   Location/Qualifiers
source                    1..996
                          mol_type = genomic DNA
                          organism = Desulfovibrio magneticus
SEQUENCE: 213
atgccaaccc tgccgccacc gtgtcgccgt ctgcgccgta gccatcgcac aagattggca    60
gcaccatggc cattagcagg tttgttggca gttgcattgg cattgtttct gacgggtcca   120
atcgcggtgg cctgggccga accggaacca gatgttggtg ttttgacatt ggatgcagca   180
gcagcaagtg cattgccaca tcgctttcgt acgtgtttct ttccgctggc gcgcccagat   240
ggtgccacca ccccgagtca ggagggcctg aacggtctgc gcatcagtgg tagtagccaa   300
ttcagtctgg cgggtctggc gattatgcgc gaacaattcc cgccacgtgc cgttatcgtg   360
gacctgcgtc gtgaaagtca tggctttctg ggtgatgcgg ccgttagctg ggctgtgccg   420
gacaatcagg gtaatccagg tcgtgaagca gcatttgttg cagcagcaga agcaggtttg   480
ttggcagcaa ttgatgaacg tccagacatt gtggttgccc gcgaggcgaa acgtggtggc   540
ccaacgccgc tgaccctggg tccgctggcc gcggtgaatg aagcccaagc cgcggcgagt   600
ctgggcctgg gttacctgcg cctggccgtt agcgatcaca cgcgtccaga cgatgccgtg   660
gttgagcgct tcgtgcgttt ttaccgcagt ctgccgccag atgtttggct gcatttccac   720
tgtcgtggcg gtgcgggtcg caccaccacg tttatgacgc tggtggatat gctgcgtaac   780
gccccagccg tggcgttcga ggacatcatt gcccgtcaaa aggccctggg cggtagcgat   840
ctggcgaaaa caacaggtgg tagtgcacca ggtcgtgatg cattggcacg tgaacgtttg   900
gatttcctgc gtcgcttcta tgattacgcc cgtgccaatc caagtggtgc accattgggt   960
tggcgtgcat ggttggcagg tggtgcaaag ccgtga                            996

SEQ ID NO: 214            moltype = DNA  length = 1194
FEATURE                   Location/Qualifiers
source                    1..1194
                          mol_type = genomic DNA
                          organism = unidentified
SEQUENCE: 214
atgaaagcga agatctgtgg cagtctgtgc ctgctgagtg ccgccgtgct gctgagtaac    60
gcgcatgccg aaacgccaag cgacgttctg caagccatcc cacacaccga ggaactgctg   120
aacgtggtgg tggttagtcg tcatggcgtg cgcagcccga cgcagagcgc cgagaagctg   180
cacggctgga gtgacaagaa atggagtgcc tggccagttg cgccgggtct gctgacgagc   240
cgtggttttt acctggtgaa ggccacgtgg aaactgaatc gtagccgtgc gccatttacg   300
tacggtgttt gtccgaagcc agaagacgtg caaattattg cggatgttga cgagcgtacg   360
cgcaagacgc ccgaagccct gaatgagggt ctgtatccaa cgtgcggcta caaagttaag   420
gtgaccagca gtgaacatag tgccattttc agccgctga aggcgaaagt gtgtcgcatc   480
gattatccaa aggaactgga agaaaaactg acgcagaagg tggtgggtat caatgagaaa   540
ttcgccgccc aaatgccga atcagtaaa ctgacgggtc acgaattcac cggtccgatg   600
cgtgccaaag tgagtaaata caaggtgggc ttcaagggcg ccccgtacga ctgtagcagt   660
atcacggaga tttttgccct ggaatggggt cagaatccag aaaaaaaggt tgcgtgggat   720
cagctggact ggaacggtat cctgcacctg atgccgatcc gtgtgagtgt tttcagcgcc   780
ctgaatgcgc acatggaagt ggcgcgctat aagggcacgg cgctgcgaa caaaattatt   840
gagagtctgg atcacggtcc gaaatacacg tatctgattg tcatgacac caatctggcc   900
aatctgggcg aaattttcga tctgaattgg aagctgccgg gccgcgacca aaatgaaaat   960
acgcaggtg gttatctgac gtttgagaag tggagcgtta tggccaacc ggaaatccgc  1020
gtgttctata gtgccctgag tccggagcaa atccacgcgg agcgcgtgac gcaaccgacg  1080
gacgactttg aaaattctgcc gcgcggtacc aagttcgatg agtggaagac gacctacggt  1140
cgtcgtctgc aaagtaattg tattgcggac gataaatatg aaaaccgcaa gtaa        1194
```

```
SEQ ID NO: 215          moltype = DNA  length = 1275
FEATURE                 Location/Qualifiers
source                  1..1275
                        mol_type = genomic DNA
                        organism = Acinetobacter nectaris
SEQUENCE: 215
atgatcaaaa ataagctgat ttgtgcgatc ctgaccagta ttaccgccct gacgggtacg    60
acggtttatg ccgcgaccaa tgattaccaa ctggaacagg tggttacgct ggttcgccac   120
ggtattcgtc cacaaaccaa tctgcaaagg ctgaatgacg ccacgggcaa ggattggccg   180
aaatggagcg ttccagatgg ttatctgacg cagcgcggtt acgacggcat tctgaatcag   240
agccaatatc agctgaagac ctggcaagag gccggcctgc cgatcagtct gaaccaagag   300
aattgtagta atcaaaatca agtgtttatt tgggcggcgc cagaccagcg cacgcgtaag   360
accgccgatg cgatcgccga aagcattagt caaacgtgtc acccggaggt tggtgtgagc   420
ggttataaac atgatccgct gttcgatgcc ctgaagatgg gtagtgcgac cgaccaattc   480
gacgagatta agaaagaatt caaggcccgt atcgtgagtc aagatgacat ccaggcgaaa   540
tacgcccaga gcaaccaaca tctgaaagcg acggtgtgtg cgccaaatgg ttgtgacttc   600
ctggacaaag actggaaact gaagctgaac aagaatggtc aaccgaagct gaacggtcca   660
gccgacgagg gcagtaatat tggtgaaacg attcgcctgc agtatagtga gaatttccca   720
ctgagtcaag tggcgtttgg tcatgtgaag aatgccaatg atgttaaaaa gctgatggtt   780
ttgcacgacg ccaaatacaa atatctgaat gaaatcccgc tgttcgccca acgcggcggt   840
agcattctgt accaacaaat tctggatgcg ctggataata gtaaggccac cgaggcgcaa   900
ctgcatcgtc cgctggttgt ttttgttggt cacgacacga atattagcga gatcaaaacc   960
ctgctgcaat tcaattggca gctgccacaa tatctggcca acgacatccc gccaggcggt  1020
acgctgagtt ttgaaaaata caaggagaaa agcacgggcc aatattttgt gaaaattggc  1080
ttcagtgccc gtaccctgga tcaatggcgc cacctgaccg cgctgagtaa ggcgcaaccg  1140
ctgcacgaag acgttctgaa atacagttat tgtaaaacca ccagtgttgg cgtgctgtgc  1200
ccgctgaatc agttcctgca aaatgcccag aagcaaatcg tgcgtctgaa catcgaccaa  1260
ccactgtaca agtaa                                                   1275

SEQ ID NO: 216          moltype = DNA  length = 1296
FEATURE                 Location/Qualifiers
source                  1..1296
                        mol_type = genomic DNA
                        organism = Dyella marensis
SEQUENCE: 216
atgcgtccac caggtagatt tgcaagagca gcattgttgg gtgcagcatt gttggcacca    60
gttttggcac aagcagatga tgcaacgctg cgtctgcgcg ttgtggttct gcgccatggc   120
gtgcgtgccc caacgaaggc cccggatgcc ctggcgccat atgccagtcg tccatgggag   180
acgtggccgg tggcgccggg tcagctgacg ccacacggta ttgagggtat gcgcgccctg   240
ggtgcgaatt accgtcgcac cctggccgcc gacggcctgt ggagtggcgc ctgtgaccgt   300
atggatcaac tggtggttat cgccgacagt accccgcgta atcatgccag tggcgcggcc   360
ctggttcaag gtctggcccc agcctgcgac ggtacctacc tggccctgcc gacggatcaa   420
aacaacccac tgtttcactt tggcggtaaa gatgacgaca aggatgagga cgataaacca   480
gcattgccag ttacatggcc accagcagtt ttggcacaac tgcaacgcgt gctgctgggc   540
tgcgagggtc aagcctgcct ggcgaaagcc catgccgacg gccgcaagac cctgctggac   600
gccgcggacg atgccgcccg cgcgaaagcc ctgaagaccg ccggtagtct gagtgaaaat   660
ctgatgctgg aatatgccca aggcttccca agtgcgcagg ttgcctgggg tcaaggcgac   720
gaggcgacca tcggtcgtct ggtgacgctg cacaatctgc agtttgccct gagtaagaaa   780
gcgatgccag ccgccgcccg cggcggtagt aacctgctgg cccacgttct ggccacgctg   840
caacaagcag atggtgaaaa accagatgca gcagcattgg caccagcaag tgcacgtgca   900
gttttggttg ttggtcatga taccaatctg gcgcaactgg cgggtctgct ggatgtggac   960
tggcacgacg ccgcccaccc agacgactat ccgccgggcg gtgccctggt gttcgacctg  1020
tggcaaacgc atgacacgta cagtgtgacc gtgagtacgg ccatgccaac gctggatgcc  1080
ctgcgccgcg ccgatgttgc gcgtccaacc gccctgacgc gtaaaaccct gcgcctgacg  1140
ccgtgtccgg tgacggacca ttgtccactg gacaagctga gtagctggct gcgtggccgt  1200
ctggatgcga cgcgcattga cccggcgctg ccggacatgc gtgcctggag tgcgagtagt  1260
caagaggcgc acatgaacc agcggttagt aagtaa                             1296

SEQ ID NO: 217          moltype = DNA  length = 1299
FEATURE                 Location/Qualifiers
source                  1..1299
                        mol_type = genomic DNA
                        organism = Escherichia coli
SEQUENCE: 217
atgaaagcga ttctgatccc attcctgagt ctgctgattc cgctgacgcc acaaagtgcc    60
tttgcccaaa gcgagccgga actgaaactg gagagcgttg tgatcgtgag tcgccatggc   120
gtgcgtgcgc cgacgaaggc cacccaactg atgcaagatg tgacgccgga cgcctggcca   180
acgtggccag tgaagctggg ctggctgacg ccgctggtg cgtgagctgat tgcctatctg   240
ggccattacc aacgccagcg cctggttgcg gatggtctgc tggccaagaa aggctgtccg   300
caaagcggtc aagttgcgat catcgccgac gtggatgagc gtaccgcaa gacgggcgaa   360
gcctttgccg cgggtctggc gccagattgt gcgatcacgg ttcacacgca agcggatacg   420
agtagcccgg acccgctgtt taatccactg aaaacgggcg tgtgtcaact ggacaatgcg   480
aatgtgacga atcgatcct gagtcgtgcc ggcggcagta tgccgactt cacgggtcat   540
cgccagacgc cgttccgtga actggagcgc gttctgaatt ttccgcaaag taatctgtgt   600
ctgaagcgta aaaagcagga tgagagctgc agtctgacgc aagccctgcc gagcgagctg   660
aaagtgagcg cggacaatgt tagcctgacc ggcgcggtga gcctggcgag tatgctgacc   720
gagatttttc tgctgcaaca ggcccaaggt atgccggaac aggttggggg tcgcattacg   780
gacagtcacc agtggaacac gctgctgagc ctgcataatg cgcagtttta tctgctgcaa   840
```

-continued

```
cgcacgccgg aggttgcccg cagccgtgcc accccgctgc tggatctgat caagaccgcc    900
ctgacgccgc atccgccgca gaagcaagcg tatggtgtga cgctgccaac cagtgttctg    960
ttcattgccg gtcatgacac gaacctggcc aatctgggtg gtgccctgga gctgaattgg   1020
acgctgccgg gtcaaccgga caacacgccg ccaggtggcg agctggtgtt tgaacgttgg   1080
cgtcgcctga gcgacaatag tcaatggatc caggttagtc tggtgttcca aaccctgcag   1140
caaatgcgcg ataaaacgcc gctgagtctg aataccccgc cgggtgaagt taagctgacg   1200
ctggccggtt gtgaagagcg taatgcgcag ggtatgtgta gtctggccgg tttcacccaa   1260
atcgtgaacg aggcccgcat tccggcctgt agcctgtga                          1299

SEQ ID NO: 218          moltype = DNA   length = 1311
FEATURE                 Location/Qualifiers
source                  1..1311
                        mol_type = genomic DNA
                        organism = Anaerovibrio sp.
SEQUENCE: 218
atgcaaccac tgaactatac gattaaaaag tgtctgggtc tgctgggccc agcggccatc     60
agtgcgctgc tgctgctgag ctggagtacc tggacggaag ccgcgagtga actgaccgat    120
aagggttacc agctggacca aattgtgatg ttcagccgtc acaatctgcg taccagtatt    180
acgagcgaag acagtagtgc cgccacgatg atgacccatc cgatgccgaa atggcaagtg    240
ccgcgcggca acctgacgat gaagggtggc gttaatgaga ccattctggg tcagtatttt    300
cagctgtatc tgatggatga aggcttcatg gcggatagtt ggcaaccggg ttacggccaa    360
gttgacttct atgccaacag ttacgaacgc acgatcgccg cgcgtta ttttgccacg        420
ggtctgctgc caacggccaa tattaccatc aaacacacca aggccgtggg tggtagtgat    480
gccgttttca ataaaccgtt tgccatggac acgccaaaac tgatggagct ggcgatggag    540
tatcataacg agtacttcca aagttataaa gatgtgttta gcaagtgcta cgacagcttc    600
gcccgtgtta ccgactttcc gaatagcccg tatgccaaga acgacggcat tgaccacatt    660
aatacggatg acctggccct gacctttagt ggtaaggaga agaatgtgat caattacgac    720
ggtaccgccc gcaaggccta taaactgctg gatccaatta ttatgaatta ttaccaggaa    780
gccgataaca gtaaggcgga cttcggtacc ggcctgaccc gtaaggactg ggagaatctg    840
ggtgccgtga agacgaagag catcgaaatg gtggttggca atccagccgt ggcgctgaat    900
cacagtcacg acattctgaa catcatggaa agcgacctga aaaatgatac gctgaagttt    960
gccttcattt gtggtcacga caccaacatc tttacgattc tgacggccct ggagaccgag   1020
gattacagtc tgccggagac gatcctgacc aaggcgcccc tgggcgttaa aattgtgttc   1080
gagaagcgcc gtaatccgca gggcgacctg tttatctacc catacattgc gtatatgacg   1140
gacgaccaac agcgcaatag tcgtcagctg agtctgcacg aaccgccaat gatctacccg   1200
ctgaatttcc gcggtctggc gaagaatggt gatggcctgt accgctatga ggatattctg   1260
accctgatgg accgtgtgaa cgccaaatat gaggagtatt gcctgcattg a             1311

SEQ ID NO: 219          moltype = DNA   length = 1311
FEATURE                 Location/Qualifiers
source                  1..1311
                        mol_type = genomic DNA
                        organism = Avibacterium paragallinarum
SEQUENCE: 219
atgaagaagc tgacgctgag tctgaatctg gttagtctgc tgagtggtag cctgtttttac    60
ccaaccaatc tgagtgccgc gccgaacgtg ccggataatc atcaagccca agccctgcaa    120
ctgaagaaaa tcgtgatctt cagtcgtcac ggcattcgaa ccccactggt gggtaaagag    180
agtattctga gtcaggcgac gccatatcgc tgggttaagt ggcaagataa gaccggttac    240
ctgacggcca aaggcgcccg cctggagaag ctgttcgcgg cctattggag cgaatggctg    300
cagcaaacgg gtattctgag tagtcaatgt ccaaaggatg atctgttcat ttacaccaat    360
gcgcgtccac gcacgattga cacggcgtgtg agttttgcca aaggtgcgta cagccactgt    420
gccatccgcg tgaattatct gggtgaatat aacaccatgg ataatacctt caacccagtt    480
attcgcagta aggtggataa agcgttcgag caaaaggccc gtaaagccgt ggatgaactg    540
gtgggcgaag gcggtttcgc gcaactgaac cgtcatctgc aaagcaattt taatgcgctg    600
agtcaagccc tgaatcaagg tcaaagtccg ctgtgtcaag agagcaact gtgcaatctg      660
gaccaagagg ccaatacgct gacgttcacc caaggtaaag agccgaagac gaccggcgcg     720
ctgcgtgatg gtacgggcgc cgccgatagt ttcctgctgc aatattatga aggctttccg    780
gcgaaagacg ttgcctgggg tcgtatcgac aatcaagaaa gttggaaaaa gattgtggac    840
atcaaagagc gctacaacca gctgctgttc ggtacgcaag tgatggcgaa agaagcggcc    900
acgccgctgc tgaccttcat ccaaaacagt tttaaggatt acggctacca gcacccatat    960
attgaaaagg cgcgtaatgc gaaggtggtg ctgctggttg ccacgacag caatgtgggt    1020
agtctgctgc cactgctgaa agtgaaaccg tattatctgc cggatcaact ggagaccacg   1080
ccgatcagtg gtaaggtggc cttcgagaag tgggtgaatg ccaaaggtga agccttcatg   1140
aaggtggaat atgtttatca aaccattgac caactgcgca cggcgcacgaa actgagtctg  1200
accaatccgc cgaaccgtat cacgctgcag ctggaagact gtccaacgaa tgcgcaaggt   1260
ctgtgcaaga tggatgactt ctataatgcc gttaagaacg cgctgaaatg a             1311

SEQ ID NO: 220          moltype = DNA   length = 1317
FEATURE                 Location/Qualifiers
source                  1..1317
                        mol_type = genomic DNA
                        organism = Cronobacter sakazakii
SEQUENCE: 220
atgaaaaacgc tgttcctgca tctgttcctg ttcatcttca ttttcatgcc aggtgtgttc    60
ccgctgcacg cccaaggtgc cgataaaatg aaactggaac gcgtggtgat cgttagccgc    120
catggtgtgc gtgcgccgac caagtttacg ccgctgatgc aagagatcac cccgtaccca    180
tggccgcaat gggacgttcc cctgggctgg ctgacgaccc gcggtggtga gctggccagt    240
gagctgggcc gctatcaaaa agcgcgttct ctggataaag gcatcctgga aagtcatggt    300
tgcccgagtc cggaacaagt tgcggtgatt gcggatacgg accagcgtac gcgtaaaacc    360
```

-continued

```
ggcgaagcct ttctggccgg cttcgcccca ggctgccaaa ataaggtgca ctaccagaaa   420
gagctggata agaaggaccc gctgtttaac ccagtgaaga tgggcgtgtg tagtttttaac  480
gtgagcaaaa cgcgcgaggc catcctgacg cgtgccgagg gtaatatcga acgctatacg   540
caacgttacg atagcgcgtt ccgcaccctg gagcaagtgc tgaatttcag tcagagtgcc   600
gcctgcaaga gtccgcgcca accaggttgt acgctgacgg gtgtgctgcc gagtgagctg   660
agtgtgagtc aggacaacgt gagcctgttc ggtgcctgga gtctgagtag caccctgacg   720
gagatcttcc tgctgcaaga agcgcagggc atggcggaag tggcctgggg tcgcattcat   780
ggcgagaaac aatggacgga actgctgcgt ctgcacaatg cgcaatttga cctgctgcaa   840
cgcaccccgg atgtggcccg cacgcgcgcc acgccactgc tggacctgat cagtcgtgcg   900
ctgattagta acggtagtac cgagagtcac tatggtatca agctgccagt gagtctgctg   960
ttcatcgccg gtcacgatac gaatatcgcg aacctgagcg gcgtgtttgc cctgaattgg  1020
agtctgccgg gtcagccgga caataccccca ccaggtggcg aactggtttt cgagcgctgg  1080
aaacgtgtga gcgacaatac cgactggatt caaatcagtt ttgtttacca gacgctgcaa  1140
cagatgcgcg aatttaagag cagcagtagc agtagtctgc cacataaaat tgtgctgcca  1200
ctgccgagct gtcaagagaa aaacgcggaa ggtatgtgta gtctgaaacg tttcaatgac  1260
attgttcaaa cgatccgcgt gccacaatgt gccgttatgg cggagaagga ccaatga     1317
```

SEQ ID NO: 221          moltype = DNA  length = 1362
FEATURE                 Location/Qualifiers
source                  1..1362
                        mol_type = genomic DNA
                        organism = unidentified
SEQUENCE: 221

```
atgatcatgc tgggtagccg caatctgctg accgttttc tgttcacgtt cacgagtctg    60
agctttgcgc aaaccaatgt gattgccggc agtaaaacgg cgtatcagta taatagcaac  120
caaaccctga cgctggcccc aacgggttac caggccttct atatcgatca tgttggtcgt   180
cacggcagtc gctacattag caagagtaag tacgaagacc tggcgtatca tattctgctg   240
ctggcggaca gccaacacca actgaccgac agtggtaaag atctgctgcg ccaggtgacg   300
atcctgaagc aactgaatca gaaccattat ggccaactga ccaatctggg tcgtaaagac   360
attagtctga tcagtaatcg tatgctggag aacaatcgca cggtgttcaa gggtcaaaaa   420
attgaggtta tcagcagcag tagcccgcgc gccaaggaga ccgcggagat tttcatcgat   480
agttttaagg cgaagtatcc gaatatccac gtgatccaac agccagacaa tgaacaaacg   540
ctgctgcgtt tctttgaata cagtccggcc tatagcgagt ataagaaaag caaagcggtt   600
aaagatgccg ttaaaagtat tgagtatgcc agccaaacca agcaaatgag taaacaggtg   660
gccaagggca tctttaaaaa gagtttcctg atcaaactga agaaaggtct ggacgaaagc   720
gaggatacgc tggttaagac gagcgacttt gtgattgcca tttatcaact gtatcaagaa   780
ctgcaagcgt tcagcccgca agtgctgacc gataaccacc tggacctggg ccgctatttt   840
agtacggaac aaaaaaatttg gctgaacacg gttgtgaccg ccaagaacta tctgcagatc   900
ggtccagcct tcgatgccac gggcattcaa attaagatcg cggcccccgct gctgtgggac   960
atgattcata gtgcggataa agccatcgtt gataataatg tggacgccaa tctgcgtttt  1020
gcccatgccg aaaccgtgag tccgctggcg acgctgctgg aaattgaagg tagcgcgaac  1080
gtgaccaaaa cgctgttcaa ttatccaacc atctggcgcg ccgataagat tatcccaatg  1140
ggtgccaata tccagtggat tttctataaa agtaagcaaa cccatcaacc gatcctgatc  1200
aaagtgctgc tgaacgaacg cgaagttcac ctgccgatta aaacggacag ttatccgtac  1260
taccgctgga ataatgtgaa gcaattctat gttaataaac tgaataagct gggcctggac  1320
gagaatcaaa gcgccatcga aatgctgaaa aacctgaaat aa                     1362
```

SEQ ID NO: 222          moltype = DNA  length = 1635
FEATURE                 Location/Qualifiers
source                  1..1635
                        mol_type = genomic DNA
                        organism = Corynebacterium singulare
SEQUENCE: 222

```
atgcgtatcc gtaccctggc cctggcgacc gccattgcct gcacgctgac gccggttcag    60
gcgctggccg ccgatgacac cacgtactat agcaccaagc aacattacga accgcaaggt   120
agtaactata gtacggcccc aacgggcttt catcaaatct atacgagtac ggttaaccgc   180
cacggtagtc gtggtctgag tggttttaaa tacgatgacc tggcccagca aatgctggag   240
tatgcgaaag agcatgatca actgaccgag ctgggcgaaa agctgatccc gcaagtggaa   300
gcgatgatta cggttaataa ggaactggcg ggtggcccag gtcaggaagc cggttatggc   360
aatctgaccg ttgtgggtcg cgaggagctg caaggtatcg gtcaacgtaa tgcgcaacgc   420
aacgccgccc tgatggagag cattgaagag gacaacctga aagtgaagta catgagtagc   480
ggcgcggatc gtgccaacga cagtggttgg agtttcggtg aagcctggct gagccataat   540
agtaaactga gcgacaatct ggtggatggc atggaagacg gccacgtggc cattgagacc   600
cgcacggatc tgctgcatgc ccacaaggat aaaaagagtc cgagttacga gcgttacagc   660
aagtggaaag acagcgagac gctggatagc aaagttcagg aagcctatgc gaaaccagcc   720
agtcaaaccg cggcccgcag cctgctgaac aaaatcttta cggaggactt catcgccggt   780
ctggaagacg gcaccatcac gtttgttggt cgcgacaata agggcaagag tgtggagggt   840
attgtggaag cggcgctgca attttataac ctgtacatta ttgccccggc gctggcgcat   900
gaagagcaga cgccaagcga aggttggatc tttgaccaat atatggacaa tgccagtagc   960
ccgaccttg cctatctgct ggacgtggag gattattatc aaaaaaaggccc agccatcgag  1020
ggtcaaaccg ttgcctatga caattatgag ccactgctgg aggaaatgat ccaaggcgtt  1080
aaagatcgtc cgaaggtgg cgacgtggcc gcggagtacc gcttcggtca cgccgaaacg  1140
attatcccac tggccgccct gctgaagctg ccgggtagtg aaaaaggcac gccagccgat  1200
gagctgtata cgtgggagaa tagcgagtgg cgcggtacga ggttgcccc aatggtgacc  1260
aacattcagt gggacgcctt tcaaaacgaa cgcggcgaga ccctggtgcg catgctgtac  1320
aatgaaaaag aaatcgcgtt ccatgacggt tgcgagccga tcgagacggg cagtaccttc  1380
tataccattg atgaactgag tgactgtctg ccactgggtg ccacgagtga ccacagtaag  1440
gcgcgcctgc aagaagacaa aacccatgag accgcccagc aagcccgag tgatgccgtt   1500
agtagtaagg ccaaagtgtg gggtattgtt gcagcagttt tgggtgcatt ggcaattgca  1560
```

```
gttggtgcag caaccgccaa tgcccaacag atcaaggaca ttctgaataa gtttggtatc   1620
cacgtgccgt tctga                                                     1635

SEQ ID NO: 223           moltype = AA  length = 417
FEATURE                  Location/Qualifiers
source                   1..417
                         mol_type = protein
                         organism = Pseudomonas putida
SEQUENCE: 223
MSMKTLLIAT LVLGAGAAAQ AVANDDAQVR LGEYLARAGD CVACHTAKGG KPFAGGLPME   60
TPIGTVYSTN ITPAASGIGQ YSFEDFDQAV RRGIGKDGST LYPAMPYPSY ARVSEQDMQA   120
LYAYFMKGVA PVEQANKASD IPWPLSMRWP LAIWRGVFAP EAKPWQASAT ADPVVNRGAY   180
LVEGLGHCGA CHTPRALTMQ EKALSAADGE QFLAGSAPLE GWIAKNLRGD HKDGLGSWSE   240
AQLVQFLKTG RSDRSAVFGG MSDVVEHSMQ HMSDADLTAI ARYLKTLPPS NPDDQLHVYD   300
KQVADALWKG DDSKPGAAVY IDNCAACHRT DGQGYTRVFP ALAGNPVVQT ADATSLIHVV   360
LAGGTVPATH SAPSNFTMPA FGWRLSDQEV AEVVNFIRSS WGNQGSAVTA GDVKSLR     417

SEQ ID NO: 224           moltype = AA  length = 594
FEATURE                  Location/Qualifiers
source                   1..594
                         mol_type = protein
                         organism = Pseudomonas putida
SEQUENCE: 224
MATVLNKVDA VIVGFGWAGA IMAKELTEAG LHVVALERGP MQDTYPEGSY PQVIDELTYS   60
VRKKLFVDVS KETVTVRHSV NDVALPNRQL GAFLPGKGVG GAGLHWSGVH FRVDPVELRL   120
RSHYEERYGR TFIPEGMTIQ DFGVSYEELE PYFDFAEKVF GTSGQAWTVK GQVVGEGKGG   180
NPYAPDRSNP FPLPAQKNVV SARLFEKAAT SLGYKPYNLP SANTSGPYTN PYGAQMGPCN   240
FCGFCSGYVC YMYSKASPNV NILPALRQVP NFELRPNAHV LRVNLDDSKR RATGVTYIDA   300
QGREVEQPAE LVILAAFQFN NVRLMLLSGI GKPYDPVKNE GVVGRNFAYQ NMGTVKAFFD   360
KDTYTNNFIG AGGNGIAIDD FNADNFDHGP HGFVGGSPMW VNQAGSRPIA GTSNPPGTPA   420
WGSAWKKATA DYYTHQVSMD AHGAHQSYRG NYLDLDPTYR DAYGQPLLRM TFDWQENDIK   480
MNQFMVDKLS KIAQAMNPKA IAVLGKQVKD HFNTTSYQTT HLNGGAIMGT DPKTSALNRY   540
LQSWDVHNVF VPGASAFPQG LGYNPTGLVA ALTYWSARAI REQYLKNPGP LVQA         594

SEQ ID NO: 225           moltype = AA  length = 246
FEATURE                  Location/Qualifiers
source                   1..246
                         mol_type = protein
                         organism = Pseudomonas putida
SEQUENCE: 225
MPEHAPDNSR RDFLRKTLTL IPVVTVASTG LGAGASQLLA APQQQPNVPA TPPAGDYRPT   60
FFSAEEWAFV QAAVSRIIPA DELGPGALEA GAAEFIDRQM NTPYATGAQW YMQGPFNADA   120
PPELGYQLQL SPQQIYRLGI AAVDGWCKAN GGQVFAAQDS ATRDRILSKL EAGELVFESV   180
PAKVFFSLLV QNTREGFFCD PIHGGNKGMV GWTQIGFPGA RADFMDWVER NEPYPFPAVS   240
IRGERA                                                              246

SEQ ID NO: 226           moltype = AA  length = 527
FEATURE                  Location/Qualifiers
source                   1..527
                         mol_type = protein
                         organism = Burkholderia pseudomallei
SEQUENCE: 226
MNKHWIRVSP IALAAAIGLT ACGGDDVTSP GLSAVKNVVV IYAENRSFDN LYGNFPGANG   60
LQNVTAASAA QVDRDGTPLA TLPKIWGGLT AAGVTPAVTE AMTANLPNAP FAIDDPNGFN   120
TPMSVTTRDL VHRFYENQMQ IDGGKNDKYA AWSDAGGLVM GHYTADPSKL PLWKLAQQYT   180
LADNFFMGTF GGSFLNHQYL ICACAPFYPN ADKSPAASQI SVVNPDGVTL TTASNSPASA   240
LSGPPKFVKS GGLTPDFYAV NTMQPPYQPS ANAAPTGGDP NLADPANPST LPPQTQQNIG   300
DLLTSAGVSW AWYAGAWGAA LQAAQSGTSG VIYGPNMTSP NFQPHHQPFN YYANQAPGSA   360
NRAQHLLDAG SNGAALIQAI DAGKLPQVTF YKPQGNLNEH PGYTDVASGD QHIADVIAHL   420
QKSPQWNNMV VIVTYDENGG FWDHVAPPKG DRWGPGTRIP AFVISPFAKQ GFVDHTQYDT   480
ASILRFITRR FALPKLAGLK QRDDALVANG FKPMGDLTNA LTLSTGN               527

SEQ ID NO: 227           moltype = AA  length = 256
FEATURE                  Location/Qualifiers
source                   1..256
                         mol_type = protein
                         organism = Acetobacter pomorum
SEQUENCE: 227
MRFRNAVFYA VSLSLAHTFF GHTAQAQQFT LPDGRAFLPP PPRAEEPAQQ ADLRAFEKTR   60
GLKDKARWKL AQNDANLNPD HVIKDFSCAA GFNLDPAKLP AMVDLLTSLA QPVEQDVSNE   120
KDFWKRRRPF VGTDKDICTA HSDGLDHSYA YPSGHTTWGW LTASILASAL PDRATQIMQR   180
GRIFGESRIV CGVHWKSDVQ AGYMNGSAMF ATLQEQPAFT QKMAKVRQEL LALRNAKTEP   240
DTKTCAVEQQ AAQDIF                                                   256

SEQ ID NO: 228           moltype = AA  length = 236
FEATURE                  Location/Qualifiers
source                   1..236
                         mol_type = protein
                         organism = Morganella morganii
```

```
SEQUENCE: 228
MRKLTLTLSA LALALSLNSV ADAKVYMPEK VSDGVTVAQL AEQHAIHWIS VEQIEESLKG    60
QPMAVGFDID DTVLFSSPGF YRGKLEYSPN DYSYLKNPEF WEKMNNEWDK FSMPKKSGME   120
LVQMHLKRGD TVYFITGRSK TKTETVTKYV QEGLRIPADK MNPVIFAGDE EGQNNKVSWM   180
RDHKLKIYYG DADADIAAAR ELNIRGIRVL RASNSSYQPL PKAGQFGEEV VINSEY       236

SEQ ID NO: 229           moltype = AA   length = 469
FEATURE                  Location/Qualifiers
source                   1..469
                         mol_type = protein
                         organism = Azospirillum brasilense
SEQUENCE: 229
MSDISKVFDL IKEHDVKYVD LRFTDPRGKL HHTAQHVSTI DEDVFEDGIM FDGSSIAGWK    60
AINESDMILQ LDPTTAVMDP FSAQPTLNIL CDVYEPSTGQ PYARCPRGIA KAAEKYMASA   120
GIGDTAYFGP EAEFFVFDDV KFKVEMNKVS YEFDSEEGPY TSDKDYEDGN LGHRPGVKGG   180
YFPVAPVDSG SDLRAEMLSV LAEMGVPVEK HHHEVAASQH ELGIKFDTLV RTGDNMQYYK   240
YVVHNVAHAY GKTATFMPKP VFGDNGSGMH MHQSIWKEGQ PLFAGNQYAD LSELALYYIG   300
GIIKHAKALN AFTNPTTNSY KRLVPGYEAP VLLAYSARNR SASCRIPYVA SPKGKRVEVR   360
FPDPSANPYL AFAALLMAGL DGIQNKIHPG EAMDKNLYDL PAEELAKVPT VCGSLREALD   420
SLKADSAFLQ KGDVFTKDMI ESYIDLRTEE LLAFETMPHP IEYKMYYSV              469

SEQ ID NO: 230           moltype = AA   length = 468
FEATURE                  Location/Qualifiers
source                   1..468
                         mol_type = protein
                         organism = Pseudomonas stutzeri
SEQUENCE: 230
MSKSLQLIKD YDVKWIDLRF TDTKGKQHHV TVPARDAQDE DFFEHGKMFD GSSIHGWKGI    60
EASDMILMPV DETAVLDPFT EEPTLILVCD IVEPSTMQGY DRDPRSIAKR AEEFLKTTGI   120
GDTVFVGPEP EFFIFDQVKF KSDISGSMFK IYSEQGSWMT DQDVEGGNKG HRPAVKGGYF   180
PVPPCDHDHE IRTAMCNAME EMGLVVEVHH HEVATAGQNE IGVKFNTLVA KADEVQTLKY   240
CVHNVADAYG KTATFMPKPL YGDNGSGMHV HMSISKDGKN TFAGEGYAGL SETALYFIGG   300
IIKHGKALNG FTNPSTNSYK RLVPGFEAPV MLAYSARNRS ASIRIPYVSS PKARRIEARF   360
PDPAANPYLC FAALLMAGLD GIQNKIHPGD AADKNLYDLP PEEGKLIPQV CGSLKEALEE   420
LDKGRAFLTK GGVFSDEFID AYIELKSEEE IKVRTFVHPL EYDLYYSV              468

SEQ ID NO: 231           moltype = AA   length = 1003
FEATURE                  Location/Qualifiers
source                   1..1003
                         mol_type = protein
                         organism = Azospirillum brasilense
SEQUENCE: 231
MTTTLPKPFD TALAGRGLER WRAEAATAAD GTGDDDLGAW AEAYADSAEG RALIDAVCGN    60
SPYLGQILTR ELPFVREMVS EGYDAAFAAL LRRLETDCAE ERNIDRLMTA LRIAKRRAAL   120
LIAMADITGA WELEAVTGAL SDIAETSVRM AANHLLRRAA EAGTLTLPEP QRPWVGSGLI   180
VLGMGKLGAR ELNYSSDIDL IVLYDDAVVQ TPQPDNLART FIRIARDLVR IMDERTKDGY   240
VFRTDLRLRP DPGATPLAVS VSAAEIYYGS VGQNWERAAM IKARPIAGDP EAGAHFLRFL   300
EPFVWRRHLD FAAIQDIHSI KRQINAHKGH REVTVNGHDI KVGRGGIREI EFFAQTQQLI   360
FGGRDIRVRI APTLLANKAL CAVGRVPEAA VEELEEAYRF LRRVEHRIQM TDDRQTHQIP   420
ADDEGVAHLA TFLGYERVED FRADLLAQLG RVEDRYAELF EEAPSLSGPG NLVFTGTDDD   480
PGTVKTLAGM GYRDPSRVIA VVSTWHRGRY RSTRSGRARE LLTELVPAML NELAKTPAPD   540
DALVKFDSFL ERLPAGVGLF SLFIANPWLL ALVAEIMGTA PQLAETLSRN PSLLDAVLSP   600
DFFDPLPDAA GLTPEYQRFI AGAHNFEDVL TLSRRWTNDQ RFFRAGAHILR GITDGDRCGP   660
FLADLADVVV PELAARVEEE FAARHGRIPG GAWVVVAMGK LGSRQLTITS DIDLIVVYEV   720
PPGTRQSDGA KPLAPNEYYI KLTQRLTNAI TAPMADGRLY EVDMRLRPSG NAGPLATALD   780
AFTAYQAKDA WTWEHMALTR ARVIGSDSGG GDPALGHKVE SAIRGVLTGP RDPAKVLRDV   840
ADMRRRIDKE FGTTNPWNVK YARGGLIDIE FTAQYLQLRH GHAHPDILSI ATSRALLNAA   900
AAGLLAPEVA EELVATLKLW RRVQGFLRLT TDGVLDPRQV SPTLREGLSR AAFPDEEPAV   960
DFAALDSRIR DIAARAHRHF VALVEEPASR LPPPETNEEA KLP                  1003

SEQ ID NO: 232           moltype = AA   length = 996
FEATURE                  Location/Qualifiers
source                   1..996
                         mol_type = protein
                         organism = Azorhizobium caulinodans
SEQUENCE: 232
MPLRQAMTAL TSPSPELGPG LAAAIREAPV LFDEAAAAVK LSHTLERFAD HDRASLDALL    60
VAHPMARQVV LGVMEGAPFL TDVIRREPAR LLRALETDPV ARVAALVAAA GVQVREAEDE   120
AAVMRALRRM RSEAALVIAL ADIGGVLPLM DVTRALTRVA DTAVALALDF LLREAAGSGK   180
LLLPDLNVPG KGSGLAAIAM GKHGAGELNY SSDVDLILVY DRAVAPLGPD AEASPTYVRI   240
AKGLVRLLQE RTEDGYVLRV DLRLRPDPGS TQVALSTASA LAYYEREGAT WERAAYIKAR   300
PVAGDLVVGR EYLDELAPFV WRRVLDYQAI SDVHAMKREI HAFRGHEVVA VEGHNVKLGR   360
GGIREVEFFV QTQQLIAGGR DRDLRSPRTL EALGALVDHR WIAPEVRDDL SEAYVFLRRV   420
EHRLQMVADA QTHTLPEGRE ALEAFARFMG YKRDSFAAA LVERLQRVQG HYAHLFEDSV   480
THPCLQGELH FPLDRDDRAT LGTLSRLGFR DPPAASRLVR EWLAGQPRAL RTDAAREHLA   540
RIVALLIEQL SHGGDPDGAL NAMDSFLRDL PGPHLLAALE HNPDLVRLIA TIVSAAPRLG   600
ETLARRPSLA DALLDPAFFD VLPDEPALAA HLEALLDAAP NEEEQFDRAR RFFRQEQHVLI   660
GVRIVSGTLP AARAGEAYAR VAEVIIRALH ARVWARFVEA HGSIPGADTA VLSMGKLGSR   720
EMTAGSDLDL IVLYDFDPAS DGTSDGPRPL VGAQYFARFT QRLVTALTSL TNAGKLYDVD   780
```

```
LRLRPSGRSG PVATRIGSFE NYQRTEAWTW EHMALTRARI ISASPAFARR VEQVILQVLA    840
HPRDPRRIAG DILDMRRAIA AEKGESDRWN LKHAAGGQVD AEFLAQFLVL IHAERHPEIV    900
DTATARILTV AGWLQLLSPE DCQTLSNACR LYQDLTQVLR LAIDRPFVPA QASPALKALL    960
ARAGEMPDFS SLDAHLTDTE ARVRAIFERI LEAASA                             996

SEQ ID NO: 233            moltype = AA   length = 946
FEATURE                   Location/Qualifiers
source                    1..946
                          mol_type = protein
                          organism = Escherichia coli
SEQUENCE: 233
MKPLSSPLQQ YWQTVVERLP EPLAEESLSA QAKSVLTFSD FVQDSISAHP EWLTELESQP    60
PQADEWQHYA AWLQEALCNV SDEAGLMREL RLFRRRIMVR IAWAQTLALV TEESILQQLS    120
YLAETLIVAA RDWLYDACCR EWGTPCNAQG EAQPLLILGM GKLGGGELNF SSDIDLIFAW    180
PEHGCTQGGR RELDNAQFFT RMGQRLIKVL DQPTQDGFVY RVDMRLRPFG ESGPLVLSFA    240
ALEDYYQEQG RDWERYAMVK ARIMGDSDGV YANELRAMLR PFVFRRYIDF SVIQSLRNMK    300
GMIAREVRRR GLTDNIKLGA GGIREIEFIV QVFQLIRGGR EPSLQSRSLL PTLSAIAELH    360
LLSENDAEQL RVAYLFLRRL ENLLQSINDE QTQTLPSDEL NRARLAWAMD FADWPQLTGA    420
LTAHMTNVRR VFNELIGDDE SETQEESLSE QWRELWQDAL QEDDTTPVLA HLSEDDRKQV    480
LTLIADFRKE LDKRTIGPRG RQVLDHLMPH LLSDVCARED AAVTLSRITA LLVGIVTRTT    540
YLELLSEFPA ALKHLISLCA ASPMIASQLA RYPLLLDELL DPNTLYQPTA TDAYRDELRQ    600
YLLRVPEDDE EQQLEALRQF KQAQLLRIAA ADIAGTLPVM KVSDHLTWLA EAMIDAVVQQ    660
AWVQMVARYG KPNHLNEREG RGFAVVGYGK LGGWELGYSS DLDLIFLHDC PMDAMTDGER    720
EIDGRQFYLR LAQRIMHLFS TRTSSGILYE VDARLRPSGA AGMLVTSAEA FADYQKNEAW    780
TWEHQALVRA RVVYGDPQLT AHFDAVRREI MTLPREGKTL QTEVREMREK MRAHLGNKHR    840
DRFDIKADEG GITDIEFITQ YLVLRYAHEK PKLTRWSDNV RILELLAQND IMEEQEAMAL    900
TRAYTTLRDE LHHLALQELP GHVSEDCFTA ERELVRASWQ KWLVEE                  946

SEQ ID NO: 234            moltype = DNA   length = 18
FEATURE                   Location/Qualifiers
source                    1..18
                          mol_type = genomic DNA
                          organism = Escherichia coli
SEQUENCE: 234
gttggccttc tggccgcc                                                 18

SEQ ID NO: 235            moltype = DNA   length = 18
FEATURE                   Location/Qualifiers
source                    1..18
                          mol_type = genomic DNA
                          organism = Escherichia coli
SEQUENCE: 235
gttgccggtt tgttcatg                                                 18

SEQ ID NO: 236            moltype = DNA   length = 18
FEATURE                   Location/Qualifiers
source                    1..18
                          mol_type = genomic DNA
                          organism = Escherichia coli
SEQUENCE: 236
gttgaccttc tccttacc                                                 18

SEQ ID NO: 237            moltype = DNA   length = 18
FEATURE                   Location/Qualifiers
source                    1..18
                          mol_type = genomic DNA
                          organism = Escherichia coli
SEQUENCE: 237
gttgaccttc tccttacc                                                 18

SEQ ID NO: 238            moltype = DNA   length = 18
FEATURE                   Location/Qualifiers
source                    1..18
                          mol_type = genomic DNA
                          organism = Escherichia coli
SEQUENCE: 238
gttgaccttc tccttacc                                                 18

SEQ ID NO: 239            moltype = DNA   length = 18
FEATURE                   Location/Qualifiers
source                    1..18
                          mol_type = genomic DNA
                          organism = Escherichia coli
SEQUENCE: 239
gttgaccgtg cgttcctg                                                 18
```

```
SEQ ID NO: 240           moltype = DNA   length = 18
FEATURE                  Location/Qualifiers
source                   1..18
                         mol_type = genomic DNA
                         organism = Escherichia coli SEQUENCE: 240
gttgaccggg cgttcacg                                        18

SEQ ID NO: 241           moltype = DNA   length = 18
FEATURE                  Location/Qualifiers
source                   1..18
                         mol_type = genomic DNA
                         organism = Escherichia coli SEQUENCE: 241
gttctcgccc tggttacc                                        18

SEQ ID NO: 242           moltype = DNA   length = 18
FEATURE                  Location/Qualifiers
source                   1..18
                         mol_type = genomic DNA
                         organism = Escherichia coli SEQUENCE: 242
gttgaactgg tctacacc                                        18

SEQ ID NO: 243           moltype = DNA   length = 18
FEATURE                  Location/Qualifiers
source                   1..18
                         mol_type = genomic DNA
                         organism = Escherichia coli SEQUENCE: 243
gttctcgccc tggacacg                                        18

SEQ ID NO: 244           moltype = DNA   length = 18
FEATURE                  Location/Qualifiers
source                   1..18
                         mol_type = genomic DNA
                         organism = Escherichia coli SEQUENCE: 244
gttctccggc tgttccgc                                        18

SEQ ID NO: 245           moltype = DNA   length = 18
FEATURE                  Location/Qualifiers
source                   1..18
                         mol_type = genomic DNA
                         organism = Escherichia coli SEQUENCE: 245
gttcgtgctc tgttcgtg                                        18

SEQ ID NO: 246           moltype = DNA   length = 18
FEATURE                  Location/Qualifiers
source                   1..18
                         mol_type = genomic DNA
                         organism = Escherichia coli SEQUENCE: 246
gttcggctgc tggccgcc                                        18

SEQ ID NO: 247           moltype = DNA   length = 18
FEATURE                  Location/Qualifiers
source                   1..18
                         mol_type = genomic DNA
                         organism = Escherichia coli SEQUENCE: 247
gttcggctgc tggccgcc                                        18

SEQ ID NO: 248           moltype = DNA   length = 18
FEATURE                  Location/Qualifiers
source                   1..18
                         mol_type = genomic DNA
                         organism = Escherichia coli SEQUENCE: 248
gttcgcctcc gtttcact                                        18

SEQ ID NO: 249           moltype = DNA   length = 18
FEATURE                  Location/Qualifiers
source                   1..18
                         mol_type = genomic DNA
                         organism = Escherichia coli
```

-continued

```
SEQUENCE: 249
gttcgctttg cggacacc                                                      18

SEQ ID NO: 250        moltype = DNA   length = 18
FEATURE               Location/Qualifiers
source                1..18
                      mol_type = genomic DNA
                      organism = Escherichia coli
SEQUENCE: 250
gttcgcctac ggtacgtg                                                      18

SEQ ID NO: 251        moltype = DNA   length = 18
FEATURE               Location/Qualifiers
source                1..18
                      mol_type = genomic DNA
                      organism = Escherichia coli
SEQUENCE: 251
gttcgcctcc gtttcact                                                      18

SEQ ID NO: 252        moltype = DNA   length = 18
FEATURE               Location/Qualifiers
source                1..18
                      mol_type = genomic DNA
                      organism = Escherichia coli
SEQUENCE: 252
gttccgcttc ttttcagc                                                      18

SEQ ID NO: 253        moltype = DNA   length = 18
FEATURE               Location/Qualifiers
source                1..18
                      mol_type = genomic DNA
                      organism = Escherichia coli
SEQUENCE: 253
gttcctcctc cattcact                                                      18

SEQ ID NO: 254        moltype = DNA   length = 18
FEATURE               Location/Qualifiers
source                1..18
                      mol_type = genomic DNA
                      organism = Escherichia coli
SEQUENCE: 254
gttcccgtgc tgctcatt                                                      18

SEQ ID NO: 255        moltype = DNA   length = 18
FEATURE               Location/Qualifiers
source                1..18
                      mol_type = genomic DNA
                      organism = Escherichia coli
SEQUENCE: 255
gttcatgtgc tgttcacg                                                      18

SEQ ID NO: 256        moltype = DNA   length = 18
FEATURE               Location/Qualifiers
source                1..18
                      mol_type = genomic DNA
                      organism = Escherichia coli
SEQUENCE: 256
gttcatcttc cgttcacc                                                      18

SEQ ID NO: 257        moltype = DNA   length = 18
FEATURE               Location/Qualifiers
source                1..18
                      mol_type = genomic DNA
                      organism = Escherichia coli
SEQUENCE: 257
gttcatgtct acttcatc                                                      18

SEQ ID NO: 258        moltype = DNA   length = 18
FEATURE               Location/Qualifiers
source                1..18
                      mol_type = genomic DNA
                      organism = Escherichia coli
SEQUENCE: 258
gttcatcttc cgttcacc                                                      18
```

```
SEQ ID NO: 259                moltype = DNA    length = 18
FEATURE                       Location/Qualifiers
source                        1..18
                              mol_type = genomic DNA
                              organism = Escherichia coli SEQUENCE: 259
gttcatctcc tgggcgcg                                                18

SEQ ID NO: 260                moltype = DNA    length = 18
FEATURE                       Location/Qualifiers
source                        1..18
                              mol_type = genomic DNA
                              organism = Escherichia coli SEQUENCE: 260
gttcagctcc cagccgcc                                                18

SEQ ID NO: 261                moltype = DNA    length = 18
FEATURE                       Location/Qualifiers
source                        1..18
                              mol_type = genomic DNA
                              organism = Escherichia coli SEQUENCE: 261
gttcagcgtt cgtttatc                                                18

SEQ ID NO: 262                moltype = DNA    length = 18
FEATURE                       Location/Qualifiers
source                        1..18
                              mol_type = genomic DNA
                              organism = Escherichia coli SEQUENCE: 262
gttcagatgg cggtcgtg                                                18

SEQ ID NO: 263                moltype = DNA    length = 18
FEATURE                       Location/Qualifiers
source                        1..18
                              mol_type = genomic DNA
                              organism = Escherichia coli SEQUENCE: 263
gttcacgttc tcgctgtc                                                18

SEQ ID NO: 264                moltype = DNA    length = 18
FEATURE                       Location/Qualifiers
source                        1..18
                              mol_type = genomic DNA
                              organism = Escherichia coli SEQUENCE: 264
gttcacgtgc tggacacc                                                18

SEQ ID NO: 265                moltype = DNA    length = 18
FEATURE                       Location/Qualifiers
source                        1..18
                              mol_type = genomic DNA
                              organism = Escherichia coli SEQUENCE: 265
gttcacgttc gataaacg                                                18

SEQ ID NO: 266                moltype = DNA    length = 18
FEATURE                       Location/Qualifiers
source                        1..18
                              mol_type = genomic DNA
                              organism = Escherichia coli SEQUENCE: 266
gttcacgtgc cgctcgtt                                                18

SEQ ID NO: 267                moltype = DNA    length = 18
FEATURE                       Location/Qualifiers
source                        1..18
                              mol_type = genomic DNA
                              organism = Escherichia coli SEQUENCE: 267
gttcacggcg tggttggc                                                18

SEQ ID NO: 268                moltype = DNA    length = 18
FEATURE                       Location/Qualifiers
source                        1..18
                              mol_type = genomic DNA
                              organism = Escherichia coli
```

-continued

```
SEQUENCE: 268
gttcaccttg gagccagg                                                   18

SEQ ID NO: 269           moltype = DNA   length = 18
FEATURE                  Location/Qualifiers
source                   1..18
                         mol_type = genomic DNA
                         organism = Escherichia coli
SEQUENCE: 269
gttcaccttg gagccagg                                                   18

SEQ ID NO: 270           moltype = DNA   length = 18
FEATURE                  Location/Qualifiers
source                   1..18
                         mol_type = genomic DNA
                         organism = Escherichia coli
SEQUENCE: 270
gttcacctcg gagtggtc                                                   18

SEQ ID NO: 271           moltype = DNA   length = 18
FEATURE                  Location/Qualifiers
source                   1..18
                         mol_type = genomic DNA
                         organism = Escherichia coli
SEQUENCE: 271
gttcaccttc tggccttc                                                   18

SEQ ID NO: 272           moltype = DNA   length = 18
FEATURE                  Location/Qualifiers
source                   1..18
                         mol_type = genomic DNA
                         organism = Escherichia coli
SEQUENCE: 272
gttcaccggg agttcggc                                                   18

SEQ ID NO: 273           moltype = DNA   length = 18
FEATURE                  Location/Qualifiers
source                   1..18
                         mol_type = genomic DNA
                         organism = Escherichia coli
SEQUENCE: 273
gttcaccggg agttcggc                                                   18

SEQ ID NO: 274           moltype = DNA   length = 18
FEATURE                  Location/Qualifiers
source                   1..18
                         mol_type = genomic DNA
                         organism = Escherichia coli
SEQUENCE: 274
gttcacctac gggcaacg                                                   18

SEQ ID NO: 275           moltype = DNA   length = 18
FEATURE                  Location/Qualifiers
source                   1..18
                         mol_type = genomic DNA
                         organism = Escherichia coli
SEQUENCE: 275
gttcaccgcg tgtcaagg                                                   18

SEQ ID NO: 276           moltype = DNA   length = 18
FEATURE                  Location/Qualifiers
source                   1..18
                         mol_type = genomic DNA
                         organism = Escherichia coli
SEQUENCE: 276
gttcaccgcg tgtcaagg                                                   18

SEQ ID NO: 277           moltype = DNA   length = 18
FEATURE                  Location/Qualifiers
source                   1..18
                         mol_type = genomic DNA
                         organism = Escherichia coli
SEQUENCE: 277
gttcaccctg tgtgcact                                                   18

SEQ ID NO: 278           moltype = DNA   length = 18
FEATURE                  Location/Qualifiers
```

-continued

```
source                    1..18
                          mol_type = genomic DNA
                          organism = Escherichia coli
SEQUENCE: 278
gttcaccctc tccccacc                                                18

SEQ ID NO: 279            moltype = DNA   length = 18
FEATURE                   Location/Qualifiers
source                    1..18
                          mol_type = genomic DNA
                          organism = Escherichia coli
SEQUENCE: 279
gttcacccgg cgttcatt                                                18

SEQ ID NO: 280            moltype = DNA   length = 18
FEATURE                   Location/Qualifiers
source                    1..18
                          mol_type = genomic DNA
                          organism = Escherichia coli
SEQUENCE: 280
gttcaccctc tccccacc                                                18

SEQ ID NO: 281            moltype = DNA   length = 18
FEATURE                   Location/Qualifiers
source                    1..18
                          mol_type = genomic DNA
                          organism = Escherichia coli
SEQUENCE: 281
gttcaccagg cgttcctg                                                18

SEQ ID NO: 282            moltype = DNA   length = 18
FEATURE                   Location/Qualifiers
source                    1..18
                          mol_type = genomic DNA
                          organism = Escherichia coli
SEQUENCE: 282
gttcacatcc tgttagcc                                                18

SEQ ID NO: 283            moltype = DNA   length = 18
FEATURE                   Location/Qualifiers
source                    1..18
                          mol_type = genomic DNA
                          organism = Escherichia coli
SEQUENCE: 283
gttcaactgc cgttcacc                                                18

SEQ ID NO: 284            moltype = DNA   length = 18
FEATURE                   Location/Qualifiers
source                    1..18
                          mol_type = genomic DNA
                          organism = Escherichia coli
SEQUENCE: 284
gttcaacttg cgttcagg                                                18

SEQ ID NO: 285            moltype = DNA   length = 18
FEATURE                   Location/Qualifiers
source                    1..18
                          mol_type = genomic DNA
                          organism = Escherichia coli
SEQUENCE: 285
gttcaactcc ggcccagg                                                18

SEQ ID NO: 286            moltype = DNA   length = 18
FEATURE                   Location/Qualifiers
source                    1..18
                          mol_type = genomic DNA
                          organism = Escherichia coli
SEQUENCE: 286
gttcaactgc cgttcacc                                                18

SEQ ID NO: 287            moltype = DNA   length = 18
FEATURE                   Location/Qualifiers
source                    1..18
                          mol_type = genomic DNA
                          organism = Escherichia coli
SEQUENCE: 287
gtccatcccg cggtaatc                                                18

SEQ ID NO: 288            moltype = DNA   length = 18
```

-continued

```
FEATURE               Location/Qualifiers
source                1..18
                      mol_type = genomic DNA
                      organism = Escherichia coli
SEQUENCE: 288
gttaaccggc tgttgacc                                               18

SEQ ID NO: 289        moltype = DNA   length = 18
FEATURE               Location/Qualifiers
source                1..18
                      mol_type = genomic DNA
                      organism = Escherichia coli
SEQUENCE: 289
gtccacgtgt gcgtcatg                                               18

SEQ ID NO: 290        moltype = DNA   length = 18
FEATURE               Location/Qualifiers
source                1..18
                      mol_type = genomic DNA
                      organism = Escherichia coli
SEQUENCE: 290
gtccaccgtc tggtcctc                                               18

SEQ ID NO: 291        moltype = DNA   length = 18
FEATURE               Location/Qualifiers
source                1..18
                      mol_type = genomic DNA
                      organism = Escherichia coli
SEQUENCE: 291
gtcaacgtct tgttaacg                                               18

SEQ ID NO: 292        moltype = DNA   length = 18
FEATURE               Location/Qualifiers
source                1..18
                      mol_type = genomic DNA
                      organism = Escherichia coli
SEQUENCE: 292
gtcatcgtcg tgttcatg                                               18

SEQ ID NO: 293        moltype = DNA   length = 18
FEATURE               Location/Qualifiers
source                1..18
                      mol_type = genomic DNA
                      organism = Escherichia coli
SEQUENCE: 293
ggtgacccgc cggtcaca                                               18

SEQ ID NO: 294        moltype = DNA   length = 18
FEATURE               Location/Qualifiers
source                1..18
                      mol_type = genomic DNA
                      organism = Escherichia coli
SEQUENCE: 294
ggtgacccag cggtcgtc                                               18

SEQ ID NO: 295        moltype = DNA   length = 18
FEATURE               Location/Qualifiers
source                1..18
                      mol_type = genomic DNA
                      organism = Escherichia coli
SEQUENCE: 295
ggtcgcccgc cgttcgcc                                               18

SEQ ID NO: 296        moltype = DNA   length = 18
FEATURE               Location/Qualifiers
source                1..18
                      mol_type = genomic DNA
                      organism = Escherichia coli
SEQUENCE: 296
ggtctcccgc tcgtcatg                                               18

SEQ ID NO: 297        moltype = DNA   length = 18
FEATURE               Location/Qualifiers
source                1..18
                      mol_type = genomic DNA
                      organism = Escherichia coli
SEQUENCE: 297
ggtcgcccgc cgttcgcc                                               18
```

-continued

```
SEQ ID NO: 298          moltype = DNA   length = 18
FEATURE                 Location/Qualifiers
source                  1..18
                        mol_type = genomic DNA
                        organism = Escherichia coli SEQUENCE: 298
ggtccacttc cgtccagc                                                  18

SEQ ID NO: 299          moltype = DNA   length = 18
FEATURE                 Location/Qualifiers
source                  1..18
                        mol_type = genomic DNA
                        organism = Escherichia coli SEQUENCE: 299
ggtcagcggt cggtcgtg                                                  18

SEQ ID NO: 300          moltype = DNA   length = 18
FEATURE                 Location/Qualifiers
source                  1..18
                        mol_type = genomic DNA
                        organism = Escherichia coli SEQUENCE: 300
ggtcatcgcc ccgccact                                                  18

SEQ ID NO: 301          moltype = DNA   length = 18
FEATURE                 Location/Qualifiers
source                  1..18
                        mol_type = genomic DNA
                        organism = Escherichia coli SEQUENCE: 301
ggtcacgttt cgatcacc                                                  18

SEQ ID NO: 302          moltype = DNA   length = 18
FEATURE                 Location/Qualifiers
source                  1..18
                        mol_type = genomic DNA
                        organism = Escherichia coli SEQUENCE: 302
ggtcacgccc gagaaatc                                                  18

SEQ ID NO: 303          moltype = DNA   length = 18
FEATURE                 Location/Qualifiers
source                  1..18
                        mol_type = genomic DNA
                        organism = Escherichia coli SEQUENCE: 303
ggtcaccgtg cctccaca                                                  18

SEQ ID NO: 304          moltype = DNA   length = 18
FEATURE                 Location/Qualifiers
source                  1..18
                        mol_type = genomic DNA
                        organism = Escherichia coli SEQUENCE: 304
ggtcacgccc gagaaatc                                                  18

SEQ ID NO: 305          moltype = DNA   length = 18
FEATURE                 Location/Qualifiers
source                  1..18
                        mol_type = genomic DNA
                        organism = Escherichia coli SEQUENCE: 305
ggtcacccgg gagccacc                                                  18

SEQ ID NO: 306          moltype = DNA   length = 18
FEATURE                 Location/Qualifiers
source                  1..18
                        mol_type = genomic DNA
                        organism = Escherichia coli SEQUENCE: 306
ggtcaccgcg gggccagc                                                  18

SEQ ID NO: 307          moltype = DNA   length = 18
FEATURE                 Location/Qualifiers
source                  1..18
                        mol_type = genomic DNA
                        organism = Escherichia coli SEQUENCE: 307
ggtcacccgg agctcacc                                                  18
```

```
SEQ ID NO: 308          moltype = DNA   length = 18
FEATURE                 Location/Qualifiers
source                  1..18
                        mol_type = genomic DNA
                        organism = Escherichia coli SEQUENCE: 308
ggtcacccgg agctcacc                                               18

SEQ ID NO: 309          moltype = DNA   length = 18
FEATURE                 Location/Qualifiers
source                  1..18
                        mol_type = genomic DNA
                        organism = Escherichia coli SEQUENCE: 309
ggtcacattt tcgtcaca                                               18

SEQ ID NO: 310          moltype = DNA   length = 18
FEATURE                 Location/Qualifiers
source                  1..18
                        mol_type = genomic DNA
                        organism = Escherichia coli SEQUENCE: 310
ggtcaccccc tcgacggc                                               18

SEQ ID NO: 311          moltype = DNA   length = 18
FEATURE                 Location/Qualifiers
source                  1..18
                        mol_type = genomic DNA
                        organism = Escherichia coli SEQUENCE: 311
ggtcaactgc ccgtcgcc                                               18

SEQ ID NO: 312          moltype = DNA   length = 18
FEATURE                 Location/Qualifiers
source                  1..18
                        mol_type = genomic DNA
                        organism = Escherichia coli SEQUENCE: 312
ggtcacacgg ccttcaca                                               18

SEQ ID NO: 313          moltype = DNA   length = 18
FEATURE                 Location/Qualifiers
source                  1..18
                        mol_type = genomic DNA
                        organism = Escherichia coli SEQUENCE: 313
ggtcaaccgc cggtcgct                                               18

SEQ ID NO: 314          moltype = DNA   length = 18
FEATURE                 Location/Qualifiers
source                  1..18
                        mol_type = genomic DNA
                        organism = Escherichia coli SEQUENCE: 314
ggtcaactgc ccgtcgcc                                               18

SEQ ID NO: 315          moltype = DNA   length = 18
FEATURE                 Location/Qualifiers
source                  1..18
                        mol_type = genomic DNA
                        organism = Escherichia coli SEQUENCE: 315
ggtatcccgc ccgtcacc                                               18

SEQ ID NO: 316          moltype = DNA   length = 18
FEATURE                 Location/Qualifiers
source                  1..18
                        mol_type = genomic DNA
                        organism = Escherichia coli SEQUENCE: 316
ggtatcccgc ccgtcacc                                               18

SEQ ID NO: 317          moltype = DNA   length = 18
FEATURE                 Location/Qualifiers
source                  1..18
                        mol_type = genomic DNA
                        organism = Escherichia coli
```

```
SEQUENCE: 317
ggtcaaccgc cggtaacc                                                        18

SEQ ID NO: 318         moltype = DNA   length = 18
FEATURE                Location/Qualifiers
source                 1..18
                       mol_type = genomic DNA
                       organism = Escherichia coli
SEQUENCE: 318
ggtaacacgg ggttcacc                                                        18

SEQ ID NO: 319         moltype = DNA   length = 18
FEATURE                Location/Qualifiers
source                 1..18
                       mol_type = genomic DNA
                       organism = Escherichia coli
SEQUENCE: 319
ggtaaccccg gggcaacc                                                        18

SEQ ID NO: 320         moltype = DNA   length = 18
FEATURE                Location/Qualifiers
source                 1..18
                       mol_type = genomic DNA
                       organism = Escherichia coli
SEQUENCE: 320
ggccacccCg cggtcacg                                                        18

SEQ ID NO: 321         moltype = DNA   length = 18
FEATURE                Location/Qualifiers
source                 1..18
                       mol_type = genomic DNA
                       organism = Escherichia coli
SEQUENCE: 321
ggccacgtcc tggccacc                                                        18

SEQ ID NO: 322         moltype = DNA   length = 18
FEATURE                Location/Qualifiers
source                 1..18
                       mol_type = genomic DNA
                       organism = Escherichia coli
SEQUENCE: 322
gatcacccgt cggtaagc                                                        18

SEQ ID NO: 323         moltype = DNA   length = 18
FEATURE                Location/Qualifiers
source                 1..18
                       mol_type = genomic DNA
                       organism = Escherichia coli
SEQUENCE: 323
ggccacatcc ccttcacc                                                        18

SEQ ID NO: 324         moltype = DNA   length = 18
FEATURE                Location/Qualifiers
source                 1..18
                       mol_type = genomic DNA
                       organism = Escherichia coli
SEQUENCE: 324
gatcaccctg cgtctatg                                                        18

SEQ ID NO: 325         moltype = DNA   length = 18
FEATURE                Location/Qualifiers
source                 1..18
                       mol_type = genomic DNA
                       organism = Escherichia coli
SEQUENCE: 325
gatcacacct tcttcacg                                                        18

SEQ ID NO: 326         moltype = DNA   length = 18
FEATURE                Location/Qualifiers
source                 1..18
                       mol_type = genomic DNA
                       organism = Escherichia coli
SEQUENCE: 326
gatcacccgt cggtaagc                                                        18

SEQ ID NO: 327         moltype = DNA   length = 18
FEATURE                Location/Qualifiers
```

-continued

```
source                      1..18
                            mol_type = genomic DNA
                            organism = Escherichia coli
SEQUENCE: 327
cttcgcctcc ccttcatc                                                  18

SEQ ID NO: 328              moltype = DNA   length = 18
FEATURE                     Location/Qualifiers
source                      1..18
                            mol_type = genomic DNA
                            organism = Escherichia coli
SEQUENCE: 328
cttcgcctcc ccttcatc                                                  18

SEQ ID NO: 329              moltype = DNA   length = 18
FEATURE                     Location/Qualifiers
source                      1..18
                            mol_type = genomic DNA
                            organism = Escherichia coli
SEQUENCE: 329
cttcaaccac ggtcaacc                                                  18

SEQ ID NO: 330              moltype = DNA   length = 18
FEATURE                     Location/Qualifiers
source                      1..18
                            mol_type = genomic DNA
                            organism = Escherichia coli
SEQUENCE: 330
cttcgcctcc ccttcatc                                                  18

SEQ ID NO: 331              moltype = DNA   length = 18
FEATURE                     Location/Qualifiers
source                      1..18
                            mol_type = genomic DNA
                            organism = Escherichia coli
SEQUENCE: 331
cgtcacttcg tgttcacg                                                  18

SEQ ID NO: 332              moltype = DNA   length = 18
FEATURE                     Location/Qualifiers
source                      1..18
                            mol_type = genomic DNA
                            organism = Escherichia coli
SEQUENCE: 332
cgtcacttcg tgttcacg                                                  18

SEQ ID NO: 333              moltype = DNA   length = 18
FEATURE                     Location/Qualifiers
source                      1..18
                            mol_type = genomic DNA
                            organism = Escherichia coli
SEQUENCE: 333
cgtcacgtcg cggtcacc                                                  18

SEQ ID NO: 334              moltype = DNA   length = 18
FEATURE                     Location/Qualifiers
source                      1..18
                            mol_type = genomic DNA
                            organism = Escherichia coli
SEQUENCE: 334
attcgtccat tgttcacc                                                  18

SEQ ID NO: 335              moltype = DNA   length = 18
FEATURE                     Location/Qualifiers
source                      1..18
                            mol_type = genomic DNA
                            organism = Escherichia coli
SEQUENCE: 335
attcgggtgg tgttcatc                                                  18

SEQ ID NO: 336              moltype = DNA   length = 18
FEATURE                     Location/Qualifiers
source                      1..18
                            mol_type = genomic DNA
                            organism = Escherichia coli
SEQUENCE: 336
attcgtccat tgttcacc                                                  18

SEQ ID NO: 337              moltype = DNA   length = 18
```

```
FEATURE                 Location/Qualifiers
source                  1..18
                        mol_type = genomic DNA
                        organism = Escherichia coli
SEQUENCE: 337
attcccctgg cgttcgcc                                                    18

SEQ ID NO: 338          moltype = DNA   length = 18
FEATURE                 Location/Qualifiers
source                  1..18
                        mol_type = genomic DNA
                        organism = Escherichia coli
SEQUENCE: 338
attcgggtgg tgttcatc                                                    18

SEQ ID NO: 339          moltype = DNA   length = 18
FEATURE                 Location/Qualifiers
source                  1..18
                        mol_type = genomic DNA
                        organism = Escherichia coli
SEQUENCE: 339
attcagcctg tggccact                                                    18

SEQ ID NO: 340          moltype = DNA   length = 18
FEATURE                 Location/Qualifiers
source                  1..18
                        mol_type = genomic DNA
                        organism = Escherichia coli
SEQUENCE: 340
attcagcctg tggccact                                                    18

SEQ ID NO: 341          moltype = DNA   length = 18
FEATURE                 Location/Qualifiers
source                  1..18
                        mol_type = genomic DNA
                        organism = Escherichia coli
SEQUENCE: 341
attcactcac cgttcagt                                                    18

SEQ ID NO: 342          moltype = DNA   length = 18
FEATURE                 Location/Qualifiers
source                  1..18
                        mol_type = genomic DNA
                        organism = Escherichia coli
SEQUENCE: 342
attcactcac cgttcagt                                                    18

SEQ ID NO: 343          moltype = DNA   length = 18
FEATURE                 Location/Qualifiers
source                  1..18
                        mol_type = genomic DNA
                        organism = Escherichia coli
SEQUENCE: 343
attcacgcgc cggccacc                                                    18

SEQ ID NO: 344          moltype = DNA   length = 18
FEATURE                 Location/Qualifiers
source                  1..18
                        mol_type = genomic DNA
                        organism = Escherichia coli
SEQUENCE: 344
agtaaaccct cgttcact                                                    18

SEQ ID NO: 345          moltype = DNA   length = 18
FEATURE                 Location/Qualifiers
source                  1..18
                        mol_type = genomic DNA
                        organism = Escherichia coli
SEQUENCE: 345
agtaaaccct cgttcact                                                    18

SEQ ID NO: 346          moltype = DNA   length = 18
FEATURE                 Location/Qualifiers
source                  1..18
                        mol_type = genomic DNA
                        organism = Streptomyces coelicolor
SEQUENCE: 346
attaaccaaa tcgtcaca                                                    18
```

-continued

```
SEQ ID NO: 347        moltype = DNA   length = 18
FEATURE               Location/Qualifiers
source                1..18
                      mol_type = genomic DNA
                      organism = Streptomyces coelicolor
SEQUENCE: 347
tgtcattaaa aagaaaca                                             18

SEQ ID NO: 348        moltype = DNA   length = 18
FEATURE               Location/Qualifiers
source                1..18
                      mol_type = genomic DNA
                      organism = Streptomyces coelicolor
SEQUENCE: 348
tgtaatgtaa ccgtcaat                                             18

SEQ ID NO: 349        moltype = DNA   length = 18
FEATURE               Location/Qualifiers
source                1..18
                      mol_type = genomic DNA
                      organism = Streptomyces coelicolor
SEQUENCE: 349
tttcacgccg ttgtaata                                             18

SEQ ID NO: 350        moltype = DNA   length = 18
FEATURE               Location/Qualifiers
source                1..18
                      mol_type = genomic DNA
                      organism = Streptomyces coelicolor
SEQUENCE: 350
tgtaatagtt ctgtaacg                                             18

SEQ ID NO: 351        moltype = DNA   length = 18
FEATURE               Location/Qualifiers
source                1..18
                      mol_type = genomic DNA
                      organism = Streptomyces coelicolor
SEQUENCE: 351
tgtcataaaa ctgtcata                                             18

SEQ ID NO: 352        moltype = DNA   length = 18
FEATURE               Location/Qualifiers
source                1..18
                      mol_type = genomic DNA
                      organism = Streptomyces coelicolor
SEQUENCE: 352
ttacatacaa atgtaata                                             18

SEQ ID NO: 353        moltype = DNA   length = 18
FEATURE               Location/Qualifiers
source                1..18
                      mol_type = genomic DNA
                      organism = Streptomyces coelicolor
SEQUENCE: 353
ggtcaccgag ttgtcata                                             18

SEQ ID NO: 354        moltype = DNA   length = 18
FEATURE               Location/Qualifiers
source                1..18
                      mol_type = genomic DNA
                      organism = Streptomyces coelicolor
SEQUENCE: 354
tttcacaatg ttgtcatg                                             18

SEQ ID NO: 355        moltype = DNA   length = 18
FEATURE               Location/Qualifiers
source                1..18
                      mol_type = genomic DNA
                      organism = Streptomyces coelicolor
SEQUENCE: 355
ggtaataaat atgtcact                                             18

SEQ ID NO: 356        moltype = DNA   length = 18
FEATURE               Location/Qualifiers
source                1..18
                      mol_type = genomic DNA
                      organism = Streptomyces coelicolor
SEQUENCE: 356
tgtcatcttt ctgacacc                                             18
```

```
SEQ ID NO: 357              moltype = DNA   length = 18
FEATURE                    Location/Qualifiers
source                     1..18
                           mol_type = genomic DNA
                           organism = Streptomyces coelicolor
SEQUENCE: 357
cttcacagta ccgtcatc                                                       18

SEQ ID NO: 358              moltype = DNA   length = 18
FEATURE                    Location/Qualifiers
source                     1..18
                           mol_type = genomic DNA
                           organism = Streptomyces coelicolor
SEQUENCE: 358
tgtcatacac ccgtcacg                                                       18

SEQ ID NO: 359              moltype = DNA   length = 18
FEATURE                    Location/Qualifiers
source                     1..18
                           mol_type = genomic DNA
                           organism = Streptomyces coelicolor
SEQUENCE: 359
tgacacaaat ctttaatc                                                       18

SEQ ID NO: 360              moltype = DNA   length = 18
FEATURE                    Location/Qualifiers
source                     1..18
                           mol_type = genomic DNA
                           organism = Streptomyces coelicolor
SEQUENCE: 360
agtaacaacc gtgtcaca                                                       18

SEQ ID NO: 361              moltype = DNA   length = 18
FEATURE                    Location/Qualifiers
source                     1..18
                           mol_type = genomic DNA
                           organism = Streptomyces coelicolor
SEQUENCE: 361
tttcacattt ctgtgaca                                                       18

SEQ ID NO: 362              moltype = DNA   length = 18
FEATURE                    Location/Qualifiers
source                     1..18
                           mol_type = genomic DNA
                           organism = Streptomyces coelicolor
SEQUENCE: 362
tgtcacaatt cgatcatg                                                       18

SEQ ID NO: 363              moltype = DNA   length = 18
FEATURE                    Location/Qualifiers
source                     1..18
                           mol_type = genomic DNA
                           organism = Streptomyces coelicolor
SEQUENCE: 363
tgtcatcaaa ctgccatt                                                       18

SEQ ID NO: 364              moltype = DNA   length = 18
FEATURE                    Location/Qualifiers
source                     1..18
                           mol_type = genomic DNA
                           organism = Streptomyces coelicolor
SEQUENCE: 364
tttcacagag cgaaaacg                                                       18

SEQ ID NO: 365              moltype = DNA   length = 18
FEATURE                    Location/Qualifiers
source                     1..18
                           mol_type = genomic DNA
                           organism = Streptomyces coelicolor
SEQUENCE: 365
tatcagaaaa atgtcatg                                                       18

SEQ ID NO: 366              moltype = DNA   length = 18
FEATURE                    Location/Qualifiers
source                     1..18
                           mol_type = genomic DNA
                           organism = Streptomyces coelicolor
```

-continued

```
SEQUENCE: 366
agtcatattt ctgtcaca                                              18

SEQ ID NO: 367        moltype = DNA   length = 18
FEATURE               Location/Qualifiers
source                1..18
                      mol_type = genomic DNA
                      organism = Streptomyces coelicolor
SEQUENCE: 367
tgtcatcact ctgtcatc                                              18

SEQ ID NO: 368        moltype = DNA   length = 18
FEATURE               Location/Qualifiers
source                1..18
                      mol_type = genomic DNA
                      organism = Streptomyces coelicolor
SEQUENCE: 368
tgtcacattc ctgtcaat                                              18

SEQ ID NO: 369        moltype = DNA   length = 18
FEATURE               Location/Qualifiers
source                1..18
                      mol_type = genomic DNA
                      organism = Streptomyces coelicolor
SEQUENCE: 369
tgtcaggccg ctgtcatc                                              18

SEQ ID NO: 370        moltype = DNA   length = 18
FEATURE               Location/Qualifiers
source                1..18
                      mol_type = genomic DNA
                      organism = Streptomyces coelicolor
SEQUENCE: 370
tgtcattttt ctgtcacc                                              18

SEQ ID NO: 371        moltype = DNA   length = 18
FEATURE               Location/Qualifiers
source                1..18
                      mol_type = genomic DNA
                      organism = Streptomyces coelicolor
SEQUENCE: 371
attcacagca ctgtcata                                              18

SEQ ID NO: 372        moltype = DNA   length = 18
FEATURE               Location/Qualifiers
source                1..18
                      mol_type = genomic DNA
                      organism = Streptomyces coelicolor
SEQUENCE: 372
tttcataaat ctgtcata                                              18

SEQ ID NO: 373        moltype = DNA   length = 18
FEATURE               Location/Qualifiers
source                1..18
                      mol_type = genomic DNA
                      organism = Streptomyces coelicolor
SEQUENCE: 373
tgtaacagaa atatcaca                                              18

SEQ ID NO: 374        moltype = DNA   length = 18
FEATURE               Location/Qualifiers
source                1..18
                      mol_type = genomic DNA
                      organism = Streptomyces coelicolor
SEQUENCE: 374
tgtcataaag ttgtcacg                                              18

SEQ ID NO: 375        moltype = DNA   length = 18
FEATURE               Location/Qualifiers
source                1..18
                      mol_type = genomic DNA
                      organism = Streptomyces coelicolor
SEQUENCE: 375
tgtaataaaa gcgtaaac                                              18

SEQ ID NO: 376        moltype = DNA   length = 18
FEATURE               Location/Qualifiers
```

-continued

```
source                      1..18
                            mol_type = genomic DNA
                            organism = Azorhizobium caulinodans
SEQUENCE: 376
gtgtcacgaa ccagtcat                                                      18

SEQ ID NO: 377              moltype = DNA   length = 18
FEATURE                     Location/Qualifiers
source                      1..18
                            mol_type = genomic DNA
                            organism = Azospirillum brasilense
SEQUENCE: 377
tcgtcatgaa actgtcat                                                      18

SEQ ID NO: 378              moltype = DNA   length = 18
FEATURE                     Location/Qualifiers
source                      1..18
                            mol_type = genomic DNA
                            organism = Escherichia coli
SEQUENCE: 378
ctgtcataaa gttgtcac                                                      18

SEQ ID NO: 379              moltype = DNA   length = 18
FEATURE                     Location/Qualifiers
source                      1..18
                            mol_type = genomic DNA
                            organism = Escherichia coli
SEQUENCE: 379
tcatcacatc gttgtcat                                                      18

SEQ ID NO: 380              moltype = DNA   length = 18
FEATURE                     Location/Qualifiers
source                      1..18
                            mol_type = genomic DNA
                            organism = Escherichia coli
SEQUENCE: 380
atgacaaaaa gatgacat                                                      18

SEQ ID NO: 381              moltype = DNA   length = 18
FEATURE                     Location/Qualifiers
source                      1..18
                            mol_type = genomic DNA
                            organism = Escherichia coli
SEQUENCE: 381
ctgtcataaa aatgtcat                                                      18

SEQ ID NO: 382              moltype = DNA   length = 18
FEATURE                     Location/Qualifiers
source                      1..18
                            mol_type = genomic DNA
                            organism = Escherichia coli
SEQUENCE: 382
ctgtcacctg tttgtcct                                                      18

SEQ ID NO: 383              moltype = DNA   length = 18
FEATURE                     Location/Qualifiers
source                      1..18
                            mol_type = genomic DNA
                            organism = Gluconacetobacter diazotrophicus
SEQUENCE: 383
ttcggccaca tgtgtcgt                                                      18

SEQ ID NO: 384              moltype = DNA   length = 18
FEATURE                     Location/Qualifiers
source                      1..18
                            mol_type = genomic DNA
                            organism = Gluconacetobacter diazotrophicus
SEQUENCE: 384
ttgccgaatg gctgccat                                                      18

SEQ ID NO: 385              moltype = DNA   length = 18
FEATURE                     Location/Qualifiers
source                      1..18
                            mol_type = genomic DNA
                            organism = Herbaspirillum seropedicae
SEQUENCE: 385
tgatcaaatc tgttgcag                                                      18

SEQ ID NO: 386              moltype = DNA   length = 18
```

-continued

```
FEATURE                 Location/Qualifiers
source                  1..18
                        mol_type = genomic DNA
                        organism = Kosakonia radicincitans
SEQUENCE: 386
attattgata tgccgcac                                                  18

SEQ ID NO: 387          moltype = DNA  length = 18
FEATURE                 Location/Qualifiers
source                  1..18
                        mol_type = genomic DNA
                        organism = Kosakonia radicincitans
SEQUENCE: 387
ttatcacgtt gcgctgat                                                  18

SEQ ID NO: 388          moltype = DNA  length = 18
FEATURE                 Location/Qualifiers
source                  1..18
                        mol_type = genomic DNA
                        organism = Kosakonia radicincitans
SEQUENCE: 388
ttgtgaattc tcattcgt                                                  18

SEQ ID NO: 389          moltype = DNA  length = 18
FEATURE                 Location/Qualifiers
source                  1..18
                        mol_type = genomic DNA
                        organism = Kosakonia radicincitans
SEQUENCE: 389
ttatcttttt tatatcat                                                  18

SEQ ID NO: 390          moltype = DNA  length = 18
FEATURE                 Location/Qualifiers
source                  1..18
                        mol_type = genomic DNA
                        organism = Kosakonia radicincitans
SEQUENCE: 390
tattcaaaaa tctatcaa                                                  18

SEQ ID NO: 391          moltype = DNA  length = 18
FEATURE                 Location/Qualifiers
source                  1..18
                        mol_type = genomic DNA
                        organism = Paenibacillus azotofixans
SEQUENCE: 391
tagacggatt tgcggcga                                                  18

SEQ ID NO: 392          moltype = DNA  length = 18
FEATURE                 Location/Qualifiers
source                  1..18
                        mol_type = genomic DNA
                        organism = Pseudomonas stutzeri
SEQUENCE: 392
tggctggttc tgacatcg                                                  18

SEQ ID NO: 393          moltype = DNA  length = 18
FEATURE                 Location/Qualifiers
source                  1..18
                        mol_type = genomic DNA
                        organism = Pseudomonas stutzeri
SEQUENCE: 393
gcgaagctgc tctgaagg                                                  18

SEQ ID NO: 394          moltype = DNA  length = 18
FEATURE                 Location/Qualifiers
source                  1..18
                        mol_type = genomic DNA
                        organism = Pseudomonas stutzeri
SEQUENCE: 394
ggggcttttt tttgcgac                                                  18

SEQ ID NO: 395          moltype = DNA  length = 18
FEATURE                 Location/Qualifiers
source                  1..18
                        mol_type = genomic DNA
                        organism = Pseudomonas stutzeri
SEQUENCE: 395
gcgtcatggc tccgacaa                                                  18
```

```
SEQ ID NO: 396          moltype = DNA   length = 18
FEATURE                 Location/Qualifiers
source                  1..18
                        mol_type = genomic DNA
                        organism = Pseudomonas stutzeri
SEQUENCE: 396
ctgtcacaga accgccac                                                           18

SEQ ID NO: 397          moltype = DNA   length = 18
FEATURE                 Location/Qualifiers
source                  1..18
                        mol_type = genomic DNA
                        organism = Pseudomonas stutzeri
SEQUENCE: 397
ttgtcacact tgcttcat                                                           18

SEQ ID NO: 398          moltype = AA   length = 471
FEATURE                 Location/Qualifiers
source                  1..471
                        mol_type = protein
                        organism = Kosakonia radicincitans
SEQUENCE: 398
MKQSALYLAL LPVFFTSVIY AETTDTSVLE HRAAQGDIST PGGARRLTAD QTAALLDSLI   60
DKPAKNIILL IGDGMGDSEI TAARNYAEGA GGYFKGIDAL PLTGQYTHYA LDKKTGKPDY   120
VTDSAASATA WSTGVKTYNG ALGVDIHEKD HMTILEMAKA AGLATGNVST AELQDATPAA   180
LVSHVISRRC YGPTVTSEKC ALNALEKGGK GSITEQFLNT RADVTLGGGA KTFSETATAG   240
KWQGKTLREQ AQARGYQMVS DASALAAISE ANQDKPLLGL FADGNMPVRW EGPKASLHGN   300
LDKPAVTCTP NAKRTDSVPT LAAMTEKAID LLSKNEKGFF LQVEGASIDK QDHAANPCGQ   360
IGETVDLDEA VQKALEFAKK DGNTLVIVTA DHAHASQIIP ADTKAPGLSQ ALNTKDGAVM   420
AITYGNSEEE SMEHTGTQVR IAAYGPHAGN VVGLTDQTDL FYTMKSALNL K            471

SEQ ID NO: 399          moltype = AA   length = 346
FEATURE                 Location/Qualifiers
source                  1..346
                        mol_type = protein
                        organism = Kosakonia radicincitans
SEQUENCE: 399
MNVMRTTVAT VVAATFSLSA FAVNAAASLT GAGATFPAPV YAKWADTYQK ETGNKINYQG   60
IGSSGGVKQI TAKTVDFGAS DAPLADDKLA QEGLFQFPTV IGGIVLAINV PGIKSGELVL   120
DGKTLGDIYL GNIKKWDDAA IAKLNPGLKL PSQNIAVVRR ADGSGTSFVF TNYLAKVNEE   180
WKSKVGSGST VNWPTGLGGK GNDGIAAFVQ RLPGSIGYVE YAYAKQNNLT YTKLLSADGK   240
AVSPTEQSFS NAAKNIDWSK SFAQDLTNQK GADVWPITST TFILVHKEQA KPEQGAEVLK   300
FFDWAYKKGG KQANDLDYAT LPDSVVEQVR AAWKTNVKDS SGKALY                  346

SEQ ID NO: 400          moltype = AA   length = 573
FEATURE                 Location/Qualifiers
source                  1..573
                        mol_type = protein
                        organism = Paenibacillus durus
SEQUENCE: 400
MNKGLKKVAI GGLACLILSA GSFAYAAQSA SKTQKAVKAP SKNLIVLIGD GMGPAQISAT   60
RYYEQYKKGV KHLNLDPYYV GQATTYADRG EDGGKVVSGV VTDSASAGTA FATGHKTYNA   120
GISVSNEDAS KPFASVIEAA VSSGKATGLV TTARITHATP AVYASHVRNR DNEAAIASQY   180
LESGVDVLFG GGKQFFVTKD EKGKRTDKNI LPDFKAKGYT IVESTSALKA LPASTTKALG   240
LFGNSHVAYT PDRTAEIPSL AAMTSSALKI LSKDKDGFVM MIEGGRIDHA GHANDFPTLI   300
QETLDFDAAF KTAIEFAKKD GNTSVVVTAD HETGGLSLSR DNIYELNIDL WDKQKNSSES   360
IASKLAEAKT PEEIRSIVAE NTGINDLTDE EVQAILAGDG SSYKQEGAYN AVISKRLLVG   420
WSGHGHSAVD VGIWAYGPIA GKVKGQVDNT QIARASAAIV GVNLDKRSAE LQSKYVYPKF   480
KINRENEVLY PVASLIKALG GSYSSGSSVS KAAFGKNTLN INMSALTATL NGKAVAFTVD   540
NDNGTVYLPL SAFNQLTGKN LKWDSLSERI VLR                               573

SEQ ID NO: 401          moltype = AA   length = 316
FEATURE                 Location/Qualifiers
source                  1..316
                        mol_type = protein
                        organism = Paenibacillus durus
SEQUENCE: 401
MRSKKSWIMA LALTSVLALS ACGNNGGNNT AANEGNTGAS SAPTETSGAE VSGSILASGS   60
TALQPLVEQV AEKFMEKNAG VDIQVQGGGS GTGLTQVAEK QVDIGNSDVF AEEKLKDADA   120
EKAKALVDHQ VAVVAIAAVS HPAAGVDTLT KQQLVDIFTG KITNWKEVGG ADQKIQIINR   180
PASSGTRATF EKFALGTKTE DLPGSIQEDS SGTVKKIIGE TPGAIGYLAL SYLDDSVKTL   240
NYDGVEPSVD NVVSGKYPVW AYEHMYTNGE PNATVKAFLD YFQTDEVQNG DVTELGYIPA   300
SKMQVSRDVA GNVTNK                                                   316

SEQ ID NO: 402          moltype = AA   length = 580
FEATURE                 Location/Qualifiers
source                  1..580
                        mol_type = protein
                        organism = Azorhizobium caulinodans
```

SEQUENCE: 402
MRRLLAALAL STALAGTAGA TAIYPLDRAT ILAGSPFDLK VEFDKEVQPQ DVSITINGQP    60
VEQVLGKKPD FIAKEEGVNA SAVLLRAAAF PKPGTYKVEA KAGGETKTVT WDVYATAATP   120
KAKNVIFFLG DGLSVAHRTG ARLMSKGMTE GKANGRLNID DFERMAFIGT SSTNAIATDS   180
ANTMSAYMTG HKTAVNALGV YADRTKSTLD DPKVETIAEA IRRTSKKSVG IVTGAEVEDA   240
TPAAVVAHTR ARADKADIVG MMLDVKPDVV LGGGSAYFLP KTTPGSKRKD DKDYIQLFKD   300
AGYTLATDKT ELASAAGTNT GKILGLFHPA NMDVTLDREF LKKGTVEKFP NQPGLVEMTK   360
VALNQLAKNP DGFFLMVEGA SIDKMSHPMD WERALFETIE FDQAVGVGIE FLKTHPDTLI   420
VVTGDHTHGI SIIGTIDDNK PGPDMRDKVG VYADAGFPNY EDKNGDGFPD KVDVSRRLAV   480
FASNYPDYYE TWRPKMDGPF DPAVQNEKKQ YVANEAYKNV PGATFREGNL PRSADTAVHA   540
VDDVVLQATG AGADGFKGYM EESDVYRVLV DVMALAPAKN                         580

SEQ ID NO: 403          moltype = AA  length = 347
FEATURE                 Location/Qualifiers
source                  1..347
                        mol_type = protein
                        organism = Azorhizobium caulinodans
SEQUENCE: 403
MKLTHILGAA LAVAGTLVAG NASALDFNGA GASFPAPVYQ SWGAKYKEKT GNGLNYQSIG    60
SGGGQNQIIN RTVDFGASDA PVEGPKLASN NLLQFPAVIG SIVATVNLDG IQTEQLKLTG   120
PVLADIYLGK ITKWNDKAIA DLNAGVKLPD QAIVPVYRSD ASGTSYVFTS YLAEVSADWK   180
AKVGAATSVQ WPTGAGAKGN EGVAGTVKNT KGAIGYVEFV YAAANKLVVT QLQNKAGKFV   240
APTVPAFMEA AAAADWAGSK DFAASMLNTP GANAWPIVSA TYILLPKNPT NVDASKEVMK   300
FPQWAYTKEG GEIAEKLHYI PLPEAVVKRV EEAWKAEVKA PDGKPVF                 347

SEQ ID NO: 404          moltype = AA  length = 471
FEATURE                 Location/Qualifiers
source                  1..471
                        mol_type = protein
                        organism = Escherichia coli
SEQUENCE: 404
MKQSTIALAL LPLLFTPVTK ARTPEMPVLE NRAAQGDITA PGGARRLTGD QTAALRDSLS    60
DKPAKNIILL IGDGMGDSEI TAARNYAEGA GGFFKGIDAL PLTGQYTHYA LNKKTGKPDY   120
VTDSAASATA WSTGVKTYNG ALGVDIHEKD HPTILEMAKA AGLATGNVST AELQDATPAA   180
LVAHVTSRKC YGPSATSEKC PGNALEKGGK GSITEQLLNA RADVTLGGGA KTFAETATAG   240
EWQGKTLREQ AQARGYQLVS DAASLNSVTE ANQQKPLLGL FADGNMPVRW LGPKATYHGN   300
IDKPAVTCTP NPQRNDSVPT LAQMTDKAIE LLSKNEKGFF LQVEGASIDK QDHAANPCGQ   360
IGETVDLDEA VQRALEFAKK EGNTLVIVTA DHAHASQIVA PDTKAPGLTQ ALNTKDGAVM   420
VMSYGNSEED SQEHTGSQLR IAAYGPHAAN VVGLTDQTDL FYTMKAALGL K           471

SEQ ID NO: 405          moltype = AA  length = 346
FEATURE                 Location/Qualifiers
source                  1..346
                        mol_type = protein
                        organism = Escherichia coli
SEQUENCE: 405
MKVMRTTVAT VVAATLSMSA FSVFAEASLT GAGATFPAPV YAKWADTYQK ETGNKVNYQG    60
IGSSGGVKQI IANTVDFGAS DAPLSDEKLA QEGLFQFPTV IGGVVLAVNI PGLKSGELVL   120
DGKTLGDIYL GKIKKWDDEA IAKLNPGLKL PSQNIAVVRR ADGSGTSFVF TSYLAKVNEE   180
WKNNVGTGST VKWPIGLGGK GNDGIAAFVQ RLPGAIGYVE YAYAKQNNLA YTKLISADGK   240
PVSPTEENFA NAAKGADWSK TFAQDLTNQK GEDAWPITST TFILIHKDQK KPEQGTEVLK   300
FFDWAYKTGA KQANDLDYAS LPDSVVEQVR AAWKTNIKDS SGKPLY                 346

SEQ ID NO: 406          moltype = AA  length = 524
FEATURE                 Location/Qualifiers
source                  1..524
                        mol_type = protein
                        organism = Azoarcus olearius
SEQUENCE: 406
MQPKALAISI ALALCAAQAH AAGNAVPTSA EEWFAAGRAA VETSKHVVPN RARAKNVILF    60
VGDGMGISTV TAARILEGQM RNADGEFNRL SFEKLDHMGT SVTASANQQT SDSAPTATAM   120
VTGIKTNDGA ISVDQTIERN EPSATVTRAK SVKTILEQAE ERGMSTGIVT TARLTHATPA   180
VNYAHIGNRD WEADSNLPAG ATVADIARQL LEFPYGDGLE VALGGGRSYF MPNTASDPEY   240
PSQKGRRKDG RDLTKEWTTK YKQSAYVWDK AAFDAVNPQR TKHLLGLFER SHMRYEADRK   300
DDVAGEPSLA EMTEKAIKML GQNKKGFYLM VEAGRIDHAH HAGNAYRALT DTVALSEAVE   360
VAKRLTDDQD TLIVVTADHS HVFTIAGYPS RGNPILGKSA IDGVASTDAL GLTYTTVSYA   420
NGPGWTGGFQ RKEYNPATEG TVAAPYNGSA LRPNLAGIDT TAPNYMQEAT VPMGSETHAG   480
EDVAIYASGP NAYLFRGPQE QNVIYHVMAD ALGLNKGGHG RGRD                   524

SEQ ID NO: 407          moltype = AA  length = 347
FEATURE                 Location/Qualifiers
source                  1..347
                        mol_type = protein
                        organism = Azoarcus olearius
SEQUENCE: 407
MAIRFLLLLS LAWSACVAAA PDVLRGAGSS AAQPVYAAWA AAYYAATHGTV LEYDPAGSGA    60
GIKKLLAAEV DFGASDLVPD AAALQGRDIV VVPTAVTGAV PVINLPGLRG ALRLDGATLA   120
EIFAGRIRRW DDAAIRRLNP GLTLPERAIE RVVRSDSSGT TWNFADYLAK LSPRWRAEFG   180
VAARFDWGEG VIAAKGSGGV AEAVARTPGA IGYVDYNYVV RHGLQAVTLQ NRDGAFVQAG   240

-continued

```
TDGFAAALSA SPWPRSGDFT ATLTDQPGAR SWPITMGTFI LVPRHGGGDG VRRALAFFTW   300
AYLHGDELIR SSHFVRLPDR VQAKAFRSLA AVTDANGTPI GFGGLAR                  347

SEQ ID NO: 408           moltype = AA  length = 664
FEATURE                  Location/Qualifiers
source                   1..664
                         mol_type = protein
                         organism = Stutzerimonas stutzeri
SEQUENCE: 408
MITENNDILF GNGDELPSNH STNPHIQDVI SLGRRKVLAG GAAMGALAFL GASLPGLAQA   60
AEPMSRGIKD VPFKRRTRLP FVPVAVTRAD TITVPSGYTA TTFIPWGTPI TGRYPAWLED   120
ASNTAEDQAQ QVGMHHDGMH FFPMNAKLGG RQSDHGLLVL NHEYIDAPLL HRNGPTVVDG   180
KRVNVDEVRK EINAHGVSVV EIRRGPRGEW SVLPTARNRR ITGATPMRIE GPARGHALMR   240
TRYSPSGTSV RGTLNNCANG FTPWGTYLTC EENWAGYFAT GDAELPRELS RYGVRGAGRY   300
GWETVAGDEF ERFNATRIAA TAQGDYRNEP NTFGWVVEID PFDPHSTPIK HTALGRFAHE   360
GLVFAPVKPG RPVVCYSGDD SQNEYIYKYV SRDKYRPQRS DGRLLDDGVL YVARFNPDGS   420
GDWLALDHAN PAFQRACKAA GVRFADQGEV LINTRLAADI VGATKMDRPE WGAVHPDTGE   480
VYFTLTNNSG RQQSDAANPR SPNAFGHIIR WREASRDFAG TRFTWDIYLL AGPEENSRSP   540
KGRALDATNI LASPDGLWFD DEGRLWIQTD MSGSQLSSGP FGNNQMLVSD PRTGETKRFL   600
VGPPGAEVTG ITATPDFRTL FVNIQHPGEG STSTNYTSTW PDGAGRRPRS ATVIITREDG   660
KRLM                                                               664

SEQ ID NO: 409           moltype =   length =
SEQUENCE: 409
000

SEQ ID NO: 410           moltype = AA  length = 672
FEATURE                  Location/Qualifiers
source                   1..672
                         mol_type = protein
                         organism = Pseudomonas aeruginosa
SEQUENCE: 410
MSLEKKDAIL FGDGDELPSN HSNNPHMNDL IAGLGRRQVL AGGAALGALA FLGVALPASA   60
APAEAQVPAA EGLRGLPFKR RNRLPFEAIA SGRADTIRVP AGYKATPFIP WGTPISGSYP   120
GFLDDASNSA QDQAEQIGMH HDGMHFFPID AQFGFGGGHI SNHGLLVLNH EYIDAPLLHT   180
NGPTVIDGKR TVADEVRKEI NAHGVSVVEI RRNVRGEWNV VPSQRNRRIT AATPMRIAGP   240
ARGHELLRTR HSPDGTRTRG THNNCSNGFT PWGTYLTCEE NWVGYFSTQD SELPRELTRY   300
GIRNTSRFGW ETLAGDEFER FDATRKGKQA QDDYRNEPNN FGWIVEIDPF DPQSVPVKRT   360
ALGRFAHEGL VFAPVKPGRQ VVCYSGDDSQ NEYIYKYVSR DKFRPGRSNT RLLDEGTLYV   420
ARFNADGSGQ WLPLDIADGN FRAACRKAGV SFADQGEVLI NTRLAADVLG ATKMDRPEWG   480
AVNPDNGDVY FTLTNNTSRT VADAANPRVK NAYGHIIRWR ERSRDYAGQR FTWDLFMLAG   540
PGEDSRGPDG KPLNQDNILA SPDGLWFDPE GRLWIQTDMS GSQLSSGPFG NNQMLVADPR   600
TGELKRFLTG PLGCEVTGIA ATPDFRTLFI NIQHPGEGST ADNLLSTWPD GPGRRPRSAT   660
VVITREDGRR LL                                                     672

SEQ ID NO: 411           moltype = AA  length = 651
FEATURE                  Location/Qualifiers
source                   1..651
                         mol_type = protein
                         organism = Aromatoleum aromaticum
SEQUENCE: 411
MVERVVSRRG FLKNGIGLGA AAFPAGPLSA FAKPAGTPAL HQKTPTIGFT PMAVSSGDAV   60
VVPSGYRAQV LARWGEALFA DSPEWLPDGS NTGEDQARQI GDNHDGMHFF PLNGQSSKEG   120
LLVVNHEYTN YEYLFAPEPG QPYLEPWTLD KVRKAQHAHG VSVLHIDQKS GKWEIVRDSK   180
YNRRITGNTP MAISGPASGH PLMRTSADPE GVEVLGTLNN CANGFTPWGT YLACEENFQG   240
YFGTTSGIDA RDDVMRRYGV SPLGSGYRWE EHDDRFDYVK EPNESNCFGW IVEIDPFDPD   300
SVPVKHTALG RIKHENAALT VAGTGRVVVY MGDDQTNDYI YKYVSDDRFI PGRKTANSEL   360
LDHGRLYVAK FSDGAVSGDF IGTGEWILLD KHANPILAAD PRFVDQGELL IKTRLAADAV   420
GATKMDRPEW ITVHPGSGEV YCTLTNNSGR AAANIDDANP RAANSWGQIV RWREDGDAAE   480
ATTFEWDLFV VAGNPIAFPE RADLRSGSEQ ITADNTFNSP DGLGFDSEGR LWIQTDGNFS   540
NTGNYLGQGN NQMLCADPQS GEIRRFLVGP SGCEITGIAW TPDLKTMFVN VQHPGEVGNH   600
PNRPVLPTGV SMDEYMAANP LAFSQWPEAA GGRPRSATVV ITKEDGGVIG T           651

SEQ ID NO: 412           moltype = AA  length = 629
FEATURE                  Location/Qualifiers
source                   1..629
                         mol_type = protein
                         organism = Yoonia vestfoldensis
SEQUENCE: 412
MKDIDTKTLS WDEWDELQRP ALATTDFDAV VDTALSRRGF LGGVLAFGSG AAVMGTGLLS   60
GTSAQAQATS RFGFNAIPIA TDFTVHVPEG YTWQPVAKWG QPLFSDAAPL SQETGVDLAS   120
SDRVFGENTD GMELFSIGGR QVVAVNHEYV NPDINLPHTG GETTSADDAR ILQNMQGVTV   180
MEVAEGANGW DIVVDSPFNR RITQNTPMTF SGPAAGHPLL QTAADPDGMI VLGTFNNCGS   240
GKTPWGTYLT CEENFNGYFG STDAAFARPD DYVRYGIGLE SRYGYEKFDA RPDVSQNVNE   300
PRRQGYVVEI DPSDATSTPV KHTALGRFKH ENAAVVVARD GRVVVYLGDD ERGEFLYKFV   360
SAGVYTPGGE TSSLLSDGQL YVARFATDMT GEWVALTPEA TGMDAAEIAV YTRVAASRVG   420
ATTMDRPEWV AVNPVAIEGY CALTNNSRRG ADATNAGGDA MQAVENSPNP REANRYGQIL   480
```

-continued

```
RWFPDAEDHA ATTFHWDLYV MAGNPTVHQD ANAGSANINE GNLFNSPDGM MFDSSGLLWI    540
QTDGDDSNEE GFAGMGNNQM LAGDPVTGEI ARFLTGPNGS EVTGLTWSAD RRTMFVGIQH    600
PAAPFPDGDG KLARSTVIAV KKADGAVIG                                      629

SEQ ID NO: 413           moltype = AA   length = 620
FEATURE                  Location/Qualifiers
source                   1..620
                         mol_type = protein
                         organism = Maritimibacter alkaliphilus
SEQUENCE: 413
MKDQDTSNLS WDEFDEMRDP RPATNDFDAV VERAITRRGF LGGALAFGSA ATVFGSAMLT    60
SSRAQAAAHG GFGFEPIDIA TDFDIHVPEG YEWKTLVRWG DALWSEADGA YDAETGVSPA    120
MSDKVFGENT DGMETFFVDG KELIAVNSEY VNPKINLPAA SDGTPQNADE VMLLKNLQGV    180
TVMEVAMNGG TYEVVKDSPY NRRITHETQM TMDGPAAGHA LVQTNADPEG MSPKGTMNNC    240
GSGKTLWGTY LTCEENFNGY FGATGGYDET DGLSRYGIGG EGRYAYEKFD PRYDLTAEPN    300
EPNRHGWITE IDPTDPESTP VKHTALGRFK HENAEMVQAA DGRVVVYMGD DERGEFIYRY    360
VSNGTYAEGG STEGLLSDGQ LYVAKFNDDM TGEWIALTPE ATGMSLEETL VFSRIAASAV    420
GATSMDRPEW IAANPLKAEA YCALTNNSKR GGDAMPVNAA NPRETNEYGQ IVRWAPAGDD    480
HGADTFAWDL YVMAGNPAVY DNAYGGSENV TDGNMFNSPD GMAFDSKGML WIQTDGDDSN    540
EGDFAGQGNN QMLVGNTETG EIARFLTAPN GAEVTGLCWN EDNTVAFVGI QHPGGSWPDG    600
NGKPRSSIIQ VWRTDGAPVG                                                620

SEQ ID NO: 414           moltype = AA   length = 382
FEATURE                  Location/Qualifiers
source                   1..382
                         mol_type = protein
                         organism = Bacillus subtilis
SEQUENCE: 414
MKVPKTMLLS TAAGLLLSLT ATSVSAHYVN EEHLFKVTAH TETDPVASGD DAADDPAIWV    60
HEKHPEKSKL ITTNKKSGLV VYDLDGKQLH SYEFGKLNNV DLRYDFPLNG EKIDIAAASN    120
RSEGKNTIEV YAIDGDKGKL KSITDPKHPI STNISEVYGF SLYHSQKTGA FYALVTGKQG    180
EFEQYEIVDG GKGYVTGKKV REFKLNSQTE GLVADDEYGN LYIAEEDEAI WKFNAEPGGG    240
SKGQVVDRAT GDHLTADIEG LTIYYAPNGK GYLMASSQGN NSYAMYERQG ENRYVANFEI    300
TDGEKIDGTS DTDGIDVLGF GLGPKYPYGI FVAQDGENID NGQAVNQNFK IVSWEQIAQH    360
LGEMPDLHKQ VNPRKLKDRS DG                                             382

SEQ ID NO: 415           moltype = AA   length = 349
FEATURE                  Location/Qualifiers
source                   1..349
                         mol_type = protein
                         organism = Herbaspirillum seropedicae
SEQUENCE: 415
MGFNQLIKSV AVAVAGAFAF SGAAHAAEIT GAGASFPYPV YAKWAELYKA ATGNSLNYQS    60
IGSGGGIKQI KAKTVDFGAS DAPLPQNELA EAGLTQFPAV VGGVVPVVNL DGVTPGQIKL    120
SGQVLGDIYA GKITKWNAPE ITALNPGVKL PNEDITVVYR SDASGTSYVF TSYLSKANAD    180
FKSKIGAGTA VKWPTGVGGK GNEGVAANVQ KVKGAIGYVE YAYVKKNKLN YTQLKNKDGN    240
FVSPDDSSFK AATAHGDWAK TPGFAVDFTD AAGKESWPIS SATFILLHKE QAGDGAKGKE    300
VLKFFDWAYK NGGKVAADLD YVPLPDSVTK LVEDSWKSNV KDSSGKAIW                349

SEQ ID NO: 416           moltype = AA   length = 334
FEATURE                  Location/Qualifiers
source                   1..334
                         mol_type = protein
                         organism = Gluconacetobacter diazotrophicus
SEQUENCE: 416
MRRSVTVFAA VLLGTAPVAL SVAHAANITG AGSSFAAPIY EAWGSAGRSA SGVAVNYQSV    60
GSSAGQNQIL AGTVDFGASD APMDPAKLQK GALFQFPTVM GGIVPVVNIP GIAANTLRLT    120
GEVLAGIYSG DISSWNDAKI TALNPGVNLP DLPIATVHRA DGSGTTFVFT SYLARSSQAW    180
HDGTGAGSSI SWPGGVGARG NDGVAASVRN TEGGIGYVEY AYASRNHMTT VQLKDKAGDF    240
VTADLDSFSR AAAAADWKGA ANFAVDLLDT SGKGAWPIVS ATYVLVPKQA KDAAQGAAVR    300
KFFGWAFDNG DGIARGLDYV VLPAEVKASI RAAW                                334

SEQ ID NO: 417           moltype = DNA   length = 508
FEATURE                  Location/Qualifiers
source                   1..508
                         mol_type = genomic DNA
                         organism = Azorhizobium caulinodans
SEQUENCE: 417
gggatgaact catccgcctg ttcgagaatc tggtgggagaa cgccctgaaa tacggcggca    60
ccggccagaa cgtggatgtg cgcatcgccc gcgagccggg gacgcagggt gacgtggctg    120
cggtgagcgt gcgggactat gggcgggca tcgcgccgga gcatctgccc cgcctgaccg    180
agcgcttcta tcgggtggac gttgcggcga ccgcgacca gggcgggacg ggtctcggcc    240
tcgccatcgt caagcatatc gtcgcccgcc atcgggccg gctgatggtg gagagcaccc    300
ccggaaaggg ggcaactttt accgtgcgcc tcgacctctc cgatgacgct gcgaaaaact    360
cagtaaaatac agcggcttga tccgtcattc aggtgtcacg aaccagtcat agaaggttcg    420
ggccagaccg ctatgtgtgg gcggtccaaa gttgcgtcag gacgggaacg tcccgtgtca    480
gcacctgatt ggcaatggag agaacccc                                        508

SEQ ID NO: 418           moltype = DNA   length = 192
```

```
FEATURE                Location/Qualifiers
source                 1..192
                       mol_type = genomic DNA
                       organism = Azospirillum brasilense
SEQUENCE: 418
aggttgcggt tacccccat cggcgtgacc gaaagtgggc gtcgtcatga aactgtcata    60
aaaccgtaat cagcgcgtcg cggaccccga ctagtgtccg ccccgcaagc cgcccgcccc   120
tgggggaagc ggcacggggt tgaaccatcg cgttccccgg caaagggca accggaccat    180
cggagggata cc                                                       192

SEQ ID NO: 419         moltype = DNA   length = 100
FEATURE                Location/Qualifiers
source                 1..100
                       mol_type = genomic DNA
                       organism = Escherichia coli
SEQUENCE: 419
aaagttaatc ttttcaacag ctgtcataaa gttgtcacgg ccgagactta tagtcgcttt    60
gtttttattt tttaatgtat ttgtacatgg agaaaataaa                         100

SEQ ID NO: 420         moltype = DNA   length = 563
FEATURE                Location/Qualifiers
source                 1..563
                       mol_type = genomic DNA
                       organism = Escherichia coli
SEQUENCE: 420
tattgagtgt gaaaacctgg ggatactgaa taccgatgat atcagtacgt ctttttatgc    60
taccgaaccc aatacggaca attcaatggt cgtaacttca aactctaacg tggggataaa   120
aatttacgac aaaaataata aggaaatcaa agtgaacggt ggtgagttgc caacagacat    180
gggtaaatca acagtgtatg gtgaaaaatc aggtagtgta acttttttcag ctgctcctgc   240
gagccttact ggagctcgcc cagccccggg gcaatttact gcaacagcga cgataactgt    300
tgagattgtg cgctaatagg tctgacaacg attgttcatc acatcgttgt catctcaccc    360
atttctttat cacttttaaa tgcatcatga caaaaagatg acatgtggga ttttcatctt    420
cacatttaaa atcagtaagt tatttggtaa ttccttctg tcataaaaat gtcatattcc     480
ttacatataa ctgtcacctg tttgtcctat tttgcttctc gtagccaaca aacaatgctt    540
tatgaatcct cccaggagac att                                           563

SEQ ID NO: 421         moltype = DNA   length = 386
FEATURE                Location/Qualifiers
source                 1..386
                       mol_type = genomic DNA
                       organism = Gluconacetobacter diazotrophicus
SEQUENCE: 421
tcgtttccgg ggggatgatc ccgacgggtc ctgtctggcg gctgccccg ccgccgggca     60
ggacctccgg ccgttttcgg ccacatgtgt cgttgttaat aagaaacgat ctcattccct   120
gccgatcgtg gcgcggatgc gccatgaccc ggggtcgcat agggcatcgg gatatgccgg    180
cctgcgccgt ctcgtatcat ttcaagcgcg gtttacttg ccgaatggct gccatgtgcg    240
gaatgtagag aaaagagggc ggaccatgat tgcagtacgg atgtgaagta agttagcatt    300
agggtccagt tcgaccgttc cggtcggata acgccgtctt gcgggtctct ggaccacgcc    360
gggaataaag aagaggaaag gtggcg                                        386

SEQ ID NO: 422         moltype = DNA   length = 457
FEATURE                Location/Qualifiers
source                 1..457
                       mol_type = genomic DNA
                       organism = Herbaspirillum seropedicae
SEQUENCE: 422
caagagtccc tgtccatcca gtttgagcgg gcagtgtatt gaggaggtat gacgagttta    60
tgacaagtat tatgacgctt tgtcattttt tctcagcaga aaatatcata ttttcgatgc    120
aatgaatgca agatccctgt ccccgtcagc tgactgacca acgctgcaac agaactgtca    180
ggaaagcccc tccagcccca gcctgcgccc ctttccgagc tgcttgatgg tgctcggaat    240
actttcctgc aggaaattat gacctgcccg aagatgacaa gtttgggtca taaactcgtc    300
acattagctg gttaaagttc gccctgtctc agaagtcatc cctcccaccg tgatgtttct    360
tgctgacgtc ctctctcaaa atcataggag tagttgaaat ggggtttaac caactgatca    420
aatctgttgc agtcgcagtg gccggcgctt tcgcttt                            457

SEQ ID NO: 423         moltype = DNA   length = 496
FEATURE                Location/Qualifiers
source                 1..496
                       mol_type = genomic DNA
                       organism = Kosakonia radicincitans
SEQUENCE: 423
gttcgccgat caggatgcgg gtttcaccag caacgacaat atgcacatta ttgatatgcc    60
gcacgtcgaa gaggtgattg caccgatttt ctataccgtg ccgctgcaat tgctggctta    120
tcacgttgcg ctgataaaag gcaccgatgt tgaccagccg cgtaacctgg cgaaatcagt    180
aacggtagag taaacatta ctgccataaa atgcgaaaga ggttgccggc gggcaacctc     240
tttttttttac tttattttgt gaattctcat tcgtttcaac tacttttta ttgtcacaaa    300
aataaaatat gactgaaata ttactgtgat gtttttttatt aagagtttga tttttatctt    360
```

-continued

```
ttttatatca tgcgataacg atatttttcc gctgtcatca aacagtaaca atgattgcat   420
ataactgtca tcaaagtgtc ctattttgct cgtcgtagcc actaaacaac gatttacgat   480
ccttgcagga gacatt                                                    496

SEQ ID NO: 424           moltype = DNA   length = 139
FEATURE                  Location/Qualifiers
source                   1..139
                         mol_type = genomic DNA
                         organism = Kosakonia radicincitans
SEQUENCE: 424
tgcccggagg tttttttctg ctgattgata ccgctctatt ttttgtcatg acacaaaatt   60
gtcatataag cgctctatcc ttccctccgt ccgcaaaatt attcaaaaat ctatcaactt   120
tttcgttttt ggagagatt                                                 139

SEQ ID NO: 425           moltype = DNA   length = 489
FEATURE                  Location/Qualifiers
source                   1..489
                         mol_type = genomic DNA
                         organism = Paenibacillus azotofixans
SEQUENCE: 425
tggcggcgtc tatctgaatg cgataggcgg agcggcgcag tattacgccg aatgtatcaa   60
gaaagtgaac ggcgtcgatt ttctcgaatt cggtattccc gaggcgatgt ggcatctgac   120
gatagacgga tttgcggcga ttgtgaccat ggattcccac ggcaatagcc tgcatgccga   180
cgttgagaaa gactccgcca gtaaattggc gttattccgt gaagcggtgt ttaagtaaag   240
tgtcatatgg acgatgatcc gtgtctagaa gtgcttttc gcgaaagctt ggctattttg   300
gtgtgtagcc tggacggcag cttttagcaa tgatagtgat catatgaagc ggatcggagc   360
acagatgtat acgtctggag ctccgatttt tggtttttgca tggtatgctt ttgcactggc   420
aatttcactg aaatcgggct acgatagagt aaagcagtat agtaaagcat agaaagaggc   480
atgtgccgc                                                            489

SEQ ID NO: 426           moltype = DNA   length = 437
FEATURE                  Location/Qualifiers
source                   1..437
                         mol_type = genomic DNA
                         organism = Pseudomonas stutzeri
SEQUENCE: 426
cctgatcacc ctgccgacct accacactgc tgctctgtcg accgacaacc tggccaaggg   60
ctactttgcc gaccagggca tgctggccta cgtcaagggc gttcagcgcg aggaactgcg   120
tcagggtatc gcctgcgtca agcaccagaa catggctggt tctgacatcg gcgacaacca   180
caaggagtac ttcgctggcg aagctgctct gaaggcaagc ggcaaagaca acaccatgaa   240
ccagttccac taagaacagg ttcgcagccg ccccggctgc ggtgtgaaaa aagccctggc   300
gtgagccggg gctttttttt gcgacggatt gagtggtgca cggttacgct tcgtcggtca   360
gcgctccact gtcattctct tgtcgcatac gaaccttagc gtcatggctc cgacaacaat   420
cgttatggag ctgcgcc                                                   437

SEQ ID NO: 427           moltype = DNA   length = 848
FEATURE                  Location/Qualifiers
source                   1..848
                         mol_type = genomic DNA
                         organism = Pseudomonas stutzeri
SEQUENCE: 427
cgccctgctg ggcgagtcac ttttttccaga cgcggaaaaa gtaaccaaaa acgctttgcc   60
cctgcatccg gccccgcgct ccgcgcgggg ttcgttcgct ccatcgccgc ttcagggggtc   120
ggcttacaag ggccttccat ggccctttaa gcctttcgcc gcatccatgc ggctcacccc   180
cttacgcaac gattccgctc tccctactga aggggcgagg ctgggggctg cgacgatttt   240
caacagacgg atgatgacga tcagccgacc cgtgtcgttc gttggaaacg tcctttacgg   300
ttttccctca tattggatcc tagcaatcac ggacttgcag gcgacatcga tcgcccttt   360
caggaggccg aatgtagtcg ctacgtagcg gggcgagcgg catggatgcc gcgagagaac   420
taggcgtccc cccgtaaagg gccatggatg gcccttgcac ggtgaccctc ggagaagcga   480
tggaatgagg gaagtctcgc gtagcgagac ccggatgtag ggcgcaagact ttttggttcc   540
ttttggcggg gccggccatc cgggcgactg ccaaaaggaa ctcgcgcagc agcgcgaaac   600
agaagtaccg gaacacccgg aaaatggggtt gctcccccaa cctgatccca gcgtgtctgc   660
gataggcatt tccatatcca taccgctaaa aacaggtcat atcagctcaa ccccaccccc   720
aaaatcctgc aaaacccact cttccaagct ctccccaaat ttcctgtcac agaaccgcca   780
catcccccac ctaccgtccg ctgcagttcc gggatggacc cggcaaacac cattcggggg   840
aatcgttc                                                             848

SEQ ID NO: 428           moltype = DNA   length = 1062
FEATURE                  Location/Qualifiers
source                   1..1062
                         mol_type = genomic DNA
                         organism = Pseudomonas stutzeri
SEQUENCE: 428
ccgccagccg ctgagcctgc tgttgctcga tctggatgat ttcaaggcct acaacgatac   60
cttcggccat ccggccggcg atgcgctgat ccgttcattc ggcgagctgg tggcaaagtt   120
cgcccgacgg ccgttggatc aggctgcgcg ggtcggttggc gaggagttcg cgctgctgct   180
gtacaactgc gacaacgcgg cggcgcaacg catcgcgcgg cagctggtgg ccgcgctggc   240
ggcgctggag gtcaggcatc cgcgcgatcc ggcgtcgcgc gtgggggtca gcatcggccgt   300
ggccacgctg caggatggcc agcaggccga gcagctctat cacaacgccg acatggcgct   360
```

-continued

```
gtaccaggcc aagacgaccg gcaagaaccg cttcgcggtc gccccggggc aggcgcgccg   420
cgactagctg gccaacctca gcggcgcggc gggaccgaac gcgtgcggcc gctgccgtcg   480
atggcgacga agacgaacac cgcttcggtg accttgcgcc attcgctgga cagcgggtcg   540
tcgctccaga cttccaccag catgcgaatc gagctgcgtc cgacttccag cgtctgggta   600
tagaaggaca gctgcgcgcc gacggccacc ggcaccatga aggccatgcg atcgatggac   660
accgtggcca cgcggccggc cgccacgcgg ctggccatcg cagtaccggc caggtccatc   720
tgcgacacca gccagccgcc gtagatatcg ccgaacccgt tggtttcgcg cggcaatgcg   780
gtgagctgca gggccaggtc gccctgggga atcggatctt cctgttcgta ttctttcatc   840
ggtcggactc gcggcgcgtt tgttgttctg gcgcgaaatg cccgcgctag cgcgggcgac   900
ggcgccgagt atagcggcag tgcagacgta cagcgaccgc gctgggtcaa tgggccggtt   960
cgtaatcaga ttgtcacact tgcttcatag agtgttcaca cggcctgcag atactggccc   1020
ccgttccaac acactcgagc acacacctgc taggagcaag gt                     1062
```

```
SEQ ID NO: 429            moltype = DNA   length = 88
FEATURE                   Location/Qualifiers
source                    1..88
                          mol_type = other DNA
                          organism = synthetic construct
SEQUENCE: 429
gggcccaagt tcacttaaaa aggagatcaa caatgaaagc aattttcgta ctgaaacatc   60
ttaatcatgc acaggagact ttctaatg                                      88
```

```
SEQ ID NO: 430            moltype = DNA   length = 88
FEATURE                   Location/Qualifiers
source                    1..88
                          mol_type = other DNA
                          organism = synthetic construct
SEQUENCE: 430
gggcccaagt tcacttaaaa aggagatcaa caatgaaagc aattttcgta ctgaaacatc   60
ttaatcatgc taaggaggtt ttctaatg                                      88
```

```
SEQ ID NO: 431            moltype = DNA   length = 88
FEATURE                   Location/Qualifiers
source                    1..88
                          mol_type = other DNA
                          organism = synthetic construct
SEQUENCE: 431
gggcccaagt tcacttaaaa aggagatcaa caatgaaagc aattttcgta ctgaaacatg   60
ttaaccatgc taaggaggtt ttctaatg                                      88
```

```
SEQ ID NO: 432            moltype = DNA   length = 88
FEATURE                   Location/Qualifiers
source                    1..88
                          mol_type = other DNA
                          organism = synthetic construct
SEQUENCE: 432
gggcccaagt tcacttaaaa aggagatcaa caatgaaagc aattttcgta ctgaaacatc   60
ttaatcatgc aggggagggt ttctaatg                                      88
```

```
SEQ ID NO: 433            moltype = DNA   length = 88
FEATURE                   Location/Qualifiers
source                    1..88
                          mol_type = other DNA
                          organism = synthetic construct
SEQUENCE: 433
gggcccaagt tcacttaaaa aggagatcaa caatgaaagc aattttcgta ctgaaacatc   60
ttaatcatgc gccggaggtt ttctaatg                                      88
```

```
SEQ ID NO: 434            moltype = DNA   length = 88
FEATURE                   Location/Qualifiers
source                    1..88
                          mol_type = other DNA
                          organism = synthetic construct
SEQUENCE: 434
gggcccaagt tcacttaaaa aggagatcaa caatgaaagc aattttcgta ctgaaacatc   60
ttaatcatgc tggggagggt ttctaatg                                      88
```

```
SEQ ID NO: 435            moltype = DNA   length = 88
FEATURE                   Location/Qualifiers
source                    1..88
                          mol_type = other DNA
                          organism = synthetic construct
SEQUENCE: 435
gggcccaagt tcacttaaaa aggagatcaa caatgaaagc aattttcgta ctgaaacatc   60
ttaatcatgc atcggaccgt ttctaatg                                      88
```

```
SEQ ID NO: 436            moltype = DNA   length = 88
FEATURE                   Location/Qualifiers
```

-continued

```
source                  1..88
                        mol_type = other DNA
                        organism = synthetic construct
SEQUENCE: 436
gggcccaagt tcacttaaaa aggagatcaa caatgaaagc aattttcgta ctgaaacatc  60
ttaatcatgc agaggagtct ttctaatg                                     88

SEQ ID NO: 437          moltype = DNA   length = 88
FEATURE                 Location/Qualifiers
source                  1..88
                        mol_type = other DNA
                        organism = synthetic construct
SEQUENCE: 437
gggcccaagt tcacttaaaa aggagatcaa caatgaaagc aattttcgta ctgaaacatc  60
ttaatcatgc ggaggatcgt ttctaatg                                     88

SEQ ID NO: 438          moltype = DNA   length = 88
FEATURE                 Location/Qualifiers
source                  1..88
                        mol_type = other DNA
                        organism = synthetic construct
SEQUENCE: 438
gggcccaagt tcacttaaaa aggagatcaa caatgaaagc aattttcgta ctgaaacatc  60
ttaatcatgc gggggagtgt ttctaatg                                     88

SEQ ID NO: 439          moltype = DNA   length = 88
FEATURE                 Location/Qualifiers
source                  1..88
                        mol_type = other DNA
                        organism = synthetic construct
SEQUENCE: 439
gggcccaagt tcacttaaaa aggagatcaa caatgaaagc aattttcgta ctgaaacatc  60
ttaatcatgc tgcggagggt ttctaatg                                     88

SEQ ID NO: 440          moltype = DNA   length = 88
FEATURE                 Location/Qualifiers
source                  1..88
                        mol_type = other DNA
                        organism = synthetic construct
SEQUENCE: 440
gggcccaagt tcacttaaaa aggagatcaa caatgaaagc aattttcgta ctgaaacatc  60
ttaatcatgc aatggaggct ttctaatg                                     88

SEQ ID NO: 441          moltype = DNA   length = 88
FEATURE                 Location/Qualifiers
source                  1..88
                        mol_type = other DNA
                        organism = synthetic construct
SEQUENCE: 441
gggcccaagt tcacttaaaa aggagatcaa caatgaaagc aattttcgta ctgaaacatc  60
ttaatcatgc ggtggagggt ttctaatg                                     88

SEQ ID NO: 442          moltype = DNA   length = 88
FEATURE                 Location/Qualifiers
source                  1..88
                        mol_type = other DNA
                        organism = synthetic construct
SEQUENCE: 442
gggcccaagt tcacttaaaa aggagatcaa caatgaaagc aattttcgta ctgaaacatc  60
ttaatcatgc gggggagtct ttctaatg                                     88

SEQ ID NO: 443          moltype = DNA   length = 88
FEATURE                 Location/Qualifiers
source                  1..88
                        mol_type = other DNA
                        organism = synthetic construct
SEQUENCE: 443
gggcccaagt tcacttaaaa aggagatcaa caatgaaagc aattttcgta ctgaaacatc  60
ttaatcatgc ttaggagtct ttctaatg                                     88

SEQ ID NO: 444          moltype = DNA   length = 88
FEATURE                 Location/Qualifiers
source                  1..88
                        mol_type = other DNA
                        organism = synthetic construct
SEQUENCE: 444
gggcccaagt tcacttaaaa aggagatcaa caatgaaagc aattttcgta ctgaaacatc  60
ttaatcatgc ggaggagggt ttctaatg                                     88
```

-continued

```
SEQ ID NO: 445            moltype = DNA   length = 88
FEATURE                   Location/Qualifiers
source                    1..88
                          mol_type = other DNA
                          organism = synthetic construct
SEQUENCE: 445
gggcccaagt tcacttaaaa aggagatcaa caatgaaagc aattttcgta ctgaaacatc   60
ttaatcatgc gacggagcgt ttctaatg                                      88

SEQ ID NO: 446            moltype = DNA   length = 88
FEATURE                   Location/Qualifiers
source                    1..88
                          mol_type = other DNA
                          organism = synthetic construct
SEQUENCE: 446
gggcccaagt tcacttaaaa aggagatcaa caatgaaagc aattttcgta ctgaaacatc   60
ttaatcatgc tatggaggtt ttctaatg                                      88

SEQ ID NO: 447            moltype = DNA   length = 88
FEATURE                   Location/Qualifiers
source                    1..88
                          mol_type = other DNA
                          organism = synthetic construct
SEQUENCE: 447
gggcccaagt tcacttaaaa aggagatcaa caatgaaagc aattttcgta ctgaaacatc   60
ttaatcatgc tgaggaaagt ttctaatg                                      88

SEQ ID NO: 448            moltype = DNA   length = 88
FEATURE                   Location/Qualifiers
source                    1..88
                          mol_type = other DNA
                          organism = synthetic construct
SEQUENCE: 448
gggcccaagt tcacttaaaa aggagatcaa caatgaaagc aattttcgta ctgaaacatc   60
ttaatcatgc gagggatggt ttctaatg                                      88

SEQ ID NO: 449            moltype = DNA   length = 88
FEATURE                   Location/Qualifiers
source                    1..88
                          mol_type = other DNA
                          organism = synthetic construct
SEQUENCE: 449
gggcccaagt tcacttaaaa aggagatcaa caatgaaagc aattttcgta ctgaaacatc   60
ttaatcatgc ctaggaagtt ttctaatg                                      88

SEQ ID NO: 450            moltype = DNA   length = 85
FEATURE                   Location/Qualifiers
source                    1..85
                          mol_type = other DNA
                          organism = synthetic construct
SEQUENCE: 450
gggcccaagt tcacttaaaa aggagatcaa caatgaaagc aattttcgta ctgaaacatg   60
ttaaccatgc ctaggaagtt ttcta                                         85

SEQ ID NO: 451            moltype = DNA   length = 88
FEATURE                   Location/Qualifiers
source                    1..88
                          mol_type = other DNA
                          organism = synthetic construct
SEQUENCE: 451
gggcccaagt tcacttaaaa aggagatcaa caatgaaagc aattttcgta ctgaaacatc   60
ttaatcatgc gaaggacagt ttctaatg                                      88

SEQ ID NO: 452            moltype = DNA   length = 88
FEATURE                   Location/Qualifiers
source                    1..88
                          mol_type = other DNA
                          organism = synthetic construct
SEQUENCE: 452
gggcccaagt tcacttaaaa aggagatcaa caatgaaagc aattttcgta ctgaaacatc   60
ttaatcatgc gatggacggt ttctaatg                                      88

SEQ ID NO: 453            moltype = DNA   length = 15
FEATURE                   Location/Qualifiers
source                    1..15
                          mol_type = other DNA
                          organism = synthetic construct
SEQUENCE: 453
ttcacacagg aaacc                                                    15
```

-continued

```
SEQ ID NO: 454          moltype = DNA  length = 15
FEATURE                 Location/Qualifiers
source                  1..15
                        mol_type = other DNA
                        organism = synthetic construct
SEQUENCE: 454
attaaagagg agaaa                                             15

SEQ ID NO: 455          moltype = DNA  length = 12
FEATURE                 Location/Qualifiers
source                  1..12
                        mol_type = other DNA
                        organism = synthetic construct
SEQUENCE: 455
aaagaggaga aa                                                12

SEQ ID NO: 456          moltype = DNA  length = 34
FEATURE                 Location/Qualifiers
source                  1..34
                        mol_type = other DNA
                        organism = synthetic construct
SEQUENCE: 456
cgcaaaaaac cccgcttcgg cggggttttt tcgc                        34

SEQ ID NO: 457          moltype = DNA  length = 39
FEATURE                 Location/Qualifiers
source                  1..39
                        mol_type = other DNA
                        organism = synthetic construct
SEQUENCE: 457
aaaaaaaaac cccgcccctg acagggcggg gtttttttt                   39

SEQ ID NO: 458          moltype = DNA  length = 129
FEATURE                 Location/Qualifiers
source                  1..129
                        mol_type = other DNA
                        organism = synthetic construct
SEQUENCE: 458
ccaggcatca ataaaacga aaggctcagt cgaaagactg ggcctttcgt tttatctgtt  60
gtttgtcggt gaacgctctc tactagagtc acactggctc accttcgggt gggcctttct  120
gcgtttata                                                        129

SEQ ID NO: 459          moltype = DNA  length = 42
FEATURE                 Location/Qualifiers
source                  1..42
                        mol_type = other DNA
                        organism = synthetic construct
SEQUENCE: 459
gttgtcacat atctgtcatc gcggccaggt ataattgcac ga                42

SEQ ID NO: 460          moltype = AA  length = 481
FEATURE                 Location/Qualifiers
source                  1..481
                        mol_type = protein
                        organism = Acetobacter malorum
SEQUENCE: 460
MVKKTTTAGD SKAAAIAKVF DLIQENSVEF VDLRFTDPRG KWHHTTQYVT TIEEDTFTEG  60
FMFDGSSIAG WKAINESDMV LLPDPETAVM DPFTARPQLI LFCDIIEPST GQPYNRDPRS  120
TAKLAEQYLK SSGLGDTAFF GPEAEFFIFD NVRFGTGPNF GKYQLDSIEG PGASLKDYPE  180
GNMGHRPGVK GGYFPVPPVD SENDLRAEML ATMGEMGLPI EKQHHEVAQS QHELGTKFDT  240
LVRSADFMQI YKYCVHNVAH SYGKTATFMP KPIYGDNSSG MHVHQSIWKD GKPTFAGNGY  300
ADLSDTALYY IGGIIKHAKA LNAFTNPSTN SYKRLIPGFE APVLLAYSAR NRSASCRIPY  360
ATNPKAKRVE VRFPDPTANP YLAFSAMLMA GIDGIKNKIH PGDAMDKDLY DLPPEELKQI  420
PTVAGSLREA LEALAADHEF LLAGGVFTKD QIESYLTVKW EDVYRFEHTP HPVEFEMYYS  480
V                                                                481

SEQ ID NO: 461          moltype = AA  length = 481
FEATURE                 Location/Qualifiers
source                  1..481
                        mol_type = protein
                        organism = Acetobacter tropicalis
SEQUENCE: 461
MVKKTTSASD AKAAAIAKVF DLIQENSVEL VDLRFTDPRG KWHHTTQYVT TIEDDTFTEG  60
FMFDGSSIAG WKAINESDMV LLPDPETAVM DPFSARPQLI LFCDIIEPST GQPYNRDPRS  120
TAKLAEQYLK STGLGDTAFF GPEAEFFIFD NVLFGTGPNF GKYQLDSIEG PGASLKEYPE  180
GNMGHRPGVK GGYFPVAPVD SESDLRAEML ATMGEMGLPI EKHHHEVAQS QHELGTKFDT  240
LVRSADFMQI YKYCIHNVAQ SYGKTATFMP KPIYGDNSSG MHVHQSIWKD GKPTFAGNGY  300
ADLSDTALYY IGGIIKHAKA LNAFTNPSTN SYKRLIPGFE APVLLAYSAR NRSASCRIPY  360
```

-continued

```
ATNPKAKRVE VRFPDPTANP YLAFAAMLMA GLDGIKNKIH PGDAMDKDLY DLPPEELKQI   420
PTVAGSLREA LEALQADHEF LLAGGVFTKD QIESYINIKW EDVYRFEHTP HPVEFEMYYS   480
V                                                                  481

SEQ ID NO: 462           moltype = AA  length = 481
FEATURE                  Location/Qualifiers
source                   1..481
                         mol_type = protein
                         organism = Acetobacter pasteurianus
SEQUENCE: 462
MVKKTAPAGD SKAAAIAKVF DLIQEHSVEL VDLRFTDPKG KWHHTCQYVS TIEEDSFTDG   60
FMFDGSSIGG WKAINESDMV LLPDPTSAVM DPFSARPQLI LFCDIIEPST GQPYNRDPRS   120
TAKLAEQYLK SSGLGDTAFF GPEAEFFIFD NVLFGTGPNY GKYQLDSIEG PDASLKEYPE   180
GNMGHRPGVK GGYFPVPPVD SESDLRAEML AAMGEMGLAI EKHHHEVAQS QHELGTKFET   240
LVRAADFMQI YKYCVHNVAN SYGKTATFMP KPIYGDNGSG MHVHQSIWKD GKPTFAGNGY   300
ADLSDTALYY IGGIIKHAKA LNAFTNPSTN SYKRLIPGFE APVLLAYSAR NRSASCRIPY   360
ATSPKAKRVE VRFPDPTANP YLAFAAMLMA GMDGIKNKIH PGDAMDKDLY DLPPEELKQI   420
PTVAGSLREA LEALAADHEF LLAGGVFTKD QIESYITLKW DDVYRFEHTP HPVEFEMYYS   480
V                                                                  481

SEQ ID NO: 463           moltype = AA  length = 474
FEATURE                  Location/Qualifiers
source                   1..474
                         mol_type = protein
                         organism = Acidothermus cellulolyticus
SEQUENCE: 463
MFRNADEVLA FIRDNDVKSV DVRFCDLPGI MQHFTVPAES FDESVFTDGL AFDGSSIRGF   60
QAIHESDMQL LPDPTTAFID PFRTEKTLAM NFFIHDPLTG EAYSRDPRNV ARKAEAYLVS   120
TGIADTAYFG PEAEFYIFDE VRFETSAHQS YYHIDSVAGA WNTGRIEDNG NRGYKVRYKG   180
GYFPVPPTDH FADLRAEMAR ELIRAGILVE KQHHEVGTAG QAEINYKFNT LLRAADDMQL   240
FKYIVKNVAW RAGKTVTFMP KPIFGDNGSG MHTHQSLWKD GSPLFYDELG YAGLSDTARY   300
YIGGLLRHAP SLLAFTNPTV NSYHRLVPGF EAPVNLVYSQ RNRSACIRIP ITGTNPKAKR   360
LEFRVPDPSC NPYLAFAAML MAGLDGIKNK IEPPEPIDKD LYELPPEEHA AVPQVPGSLP   420
EVLAALEADH DYLLEGGVFT PDLIATWLEY KRTKEVDSIR LRPHPHEFEL YFDV         474

SEQ ID NO: 464           moltype = AA  length = 471
FEATURE                  Location/Qualifiers
source                   1..471
                         mol_type = protein
                         organism = Acinetobacter baumannii
SEQUENCE: 464
MSMANKVLQL IQESGAKWVD FRFTDTKGKE QHVTYPADSI DEDTFEDGKM FDGSSIAGWK   60
GIEASDMILR PDAETGFIDP FFAEPTVVVT CDVIEPSTGH GYERDPRSIA RRAEEYLKST   120
GIGDTAFFGP EPEFFVFDEV KWDIDMSGAR HTLIAEEAAW STGKDYESGN SGHRPRVKGG   180
YFPVPPVDSA QDMRAEMCAK IEDIMGPGRV EVHHHEVASC QLEIGVSFNT LVRKADEVQQ   240
FKYAVWNVAH QYAKTATFMP KPMVGDNGSG MHVHMSISKD GKNLFAGDEY AGLSEMALYF   300
IGGIIKHARA LNAITNPSTN SYKRLVPHFE APIMLAYSAR NRSASIRIPY VSNPKGKRIE   360
ARFPDPMMNP YLGFAALLMA GIDGIQNKIH PGEAADKNLY DLPPEEEVKI PTVAHSLDMA   420
LEALQADHEF LLKGGVFTKE MLDAYIELKT EDVRRLNTTT HPVEFDMYYS L            471

SEQ ID NO: 465           moltype = AA  length = 471
FEATURE                  Location/Qualifiers
source                   1..471
                         mol_type = protein
                         organism = Acinetobacter calcoaceticus
SEQUENCE: 465
MSMANKVLQL IQESGAKWVD FRFTDTKGKE QHVTYPADSI DEDTFEDGKM FDGSSIAGWK   60
GIEASDMILR PDAETGFVDP FFAEPTVVVT CDVIEPSTGQ GYERDPRSIA RRAEEYLKST   120
GIGDTAFFGP EPEFFVFDEV KWDIDMSGAR HTLIAEEAAW STGKDYESGN SGHRPRVKGG   180
YFPVPPVDSS QDMRAEMCAK IEDIMGPGRV EVHHHEVASC QLEIGVSFNT LVRKADEVQQ   240
FKYAVWNVAH QYAKTATFMP KPMVGDNGSG MHVHMSISKD GKNLFAGDEY AGLSEMALYF   300
IGGVIKHARA LNAITNPSTN SYKRLVPHFE APIMLAYSAR NRSASIRIPY VSSPKGKRIE   360
ARFPDPMMNP YLGFAALLMA GIDGIQNKIH PGEAADKNLY DLPPEEAAKI PTVAHSLDMA   420
LEALQADHEF LLKGGVFTKE MLDAYIELKT EDVRRLNTTT HPVEFDMYYS L            471

SEQ ID NO: 466           moltype = AA  length = 344
FEATURE                  Location/Qualifiers
source                   1..344
                         mol_type = protein
                         organism = Agrobacterium deltaense
SEQUENCE: 466
MTKFKLEYIW LDGYKPVPNL RGKTQIKEFD EFPTLEQLPL WGFDGSSTQQ AEGHSSDCVL   60
KPVAIYPDPA RSNGALVMCE VMMPDGVTPH ASNSRATILD DEDAWFGFEQ EYFFYQDGRP   120
LGFPEQGYPA PQGPYYTGVG FKNVGSVARE IVEEHLDLCL EAGINHEGIN AEVAKGQWEF   180
QVFGKGSKRA ADQIWIARYL LLRLCEQYGI DVEFHCKPLG DTDWNGSGMH CNFSTKFMRE   240
VGGKDYFEAL MAAFAKNWKE HIDVYGPDNH LRLTGKHETA PWNKFSYGVA DRGASIRVPH   300
SFVNNGYKGY LEDRRPNSQG CPYQIASVVL KTIAEVPLAK SAAA                    344

SEQ ID NO: 467           moltype = AA  length = 469
```

-continued

```
FEATURE            Location/Qualifiers
source             1..469
                   mol_type = protein
                   organism = Aromatoleum aromaticum
SEQUENCE: 467
MNAQEVMKMI QENEVRFVDL RFTDTRGKEH HVGLPVSAFE EDHFEHGHPF DGSSLAGWKG    60
IQASDMILLP EAGSAYIDPF FDETTVVLTC DVIEPSDGKG YDRDPRSIAK RAEAYLKSTG   120
VGDTAFFGPE PEFFIFDSVE WSVDMSGVYS KIISEEAAWS TADKFEGGNT GHRPRIKGGY   180
FPVPPVDSLN DIRAAMVLAL EACGVPVEVH HHEVANAGQC EIGTKFSTLT KRADWTQVLK   240
YIVHNVAHQY GKTATFMPKP IVGDNGSGMH VHQSIWKDGQ NLFAGNGYAG LSEMALYYIG   300
GIIKHARALN AITNPGTNSY KRLVPHYEAP TKLAYSARNR SASIRIPYVA NPKGRRIEAR   360
FPDPLANPYL AFSALMMAGL DGIQNKIHPG DPADKNLYDL PPEEDAKIPT VCTSLDQALE   420
YLDNDREFLT RGGVFSNDFI DAYLALKGEE VDRMRITTHP VEFDMYYSL                469

SEQ ID NO: 468        moltype = AA   length = 446
FEATURE            Location/Qualifiers
source             1..446
                   mol_type = protein
                   organism = Arthrobacer sp.
SEQUENCE: 468
MDRQQEFVLR TIEERDVRFV RLWFTDVVGS LKSVALAPAE VEGAFEEGLG FDGSAIEGLA    60
RVFESDMLAQ PDPSTFQILP WRGETEQTSR MYCDILTPDG EPSAADPRNV LKRTLAKAAD   120
MGFTCYTHPE IEFYLLKSQE PGPDGSPVPV DEGGYFDHVP GGVAQDFRRT AVTMLESVGI   180
SVEFSSHHEAG PGQNEIDLRY ADALQTADNI MTFRTVIKEV ALQQGTYATF MPKPFTAHPG   240
SGMHTHFSLF EGDTNAFYEA GAEFQLSKTA KQFIAGILKH APEFTAVTNQ FVNSYKRLWG   300
GGEAPSYLSW GHNNRSALVR VPLYKPGKGQ SARIEYRGID SAANPYLAYA VLLGAGLKGI   360
EEGYEIPAAA EDDIWSLSSA ERRAMGHDPL PASLHDAIRT MEDSELMPQI LGEQVFEYFL   420
RNKRAEWQDY RLQVTPYELQ RNLGIL                                         446

SEQ ID NO: 469        moltype = AA   length = 469
FEATURE            Location/Qualifiers
source             1..469
                   mol_type = protein
                   organism = Azoarcus sp.
SEQUENCE: 469
MNAQDVMKMI QENEVRFVDL RFTDTRGKEQ HVGLPVSAFE EDHFEHGHPF DGSSIAGWKG    60
IQASDMILMP EAGSAYIDPF FDETTLVLTC DVIEPSDGKG YDRDPRSIAK RAEAYLKSTG   120
IGDTAYFGPE PEFFIPDAVE WSVDMSGVYS KIISEEAAWS TADKFEGGNT GHRPRVKGGY   180
FPVPPVDSLN DVRAAMVLAL EGAGVPVEVH HHEVANAGQC EIGTKFNTLT KRADWTQVLK   240
YIVHNVAHQY GKTATFMPKP IVGDNGSGMH VHQSIWKDGQ NLFAGNGYAG LSETALYYIG   300
GIIKHARALN AITNPGTNSY KRLVPHYEAP TKLAYSARNR SASIRIPYVA NPKGRRIEAR   360
FPDPLANPYL AFAALMMAGL DGIQNKIHPG DPADKNLYDL PPEEDALIPT VCTSLEQALE   420
YLDKDREFLT RGGVFSNDFI DAYIALKMEE VDRMRITTHP VEFDMYYSL                469

SEQ ID NO: 470        moltype = AA   length = 469
FEATURE            Location/Qualifiers
source             1..469
                   mol_type = protein
                   organism = Azorhizobium caulinodans
SEQUENCE: 470
MKTAKEVLDF IKSNDVKYVD LRFTDPRGKW QHVTFDITMV DEDFFAEGQA FDGSSIAGWK    60
AINESDMLLM PDVTTACVDP FFSETTLSVV CDVLEPTTGE PYGRDPRGIA KKAMAYLQST   120
GIGDTVFFGP EAEFFIFDDV KFKADPYNTG FKLDSIELPT NGDTDYEGGN LGHRIKTKGG   180
YFPVPPLDSA QDMRSEMLAS MAKMGAKVEK HHHEVASAQH ELGLKFGQLV TMADHLQVYK   240
YCIHQVANIY GKTATFMPKP VYGDNGSGMH VHQSIWKDGK PLFAGDKYAD LSQECLWYIG   300
GVIKHAKSLN AFTNPLTNSY KRLVPGYEAP VLLAYSARNR SASCRIPYTN NPKAKRVEVR   360
FPDPGANPYL AFSALFMAGM DGILNKIDPG SAMDKDLYDL PPAELKQIPT VCGSLREALE   420
SLAKDHDYLL KGDVFQKDFI ESYIDLKMQE VARFEMTPHP VEFEMYYSV                469

SEQ ID NO: 471        moltype = AA   length = 467
FEATURE            Location/Qualifiers
source             1..467
                   mol_type = protein
                   organism = Azotobacter vinelandii
SEQUENCE: 471
MSKSLQLIKE HDVKWIDLRF TDTKGKQQHV TMPARDVDDD FFEYGKMFDG SSIAGWKGIE    60
ASDMILMPDD STAVLDPFTE EPTLIIVCDI IEPSTMQGYD RDPRAIARRA EEYLKSTGIG   120
DTAFFGPEPE FFIFDEVKYK SDISGSMFKI FSEQAAWNTD ADFEGGNKGH RPGVKGGYFP   180
VPPVDHDHEI RTAMCNALEE MGLKVEVHHH EVATAGQNEI GVSFNTLVAK ADEVQTLKYC   240
VHNVADAYGK TVTFMPKPLY GDNGSGMHVH MSIAKDGKNT FAGEGYAGLS DTALYFIGGI   300
IKHGKALNGF TNPSTNSYKR LVPGFEAPVM LAYSARNRSA SIRIPYVNSP KARRIEARFP   360
DPSANPYLAF AALLMAGLDG IQNKIHPGDA ADKNLYDLPP EEAKEIPQVC GSLKEALEEL   420
DKGRAFLTKG GVFSDDFIDA YLELKSEEEI KVRTFVHPLE YDLYYSV                  467

SEQ ID NO: 472        moltype = AA   length = 444
FEATURE            Location/Qualifiers
source             1..444
                   mol_type = protein
                   organism = Bacillus subtilis
```

```
SEQUENCE: 472
MAKYTREDIE KLVKEENVKY IRLQFTDILG TIKNVEIPVS QLGKALDNKV MFDGSSIEGF  60
VRIEESDMYL YPDLNTFVIF PWTAEKGKVA RFICDIYNPD GTPFEGDPRN NLKRILKEME  120
DLGFSDFNLG PEPEFFLFKL DEKGEPTLEL NDKGGYFDLA PTDLGENCRR DIVLELEEMG  180
FEIEASHHEV APGQHEIDFK YAGAVRSCDD IQTFKLVVKT IARKHGLHAT FMPKPLFGVN  240
GSGMHCNLSL FKNGVNAFFD ENADLQLSET AKHFIAGIVK HATSFTAVTN PTVNSYKRLV  300
PGYEAPCYVA WSAQNRSPLI RIPASRGIST RVEVRSVDPA ANPYLALSVL LAAGLDGIKN  360
KLEAPAPIDR NIYVMSKEER MENGIVDLPA TLAEALEEFK SNEVMVKALG EHLFEHFIEA  420
KEIEWDMFRT QVHPWEREQY MSQY                                         444

SEQ ID NO: 473          moltype = AA  length = 478
FEATURE                 Location/Qualifiers
source                  1..478
                        mol_type = protein
                        organism = Bifidobacterium adolescentis
SEQUENCE: 473
MTALETKADA EALINKEGIE YVSVRFTDLI GVQQHFTVPA SEFLKDAFTD GMPFDGSSVE  60
GFQAINESDM KLVPDVSTAF IDPFRKHKTL DVAFSIVDPL TDEPYSRDPR QVAGKAEAYL  120
KSTGIADTAS FAPEAEFFIF DKVRFENSMQ RSFYEVDSIE APWNSGIDTE DDGTPNIAFK  180
NRVKKGYFPV PPIDHTQDLR DDMVANLQKV GLILERSHHE VAGAGQQEIN YRFNSLQHAG  240
DDLMKYKYVV HETAALAGKA ATFMPKPIAG DNGTGMHCHQ SLWKDGKPLF YDEKNYGGLS  300
DLARWYIGGL IKHSSSVLAF TNPSLNSYHR LVPGFEAPVN LVYSARNRSA AIRIPLAGTS  360
PAAKRIEFRA PDPSCNPFLA FSAQLMAGLD GILNHIEPPA PVDKDLYELP PEEHAGIKQV  420
PSSLAEAMDA LEEDHDFLTA GDVFTDDLID TWISIKRGEI DQARLAPTPL EYELYFHI    478

SEQ ID NO: 474          moltype = AA  length = 478
FEATURE                 Location/Qualifiers
source                  1..478
                        mol_type = protein
                        organism = Bifidobacterium asteroides
SEQUENCE: 474
MSELKSKADC EALINQEGVE YVSVRFTDLI GVQQHFTVPA SEFLKDAFTD GMAFDGSSVQ  60
GFQAINESDM KLIPDPETAY LDPFRRHRTL NVAFSIVDPV TDEPYSRDPR QIAAKAEAYL  120
RSTGIADTAS FAPEAEFFIF DKVRFENSMQ RSFYEVDSIE APWNSGVDVE EDGSDNIGFK  180
NRVKKGYFPV PPIDHYQDLR DDMVANLQKV GLILERSHHE VGGAGQQEIN YRFNTLLHAG  240
DDLMKYKYVV HETAALAGKA ATFMPKPIAG DNGTGMHCHQ SLWKDGKPLF YDENGYGGLS  300
DIARWYVGGL IEHASSVLAF TNPSTNSYKR LVPGYEAPVN LVYSARNRSA AIRIPLAGTS  360
PAAKRIEFRA PDPSCNPFLA FSAQLMAGLD GILNHTEPPA PIDKDLYELP PEEHAQIKQV  420
PGSLEEALNA LEEDHDFLSE GDVFTDDLIQ TWLDLKRGEL DQTRLAPTPL EYELYFHI    478

SEQ ID NO: 475          moltype = AA  length = 469
FEATURE                 Location/Qualifiers
source                  1..469
                        mol_type = protein
                        organism = Bradyrhizobium diazoefficiens
SEQUENCE: 475
MKTAKDVLKS IKDNDVKYVD LRFTDPRGKW QHVTFDVSMI DEDIFAEGTM FDGSSIAGWK  60
AINESDMCLM PDPVTATIDP FFAETTMVIT CDVLEPTTGE PYNRDPRGIA KKAEAMVKSM  120
GVGDSVFVGP EAEFFVFDDV RFSSDPYNTG FRLDSSELPV NSNTEYEGGN LGHRVRTKGG  180
YFPVPPQDSV QDMRSEMLGA MAKMGVKVEK HHHEVASAQH ELGMKFDTLT LMADHMQIYK  240
YCIHQVAHIY GKTATFMPKP VYGDNGSGMH VHQSIWKDGK PVFAGNKYAD LSETCLHYIG  300
GIIKHAKAIN AFTNPSTNSY KRLVPGYEAP VLLAYSARNR SASCRIPYTA SPKAKRVEVR  360
FPDPLANPYL GFAAMLMAGL DGIKNKIDPG PAMDKDLYDL PKEELKQIPT VCGSLREALE  420
NLDKDRSFLK AGGVFDDDFI DAYIELKMTE VARFEMTPHP IEFDMYYSG              469

SEQ ID NO: 476          moltype = AA  length = 469
FEATURE                 Location/Qualifiers
source                  1..469
                        mol_type = protein
                        organism = Bradyrhizobium frederickii
SEQUENCE: 476
MKTAKDVLKS IKDNDVKYVD LRFTDPRGKW QHVTFDVTMI DEDIFAEGTM FDGSSIAGWK  60
AINESDMCLM PDPVTATIDP FFAETTMVIT CDVLEPTTGE PYNRDPRGIA KKAEAMVKSM  120
GVGDSVFVGP EAEFFVFDDV RYSADPYKTG FRLDSSELPT NSDTEYEGGN LGHRIRTKGG  180
YFPVPPQDSV QDMRSEMLGA MAKMGVKVEK HHHEVASAQH ELGMKFDTLT LMADHMQIYK  240
YCIHQVAHIY GKTATFMPKP IFGDNGSGMH VHQSIWKDGK PVFAGNKYAD LSETCLHYIG  300
GIIKHAKAIN AFTNPSTNSY KRLVPGYEAP VLLAYSARNR SASCRIPYTA SPKAKRVEVR  360
FPDPMANPYL GFAAMLMAGL DGIKNKIDPG PAMDKDLYDL PKEELKQIPT VCGSLREALE  420
NLDKDRGFLK AGGVFDDDFI DAYIELKMTE VARFEMTPHP VEFEMYYSG              469

SEQ ID NO: 477          moltype = AA  length = 471
FEATURE                 Location/Qualifiers
source                  1..471
                        mol_type = protein
                        organism = Burkholderia cenocepacia
SEQUENCE: 477
MSKTVADVMQ LVKDEDVKFV DFRFTDTRGK EQHVSVPVSA FDEDKFESGH AFDGSSIAGW  60
KGIEASDMLL MPDPSAAFVD PFYEESTLVL TCDVVEPADG KGYERDPRSL AKRGEAYLKS  120
TGIGDTAYFG PEPEFFIFDS VQWNTDMSGC FVKINSEEAP WSAGKEFEGG NTGHRPGTKG  180
```

```
GYFPVAPVDT FQDMRSEMCL LLEQLGIPVE VHHHEVAGQG QNEIGTKFST LVQRADWTQW  240
SKYIIHNVAH SYGKTATFMP KPVVGDNGSG MHVHQSIWKD GQNLFAGNGY AGLSELALFY  300
IGGIIKHARA LNAITNPTTN SYKRLVPHFE APVKLAYSAR NRSASIRIPH VSNPKGRRIE  360
TRFPDPMANP YLCFTALMMA GLDGIQNKIH PGEAADKNLY DLPPEEDAKI PTVCAGLDQA  420
LEALDKDREF LTRGGVFTDG MIDAYLALKE QELAKFRMTT HPIEFEMYYS L           471

SEQ ID NO: 478        moltype = AA  length = 471
FEATURE               Location/Qualifiers
source                1..471
                      mol_type = protein
                      organism = Burkholderia stagnalis
SEQUENCE: 478
MSKTVADVMQ LVKDEDVKFV DFRFTDTRGK EQHVSVPVSA FDEDKFESGH AFDGSSIAGW  60
KGIEASDMLL MPDPSAAFVD PFYEESTLVL TCDVVEPADG KGYERDPRSL AKRGEAYLKS  120
TGIGDTAYFG PEPEFFIFDS VQWNTDMSGC FVKINSEEAP WSAGKEFEGG NTGHRPGTKG  180
GYFPVAPVDT FQDMRSEMCL LLEQLGIPVE VHHHEVAGQG QNEIGTKFST LVQRADWTQW  240
SKYIIHNVAH SYGKTATFMP KPVVGDNGSG MHVHQSIWKD GQNLFAGNGY AGLSELALFY  300
IGGIIKHARA LNAITNPTTN SYKRLVPHFE APVKLAYSAR NRSASIRIPH VSNPKGRRIE  360
TRFPDPMANP YLCFTALMMA GLDGIQNKIH PGEAADKNLY DLPPEEDAKI PTVCAGLDQA  420
LEALDKDREF LTRGGVFTDG MIDAYLALKE QELAKFRMTT HPIEFEMYYS L           471

SEQ ID NO: 479        moltype = AA  length = 445
FEATURE               Location/Qualifiers
source                1..445
                      mol_type = protein
                      organism = Conexibacter sp.
SEQUENCE: 479
MPDQPKTRED VKALVQEHRI RFIRLWFTDI LGQLKSFSIN SEELDDAFEG GMGFDGSSIT  60
GFNAIEESDM IAMPDATTFS ILPWRPEEQG VARMFCDVQT PERTPYEGDP RHVLRRAVDR  120
ANAMGFETFN VGPELEYFLF KDKNGTEVLD EGGYFDLTTL DAGSDVRRET SLALEQLGIK  180
VEYSHHEVGP SQHEIDMRYA DALKMADDCM TYRITVKEYA MKYGWHATFM PKPLFAENGS  240
GMHTHMSLFK DGRNAFFDAD DPYFLSDIGK AFIAGQLRHA RELSSIFAQW VNSYKRLVPG  300
YEAPVYVAWS RRNRSALVRV PLYHPGKEQA TRMELRCPDP ACNPYLTFAA LLHAGLEGIE  360
KGYELPEPME KNLYHLSPDD RRRLGIEQLP ETLGEAIELT AESELVLRTL GEHMFNRYIE  420
IKRQEWEDYR VQVTQWELDR YLPVL                                         445

SEQ ID NO: 480        moltype = AA  length = 474
FEATURE               Location/Qualifiers
source                1..474
                      mol_type = protein
                      organism = Curtobacterium albidum
SEQUENCE: 480
MFSDSSEVLA FIKDTDVKFL DIRFTDLPGV QQHFNIPAST VDEDFFSVGQ LFDGSSIRGF  60
ASIHESDMQL IPDVTTAYID QFRAERTLIM IFDIYNPRNG EIYGRDPRQV AKKAEKYLAS  120
TGIADTAFFA PEAEFYIFDD VRYSVTQNKS FYSVDSEEGA WNTGREEEGG NLANKTPYKG  180
GYFPVSPVDK TADLRDDITL KLIEAGFELE RSHHEVGTGG QQEINYKFDT MVHAADDILK  240
FKYIVKNTAD QWGKVATFMP KPLFGDNGSG MHTHQSLWND GKPLFYDENG YGGLSDLARW  300
YIGGILKHAP ALLAFTNPSI NSYHRLVKGF EAPVNLVYSA GNRSAAIRIP ITGTNPKAKR  360
IEFRAPDASG NPYLAFAAQL MAGLDGIQNR IEPHEPVDKD LYELPPEEAK GIPQVPGSLD  420
EALEALEADH EFLTKGNVFT EDLIQTWIDY KRENEILPLA QRPHPFEYEL YFGV          474

SEQ ID NO: 481        moltype = AA  length = 469
FEATURE               Location/Qualifiers
source                1..469
                      mol_type = protein
                      organism = Ensifer adhaerens
SEQUENCE: 481
MTTASDILKQ IKDNDVKFVD LRFTDPKGKL QHVTMDVVCV DEDMFADGVM FDGSSIGGWK  60
AINESDMVLM PDPETAHMDP FFAQSTMVII CDILDPVSGE SYNRDPRGTA KKAEAYLKAS  120
GIGDTVFVGP EAEFFVFDDV KYKADPYNTG FKLDSSELPS NDDTDYETGN LGHRPRVKGG  180
YFPVPPIDSC QDMRSEMLTV LSEMGVTVEK HHHEVAAAQH ELGVKFDALV RNADKMQIYK  240
YVVHQVANAY GKTATFMPKP IFGDNGSGMH VHLSIWKDGK PTFAGDEYAG LSESCLYFIG  300
GIIKHAKSLN AFTNPSTNSY KRLVPGYEAP VLLAYSARNR SASCRIPFGT NPKAKRVEVR  360
FPDPTANPYL AFAAMLMAGL DGIKNKLHPG KAMDKDLYDL PPKELKKIPT VCGSLREALE  420
SLDKDRKYLT AGGVFDDDQI DSFIELKMQE VMRYDMTPHP VEYDMYYSV              469

SEQ ID NO: 482        moltype = AA  length = 469
FEATURE               Location/Qualifiers
source                1..469
                      mol_type = protein
                      organism = Enterobacter agglomerans
SEQUENCE: 482
MSAEHVLTML NEHEVKFVDL RFTDTKGKEQ HVTIPAHQVN AEFFEEGKMF DGSSIGGWKG  60
INESDMVLMP DATTAVIDPF FEEPTLIIRC DILEPGTLQG YDRDPRSIAK RAEEYLRSTG  120
IADTVLFGPE PEFFLFDDIR FGASISGSHV AIDDIEGAWN SSTKYEGGNK GHRPGVKGGY  180
FPVPPVDSAQ DIRSTMCLVM EEMGLVVEAH HHEVATAGQN EVATRFNTMT KKADEIQIYK  240
YVVHNVAHRF GKTATFMPKP MFGDNGSGMH CHMSLSKNGT NLFSGDKYAG LSEQALYYIG  300
GVIKHAKAIN ALANPTTNSY KRLVPGYEAP VMLAYSARNR SASIRIPVVA SPKARRIEVR  360
```

```
FPDPAANPYL CFAALLMAGL DGIKNKIHPG EAMDKNLYDL PPEEAKEIPQ VAGSLEEALQ  420
ALDADREFLT AGGVFTDDAI DAYIALRTEE NDRVRMTPHP VEFELYYSV              469

SEQ ID NO: 483        moltype = AA  length = 469
FEATURE               Location/Qualifiers
source                1..469
                      mol_type = protein
                      organism = Erwinia amylovora
SEQUENCE: 483
MSAEHVLSMM NEHEVKFVDL RFTDTKGKEQ HVTIPAHQVN ADFFEEGKMF DGSSIGGWKG  60
INESDMVLMP DATTAVLDPF FEDATLIIRC DILEPGTMQG YDRDPRSIAK RAEDFLRSSG  120
IADTVLFGPE PEFFLFDDIR FGSSTSGSHV AIDDIEASWN TGKQYEGGNK GHRPGLKGGY  180
FPVPPVDSSQ DIRSAMCLTM EQMGLVVEAH HHEVATAGQN EVATRFNTMT KKADEIQIYK  240
YVVHNVAHAY GKTATFMPKP IFGDNGSGMH CHMSLSKGGT NLFAGDKYGG LSETALFYIG  300
GVIKHAKAIN ALANPTTNSY KRLVPGYEAP VMLAYSARNR SASIRIPVVA SPKARRIEAR  360
FPDPAANPYL CFAALLMAGL DGIINKIHPG DAMDKNLYDL PPEEEAEIPK VAASLDEALA  420
ALNEDREFLT RGGVFTDDAI EAYIELRKAE MERVRMTPHP VEFELYYSV              469

SEQ ID NO: 484        moltype = AA  length = 469
FEATURE               Location/Qualifiers
source                1..469
                      mol_type = protein
                      organism = Escherichia coli
SEQUENCE: 484
MSAEHVLTML NEHEVKFVDL RFTDTKGKEQ HVTIPAHQVN AEFFEEGKMF DGSSIGGWKG  60
INESDMVLMP DASTAVIDPF FADSTLIIRC DILEPGTLQG YDRDPRSIAK RAEDYLRSTG  120
IADTVLFGPE PEFFLFDDIR FGSSISGSHV AIDDIEGAWN SSTQYEGGNK GHRPAVKGGY  180
FPVPPVDSAQ DIRSEMCLVM EQMGLVVEAH HHEVATAGQN EVATRFNTMT KKADEIQIYK  240
YVVHNVAHRF GKTATFMPKP MFGDNGSGMH CHMSLSKNGV NLFAGDKYAG LSEQALYYIG  300
GVIKHAKAIN ALANPTTNSY KRLVPGYEAP VMLAYSARNR SASIRIPVVS SPKARRIEVR  360
FPDPAANPYL CFAALLMAGL DGIKNKIHPG EAMDKNLYDL PPEEAKEIPQ VAGSLEEALN  420
ELDLDREFLK AGGVFTDEAI DAYIALRREE DDRVRMTPHP VEFELYYSV              469

SEQ ID NO: 485        moltype = AA  length = 729
FEATURE               Location/Qualifiers
source                1..729
                      mol_type = protein
                      organism = Flavobacterium glycines
SEQUENCE: 485
MSTIRFQALR EASNRKVVSF EEANRKSNIF GLNVFNEKAM KQYLTSDAFK AVQGAIENGT  60
KIERKLADYI AMGMKEWALS KGVTHYTHWF QPLTGTTAEK HDAFFETSFD GSDPVEKFGG  120
AQLVQQEPDA SSFPNGGIRN TFEARGYTAW DPTSPAFIYG TTLCIPTVFI SYTGEALDNK  180
IPLLRALAAM DEAATEVCRY FDKNVKKVTA TLGWGEQEYFL VDKALAHSRP DLMMTGRTLL  240
GHTSAKGQQL DDHYFGSIPT RALTYMRDLE QECMLLGIPV KTRHNEVAPN QFELAPIFEE  300
TNLAVDHNCL LMDIMQKVAE RHDFKVLLHE KPFQGVNGSG KHNNWSLATD TGVNLLSPSK  360
TPMSNLQFLT FFINTIKAVN DYEELLRASI ATASNDHRLG ANEAPPAIIS VFIGEQLTKV  420
LAELESVTRG KLSPEEKTDL KLNVVGKIPE VILDNTDRNR TSPFAFTGNK FEFRAVGSSA  480
NCSNAMTTLN TIVAKQLRDF KAEVDTLIDS KAMKKDDAIF NVLREYIKVS KDILFEGDGY  540
SEAWEKEAKK RGLSNFKTTP EALKAKVSKR ALDLFSELGI MNHVEVEARY EIELEEYTKK  600
IQIESRVLGD ISKNHVIPTA IRYQNTLIEN VKGLKDIFGK EFESIAKEQI GLIKEISTHI  660
EGINAKVEEM RNERKNANAL NNAQKTAEAY CNKVKPYFEI IRNHCDKLEL LVDNELWTLT  720
KYRELLFTK                                                         729

SEQ ID NO: 486        moltype = AA  length = 474
FEATURE               Location/Qualifiers
source                1..474
                      mol_type = protein
                      organism = Frankia canadensis
SEQUENCE: 486
MFTKAEDVLR YIRDEKVQFI DVRFCDLPGI MQHFTIPTQV FAESVFTDGL MFDGSSIRGF  60
QAIHESDMLL LPDPQTAFVD PFREHKTLAM TFFIHDPITK EQYSRDPRNI AKKAETYLRG  120
TGIADTAYFG PEAEFYIFDD VRYDYNPYGS LHQVDSVEAA WNTARKEEGG NLGYKPRFKG  180
GYFPVPPTDH FTDLRSEMTR VLYETGITVE MQHHEVGTAG QAEIDIRYDT LLKTADNLML  240
YKYVIRNVAR ERGKTVTFMP KPLFEDNGSG MHVHSSLWKD GEPLFYSANG YGGLSDIARY  300
YIGGLLHHAP ALLAFTNPTT NSYRRLVPGY EAPVNLVYSA RNRSACCRIP LGGDSPKAKR  360
VEFRVPDPSC NPYLAFAAML MAGLDGIRNK IDPPEPIDKD LYELPPDELA AVPQVPGSLE  420
KVLDALEADH EFLREGDVFT TDLIETWLDY KRRNEVDAIR LRPHPYEFTL YYDI         474

SEQ ID NO: 487        moltype = AA  length = 486
FEATURE               Location/Qualifiers
source                1..486
                      mol_type = protein
                      organism = Gluconacetobacter diazotrophicus
SEQUENCE: 487
MAKKAPSSAP TTTPSPSAEA VAKVFSLIQE HSVELVDLRF TDPRGKWHHT TQHISTIEQD  60
TFRDGFMFDG SSIVGWKAIN ESDMVLLPDP TTAVMDPFSA KPQLILICDI IEPSTGQFYN  120
RDPRATAKLA EAYLKSTGLG DTAFFGPEAE FFVFDSVKFG TGPNFGIYQL DSIEGPGASL  180
KDYPEGNMGH RPTVKGGYFP VPPVDSENDL RAEMLSTMGE MGLPIEKHHH EVAQSQHELG  240
TKFATLVKSA DFMQIYKYCV HNVAHSYGKS ATFMPKPIYG DNGSGMHVHQ SIWKSGKPVF  300
```

```
AGNGYADLSD QALYYIGGII KHAKALNAFT NPSTNSYKRL IPGFEAPVLL AYSARNRSAS  360
CRIPYATSPK AKRVEVRFPD PTANPYLAFA AMLMAGLDGI KNKIHPGDAM DKDLYDLPPD  420
ELKQIPTVCG SLREALEALT ADHEFLLAGG VFTKDQIESY IDIKWQEVFK FEHTPHPAEF  480
EMYYSV                                                            486

SEQ ID NO: 488            moltype = AA  length = 460
FEATURE                   Location/Qualifiers
source                    1..460
                          mol_type = protein
                          organism = Gluconobacter oxydans
SEQUENCE: 488
MIQEHAAEFV DLRFTDPKGK WHHTTQTVST IEDDTFVEGF MFDGSSIQGW KAINESDMVL  60
LPDPETAVMD PFSAKPQLIL FCDIIDPKTG NFYNRDPRST AKLAEAYLKH AGFGDTAFFG  120
PEAEFFIFDN VQFGTGPNFG MYQLDSIEGP GASLKAYPEG NMGHRPVVKG GYFPVPPVDS  180
ENDLRAEMLS TMGEMGLPIE KHHHEVAQSQ HELGTKFDTL VKSADFMQIY KYCVHNVAHS  240
YGKTATFMPK PISGDNGSGM HVHQSIWKDG KPTFAGDKYA DLSDEALYYI GGIIKHAKAL  300
NAFTNPSTNS YKRLIPGFEA PVLLAYSAAN RSASCRIPHA TNPKAKRVEV RFPDPTANPY  360
LAFAAMLMAG LDGIRNKIHP GDAMDKDLYE LPKEELAQIP TVCGSLREAL EALKEDHAFL  420
LEGGVFTKDQ IESYIDIKWP EVYKFEHTPH PAEFEMYYSV                        460

SEQ ID NO: 489            moltype = AA  length = 471
FEATURE                   Location/Qualifiers
source                    1..471
                          mol_type = protein
                          organism = Herbaspirillum seropedicae
SEQUENCE: 489
MARTAAEVLK MVKDNEVKFV DFRFADTRGK EQHVSVPVSH FDIDKFESGH AFDGSSIAGW  60
KGIEASDMLL IPDPNTANID PFMEETTLFM QCDVIEPSDG KGYDRDPRSI AKRAEAYLKS  120
SGLGDTAYFG PEPEFFIFDG VRWGADMSGS FVKIDSEEAS WSTGAKIEGG NSGHRPTVKG  180
GYFPVPPVDS FQDMRSEMSL IIESLGIPVE VHHHEVAGAG QNELGTKFST LVERADWTGT  240
MKYVIWNVAH TYGKTATFMP KPLVGDNGSG MHVHQSVWKD GKNLFAGDGY AGLSEFALYY  300
IGGIIKHAKA LNAITNPGTN SYKRLVPGFE APVKLAYSAR NRSASIRIPH VANPKGRRIE  360
TRFPDPLANP YLCFSALLMA GLDGVQNKIH PGEAATKDLY HLPPEEDKLI PTVCSSLDEA  420
LEHLDKDREF LTRGGVFTDS MIDAYIDLKM QEVQRFRMTT HPIEFDMYYS L           471

SEQ ID NO: 490            moltype = AA  length = 469
FEATURE                   Location/Qualifiers
source                    1..469
                          mol_type = protein
                          organism = Klebsiella oxytoca
SEQUENCE: 490
MSAEHVLTML NEHEVKFVDL RFTDTKGKEQ HVTIPSHQVN AEFFEEGKMF DGSSIGGWKG  60
INESDMVLMP DATTALIDPF YEEPTLIIRC DILEPGTLQG YDRDPRSIAK RAEEYLRSTG  120
LADTVLFGPE PEFFLFDDIR FGASISGSHV AIDDIEGAWN SSTKYEGGNK GHRPGVKGGY  180
FPVPPVDSSQ DIRSTMCMIM EEMGLVVEAH HHEVATAGQN EIATRFNTMT KKADEIQIYK  240
YVVHNVAHRF GKTATFMPKP MFGDNGSGMH CHMSLSKNGV NLFSGDKYAG LSEQALYYIG  300
GVIKHAKAIN ALANPTTNSY KRLVPGYEAP VMLAYSARNR SASIRIPVVT SPKARRIEVR  360
FPDPAANPYL CFAALLMAGL DGIKNKIHPG EAMDKNLYDL PPEEAKEIPQ VAGSLEEALN  420
ALDADREFLT AGGVFTNDAI DAYIALRMEE NDRIRMTPHP VEFELYYSV              469

SEQ ID NO: 491            moltype = AA  length = 273
FEATURE                   Location/Qualifiers
source                    1..273
                          mol_type = protein
                          organism = Klebsiella variicola
SEQUENCE: 491
CMIMEEMGLV VEAHHHEVAT AGQNEVATRF NTMTKKADEI QIYKYVVHNV AHRFGKTATF  60
MPKPMFGDNG SGMHCHMSLA KNGTNLFSGD KYAGLSEQAL FYIGGVIKHA KAINALANPT  120
TNSYKRLVPG YEAPVMLAYS ARNRSASIRI PVVTSPKARR IEVRFPDPAA NPYLCFAALL  180
MAGLDGIKNK IHPGEAMDKN LYDLPPEEAK EIPQVAGSLE EALQALDADR EFLTAGGVFT  240
NDAIDAYIAL RLEENDRVRM TPHPVEFELY YSV                               273

SEQ ID NO: 492            moltype = AA  length = 469
FEATURE                   Location/Qualifiers
source                    1..469
                          mol_type = protein
                          organism = Kosakonia sp.
SEQUENCE: 492
MSAEHVLTML NEHEVKFVDL RFTDTKGKEQ HVTIPAHQVN ADFFEEGKMF DGSSIGGWKG  60
INESDMVLMP DATTAVIDPF YEETTLIIRC DILEPGTMQG YDRDPRSIAK RAEEYLRSTG  120
LADTVLFGPE PEFFLFDDVR FGSSISGSSV AIDDIEGAWN TSTKYEGGNK GHRPAVKGGY  180
FPVPPVDSSQ DLRSTMCLVM EEMGLVVEAH HHEVATAGQN EVATRFNTMT KKADEIQIYK  240
YVVHNVAHRF GKTATFMPKP MFGDNGSGMH CHMSLSKNGT NLFSGDKYAG LSEMALYYIG  300
GVIKHAKAIN ALSNPTTNSY KRLVPGYEAP VMLAYSARNR SASIRIPVVA SPKARRIEVR  360
FPDPAANPYL CFAALMMAGL DGIKNKIHPG EAMDKNLYDL PPEEAKEIPQ VAGSLEEALN  420
ALDADREFLT AGGVFTDDAI DAYIALRLEE NDRVRMTPHP VEFELYYSV              469

SEQ ID NO: 493            moltype = AA  length = 445
FEATURE                   Location/Qualifiers
```

```
source                   1..445
                         mol_type = protein
                         organism = Lactobacillus helveticus
SEQUENCE: 493
MSKQYTAEEI RKEVEDKDVR FLRLCFTDIN GTEKAVEVPK SQLDKVLNND IRFDGSSIDG   60
FVRLEESDMV LYPDFSTWTV LPWGDEHGGK IGRLICSVHT TDGKPFAGDP RNNLKRVLGQ  120
MKDAGFDTFD IGFEMEFHLF KLDENGNWTT EVPDHASYFD MTSDDEGARC RREIVETLEG  180
IGFEVEAAHH EVGDGQQEID FRFDDALTTA DRCQTFKMVA RQIARKHGLF ATFMAKPVEG  240
QAGNGMHNNM SLFKGKHNVF YDENGEFHLS DTALYFLNGI LEHARAITAI GNPTVNSYKR  300
LIPGFEAPVY IAWAAKNRSP LVRIPSASEI NTRLEMRSAD PTANPYLLLA ACLTAGLNGI  360
KEQKMPMKPV EENIFEMTEE ERAEHGIKPL PTTLHNAIKE FKEDDLIKSA LGDHLTHSFI  420
ESKELEWSKY SQSVSDWERQ RYMNW                                        445

SEQ ID NO: 494             moltype = AA  length = 446
FEATURE                    Location/Qualifiers
source                     1..446
                           mol_type = protein
                           organism = Lactococcus laudensis
SEQUENCE: 494
MTITPADILS EVKEKNVTFL RLMFTDILGT LKNVEVPATE EQLEKILDNK MMFDGSSIEG   60
FVRINESDMY LYPDLDTWII FPWGDENGKV AGLICDVYNP DGTPFAGDPR GNLKRALTHM  120
ETTGFKSFNL GPEPEFFLFK LDEKGNPTLE VNDQGGYFDL APTDTADNTR REIVNVLTDL  180
GFEVEASHHE VAVGQHEIDF KYTNVLEACD NIQIFKLVVK TIAREHGLYA TFMAKPKFGI  240
NGSGMHCNMS LFDQEGNNAF YDPKGELELS ETAYHFLGGI LDHAYNFTAI TNPTVNSYKR  300
LVPGYEAPVY IAWAGRNRSP LVRVPASRGK GTRLELRAVD PTANPYLALA VLLECGLDGI  360
ERKLEAPAPV ENNIYMMSGD ERKAVGITDL PSTLHNAVKA LREDDVVKAA LGQHIYTNFV  420
ETKKVEWASY AQFVSQWEID NYLYLY                                       446

SEQ ID NO: 495             moltype = AA  length = 444
FEATURE                    Location/Qualifiers
source                     1..444
                           mol_type = protein
                           organism = Lysinibacillus halotolerans
SEQUENCE: 495
MAKYTRDDIK RLVEEKEVKY IRLQFTDILG TIKNVEIPVS QLDKALDNKM MFDGSSIEGF   60
VRIEESDMYL YPDLDTFMVF PWTAEKGKVA RFICDIVNPD GTPFAGDPRS NLKRVLANME  120
ELGFTSFNLG PEPEFFLFKL DQKGEPTLEL NDDGGYFDLA PTDLGENCRR DIVLELEEMG  180
FEIEASHHEV APGQHEIDFK YANVVEACDN IQTFKLVVKT IARKHGLHAT FMPKPLYGVN  240
GSGMHCNVSL FRGKENAFFD EKAEIGLSET AMQFMAGVLA HVQGFTAITN PTVNSYKRLV  300
PGYEAPCYVA WSAQNRSPLI RVPASRGLST RIELRSVDPS ANPYLALAVI LESGLEGIRQ  360
KMTPPAAINR NIYIMSEEER KANGIDNLPA SLSDALVALE NDEVVKRALG EHIYANFREA  420
KEIEFDMFRT AVHPWEREQY MKMY                                         444

SEQ ID NO: 496             moltype = AA  length = 468
FEATURE                    Location/Qualifiers
source                     1..468
                           mol_type = protein
                           organism = Maritimibacter harenae
SEQUENCE: 496
MSNADVLKLI KDEDIAYVDI RFTDPRGKLQ HVTVMSDQVD EDFLEEGFMF DGSSVAGWKS   60
IEASDMKLMP DSESVYIDPF YAEKTLAVHC SIVEPDTGEP YERDPRGTAE KAEAYLKSSG  120
IGDAAFFGPE AEFFLFDDVK YSVAPNKVGY EIDADGAAWN TDTDFEMGNL GHRPDYKGGY  180
FPVNPSDDGQ DIRSEMLTTM KMIGMKVDKH HHEVATTQHE LGLIFDSLTK QADELQKYKY  240
VIHNVALSYG RSATFMPKPI KGDNGSGMHV NMSIWKDNKP LFAGDKYADL SQEALYFIGG  300
ILKHAKTLNA FTNPSTNSYK RLIPGFEAPV LRAYSARNRS GCVRIPWTES PKAKRVEARF  360
PDPAANPYLC FAALLMAGLD GIKNKIDPGP SSDKNLYDLP PEELQGIPTV CGSLREALES  420
LADDHDFLLA GDVFTKDQIE GYLELKWEEV YEFEHTPHPI EYKMYYSC              468

SEQ ID NO: 497             moltype = AA  length = 344
FEATURE                    Location/Qualifiers
source                     1..344
                           mol_type = protein
                           organism = Methylobacterium aquaticum
SEQUENCE: 497
MTKYKLEYIW LDGYTPTPNL RGKTQIKAFD SFPTLEQLPL WGFDGSSTQQ AEGSSSDCVL   60
KPVRHFPDPA RTNGVLVLCE VMMPDGKTPH PSNKRATILD DEGAWFGFEQ EYFFYKNGRP  120
LGFPETGYPA PQGPYYTGVG YSNVGSVARQ IVEEHLDLCL AAGINHEGIN AEVAKGQWEF  180
QIFGKGSKRA ADEMWMARYL MQRLCEKYEI DIEYHCKPLG DTDWNGSGMH ANFSTAYMRD  240
VGGKAYFEKL MAAFGDARED HIAVYGPDNH MRLTGKHETA SIHTFSWGVA DRGASIRVPH  300
SFVNNDYKGY LEDRRPNSMG DPYQIASQIL KTISTVPTEV SAAA                   344

SEQ ID NO: 498             moltype = AA  length = 442
FEATURE                    Location/Qualifiers
source                     1..442
                           mol_type = protein
                           organism = Paenibacillus polymyxa
SEQUENCE: 498
MSYSREDILR IAKEENVRFI RLQFTDLLGT IKNVEIPVSQ LEKALDNKMM FDGSSIEGYV   60
RIEESDMYLY PDLDTWVVFP WVTSDRVARL ICDIYKPDGV PFAGDPRGIL KRVLKEAEEL  120
```

```
GYTSMNVGPE PEFFLFKTDE KGEPTTELND QGGYFDLAPM DLGENCRREI VLKLEEMGFE 180
IEASHHEVAP GQHEIDFKYA DAIKAADQIQ TFKLVVKTIA RQHGLHATFM PKPLFGVNGS 240
GMHCNQSLFK DNENVFYDET DELGLSQTAR HYMAGILKHA RAMAAITNPT VNSYKRLVPG 300
YEAPCYVAWS ASNRSPMIRI PASRGLSTRV EVRNPDPAAN PYLALAVMLR AGLDGIKRQL 360
ALPAPIDRNI YVMSEEERIE EGIPSLPADL KEALSELIRS EVISDALGDH ALAYFYELKE 420
IEWDMYRTQV HQWERDQYLT LY                                          442

SEQ ID NO: 499          moltype = AA  length = 444
FEATURE                 Location/Qualifiers
source                  1..444
                        mol_type = protein
                        organism = Priestia megaterium
SEQUENCE: 499
MAKYTKEDIF RKVQEENVKY IRLQFTDILG TIKNVEIPVS QLEKALDNKM MFDGSSIEGF 60
VRIEESDMYL FPDIDTFVIF PWTSEKGKVA RFICDIYNAD RTPFDGDPRN NLKRVLKEME 120
ELGFTDFNLG PEPEFFLFKL DEKGEPTLEL NDKGGYFDLA PTDLGENCRR DIVLELEEMG 180
FEIEASHHEV APGQHEIDFK YAAALKACDD IQTFKLVVKT IARKHGLHAT FMPKPLFGVN 240
GSGMHCNVSL FKDGQNAFYD ENGNLELSDT ARQFIAGIIK HAHSFTAVTN PTVNSYKRLV 300
PGYEAPCYVA WSARNRSPLI RIPASRGVGT RVEVRSVDPA ANPYLAMAVL LKAGLDGIKN 360
NLEAPKPIDR NIYVMTKEER VEEGIVDLPA TLAQALDSFQ SNEVMVSALG EHLAEHFVEA 420
KEIEWDMFRT QVHPWERDQY MSQY                                        444

SEQ ID NO: 500          moltype = AA  length = 474
FEATURE                 Location/Qualifiers
source                  1..474
                        mol_type = protein
                        organism = Pseudarthrobacter siccitolerans
SEQUENCE: 500
MFKTADEVLK FIKDEDIKFV DIRFTDLPGV QQHFNVPAKS VDADFFINGQ LFDGSSIRGF 60
QGIAESDMQL IPDVTTAFLD TFRMEKTLAL NFSIVNPRTG DPYHRDPRGV AEKAEAYLAS 120
TGIADTAFFA PEAEFFVFDN VQYQSSPQGS FYKIDSEEAH WNTGREEEGG NLGYKTPVKG 180
GYFPVSPTDK QADLRDAMCV ALDEAGLEVE RSHHEVGSAG QAEINYKFTT LTHAADDLQK 240
FKYVIKNTAD AWGKSVTFMP KPVFGDNGSG MHCHQSLWNG GEPLFYDEKG YAGLSDTARW 300
YIGGLLKHAS AVLAFTNPTV NSYRRLVKGF EAPVNMVYSQ GNRSAGIRIP ITGTNPKAKR 360
IEFRAPDPSS NPYLAFAAQL MAGIDGIRNR IEPPAPIDKD LYELPAEEAK DIPKAPGTLE 420
EALEALAEDN EFLQAGGVFT QDLIDTWIEY KYENEIRPLS LRPNPYEFEL YYGV        474

SEQ ID NO: 501          moltype = AA  length = 468
FEATURE                 Location/Qualifiers
source                  1..468
                        mol_type = protein
                        organism = Pseudomonas azotoformans
SEQUENCE: 501
MSKSVQLIKD HDVKWIDLRF TDTKGTQHHV TMPARDALDE AFFEEGKMFD GSSIAGWKGI 60
EASDMILMPD DSTAVLDPFT EEPTLILVCD VIEPSTMQGY DRDPRAIAKR AEEYLKSTGI 120
GDTVFVGPEP EFFIFDQVKF KSDISGSMFK IYSEQGSWMS DQDVEGGNHG HRPGIKGGYF 180
PVPPFDHDHE IRTSMCNAME DMGLVIEVHH HEVATAGQNE IGVKFNTLVA KADEVQTLKY 240
CVHNTAVAYG RTATFMPKPL YGDNGSGMHV HLSIAKDGKN TFAGEGYAGL SDTALYFIGG 300
IIKHGKALNG FTNPSTNSYK RLVPGFEAPV MLAYSARNRS ASIRIPYVSS PRARRIEARF 360
PDPAANPYLA FAALVMAGLD GIQNKIHPGD AADKNLYDLP PEEAKEIPQV CGSLKEALEE 420
LDKGRAFLTK GGVFSDDFID AYIGLKSEEE IKVRTFVHPL EYELYYSC              468

SEQ ID NO: 502          moltype = AA  length = 468
FEATURE                 Location/Qualifiers
source                  1..468
                        mol_type = protein
                        organism = Pseudomonas putida
SEQUENCE: 502
MSKSVQLIKD HDVKWIDLRF TDTKGTQHHV TMPARDALED DFFEVGKMFD GSSIAGWKGI 60
EASDMILMPV DETAVLDPFT EEPTLIITCD IVDPSSMQGY DRDPRAIAKR AEEYLKSTGI 120
GDTVFAGPEP EFFIFDEVKF QSDISGSMFK IFSEQGSWMT GADVEGGNKG HRPGVKGGYF 180
PVPPFDHDHE IRTAMCNALE EMGQTVEVHH HEVATAGQNE IGVKFNTLVK KADEVQALKY 240
VVHNVADAYG RTATFMPKPL YGDNGSGMHV HMSIWKDGKN TFSGEGYAGL SDTALYFIGG 300
IIKHGKALNG FTNPSTNSYK RLVPGFEAPV MLAYSARNRS ASIRIPYVGS PKARRIEARF 360
PDPSANPYLA FAALLMAGLD GIQNKIHPGD AADKNLYDLP PEEAKDIPQV CGSLKEALEE 420
LDKGRAFLTK GGVFSDDFID AFIELKSEEE IKVRTFVHPL EYELYYSC              468

SEQ ID NO: 503          moltype = AA  length = 468
FEATURE                 Location/Qualifiers
source                  1..468
                        mol_type = protein
                        organism = Pseudomonas syringae
SEQUENCE: 503
MSKSVQLIKD HDVKWIDLRF TDTKGTQHHV TMPARDALDE DFFEIGKMFD GSSIAGWKGI 60
EASDMILMPD DSTAVLDPFT EEPTIILVCD IIEPSTMQGY DRDPRAIAHR AEEYLKSTGI 120
GDTVFVGPEP EFFIFDEVKF KSDISGSMFK IFSEQGSWMS DQDVEGGNKG HRPGVKGGYF 180
PVPPFDHDHE IRTSMCNAME EMGLVIEVHH HEVATAGQNE IGVKFNTLVK KADEVQTLKY 240
CVHNVADAYG RTATFMPKPL YGDNGSGMHV HMSISKDGKN TFAGEGYAGL SDTALFFIGG 300
IIKHGKALNG FTNPSTNSYK RLVPGFEAPV MLAYSARNRS ASIRIPYVSS PKARRIEARF 360
```

-continued

```
PDPAANPYLG FAALLMAGLD GIQNKIHPGD AADKNLYDLP PEEAKEIPQV CGSLKEALEE   420
LDKGRAFLTK GGVFSDDFID AYIALKSEEE IKVRTFVHPL EYELYYSC                 468

SEQ ID NO: 504          moltype = AA  length = 469
FEATURE                 Location/Qualifiers
source                  1..469
                        mol_type = protein
                        organism = Rahnella contaminans
SEQUENCE: 504
MSAEHVLTML NEHEVKFVDL RFTDTKGKEQ HVTIPAHQVS ADFFEEGKMF DGSSIGGWKG   60
INESDMVLMP DASTAVLDPF YEETTLIIRC DILEPTTLQG YDRDPRSTAK RAEDFLRSSG   120
IADTVLFGPE PEFFLFDDVR FGSSISGSHV AIDDIEGAWN SSTKYEGGNK GHRPAVKGGY   180
FPVPPVDSSQ DLRSTMCLTM EEMGLVVEAH HHEVATAGQN EVATRFNTLT KKADEIQIYK   240
YVVHNVAHAF GKTATFMPKP MFGDNGSGMH CHMSLSKNGN NLFAGDKYGG LSEMALFYIG   300
GIIKHAKAIN AYANPTTNSY KRLVPGYEAP VMLAYSARNR SASIRIPHVS SPKAMRIEAR   360
FPDPAANPYL AFAALMMAGL DGIINKIHPG DAMDKNLYDL PPEEEAEIPK VAGSLEEALN   420
ALNEDREFLT RGGVFTDDAI DAYIGLRKEE MDRVRMTPHP VEFELYYSV               469

SEQ ID NO: 505          moltype = AA  length = 469
FEATURE                 Location/Qualifiers
source                  1..469
                        mol_type = protein
                        organism = Rahnella sp.
SEQUENCE: 505
MSAEHVLTML NEHEVKFVDL RFTDTKGKEQ HVTIPAHQVS ADFFEEGKMF DGSSIGGWKG   60
INESDMVLMP DASTAVLDPF YEETTLIIRC DILEPTTLQG YDRDPRSTAK RAEDFLRSSG   120
IADTVLFGPE PEFFLFDDVR FGSSISGSHV AIDDIEGAWN SSTKYEGGNK GHRPAVKGGY   180
FPVPPVDSSQ DLRSTMCLTM EEMGLVVEAH HHEVATAGQN EVATRFNTLT KKADEIQIYK   240
YVVHNVAHAF GKTATFMPKP MFGDNGSGMH CHMSLSKNGN NLFSGDKYGG LSEMALFYIG   300
GIIKHAKAIN AYANPTTNSY KRLVPGYEAP VMLAYSARNR SASIRIPHVS SPKAMRIEAR   360
FPDPAANPYL AFAALMMAGL DGIINKIHPG DAMDKNLYDL PPEEEAEIPK VAGSLEEALN   420
ALNEDREFLT RGGVFTDDAI DAYIGLRKEE MDRVRMTPHP VEFELYYSV               469

SEQ ID NO: 506          moltype = AA  length = 469
FEATURE                 Location/Qualifiers
source                  1..469
                        mol_type = protein
                        organism = Rhizobium leguminosarum
SEQUENCE: 506
MATASEILKQ IKENDVKFVD LRFTDPKGKL QHVTMDVVCV DEDMFADGVM FDGSSIGGWK   60
AINESDMVLM PDTETVHMDP FFAQSTMVIV CDILDPVSGE AYNRDPRGTA KKAEAYLKAS   120
GIGDTIFVGP EAEFFVFDDV KYKADPYNTG FKLDSTELPS NDDTDYETGN LGHRPRVKGG   180
YFPVPPVDSA QDMRSEMLTV LSEMGVVVEK HHHEVAAAQH ELGIKFDTLV RNADKMQIYK   240
YVVHQVANAY GKTATFMPKP IFGDNGSGMH VHQSIWKGGK PTFAGDEYAG LSESCLFYIG   300
GIIKHAKAIN AFTNPSTNSY KRLVPGYEAP VLLAYSARNR SASCRIPFGS NPKAKRVEVR   360
FPDPTANPYL AFAAMLMAGL DGIKNKIHPG KAMDKDLYDL PPKELKKIPT VCGSLREALE   420
SLDKDRKFLT AGGVFDDDQI DAFIELKMAE VMRFEMTPHP VEYDMYYSA               469

SEQ ID NO: 507          moltype = AA  length = 478
FEATURE                 Location/Qualifiers
source                  1..478
                        mol_type = protein
                        organism = Rhodococcus oryzae
SEQUENCE: 507
MAFTTAEEVI NYIADEKIEY VDIRFSDLPG VQQHFSIPAS AFNKDVFEDG LAFDGSSVRG   60
FQSIHESDMM LLPDVSTARV DPFRAAKTLN MDFFVHDPFT RESYSRDPRN VARKAEEYLV   120
STGIADTAFF GAEAEFYIFD SVRYDSGMNG AFYELDSISG SWNTGNEVNA DGSPNLGYKV   180
RPKGGYFPVA PYDHYVDLRD EISTNLQNAG FELERGHHEV GTGGQQEINY KFNTLLAAAD   240
DLQLFKYIVK NTCWQNGKSA TFMPKPLFGD NGSGMHVHQS IHDGKPLFH DESGYAGLSD    300
MARHYIGGIL HHAPSLLAFT NPTVNSYHRL VPGYEAPINL VYSQRNRSAA VRIPITGNNP   360
KAKRIEFRAP DSSGNPYLNF AAQMMAGLD IKNKIEPMAP VDKDLYELPP EEARNIPQAP    420
TSLATVIDRL EADHEYLTEG GVFTTDLIES WISIKREQEI APVNLRPHPY EFQLYYDV     478

SEQ ID NO: 508          moltype = AA  length = 473
FEATURE                 Location/Qualifiers
source                  1..473
                        mol_type = protein
                        organism = Sphingomonas glacialis
SEQUENCE: 508
MAKAPNTASD VLKMIKEQEI EWVDLRFTDP KGKWQHLTMV ASVVGEDELT DGFMFDGSSI   60
EGWKAINESD MILMPDLDAI WTDPFSATPM LILVCDIVEP STGELYARDP RSTAKRAEAY   120
LKTTGIGDTI FIGPEAEFFM FDNVQFENSY STSYYKIDDI ELPTNTGTSY DGGNLGHRPR   180
AKGGYFPVAP VDSAVDIRGE MVSTMLEMGL PCDKHHHEVA AAQHELGLTF GTMTVTADRM   240
QIYKYVCHNV AQAYGKTVTF MPKPIKEDNG SGMHTHLSIW DKGNPLFAGN GYAGLSDMCL   300
YFIGGIIKHA KAVNAFTNPT TNSYKRLVPG YEAPVLLAYS ARNRSASCRI PYGTGPKAKR   360
VEVRFPDAMA NPYLCYAALF MAGLDGIQNR IHPGEAMDKN LYDLPPEELA EVPTVCGSLR   420
EALDCLAADH DFLLKGDVFS KDQIESYIEL KMEDVKRWEM TPSPVEFDMY YSY           473

SEQ ID NO: 509          moltype = AA  length = 469
```

-continued

```
FEATURE              Location/Qualifiers
source               1..469
                     mol_type = protein
                     organism = Stenotrophomonas maltophilia
SEQUENCE: 509
MSVENVEKLV KDNQIEFVDL RFVDMRGIEQ HVTFPVSIIE ASLFEEGKMF DGSSIAGWKG    60
INESDMVLLP DPSSAYVDPF YADPTIVISC DILDPATMQP YGRCPRGIAK RAEAFLKSSG   120
IAEQAFFGPE PEFFIFDSVR FANDMGNTFF KVDSEEAAWN TGAKYDGANS GYRPGVKGGY   180
FPVPPTDSLH DLRAEMCKTL EQVGIEVEVQ HHEVATAGQC EIGTKFSTLV QKADELLRMK   240
YVIKNVAHRN GKTATFMPKP IVGDNGSGMH VHQSLSKGGT NLFSGDGYGG LSQLALWYIG   300
GIFKHAKAIN AFANAGTNSY KRLVPGFEAP VMLAYSARNR SASCRIPFVT NPKARRIEMR   360
FPDPIQSGYL TFTVLMMAGL DGIRNQIDPG APSDKDLYDL PPEEEKLIPQ VCSSLDQALE   420
ALDKDREFLK AGGVMDDDFI DGYIALKMQE VTKFRAATHP LEYQLYYAS              469

SEQ ID NO: 510         moltype = AA  length = 468
FEATURE                Location/Qualifiers
source                 1..468
                       mol_type = protein
                       organism = Stutzerimonas stutzeri
SEQUENCE: 510
MSKSLQLIKD YDVKWIDLRF TDTKGKQHHV TVPARDAQDE DFFEHGKMFD GSSIHGWKGI    60
EASDMILMPV DETAVLDPFT EEPTLILVCD IVEPSTMQGY DRDPRSIAKR AEEFLKGTGI   120
GDTVFVGPEP EFFIFDQVKF KSDISGSMFK IYSEQGSWMT DQDVEGGNKG HRPAVKGGYF   180
PVPPCDHDHE IRTAMCNAME EMGLVVEVHH HEVATAGQNE IGVKFNTLVA KADEVQTLKY   240
CVHNVADAYG KTATFMPKPL YGDNGSGMHV HMSISKDGKN TFAGEGYAGL SETALYFIGG   300
IIKHGKALNG FTNPSTNSYK RLVPGFEAPV MLAYSARNRS ASIRIPVSS PKARRIEARF   360
PDPAANPYLC FAALLMAGLD GIQNKIHPGD AADKNLYDLP PEEGKLIPQV CGSLKEALEE   420
LDKGRAFLTK GGVFSDEFID AYIELKSEEE IKVRTFVHPL EYDLYYSV               468

SEQ ID NO: 511         moltype = AA  length = 471
FEATURE                Location/Qualifiers
source                 1..471
                       mol_type = protein
                       organism = Variovorax paradoxus
SEQUENCE: 511
MAKTVADVLK LVKENEVKFI DFRFTDTRGK EQHVTVPVSA FDEDKFTSGH AFDGSSIAGW    60
KGIEASDMQL MPDPNTANID PFFEETTLIL TCDVIDPADG KAYERDPRSL AKRAEAYMKA   120
SGLGDTAFFG PEPEFFVFDG VRWKNDMSGC FVKIDSEEAS WNTDKEYEHG NTGHRPAVKG   180
GYFPVPPVDS FQDMRSEMCL VLESLGIPVE VHHHEVANAG QMELGTKFST LVQORADWVQL   240
QKYVIHNVAH AYGKTATFMP KPIVGDNGSG MHVHQSVWKD GKNLFAGDGY AGLSDFALHY   300
IGGIIKHARA LNAITNPGTN SYKRLVPGFE APVKLAYSAK NRSASIRIPF VANPKGRRVE   360
ARFPDPLMNP YLGFAALLMA GLDGVENKIH PGEAASKDLY HLPPEEDALI PTVCHSLDQA   420
LEYLDKDRAF LTKGGVFTDA YIDAYIELKM QEVTRFRMAT HPVEFDMYYS L           471

SEQ ID NO: 512         moltype = AA  length = 468
FEATURE                Location/Qualifiers
source                 1..468
                       mol_type = protein
                       organism = Yoonia vestfoldensis
SEQUENCE: 512
MDKKAVLKLI KDEEVDYVDI RFTDPRGKLQ HVTVVADLVD EDFLDEGFMF DGSSIAGWKS    60
IDQSDMKLMP DASSAYVDPF YAEKTICIHC NVVEPDTMEP YDRDPRGTAV KAEEYLKSSG   120
IGDSAFFGPE AEFFVFDDVR FSVSMNKVSY QVDALDGAWN TDTEYEMGNT GHRPGIKGGY   180
FPVNPIDDAQ EMRSEMLSTM KRMGMKVDKH HHEVASCQHE LGLIFGTLTH QADEIQKYKY   240
VIHNVAQAYG KSATFMPKPI AGDNGTGMHV NMSIWKDGKN LFAGDKYADL SQEALYFIGG   300
ILKHAKALNA ITNPTTNSYK RLIPGFEAPV LRAYSARNRS GCVRIPWAES PKAKRVEARF   360
PDPAANPYLA FAALLMAGLD GIKNKIDPGP SSDKDLYDLP PEELASIPTV CGSLREALES   420
LEADHEFLLA GDVFTKSQLE GYMALKWEEV YAYEHTPHPI EFKMYYSC               468

SEQ ID NO: 513         moltype = AA  length = 346
FEATURE                Location/Qualifiers
source                 1..346
                       mol_type = protein
                       organism = Rahnella aceris
SEQUENCE: 513
MKLMRNTVAG LVAATFSLTA MSAFAAANLT GAGGTFPAPV YAKWADAYQK ATGTQVNYQG    60
IGSSGGVKQI IAKTVDFGAS DAPMKEEDLN KNGLFQFPTV IGGVVLAVNI PGIKSGQLTL   120
DGATLGDIYL GKIKKWNDTA ITKLNPGVKL PDTNIAVVRR ADGSGTSFVF TSYLAKVNSE   180
WKDKIGAGST VNWPTGLGGK GNDGVAAFVQ RLPGSIGYVE YAYAKQNNLA YTKLVDADGK   240
AISPTEESFS AAAKGADWSK TFAQDLTNQK GDNAWPISST TFILIYKDQQ DAAKGTEVLK   300
FFDWAYKNGN KLTTDLDYAA LPASVVEQIR AAWKTNIKDS SGKALY                346

SEQ ID NO: 514         moltype = AA  length = 53
FEATURE                Location/Qualifiers
source                 1..53
                       mol_type = protein
                       organism = synthetic construct
VARIANT                8
                       note = X is T or V
```

```
VARIANT               18
                      note = X is V or I
VARIANT               43
                      note = X is A or T
VARIANT               44
                      note = X is Y or W
VARIANT               48
                      note = X is V or F
VARIANT               49
                      note = X is D or S
SEQUENCE: 514
GSTVNWPXGL GGKGNDGXAA FVQRLPGSIG YVEYAYAKQN NLXXTKLXXA DGK          53

SEQ ID NO: 515        moltype = DNA   length = 458
FEATURE               Location/Qualifiers
source                1..458
                      mol_type = genomic DNA
                      organism = Klebsiella variicola
SEQUENCE: 515
gacgatcgcc cctatcttct atacggtacc gctgcagctg ttggcttatc acgtcgcgct   60
gatcaaaggc actgacgttg accagccgcg taacctggcg aaatcggtaa cggttgagta  120
aaaccatcat tacttgcaaa gggctgccgg cggcggccct ttttattttc acctgctgtt  180
tattaccgaa cttgcgcgaa atattttggc tggcggtagg tgacaaacga acgttttgcg  240
gtccgatttc gctgtcataa aaagaaaatt attctgtcat tgcacggtca tgattacaga  300
taactatctg agttatatat ttattatttg ctgtaaaatc ccttctttct gcctgtcata  360
aaaactgtcat aattcgtaca ttttactgtc acctctttga cctattttgc tcaccatagc  420
ctcgaaacaa tgatttacga atcccagcag gagacatt                          458

SEQ ID NO: 516        moltype = AA   length = 207
FEATURE               Location/Qualifiers
source                1..207
                      mol_type = protein
                      organism = synthetic construct
SEQUENCE: 516
MSRLDKSKVI NSALELLNEV GIEGLTTRKL AQKLGVEQPT LYWHVKNKRA LLDALAIEML   60
DRHHTHFCPL EGESWQDFLR NNAKSFRCAL LSHRDGAKVH LGTRPTEKQY ETLENQLAFL  120
CQQGFSLENA LYALSAVGHF TLGCVLEDQE HQVAKEERET PTTDSMPPLL RQAIELFDHQ  180
GAEPAFLFGL ELIICGLEKQ LKCESGS                                      207

SEQ ID NO: 517        moltype = DNA   length = 460
FEATURE               Location/Qualifiers
source                1..460
                      mol_type = genomic DNA
                      organism = Kosakonia sacchari
SEQUENCE: 517
caggatggct tctcattgcg ccgtttttccg tactgtctct gattttttgg gggattggga   60
tggtgctgtt atggctggcg cgacaagtga tgaatggacc ggaacttagc aaattagtgc  120
agtggcgcgt atcgctaaaa atcgcccaat tccggcgcca ggcgctgaca caatctaagc  180
gtaaataaat cgataagcgg tggctttttc tcgcgttttg ttaggacttc ttgtcagatt  240
cagctacgtt tttaatgtca taaaactaaa atcttgctga catcttatcg tcatcaacct  300
ttttatctcg ctgataaatc atccaggatt cgttaaatct ggccgcaatt cgttgctgtc  360
ataaaacagt aacaatcttt gcatataact gtcatcaaag tgtcctattt tgctcatcgt  420
agccactaaa caacgattta cgattcttgc aggagacatt                        460

SEQ ID NO: 518        moltype = DNA   length = 345
FEATURE               Location/Qualifiers
source                1..345
                      mol_type = genomic DNA
                      organism = Rahnella aceris
SEQUENCE: 518
gtgccatcaa aacctgctca ggctaaaaaa ccggctgtca ctaaaacgaa aaacagtgaa   60
aaacctgaag tgaattccgc atcccgcaag cgttttgccc agcctggccg taagaagaag  120
gggcgttaat ttacctgctt ttcattatcc gccggtgtaa taaccggctt tttctgctta  180
aaactcccgc attttgcccg tatggttcga attgtgacca gtgtcataaa actgtcatat  240
aacgtacatt ttactgtcac taaactgtcc tattttcctc ctgtgccaaa cactttaatt  300
aacgtcgaca tcagtcggga agtttaaaac caccaggagt ggaac                  345

SEQ ID NO: 519        moltype = AA   length = 469
FEATURE               Location/Qualifiers
source                1..469
                      mol_type = protein
                      organism = Kosakonia sacchari
SEQUENCE: 519
MSAEHVLTML NEHEVKFVDL RFTDTKGKEQ HVTIPAHQVN ADFFEEGKMF DGSSIGGWKG   60
INESDMVLMP DATTAVIDPF YEESTLIIRC DILEPGTMQG YDRDPRSIAK RAEEYLRSTG  120
LADTVLFGPE PEFFLFDDVR FGSSISGSSV AIDDIEGAWN TSTKYEGGNK GHRPAVKGGY  180
FPVPPVDSSQ DLRSTMCLVM EEMGLVVEAH HHEVATAGQN EVATRFNTMT KKADEIQIYK  240
YVHNVAHRF GKTATFMPKP MFGDNGSGMH CHMSLSKNGT NLFSGDKYAG LSEMALYYIG  300
GVIKHAKAIN ALSNPTTNSY KRLVPGYEAP VMLAYSARNR SASIRIPVVA SPKARRIEVR  360
```

```
FPDPAANPYL CFAALLMAGL DGIKNKIHPG EAMDKNLYDL PAEEAKEIPQ VAGSLEEALN   420
ALDADREFLT AGGVFTDDAI DAYIALRIEE NDRVRMTPHP VEFELYYSV               469

SEQ ID NO: 520          moltype = AA  length = 469
FEATURE                 Location/Qualifiers
source                  1..469
                        mol_type = protein
                        organism = Klebsiella variicola
SEQUENCE: 520
MSAEHVLTML NEHEVKFVDL RFTDTKGKEQ HVTIPSHQVN AEFFEEGKMF DGSSIGGWKG   60
INESDMVLMP DASTAVIDPF YEEPTLIIRC DILEPGTLQG YDRDPRSIAK RAEEYLRATG   120
IADTVLFGPE PEFFLFDDIR FGASISGSHV AIDDIEGAWN SSTKYEGGNK GHRPGVKGGY   180
FPVPPVDSSQ DIRSTMCMIM EEMGLVVEAH HHEVATAGQN EVATRFNTMT KKADEIQIYK   240
YVVHNVAHRF GKTATFMPKF MFGDNGSGMH CHMSLAKNGT NLFSGDKYAG LSEQALFYIG   300
GVIKHAKAIN ALANPTTNSY KRLVPGYEAP VMLAYSARNR SASIRIPVVT SPKARRIEVR   360
FPDPAANPYL CFAALLMAGL DGIKNKIHPG EAMDKNLYDL PPEEAKEIPQ VAGSLEEALQ   420
ALDADREFLT AGGVFTNDAI DAYIALRLEE NDRVRMTPHP VEFELYYSV               469

SEQ ID NO: 521          moltype = AA  length = 469
FEATURE                 Location/Qualifiers
source                  1..469
                        mol_type = protein
                        organism = Rahnella aceris
SEQUENCE: 521
MSAEHVLTML NEHEVKFVDL RFTDTKGKEQ HVTIPAHQVS ADFFEEGKMF DGSSIGGWKG   60
INESDMVLMP DASTAVLDPF YEETTLIIRC DILEPTTLQG YDRDPRSTAK RAEDFLRSSG   120
IADTVLFGPE PEFFLFDDVR FGSSISGSHV AIDDIEGAWN SSTKYEGGNK GHRPAVKGGY   180
FPVPPVDSSQ DLRSTMCLTM EEMGLVVEAH HHEVATAGQN EVATRFNTLT KKADEIQIYK   240
YVVHNVAHAF GKTATFMPKP MFGDNGSGMH CHMSLSKNGN NLFAGDKYGG LSEMALFYIG   300
GIIKHAKAIN AYANPTTNSY KRLVPGYEAP VMLAYSARNR SASIRIPHVS TPKAMRIEAR   360
FPDPAANPYL AFAALMMAGL DGIINKIHPG DAMDKNLYDL PPEEEAEIPK VAGSLEEALN   420
ALNEDREFLT RGGVFTDDAI DAYIGLRKEE MDRVRMTPHP VEFELYYSV               469

SEQ ID NO: 522          moltype = DNA  length = 1653
FEATURE                 Location/Qualifiers
source                  1..1653
                        mol_type = other DNA
                        organism = synthetic construct
SEQUENCE: 522
ggacatgcga tcgtattgcc tatgaggacc aaaacgaaaa aaggcccccc tttcgggagg   60
cctcttttct ggaatttggt accgagctat ctaaggatgg agggccaagg agcgcaataa   120
aaaagccccc ggaaggtgat cttccggggg ctttctcatg cgtttcggcc cgggcaacat   180
cagatgccga catattcggg agttccctca tttaggaccc taccaggtct cagtcaacat   240
tgcgacgatc gcccctatct tctatacggt accgctgcag ctgttggctt atcacgtcgc   300
gctgatcaaa ggcactgacg ttgaccagcc gcgtaacctg gcgaaatcgg taacggttga   360
gtaaaaccat cattacttgc aaagggctgc cggcggcggc cctttttatt ttcacctgct   420
gtttattacc gaacttgcgc gaaatatttt ggctggcggt aggtgacaaa cgaacgtttt   480
gcggtccgat ttcgctgtca taaaaagaaa attattctgt cattgcacgg tcatgattac   540
agataaactg t ctgagttata tatttattat ttgctgtaaa atcccttctt tctgcctgtc   600
ataaaactgt cataattcgt acatttact gtcacctctt tgacctattt tgctcaccat   660
agcctcgaaa caatgattta cgaatcccag caggagacat tgcggtatat gaatgcgacc   720
tcgggcccaa gttcacttaa aaaggagatc aacaatgaaa gcaattttcg tactgaaaca   780
tcttaatcat gctaaggagg ttttctaatg agcaagggcg aggaactctt taccggagtc   840
gtgccgattt tggtggaact ggacggtgac gtgaatgggc ataaattcag tgtacggggt   900
gagggcgaag gcgatgcaac caacggcaag ctgacactta aatttatctg cacgaccggc   960
aaactaccgg ttccttggcc gacgctggtt acgacgctgt cctacggtgt tcagtgtttt   1020
tcccgttacc cggatcatat gaaacgtcac gatttcttta aatcggcaat gccagaagga   1080
tatgtccaag agcgaaccat tagctttaaa gacgatggga cctataaaac gcgcgcggag   1140
gttaaattcg agggcgacac tttggtcaac cgtatcgaac tgaagggtat cgactttaag   1200
gaagatggta atatttttagg tcataaactg gaatacaact tcaacagtca taatgtctat   1260
ataactgccg ataagcaaaa aaacggcatt aaagcgaatt tcaagattcg ccataatgtg   1320
gaagatggat ccgttcagtt ggcggatcac tatcagcaga cactcccat cggccgatggg   1380
ccagtactgt tacctgacaa tcactatctg tctacccagt cagtgctgag caaagatccg   1440
aacgaaaaac gcgatcacat ggtactgctc gaattcgtga cagcggctgg cattacacat   1500
ggtatggatg aactttacaa ataaccaggc atcaaataaa acgaaaggct cagtcgaaag   1560
actgggcctt tcgttttatc tgttgtttgt cggtgaacgc tctctactag agtcacactg   1620
gctcaccttc gggtgggcct ttctgcgttt ata                                1653

SEQ ID NO: 523          moltype = AA  length = 346
FEATURE                 Location/Qualifiers
source                  1..346
                        mol_type = protein
                        organism = Klebsiella variicola
SEQUENCE: 523
MNVMRTTVAT VVAATLSMSA FSAFAAASLT GAGATFPAPV YAKWADTYQK ETGNKVNYQG   60
IGSSGGVKQI IANTVDFGAS DAPLADDKLT QEGLFQFPTV IGGVVLAVNL PGVKSGELVL   120
DGKTLGDIYL GKIKKWDDAA IAKLNPGLKL PSQNIAVVRR ADGSGTSFVF TSYLSKVNEE   180
```

-continued

```
WKSKIGAGST VNWPTGLGGK GNDGIAAFVQ RLPGSIGYVE YAYAKQNNLA YTKLVSADGK   240
PVSPTEDNFA NAAKGVDWSK SFAQDLTNQK GENAWPITST TFILVHKATN KPEQTAEVLK   300
FFDWAYKNGG KEANALDYAT LPESVVEQVR AAWKTNVKDS SGKALY                  346

SEQ ID NO: 524            moltype = AA  length = 345
FEATURE                   Location/Qualifiers
source                    1..345
                          mol_type = protein
                          organism = Kosakonia sacchari
SEQUENCE: 524
MAMLNASVRL MAAALALSTT TIFAATNVTG AGGTFPAPVY AKWAAEYQKQ TGSQVNYQGI   60
GSSGGIKQII AKTVDFGASD APMSDDDLAK NGLFQFPTVI GGVVLAVNIP GVKSGELTLD   120
GKTLGDIYLG TVKKWNDPEI TKLNPKVKLP DTNINVVRRA DGSGTSFVFT SYLSKVNADW   180
ASKVGKGSTV NWPVGLGGKG NDGVAAFVQR LPGSIGYVEY AYAKQNNLTW TKLFDADGKV   240
VEPSQQSFSN SAKGADWSKS FAQDLTFQKG KEAWPISSTT FILVYKKQDN AAKGAEVLKF   300
FDWSYKNGST IATDLDYAPL PDSVTAQVRA AWKANVQDAS GKPLF                   345

SEQ ID NO: 525            moltype = DNA  length = 17
FEATURE                   Location/Qualifiers
source                    1..17
                          mol_type = genomic DNA
                          organism = Klebsiella variicola
SEQUENCE: 525
tgtcataaaa ctgtcat                                                  17

SEQ ID NO: 526            moltype = DNA  length = 17
FEATURE                   Location/Qualifiers
source                    1..17
                          mol_type = genomic DNA
                          organism = Klebsiella variicola
SEQUENCE: 526
tgtcataatt cgtacat                                                  17

SEQ ID NO: 527            moltype = DNA  length = 17
FEATURE                   Location/Qualifiers
source                    1..17
                          mol_type = genomic DNA
                          organism = Klebsiella variicola
SEQUENCE: 527
tgtcacctct ttgacct                                                  17

SEQ ID NO: 528            moltype = DNA  length = 17
FEATURE                   Location/Qualifiers
source                    1..17
                          mol_type = genomic DNA
                          organism = Klebsiella variicola
SEQUENCE: 528
tccgatttcg ctgtcat                                                  17

SEQ ID NO: 529            moltype = DNA  length = 17
FEATURE                   Location/Qualifiers
source                    1..17
                          mol_type = genomic DNA
                          organism = Klebsiella variicola
SEQUENCE: 529
tgtcattgca cggtcat                                                  17

SEQ ID NO: 530            moltype = AA  length = 474
FEATURE                   Location/Qualifiers
source                    1..474
                          mol_type = protein
                          organism = Paenibacillus graminis
SEQUENCE: 530
MSVEKVLQTI KENNIEWVDF RFVDLGGRAH HISLPASAVD DETFVNGVAF DGSSIAGFRG   60
IEESDMVMMP DPSTIYIDPF TAHPTLNIMC DIFTPDGERY ERDPRGIAVK AEEFLQASGV   120
GTAAFFAPES EFFIFDDVRY ESGMNSSSYF VDSEEAVWNT NRKDEGGNMA FKVGVKGGYV   180
PVAPVDSQQD IRSEMCRLLS EAGLEIERHH HEVATAGQAE INFRFDTLKK TADNLLTYKY   240
IVQNTARQYG KVATFMPKPL FGDNGSGMHV HQSIFNGDSP LFYEKGAYAN LSEMALHYIG   300
GILYHAPALI ALTNPSTNSF KRLVPGYEAP VNLVFSKGNR SAAVRIPVAA VTPKGCRIEF   360
RTPDSTANPY LAFSAMLMAG LDGIKKKINP VELGYGPLDK NIYELADEDK EKIRSVPGTL   420
EEALDSLEAD YEFLTEGGVF TKDFIDNYIA LKRSEAQAVA IRVHPHEYSL YFDV          474

SEQ ID NO: 531            moltype = AA  length = 469
FEATURE                   Location/Qualifiers
source                    1..469
                          mol_type = protein
                          organism = Enterobacter sp
```

-continued

```
SEQUENCE: 531
MSAEHVLTML NEHEVKFVDL RFTDTKGKEQ HVTIPAHQVN ADFFEEGKMF DGSSIGGWKG   60
INESDMVLMP DATTAVIDPF YEEPTLIIRC DILEPGTMQG YDRDPRSIAK RAEEYLRATG  120
IADTVLFGPE PEFFLFDDVR FGSSISGSHV AIDDIEGAWN SATKYEGGNK GHRPAVKGGY  180
FPVPPVDSAQ DLRSTMCLVM EEMGLVVEAH HHEVATAGQN EVATRFNTMT KKADEIQIYK  240
YVVHNVAHRF GKTATFMPKP MFGDNGSGMH CHMSLSKNGT NLFSGDKYAG LSEQALFYIG  300
GVIKHAKAIN ALANPTTNSY KRLVPGYEAP VMLAYSARNR SASIRIPVVA SPKARRIEVR  360
FPDPAANPYL CFAALLMAGL DGIKNKIHPG EAMDKNLYDL PPEEAAEIPQ VAGSLEEALN  420
ALDADREFLT AGGVFTDDAI DAYIALRVEE NDRVRMTPHP VEFELYYSV              469

SEQ ID NO: 532        moltype = AA  length = 469
FEATURE               Location/Qualifiers
source                1..469
                      mol_type = protein
                      organism = Phytobacter diazotrophicus
SEQUENCE: 532
MSAEHVLTML NEHEVKFVDL RFTDTKGKEQ HVTIPAHQVN ADFFEEGKMF DGSSIGGWKG   60
INESDMVLMP DASTAVIDPF YEEPTLIIRC DILEPGTMQG YDRDPRSIAK RAEEYLRATG  120
IADTVLFGPE PEFFLFDDVR FGSSISGSHV AIDDIEGAWN SSTKYEGGNK GHRPAVKGGY  180
FPVPPVDSAQ DLRSTMCLVM EEMGLVVEAH HHEVATAGQN EVATRFNTMT KKADEIQIYK  240
YVVHNVAHRF GKTATFMPKP MFGDNGSGMH CHMSLSKNGV NLFSGDKYAG LSEQALYYIG  300
GVIKHAKAIN ALSNPTTNSY KRLVPGYEAP VMLAYSARNR SASIRIPVVA SPKARRIEVR  360
FPDPAANPYL CFAALLMAGL DGIKNKIHPG EAMDKNLYDL PAEEAKEIPQ VAGSLEEALN  420
CLNEDREFLT AGGVFTDDAI DAYIALRIEE NDRVRMTPHP VEFELYYSV              469

SEQ ID NO: 533        moltype = AA  length = 469
FEATURE               Location/Qualifiers
source                1..469
                      mol_type = protein
                      organism = Enterobacter dykesii
SEQUENCE: 533
MSAEHVLTML NEHEVKFVDL RFTDTKGKEQ HVTIPAHQVN AEFFEEGKMF DGSSIGGWKG   60
INESDMVLMP DATTAVIDPF FEEPTLIIRC DILEPGTLQG YDRDPRSIAK RAEEYLRSTG  120
IADTVLFGPE PEFFLFDDIR FGASISGSHV AIDDIEGAWN SSTKYEGGNK GHRPGVKGGY  180
FPVPPVDSAQ DIRSTMCLVM EEMGLVVEAH HHEVATAGQN EVATRFNTMT KKADEIQIYK  240
YVVHNVAHRF GKTATFMPKP MFGDNGSGMH CHMSLSKNGT NLFSGDKYAG LSEQALYYIG  300
GVIKHAKAIN ALANPTTNSY KRLVPGYEAP VMLAYSARNR SASIRIPVVA SPKARRIEVR  360
FPDPAANPYL CFAALLMAGL DGIKNKIHPG EAMDKNLYDL PPEEAKEIPQ VAGSLEEALQ  420
ALDADREFLT AGGVFTDDAI DAYIALRMEE NDRVRMTPHP VEFELYYSV              469
```

PHOSPHATE SENSING MICROBIAL GENE SWITCH

CROSS-REFERENCE TO RELATED APPLICATIONS

This non-provisional US patent application claims benefit of U.S. Provisional Patent Application Ser. No. 63/627,673, filed Jan. 31, 2024, which is incorporated herein by reference in its entirety.

STATEMENT REGARDING FEDERALLY SPONSORED RESEARCH

Not applicable.

INCORPORATION OF SEQUENCE LISTINGS

A substitute sequence listing contained in the xml file named "P14613US02_R.xml" which is 686,947 bytes in size (measured in MS-Windows), which was created on Feb. 26, 2025, and which comprises 533 sequences, and is incorporated herein by reference in its entirety. A sequence listing contained in the xml file named "P14613US02.xml" which is 686,780 bytes in size (measured in MS-Windows), which was created on Jan. 28, 2025, and which comprises 533 sequences, is electronically filed herewith and is incorporated herein by reference in its entirety. The sequence listing contained in the xml file named "P14613US00.xml" which is 658,989 bytes in size (measured in MS-Windows), which was created on Jan. 31, 2024, which comprises 512 sequences, and which was filed in U.S. Provisional Patent Application Ser. No. 63/627,673 on Jan. 31, 2024, is also incorporated herein by reference in its entirety.

BACKGROUND

The expression of certain proteins or production of certain metabolites can be inhibitory to a host strain and reduce its growth rate. Under lab conditions this issue can be overcome by using inducible expression systems with chemical inducers such as tetracycline. However, for bacteria in their natural environments (e.g., soil-borne bacteria in soil) such systems are not suitable either because these inducers are not compatible with environmental requirements and laws, are very expensive, or can simply not reach the host (e.g., in soil). For example, bacteria that are producing and releasing large quantities of ammonia which can be used by crop plants suffer a marked fitness defect that would render them non-competitive and unable to persist in the environment. Therefore, there is a need to provide alternative solutions which allow expression of proteins or production of certain metabolites in bacteria in their natural environments after a desirable delay and/or under certain conditions.

SUMMARY

Methods of providing at least one agriculturally relevant compound to a plant comprising placing at least one genetically engineered bacterium into a plant growth medium, wherein the genetically engineered bacterium comprises a heterologous gene expression cassette comprising at least one nucleic acid sequence coding for at least one RNA sequence or protein of interest, wherein the heterologous gene expression cassette is operably linked to a control element comprising a phosphate-sensitive promoter, wherein said at least one RNA sequence or protein of interest is or causes the production of said at least one agriculturally relevant compound when a decrease in phosphate concentration in the plant growth medium activates expression of said at least one RNA sequence or protein of interest are provided.

Genetically engineered bacterium comprising a heterologous gene expression cassette comprising at least one nucleic acid sequence coding for at least one RNA sequence or protein of interest operably linked to a control element comprising a phosphate-sensitive promoter, wherein said at least one RNA sequence or protein of interest is or causes the production of at least one agriculturally relevant compound are provided.

Compositions comprising the genetically engineered bacterium and an agriculturally acceptable carrier are also provided.

Plant parts or plant propagules which are at least partially coated, imbibed, or mixed with the compositions are also provided. Use of the plant parts or plant propagules which are at least partially coated, imbibed, or mixed with the compositions to grow a crop are also provided.

Agricultural systems comprising: (i) at least one of the engineered bacteria; (ii) at least one plant growth medium; and (iii) at least one crop plant, crop plant seed, or crop plant vegetative propagule; wherein the plant growth medium, crop plant, crop seed, and/or crop plant propagule comprise, are at least partially coated, imbibed, and/or are mixed with the engineered bacterium or a composition comprising the engineered bacterium and an agriculturally acceptable carrier, are provided.

Treated plant seed or plant propagule systems comprising: (i) at least one crop plant seed or crop plant vegetative propagule; and (ii) at least one of the engineered bacteria, wherein the crop plant seed or crop plant propagule are at least partially coated, imbibed, and/or mixed with the engineered bacterium or a composition comprising the engineered bacterium and an agriculturally acceptable carrier, are provided.

BRIEF DESCRIPTION OF THE DRAWINGS

FIG. 12 also shows ammonia production (mM NH₃/OD600) at 0 mM or 20 mM Pi for *Kosakonia sacchari* (Ks) strains with different constructs with various combinations of RBS in the glnA and tetR transcription units.

FIG. 13 also shows ammonia production (mM NH₃/OD600) at 0 mM or 20 mM Pi for *Rahnella aceris* strains with different constructs with various combinations of RBS in the glnA and tetR transcription units.

FIG. 14 also shows ammonia production (mM NH3/OD600) at 0 mM or 20 mM Pi for *Klebsiella variicola* strains with different constructs with various combinations of RBS in the glnA and tetR transcription units.

*konia sacchari* soil isolates were tested with either native PstS or heterologous PstS promoters fused to GFP.

Figure 16:
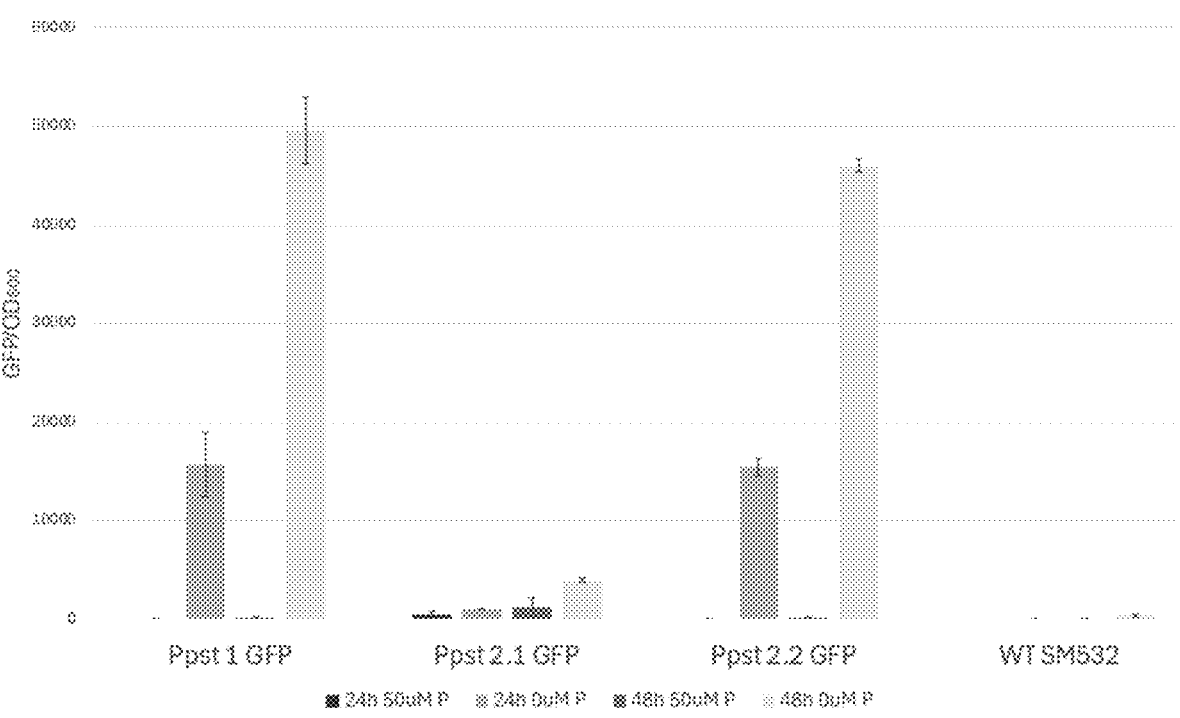

FIG. 16 shows low-Pi inducible expression of GFP by two pstS promoters in *Paenibacillus graminis*. In the figure for each tested construct (Ppst1 GFP, Ppst2.1 GFP, Ppst2.2 GFP) or negative control (WT SM532), GFP expression normalized to the OD600 was determined from left to right as follows: 24 hours at 50 μM Pi, 24 hours at 0 μM Pi, 48 hours at 50 μM Pi, and 48 hours at 0 μM Pi.

Figure 17:
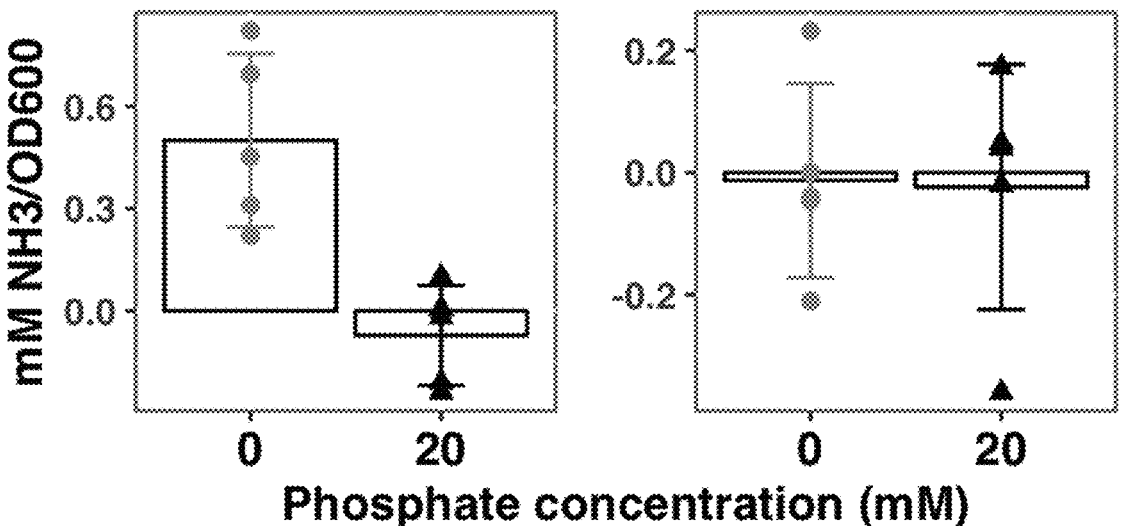

FIG. 17 shows low-Pi control of a unidirectional adenylyl transferase (uAT) fused to the PstS promoter drives ammonia release (mM NH₃/OD600) for *Kosakonia sacchari* in liquid culture (left panel). The right panel shows results from a wild-type (WT) negative control lacking the PstS promoter fusion to the uAT.

Figure 18A:
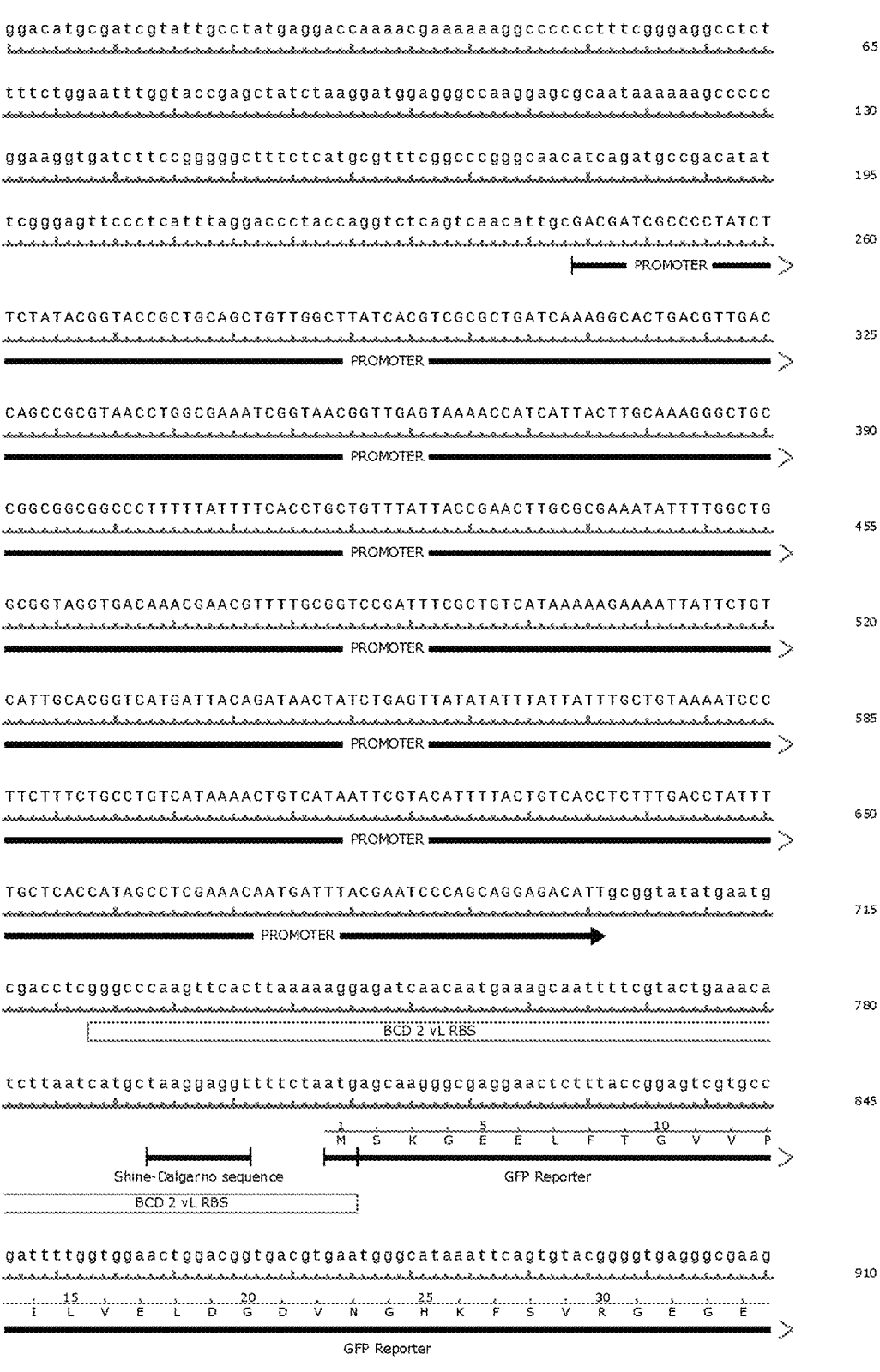
Figure 18C:
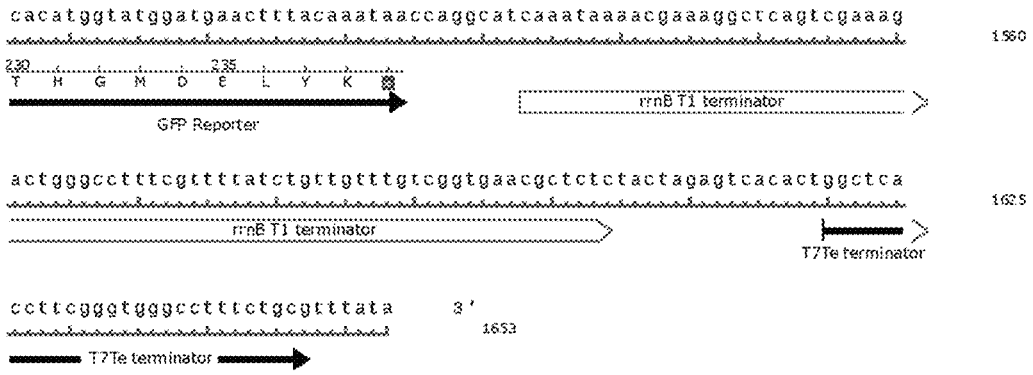

FIGS. 18A, B, C show the control GFP expression cassette of SEQ ID NO: 522 containing the BCD 2 vL ribosome binding site.

DETAILED DESCRIPTION

Methods, genetically engineered bacteria (GEB), and related systems which use phosphate-sensitive promoters (PS-P) which are expressed under low phosphate conditions to drive expression of proteins or RNAs which are agriculturally relevant or which cause the production of at least one agriculturally relevant compound are disclosed herein. In plant growth media including soil, phosphate is consumed over time by plants and microorganisms. Once phosphate concentrations fall below a certain threshold level (e.g. about 50 μM, 40 μM, 30 μM, 20 μM, or 10 μM to about 1 μM), the desired production of proteins, RNAs, and/or agriculturally relevant compounds by the genetically engineered bacteria occurs. As the consumption of phosphate by the plants and microorganisms takes time, a desired delay in production of proteins, RNAs, and/or agriculturally relevant compounds by the genetically engineered bacteria is achieved. In certain embodiments, the genetically engineered bacteria are placed in the plant growth medium (e.g., soil) and then grow to a higher titer until the phosphate is consumed and expression of the protein or RNA of interest which is or causes the production of an agriculturally relevant compound is switched on. In comparison, other bacteria which have the protein or RNA of interest under the control of another promoter which is not phosphate-sensitive (e.g., a constitutive promoter) will express the protein, RNA, and/or compound before and/or shortly after placement in the plant growth media and will not grow to the higher titers achieved by the genetically engineered bacteria provided herein. Higher titers of the engineered bacteria provided herein can thus provide for higher titers of the desired proteins, RNAs, and/or agriculturally relevant compounds in the plant growth media in comparison to bacteria lacking the phosphate-sensitive promoter controlled genes.

Phosphate-sensitive promoter controlled gene expression systems provided herein are especially useful for the production of ammonia by bacteria which can act as biofertilizers. Constitutively active ammonia release can significantly inhibit bacteria growth as protein synthesis is effectively shut down. To obtain effective biofertilizers, bacteria provided herein are engineered to grow first to a high density in soil before the ammonia release mechanism is activated. The phosphate-sensing gene expression systems provided herein allow a desirable delay in ammonia production as phosphate is only slowly consumed by the plant and bacteria.

Definitions

As used herein, the terms "about" or "approximately" indicate values slightly above or below the cited values, e.g., plus or minus 0.1% to 10% of the cited value.

As used herein, the phrase "agriculturally relevant compound" refers to a compound that provides for plant growth, altered plant morphology (e.g., increased branching/surface area of root systems), plant nutrition, plant growth regulation, or plant protection from abiotic (e.g., drought, salinity, cold, heat, or excess water stress) or biotic stress (e.g., plant pests including bacterial, fungal, insect, nematode, and viral plant pests).

As used herein, the phrase "agriculturally useful bacteria" or acronym "AUB" refers to bacteria which can grow in plant growth media (e.g., soil) and/or which can colonize crop plants The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

As used herein, the phrase "constitutive promoter" refers to a promoter, which is active under most growth and/or stationary phase conditions (e.g., in biofilms) in a given organism.

As used herein, the phrase "control element" refers to a promoter, a 5' untranslated region (5' UTR), a ribosome binding site, an enhancer, an insulator, a silencer, or a terminator. Control elements comprising a promoter, 5' UTR, an enhancer, an insulator, and/or a silencer can contain transcriptional repressor binding sites, transcriptional activator binding sites, ribozymes, protein recognition sites, and/or sites for chemical modification of nucleobases.

The term "gene," as used herein, refers to a hereditary unit consisting of a sequence of DNA located on a chromosome, plasmid, or other extra-chromosomal element that contains the genetic instruction for a particular characteristic or trait in an organism. The term "gene" thus includes a nucleic acid (for example, DNA or RNA) sequence that comprises coding and/or non-coding sequences necessary for the production of an RNA, a polypeptide, or a precursor of the RNA or protein. A functional polypeptide can be encoded by a full-length coding sequence or by any portion of the coding sequence as long as the desired activity or functional properties (e.g., enzymatic activity, DNA-binding activity, transcriptional activation, transcriptional repression, pesticidal activity, ligand binding, and/or signal transduction) of the polypeptide are retained.

The term "heterologous" is used herein to refer to any polynucleotide (e.g., DNA molecule) that has been introduced into a microorganism (e.g., a bacterium) where the polynucleotide is not sourced from the microorganism and/or has been inserted into a new location (e.g., in a distinct DNA sequence in the chromosome, plasmid, or other extra-chromosomal element) in the microorganism (e.g., the bacterium). Non-limiting examples of heterologous DNA molecules that can be introduced into a microorganism include a non-naturally occurring (e.g., synthetic and/or recombinant) DNA molecule, a DNA molecule found in another microorganism (e.g., an intergeneric transfer of a DNA molecule comprising DNA from an organism of a different taxonomic genus), a DNA molecule found in another species (e.g., an intrageneric transfer of a DNA molecule comprising DNA from an organism of the same taxonomic genus), a DNA molecule found in a different location in the same species, and/or a DNA molecule found in the same strain or isolate of a species, where the DNA molecule has been inserted at a new location.

As used herein, the terms "include," "includes," and "including" are to be construed as at least having the features or items to which they refer while not excluding any additional unspecified features or items.

Unless otherwise stated, nucleic acid sequences in the text of this specification are given, when read from left to right, in the 5' to 3' direction. Nucleic acid sequences may be provided as DNA or as RNA, as specified; disclosure of a DNA or an RNA obtained therefrom also defines the exact complement of that DNA or RNA.

As used herein, the term "operably linked" refers to the association of nucleic acid sequences on a single nucleic acid fragment so that the function of one is or can be regulated by the other. For instance, a promoter is operably linked to an RNA or protein coding sequence if the promoter provides for transcription of the RNA or an mRNA encoding the protein.

As used herein, the term "phosphate," when used in the context of phosphate concentration in a plant growth medium and/or phosphate concentrations which can activate a phosphate-sensitive promoter, refers to inorganic and soluble phosphate which is available to plants and microorganisms.

As used herein, the phrase "phosphate-sensitive promoter" refers to a promoter which is activated (e.g., up-regulated) or repressed (e.g., down-regulated) when phosphate concentration changes. In certain embodiments, a phosphate-sensitive promoter is activated or repressed when phosphate concentration crosses a threshold value. In certain embodiments, a phosphate-sensitive promoter is up-regulated or down-regulated proportionally in response to a change in phosphate concentration. In certain embodiments, a phosphate-sensitive promoter is activated when phosphate concentrations decrease below a threshold value of about 50 $\mu M$, 40 $\mu M$, 30 $\mu M$, 20 $\mu M$, or 10 $\mu M$ to about 1 $\mu M$. In certain embodiments, a phosphate-sensitive promoter will be active at a concentration of phosphate from 0 $\mu M$ to about 1 $\mu M$, 2 $\mu M$, 5 $\mu M$, 7 $\mu M$, or 10 $\mu M$.

As used herein, the term "refactored" refers to a gene, gene cluster, or operon that has been restructured. In some embodiments, restructuring may include changing a DNA coding sequence to a DNA sequence divergent from the wild-type gene while still encoding the same polypeptide. In some embodiments, restructuring may include computationally scanning genes to identify control elements, removing them, and optionally replacing them with different control elements. In some embodiments, "refactored" refers to a gene, gene cluster, or operon wherein the naturally-occurring promoter has been modified to contain a new promoter which exhibits different regulatory characteristics. Examples of such refactored gene clusters include refactored nif and/or fix gene clusters which allow nitrogenase to be expressed without transcriptional down-regulation by fixed nitrogen. Examples of refactoring methods and refactored nif gene clusters include those disclosed in U.S. Pat. No. 11,479,516, incorporated herein by reference in its entirety.

As used herein, the phrase "ribosome binding site" and corresponding acronym "RBS" refers to RNA comprising a Shine-Dalgarno sequence. In certain embodiments, a ribosome binding site can comprise a Shine-Dalgarno sequence and the translational initiation codon.

As used herein, the phrase "segment of a 5' UTR" refers to one or more nucleotides of DNA encoding a 5' UTR (5' untranslated region) of a transcript and/or RNA comprising one or more nucleotides of a 5' UTR. In certain embodiments, the segment of a 5' UTR will comprise at least the first nucleotide of the 5' UTR but can also comprise at least a Shine-Dalgarno sequence of a ribosome binding site in a 5' UTR or the entire 5' UTR.

As used herein, the phrase "transcriptional activator" refers to proteins or ribonucleoprotein (RNP) complexes capable of activating expression of a particular target gene. Transcriptional activators can thus include: (i) transcription factors comprising a DNA binding domain and a transcriptional activation domain; (ii) sigma factors which bind both a target promoter and RNA polymerase; and (iii) a catalytically inactive RNA-guided DNA binding protein which further comprises a transcriptional activator domain and a guide RNA which targets the RNP complex to the promoter.

Sequence identity or percent sequence identity can be measured with the BLASTN program (for nucleotide sequence percent identity determinations) or BLASTP program (for protein sequence percent identity determinations) using the BLAST (Basic Local Alignment Search Tool) available on the internet at blast.ncbi.nlm.nih.gov/Blast.cgi with default settings.

To the extent to which any of the preceding definitions is inconsistent with definitions provided in any patent or non-patent reference incorporated herein by reference, any patent or non-patent reference cited herein, or in any patent or non-patent reference found elsewhere, it is understood that the preceding definition will be used herein.

In certain embodiments, one or more bacterial genes are down-regulated to cause the production of the agriculturally relevant compounds. Examples of bacterial genes which can be downregulated to produce ammonia include glnA, glnB, glnK, glnZ, nifL, and/or draT genes. Target glnA, glnB, glnK, glnZ, nifL, and/or draT gene sequences which can be down-regulated include those set forth in Table 5, in the sequence listing, and in US Patent Application No. US20210315212, which is incorporated herein by reference in its entirety. Target glnA, glnB, glnK, glnZ, nifL, or draT gene sequences which can be down-regulated further include sequences having at least 75%, 80%, 85%, 90%, 95%, or 99% sequence identity across the entire length of the sequences set forth in Table 1, in Table 5, in the sequence listing, and in US Patent Application No. US20210315212. Target glnA, glnB, glnK, glnZ, nifL, and/or draT gene sequences which can be down-regulated also include sequences which encode GlnA, GlnB, GlnK, GlnZ, NifL, or DraT proteins having at least 75%, 80%, 85%, 90%, 95%, or 99% sequence identity across the entire length of GlnA, GlnB, GlnK, GlnZ, NifL, or DraT proteins encoded by genes set forth in Table 1, in Table 5, in the sequence listing, and in US Patent Application No. US20210315212 or to GlnA, GlnB, GlnK, GlnZ, NifL, or DraT proteins in US Patent Application No. US20210315212.

TABLE 1

Non-limiting summary of target genes for down-regulation and ammonia production.

| Target Gene Name | Representative Genes | Comments |
|---|---|---|
| amtB | | Down-regulation of the amtB gene can inhibit uptake of ammonium from the extracellular environment and also result in excretion of ammonia from the cells under diazotrophic growth conditions. In certain embodiments of the methods, systems, and genetically engineered bacteria (GEB) provided herein, amtB down-regulation is combined with down-regulation of glnA, glnB, glnK, glnZ, nifL, and/or draT. |
| draT | | Nitrogenase is regulated by feedback repression at the transcriptional and post translational level by ADP-ribosylation via the DraT-DraG system. DraT catalyzes the ADP-ribosylation of the nitrogenase Fe protein and shuts off of nitrogenase under nitrogen excessive conditions, whereas DraG catalyzes the removal of ADP ribose and reactivation of nitrogenase under nitrogen starvation. Down-regulation of DraT in a cell where nitrogenase is not regulated by feedback repression at the transcriptional level can result in nitrogenase activity that escapes feedback repression. In certain embodiments of the methods, systems, and GEB provided herein, draT down-regulation is combined with down-regulation of glnA, amtB, glnB, glnK, glnZ, and/or nifL. |
| glnA | Genes encoding the GlnA proteins of SEQ ID NOs 229-230, 460-512, 519-521, 530-533 | Down-regulation of the glnA gene encoding glutamine synthetase can block assimilation of fixed nitrogen into glutamine, allow de-repression of nitrogen-fixing catalyst nitrogenase, and result in ammonia excretion. In certain embodiments of the methods, systems, and GEB provided herein, glnA down-regulation is combined with down-regulation of amtB, glnB, glnK, glnZ, nifL, and/or draT. |
| PII (glnB, glnK, glnZ) | | The PII proteins are the global nitrogen response regulators of the cell, acting on a suite of nitrogen metabolism proteins. Down-regulation of PII genes or proteins can result in ammonia release. For example, down-regulation of PII genes or proteins can force the adenylyl transferase (AT) to adeny late the GS protein, leading to de-repressed nitrogenase |

TABLE 1-continued

Non-limiting summary of target genes for down-regulation and ammonia production.

| Target Gene Name | Representative Genes | Comments |
|---|---|---|
| | | activity in the presence of ammonia. In certain embodiments of the methods, systems, and GEB provided herein, PII down-regulation (e.g., glnB, glnK, and/or glnZ down-regulation), is combined with down-regulation of glnA, amtB, nifL, and/or draT. |
| nifL | | The nifL gene is common amongst gamma-proteobacteria and acts as an anti-activator of the nitrogenase master regulator NifA. In conditions of low oxygen and low glutamine, NifL represses activity of NifA, preventing nitrogenase expression and nitrogen fixation. Down-regulation of NifL can lead to increased NifA activity and subsequently nitrogenase activity that is no longer repressed by glutamine. Removal of nitrogenase feedback inhibition leads to ammonia release. In certain embodiments of the methods, systems, and GEB provided herein, nifL down-regulation is combined with down-regulation of glnA, amtB, glnB, glnK, glnZ, and/or draT and/or with upregulation of nifA. |

In certain embodiments, one or more genes set forth in Table 1 can be down-regulated by one or more of the phosphate-sensitive systems or genes set forth in Table 2, Table 3, and/or Table 4. Examples of such combinations include down-regulation of GlnA (glutamine synthetase) by phosphate-sensitive promoter-controlled expression of a modified glnE gene encoding a GlnE protein lacking an adenylyl removing domain which exhibits unidirectional adenylyltransferase (uAT) activity. Particular embodiments of the systems for down-regulation of genes set forth in Table 1 are also disclosed within numbered embodiments 1-145.

Another example of such a combination is down-regulation of target genes set forth in Table 1 which include glnA (glutamine synthetase; e.g., as in Table 1 and SEQ ID NO: 229-230, 460-512, 519-521, 530-533) through phosphate-sensitive promoter (P-SP) controlled expression of a repressor protein (e.g., TetR repressor) which binds a natural or synthetic DNA motif in the promoter and/or 5' UTR of the target gene (e.g., glnA). In certain embodiments, the P-SP is operably linked to DNA encoding a transcript comprising a relatively weak ribosome binding site (RBS) which is operably linked to the transcriptional repressor protein coding region and supports lower levels of repressor protein expression in comparison to strong RBS. Relatively weak RBS include the BCD22 (SEQ ID NO: 449) RBS set forth herein and in Mutalik et al., 2013, doi:10.1038/nmeth.2404) as well as the BCD8 and BCD24 RBS set forth in Mutalik et al., 2013, doi:10.1038/nmeth.2404. Relatively weak RBS can also comprise other procaryotic RBS binding sites (e.g., obtainable from alpha-, beta-, or gamma-proteobacteria) comprising modifications of the Shine-Dalgarno 2 (SD2) sequence of the RBS that reduce translational initiation of operably linked protein coding regions (Mutalik et al., 2013, doi:10.1038/nmeth.2404). Additional weak RBS binding sites are disclosed in Wen et al., 2020, doi.org/10.1080/15476286.2020.1861406. Relatively strong RBS include the BCD2vL RBS encoded by SEQ ID NO: 430 and disclosed in Mutalik et al., 2013. A green fluorescent protein (GFP) reporter gene cassette where the strong BCD2vL RBS encoded by SEQ ID NO: 430 is operably linked to a promoter and the GFP reporter is set forth in SEQ ID NO: 522. Relatively weak RBS suitable for operable linkage to the transcriptional repressor protein coding region thus include RBS which when substituted in place of the BCD2vL RBS located at nucleotides 723 to 810 of control green fluorescent protein (GFP) reporter gene expression cassette of SEQ ID NO: 522 provide 0.1% to 44% of GFP reporter gene expression cassette of SEQ ID NO: 522 when expressed under otherwise identical conditions. In certain embodiments, RBS suitable for operable linkage to the transcriptional repressor protein coding region include RBS which when substituted in place of the BCD2vL RBS located at nucleotides 723 to 810 of control green fluorescent protein (GFP) reporter gene expression cassette of SEQ ID NO: 522 provide (i) 0.1%, 0.5%, 1%, 2%, 3%, 4%, 5%, 6%, 7%, or 8% to 10%, 15%, 20%, 25%, 30%, 35%, 40%, or 44%; or (ii) 10%, 15%, or 20% to 25%, 30%, 35%, 40%, or 44%; of GFP reporter gene expression cassette of SEQ ID NO: 522 when expressed under otherwise identical conditions. In certain embodiments, determination of percent (%) operably linked reporter gene expression for any given test candidate RBS relative to the SEQ ID NO: 430 RBS can be determined by: (i) inserting the test candidate RBS and the control strong RBS (SEQ ID NO: 430) at the same position (e.g., nucleotides 723 to 810) in the 5' UTR of the same reporter gene in the test candidate gene expression cassette and control gene expression cassette (e.g., SEQ ID NO: 522), where the only difference between the test candidate and control gene expression cassette is the RBS sequence (i.e., the promoters, 5' UTR, reporter gene, and terminator are otherwise identical); (ii) recovering transformed bacteria where the test candidate and control gene expression cassette are both inserted at the same position and orientation in the bacterial chromosome of an otherwise identical bacterial strain; and (iii) growing the transformed bacteria with the test candidate and control gene expression cassette under identical conditions, harvesting the bacteria at the same density during exponential growth (e.g., in mid-exponential growth phase), and assaying for reporter gene expression in identical assays. In certain embodiments, the bacteria comprising the test candidate gene expression cassette with a suitable weak RBS will provide 0.1%, 0.5%, 1%, 2%, 3%, 4%, 5%, 6%, 7%, or 8% to 10%, 15%, 20%, 25%, 30%, 35%, 40%, or 44% of the reporter gene expression provided by the control gene cassette (e.g., the GFP reporter gene expression cassette of SEQ ID NO: 522) having the strong RBS (SEQ ID NO: 430).

Target genes (e.g., a target gene of Table 1 such as glnA) that are down-regulated by phosphate-sensitive promoter (P-SP) controlled expression of a repressor protein (e.g., TetR or LacI repressor) can be modified in host bacteria to provide a host where the functional copy of the target gene is under control of the repressible promoter. In certain embodiments, the endogenous target gene is disrupted (e.g., contains an insertion, deletion, and/or substitution which results in a null allele of the endogenous target gene) and a modified target gene comprising a repressible promoter (e.g., TetR repressible promoter) which is operably linked to a target gene coding region (e.g., a glnA gene from the host bacterium or another source) is inserted in the chromosome of the host bacterium. In other embodiments, the target gene (e.g., a target gene of Table 1 such as glnA) is encoded by the endogenous target gene and the endogenous target gene (e.g., glnA) is operably linked to the promoter which is repressed by the repressor protein (e.g., a TetR or LacI repressor). Examples of such embodiments include those where endogenous glnA gene promoter which is operably linked to the endogenous glnA gene coding region is replaced with a promoter that is under control of the repressor. In certain embodiments, the target gene (e.g., the entire promoter and coding region of a glnA gene in a target bacterium such as a *Kosakonia* sp.) is substituted with a heterologous target gene comprising the repressible promoter (e.g., TetR repressible promoter) which is operably linked to a heterologous target gene coding region (e.g., a glnA gene from a bacterium other than *Kosakonia* sp. or variant thereof including an *Azospirillum* glnA coding region). Suitable promoters under control of the repressor include: (i) recombinant target gene (e.g., glnA) promoter containing a natural or synthetic DNA motif inserted within the promoter at a position which will result in inhibition of transcription when bound by the repressor; or (ii) wild-type promoters or variants thereof which are repressed by the repressor protein (e.g., a Tet operon promoter which is repressed by a TetR repressor protein).

TABLE 2

| | Non-limiting summary of systems for down-regulating target genes under decreased phosphate concentrations | | |
|---|---|---|---|
| System | Non-limiting materials which can be used to implement system | Non-limiting descriptions of materials and methods which can be adapted for use in the mechanism | |
| Phosphate-sensitive promoter (P-SP) controlled expression of a repressor protein which binds a natural or synthetic DNA motif in the promoter and/or 5′ UTR of a target gene. | P-SP described in Table 5, SEQ ID NO: 417-428, 515, 517, or 518; Lambda phage repressor (cI) (SEQ ID NO: 26), the tet repressor (TetR) (SEQ ID NO: 27, the lac repressor (LacI) SEQ ID NO: 29, PhlF (SEQ ID NO: 30), (e.g., in Table 5), a catalytically inactive RNA-guided DNA binding protein, proteins comprising a DNA-binding zinc finger domain, a transcription activator-like effector (TALE) lacking a transcription activation domain (TAD), and/or any variant thereof. | Ramos et al., 2005, doi.org/10.1128/mmbr.69.2.326-356.2005 | |
| P-SP controlled expression of a repressor which controls a second gene encoding a second repressor in a repressor cascade comprising an odd number (1, 3, 5, 7, 9, or more) of repressors and repressed genes encoding repressors, where the last repressor in the cascade can repress expression of the gene targeted for down regulation when the P-SP is active. | Lambda phage repressor (cI), the tet repressor (TetR), the lac repressor (LacI), and PhlF (e.g., in Table 5) | Hooshangi et al., 2004, doi: 10.1073pnas.0408507102; Ramos et al., 2005, doi.org/10.1128/mmbr.69.2.326-356.2005 | |
| P-SP controlled expression of a non-coding synthetic small RNA (sRNA) | P-SP described in Table 5, SEQ ID NO: 417-428; Guide RNA molecules that hybridize to a DNA sequence in target gene and allow: (1) site-specific cleavage by an RNA-guided DNA endonuclease (e.g., Cas9 or Cas12); (2) site-specific binding and transcriptional repression by a protein comprising dCas9 or dCas12, | Arroyo-Olarte et al. 2021, doi: 10.3390/microorganisms9040844. Cytosine base editing: U.S. Pat. No. 9,840,699B2 incorporated herein by reference in its entirety. Adenosine base editing: | |

TABLE 2-continued

Non-limiting summary of systems for down-regulating
target genes under decreased phosphate concentrations

| System | Non-limiting materials which can be used to implement system | Non-limiting descriptions of materials and methods which can be adapted for use in the mechanism |
| --- | --- | --- |
| | (3) site-specific base editing with a catalytically inactive RNA-guided DNA binding protein coupled to a cytidine or adenine deaminase, (4) site-specific chemical modification of DNA nucleobases (including methylation, demethylation, hydroxymethylation, carboxymethylation) by a catalytically inactive RNA-guided DNA binding protein coupled to a DNA modifying enzyme (including methyltansferases, TET enzymes, and carboxymethylation enzymes such as M.MpeI N374K), or (5) site-specific DNA mutagenesis with a catalytically inactive RNA-guided DNA binding protein coupled to a reverse transcriptase or error-prone DNA polymerase. | U.S. Pat. No. 10,113,163B2 incorporated herein by reference in its entirety. Prime editing: U.S. Pat. No. 11,643,652B2 incorporated herein by reference in its Entirety. Prime editing: U.S. Pat. No. 11,643,652B2 incorporated herein by reference in its entirety. Site-specific DNA methylation: doi: 10.1016/j.cell.2016.08.056 DNA carboxymethylation: doi: 10.1016/j.chembiol.2020.09.006. |
| P-SP controlled expression of a non-coding synthetic small RNA (sRNA) | P-SP described in Table 5, SEQ ID NO: 417-428, 515, 517, or 518; RNA molecules that hybridize to an RNA sequence expressed by target gene | |
| P-SP controlled expression of a non-coding synthetic small RNA (sRNA) | P-SP described in Table 5, SEQ ID NO: 417-428, 515, 517, or 518; Expression of sRNA which hybridize to target gene mRNA Shine-Dalgarno sequence of a ribosome binding site and/or start codon | Good L, Stach J E. Front Microbiol. 2011, doi: 10.3389/fmicb.2011.00185 Lee J L, Moon T S. Methods. 2018, doi: 10.1016/j.ymeth.2018.01.001 Na D et al. *Nat Biotechnol.* 2013, doi: 10.1038/nbt.2461 |
| P-SP controlled expression of a site-specific recombinase (SSR) or integrase protein (INTP) which can excise a target gene or region within the target gene flanked by site-specific recombinase recognition sites (SSRRS) in a direct configuration | P-SP described in Table 5, SEQ ID NO: 417-428, 515, 517, or 518; SSR, INTP, and SSRRS including PhiC31 serine integrase, IntS, IntM, IntG - ICEMcSym 1271, YdcL - ICEBs, or Int - ICE SXT/R39 integrase, and corresponding attL and attR sites and the genetically engineered bacterium comprises a gene encoding a recombinase directionality factor (RDF); FLP recombinase and FRT sites or Cre-recombinase and loxP sites. | U.S. Pat. No. 10,614,353, incorporated herein by reference in its entirety. |
| P-SP controlled expression of a site-specific recombinase (SSR) or integrase protein (INTP), an integrative SSRRS in the target gene, and an integrative element comprising an SSRRS that provides for insertional inactivation. | P-SP described in Table 5, SEQ ID NO: 417-428, 515, 517, or 518; SSR, INTP, and SSRRS including: PhiC31 serine integrase, IntS, IntM, IntG - ICEMcSym 1271, YdcL - ICEBs, or Int - ICE SXT/R39 integrase, and corresponding recognition sites (attB and attP) including those in Table 5; FLP recombinase and FRT sites; or Cre-recombinase and loxP sites. | U.S. Pat. No. 10,614,353, incorporated herein by reference in its entirety. |
| P-SP controlled expression of a site-specific recombinase (SSR) or integrase protein (INTP), in a cell comprising an | P-SP described in Table 5, SEQ ID NO: 417-428, 515, 517, or 518; SSR, INTP, and SSRRS including: PhiC31 serine integrase, IntS, IntM, IntG - | U.S. Pat. No. 10,614,353, incorporated herein by reference in its entirety. |

TABLE 2-continued

| | Non-limiting summary of systems for down-regulating target genes under decreased phosphate concentrations | |
|---|---|---|
| System | Non-limiting materials which can be used to implement system | Non-limiting descriptions of materials and methods which can be adapted for use in the mechanism |
| SSR- or integrase-controlled promoter switch where inversion of promoter in switch by SSR or INTP inverts promoter and down-regulates gene. | ICEMcSym 1271, YdcL - ICEBs, or Int - ICE SXT/R39 integrase, and corresponding recognition sites, including those in Table 5; FLP recombinase and FRT sites, or Cre-recombinase and loxP sites. Constitutive and inducible promoters used in the SSR or integrase controlled promoter switch. | Siuti et al. 2013, doi: 10.1038/nbt.2510 Bernabé-Orts et al. 2020, doi.org/10.1093/nar/gkaa104 |
| P-SP controlled expression of a site-specific RNA-guided RNA endonuclease which specifically cleaves one or more RNA transcripts of the target gene. | P-SP described in Table 5, SEQ ID NO: 417-428, 515, 517, or 518; RNA-guided RNA endonuclease (e.g., Cas Type III systems and Cas Type VI systems including Cas13) | Arroyo-Olarte et al. 2021, doi: 10.3390/microorganisms9040844; Gasiunas et al. 2014, doi: 10.1007/s00018-013-1438-6; Hale et al. 2012, doi: 10.1016/j.molcel.2011.10.023; Hillary and Ceasar, 2022, doi: 10.1007/s12033-022-00567-0; U.S. Pat. No. 11,788,083, incorporated herein by reference in its entirety. |
| P-SP controlled expression of a site-specific DNA endonuclease which specifically cleaves one or more DNA sequences in the target gene. | P-SP described in Table 5, SEQ ID NO: 417-428, 515, 517, or 518; RNA-guided DNA endonuclease, a protein comprising a DNA-binding zinc finger domain and endonuclease domain, a transcription activator-like effector (TALE) and endonuclease domain, a meganuclease, a homing endonuclease, or a restriction endonuclease | Arroyo-Olarte et al. 2021, doi: 10.3390/microorganisms9040844. Hillary and Ceasar, 2022, doi: 10.1007/s12033-022-00567-0. |
| P-SP controlled expression of a protease which cleaves a protease specific recognition sequence (PSRS) in the target gene. | P-SP described in Table 5, SEQ ID NO: 417-428, 515, 517, or 518; TEV, TVMV, SMMV, TrMV, SMV, PPV, HCV, enterokinase, Factor Xa, furin proteases (e.g., SEQ ID Nos: 45, 46, 47, 48, 49, 50, 51, 52, and 53) and corresponding PSRS. | |
| P-SP controlled expression of a ClpAP ATP-dependent protease and a ClpS Leu/N-recognin where the target gene protein has an N-terminal -Leu, -Phe, -Trp, or -Tyr residue | P-SP described in Table 5, SEQ ID NO: 417-428, 515, 517, or 518; ClpAP ATP-dependent protease and a ClpS Leu/N-recognin | |
| P-SP controlled expression of a protease which cleaves a PSRS in the N-terminus of the target gene to expose an N-terminal -Leu, -Phe, -Trp, or -Tyr residue, allowing degradation by native ClpS and ClpAP. | P-SP described in Table 5, SEQ ID NO: 417-428, 515, 517, or 518; TEV, TVMV, SMMV, TrMV, SMV, PPV, HCV, enterokinase, Factor Xa, furin proteases and corresponding PSRS. | |
| P-SP controlled expression of a transcriptional activator (TA) which upregulates expression of a protease which cleaves a PSRS in the target gene. | P-SP described in Table 5, SEQ ID NO: 417-428, 515, 517, or 518; tet responsive element-binding TA transcription factor, or a transcriptional activator domain fused to a | Pinto et al., doi: 10.1093/nar/gky614 |

TABLE 2-continued

| | | Non-limiting descriptions of materials and |
| | Non-limiting materials which can be used to implement | methods which can be adapted for use |
| System | system | in the mechanism |
|---|---|---|
| | DNA targeting protein or ribonucleoprotein (e.g., DNA sequence-specific binding protein or ribonucleoprotein). TA also include sigma factors which bind the core promoter and RNA polymerase. | |
| P-SP controlled expression of a repressor which inhibits expression of a protease which activates the target gene by cleaving a PSRS located C-terminal to an N-terminal amino acid tag designed to render the target protein inactive. | P-SP described in Table 5, SEQ ID NO: 417-428, 515, 517, or 518; N-terminal tag which renders the target protein inactive by (i) sterically blocking the active site, (ii) binding the active site, or (iii) preventing multimer formation. | |
| P-SP controlled expression of a nanobody which binds and inactivates the target protein. | P-SP described in Table 5, SEQ ID NO: 417-428, 515, 517, or 518; Nanobodies directed against GlnA, GlnB, GlnK, GlnZ, NifL, or DraT proteins | Muyldermans 2013, doi: 10.1146/annurev-biochem-063011-092449 |
| P-SP controlled expression of an aptamer which binds and inactivates the target protein. | P-SP described in Table 5, SEQ ID NO: 417-428, 515, 517, or 518; Aptamers directed against glnA, glnB, glnK, glnZ, nifL, or draT genes, gene transcripts, or encoded proteins. | |

In certain embodiments, one or more bacterial genes are up-regulated to cause the production of the agriculturally relevant compounds. Examples of bacterial genes which can be up-regulated to produce ammonia include nifA, ntrC, glnR, a gene encoding a glutaminase enzyme, a gene encoding a GlnE protein lacking an adenylyl removing domain which exhibits unidirectional adenylyltransferase (uAT) activity (also referred to herein as GlnE-uAT), one or more nif cluster gene(s), and/or one or more fix cluster gene(s). Target nifA, ntrC, glnR, glutaminase encoding genes, GlnE-uAT genes, nif cluster gene(s), and/or fix cluster gene sequences which can be up-regulated include those set forth in Table 3, in the sequence listing, and in US Patent Application No. US20210315212, which is incorporated herein by reference in its entirety. Target nifA, ntrC, glnR, glutaminase encoding genes, GlnE-uAT genes, nif cluster gene(s), and/or fix cluster genes which can be up-regulated further include sequences having at least 75%, 80%, 85%, 90%, 95%, or 99% sequence identity across the entire length of the sequences set forth in Table 3, in the sequence listing, and in US Patent Application No. US20210315212. Target nifA, ntrC, glnR, glutaminase encoding genes, GlnE-uAT genes, nif cluster gene(s), and/or fix cluster gene sequences which can be up-regulated also include sequences which encode NifA, NtrC, GlnR, glutaminase, GlnE-uAT, nif cluster, and/or fix cluster proteins having at least 75%, 80%, 85%, 90%, 95%, or 99% sequence identity across the entire length of NifA, NtrC, GlnR, glutaminase, GlnE-uAT, nif cluster, and/or fix cluster proteins encoded by genes set forth in Table 3, in the sequence listing, and/or in US Patent Application No. US20210315212 or to NifA, NtrC, GlnR, Glutaminase, GlnE-uAT, nif cluster, and/or fix cluster proteins in Table 3, in Table 5, in the sequence listing, and/or in US Patent Application No. US20210315212.

In certain embodiments, one or more bacterial genes are up-regulated to cause the production of phosphate from insoluble forms of phosphate (e.g., present in plant growth media). Examples of bacterial genes which can be up-regulated to produce phosphate include genes encoding a phytase enzyme (e.g., a cysteine phytase, a histidine acid phytase, or a beta-propeller phytase), genes encoding an acid phosphatase enzyme (e.g., an acpA, aphA, phoC, napA, napD, or napE gene), and/or genes encoding a protein which stimulates organic acid release from the bacterium, (e.g., a gluconate dehydrogenase (GAD), a glucose dehydrogenase (GDH), or a pyrroloquinoline (PQQ) synthase encoding gene). Target phytase-, acid phosphatase- (e.g., an acpA, aphA, phoC, napA, napD, or napE gene), GAD-, GDH-, or pyrroloquinoline (PQQ) synthase-encoding genes which can be up-regulated include those set forth in Table 3, in the sequence listing, and in US Patent Application No. US20210345618, which is incorporated herein by reference in its entirety. Target phytase-, acid phosphatase- (e.g., an acpA, aphA, phoC, napA, napD, or napE gene), GAD-, GDH-, or pyrroloquinoline (PQQ) synthase-encoding genes which can be up-regulated further include sequences having at least 75%, 80%, 85%, 90%, 95%, or 99% sequence identity across the entire length of the sequences set forth in Table 3, in the sequence listing, and in US Patent Application No. US20210345618. Target phytase-, acid phosphatase- (e.g., an acpA, aphA, phoC, napA, napD, or napE gene), GAD-, GDH-, or pyrroloquinoline (PQQ) synthase-encoding genes which can be up-regulated also include sequences which encode phytase, acid phosphatase (e.g., an AcpA, AphA, PhoC, NapA, NapD, or NapE protein), GAD, GDH, or pyrroloquinoline (PQQ) synthase proteins having at least 75%, 80%, 85%, 90%, 95%, or 99% sequence identity across the entire length of phytase, acid phosphatase (e.g., an AcpA, AphA, PhoC, NapA, NapD, or NapE protein), GAD, GDH, or pyrroloquinoline (PQQ) synthase proteins encoded by genes set forth in Table 3, in the sequence listing, and in US Patent Application No. US20210345618 or to phytase, acid phosphatase (e.g., an AcpA, AphA, PhoC, NapA, NapD, or NapE protein), GAD, GDH, or pyrroloquinoline (PQQ) synthase proteins in Table 3, in the sequence listing, and/or in US Patent Application No. US20210345618.

TABLE 3

| Non-limiting summary of target genes for up-regulation and agriculturally relevant compounds produced by up-regulation | | |
|---|---|---|
| Target Gene or Target Gene encoded protein (non-limiting examples) | Agriculturally relevant compound | Comment |
| nifA | ammonia | NifA is the master transcriptional regulator of genes involved in nitrogenase assembly, function and maintenance (nif, fix). The nifA gene in bacteria is typically regulated at the transcriptional and often posttranslational level by nitrogen, oxygen, and in some cases, carbon. In *Azotobacter vinlandii*, overexpression of nifA from a heterologous promoter drives constitutive nitrogenase activity and stimulates ammonia release. In certain embodiments, nifA up-regulation is combined with: (i) nifL down-regulation (e.g., mutants that are unable to regulate NifA at the protein level); (ii) in draT down-regulation; and/or (iii) nif/fix gene cluster up-regulation. In certain embodiments of the methods, systems, and GEB provided herein, nifA up-regulation is combined with: (i) down-regulation of glnA, amtB, glnB, glnK, glnZ, nifL, and/or draT; and/or (ii) up-regulation of ntrC, glnR, uAT, GLS, one or more nif cluster gene(s), and/or one or more fix cluster genes |
| ntrC | ammonia | Kukolj et al., 2020, doi:: 10.1021/acs.jproteome.9b00397 |
| glnR | ammonia | The glnR gene acts as a regulator of nitrogen metabolism genes in gram-positive bacteria. Up-regulation of glnR can drive nitrogenase activity and promote ammonia release. In certain embodiments of the methods, systems, and GEB provided herein, glnR up-regulation is combined with: (i) down-regulation of glnA, amtB, glnB, glnK, glnZ, nifL, and/or draT; and/or (ii) up-regulation of nifA, ntrC, uAT, GLS, one or more nif cluster gene(s), and/or one or more fix cluster genes to promote ammonia release. |
| nif/fix cluster genes | ammonia | The nif/fix genes are required for iron molybdenum nitrogenase assembly, function, and maintenance. Up-regulation of nif/fix cluster genes can promote ammonia release. In certain embodiments of the methods, systems, and GEB provided herein, up-regulation of one or more nif cluster gene(s) and/or one or more fix cluster genes is combined with: (i) down-regulation of glnA, amtB, glnB, glnK, glnZ, nifL, and/or draT; and/or (ii) up-regulation of nifA, ntrC, glnR, GLS, and/or a uAT. |
| GlnE protein lacking an adenylyl removing domain which exhibits unidirectional adenylyltransferase (uAT) activity (GlnE-uAT protein). GlnE-uAT proteins include SEQ ID NO: 16-25; GlnE-uAT encoding genes include SEQ ID NO: 1-15. | ammonia | Up-regulation of GlnE-uAT proteins can result in the down-regulation of glutamine synthetase by adenylation and result in ammonia release. In certain embodiments of the methods, systems, and GEB provided herein, uAT up-regulation is combined with: (i) down-regulation of glnA, amtB, glnB, glnK, glnZ, nifL, and/or draT; and/or (ii) up-regulation of nifA, ntrC, glnR, GLS, one or more nif cluster gene(s), and/or one or more fix cluster genes to promote ammonia release. |
| Glutaminase (GLS) enzymes | ammonia | GLS enzymes catalyze the conversion of glutamine into glutamate. Up-regulation of GLS can reduce glutamine levels in the cell and force a nitrogen starvation response, resulting in de-repression of nitrogenase and promoting nitrogen release. In certain embodiments of the methods, |

TABLE 3-continued

| | | |
|---|---|---|
| Non-limiting summary of target genes for up-regulation and agriculturally relevant compounds produced by up-regulation | | |

| Target Gene or Target Gene encoded protein (non-limiting examples) | Agriculturally relevant compound | Comment |
|---|---|---|
| | | systems, and GEB provided herein, GLS up-regulation is combined with: (i) down-regulation of glnA, amtB, glnB, glnK, glnZ, nifL, and/or draT; and/or (ii) up-regulation of nifA, ntrC, glnR, uAT, one or more nif cluster gene(s), and/or one or more fix cluster genes. |
| Acid phosphatases (e.g., acpA, phoC, napA, napD, napE) | phosphate | Acid phosphatases catalyze dephosphorylation of phosphor-ester or phospho-anhydride bond of organic compounds to release phosphate. Acid phosphatase gene sources include genes in US20210345618A1, incorporated herein by reference in its entirety. |
| aphA | phosphate | |
| phytase (including a cysteine phytase, histidine acid phytase, or beta-propeller phytase; including phytases in Table 5 and phytases comprising a protein sequence having at least 70%, 75%, 80%, 85%, 90%, 95%, 98%, or 99% sequence identity to SEQ ID NO: 58-138, or 139. | phosphate | Phytase-mediated hydrolysis of phytic acid in different positions of the inositol ring to release phosphorus, zinc, and other minerals in inorganic form; US20210345618A1 |
| gluconate dehydrogenase (GAD) | phosphate | Conversion of the insoluble inorganic phosphate to plant-available phosphate through H+ excretion and organic acid production. GAD gene sources include genes in US20210345618A1, incorporated herein by reference in its entirety. |
| glucose dehydrogenase (GDH) | phosphate | Conversion of the insoluble inorganic phosphate to plant-available phosphate through H+ excretion and gluconic acid production. |
| gluconic acid biosynthetic gene(s) (e.g., pyrroloquinoline (PQQ) synthase | phosphate | Conversion of the insoluble inorganic phosphate to plant-available phosphate through H+ excretion and gluconic acid production. Gluconic acid biosynthetic genes include pqqA, pqqB, pqqC, pqqD, pqqE, gcd, gabY, variants thereof, and combinations thereof disclosed in US20210345618A1, incorporated herein by reference in its entirety. |
| B. thuringiensis Cry endotoxins, variants thereof, and chimeras thereof | Protein based insecticide | Cry1, Cry2, Cry3, Cry4, Cry5, Cry6, Cry7, Cry8, Cry9, Cry10, Cry11, Cry12, Cry13, Cry14, Cry15, Cry16, Cry17, Cry18, Cry19, Cry20, Cry21, Cry22, Cry23, Cry24, Cry25, Cry26, Cry27, Cry28, Cry29, Cry30, Cry31, Cry32, Cry33, Cry34, Cry35, Cry36, Cry37, Cry38, Cry39, Cry40, Cry41, Cry42, Cry43, Cry44, Cry45, Cry46, Cry47, Cry49, Cry51, Cry52, Cry53, Cry 54, Cry55, Cry56, Cry57, Cry58, Cry59, Cry60, Cry61, Cry62, Cry63, Cry64, Cry65, Cry66, Cry67, Cry68, Cry69, Cry70 and Cry71 endotoxins, variants thereof, and chimeras thereof, including those disclosed in U.S. Pat. Application No. US20210315212, incorporated herein by reference in its entirety |
| B. thuringiensis Cyt proteins | Protein based insecticide | B. thuringiensis cytolytic cyt1 and cyt2 genes including those disclosed in U.S. Pat. Application No. US20210315212, incorporated herein by reference in its entirety. |
| VIP (vegetative insecticidal proteins) toxins | Protein based insecticide | VIP1, VIP2, VIP3 proteins disclosed in U.S. Pat. Nos. 5,877,012, 6,107,279 6,137,033, 7,244,820, 7,615,686, and 8,237,020, incorporated herein by reference in their entireties. |

TABLE 3-continued

| Non-limiting summary of target genes for up-regulation and agriculturally relevant compounds produced by up-regulation | | |
| --- | --- | --- |
| Target Gene or Target Gene encoded protein (non-limiting examples) | Agriculturally relevant compound | Comment |
| Toxin complex (TC) proteins, obtainable from organisms such as *Xenorhabdus*, *Photorhabdus* and *Paenibacillus* | Protein based insecticide | TC Class A proteins including TcbA, TcdA, XptA1 and XptA2; TC Class B proteins including TcaC, TcdB, XptB1Xb and XptC1; TC Class C proteins including TccC, XptClXb and XptBl Wi (U.S. Pat. Nos. 7,491,698 and 8,084,418, incorporated herein by reference in their entireties). |
| Anti-microbial proteins including defensin proteins | Protein-based fungicides | Defensin and defensin-multimers disclosed in U.S. Pat. Applic. Publ. No. 20190185877, incorporated herein by reference in its entirety. |
| Genes encoding dsRNA to produce RNAi response directed against insect target genes | RNA based insecticides | dsRNA directed against insect target proteins including those disclosed in U.S. Pat. No. 11,312,975, incorporated herein by reference in its entirety. |
| Genes encoding dsRNA to produce RNAi response directed against fungal target genes | RNA based fungicides | dsRNA directed against fungal target proteins including those disclosed in U.S. Pat. No. 8,865,968, incorporated herein by reference in its entirety. |
| Genes encoding dsRNA to produce RNAi response directed against nematode target genes | RNA based nematicides | dsRNA directed against nematode target proteins including those disclosed in U.S. Pat. No. 9,388,409, incorporated herein by reference in its entirety. |
| gluconate dehydrogenase (GAD), optionally in strain selected for zinc solubilization activity | Zinc | Conversion of the insoluble zinc to plant-available zinc through $H+$ excretion and organic acid production (Eshagi et al., Iran J Microbiol. 2019 October; 11(5): 419-430). GAD gene sources include genes in US20210345618A1, incorporated herein by reference in its entirety. |
| gluconate dehydrogenase (GAD), optionally in a strain selected for potassium solubilization activity | Potassium | Conversion of the insoluble potassium to plant-available zinc through $H+$ excretion and organic acid production (Kumar etal., 2013, DOI: 10.1007/s00284-013-0372-z; Rajawat et al., 2016, doi: 10.1016/S1002-0160(15)60080-7). GAD gene sources include genes in US20210345618A1, incorporated herein by reference in its entirety. |
| Genes encoding siderophore biosynthetic and transport proteins including dnbACDEBF gene clusters, genes encoding non-ribosomal peptide synthetase (NRPS), polyketide synthase (PKS), and NRPS-independent siderophore synthetase (NIS); and major facilitator superfamily (MFS) transporters (ymfE), TonB, ExbD, and ExbB (gram-negatives) | Iron | Production of catecholates and phenolates, hydroxamates, carboxylates, and mixed-type siderophores which chelate iron and permit uptake by plants; Timofeeva et al., 2022, doi: 10.3390/plants11223065 |
| ipdC, iaaM | Auxin | |
| GA operon containing core genes cyp112, cyp114, cyp117 (cytochrome P450 (CYP) monooxygenases), fd (ferredoxin), sdr (short-chain dehydrogenase/reductase), ggps | Gibberelin | GA operon sources include those disclosed in Nett et al., 2020, doi: 10.1128/mSphere.00292-20 |

TABLE 3-continued

| Non-limiting summary of target genes for up-regulation and agriculturally relevant compounds produced by up-regulation | | |
|---|---|---|
| Target Gene or Target Gene encoded protein (non-limiting examples) | Agriculturally relevant compound | Comment |
| (geranylgeranyl diphosphate synthase), cps and ks (two diterpene synthases/cyclases) | | |
| ACC deaminase, AcdS | ammonia and α-ketobutyrate | Down-regulation of ethylene by degradation of ethylene precursor 1-aminocyclopropane-1-carboxylate (ACC). AcdS sources include those in Gao et al., 2020, doi: 10.3390/microorganisms8010071 |
| Glyceraldehyde-3-Phosphate Dehydrogenase (GAPDH) and 2,3-butanediol Dehydrogenase (BDH) | Volatile Organic compounds (VOC) | Production of 2,3-Butanediol. GAPDH and BDH sources include those disclosed in Yang et al., 2013, doi: 10.1371/journal.pone.0076149 |
| OtsA, OtsB, and TreS; TreS alone. gene encoding a carbonic anhydrase (CA) (beta-CA or alpha-CA) | Trehalose<br><br>carbon-containing compound (calcium carbonate) | TreS sources include those disclosed in Orozco-Mosqueda, 2019, doi: 10.3389/fmicb.2019.01392. CA gene sources include those disclosed in Chen et al., 2019, doi: 10.1007/s12088-018-0773-6; Clemente Capasso et al., 2012, doi: 10.3109/14756366.2012.703185 |

In certain embodiments, one or more genes set forth in Table 3 can be up-regulated by one or more of the phosphate-sensitive systems or genes set forth in Table 4. Particular embodiments of the systems for up-regulation of genes set forth in Table 3 are also disclosed within the following numbered embodiments 1-119 and 123.

TABLE 4

| Non-limiting summary for gene up-regulation mechanisms under decreased phosphate concentrations | | |
|---|---|---|
| System | Non-limiting materials which can be used to implement system | Non-limiting descriptions of materials and methods which can be adapted for use in the system |
| P-SP controlled expression of a GlnE protein lacking an adenylyl removing domain which exhibits unidirectional adenylyltransferase (uAT) activity (GlnE-uAT) | P-SP described in Table 5, SEQ ID NO: 417-428, 515, 517, or 518; GlnE-uAT proteins comprising a protein sequence having at least 70%, 80%, 85%, 90%, 95%, 98%, or 99% identity to SEQ ID NO: 16-24, or 25. | GlnE-uAT described in: US20210315212 incorporated herein by reference in its entirety. Schnabel and Sattely 2021, doi: 10.1128/AEM.00582-21 Schnabel and Sattely 2021, doi: 10.1021/acssynbio.1c00287 |
| P-SP controlled expression of a NifA protein | P-SP described in Table 5, SEQ ID NO: 417-428, 515, 517, or 518; | NifA described US20210315212 incorporated herein by reference in its entirety. |
| P-SP controlled expression of a GlnR protein | P-SP described in Table 5, SEQ ID NO: 417-428, 515, 517, or 518 | GlnR described US20210315212 incorporated herein by reference in its entirety. |
| P-SP controlled expression of a glutaminase enzyme | Table 5 P-SP described in Table 5, SEQ ID NO: 417-428, 515, 517, or 518 | Glutaminase enzymes disclosed in US20210315212 incorporated herein by reference in its entirety. |
| P-SP controlled expression of a refactored nif or fix gene cluster | Table SP-SP described in Table 5, SEQ ID NO: 417-428, 515, 517, or 518 | Nif gene clusters disclosed in US20210315212 incorporated herein by reference in its entirety. |
| P-SP controlled expression of a repressor which controls a second gene encoding a | P-SP described in Table 5, SEQ ID NO: 417-428, 515, 517, or 518; Lambda phage repressor (cI), the tet | Hooshangi et al., 2004, doi: 10.1073pnas.0408507102;; Ramos et al., 2005, doi.org/10.1128/mmbr.69.2.326-356.2005 |

TABLE 4-continued

| | | |
|---|---|---|
| Non-limiting summary for gene up-regulation mechanisms under decreased phosphate concentrations | | |
| System | Non-limiting materials which can be used to implement system | Non-limiting descriptions of materials and methods which can be adapted for use in the system |
| second repressor in a repressor cascade comprising an even number (2, 4, 6, 8, or more) of repressors and repressed genes encoding repressors, where the last repressor in the cascade can repress expression of the gene targeted for up-regulation when the P-SP is inactive. | repressor (TetR), the lac repressor (LacI), and PhlF and respective binding sites (e.g., in Table 5) | |
| P-SP controlled expression of a transcriptional activator (TA) which activates expression of the gene encoding the RNA or protein of interest | P-SP described in Table 5, SEQ ID NO: 417-428, 515, 517, or 518; Transcriptional activators including tet responsive element-binding tTA transcription factor or an activator domain fused to a DNA targeting protein; TA also include sigma factors which bind the core promoter and RNA polymerase. | Pinto et al., doi: 10.1093/nar/gky614 |
| P-SP controlled expression of a transcriptional activator (TA) which controls a second gene encoding a second activator in a transcriptional activator cascade comprising of transcriptional activators and activated genes encoding activators where the last activator in the cascade can activate expression of the gene targeted for up-regulation when the P-SP is active. | P-SP described in Table 5, SEQ ID NO: 417-428, 515, 517, or 518; Transcriptional activators including tet responsive element-binding tTA transcription factor or an activator domain fused to a DNA targeting protein; TA also include sigma factors which bind the core promoter and RNA polymerase. | Pinto et al., doi: 10.1093/nar/gky614 |
| P-SP controlled expression of a site-specific recombinase (SSR) or integrase protein in a cell containing an SSR- or integrase-controlled promoter switch (promoter is operably linked to target gene(s) upon inversion by the SSR or integrase). | P-SP described in Table 5, SEQ ID NO: 417-428, 515, 517, or 518; | U.S. Pat. No. 10,614,353, incorporated herein by reference in its entirety. Siuti et al. 2013, doi: 10.1038/nbt.2510 Bernabé-Orts et al. 2020, doi.org/10.1093/nar/gkaa104 |
| P-SP controlled expression of a transcriptional activator protein which binds a natural or synthetic DNA motif in a | P-SP described in Table 5, SEQ ID NO: 417-428, 515, 517, or 518; | Transcriptional activators disclosed in U.S. Pat. No. 10,614,353, incorporated herein by reference in its entirety. |

TABLE 4-continued

Non-limiting summary for gene up-regulation mechanisms
under decreased phosphate concentrations

| System | Non-limiting materials which can be used to implement system | Non-limiting descriptions of materials and methods which can be adapted for use in the system |
|---|---|---|
| promoter of the target gene P-SP controlled expression of a site-specific recombinase (SSR) or integrase protein in a cell containing an SSR- or integrase-controlled promoter switch where the promoter is operably linked to a first gene prior to inversion by the SSR or integrase and is operably linked to a up-regulation gene target upon inversion. | P-SP described in Table 5, SEQ ID NO: 417-428, 515, 517, or 518; Constitutive and inducible promoters used in the SSR or integrase controlled promoter switch. | U.S. Pat. No. 10,614,353, incorporated herein by reference in its entirety. Siuti et al. 2013, doi: 10.1038/nbt.2510 Bernabé-Orts et al. 2020, doi.org/10.1093/nar/gkaa104 |

In certain embodiments, target genes encoding an RNA or protein of interest can be upregulated or down regulated by an SSR- or integrase-controlled promoter switch where a control element comprising a promoter can be inverted. Examples of such promoter switches include those in Tables 1-4 or the numbered embodiments. In certain embodiments, inversion of the promoter by the SSR- or integrase- can result in the down-regulation of the RNA sequence or protein of interest by disrupting operable linkage of the promoter to DNA encoding the RNA or protein. In certain embodiments, inversion of the promoter by the SSR- or integrase- can result in the up-regulation of the RNA sequence or protein of interest by operably linking the promoter to DNA encoding the RNA or protein (e.g., an SSR- or integrase-controlled promoter switch). Control elements used in the promoter switch can comprise a constitutive promoter, an inducible promoter, or phosphate-sensitive promoter and at least a segment of a 5' UTR. In still other embodiments, an SSR- or integrase-controlled promoter switch can be designed to express a first gene before expression of the SSR or integrase and a second gene after expression of the SSR or integrase by the PS-P. In certain embodiments, the first gene can be selected from genes targeted for down-regulation in Table 1 and the second gene can be selected from a gene targeted for up-regulation in Table 3. In certain embodiments, the first gene can be a wild-type or even improved copy of a gene targeted for down-regulation in Table 1 and the second gene can be a wild-type copy of that same first gene from Table 1 which is expressed at levels lower than the wild-type or first gene, a mutated variant of that same first gene from Table 1 with reduced enzymatic or biological activity, or a mutated variant of that same first gene from Table 1 which is also expressed at levels lower than the wild-type or first gene.

In one embodiment, the SSR- or integrase-controlled promoter switch is placed between a first gene encoding a GlnA (glutamine synthetase (GS)) protein with wild-type or improved catalytic activity in comparison to wild-type GS and a second gene encoding: (i) a wild-type GS with reduced levels of expression in comparison to the wild-type glnA gene, (ii) a GS variant with decreased catalytic activity in comparison to wild-type GS, or (iii) a GS variant with decreased catalytic activity in comparison to wild-type GS and reduced levels of expression in comparison to the wild-type glnA gene, where the promoter in the SSR- or integrase-controlled promoter switch is operably linked to the first gene prior to SSR- or integrase-mediated promoter inversion resulting from PS-P promoter activation of the SSR or integrase. GEB comprising this promoter switch will express wild-type or catalytically improved GS prior to PS-P promoter-mediated activation of the SSR or integrase, promoting growth of the GEB in plant growth media. After PS-P promoter-mediated activation of the SSR or integrase, the promoter in the promoter switch is inverted and operably linked to the wild-type GS with reduced expression, variant GS with reduced catalytic activity, or variant GS with reduced catalytic activity and reduced expression, resulting in ammonia production. Reductions in expression of the second gene encoding a wild-type or GS variant can be achieved in a variety of ways including use of weak ribosome binding sites in the 5' UTR, use of non-preferred codons, substitution of the ATG start codon with a GTG start codon, mutations that result in decrease protein or mRNA and/or protein stability, and combinations thereof. Certain methods of reducing expression of a glnA gene disclosed in US20200331820 can be adapted for use in embodiments disclosed herein.

In one embodiment, the SSR- or integrase-controlled promoter switch is placed between a first gene comprising a glnE gene encoding a wild-type GS adenylyltransferase protein and a second gene comprising a glnE gene encoding a GS adenylyltransferase protein lacking an adenylyl removing domain which exhibits unidirectional adenylyltransferase (uAT) activity (e.g., a GlnE-uAT gene), where the promoter in the SSR- or integrase-controlled promoter switch is operably linked to the first gene prior to SSR- or integrase-mediated promoter inversion resulting from PS-P promoter activation of the SSR or integrase. GEB comprising this promoter switch will express wild-type GlnE protein prior to PS-P promoter-mediated activation of the SSR or integrase, promoting growth of the GEB in plant growth media. After PS-P promoter-mediated activation of the SSR or integrase, the promoter in the promoter switch is inverted and operably linked to the GlnE-uAT gene, resulting in the adenylation and inactivation of GS and ammonia production. Sources of GlnE-uAT genes are set forth in Table 3.

In one embodiment, the SSR- or integrase-controlled promoter switch is placed between a first gene comprising a nifL gene and a second gene comprising a nifA gene, where the promoter in the SSR- or integrase-controlled promoter switch is operably linked to the first nifL gene prior to SSR- or integrase-mediated promoter inversion resulting from PS-P promoter activation of the SSR or integrase. GEB comprising this promoter switch will express wild-type NifL protein prior to PS-P promoter-mediated activation of the SSR or integrase, promoting growth of the GEB in plant growth media. After PS-P promoter-mediated activation of the SSR or integrase, the promoter in the promoter switch is inverted and operably linked to the nifA gene, resulting in the down-regulation of nifL, the up-regulation of nifA, and ammonia production.

In certain embodiments, it is desirable to delay expression of genes encoding an RNA or protein of interest (e.g., genes disclosed in Table 1 or 3) by constructing a PS-P controlled cascade of repressors/repressor-controlled genes encoding repressors and/or a PS-P controlled cascade of transcriptional activators/transcriptional activator-controlled genes encoding transcriptional activators in the GEB. In certain embodiments, a gene encoding the RNA or protein of interest or which regulates expression of the gene encoding the RNA or protein of interest is at the end of the cascade. At the head of the repressor and/or transcriptional-activator cascade is a PS-P promoter that drives expression of the first repressor or transcriptional activator, respectively. In certain embodiments, a repressor cascade can further comprise a gene encoding a transcriptional activator which is controlled by a repressor in the cascade (e.g., the terminal repressor in the cascade which regulates the RNA or protein of interest is at the end of the cascade). In certain embodiments, a transcriptional activator cascade can further comprise a gene encoding a repressor which is controlled by a transcriptional activator in the cascade (e.g., the terminal repressor in the cascade). In a repressor cascade, each repressor represses the subsequent repressor in the cascade. In a transcriptional activator cascade, each transcriptional activator activates the subsequent transcriptional activator in the cascade. Descriptions of such regulatory cascades which can be adapted for use in the PS-P controlled regulatory cascades described herein include regulatory cascades disclosed in Tables 2 and 4 as well as in those disclosed in Hooshangi et al., 2004, doi: 10.1073pnas.0408507102 and Pinto et al., doi:10.1093/nar/ gky614.

Without being limited by theory, it is believed that the delay in expression of the gene encoding the RNA or protein of interest is a factor of the number of repressor modules and/or transcriptional activator modules are in the cascade, the rate at which each of the repressors and/or transcriptional activator degrade and/or accumulate in the cell. It is further believed that delaying expression of RNAs or proteins of interest is beneficial insofar as expression of those RNAs, proteins, or the agriculturally relevant compounds they produce can in certain embodiments reduce the GEB's ability to compete against other microorganisms in the plant growth media and/or on the plant (e.g., root system). It is thus believed that such delays in expression can promote growth of the GEB to sufficient cell density in the plant growth media and/or plant before the agriculturally relevant compound is produced.

Bacteria selected from the groups of bacteria of the taxonomic classes of alphaproteobacteria, betaproteobacteria, and gammaproteobacteria can be modified to obtain the GEB disclosed herein. In certain embodiments, the bacteria selected for modification to obtain the GEB are bacteria in the taxonomic genera of *Acetobacter, Acidothermus, Acinetobacter, Agrobacterium, Aromatoleum, Arthrobacter, Azoarcus, Azorhizobium, Azospirillum, Azotobacter, Bacillus, Bifidobacterium, Bradyrhizobium, Burkholderia, Conexibacter, Curtobacterium, Ensifer, Enterobacter, Erwinia, Escherichia, Flavobacterium, Frankia, Gaiella, Gluconacetobacter, Gluconobacter, Herbaspirillum, Klebsiella, Kosakonia, Lactobacillus, Lactococcus, Lysinibacillus, Maritimibacter, Methylobacterium, Nitrosocosmicus, Nitrososphaera, Paenarthrobacter, Paenibacillus, Pantoea, Pediococcus, Peribacillus, Phytobacter, Priestia, Pseudarthrobacter, Pseudomonas, Rahnella, Rhizobium, Rhodococcus, Rhodoplanes, Rhodopseudomonas, Rhodospirillum, Serratia, Solirubrobacter, Sphingobacterium, Sphingomonas, Stenotrophomonas, Streptomyces, Stutzerimonas, Variovorax, Xanthobacter,* and *Yoonia,* optionally wherein the bacteria are selected from at least one of the taxonomic genera selected from the group consisting of *Azospirillum, Enterobacter, Herbaspirillum, Kosakonia, Klebsiella, Paenibacillus, Phytobacter, Pseudomonas, Rahnella, Sphingomonas,* or *Variovorax.* In certain embodiments, the GEB and/or bacteria used to obtain the GEB are bacteria which have been modified and/or selected for increased potential to colonize the roots of target crop plants (e.g., maize, rice, wheat, and the like). Genes which have been modified for improved colonization include bcsll, bcslll, yjbE, fhaB, pehA, glgA, otsB, treZ, and cysZ genes (US Patent. Applic. Publ. No. 20210315212 and WO2019032926, both incorporated herein by reference in their entireties). In certain embodiments, the genetically engineered strains disclosed herein can be obtained by modification of *Klebsiella, Kosakonia,* or *Rahnella* strains, and include such strains deposited as NCMA 201701002, a bacterium deposited as NCMA 201708004, a bacterium deposited as NCMA 201708003, a bacterium deposited as NCMA 201708002, a bacterium deposited as NCMA 201712001, or a bacterium deposited as NCMA 201712002. These strains were deposited with the Bigelow National Center for Marine Algae and Microbiota (NCMA), located at 60 Bigelow Drive, East Boothbay, Me. 04544, USA under the terms of the Budapest Treaty as described in US Patent. Applic. Publ. No. 20210315212. In certain embodiments, the genetically engineered bacteria disclosed herein can be selected for improved plant colonization and/or improved production of nitrogenous compounds (e.g., ammonia) by various methods including those disclosed in US Patent Application No. 20240010576, incorporated herein by reference in its entirety. Examples of other bacteria that can be modified to obtain the GEB disclosed herein also include *Rahnella aquatilis* and *Enterobacter sacchari* strains were deposited with the American Type Culture Collection and assigned ATTC Patent Deposit Designation numbers PTA-122293 and PTA-122294, respectively, as described in US Patent Application No. 20240010576.

A variety of control elements comprising PS-P promoters and optionally 5' UTR segments can be used in the GEB, methods, and systems provided herein. Desirable characteristics of such control elements include activation of expression of operably linked RNAs or proteins in agriculturally useful bacteria in response to decreases in phosphate concentration in the plant growth medium. Such agriculturally useful bacteria include bacteria capable of growth in plant growth media and in particular growth in plant growth media used to grow crop plants and/or growth on and/or in crop plants. In certain embodiments, the control elements comprising Pho boxes and/or PS-P promoters will be derived in whole or in part from agriculturally useful bacteria which include: (i) alphaproteobacteria, betaproteobacteria, and gammaproteobacteria; (ii) bacteria in the genus *Acetobacter, Acidothermus, Acinetobacter, Agrobacterium, Aromatoleum, Arthrobacter, Azoarcus, Azorhizobium, Azospirillum, Azotobacter, Bacillus, Bifidobacterium, Bradyrhizobium, Burkholderia, Conexibacter, Curtobacterium, Ensifer, Enterobacter, Erwinia, Escherichia, Flavobacterium, Frankia, Gaiella, Gluconacetobacter, Gluconobacter, Herbaspirillum, Klebsiella, Kosakonia, Lactobacillus, Lactococcus, Lysinibacillus, Maritimibacter, Methylobacterium, Nitrosocosmicus, Nitrososphaera, Paenarthrobacter, Paenibacillus, Pantoea, Pediococcus, Peribacillus, Phytobacter, Priestia, Pseudarthrobacter, Pseudomonas, Rahnella, Rhizobium, Rhodococcus, Rhodoplanes, Rhodopseudomonas, Rhodospirillum, Serratia, Solirubrobacter, Sphingobacterium, Sphingomonas, Stenotrophomonas, Streptomyces, Stutzerimonas, Variovorax, Xanthobacter,* and *Yoonia;* (iii) *Azospirillum, Enterobacter, Herbaspirillum, Kosakonia, Klebsiella, Paenibacillus, Phytobacter, Pseudomonas, Rahnella, Sphingomonas,* or *Variovorax.* In certain embodiments, the control elements comprising the PS-P are used in bacteria of the genus or the species from which they were derived in whole or in part.

In certain embodiments, the control elements comprising PS-P promoters and optionally 5' UTR segments will comprise "Pho box" elements or the corresponding PS-P promoters obtained from *E. coli.* Such *E. coli* Pho Box sequences can comprise those set forth in SEQ ID NO: 234-345, 378-382, and variants thereof comprising 1, 2, or 3 nucleotide substitutions. Such *E. coli* PS-P promoters can comprise DNA molecules having at least 85%, 90%, 95%, 98%, or 99% sequence identity across the entire length of any of SEQ ID NO: 419 and 420. In certain embodiments, the control elements comprising the *E. coli* Pho Box sequences provided herein can activate expression of operably linked RNAs or proteins in agriculturally useful bacteria including various gram-negative bacteria (e.g., *Klebsiella, Escherichia,* or *Serratia*) in response to decreases in phosphate concentration.

In certain embodiments, the control elements comprising PS-P promoters and optionally 5' UTR segments will comprise "Pho box" elements or the corresponding PS-P promoters obtained from *S. coelicolor.* Such *S. coelicolor* Pho box sequences can comprise those set forth in SEQ ID NO: 346-375, and variants thereof comprising 1, 2, or 3 nucleotide substitutions. In certain embodiments, the control elements comprising the *S. coelicolor* Pho Box sequences provided herein can activate expression of operably linked RNAs or proteins in agriculturally useful bacteria including various gram-positive bacteria and actinomycetes (e.g., *Streptomyces* sp.) in response to decreases in phosphate concentration.

In certain embodiments, the control elements comprising PS-P promoters and optionally 5' UTR segments will comprise "Pho box" elements (specific regulator-binding DNA sequences that facilitate the activation or inhibition of gene expression in a phosphate-sensitive manner) or the corresponding PS-P promoters are obtained in whole or in part from various agriculturally useful bacteria (AUB). AUB include bacteria in the taxonomic genera of *Acetobacter, Acidothermus, Acinetobacter, Agrobacterium, Aromatoleum, Arthrobacter, Azoarcus, Azorhizobium, Azospirillum, Azotobacter, Bacillus, Bifidobacterium, Bradyrhizobium, Burkholderia, Conexibacter, Curtobacterium, Ensifer, Enterobacter, Erwinia, Escherichia, Flavobacterium, Frankia, Gaiella, Gluconacetobacter, Gluconobacter, Herbaspirillum, Klebsiella, Kosakonia, Lactobacillus, Lactococcus, Lysinibacillus, Maritimibacter, Methylobacterium, Nitrosocosmicus, Nitrososphaera, Paenarthrobacter, Paenibacillus, Pantoea, Pediococcus, Peribacillus, Phytobacter, Priestia, Pseudarthrobacter, Pseudomonas, Rahnella, Rhizobium, Rhodococcus, Rhodoplanes, Rhodopseudomonas, Rhodospirillum, Serratia, Solirubrobacter, Sphingobacterium, Sphingomonas, Stenotrophomonas, Streptomyces, Stutzerimonas, Variovorax, Xanthobacter,* and *Yoonia.* Such AUB Pho Box sequences can comprise those set forth in SEQ ID NO: 376, 377, 383-397, and 525-529, and variants thereof comprising 1, 2, or 3 nucleotide substitutions. Such AUB PS-P promoters can comprise DNA molecules having at least 85%, 90%, 95%, 98%, or 99% sequence identity across the entire length of any one of SEQ ID NO: 417-418, 421-428, 515, 517, and 518. Such Pho boxes and PS-P promoters can also include those which are operably linked to a phoA, phoX, phy, or pstS gene encoding a protein having at least 76%, 80%, 85%, 90%, 95%, 98%, or 99% sequence identity to a PhoA, PhoX, Phy (phytase), or PstS protein set forth in Table 5 and the sequence listing. In certain embodiments, the control elements comprising the AUB Pho box sequences and AUB PS-P promoters provided herein can activate expression of operably linked RNAs or proteins in agriculturally useful bacteria including *Gluconacetobacter* sp., *Azorhizobium* sp., *Azospirillum* sp., *Herbaspirillum* sp., *Kosakonia* sp., *Paenibacillus* sp., *Pseudomonas* sp. *Enterobacter* sp., *Klebsiella* sp., *Paenibacillus* sp., *Phytobacter* sp., *Rahnella* sp., *Sphingomonas* sp., or *Variovorax* sp. in response to decreases in phosphate concentration. In certain embodiments, the control elements comprising the AUB Pho box sequences and AUB PS-P promoters provided herein can activate expression of operably linked RNAs or proteins in: (i) a bacterium of the genus *Azospirillum, Enterobacter, Herbaspirillum, Kosakonia, Klebsiella, Paenibacillus, Phytobacter, Pseudomonas, Rahnella, Sphingomonas,* or *Variovorax;* and/or (ii) a *Gluconacetobacter diazotrophicus, Azorhizobium caulinodans, Azospirillum brasilense, Herbaspirillum seropedicae, Kosakonia radicincitans, Paenibacillus azotofixans,* and *Pseudomonas stutzeri* isolate, strain, or derivative thereof. In certain embodiments, a control element comprising an AUB Pho box sequence or AUB PS-P promoters derived in whole or in part from *Gluconacetobacter* sp., *Azorhizobium* sp., *Azospirillum* sp., *Herbaspirillum* sp., *Kosakonia* sp., *Klebsiella* sp., *Paenibacillus* sp., or *Pseudomonas* sp. (e.g., the corresponding AUB Pho box sequences and AUB PS-P promoters set forth in Table 5) are respectively used in a GEB obtained from: (i) a *Gluconacetobacter* sp., *Azorhizobium* sp., *Azospirillum* sp., *Herbaspirillum* sp., *Kosakonia* sp., *Paenibacillus* sp., or *Pseudomonas* sp.; and/or (ii) a bacterium of the genus *Azospirillum, Enterobacter, Herbaspirillum, Kosakonia, Klebsiella, Paenibacillus, Phytobacter, Pseudomonas, Rahnella, Sphingomonas,* or *Variovorax.* In certain embodiments, a control element comprising an AUB Pho box sequences or AUB PS-P promoter derived in whole or in part from *Gluconacetobacter diazotrophicus, Azorhizobium cau-*

*linodans, Azospirillum brasilense, Herbaspirillum serope-dicae, Kosakonia radicincitans, Klebsiella* sp., *Paenibacillus azotofixans*, or *Pseudomonas stutzeri* (e.g., the corresponding AUB Pho box sequences and AUB PS-P promoters set forth in Table 5) are respectively used in a GEB obtained from: (i) a *Gluconacetobacter diazotrophicus, Azorhizobium caulinodans, Azospirillum brasilense, Herbaspirillum seropedicae, Kosakonia radicincitans, Paenibacillus azotofixans*, or *Pseudomonas stutzeri* isolate, strain, or derivative thereof; and/or (ii) a bacterium of the genus *Azospirillum, Enterobacter, Herbaspirillum, Kosakonia, Klebsiella, Paenibacillus, Phytobacter, Pseudomonas, Rahnella, Sphingomonas*, or *Variovorax*. In certain embodiments, the AUB Pho Box sequence can comprise a DNA molecule set forth in SEQ ID NO: 383-391, 397, 525-529, and variants thereof comprising 1, 2, or 3 nucleotide substitutions. In certain embodiments, the AUB Pho Box sequence or PS-P promoter can comprise a DNA molecule having at least 85%, 90%, 95%, 98%, or 99% sequence identity across the entire length of any one of SEQ ID NO: 417-418, 421-425, 428, 515, 517, or 518.

In certain embodiments, the heterologous gene expression cassette comprising the control elements comprising the Pho box sequences and PS-P promoters (e.g., the corresponding AUB Pho box sequences and AUB PS-P promoters set forth in Table 5) is integrated at a location in the chromosome of the genetically engineered bacterium which does not comprise the location of an endogenous phosphate-sensitive promoter in the unmodified agriculturally relevant bacterium. In certain embodiments, a control element comprising a phoA Pho box or phoA PS-P promoter (e.g., a phoA box or phoA PS-P promoter in Table 5) is integrated in the genome of the GEB at a location other than the location of the endogenous (e.g., wild-type) phoA box or phoA PS-P promoter in the GEB. In certain embodiments, a control element comprising a phoX Pho box or phoX PS-P promoter (e.g., a PhoX box or phoX PS-P promoter in Table 5) is integrated in the genome of the GEB at a location other than the location of the endogenous (e.g., wild-type) phoX box or phoX PS-P promoter in the GEB. In certain embodiments, a control element comprising a phy Pho box or phy PS-P promoter (e.g., a phy Pho box or phy PS-P promoter in Table 5) is integrated in the genome of the GEB at a location other than the location of the endogenous (e.g., wild-type) phy Pho box or phy PS-P promoter in the GEB. In certain embodiments, a control element comprising a pstS Pho box or pstS PS-P promoter (e.g., a pstS Pho box or pstS PS-P promoter in Table 5) is integrated in the genome of the GEB at a location other than the location of the endogenous (e.g., wild-type) pstS Pho box or pstS PS-P promoter in the GEB. Methods for inserting control elements comprising Pho boxes or PS-P promoters at sites distinct from the endogenous gene include Tn7 transposon mediated insertion (McKenzie and Craig, N. L., 2006, doi:10.1186/1471-2180-6-39).

Methods of producing preparations of the genetically engineered bacterium (GEB) for use in treating plant growth media, plants, plant parts, plant propagules, and/or for formulating a composition comprising the GEB are provided herein. In certain embodiments, the methods can comprising growing the GEB in a bacterial growth medium comprising a carbon and nitrogen source and harvesting the GEB from the media. Conditions for growing the GEB include axenic growth in continuous stirred tank reactors, batch fermentation reactors, and the like. In certain embodiments, phosphate concentrations in the bacterial growth medium are kept at a level sufficient to suppress the expression of the phosphate-sensitive promoter(s) which drive expression of the protein or RNA of interest. Phosphate concentrations sufficient to suppress the expression of the phosphate-sensitive promoter(s) include phosphate concentrations of at least about 20 μM, 50 μM, or 100 μM. In certain embodiments, the GEB are grown in a bacterial growth media comprising phosphate concentrations of at least 1 mM, 5 mM, 10 mM, or 20 mM. In certain embodiments, the GEB are grown in a bacterial growth media comprising phosphate concentrations of about 1 mM, 5 mM or 10 mM to about 30 mM, 50 mM, or 100 mM.

Compositions comprising one or more of the genetically engineered bacterium (GEB) are also provided herein. Such compositions can be adapted for storage of the GEB and/or for use of the GEB in the methods and agricultural systems disclosed herein. In certain embodiments, the compositions comprising the GEB can be used to treat a plant part including a leaf, stem, root, and/or seed by least partially coating the plant part with the composition. In certain embodiments, the compositions comprising the GEB can placed in plant growth medium (e.g., soil and/or water) prior to, during, and/or after depositing or establishing a seed, a seedling, plant, or vegetative propagule in the plant growth medium. In certain embodiments, a composition comprising the GEB is in a solid form. Such solid compositions can include those comprising a wettable powder, granules, a gel, pellets, or microencapsulated particles. In certain embodiments, a composition comprising the GEB is in a liquid form. Such liquid compositions can include those comprising an aqueous solution, aqueous suspension, water-in-oil emulsion, an oil, or an alcohol. Descriptions of compositions and components thereof which can be adapted for use with the GEB, related methods, agricultural systems, seedlings, plant parts, and vegetative propagules provided herein include those described below and/or in US Patent Application Publication Nos. US20210315212A1 and 20230148607, which are incorporated herein by reference in their entirety.

Compositions comprising the GEB provided herein can comprise an agriculturally acceptable carrier. Such carriers include liquid carriers comprising water, aqueous solutions, plant oils, and combinations thereof. Such carriers can in other embodiments comprise one of more solids including diatomaceous earth, loam, silica, clay, bentonite, vermiculite, seed cases, plant products (e.g., ground hulls, husk, stalks, stems, leaves, and the like), animal products, or combinations thereof.

Compositions comprising the GEB provided herein can comprise an agriculturally acceptable adjuvant.

In certain embodiments, the agriculturally acceptable adjuvant is an adhesive agent (e.g., an agent which promotes adherence of the composition and/or GEB to a plant part). In certain embodiments, the adhesive agents comprise one or more alginates, gums, starches, lecithins, formononetin, polyvinyl alcohol, alkali formononetinate, hesperetin, polyvinyl acetate, cephalins, Gum Arabic, Xanthan Gum, Mineral Oil, Polyethylene Glycol (PEG), Polyvinyl pyrrolidone (PVP), Arabino-galactan, Methyl Cellulose, PEG 400, Chitosan, Polyacrylamide, Polyacrylate, Polyacrylonitrile, Glycerol, Triethylene glycol, Vinyl Acetate, Gellan Gum, Polystyrene, Polyvinyl, Carboxymethyl cellulose, Gum Ghatti, and/or polyoxyethylene-polyoxybutylene block copolymers. In certain embodiments, the adhesive agents can comprise one or more waxes (e.g., carnauba wax, beeswax, or Chinese wax, shellac wax, spermaceti wax, candelilla wax, castor wax, ouricury wax, or rice bran wax), a polysaccharide (e.g., starch, dextrins, maltodextrins, alginate, and chitosans), a fat, oil, a protein (e.g., gelatin and zeins), gum ambles, and/or a shellac. In certain embodiments, adhesive agents can comprise one or more polymers or copolymers including polyvinyl acetates, polyvinyl acetate copolymers, ethylene vinyl acetate (EVA) copolymers, polyvinyl alcohols, polyvinyl alcohol copolymers, celluloses (e.g., ethylcelluloses, methylcelluloses, hydroxymethylcelluloses, hydroxypropylcelluloses, and carboxymethylcelluloses), polyvinylpyrrolidones, vinyl chloride, vinylidene chloride copolymers, calcium lignosulfonates, acrylic copolymers, polyvinylacrylates, polyethylene oxide, acylamide polymers and copolymers, polyhydroxyethyl acrylate, methylacrylamide monomers, and/or polychloroprene.

In certain embodiments, the agriculturally acceptable adjuvant is a desiccant or mixture thereof. In certain embodiments, the desiccant comprises one or more of trehalose, sucrose, glycerol, and/or methylene glycol. In certain embodiments, the desiccant comprises one or more non-reducing sugars and sugar alcohols (e.g., mannitol or sorbitol). In certain embodiments, desiccants are provided at about 5% to about 50% by weight/volume (w/v), about 10% to about 40% (w/v), about 15% to about 35% (w/v), or about 20% to about 30% (w/v) in the composition.

In certain embodiments, the agriculturally acceptable adjuvant is a dispersant (e.g., a surfactant). In certain embodiments, the dispersant comprises one or more of a nitrogen-surfactant blend (e.g., Prefer 28 (Cenex), Surf-N (US), Inhance (Brandt), P-28 (Wilfarm) and Patrol (Helena)), an esterified seed oil (e.g., Sun-It II (AmCy), MSO (UAP), Scoil (Agsco), Hasten (Wilfarm) and Mes-100 (Drexel)), and/or an organo-silicone surfactant (e.g., Silwet L77 (UAP), Silikin (Terra), Dyne-Amic (Helena), Kinetic (Helena), Sylgard 309 (Wilbur-Ellis) and Century (Precision)). In one embodiment, the surfactant or mixture of surfactants are at a concentration of about 0.01% volume/volume (v/v) to about 10% v/v in the composition. In another embodiment, the surfactant or mixture of surfactants are at a concentration of 0.1% (v/v) to 1% (v/v) in the composition.

In certain embodiments, the agriculturally acceptable adjuvant is a fungicide, insecticide, a nematicide, a rodenticide, and/or a bacteriocide. When the adjuvant is a bacteriocide, it is a bacteriocide selected for compatibility with the GEB and/or provided at a concentration or in a form which does not compromise the viability of the GEB.

Numbered Embodiments

Additionally, the following numbered embodiments are included in the disclosure.

1. A method of providing at least one agriculturally relevant compound to a plant comprising placing at least one genetically engineered bacterium into a plant growth medium, wherein the genetically engineered bacterium comprises a heterologous gene expression cassette comprising at least one nucleic acid sequence coding for at least one RNA sequence or protein of interest, wherein the heterologous gene expression cassette is operably linked to a control element comprising a phosphate-sensitive promoter, wherein said at least one RNA sequence or protein of interest is or causes the production of said at least one agriculturally relevant compound when a decrease in phosphate concentration in the plant growth medium activates expression of said at least one RNA sequence or protein of interest.

2. The method of embodiment 1, wherein the plant growth medium comprises soil and/or water, optionally wherein the soil and/or water is non-axenic.

3. The method of embodiment 1 or 2, wherein the placing is prior to, during, and/or after depositing a seed in the plant growth medium.

4. The method of embodiment 1 or 2, wherein the placing is prior to, during, and/or after depositing a vegetative propagule in the plant growth medium.

5. The method of embodiment 1, 2, or 3, wherein the placing comprises depositing a seed which is at least partially coated with the genetically engineered bacterium in the plant growth medium or depositing both the seed and a composition comprising the genetically engineered bacterium in the plant growth medium.

6. The method of embodiment 1, 2, or 3, wherein the placing comprises depositing the seed in furrow and contacting the seed in the furrow with a composition comprising the genetically engineered bacterium.

7. The method of any one of embodiments 1-6, wherein the placing of the genetically engineered bacterium in the plant growth medium is prior to, during, and/or after establishment of a plant in the plant growth medium.

8. The method of any one of embodiments 1-7, wherein the control element and/or the heterologous gene expression cassette further comprises at least a segment of a 5' untranslated region (5' UTR) which is operably linked to the phosphate-sensitive promoter and/or the heterologous gene expression cassette, optionally wherein the 5' UTR comprises a 5' UTR sequence which has at least 85%, 90%, 95%, 98%, or 99% sequence identity to an endogenous 5' UTR sequence which is operably linked to an endogenous phosphate-sensitive promoter.

9. The method of embodiment 8, wherein the phosphate-sensitive promoter and/or the segment of the 5' UTR which is operably linked to the phosphate-sensitive promoter comprises at least one copy of an operably linked Pho box, wherein the Pho box comprises the sequence of SEQ ID NO: 234-397, 525-528, or 529, and sequences with at least 95%, 98%, or 99% identity to any one of SEQ ID NO: 234-397, 525-528, or 529, optionally wherein the Pho box comprises SEQ ID NO: 376, 377, 383-397, 525-528, or 529.

10. The method of embodiment 8 or 9, wherein the phosphate-sensitive promoter and/or the segment of the 5' UTR is a promoter and/or 5' UTR derived from at least one gram-negative bacterium.

11. The method of embodiment 8, 9, or 10, wherein the phosphate-sensitive promoter and/or the segment of the 5' UTR is a promoter and/or 5' UTR derived from at least one bacterium of the taxonomic classes of alphaproteobacteria, betaproteobacteria, and gammaproteobacteria.

12. The method of any one of embodiments 8-11, wherein the phosphate-sensitive promoter and/or the segment of the 5' UTR is a promoter and/or segment of a 5' UTR derived from at least one bacterium of a genus selected from the group consisting of *Acetobacter, Acidothermus, Acinetobacter, Agrobacterium, Aromatoleum, Arthrobacter, Azoarcus, Azorhizobium, Azospirillum, Azotobacter, Bacillus, Bifidobacterium, Bradyrhizobium, Burkholderia, Conexibacter, Curtobacterium, Ensifer, Enterobacter, Erwinia, Escherichia, Flavobacterium, Frankia, Gaiella, Gluconacetobacter, Gluconobacter, Herbaspirillum, Klebsiella, Kosakonia, Lacto-*

*bacillus, Lactococcus, Lysinibacillus, Maritimibacter, Methylobacterium, Nitrosocosmicus, Nitrososphaera, Paenarthrobacter, Paenibacillus, Pantoea, Pediococcus, Peribacillus, Phytobacter, Priestia, Pseudarthrobacter, Pseudomonas, Rahnella, Rhizobium, Rhodococcus, Rhodoplanes, Rhodopseudomonas, Rhodospirillum, Serratia, Solirubrobacter, Sphingobacterium, Sphingomonas, Stenotrophomonas, Streptomyces, Stutzerimonas, Variovorax, Xanthobacter,* and *Yoonia,* optionally wherein the phosphate-sensitive promoter and/or the segment of the 5′UTR is derived from at least one bacterium of a genus selected from the group consisting of *Azospirillum, Enterobacter, Herbaspirillum, Paenibacillus, Phytobacter, Pseudomonas, Klebsiella, Rahnella, Kosakonia, Sphingomonas,* and *Variovorax.*

13. The method of any one of embodiments 8-12, wherein the phosphate-sensitive promoter and/or the segment of the 5′ UTR comprises a promoter and/or a segment of a 5′UTR of a phoA, phoX, phy, pstS gene, a variant thereof, or a combination thereof.

14. The method of any one of embodiments 8-13, wherein the phosphate-sensitive promoter and/or the segment of the 5′ UTR comprises a promoter and/or a segment of a 5′UTR of a promoter comprising the DNA sequence of SEQ ID NO: 417-428, 515, 516, or 518, a phosphate-sensitive promoter element of a promoter comprising the DNA sequence of SEQ ID NO: 417-428, 515, 516, 517, 518, a variant thereof, or a combination thereof, optionally wherein the variant has at least 76%, 80%, 85%, 90%, 95%, 98%, or 99% sequence identity to SEQ ID NO: 417-428, 515, 516, or 518.

15. The method of any one of embodiments 8-14, wherein the phosphate-sensitive promoter and/or the segment of the 5′ UTR comprises a promoter of a gene encoding:

i. a PhoA protein comprising a protein sequence selected from the group consisting of SEQ ID NO: 398, 400, 402, 404, and 406 or having an identity of at least 80%, 85%, 90%, 95%, 98%, or 99% with any one of SEQ ID NO: 398, 400, 402, 404, or 406;

ii. a PhoX protein comprising a protein sequence selected from the group consisting of SEQ ID NO: 408, 410, 411, 412, and 413 or having an identity of at least 80%, 85%, 90%, 95%, 98%, or 99% with any one of SEQ ID NO: 408, 410, 411, 412, and 413;

iii. a Phy protein comprising a protein sequence selected from the group consisting of SEQ ID NO: 414, 57-138, and 139 or having an identity of at least 80%, 85%, 90%, 95%, 98%, or 99% with any one of SEQ ID NO: 414, 57-138, or 139; and/or iv. a PstS protein comprising a protein sequence selected from the group consisting of SEQ ID NO: 399, 401, 403, 405, 407, 409, 415, 416, 513, 523, and 524 or having an identity of at least 76%, 80%, 85%, 90%, 95%, 98%, or 99% with any one of SEQ ID NO: 399, 401, 403, 405, 407, 409, 415, 416, 513, 523, or 524.

16. The method of any one of embodiments 8-15, wherein the promoter region and/or the segment of the 5′ UTR comprises at least 50 nucleotides of DNA located upstream of a start codon of a gene encoding a PhoA, PhoX, Phy, or PstS protein, optionally wherein the promoter region and/or the segment of the 5′ UTR comprises about 50 to about 250 nucleotides of DNA located upstream of said start codon of said gene encoding said PhoA, PhoX, Phy, or PstS protein.

17. The method of embodiment 8, wherein the phosphate-sensitive promoter and/or the segment of the 5′ UTR comprises:

i. a phoA promoter comprising the DNA sequence of SEQ ID NO: 419;

ii. a phoX promoter comprising the DNA sequence of SEQ ID NO: 426;

iii. a phy promoter comprising the DNA sequence of SEQ ID NO: 427;

iv. a pstS promoter comprising a DNA sequence selected from the group consisting of SEQ ID NO: 417, 418, 420, 421, 422, 423, 424, 425, 428, 515, 517, and 518; and/or v. a Pliar53 promoter comprising the DNA sequence of SEQ ID NO: 459;

vi. a variant of the promoters under i. to v. having an identity of at least 76%, 80%, 90%, 95%, 98%, or 99% with any of SEQ ID NO: 417, 418-428, 459, 515, 517, or 518, wherein said variant comprises at least one Pho box and/or retains at least one Pho box present in each promoter and wherein said variant promoters are activated by a decrease in phosphate concentration to about 0 µM to about 1 µM, 2 µM, 5 µM, 7 µM, 10 µM, 20 µM, 30 µM, 40 µM, or 50 µM.

18. The method of any one of embodiments 8-17, wherein the phosphate-sensitive promoter and/or the segment of the 5′ UTR or its variant is derived from the same genus or species as the genetically engineered bacterium.

19. The method of any one of embodiments 1-18, wherein the heterologous gene expression cassette is integrated at a location in the chromosome of the genetically engineered bacterium which does not comprise the location of an endogenous phosphate-sensitive promoter.

20. The method of any one of embodiments 1-19, wherein the heterologous gene expression cassette comprises one or more elements comprising:

a. a ribosome binding site (RBS), wherein the RBS is operably linked to the nucleic acid sequence coding for the protein of interest and optionally wherein the RBS is an RBS having at least 95% sequence identity to SEQ ID NO: 429-454, or 455; and/or b. a terminator sequence (TS), wherein the TS is operably linked to the nucleic acid sequence coding for the RNA sequence or protein of interest and optionally wherein the TS is a TS having at least 95% sequence identity to SEQ ID NO: 456, 457, or 458.

21. The method of any one of embodiments 1 to 20, wherein the at least one agriculturally relevant compound is selected from the group consisting of:

a. at least one fertilizer or plant nutrient, optionally wherein the fertilizer or plant nutrient is selected from the group consisting of ammonia, ammonium, bioavailable carbon, calcium, iron, nitrate, nitrite, nitrogen, potassium, phosphate, sulfur, urea, zinc, a combination thereof, and a mixture thereof;

b. at least one pesticide, optionally wherein the pesticide is an RNA- and/or protein-based fungicide, insecticide, nematicide, antibacterial agent, and/or antiviral agent;

c. at least one phytohormone or plant growth regulator, optionally wherein the phytohormone or plant growth regulator is an auxin, a cytokinin, a gibberellin, abscisic acid, a brassinosteroid, jasmonic acid, a polyamine, a strigolactone, trehalose, and/or a volatile organic compound, or optionally wherein the phytohormone or plant growth regulator is cytokinin, indole butyric acid, and/or combinations thereof; and d. at least one carbon-containing compound, optionally wherein the carbon-containing compound is bicarbonate, carbonate, CaCO$_3$, MgCO$_3$, CaMg(CO$_3$)$_2$, polyhydroxybutyrate, melanin, chitin, and/or combinations thereof.

22. The method of any one of embodiments 1-21, wherein the RNA sequence or protein of interest encoded by the heterologous gene expression cassette and operably linked to the control element comprises:

(a) a GlnE protein lacking an adenylyl removing domain which exhibits unidirectional adenylyltransferase (uAT) activity and the fertilizer is ammonia, optionally wherein the GlnE protein lacking an adenylyl removing domain comprises a protein sequence having at least 70%, 80%, 85%, 90%, 95%, 98%, or 99% identity to SEQ ID NO: 16-24, or 25 or optionally wherein the gene encoding the GlnE protein lacking an adenylyl removing domain comprises a DNA sequence having at least 70%, 80%, 85%, 90%, 95%, 98%, or 99% identity to SEQ ID NO: 1-14, or 15;

(b) a NifA protein, wherein the genetically engineered bacterium optionally comprises a loss-of-function mutation in any one or more of the amtB, draT, glnA, glnB, glnK, glnR, glnZ, or nifL genes, wherein the genetically engineered bacterium optionally comprises one or more heterologous genes from a wild-type or refactored nif or fix gene cluster and the fertilizer is ammonia;

(c) a GlnR protein and the fertilizer is ammonia;

(d) a glutaminase enzyme and the fertilizer is ammonia;

(e) a protein product of a refactored nif or fix gene cluster and the fertilizer is ammonia;

(f) a repressor protein, wherein the repressor protein binds a natural or synthetic DNA motif in the promoter of any one or more first target gene(s) of the genetically engineered bacterium and inhibits expression of any one or more of the protein products of the first target genes and/or wherein the repressor protein optionally comprises the lambda repressor (cI), the tet repressor (TetR), the lac repressor (LacI), a catalytically inactive RNA-guided DNA binding protein, a protein comprising a DNA-binding zinc finger domain, a transcription activator-like effector (TALE), or any variant thereof and/or optionally wherein the first target gene(s) is/are a glnA, amtB, glnB, glnK, glnZ, nifL, and/or draT gene and the fertilizer is ammonia;

(g) a non-coding synthetic small RNA (sRNA); optionally wherein the non-coding synthetic small RNA (sRNA) binds a natural or synthetic DNA and/or RNA motif in the promoter, 5' UTR, and/or coding region of any one or more first target gene(s) of the genetically engineered bacterium, optionally wherein the non-coding synthetic small RNA (sRNA) comprises a guide RNA that additionally binds an RNA-guided DNA or RNA endonuclease or variant thereof and/or optionally wherein the first target gene(s) is/are a glnA, amtB, glnB, glnK, glnZ, nifL, and/or draT gene and the fertilizer is ammonia;

(h) a site-specific recombinase (SSR) or integrase protein: wherein any one or more first target gene(s) of the genetically engineered bacterium and/or a promoter operatively linked thereto are flanked by site-specific recombinase recognition sites (SSRRS) in a direct configuration, optionally wherein the SSRRS comprise attL and attR sites and the genetically engineered bacterium comprises a gene encoding a recombinase directionality factor (RDF) and/or optionally wherein the first target gene(s) is/are a glnA, amtB, glnB, segment of glnE encoding an adenylyl-removing domain of a glutamine synthetase adenylyltransferase, glnK, glnZ, nifL, and/or draT gene and the fertilizer is ammonia;

(i) a site-specific recombinase (SSR) or integrase protein: wherein any one or more first target gene(s), the promoter(s) thereof, and/or the 5' UTR(s) thereof of the genetically engineered bacterium comprise(s) one or more internal synthetic SSRRS and wherein the gene(s), promoter(s), the 5' UTR(s), and/or a segment(s) thereof is/are excised or inactivated after a recombination event; optionally wherein the genetically engineered bacterium further comprises a plasmid comprising an SSRRS; optionally wherein the genetically engineered bacterium further comprises one or more genes encoding a recombinase directionality factor (RDF); and/or optionally wherein the first target gene(s) is/are a glnA, amtB, glnB, glnE, glnK, glnZ, nifL, and/or draT gene and the fertilizer is ammonia;

(j) a site-specific recombinase (SSR) or integrase protein, wherein any one or more first target gene(s), the promoter(s) thereof, and/or the 5' UTR(s) thereof of the genetically engineered bacterium comprise(s) one or more internal integrative SSRRS and retain(s) activity of said first target gene(s), promoter(s), and/or 5' UTR(s) and wherein the genetically engineered bacterium further comprises an integrative element comprising an SSRRS; optionally wherein the internal integrative SSRRS is/are an attB site(s) and the integrative element comprises an SSRRS comprising an attP site; and/or optionally wherein the target gene(s) is/are glnA, amtB, glnB, glnK, glnZ, nifL, and/or draT and the fertilizer is ammonia;

(k) a site-specific recombinase (SSR) or integrase protein, wherein a control element comprising a promoter and/ or at least a segment of a 5' UTR: (i) is flanked by site-specific recombinase recognition sites (SSRRS) in an inverted configuration; and (ii) is operably linked to one or more first target gene(s) of the genetically engineered bacterium; optionally wherein the control element which is operably linked to said first target gene(s) comprises a constitutive promoter, an inducible promoter, or phosphate sensitive promoter; and/or optionally wherein the first target gene(s) is/are glnA, amtB, glnB, glnK, glnZ, nifL, and/or draT and the fertilizer is ammonia;

(l) a site-specific recombinase (SSR) or integrase protein, wherein a control element comprising a promoter and at least a segment of a 5' UTR: (i) is flanked by site-specific recombinase recognition sites (SSRRS) in an inverted configuration; and (ii) is operably linked to one or more first target gene(s) of the genetically engineered bacterium upon inversion by the SSR or integrase; optionally wherein the control element which is operably linked to said first target gene(s) upon inversion by the SSR or integrase comprises a constitutive promoter, an inducible promoter, or phosphate-sensitive promoter; and/or optionally wherein the first target gene(s) is/are: (a) nifA, ntrC, glnR, a gene encoding a glutaminase enzyme, a gene encoding a GlnE protein lacking an adenylyl removing domain which exhibits unidirectional adenylyltransferase (uAT) activity, one or more nif cluster gene(s), and/or one or more fix cluster gene(s) and the agriculturally relevant compound is ammonia; or (b) a gene encoding a phytase enzyme, optionally wherein the phytase enzyme comprises a cysteine phytase, a histidine acid phytase, or a beta-propeller phytase, a gene encoding an acid phosphatase enzyme, optionally wherein the acid phosphatase is encoded by an acpA, aphA, phoC, napA, napD, or napE gene or variant thereof, or a gene encoding a protein which stimulates organic acid release from the bacterium, optionally wherein the protein which stimulates organic acid release comprises a gluconate dehydrogenase (GAD), a glucose dehydrogenase (GDH), or a pyrroloquinoline (PQQ) synthase, and the agriculturally relevant compound is phosphate;

(m) a site-specific DNA endonuclease, wherein any one or more first target gene(s) of the genetically engineered bacterium comprise(s) one or more specific DNA sequence(s) recognized by the site-specific DNA endonuclease, optionally wherein the site-specific DNA endonuclease comprises an RNA-guided DNA endonuclease, a protein comprising a DNA-binding zinc finger domain, a transcription activator-like effector (TALE), a meganuclease, a homing endonuclease, or a restriction endonuclease, and/or optionally wherein the first target gene(s) is/are glnA, amtB, glnB, glnK, glnZ, nifL, and/or draT and the fertilizer is ammonia;

(n) a protease which cleaves a protease specific recognition sequence (PSRS), wherein any one or more first target gene(s) of the genetically engineered bacterium comprise(s) one or more in-frame insertion(s) comprising DNA encoding the PSRS in the protein coding region of the first target gene(s), wherein the target protein product comprising the one or more in-frame insertion(s) has activity, and wherein cleavage of the target protein product(s) by the protease deactivates the target protein product(s), optionally wherein the location of the one or more in-frame insertion is given by Table 6, optionally wherein the first target gene(s) is/are under the control of a constitutive promoter, and/or optionally wherein the first target gene(s) is/are glnA, amtB, glnB, glnK, glnZ, nifL, and/or draT and the fertilizer is ammonia;

(o) a first protein of interest comprising a ClpAP ATP-dependent protease and a second protein of interest comprising a ClpS Leu/N-recognin, wherein any one or more first target gene(s) of the genetically engineered bacterium encodes a protein comprising an N-terminal -Leu, -Phe, -Trp, or -Tyr residue, and optionally wherein the first and second protein of interest are operably linked to distinct control elements, and/or optionally wherein the first target gene(s) is/are glnA, amtB, glnB, glnK, glnZ, nifL, and/or draT and the fertilizer is ammonia;

(p) a protease which cleaves a protease specific recognition sequence (PSRS), wherein any one or more first target gene(s) of the genetically engineered bacterium comprise(s) an in-frame insertion(s) of DNA encoding the PSRS at the N-terminus of the protein coding region of the gene followed by a -Leu, -Phe, -Trp, or -Tyr residue and wherein cleavage of PSRS from the N-terminus of the protein(s) encoded by the gene(s) by the protease results in a protein comprising an N-terminal -Leu, -Phe, -Trp, or -Tyr residue which is degraded by native ClpS and ClpAP, optionally wherein the first target gene(s) is/are glnA, amtB, glnB, glnK, glnZ, nifL, and/or draT and the fertilizer is ammonia;

(q) a transcriptional activator protein, wherein the transcriptional activator protein binds a natural or synthetic DNA motif in a promoter of a heterologous protease gene of the genetically engineered bacterium and activates expression of the protease, wherein any one or more first target gene(s) of the genetically engineered bacterium comprise(s) one or more in-frame insertion(s) of DNA encoding a PSRS, optionally wherein the transcriptional activator protein comprises a tet responsive element-binding tTA transcription factor or a transcriptional activator domain fused to a DNA targeting protein, optionally wherein the DNA targeting protein is a catalytically inactive RNA-guided DNA binding protein, a protein comprising a DNA-binding zinc finger domain, a transcription activator-like effector (TALE), or any variant thereof, optionally wherein the transcriptional activator domain is VP16, and/or optionally wherein the first target gene(s) is/are: glnA, amtB, glnB, glnK, glnZ, nifL, and/or draT and the fertilizer is ammonia;

(r) a repressor protein, wherein the repressor protein binds a natural or synthetic DNA motif in a promoter of a heterologous protease gene of the genetically engineered bacterium and inhibits expression of the protease, wherein any one or more first target gene(s) of the genetically engineered bacterium comprise(s) an in-frame insertion of DNA encoding an N-terminal amino acid tag designed to render the protein product(s) of the first target gene(s) inactive, followed by a PSRS, optionally wherein the repressor protein comprises the lambda repressor (cI), the tet repressor (TetR), the lac repressor (LacI), a catalytically inactive RNA-guided DNA binding protein, a protein comprising a DNA-binding zinc finger domain, a transcription activator-like effector (TALE), or any variant thereof, and/or optionally wherein the first target gene(s) is/are glnA, amtB, glnB, glnK, glnZ, nifL, and/or draT and the fertilizer is ammonia;

(s) a nanobody, wherein the nanobody binds a protein product of any one or more first target gene(s) of the genetically engineered bacterium, wherein binding of the nanobody to such protein product inhibits function of the protein product, optionally wherein the first target gene(s) is/are glnA, amtB, glnB, glnK, glnZ, nifL, and/or draT and the fertilizer is ammonia;

(t) an aptamer, wherein the aptamer binds a protein product of any one or more first target gene(s) of the genetically engineered bacterium and inhibits function of any one or more of the protein product(s) of the first target gene(s), optionally wherein the first target gene(s) is/are glnA, amtB, glnB, glnK, glnZ, nifL, and/or draT and the fertilizer is ammonia; or (u) a transcriptional activator protein, wherein the transcriptional activator protein binds a natural or synthetic DNA motif in a promoter of any one or more first target gene(s) and increases expression of any one or more of the first target gene(s), optionally wherein the transcriptional activator protein comprises the tet responsive element-binding tTA transcription factor or a transcriptional activator domain fused to a DNA targeting protein, wherein the DNA targeting protein is optionally a catalytically inactive RNA-guided DNA binding protein, a protein comprising a DNA-binding zinc finger domain, a transcription activator-like effector (TALE), or any variant thereof, wherein the transcriptional activator domain is optionally VP16 and/or optionally wherein the first target gene(s) is/are any one or more of: (a) nifA, ntrC, glnR, a gene encoding a glutaminase enzyme, a gene encoding a GlnE protein lacking an adenylyl removing domain which exhibits unidirectional adenylyltransferase (uAT) activity, one or more nif cluster gene(s), and/or one or more fix cluster gene(s) and the agriculturally relevant compound is ammonia; or (b) a gene encoding a phytase enzyme, optionally wherein the phytase enzyme comprises a cysteine phytase, a histidine acid phytase, or a beta-propeller phytase, a gene encoding an acid phosphatase enzyme, optionally wherein the acid phosphatase is encoded by an acpA, aphA, phoC, napA, napD, or napE gene or variant thereof, and/or a gene encoding a protein which stimulates organic acid release from the bacterium, optionally wherein the protein which stimulates organic acid release comprises a gluconate dehydrogenase (GAD), a glucose dehydrogenase (GDH), or a pyrroloquinoline (PQQ) synthase and the agriculturally relevant compound is phosphate.

23. The method of embodiment 22, wherein the integrase is a serine integrase, optionally wherein the serine integrase is a phage PhiC31 serine integrase, IntS, IntM, IntG-ICEMcSym 1271, YdcL-ICEBs, or Int-ICE SXT/R39 integrase, and the SSRRS are attB and attP sites recognized respectively by the PhiC31, IntS, IntM, IntG, YdcL, or Sxt/R39 integrase.

24. The method of embodiment 22, wherein: (i) one or more SSR is a yeast flippase (FLP) recombinase and the SSRRS are FRT sites; or (ii) one or more SSR is a Cre-recombinase and the SSRRS are loxP sites.

25. The method of embodiment 22, wherein the PSRS is inserted in a glutamine synthetase (GS) polypeptide between any one or more of the pairs of amino acid residues corresponding to:

(i) amino acid residues 98 and 99, 121 and 122, 279 and 280, and/or 285 and 286 of the glutamine synthetase (GS) polypeptide of SEQ ID NO: 229;

(ii) amino acid residues 98 and 99, 119 and 120, 283 and 284, and/or 298 and 299 of the glutamine synthetase (GS) polypeptide of SEQ ID NO: 230;

(iii) amino acid residues 448 and 449, 480 and 481, 505 and 506, 528 and 529, and/or 624 and 625 of the GlnE polypeptide of SEQ ID NO: 231;

(iv) amino acid residues 527 and 528, 537 and 538, and/or 547 and 548 of the GlnE polypeptide of SEQ ID NO: 232; or (v) amino acid residues 422 and 423 and/or 608 and 609 of the GlnE polypeptide of SEQ ID NO: 233.

26. The method of embodiment 22 or 25, wherein the protease or heterologous protease:

a. comprises a tobacco etch virus (TEV) protease and the PSRS comprises the peptide EXXYXQ-(S/G) or ENLYFQ-(S/G/A/M/C/H), wherein X is any amino acid and the TEV protease cleaves between the Q and the S, G, A, M, C, or H residues;

b. comprises a tobacco vein mottling virus (TVMV) protease and the PSRS comprises the peptide ETVRFQ-(G/S), wherein the TVMV protease cleaves between the Q and S or G residues;

c. comprises a sunflower mild mosaic virus (SMMV) protease and the PSRS comprises the peptide EEIHLQ-(S/G), wherein the SMMV protease cleaves between the Q and S or G residues;

d. comprises a turnip mosaic virus (TrMV) protease and the PSRS comprises the peptide VXHQ or VRHQ-S, wherein X is any amino acid and the TrMV protease cleaves C-terminal to the Q residue;

e. comprises a soybean mosaic virus (SMV) protease and the PSRS comprises the peptide XVXXQ-(G/S), wherein X is any amino acid and the SMV protease cleaves between Q and S or G residues;

f. comprises a plum pox virus (PPV) protease and the PSRS comprises the peptide NVVVHQ-A, wherein the PPV protease cleaves between the Q and the A residue;

g. comprises a hepatitis C virus (HCV) NS3 protease and the PSRS comprises the peptide (D/E)XXXXC(A/S), wherein X is any amino acid and the HCV protease cleaves between the C and the A or S residues;

h. comprises an enterokinase and the PSRS comprises the peptide DDDDK, wherein the enterokinase cleaves C-terminal to the K residue;

i. comprises a Factor Xa protease and the PSRS comprises the peptide I(D/E)GR, wherein the Factor Xa protease cleaves C-terminal to the R residue; or j. comprises a furin protease and the PSRS comprises the peptide RX(K/R)R, wherein the furin protease cleaves C-terminal to the C-terminal R residue.

27. The method of embodiment 21 or 22, wherein:

(i) the plant nutrient is zinc or potassium and the protein of interest or protein encoded by the target gene is a gluconate dehydrogenase (GAD) enzyme;

(ii) the plant nutrient is iron and the protein of interest or protein encoded by the target gene is a siderophore biosynthetic and transport protein optionally selected from a dhbACDEBF gene cluster; a non-ribosomal peptide synthetase (NRPS), polyketide synthase (PKS), and NRPS-independent siderophore synthetase (NIS); and major facilitator superfamily (MFS) transporters (ymfE), TonB, ExbD, and/or ExbB;

(iii) the phytohormone is auxin and the protein of interest or protein encoded by the target gene is an IpdC or IaaM protein;

(iv) the plant nutrient is ammonia and α-ketobutyrate and the protein of interest or protein encoded by the target gene is ACC deaminase;

(v) the plant growth regulator is a volatile organic compound and the proteins of interest or proteins encoded by the target genes are Glyceraldehyde-3-Phosphate Dehydrogenase (GAPDH) and 2,3-butanediol Dehydrogenase (BDH);

(vi) the agriculturally relevant compound is trehalose and the protein(s) of interest or proteins encoded by the target gene are OtsA, OtsB, and TreS or TreS; or (vii) the carbon containing compound is calcium carbonate and the protein of interest is a beta-carbonic anhydrase or alpha-carbonic anhydrase.

28. The method of any one of embodiments 1-22, wherein the protein of interest comprises a site-specific recombinase (SSR) or integrase protein, wherein a control element comprising a promoter and/or at least a segment of a 5' UTR: (i) is flanked by site-specific recombinase recognition sites (SSRRS) in an inverted configuration; (ii) is operably linked to one or more first target gene(s) of the genetically engineered bacterium; and (iii) is operably linked to one or more second target gene(s) of the genetically engineered bacterium upon inversion by the SSR or integrase; and wherein:

(a) the first target gene is a glnA gene encoding a wild-type glutamine synthetase (GS) or variant thereof with improved catalytic activity in comparison to wild-type GS and the second target gene is a glnA gene encoding a wild-type GS with reduced levels of expression in comparison to the wild-type glnA gene or a GS variant with decreased catalytic activity in comparison to wild-type GS, and the fertilizer is ammonia, optionally wherein the wild-type GS comprises a protein sequence having at least 70%, 80%, 85%, 90%, 95%, 98%, or 99% identity to SEQ ID NO: 229, 230, 460-512, 519-521, or 530-533;

(b) the first target gene is a glnE gene encoding a wild-type GS adenylyltransferase protein and the second target gene is a glnE gene encoding a GS adenylyltransferase protein lacking an adenylyl removing domain which exhibits unidirectional adenylyltransferase (uAT) activity, and the fertilizer is ammonia, optionally wherein the protein encoded by the second target gene comprises a protein sequence having at least 70%, 80%, 85%, 90%, 95%, 98%, or 99% identity to SEQ ID NO: 16-24, or 25 or optionally wherein the second target gene comprises a DNA sequence having at least 70%, 80%, 85%, 90%, 95%, 98%, or 99% identity to SEQ ID NO: 1-14, or 15; or (c) the first target gene is a nifL gene and the second target gene is a nifA gene, and the fertilizer is ammonia.

29. The method of embodiment 28, wherein the control element which is operably linked to said target genes comprises a constitutive promoter, an inducible promoter, or phosphate-sensitive promoter.

30. The method of embodiment 28 or 29, wherein the integrase is a serine integrase, optionally wherein the serine integrase is a phage PhiC31 serine integrase, IntS, IntM, IntG-ICEMcSym 1271, YdcL-ICEBs, or Int-ICE SXT/R39 integrase, and the SSRRS are attB and attP sites recognized respectively by the PhiC31, IntS, IntM, IntG, YdcL, or Sxt/R39 integrase.

31. The method of embodiment 28, wherein: (i) one or more SSR is a yeast flippase (FLP) recombinase and the SSRRS are FRT sites; or (ii) one or more SSR is a Cre-recombinase and the SSRRS are loxP sites.

32. The method of any one of embodiments 1-22, wherein the protein of interest is a first repressor protein and wherein the genetically engineered bacterium further comprises:

(i) a second control element comprising a promoter which is repressed by the first repressor protein and operably linked to a gene encoding a second repressor protein;

(ii) optionally a third control element comprising a promoter which is repressed by the second repressor protein and operably linked to a gene encoding a third repressor protein;

(iii) optionally a fourth control element comprising a promoter which is repressed by the third repressor protein and operably linked to a gene encoding a fourth repressor protein; and (iv) a control element comprising a promoter which is repressed by the second, third, or fourth repressor protein and which is operably linked to a first target gene, optionally wherein the first, second, third, and/or fourth repressor protein(s) comprise(s) the lambda repressor (cI), the tet repressor (TetR), the lac repressor (LacI), a catalytically inactive RNA-guided DNA binding protein, a protein comprising a DNA-binding zinc finger domain, a transcription activator-like effector (TALE), or any variant thereof.

33. The method of embodiment 32, wherein the genetically engineered bacterium lacks (ii) and (iii), and the first target gene comprises: (a) nifA, ntrC, glnR, a gene encoding a glutaminase enzyme, a gene encoding a GlnE protein lacking an adenylyl removing domain which exhibits unidirectional adenylyltransferase (uAT) activity, one or more nif cluster gene(s), and/or one or more fix cluster gene(s), and the agriculturally relevant compound is ammonia; or (b) a gene encoding a phytase enzyme, optionally wherein the phytase enzyme comprises a cysteine phytase, a histidine acid phytase, or a beta-propeller phytase, a gene encoding an acid phosphatase enzyme, optionally wherein the acid phosphatase is encoded by an acpA, aphA, phoC, napA, napD, or napE gene or variant thereof, or a gene encoding a protein which stimulates organic acid release from the bacterium, optionally wherein the protein which stimulates organic acid release comprises a gluconate dehydrogenase (GAD), a glucose dehydrogenase (GDH), or a pyrroloquinoline (PQQ) synthase, and the agriculturally relevant compound is phosphate.

34. The method of embodiment 32, wherein the genetically engineered bacterium further comprises (ii) and (iii), and the first target gene comprises: (a) nifA, ntrC, glnR, a gene encoding a glutaminase enzyme, a gene encoding a GlnE protein lacking an adenylyl removing domain which exhibits unidirectional adenylyltransferase (uAT) activity, one or more nif cluster gene(s), and/or one or more fix cluster gene(s) and the agriculturally relevant compound is ammonia; or (b) a gene encoding a phytase enzyme, optionally wherein the phytase enzyme comprises a cysteine phytase, a histidine acid phytase, or a beta-propeller phytase, a gene encoding an acid phosphatase enzyme, optionally wherein the acid phosphatase is encoded by an acpA, aphA, phoC, napA, napD, or napE gene or variant thereof, or a gene encoding a protein which stimulates organic acid release from the bacterium, optionally wherein the protein which stimulates organic acid release comprises a gluconate dehydrogenase (GAD), a glucose dehydrogenase (GDH), or a pyrroloquinoline (PQQ) synthase, and the agriculturally relevant compound is phosphate.

35. The method of embodiment 32, wherein the genetically engineered bacterium further comprises (ii) and lacks (iii), and the first target gene is amtB, draT, glnA, glnB, glnK, glnZ, and/or nifL, and the agriculturally relevant compound is ammonia.

36. The method of embodiment 32, wherein first target gene encodes a transcriptional activator protein and wherein the genetically engineered bacterium further comprises a control element comprising a promoter which is activated by the transcriptional activator protein and operably linked to at least one second target gene.

37. The method of embodiment 32, wherein the genetically engineered bacterium comprises an even number of repressors and the first target gene comprises: (a) nifA, ntrC, glnR, a gene encoding a glutaminase enzyme, a gene encoding a GlnE protein lacking an adenylyl removing domain which exhibits unidirectional adenylyltransferase (uAT) activity, one or more nif cluster gene(s), and/or one or more fix cluster gene(s) and the agriculturally relevant compound is ammonia; or (b) a gene encoding a phytase enzyme, optionally wherein the phytase enzyme comprises a cysteine phytase, a histidine acid phytase, or a beta-propeller phytase, a gene encoding an acid phosphatase enzyme, optionally wherein the acid phosphatase is encoded by an acpA, aphA, phoC, napA, napD, or napE gene or variant thereof, or a gene encoding a protein which stimulates organic acid release from the bacterium, optionally wherein the protein which stimulates organic acid release comprises a gluconate dehydrogenase (GAD), a glucose dehydrogenase (GDH), a pyrroloquinoline (PQQ) synthase, and the agriculturally relevant compound is phosphate.

38. The method of embodiment 32, wherein the genetically engineered bacterium comprises an even number of repressors and the first target gene encodes an RNA sequence or protein comprising:

a. a GlnE protein lacking an adenylyl removing domain which exhibits unidirectional adenylyltransferase (uAT) activity and the fertilizer is ammonia;

b. a NifA protein, wherein the genetically engineered bacterium optionally comprises a loss-of-function mutation in any one or more of the amtB, draT, glnA, glnB, glnK, glnR, glnZ, or nifL genes, wherein the genetically engineered bacterium optionally comprises one or more heterologous genes from a wild-type or refactored nif or fix gene cluster and the fertilizer is ammonia;

c. a GlnR protein and the fertilizer is ammonia;

d. a glutaminase enzyme and the fertilizer is ammonia;

e. a protein product of a refactored nif or fix gene cluster and the fertilizer is ammonia;

f. a phytase enzyme and the agriculturally relevant compound is phosphate, optionally wherein the phytase enzyme comprises a cysteine phytase, a histidine acid phytase, or a beta-propeller phytase;

g. an acid phosphatase enzyme and the agriculturally relevant compound is phosphate, optionally wherein the acid phosphatase enzyme is encoded by an acpA, aphA, phoC, napA, napD, or napE gene or variant thereof;

h. a protein which stimulates organic acid release from the bacterium and the agriculturally relevant compound is phosphate, optionally wherein the protein which stimulates organic acid release comprises a gluconate dehydrogenase (GAD), a glucose dehydrogenase (GDH), or a pyrroloquinoline (PQQ) synthase;

i. a repressor protein, wherein the repressor protein binds a natural or synthetic DNA motif in the promoter of any one or more second target gene(s) of the genetically engineered bacterium and inhibits expression of any one or more of the protein product(s) of the second target gene(s) and/or wherein the repressor protein optionally comprises the lambda repressor (cI), the tet repressor (TetR), the lac repressor (LacI), a catalytically inactive RNA-guided DNA binding protein, a protein comprising a DNA-binding zinc finger domain, a transcription activator-like effector (TALE), or any variant thereof and/or optionally wherein the second target gene(s) is/are a glnA, amtB, glnB, glnK, glnZ, nifL, and/or draT gene and the fertilizer is ammonia;

j. a non-coding synthetic small RNA (sRNA); optionally wherein the non-coding synthetic small RNA (sRNA) binds a natural or synthetic DNA and/or RNA motif in the promoter, 5' UTR, and/or coding region of any one or more second target gene(s) of the genetically engineered bacterium, optionally wherein the non-coding synthetic small RNA (sRNA) comprises a guide RNA that additionally binds an RNA-guided DNA endonuclease, an RNA-guided RNA endonuclease, or variant thereof and/or optionally wherein the second target gene(s) is/are a glnA, amtB, glnB, glnK, glnZ, nifL, and/or draT gene and the fertilizer is ammonia;

k. a site-specific recombinase (SSR) or integrase protein: wherein any one or more second target gene(s) of the genetically engineered bacterium and/or a promoter operatively linked thereto are flanked by site-specific recombinase recognition sites (SSRRS) in a direct configuration, optionally wherein the SSRRS comprise attL and attR sites and the genetically engineered bacterium comprises a gene encoding a recombinase directionality factor (RDF) and/or optionally wherein the second target gene(s) is/are a glnA, amtB, glnB, segment of glnE encoding an adenylyl-removing domain of a glutamine synthetase adenylyltransferase, glnK, glnZ, nifL, and/or draT gene and the fertilizer is ammonia;

l. a site-specific recombinase (SSR) or integrase protein: wherein any one or more second target gene(s), the promoter(s) thereof, and/or the 5' UTR(s) thereof of the genetically engineered bacterium comprise(s) one or more internal synthetic SSRRS and wherein the gene(s), promoter(s), the 5' UTR(s), and/or a segment(s) thereof is/are excised or inactivated after a recombination event; optionally wherein the genetically engineered bacterium further comprises a plasmid comprising an SSRRS; optionally wherein the genetically engineered bacterium further comprises one or more genes encoding a recombinase directionality factor (RDF); and/or optionally wherein the second target gene(s) is/are a glnA, amtB, glnB, glnE, glnK, glnZ, nifL, and/or draT gene and the fertilizer is ammonia;

m. a site-specific recombinase (SSR) or integrase protein, wherein any one or more second target gene(s), the promoter(s) thereof, and/or the 5' UTR(s) thereof of the genetically engineered bacterium comprise(s) one or more internal integrative SSRRS and retain(s) activity of said second target gene(s), promoter(s), and/or 5' UTR(s) and wherein the genetically engineered bacterium further comprises an integrative element comprising an SSRRS; optionally wherein the internal integrative SSRRS is/are an attB site(s), the integrative element comprises an SSRRS comprising an attP site; and/or optionally wherein the second target gene(s) is/are glnA, amtB, glnB, glnK, glnZ, nifL, and/or draT and the fertilizer is ammonia;

n. a site-specific recombinase (SSR) or integrase protein, wherein a control element comprising a promoter and/or at least a segment of a 5' UTR: (i) is flanked by site-specific recombinase recognition sites (SSRRS) in an inverted configuration; and (ii) is operably linked to one or more second target gene(s) of the genetically engineered bacterium; optionally wherein the control element which is operably linked to said second target gene(s) comprises a constitutive promoter, an inducible promoter, or phosphate-sensitive promoter; and/or optionally wherein the second target gene(s) is/are glnA, amtB, glnB, glnK, glnZ, nifL, and/or draT and the fertilizer is ammonia;

o. a site-specific recombinase (SSR) or integrase protein, wherein a control element comprising a promoter and at least a segment of a 5' UTR: (i) is flanked by site-specific recombinase recognition sites (SSRRS) in an inverted configuration; and (ii) is operably linked to one or more second target gene(s) of the genetically engineered bacterium upon inversion by the SSR or integrase; optionally wherein the control element which is operably linked to said second target gene(s) upon inversion by the SSR or integrase comprises a constitutive promoter, an inducible promoter, or phosphate-sensitive promoter; and/or optionally wherein the second target gene(s) is/are: (a) nifA, ntrC, glnR, a gene encoding a glutaminase enzyme, a gene encoding a GlnE protein lacking an adenylyl removing domain which exhibits unidirectional adenylyltransferase (uAT) activity, one or more nif cluster gene(s), and/or one or more fix cluster gene(s) and the agriculturally relevant compound is ammonia; or (b) a gene encoding a phytase enzyme, optionally wherein the phytase enzyme comprises a cysteine phytase, a histidine acid phytase, or a beta-propeller phytase, a gene encoding an acid phosphatase enzyme, optionally wherein the acid phosphatase is encoded by an acpA, aphA, phoC, napA, napD, or napE gene or variant thereof, or a gene encoding a protein which stimulates organic acid release from the bacterium, optionally wherein the protein which stimulates organic acid release comprises a gluconate dehydrogenase (GAD), a glucose dehydrogenase (GDH), or a pyrroloquinoline (PQQ) synthase, and the agriculturally relevant compound is phosphate;

p. a site-specific DNA endonuclease, wherein any one or more second target gene(s) of the genetically engineered bacterium comprise(s) one or more specific DNA sequence(s) recognized by the site-specific DNA endonuclease, optionally wherein the site-specific DNA endonuclease comprises an RNA-guided DNA endonuclease, a protein comprising a DNA-binding zinc finger domain, a transcription activator-like effector (TALE), a meganuclease, a homing endonuclease, or a restriction endonuclease, and/or optionally wherein the second target gene(s) is/are glnA, amtB, glnB, glnK, glnZ, nifL, and/or draT and the fertilizer is ammonia;

q. a protease which cleaves a protease specific recognition sequence (PSRS), wherein any one or more second target gene(s) of the genetically engineered bacterium comprise(s) one or more in-frame insertion(s) comprising DNA encoding the PSRS in the protein coding region of the second target gene(s), wherein the target protein product comprising the one or more in-frame insertion(s) has activity, and wherein cleavage of the target protein product(s) by the protease deactivates the target protein product(s), optionally wherein the location of the one or more in-frame insertion is given by Table 6, optionally wherein the second target gene(s) is/are under the control of a constitutive promoter, and/or optionally wherein the second target gene(s) is/are glnA, amtB, glnB, glnK, glnZ, nifL, and/or draT and the fertilizer is ammonia;

r. a first protein comprising a ClpAP ATP-dependent protease and a second protein comprising a ClpS Leu/N-recognin, wherein any one or more second target gene(s) of the genetically engineered bacterium encodes a third protein comprising an N-terminal -Leu, -Phe, -Trp, or -Tyr residue, and optionally wherein the first and second protein are operably linked to distinct control elements, and/or optionally wherein the second target gene(s) is/are glnA, amtB, glnB, glnK, glnZ, nifL, and/or draT and the fertilizer is ammonia;

s. a protease which cleaves a protease specific recognition sequence (PSRS), wherein any one or more second target gene(s) of the genetically engineered bacterium comprise(s) an in-frame insertion(s) of DNA encoding the PSRS at the N-terminus of the protein coding region of the gene(s) followed by a -Leu, -Phe, -Trp, or -Tyr residue and wherein cleavage of PSRS from the N-terminus of the protein(s) encoded by the gene(s) by the protease results in a protein comprising an N-terminal -Leu, -Phe, -Trp, or -Tyr residue which is degraded by native ClpS and ClpAP, optionally wherein the second target gene(s) is/are glnA, amtB, glnB, glnK, glnZ, nifL, and/or draT and the fertilizer is ammonia;

t. a transcriptional activator protein, wherein the transcriptional activator protein binds a natural or synthetic DNA motif in a promoter of a heterologous protease gene of the genetically engineered bacterium and activates expression of the protease, wherein any one or more second target gene(s) of the genetically engineered bacterium comprise(s) one or more in-frame insertion(s) of DNA encoding a PSRS, optionally wherein the transcriptional activator protein comprises a tet responsive element-binding tTA transcription factor or a transcriptional activator domain fused to a DNA targeting protein, optionally wherein the DNA targeting protein is a catalytically inactive RNA-guided DNA binding protein, a protein comprising a DNA-binding zinc finger domain, a transcription activator-like effector (TALE), or any variant thereof, optionally wherein the transcriptional activator domain is VP16, and/or optionally wherein the second target gene(s) is/are: glnA, amtB, glnB, glnK, glnZ, nifL, and/or draT and the fertilizer is ammonia;

u. a repressor protein, wherein the repressor protein binds a natural or synthetic DNA motif in a promoter of a heterologous protease gene of the genetically engineered bacterium and inhibits expression of the protease, wherein any one or more second target gene(s) of the genetically engineered bacterium comprise(s) an in-frame insertion of DNA encoding an N-terminal amino acid tag designed to render the protein product(s) of the second target gene(s) inactive, followed by a PSRS, optionally wherein the repressor protein comprises the lambda repressor (cI), the tet repressor (TetR), the lac repressor (LacI), a catalytically inactive RNA-guided DNA binding protein, a protein comprising a DNA-binding zinc finger domain, a transcription activator-like effector (TALE), or any variant thereof, and/or optionally wherein the second target gene(s) is/are glnA, amtB, glnB, glnK, glnZ, nifL, and/or draT and the fertilizer is ammonia;

v. a nanobody, wherein the nanobody binds a protein product of any one or more second target gene(s) of the genetically engineered bacterium, wherein binding of the nanobody to such protein product inhibits function of the protein product, optionally wherein the second target gene(s) is/are glnA, amtB, glnB, glnK, glnZ, nifL, and/or draT and the fertilizer is ammonia;

w. an aptamer, wherein the aptamer binds a protein product of any one or more second target gene(s) of the genetically engineered bacterium and inhibits function of any one or more of the protein product(s) of the second target gene(s), optionally wherein the second target gene(s) is/are glnA, amtB, glnB, glnK, glnZ, nifL, and/or draT and the fertilizer is ammonia; or x. a transcriptional activator protein, wherein the transcriptional activator protein binds a natural or synthetic DNA motif in a promoter of any one or more second target gene(s) and increases expression of any one or more of the second target gene(s), optionally wherein the transcriptional activator protein comprises the tet responsive element-binding tTA transcription factor or a transcriptional activator domain fused to a DNA targeting protein, wherein the DNA targeting protein is optionally a catalytically inactive RNA-guided DNA binding protein, a protein comprising a DNA-binding zinc finger domain, a transcription activator-like effector (TALE), or any variant thereof, wherein the transcriptional activator domain is optionally VP16 and/or optionally wherein the second target gene(s) is/are any one or more of: (a) nifA, ntrC, glnR, a gene encoding a glutaminase enzyme, a gene encoding a GlnE protein lacking an adenylyl removing domain which exhibits unidirectional adenylyltransferase (uAT) activity, one or more nif cluster gene(s), and/or one or more fix cluster gene(s) and the agriculturally relevant compound is ammonia; or (b) a gene encoding a phytase enzyme, optionally wherein the phytase enzyme comprises a cysteine phytase, a histidine acid phytase, or a beta-propeller phytase, a gene encoding an acid phosphatase enzyme, optionally wherein the acid phosphatase is encoded by an acpA, aphA, phoC, napA, napD, or napE gene or variant thereof, and/or a gene encoding a protein which stimulates organic acid release from the bacterium, optionally wherein the protein which stimulates organic acid release comprises a gluconate dehydrogenase (GAD), a glucose dehydrogenase (GDH), or a pyrroloquinoline (PQQ) synthase and the agriculturally relevant compound is phosphate.

39. The method of embodiment 32, wherein the genetically engineered bacterium comprises an odd number of repressors and the second target gene is amtB, draT, glnA, glnB, glnK, glnZ, and/or nifL, and the agriculturally relevant compound is ammonia.

40. The method of embodiment any one of embodiments 1-21, wherein the protein of interest is a first transcriptional activator protein and wherein the genetically engineered bacterium further comprises:

(i) a second control element comprising a promoter which is activated by the first transcriptional activator protein and operably linked to a gene encoding a second transcriptional activator protein;

(ii) optionally a third control element comprising a promoter which is activated by the second transcriptional activator protein and operably linked to a gene encoding a third transcriptional activator protein;

(iii) optionally a fourth control element comprising a promoter which is activated by the third transcriptional activator protein and operably linked to a gene encoding a fourth transcriptional activator protein; and (iv) a control element comprising a promoter which is activated by the second, third, or fourth transcriptional activator protein and which is operably linked to a first target gene, optionally wherein the first, second, third, and/or fourth transcriptional activator protein comprise(s) the tet responsive element-binding tTA transcription factor or an activator domain fused to a DNA targeting protein, optionally wherein the DNA targeting protein is a catalytically inactive RNA-guided DNA binding protein, a protein comprising a DNA-binding zinc finger domain, a transcription activator-like effector (TALE), and/or any variant thereof, optionally wherein the activator domain is VP16.

41. The method of embodiment 40, wherein the first target gene comprises: (a) nifA, ntrC, glnR, a gene encoding a glutaminase enzyme, a gene encoding a GlnE protein lacking an adenylyl removing domain which exhibits unidirectional adenylyltransferase (uAT) activity, one or more nif cluster gene(s), and/or one or more fix cluster gene(s) and the agriculturally relevant compound is ammonia; or (b) a gene encoding a phytase enzyme, optionally wherein the phytase enzyme comprises a cysteine phytase, a histidine acid phytase, or a beta-propeller phytase, a gene encoding an acid phosphatase enzyme, optionally wherein the acid phosphatase is encoded by an acpA, aphA, phoC, napA, napD, or napE gene or variant thereof, or a gene encoding a protein which stimulates organic acid release from the bacterium, optionally wherein the protein which stimulates organic acid release comprises a gluconate dehydrogenase (GAD), a glucose dehydrogenase (GDH), or a pyrroloquinoline (PQQ) synthase, and the agriculturally relevant compound is phosphate.

42. The method of any one of embodiments 1-22, wherein the protein of interest is a repressor protein and wherein the genetically engineered bacterium further comprises:

(i) a second control element comprising a promoter which is repressed by the repressor protein and operably linked to a gene encoding a transcriptional activator protein; and (ii) a third control element comprising a promoter which is activated by the transcriptional activator protein and operably linked to a target gene.

43. The method of embodiment 42, wherein the target gene is a glnA, amtB, glnB, glnK, glnZ, nifL, and/or draT gene and the agriculturally relevant compound is ammonia.

44. The method of any one of embodiments 1-22, wherein the protein of interest is a transcriptional activator protein and wherein the genetically engineered bacterium further comprises:

(i) a second control element comprising a promoter which is activated by the transcriptional activator protein and operably linked to a gene encoding a repressor protein; and (ii) a third control element comprising a promoter which is repressed by the repressor and operably linked to a target gene.

45. The method of embodiment 44, wherein the target gene is a glnA, amtB, glnB, glnK, glnZ, nifL, and/or draT gene and the agriculturally relevant compound is ammonia.

46. The method of embodiment 22, wherein the glnA, amtB, glnB, glnK, glnZ, nifL, and/or draT gene in (n), (o), (p), or (q) is under the control of a heterologous constitutive promoter.

47. The method of embodiment 38, wherein the glnA, amtB, glnB, glnK, glnZ, nifL, and/or draT gene in (q), (r), (s), or (t) is under the control of a heterologous constitutive promoter.

48. The method of any one of embodiments 1-21, wherein the plant nutrient is phosphate and the protein of interest comprises:

a. a phytase enzyme, optionally wherein the phytase enzyme comprises a cysteine phytase, a histidine acid phytase, or a beta-propeller phytase, optionally wherein the phytase enzyme comprises a protein sequence having at least 70%, 75%, 80%, 85%, 90%, 95%, 98%, or 99% sequence identity to SEQ ID NO: 58-138, or 139;

b. an acid phosphatase enzyme, optionally wherein the acid phosphatase is encoded by an acpA, aphA, phoC, napA, napD, or napE gene or variant thereof;

c. a protein which stimulates organic acid release from the bacterium, optionally wherein the protein comprises a gluconate dehydrogenase (GAD), a glucose dehydrogenase (GDH), a pyrroloquinoline (PQQ) synthase including pqqFABCDEG, or any combination of GAD, GDH, and PQQ; or, d. any combination of proteins of a, b, or c.

49. The method of any one of embodiments 1 to 48, wherein the heterologous gene expression cassette is introduced into bacteria originally isolated from a plant growth medium or a plant to obtain the genetically engineered bacteria.

50. The method of any one of embodiments 1 to 49, wherein the bacterium is selected from the group of gram-negative bacteria.

51. The method of any one of embodiments 1 to 49, wherein the bacteria are selected from the groups of bacteria of the taxonomic classes of alphaproteobacteria, betaproteobacteria, and gammaproteobacteria.

52. The method of any one of embodiments 1 to 49, wherein the bacteria are selected from the groups of bacteria in the taxonomic genera of *Acetobacter, Acidothermus, Acinetobacter, Agrobacterium, Aromatoleum, Arthrobacter, Azoarcus, Azorhizobium, Azospirillum, Azotobacter, Bacillus, Bifidobacterium, Bradyrhizobium, Burkholderia, Conexibacter, Curtobacterium, Ensifer, Enterobacter, Erwinia, Escherichia, Flavobacterium, Frankia, Gaiella, Gluconacetobacter, Gluconobacter, Herbaspirillum, Klebsiella, Kosakonia, Lactobacillus, Lactococcus, Lysinibacillus, Maritimibacter, Methylobacterium, Nitrosocosmicus, Nitrososphaera, Paenarthrobacter, Paenibacillus, Pantoea, Pediococcus, Peribacillus, Phytobacter, Priestia, Pseudarthrobacter, Pseudomonas, Rahnella, Rhizobium, Rhodococcus, Rhodoplanes, Rhodopseudomonas, Rhodospirillum, Serratia, Solirubrobacter, Sphingobacterium, Sphingomonas, Stenotrophomonas, Streptomyces, Stutzerimonas, Variovorax, Xanthobacter*, and *Yoonia*, optionally wherein the bacteria are selected from at least one of the taxonomic genera selected from the group consisting of *Herbaspirillum, Azospirillum, Kosakonia, Pseudomonas, Enterobacter, Klebsiella, Paenibacillus, Phytobacter, Rahnella, Sphingomonas*, or *Variovorax*.

53. The method of any one of embodiments 1 to 52, wherein the phosphate concentration in the plant growth medium is reduced as a consequence of:

i. growth of resident soil organisms, microorganisms, and/or the genetically engineered bacterium in the plant growth medium, and/or ii. growth of a plant in the plant growth medium.

54. The method of any one of embodiments 1 to 53, wherein the plant growth medium has been treated by adding inorganic phosphate to the plant growth medium at a rate of about 3 $g/m^2$ to about 15 $g/m^2$.

55. The method of any one of embodiments 1 to 54, wherein the threshold concentration of phosphate in the plant growth medium which activates expression of the RNA or protein of interest is about 0 $\mu M$ to any one of about 1 $\mu M$, 2 $\mu M$, 5 $\mu M$, 7 $\mu M$, 10 $\mu M$, 20 $\mu M$, 30 $\mu M$, 40 $\mu M$, or 50 $\mu M$.

56. The method of any one of embodiments 1 to 55, wherein the genetically engineered bacterium is placed into the plant growth medium and/or in contact with the plant:

(i) by foliar application to the plant;

(ii) by an in furrow application, fumigation, and/or soil drench;

(iii) with a seed in form of a seed treatment wherein the seed is at least partially coated with a composition comprising the genetically engineered bacterium;

(iv) with a seed in the form of bio-priming where the seed is imbibed with an aqueous composition comprising the genetically engineered bacterium before planting; and/or (v) with a root dip transplant whereby a seedling root system is dipped in an aqueous composition comprising the genetically engineered bacterium.

57. The method of any one of embodiments 1 to 56, further comprising;

a. determining leaf nitrogen and/or chlorophyll concentrations in a plant grown in the plant growth medium; and b. placing or re-applying the genetically engineered bacterium into the plant growth medium and/or in contact with the plant when the leaf nitrogen and/or chlorophyll concentrations in the plant are sub-optimal for yield.

58. A genetically engineered bacterium comprising a heterologous expression cassette comprising at least one nucleic acid sequence coding for at least one RNA sequence or protein of interest operably linked to a to a control element comprising a phosphate-sensitive promoter, wherein said at least one RNA sequence or protein of interest is or causes the production of at least one agriculturally relevant compound.

59. The genetically engineered bacterium of embodiment 58, wherein the control element and/or the heterologous gene expression cassette further comprises at least a segment of a 5' untranslated region (5' UTR) which is operably linked to the phosphate-sensitive promoter and/or the heterologous gene expression cassette, optionally wherein the 5' UTR comprises a 5' UTR sequence which has at least 85% sequence identity to an endogenous 5' UTR sequence which is operably linked to an endogenous phosphate-sensitive promoter.

60. The genetically engineered bacterium of embodiment 59, wherein the phosphate-sensitive promoter and/or the segment of the 5' UTR which is operably linked to the phosphate-sensitive promoter comprises at least one copy of an operably linked Pho box, wherein the Pho box comprises the sequence of SEQ ID NO: 234-397, 525-528, or 529, and sequences with at least 95% identity to any one of SEQ ID NO: 234-397, 525-528, or 529, optionally wherein the Pho box comprises SEQ ID NO: 376, 377, 383-396, 397, 525-528, or 529.

61. The genetically engineered bacterium of embodiment 59 or 60, wherein the phosphate-sensitive promoter and/or segment the of the 5' UTR is a promoter and/or 5' UTR derived from at least one gram-negative bacterium.

62. The genetically engineered bacterium of embodiment 59 or 60, wherein the phosphate-sensitive promoter and/or the segment of the 5' UTR is a promoter and/or 5' UTR derived from at least one bacterium of the taxonomic classes of alphaproteobacteria, betaproteobacteria, and gammaproteobacteria.

63. The genetically engineered bacterium of embodiment 59 or 60, wherein the phosphate-sensitive promoter and/or the segment of the 5' UTR is a promoter and/or segment of a 5' UTR derived from at least one bacterium of a genus selected from the group consisting of *Acetobacter, Acidothermus, Acinetobacter, Agrobacterium, Aromatoleum, Arthrobacter, Azoarcus, Azorhizobium, Azospirillum, Azotobacter, Bacillus, Bifidobacterium, Bradyrhizobium, Burkholderia, Conexibacter, Curtobacterium, Ensifer, Enterobacter, Erwinia, Escherichia, Flavobacterium, Frankia, Gaiella, Glu-* conacetobacter, Gluconobacter, Herbaspirillum, Klebsiella, Kosakonia, Lactobacillus, Lactococcus, Lysinibacillus, Maritimibacter, Methylobacterium, Nitrosocosmicus, Nitrososphaera, Paenarthrobacter, Paenibacillus, Pantoea, Pediococcus, Peribacillus, Phytobacter, Priestia, Pseudarthrobacter, Pseudomonas, Rahnella, Rhizobium, Rhodococcus, Rhodoplanes, Rhodopseudomonas, Rhodospirillum, Serratia, Solirubrobacter, Sphingobacterium, Sphingomonas, Stenotrophomonas, Streptomyces, Stutzerimonas, Variovorax, Xanthobacter, and Yoonia, optionally wherein the phosphate-sensitive promoter and/or the segment of the 5' UTR is derived from at least one bacterium of a genus selected from the group consisting of Azospirillum, Herbaspirillum, Pseudomonas, Kosakonia, Enterobacter, Klebsiella, Paenibacillus, Phytobacter, Pseudomonas, Rahnella, Sphingomonas, and Variovorax.

64. The genetically engineered bacterium of any one of embodiments 59-63, wherein the phosphate-sensitive promoter and/or the segment of the 5' UTR comprises a promoter and/or a segment of a 5' UTR of a phoA, phoX, phy, pstS gene, a variant thereof, or a combination thereof.

65. The genetically engineered bacterium of any one of embodiments 59-63, wherein the phosphate-sensitive promoter and/or the segment of the 5' UTR comprises a promoter and/or a segment of a 5' UTR of a promoter comprising the DNA sequence of SEQ ID NO: 417-428, 515, 516, or 518, a phosphate-sensitive promoter element of a promoter comprising the DNA sequence of SEQ ID NO: 417-428, 515, 516, 518, a variant thereof, or a combination thereof, optionally wherein the variant has at least 76%, 80%, 85%, 90%, 95%, 98%, or 99% sequence identity to SEQ ID NO: 417-428, 515, 516, or 518.

66. The genetically engineered bacterium of any one of embodiments 59-65, wherein the phosphate-sensitive promoter and/or the segment of the 5' UTR comprises a promoter of a gene encoding:

i. a PhoA protein comprising a protein sequence selected from the group consisting of SEQ ID NO: 398, 400, 402, 404, and 406 or having an identity of at least 80%, 85%, 90%, 95%, 98%, or 99% with any one of SEQ ID NO: 398, 400, 402, 404, or 406;

ii. a PhoX protein comprising a protein sequence selected from the group consisting of SEQ ID NO: 408, 410, 411, 412, and 413 or having an identity of at least 80%, 85%, 90%, 95%, 98%, or 99% with any one of SEQ ID NO: 408, 410, 411, 412, and 413;

iii. a Phy protein comprising a protein sequence selected from the group consisting of SEQ ID NO: 414, 57-138, and 139 or having an identity of at least 80%, 85%, 90%, 95%, 98%, or 99% with any one of SEQ ID NO: 414, 57-138, or 139; and/or iv. a PstS protein comprising a protein sequence selected from the group consisting of SEQ ID NO: 399, 401, 403, 405, 407, 409, 415, 416, 513, 523, and 524 or having an identity of at least 76%, 80%, 85%, 90%, 95%, 98%, or 99% with any one of SEQ ID NO: 399, 401, 403, 405, 407, 409, 415, 416, 513, 523, or 524.

67. The genetically engineered bacterium of any one of embodiments 59-66, wherein the promoter region and/or the segment of the 5' UTR comprises at least 50 nucleotides of DNA located upstream of a start codon of a gene encoding a PhoA, PhoX, Phy, or PstS protein, optionally wherein the promoter region and/or the segment of the 5' UTR comprises about 50 to about 250 nucleotides of DNA located upstream of said start codon of said gene encoding said PhoA, PhoX, Phy, or PstS protein.

68. The genetically engineered bacterium of any one of embodiments 59-67, wherein the phosphate-sensitive promoter and/or the segment of the 5' UTR comprises:

i. a phoA promoter comprising the DNA sequence of SEQ ID NO: 419;

ii. a phoX promoter comprising the DNA sequence of SEQ ID NO: 426;

iii. a phy promoter comprising the DNA sequence of SEQ ID NO: 427;

iv. a pstS promoter comprising a DNA sequence selected from the group consisting of SEQ ID NO: 417, 418, 420, 421, 422, 423, 424, 425, 428, 515, 517, and 518; and/or v. a Pliar53 promoter comprising the DNA sequence of SEQ ID NO: 459;

vi. a variant of the promoters under i. to v. having an identity of at least 76%, 80%, 90%, 95%, 98%, or 99% with any of SEQ ID NO: 417, 418-428, 459, 515, 517, or 518 515, 517, or 518, wherein said variant comprises at least one Pho box and/or retains at least one Pho box present in each promoter and wherein said variant promoters are activated by a decrease in phosphate concentration to about 1 µM to about 1 µM, 2 µM, 5 µM, 7 µM, 10 µM, 20 µM, 30 µM, 40 µM, or 50 µM.

69. The genetically engineered bacterium of any one of embodiments 59-68, wherein the phosphate-sensitive promoter and/or the segment of the 5' UTR or its variant is derived from the same genus or species as the genetically engineered bacterium.

70. The genetically engineered bacterium of any one of embodiments 58-69, wherein the heterologous gene expression cassette is integrated at a location in the chromosome of the genetically engineered bacterium which does not comprise the location of an endogenous phosphate-sensitive promoter.

71. The genetically engineered bacterium of any one of embodiments 58-70, wherein the expression cassette further comprises one or more elements comprising:

a. a ribosome binding site (RBS), wherein the RBS is operably linked to the nucleic acid sequence coding for the protein of interest and optionally wherein the RBS is an RBS having at least 95% sequence identity to SEQ ID NO: 429-454, or 455; and/or b. a terminator sequence (TS), wherein the TS is operably linked to the nucleic acid sequence coding for the RNA sequence or protein of interest and optionally wherein the TS is a TS having at least 95% sequence identity to SEQ ID NO: 456, 457, or 458.

72. The genetically engineered bacterium of any one of embodiments 58 to 71, wherein the at least one agriculturally relevant compound is selected from the group consisting of:

a. at least one fertilizer or plant nutrient, optionally wherein the fertilizer or plant nutrient is selected from the group consisting of ammonia, ammonium, bioavailable carbon, calcium, iron, nitrate, nitrite, nitrogen, potassium, phosphate, sulfur, urea, zinc, a combination thereof, and a mixture thereof;

b. at least one pesticide, optionally wherein the pesticide is an RNA- and/or protein-based fungicide, insecticide, nematicide, antibacterial agent, and/or antiviral agent;

c. at least one phytohormone or plant growth regulator, optionally wherein the phytohormone or plant growth regulator is an auxin, a cytokinin, a gibberellin, abscisic acid, a brassinosteroid, jasmonic acid, a polyamine, a strigolactone, trehalose, and/or a volatile organic compound, or optionally wherein the phytohormone or plant growth regulator is cytokinin, indole butyric acid, and/or combinations thereof; and d. at least one carbon-containing compound, optionally wherein the carbon-containing compound is bicarbonate, carbonate, $CaCO_3$, $MgCO_3$, $CaMg(CO_3)_2$, polyhydroxybutyrate, melanin, chitin, and/or combinations thereof.

73. The genetically engineered bacterium of embodiment 72, wherein the RNA sequence or protein of interest encoded by the heterologous gene expression cassette and operably linked to the control element comprises:

(a) a GlnE protein lacking an adenylyl removing domain which exhibits unidirectional adenylyltransferase (uAT) activity and the fertilizer is ammonia, optionally wherein the GlnE protein lacking an adenylyl removing domain comprises a protein sequence having at least 70%, 80%, 85%, 90%, 95%, 98%, or 99% identity to SEQ ID NO: 16-24, or 25 or optionally wherein the gene encoding the GlnE protein lacking an adenylyl removing domain comprises a DNA sequence having at least 70%, 80%, 85%, 90%, 95%, 98%, or 99% identity to SEQ ID NO: 1-14, or 15;

(b) a NifA protein, wherein the genetically engineered bacterium optionally comprises a loss-of-function mutation in any one or more of the amtB, draT, glnA, glnB, glnK, glnR, glnZ, or nifL genes, wherein the genetically engineered bacterium optionally comprises one or more heterologous genes from a wild-type or refactored nif or fix gene cluster and the fertilizer is ammonia;

(c) a GlnR protein and the fertilizer is ammonia;

(d) a glutaminase enzyme and the fertilizer is ammonia;

(e) a protein product of a refactored nif or fix gene cluster and the fertilizer is ammonia;

(f) a repressor protein, wherein the repressor protein binds a natural or synthetic DNA motif in the promoter of any one or more first target gene(s) of the genetically engineered bacterium and inhibits expression of any one or more of the protein products of the first target genes and/or wherein the repressor protein optionally comprises the lambda repressor (cI), the tet repressor (TetR), the lac repressor (LacI), a catalytically inactive RNA-guided DNA binding protein, a protein comprising a DNA-binding zinc finger domain, a transcription activator-like effector (TALE), or any variant thereof and/or optionally wherein the first target gene(s) is/are a glnA, amtB, glnB, glnK, glnZ, nifL, and/or draT gene and the fertilizer is ammonia;

(g) a non-coding synthetic small RNA (sRNA); optionally wherein the non-coding synthetic small RNA (sRNA) binds a natural or synthetic DNA and/or RNA motif in the promoter, 5' UTR, and/or coding region of any one or more first target gene(s) of the genetically engineered bacterium, optionally wherein the non-coding synthetic small RNA (sRNA) comprises a guide RNA that additionally binds an RNA-guided DNA endonuclease, RNA-guided RNA endonuclease, or variant thereof and/or optionally wherein the first target gene(s) is/are a glnA, amtB, glnB, glnK, glnZ, nifL, and/or draT gene and the fertilizer is ammonia;

(h) a site-specific recombinase (SSR) or integrase protein: wherein any one or more first target gene(s) of the genetically engineered bacterium and/or a promoter operatively linked thereto are flanked by site-specific recombinase recognition sites (SSRRS) in a direct configuration, optionally wherein the SSRRS comprise attL and attR sites and the genetically engineered bacterium comprises a gene encoding a recombinase directionality factor (RDF) and/or optionally wherein the first target gene(s) is/are a glnA, amtB, glnB, segment of glnE encoding an adenylyl-removing domain of a glutamine synthetase adenylyltransferase, glnK, glnZ, nifL, and/or draT gene and the fertilizer is ammonia;

(i) a site-specific recombinase (SSR) or integrase protein: wherein any one or more first target gene(s), the promoter(s) thereof, and/or the 5' UTR(s) thereof of the genetically engineered bacterium comprise(s) one or more internal synthetic SSRRS and wherein the gene(s), promoter(s), the 5' UTR(s), and/or a segment(s) thereof is/are excised or inactivated after a recombination event; optionally wherein the genetically engineered bacterium further comprises a plasmid comprising an SSRRS; optionally wherein the genetically engineered bacterium further comprises one or more genes encoding a recombinase directionality factor (RDF); and/or optionally wherein the first target gene(s) is/are a glnA, amtB, glnB, glnE, glnK, glnZ, nifL, and/or draT gene and the fertilizer is ammonia;

(j) a site-specific recombinase (SSR) or integrase protein, wherein any one or more first target gene(s), the promoter(s) thereof, and/or the 5' UTR(s) thereof of the genetically engineered bacterium comprise(s) one or more internal integrative SSRRS and retain(s) activity of said first target gene(s), promoter(s), and/or 5' UTR(s) and wherein the genetically engineered bacterium further comprises an integrative element comprising an SSRRS; optionally wherein the internal integrative SSRRS is/are an attB site(s) and the integrative element comprises an SSRRS comprising an attP site; and/or optionally wherein the target gene(s) is/are glnA, amtB, glnB, glnK, glnZ, nifL, and/or draT and the fertilizer is ammonia;

(k) a site-specific recombinase (SSR) or integrase protein, wherein a control element comprising a promoter and/or at least a segment of a 5' UTR: (i) is flanked by site-specific recombinase recognition sites (SSRRS) in an inverted configuration; and (ii) is operably linked to one or more first target gene(s) of the genetically engineered bacterium; optionally wherein the control element which is operably linked to said first target gene(s) comprises a constitutive promoter, an inducible promoter, or phosphate-sensitive promoter; and/or optionally wherein the first target gene(s) is/are glnA, amtB, glnB, glnK, glnZ, nifL, and/or draT and the fertilizer is ammonia;

(l) a site-specific recombinase (SSR) or integrase protein, wherein a control element comprising a promoter and at least a segment of a 5' UTR: (i) is flanked by site-specific recombinase recognition sites (SSRRS) in an inverted configuration; and (ii) is operably linked to one or more first target gene(s) of the genetically engineered bacterium upon inversion by the SSR or integrase; optionally wherein the control element which is operably linked to said first target gene(s) upon inversion by the SSR or integrase comprises a constitutive promoter, an inducible promoter, or a phosphate-sensitive promoter; and/or optionally wherein the first target gene(s) is/are: (a) nifA, ntrC, glnR, a gene encoding a glutaminase enzyme, a gene encoding a GlnE protein lacking an adenylyl removing domain which exhibits unidirectional adenylyltransferase (uAT) activity, one or more nif cluster gene(s), and/or one or more fix cluster gene(s) and the agriculturally relevant compound is ammonia; or (b) a gene encoding a phytase enzyme, optionally wherein the phytase enzyme comprises a cysteine phytase, a histidine acid phytase, or a beta-propeller phytase, a gene encoding an acid phosphatase enzyme, optionally wherein the acid phosphatase is encoded by an acpA, aphA, phoC, napA, napD, or napE gene or variant thereof, or a gene encoding a protein which stimulates organic acid release from the bacterium, optionally wherein the protein which stimulates organic acid release comprises a gluconate dehydrogenase (GAD), a glucose dehydrogenase (GDH), or a pyrroloquinoline (PQQ) synthase, and the agriculturally relevant compound is phosphate;

(m) a site-specific DNA endonuclease, wherein any one or more first target gene(s) of the genetically engineered bacterium comprise(s) one or more specific DNA sequence(s) recognized by the site-specific DNA endonuclease, optionally wherein the site-specific DNA endonuclease comprises an RNA-guided DNA endonuclease, a protein comprising a DNA-binding zinc finger domain, a transcription activator-like effector (TALE), a meganuclease, a homing endonuclease, or a restriction endonuclease, and/or optionally wherein the first target gene(s) is/are glnA, amtB, glnB, glnK, glnZ, mifL, and/or draT and the fertilizer is ammonia;

(n) a protease which cleaves a protease specific recognition sequence (PSRS), wherein any one or more first target gene(s) of the genetically engineered bacterium comprise(s) one or more in-frame insertion(s) comprising DNA encoding the PSRS in the protein coding region of the first target gene(s), wherein the target protein product comprising the one or more in-frame insertion(s) has activity, and wherein cleavage of the target protein product(s) by the protease deactivates the target protein product(s), optionally wherein the location of the one or more in-frame insertion(s) is given by Table 6, optionally wherein the first target gene(s) is/are under the control of a constitutive promoter, and/or optionally wherein the first target gene(s) is/are glnA, amtB, glnB, glnK, glnZ, nifL, and/or draT and the fertilizer is ammonia;

(o) a first protein of interest comprising a ClpAP ATP-dependent protease and a second protein of interest comprising a ClpS Leu/N-recognin, wherein any one or more first target gene(s) of the genetically engineered bacterium encodes a protein comprising an N-terminal -Leu, -Phe, -Trp, or -Tyr residue, and optionally wherein the first and second protein of interest are operably linked to distinct control elements, and/or optionally wherein the first target gene(s) is/are glnA, amtB, glnB, glnK, glnZ, nifL, and/or draT and the fertilizer is ammonia;

(p) a protease which cleaves a protease specific recognition sequence (PSRS), wherein any one or more first target gene(s) of the genetically engineered bacterium comprise(s) an in-frame insertion(s) of DNA encoding the PSRS at the N-terminus of the protein coding region of the gene followed by a -Leu, -Phe, -Trp, or -Tyr residue and wherein cleavage of the PSRS from the N-terminus of the protein(s) encoded by the gene(s) by the protease results in a protein comprising an N-terminal -Leu, -Phe, -Trp, or -Tyr residue which is degraded by native ClpS and ClpAP, optionally wherein the first target gene(s) is/are glnA, amtB, glnB, glnK, glnZ, nifL, and/or draT and the fertilizer is ammonia;

(q) a transcriptional activator protein, wherein the transcriptional activator protein binds a natural or synthetic DNA motif in a promoter of a heterologous protease gene of the genetically engineered bacterium and activates expression of the protease, wherein any one or more first target gene(s) of the genetically engineered bacterium comprise(s) one or more in-frame insertion(s) of DNA encoding a PSRS, optionally wherein the transcriptional activator protein comprises a tet responsive element-binding tTA transcription factor or a transcriptional activator domain fused to a DNA targeting protein, optionally wherein the DNA targeting protein is a catalytically inactive RNA-guided DNA binding protein, a protein comprising a DNA-binding zinc finger domain, a transcription activator-like effector (TALE), or any variant thereof, optionally wherein the transcriptional activator domain is VP16, and/or optionally wherein the first target gene(s) is/are: glnA, amtB, glnB, glnK, glnZ, nifL, and/or draT and the fertilizer is ammonia;

(r) a repressor protein, wherein the repressor protein binds a natural or synthetic DNA motif in a promoter of a heterologous protease gene of the genetically engineered bacterium and inhibits expression of the protease, wherein any one or more first target gene(s) of the genetically engineered bacterium comprise(s) an in-frame insertion of DNA encoding an N-terminal amino acid tag designed to render the protein product(s) of the first target gene(s) inactive, followed by a PSRS, optionally wherein the repressor protein comprises the lambda repressor (cI), the tet repressor (TetR), the lac repressor (LacI), a catalytically inactive RNA-guided DNA binding protein, a protein comprising a DNA-binding zinc finger domain, a transcription activator-like effector (TALE), or any variant thereof, and/or optionally wherein the first target gene(s) is/are glnA, amtB, glnB, glnK, glnZ, nifL, and/or draT and the fertilizer is ammonia;

(s) a nanobody, wherein the nanobody binds a protein product of any one or more first target gene(s) of the genetically engineered bacterium, wherein binding of the nanobody to such protein product inhibits function of the protein product, optionally wherein the first target gene(s) is/are glnA, amtB, glnB, glnK, glnZ, nifL, and/or draT and the fertilizer is ammonia;

(t) an aptamer, wherein the aptamer binds a protein product of any one or more first target gene(s) of the genetically engineered bacterium and inhibits function of any one or more of the protein product(s) of the first target gene(s), optionally wherein the first target gene(s) is/are glnA, amtB, glnB, glnK, glnZ, nifL, and/or draT and the fertilizer is ammonia; or (u) a transcriptional activator protein, wherein the transcriptional activator protein binds a natural or synthetic DNA motif in a promoter of any one or more first target gene(s) and increases expression of any one or more of the first target gene(s), optionally wherein the transcriptional activator protein comprises the tet responsive element-binding tTA transcription factor or a transcriptional activator domain fused to a DNA targeting protein, optionally wherein the DNA targeting protein is a catalytically inactive RNA-guided DNA binding protein, a protein comprising a DNA-binding zinc finger domain, a transcription activator-like effector (TALE), or any variant thereof, optionally wherein the transcriptional activator domain is VP16 and/or optionally wherein the first target gene(s) is/are any one or more of: (a) nifA, ntrC, glnR, a gene encoding a glutaminase enzyme, a gene encoding a GlnE protein lacking an adenylyl removing domain which exhibits unidirectional adenylyltransferase (uAT) activity, one or more nif cluster gene(s), and/or one or more fix cluster gene(s) and the agriculturally relevant compound is ammonia; or (b) a gene encoding a phytase enzyme, optionally wherein the phytase enzyme comprises a cysteine phytase, a histidine acid phytase, or a beta-propeller phytase, a gene encoding an acid phosphatase enzyme, optionally wherein the acid phosphatase is encoded by an acpA, aphA, phoC, napA, napD, or napE gene or variant thereof, and/or a gene encoding a protein which stimulates organic acid release from the bacterium, optionally wherein the protein which stimulates organic acid release comprises a gluconate dehydrogenase (GAD), a glucose dehydrogenase (GDH), or a pyrroloquinoline (PQQ) synthase and the agriculturally relevant compound is phosphate.

74. The genetically engineered bacterium of embodiment 73, wherein the integrase is a serine integrase, optionally wherein the serine integrase is a phage PhiC31 serine integrase, IntS, IntM, IntG-ICEMcSym 1271, YdcL-ICEBs, or Int-ICE SXT/R39 integrase, and the SSRRS are attB and attP sites recognized respectively by the PhiC31, IntS, IntM, IntG, YdcL, or Sxt/R39 integrase.

75. The genetically engineered bacterium of embodiment 73, wherein: (i) one or more SSR is a yeast flippase (FLP) recombinase and the SSRRS are FRT sites; or (ii) one or more SSR is a Cre-recombinase and the SSRRS are loxP sites.

76. The genetically engineered bacterium of embodiment 73, wherein a PSRS is inserted between any one or more of the pairs of amino acid residues corresponding to:

(i) amino acid residues 98 and 99, 121 and 122, 279 and 280, and/or 285 and 286 of the glutamine synthetase (GS) polypeptide of SEQ ID NO: 229;

(ii) amino acid residues 98 and 99, 119 and 120, 283 and 284, and/or 298 and 299 of the glutamine synthetase (GS) polypeptide of SEQ ID NO: 230;

(iii) amino acid residues 448 and 449, 480 and 481, 505 and 506, 528 and 529, and/or 624 and 625 of the GlnE polypeptide of SEQ ID NO: 231;

(iv) amino acid residues 527 and 528, 537 and 538, and/or 547 and 548 of the GlnE polypeptide of SEQ ID NO: 232; or (v) amino acid residues 422 and 423 and/or 608 and 609 of the GlnE polypeptide of SEQ ID NO: 233.

77. The genetically engineered bacterium of embodiment 73 or 76, wherein the protease or heterologous protease:

a. comprises a tobacco etch virus (TEV) protease and the PSRS comprises the peptide EXXYXQ-(S/G) or ENLYFQ-(S/G/A/M/C/H), wherein X is any amino acid and the TEV protease cleaves between the Q and S, G, A, M, C, or H residues;

b. comprises a tobacco vein mottling virus (TVMV) protease and the PSRS comprises the peptide ETVRFQ-(G/S), wherein the TVMV protease cleaves between the Q and S or G residues;

c. comprises a sunflower mild mosaic virus (SMMV) protease and the PSRS comprises the peptide EEIHLQ-(S/G), wherein the SMMV protease cleaves between the Q and S or G residues;

d. comprises a turnip mosaic virus (TrMV) protease and the PSRS comprises the peptide VXHQ or VRHQ-S, wherein X is any amino acid and the TrMV protease cleaves C-terminal to the Q residue;

e. comprises a soybean mosaic virus (SMV) protease and the PSRS comprises the peptide XVXXQ-(G/S), wherein X is any amino acid and the SMV protease cleaves between Q and S or G residues;

f. comprises a plum pox virus (PPV) protease and the PSRS comprises the peptide NVVVHQ-A, wherein the PPV protease cleaves between the Q and the A residue;

g. comprises a hepatitis C virus (HCV) NS3 protease and the PSRS comprises the peptide (D/E)XXXXC(A/S), wherein X is any amino acid and the HCV protease cleaves between the C and the A or S residues;

h. comprises an enterokinase and the PSRS comprises the peptide DDDDK, wherein the enterokinase cleaves C-terminal to the K residue;

i. comprises a Factor Xa protease and the PSRS comprises the peptide I(D/E)GR, wherein the Factor Xa protease cleaves C-terminal to the R residue; or j. comprises a furin protease and the PSRS comprises the peptide RX(K/R)R, wherein the furin protease cleaves C-terminal to the C-terminal R residue.

78. The genetically engineered bacterium of embodiment 72, wherein:

(i) the plant nutrient is zinc or potassium and the protein of interest is a gluconate dehydrogenase (GAD) enzyme;

(ii) the plant nutrient is iron and the protein of interest is a siderophore biosynthetic and transport proteins optionally selected from a dhbACDEBF gene cluster; a non-ribosomal peptide synthetase (NRPS), polyketide synthase (PKS), and NRPS-independent siderophore synthetase (NIS); and major facilitator superfamily (MFS) transporters (ymfE), TonB, ExbD, and/or ExbB;

(iii) the phytohormone is auxin and the protein is an IpdC or IaaM protein;

(iv) the plant nutrient is ammonia and α-ketobutyrate and the protein is ACC deaminase;

(v) the plant growth regulator is a volatile organic compound and the proteins are Glyceraldehyde-3-Phosphate Dehydrogenase (GAPDH) and 2,3-butanediol Dehydrogenase (BDH);

(vi) the agriculturally relevant compound is trehalose and the protein(s) of interest is OtsA, OtsB, and TreS or TreS; or (vii) the carbon containing compound is calcium carbonate and the protein of interest is a beta-carbonic anhydrase or alpha-carbonic anhydrase.

79. The genetically engineered bacterium of embodiment 72 or 73, wherein the protein of interest comprises a site-specific recombinase (SSR) or integrase protein, wherein a control element comprising a promoter and/ or at least a segment of a 5' UTR: (i) is flanked by site-specific recombinase recognition sites (SSRRS) in an inverted configuration; (ii) is operably linked to one or more first target gene(s) of the genetically engineered bacterium; and (iii) is operably linked to one or more second target gene(s) of the genetically engineered bacterium upon inversion by the SSR or integrase; and wherein: (a) the first target gene is a glnA gene encoding a wild-type glutamine synthetase (GS)

or variant thereof with improved catalytic activity in comparison to wild-type GS and the second target gene is a glnA gene encoding a wild-type GS with reduced levels of expression in comparison to the wild-type glnA gene or a GS variant with decreased catalytic activity in comparison to wild-type GS, and the fertilizer is ammonia, optionally wherein the wild-type GS comprises a protein sequence having at least 70%, 80%, 85%, 90%, 95%, 98%, or 99% identity to SEQ ID NO: 229, 230, 460-512, 519-521, 530-532, or 533;

(b) the first target gene is a glnE gene encoding a wild-type GS adenylyltransferase protein and the second target gene is a glnE gene encoding a GS adenylyltransferase protein lacking an adenylyl removing domain which exhibits unidirectional adenylyltransferase (uAT) activity, and the fertilizer is ammonia, optionally wherein the protein encoded by the second target gene comprises a protein sequence having at least 70%, 80%, 85%, 90%, 95%, 98%, or 99% identity to SEQ ID NO: 16-24, or 25 or optionally wherein the second target gene comprises a DNA sequence having at least 70%, 80%, 85%, 90%, 95%, 98%, or 99% identity to SEQ ID NO: 1-14, or 15; or (c) the first target gene is a nifL gene and the second target gene is a nifA gene, and the fertilizer is ammonia.

80. The genetically engineered bacterium of embodiment 79, wherein the control element which is operably linked to said target genes comprises a constitutive promoter, an inducible promoter, or a phosphate-sensitive promoter.

81. The genetically engineered bacterium of embodiment 79 or 80, wherein the integrase is a serine integrase, optionally wherein the serine integrase is a phage PhiC31 serine integrase, IntS, IntM, IntG-ICEMcSym 1271, Yd-L-ICEBs, or I-t-ICE SXT/R39 integrase, and the SSRRS are attB and attP sites recognized respectively by the PhiC31, IntS, IntM, IntG, YdcL, or Sxt/R39 integrase.

82. The genetically engineered bacterium of embodiment 79 or 80, wherein: (i) one or more SSR is a yeast flippase (FLP) recombinase and the SSRRS are FRT sites; or (ii) one or more SSR is a Cre-recombinase and the SSRRS are loxP sites.

83. The genetically engineered bacterium of any one of embodiments 1-73, wherein the protein of interest is a first repressor protein and wherein the genetically engineered bacterium further comprises:

(i) a second control element comprising a promoter which is repressed by the first repressor protein and operably linked to a gene encoding a second repressor protein;

(ii) optionally a third control element comprising a promoter which is repressed by the second repressor protein and operably linked to a gene encoding a third repressor protein;

(iii) optionally a fourth control element comprising a promoter which is repressed by the third repressor protein and operably linked to a gene encoding a fourth repressor protein; and (iv) a control element comprising a promoter which is repressed by the second, third, or fourth repressor protein and which is operably linked to a first target gene, optionally wherein the first, second, third, and/or fourth repressor protein(s) optionally comprise(s) the lambda repressor (cI), the tet repressor (TetR), the lac repressor (LacI), a catalytically inactive RNA-guided DNA binding protein, a protein comprising a DNA-binding zinc finger domain, a transcription activator-like effector (TALE), or any variant thereof.

84. The genetically engineered bacterium of embodiment 83, wherein the genetically engineered bacterium lacks (ii) and (iii), and the first target gene comprises: (a) nifA, ntrC, glnR, a gene encoding a glutaminase enzyme, a gene encoding a GlnE protein lacking an adenylyl removing domain which exhibits unidirectional adenylyltransferase (uAT) activity, one or more nif cluster gene(s), and/or one or more fix cluster gene(s), and the agriculturally relevant compound is ammonia; or (b) a gene encoding a phytase enzyme, optionally wherein the phytase enzyme comprises a cysteine phytase, a histidine acid phytase, or a beta-propeller phytase, a gene encoding an acid phosphatase enzyme, optionally wherein the acid phosphatase is encoded by an acpA, aphA, phoC, napA, napD, or napE gene or variant thereof, or a gene encoding a protein which stimulates organic acid release from the bacterium, optionally wherein the protein which stimulates organic acid release comprises a gluconate dehydrogenase (GAD), a glucose dehydrogenase (GDH), or a pyrroloquinoline (PQQ) synthase, and the agriculturally relevant compound is phosphate.

85. The genetically engineered bacterium of embodiment 83, wherein the genetically engineered bacterium further comprises (ii) and (iii), and the first target gene comprises: (a) nifA, ntrC, glnR, a gene encoding a glutaminase enzyme, a gene encoding a GlnE protein lacking an adenylyl removing domain which exhibits unidirectional adenylyltransferase (uAT) activity, one or more nif cluster gene(s), and/or one or more fix cluster gene(s) and the agriculturally relevant compound is ammonia; or (b) a gene encoding a phytase enzyme, optionally wherein the phytase enzyme comprises a cysteine phytase, a histidine acid phytase, or a beta-propeller phytase, a gene encoding an acid phosphatase enzyme, optionally wherein the acid phosphatase is encoded by an acpA, aphA, phoC, napA, napD, or napE gene or variant thereof, or a gene encoding a protein which stimulates organic acid release from the bacterium, optionally wherein the protein which stimulates organic acid release comprises a gluconate dehydrogenase (GAD), a glucose dehydrogenase (GDH), or a pyrroloquinoline (PQQ) synthase, and the agriculturally relevant compound is phosphate.

86. The genetically engineered bacterium of embodiment 83, wherein the genetically engineered bacterium further comprises (ii) and lacks (iii), and the first target gene is amtB, draT, glnA, glnB, glnK, glnZ, and/or nifL, and the agriculturally relevant compound is ammonia.

87. The genetically engineered bacterium of embodiment 83, wherein first target gene encodes a transcriptional activator protein and wherein the genetically engineered bacterium further comprises a control element comprising a promoter which is activated by the transcriptional activator protein and operably linked to at least one second target gene.

88. The genetically engineered bacterium of embodiment 83, wherein the genetically engineered bacterium comprises an even number of repressors and the first target gene comprises: (a) nifA, ntrC, glnR, a gene encoding a glutaminase enzyme, a gene encoding a GlnE protein lacking an adenylyl removing domain which exhibits unidirectional adenylyltransferase (uAT) activity, one or more nif cluster gene(s), and/or one or more fix cluster gene(s) and the agriculturally relevant compound is ammonia; or (b) a gene encoding a phytase enzyme, optionally wherein the phytase enzyme comprises a cysteine phytase, a histidine acid phytase, or a beta-propeller phytase, a gene encoding an acid phosphatase enzyme, optionally wherein the acid phosphatase is encoded by an acpA, aphA, phoC, napA, napD, or napE gene or variant thereof, or a gene encoding a protein which stimulates organic acid release from the bacterium, optionally wherein the protein which stimulates organic acid release comprises a gluconate dehydrogenase (GAD), a glucose dehydrogenase (GDH), a pyrroloquinoline (PQQ) synthase, and the agriculturally relevant compound is phosphate.

89. The genetically engineered bacterium of embodiment 83, wherein the genetically engineered bacterium comprises an even number of repressors and the first target gene encodes an RNA sequence or protein comprising:

(a) a GlnE protein lacking an adenylyl removing domain which exhibits unidirectional adenylyltransferase (uAT) activity and the fertilizer is ammonia;

(b) a NifA protein, wherein the genetically engineered bacterium optionally comprises a loss-of-function mutation in any one or more of the amtB, draT, glnA, glnB, glnK, glnR, glnZ, or nifL genes, optionally wherein the genetically engineered bacterium comprises one or more heterologous genes from a wild-type or refactored nif or fix gene cluster and the fertilizer is ammonia;

(c) a GlnR protein and the fertilizer is ammonia;

(d) a glutaminase enzyme and the fertilizer is ammonia;

(e) a protein product of a refactored nif or fix gene cluster and the fertilizer is ammonia;

(f) a phytase enzyme and the agriculturally relevant compound is phosphate, optionally wherein the phytase enzyme comprises a cysteine phytase, a histidine acid phytase, or a beta-propeller phytase;

(g) an acid phosphatase enzyme and the agriculturally relevant compound is phosphate, optionally wherein the acid phosphatase enzyme is encoded by an acpA, aphA, phoC, napA, napD, or napE gene or variant thereof;

(h) a protein which stimulates organic acid release from the bacterium and the agriculturally relevant compound is phosphate, optionally wherein the protein which stimulates organic acid release comprises a gluconate dehydrogenase (GAD), a glucose dehydrogenase (GDH), or a pyrroloquinoline (PQQ) synthase;

(i) a repressor protein, wherein the repressor protein binds a natural or synthetic DNA motif in the promoter of any one or more second target gene(s) of the genetically engineered bacterium and inhibits expression of any one or more of the protein product(s) of the second target gene(s) and/or wherein the repressor protein optionally comprises the lambda repressor (cI), the tet repressor (TetR), the lac repressor (LacI), a catalytically inactive RNA-guided DNA binding protein, a protein comprising a DNA-binding zinc finger domain, a transcription activator-like effector (TALE), or any variant thereof and/or optionally wherein the second target gene(s) is/are a glnA, amtB, glnB, glnK, glnZ, nifL, and/or draT gene and the fertilizer is ammonia;

(j) a non-coding synthetic small RNA (sRNA); optionally wherein the non-coding synthetic small RNA (sRNA)

binds a natural or synthetic DNA and/or RNA motif in the promoter, 5' UTR, and/or coding region of any one or more second target gene(s) of the genetically engineered bacterium, optionally wherein the non-coding synthetic small RNA (sRNA) comprises a guide RNA that additionally binds an RNA-guided DNA endonuclease, RNA-guided RNA endonuclease, or variant thereof and/or optionally wherein the second target gene(s) is/are a glnA, amtB, glnB, glnK, glnZ, nifL, and/or draT gene and the fertilizer is ammonia;

(k) a site-specific recombinase (SSR) or integrase protein: wherein any one or more second target gene(s) of the genetically engineered bacterium and/or a promoter operatively linked thereto are flanked by site-specific recombinase recognition sites (SSRRS) in a direct configuration, optionally wherein the SSRRS comprise attL and attR sites and the genetically engineered bacterium comprises a gene encoding a recombinase directionality factor (RDF) and/or optionally wherein the second target gene(s) is/are a glnA, amtB, glnB, segment of glnE encoding an adenylyl-removing domain of a glutamine synthetase adenylyltransferase, glnK, glnZ, nifL, and/or draT gene and the fertilizer is ammonia;

(l) a site-specific recombinase (SSR) or integrase protein: wherein any one or more second target gene(s), the promoter(s) thereof, and/or the 5' UTR(s) thereof of the genetically engineered bacterium comprise(s) one or more internal synthetic SSRRS and wherein the gene(s), promoter(s), the 5' UTR(s), and/or a segment(s) thereof is/are excised or inactivated after a recombination event; optionally wherein the genetically engineered bacterium further comprises a plasmid comprising an SSRRS; optionally wherein the genetically engineered bacterium further comprises one or more genes encoding a recombinase directionality factor (RDF); and/or optionally wherein the second target gene(s) is/are a glnA, amtB, glnB, glnE, glnK, glnZ, nifL, and/or draT gene and the fertilizer is ammonia;

(m) a site-specific recombinase (SSR) or integrase protein, wherein any one or more second target gene(s), the promoter(s) thereof, and/or the 5' UTR(s) thereof of the genetically engineered bacterium comprise(s) one or more internal integrative SSRRS and retain(s) activity of said second target gene(s), promoter(s), and/or 5' UTR(s) and wherein the genetically engineered bacterium further comprises an integrative element comprising an SSRRS; optionally wherein the internal integrative SSRRS is/are an attB site(s), the integrative element comprises an SSRRS comprising an attP site; and/or optionally wherein the second target gene(s) is/are glnA, amtB, glnB, glnK, glnZ, nifL, and/or draT and the fertilizer is ammonia;

(n) a site-specific recombinase (SSR) or integrase protein, wherein a control element comprising a promoter and/or at least a segment of a 5' UTR: (i) is flanked by site-specific recombinase recognition sites (SSRRS) in an inverted configuration; and (ii) is operably linked to one or more second target gene(s) of the genetically engineered bacterium; optionally wherein the control element which is operably linked to said second target gene(s) comprises a constitutive promoter, an inducible promoter, or a phosphate-sensitive promoter; and/or optionally wherein the second target gene(s) is/are glnA, amtB, glnB, glnK, glnZ, nifL, and/or draT and the fertilizer is ammonia;

(o) a site-specific recombinase (SSR) or integrase protein, wherein a control element comprising a promoter and at least a segment of a 5' UTR: (i) is flanked by site-specific recombinase recognition sites (SSRRS) in an inverted configuration; and (ii) is operably linked to one or more second target gene(s) of the genetically engineered bacterium upon inversion by the SSR or integrase; optionally wherein the control element which is operably linked to said second target gene(s) upon inversion by the SSR or integrase comprises a constitutive promoter, an inducible promoter, or a phosphate-sensitive promoter; and/or optionally wherein the second target gene(s) is/are: (a) nifA, ntrC, glnR, a gene encoding a glutaminase enzyme, a gene encoding a GlnE protein lacking an adenylyl removing domain which exhibits unidirectional adenylyltransferase (uAT) activity, one or more nif cluster gene(s), and/or one or more fix cluster gene(s) and the agriculturally relevant compound is ammonia; or (b) a gene encoding a phytase enzyme, optionally wherein the phytase enzyme comprises a cysteine phytase, a histidine acid phytase, or a beta-propeller phytase, a gene encoding an acid phosphatase enzyme, optionally wherein the acid phosphatase is encoded by an acpA, aphA, phoC, napA, napD, or napE gene or variant thereof, or a gene encoding a protein which stimulates organic acid release from the bacterium, optionally wherein the protein which stimulates organic acid release comprises a gluconate dehydrogenase (GAD), a glucose dehydrogenase (GDH), or a pyrroloquinoline (PQQ) synthase, and the agriculturally relevant compound is phosphate;

(p) a site-specific DNA endonuclease, wherein any one or more second target gene(s) of the genetically engineered bacterium comprise(s) one or more specific DNA sequence(s) recognized by the site-specific DNA endonuclease, optionally wherein the site-specific DNA endonuclease comprises an RNA-guided DNA endonuclease, a protein comprising a DNA-binding zinc finger domain, a transcription activator-like effector (TALE), a meganuclease, a homing endonuclease, or a restriction endonuclease, and/or optionally wherein the second target gene(s) is/are glnA, amtB, glnB, glnK, glnZ, nifL, and/or draT and the fertilizer is ammonia;

(q) a protease which cleaves a protease specific recognition sequence (PSRS), wherein any one or more second target gene(s) of the genetically engineered bacterium comprise(s) one or more in-frame insertion(s) comprising DNA encoding the PSRS in the protein coding region of the second target gene(s), wherein the target protein product comprising the one or more in-frame insertion(s) has activity, and wherein cleavage of the target protein product(s) by the protease deactivates the target protein product(s), optionally wherein the location of the one or more in-frame insertion is given by Table 6, optionally wherein the second target gene is under the control of a constitutive promoter, and/or optionally wherein the second target gene(s) is/are glnA, amtB, glnB, glnK, glnZ, nifL, and/or draT and the fertilizer is ammonia;

(r) a first protein comprising a ClpAP ATP-dependent protease and a second protein comprising a ClpS Leu/N-recognin, wherein any one or more second target gene(s) of the genetically engineered bacterium encodes a third protein comprising an N-terminal -Leu, -Phe, -Trp, or -Tyr residue, and optionally wherein the first and second protein are operably linked to distinct control elements, and/or optionally wherein the second target gene(s) is/are glnA, amtB, glnB, glnK, glnZ, nifL, and/or draT and the fertilizer is ammonia;

(s) a protease which cleaves a protease specific recognition sequence (PSRS), wherein any one or more second target gene(s) of the genetically engineered bacterium comprise(s) an in-frame insertion(s) of DNA encoding the PSRS at the N-terminus of the protein coding region of the gene(s) followed by a -Leu, -Phe, -Trp, or -Tyr residue and wherein cleavage of PSRS from the N-terminus of the protein(s) encoded by the gene(s) by the protease results in a protein comprising an N-terminal -Leu, -Phe, -Trp, or -Tyr residue which is degraded by native ClpS and ClpAP, optionally wherein the second target gene(s) is/are glnA, amtB, glnB, glnK, glnZ, nifL, and/or draT and the fertilizer is ammonia;

(t) a transcriptional activator protein, wherein the transcriptional activator protein binds a natural or synthetic DNA motif in a promoter of a heterologous protease gene of the genetically engineered bacterium and activates expression of the protease, wherein any one or more second target gene(s) of the genetically engineered bacterium comprise(s) one or more in-frame insertion(s) of DNA encoding a PSRS, optionally wherein the transcriptional activator protein comprises a tet responsive element-binding tTA transcription factor or a transcriptional activator domain fused to a DNA targeting protein, optionally wherein the DNA targeting protein is a catalytically inactive RNA-guided DNA binding protein, a protein comprising a DNA-binding zinc finger domain, a transcription activator-like effector (TALE), or any variant thereof, optionally wherein the transcriptional activator domain is VP16, and/or optionally wherein the second target gene(s) is/are: glnA, amtB, glnB, glnK, glnZ, nifL, and/or draT and the fertilizer is ammonia;

(u) a repressor protein, wherein the repressor protein binds a natural or synthetic DNA motif in a promoter of a heterologous protease gene of the genetically engineered bacterium and inhibits expression of the protease, wherein any one or more second target gene(s) of the genetically engineered bacterium comprise(s) an in-frame insertion of DNA encoding an N-terminal amino acid tag designed to render the protein product(s) of the second target gene(s) inactive, followed by a PSRS, optionally wherein the repressor protein comprises the lambda repressor (cI), the tet repressor (TetR), the lac repressor (LacI), a catalytically inactive RNA-guided DNA binding protein, a protein comprising a DNA-binding zinc finger domain, a transcription activator-like effector (TALE), or any variant thereof, and/or optionally wherein the second target gene(s) is/are glnA, amtB, glnB, glnK, glnZ, nifL, and/or draT and the fertilizer is ammonia;

(v) a nanobody, wherein the nanobody binds a protein product of any one or more second target gene(s) of the genetically engineered bacterium, wherein binding of the nanobody to such protein product inhibits function of the protein product, optionally wherein the second target gene(s) is/are glnA, amtB, glnB, glnK, glnZ, nifL, and/or draT and the fertilizer is ammonia;

(w) an aptamer, wherein the aptamer binds a protein product of any one or more second target gene(s) of the genetically engineered bacterium and inhibits function of any one or more of the protein product(s) of the second target gene(s), optionally wherein the second target gene(s) is/are glnA, amtB, glnB, glnK, glnZ, nifL, and/or draT and the fertilizer is ammonia; or (x) a transcriptional activator protein, wherein the transcriptional activator protein binds a natural or synthetic DNA motif in a promoter of any one or more second target gene(s) and increases expression of any one or more of the second target gene(s), optionally wherein the transcriptional activator protein comprises the tet responsive element-binding tTA transcription factor or a transcriptional activator domain fused to a DNA targeting protein, wherein the DNA targeting protein is optionally a catalytically inactive RNA-guided DNA binding protein, a protein comprising a DNA-binding zinc finger domain, a transcription activator-like effector (TALE), or any variant thereof, wherein the transcriptional activator domain is optionally VP16 and/or optionally wherein the second target gene(s) is/are any one or more of: (a) nifA, ntrC, glnR, a gene encoding a glutaminase enzyme, a gene encoding a GlnE protein lacking an adenylyl removing domain which exhibits unidirectional adenylyltransferase (uAT) activity, one or more nif cluster gene(s), and/or one or more fix cluster gene(s) and the agriculturally relevant compound is ammonia; or (b) a gene encoding a phytase enzyme, optionally wherein the phytase enzyme comprises a cysteine phytase, a histidine acid phytase, or a beta-propeller phytase, a gene encoding an acid phosphatase enzyme, optionally wherein the acid phosphatase is encoded by an acpA, aphA, phoC, napA, napD, or napE gene or variant thereof, and/or a gene encoding a protein which stimulates organic acid release from the bacterium, optionally wherein the protein which stimulates organic acid release comprises a gluconate dehydrogenase (GAD), a glucose dehydrogenase (GDH), or a pyrroloquinoline (PQQ) synthase and the agriculturally relevant compound is phosphate.

90. The genetically engineered bacterium of embodiment 83, wherein the genetically engineered bacterium comprises an odd number of repressors and the second target gene is amtB, draT, glnA, glnB, glnK, glnZ, and/or nifL, and the agriculturally relevant compound is ammonia.

91. The genetically engineered bacterium of any one of embodiments 1-73, wherein the protein of interest is a first transcriptional activator protein and wherein the genetically engineered bacterium further comprises:

(i) a second control element comprising a promoter which is activated by the first transcriptional activator protein and operably linked to a gene encoding a second transcriptional activator protein;

(ii) optionally a third control element comprising a promoter which is activated by the second transcriptional activator protein and operably linked to a gene encoding a third transcriptional activator protein;

(iii) optionally a fourth control element comprising a promoter which is activated by the third transcriptional activator protein and operably linked to a gene encoding a fourth transcriptional activator protein; and (iv) a control element comprising a promoter which is activated by the second, third, or fourth transcriptional activator protein and which is operably linked to a first target gene, optionally wherein the first, second, third, and/or fourth transcriptional activator protein comprise(s) the tet responsive element-binding tTA transcription factor or an activator domain fused to a DNA targeting protein, optionally wherein the DNA targeting protein is a catalytically inactive RNA-guided DNA binding protein, a protein comprising a DNA-binding zinc finger domain, a transcription activator-like effector (TALE), and/or any variant thereof, optionally wherein the activator domain is VP16.

92. The genetically engineered bacterium of embodiment 91, wherein the first target gene comprises: (a) nifA, ntrC, glnR, a gene encoding a glutaminase enzyme, a gene encoding a GlnE protein lacking an adenylyl removing domain which exhibits unidirectional adenylyltransferase (uAT) activity, one or more nif cluster gene(s), and/or one or more fix cluster gene(s) and the agriculturally relevant compound is ammonia; or (b) a gene encoding a phytase enzyme, optionally wherein the phytase enzyme comprises a cysteine phytase, a histidine acid phytase, or a beta-propeller phytase, a gene encoding an acid phosphatase enzyme, optionally wherein the acid phosphatase is encoded by an acpA, aphA, phoC, napA, napD, or napE gene or variant thereof, or a gene encoding a protein which stimulates organic acid release from the bacterium, optionally wherein the protein which stimulates organic acid release comprises a gluconate dehydrogenase (GAD), a glucose dehydrogenase (GDH), or a pyrroloquinoline (PQQ) synthase, and the agriculturally relevant compound is phosphate.

93. The genetically engineered bacterium of any one of embodiments 1-73, wherein the protein of interest is a repressor protein and wherein the genetically engineered bacterium further comprises:

(i) a second control element comprising a promoter which is repressed by the repressor protein and operably linked to a gene encoding a transcriptional activator protein; and (ii) a third control element comprising a promoter which is activated by the transcriptional activator protein and operably linked to a target gene.

94. The genetically engineered bacterium of embodiment 93, wherein the target gene is a glnA, amtB, glnB, glnK, glnZ, nifL, and/or draT gene and the agriculturally relevant compound is ammonia.

95. The genetically engineered bacterium of any one of embodiments 1-73, wherein the protein of interest is a transcriptional activator protein and wherein the genetically engineered bacterium further comprises:

(i) a second control element comprising a promoter which is activated by the transcriptional activator protein and operably linked to a gene encoding a repressor protein; and (ii) a third control element comprising a promoter which is repressed by the repressor and operably linked to a target gene.

96. The genetically engineered bacterium of embodiment 95, wherein the target gene is a glnA, amtB, glnB, glnK, glnZ, nifL, and/or draT gene and the agriculturally relevant compound is ammonia.

97. The genetically engineered bacterium of embodiment 73, wherein the glnA, amtB, glnB, glnK, glnZ, nifL, and/or draT gene in (n), (o), (p), or (q) is under the control of a heterologous constitutive promoter.

98. The method of embodiment 89, wherein the glnA, amtB, glnB, glnK, glnZ, nifL, and/or draT gene in (q), (r), (s), or (t) is under the control of a heterologous constitutive promoter.

99. The genetically engineered bacterium of any one of embodiments 1-72, wherein the plant nutrient is phosphate and the protein of interest operably linked to the control element comprises:

a. a phytase enzyme, optionally wherein the phytase enzyme comprises a cysteine phytase, a histidine acid phytase, or a beta-propeller phytase and/or optionally wherein the phytase enzyme comprises a protein sequence having at least 70%, 75%, 80%, 85%, 90%, 95%, 98%, or 99% sequence identity to SEQ ID NO: 58-138, or 139;

b. an acid phosphatase enzyme, optionally wherein the acid phosphatase is encoded by an acpA, aphA, phoC, napA, napD, or napE gene or variant thereof;

c. a protein which stimulates organic acid release from the bacterium, optionally wherein the protein comprises a gluconate dehydrogenase (GAD), a glucose dehydrogenase (GDH), a pyrroloquinoline (PQQ) synthase including pqqFABCDEG, or any combination of GAD, GDH, and PQQ; or, d. any combination of proteins of a, b, or c.

100. The genetically engineered bacterium of any one of embodiments 58 to 99, wherein: (i) the genetically engineered bacterium comprises the heterologous gene expression cassette in a bacterium originally isolated from a plant growth medium or a plant; and (ii) wherein the bacterium originally isolated from the plant growth medium or the plant lacks the heterologous gene expression cassette.

101. The genetically engineered bacterium of any one of embodiments 58 to 100, wherein the bacterium is selected from the group of gram-negative bacteria.

102. The genetically engineered bacterium of any one of embodiments 58 to 100, wherein the bacterium is selected from the groups of bacteria of the taxonomic classes of alphaproteobacteria, betaproteobacteria, and gammaproteobacteria.

103. The genetically engineered bacterium of any one of embodiments 58 to 100, wherein the bacterium is selected from the groups of bacteria in the taxonomic genera of *Acetobacter, Acidothermus, Acinetobacter, Agrobacterium, Aromatoleum, Arthrobacter, Azoarcus, Azorhizobium, Azospirillum, Azotobacter, Bacillus, Bifidobacterium, Bradyrhizobium, Burkholderia, Conexibacter, Curtobacterium, Ensifer, Enterobacter, Erwinia, Escherichia, Flavobacterium, Frankia, Gaiella, Gluconacetobacter, Gluconobacter, Herbaspirillum, Klebsiella, Kosakonia, Lactobacillus, Lactococcus, Lysinibacillus, Maritimibacter, Methylobacterium, Nitrosocosmicus, Nitrososphaera, Paenarthrobacter, Paenibacillus, Pantoea, Pediococcus, Peribacillus, Phytobacter, Priestia, Pseudarthrobacter, Pseudomonas, Rahnella, Rhizobium, Rhodococcus, Rhodoplanes, Rhodopseudomonas, Rhodospirillum, Serratia, Solirubrobacter, Sphingobacterium, Sphingomonas, Stenotrophomonas, Streptomyces, Stutzerimonas, Variovorax, Xanthobacter,* and *Yoonia,* optionally wherein the bacteria are selected from at least one of the taxonomic genera selected from the group consisting of *Herbaspirillum, Azospirillum, Kosakonia, Pseudomonas, Enterobacter, Klebsiella, Paenibacillus, Phytobacter, Rahnella, Sphingomonas,* or *Variovorax.*

104. A composition comprising the genetically engineered bacterium of any one of any one of embodiments 58 to 103 and an agriculturally acceptable carrier.

105. The composition of embodiment 104, wherein the composition further comprises:

(i) an agriculturally acceptable adjuvant, optionally wherein the adjuvant comprises an adhesive agent, a desiccant, and/or a dispersant;

(ii) a fungicide, an insecticide, a nematicide, a rodenticide, and/or a bacteriocide; and/or (iii) a fertilizer, optionally wherein the fertilizer comprises nitrogen, phosphorous, potassium, calcium, sulfur, magnesium, boron, chloride, manganese, iron, zinc, copper, molybdenum, and/or selenium.

106. The composition of embodiment 104 or 105, wherein the composition is in a solid form, optionally wherein the solid form comprises a wettable powder, granules, a gel, pellets, or microencapsulated particles.

107. The composition of embodiment 104, wherein the composition is in a liquid form, optionally wherein the liquid form comprises an aqueous solution, aqueous suspension, water-in-oil emulsion, an oil, or an alcohol.

108. A plant part or plant propagule which is at least partially coated, imbibed, or mixed with the composition of embodiment 104.

109. The plant part of embodiment 108, wherein the part is a leaf, stem, root, or seed.

110. The plant propagule of embodiment 108, wherein the propagule comprises a cutting, tuber, or stolon.

111. Use of the plant part or plant propagule of any one of embodiments 108-110 to grow a crop.

112. The use of embodiment 111, wherein fertilizer input is reduced in comparison to a crop grown from a plant part or plant propagule which has not been at least partially coated, imbibed, or mixed with the composition.

113. An agricultural system comprising:

(i) at least one engineered bacterium of any one of embodiments 58 to 103;

(ii) at least one plant growth medium; and (iii) at least one crop plant, crop plant seed, or crop plant vegetative propagule; wherein the plant growth medium, crop plant, crop seed, and/or crop plant propagule comprise, are at least partially coated, imbibed, and/or are mixed with the engineered bacterium or a composition comprising the engineered bacterium and an agriculturally acceptable carrier.

114. The system of embodiment 113, wherein the crop plant, seed, or vegetative propagule is an alfalfa, apple, banana, barley, bean, buckwheat, cabbage, cassava, chili, clover, coffee, corn, cotton, cowpea, cucumber, fonio, garlic, herb, lettuce, maize, melon, millet, nut, oat, oilseed rape, olive, onion, orange, sunflower, pea, *Phaseolus* bean, plantain, potato, *quinoa,* rice, rye, safflower, sorghum, soybean, sugar beet, sugar cane, sunflower, tangerine, tobacco, tomato, triticale, turnip, wheat, or yam plant, seed, or vegetative propagule.

115. The system of embodiment 113 or 114, wherein the plant growth medium comprises soil and/or water, optionally wherein the soil and/or water is non-axenic.

116. The system of embodiment 113, wherein the vegetative propagule comprises a cutting, tuber, or stolon.

117. A treated plant seed or plant propagule system comprising:

(i) at least one crop plant seed or crop plant vegetative propagule; and (ii) at least one engineered bacterium of any one of embodiments 58 to 103, wherein the crop plant seed or crop plant propagule are at least partially coated, imbibed, and/or mixed with the engineered bacterium or a composition comprising the engineered bacterium and an agriculturally acceptable carrier.

118. The system of embodiment 117, wherein the crop plant, seed, or vegetative propagule is an alfalfa, apple, banana, barley, bean, buckwheat, cabbage, cassava, chili, clover, coffee, corn, cotton, cowpea, cucumber, fonio, garlic, herb, lettuce, maize, melon, millet, nut, oat, oilseed rape, olive, onion, orange, sunflower, pea, *Phaseolus* bean, plantain, potato, *quinoa*, rice, rye, safflower, sorghum, soybean, sugar beet, sugar cane, sunflower, tangerine, tobacco, tomato, triticale, turnip, wheat, or yam plant, seed, or vegetative propagule.

119. The system of embodiment 117 or 118, wherein the vegetative propagule comprises a cutting, tuber, or stolon.

120. A genetically engineered bacterium comprising: (i) a first recombinant DNA molecule comprising a phosphate-sensitive promoter of a bacterial pstS phosphate ABC transporter gene operably linked to DNA encoding a transcript comprising a ribosome binding site (RBS) operably linked to a transcriptional repressor protein coding region, wherein the RBS, when substituted in place of nucleotides 723 to 810 of control green fluorescent protein (GFP) reporter gene expression cassette of SEQ ID NO: 522, provides 0.1% to 44% of operably linked GFP reporter gene expression provided by the control GFP reporter gene expression cassette of SEQ ID NO: 522 when expressed under otherwise identical conditions; and (ii) a second recombinant DNA molecule comprising a promoter which is repressed by the transcriptional repressor protein and which is operably linked to DNA encoding a bacterial glutamine synthetase, wherein the genetically engineered bacterium is of the genus *Kosakonia*.

121. The bacterium of embodiment 120, wherein the bacterial pstS phosphate ABC transporter gene is a *Klebsiella* sp., *Klebsiella variicola*, *Kosakonia* sp., or *Kosakonia sacchari* pstS phosphate ABC transporter gene.

122. The bacterium of embodiment 120 or 121, wherein the bacterial pstS phosphate ABC transporter gene encodes a phosphate ABC transporter protein having at least 76%, 80%, 85%, 90%, 95%, 98%, or 99% sequence identity to SEQ ID NO: 513 and comprising the polypeptide of SEQ ID NO: 514.

123. The bacterium of any one of embodiments 1 to 119, 120, or 121, wherein the phosphate-sensitive promoter comprises a sequence having at least 76%, 80%, 85%, 90%, 95%, 98%, or 99% 95% sequence identity to SEQ ID NO: 515 and comprising at least one Pho box comprising the DNA molecule of SEQ ID NO: 525, 526, 527, 528, and/or 529.

124. The bacterium of any one of embodiments 120 to 123, wherein the transcriptional repressor protein is a bacterial TetR protein.

125. The bacterium of any one of embodiments 120 to 124, wherein the ribosome binding site (RBS) which is operably linked to a transcriptional repressor protein coding region comprises a BCD22vL ribosome binding site encoded by SEQ ID NO: 449.

126. The bacterium of any one of embodiments 120 to 125, wherein transcriptional repressor protein coding region encodes a bacterial TetR transcriptional repressor protein having at least 80%, 85%, 90%, 95%, 98%, or 99% sequence identity to SEQ ID NO: 516.

127. The bacterium of embodiment 126, wherein transcriptional repressor protein coding region encodes a bacterial TetR transcriptional repressor protein comprising the amino acid sequence of SEQ ID NO: 516.

128. The bacterium of any one of embodiments 120 to 127, wherein the bacterial glutamine synthetase is an *Azospirillum* glutamine synthetase and the endogenous gene encoding the *Kosakonia* glutamine synthetase protein contains a null mutation or is deleted.

129. The bacterium of any one of embodiments 120 to 127, wherein the bacterial glutamine synthetase comprises a *Kosakonia* glutamine synthetase.

130. The bacterium of embodiment 129, wherein the *Kosakonia* glutamine synthetase is encoded by the endogenous *Kosakonia* gene and wherein the endogenous *Kosakonia* gene is operably linked to the promoter which is repressed by the TetR repressor protein.

131. The bacterium of embodiment 120, wherein: (i) the first recombinant DNA molecule comprises the *Klebsiella variicola* pstS phosphate-sensitive promoter having at least 80%, 85%, 90%, 95%, 98%, or 99% sequence identity to SEQ ID NO: 515, the BCD22vL ribosome binding site (RBS) of SEQ ID NO: 449, and the transcriptional repressor protein comprising the amino acid sequence having at least 95% sequence identity to SEQ ID NO: 516; and (ii) the second recombinant DNA molecule comprises the Ptet promoter having at least 80%, 85%, 90%, 95%, 98%, or 99% sequence identity to SEQ ID NO: 32, and the bacterial glutamine synthetase is a glutamine synthetase having at least 80%, 85%, 90%, 95%, 98%, or 99% sequence identity to SEQ ID NO: 229.

132. A composition comprising the genetically engineered bacterium of any one of embodiments 120 to 131 and an agriculturally acceptable carrier.

133. The composition of embodiment 132, wherein the composition further comprises: (i) an agriculturally acceptable adjuvant, optionally wherein the adjuvant comprises an adhesive agent, a desiccant, and/or a dispersant; (ii) a fungicide, an insecticide, a nematicide, a rodenticide, and/or a bacteriocide; and/or (iii) a fertilizer, optionally wherein the fertilizer comprises nitrogen, phosphorous, potassium, calcium, sulfur, magnesium, boron, chloride, manganese, iron, zinc, copper, molybdenum, and/or selenium.

134. A plant part or plant propagule which is at least partially coated, imbibed, or mixed with the composition of embodiment 132 or 133.

135. A method of providing nitrogen to a plant comprising placing the one genetically engineered bacterium of any one of embodiments 120 to 131 or the composition of embodiment 132 or 133 into a plant growth medium, wherein a decrease in phosphate concentration in the plant growth medium results in the production of ammonia which is provided to the plant when grown in the growth medium.

136. The method of embodiment 135, wherein the plant growth medium comprises soil and/or water, optionally wherein the soil and/or water is non-axenic.

137. The method of embodiment 135 or 136, wherein the placing is prior to, during, and/or after depositing a seed or vegetative propagule in the plant growth medium.

138. The method of any one of embodiments 135 to 137, wherein the plant growth medium has been treated by adding inorganic phosphate to the plant growth medium at a rate of about 3 g/m$^2$ to about 15 g/m$^2$.

139. The method of any one of embodiments 135 to 138, further comprising: (i) determining leaf nitrogen and/or chlorophyll concentrations in a plant grown in the plant growth medium; and (ii) placing or re-applying the genetically engineered bacterium into the plant growth medium and/or in contact with the plant when the leaf nitrogen and/or chlorophyll concentrations in the plant are sub-optimal for yield.

140. An agricultural system comprising: (i) at least one engineered bacterium of any one of embodiments 120 to 131; (ii) at least one plant growth medium; and (iii) at least one crop plant, crop plant seed, or crop plant vegetative propagule; wherein the plant growth medium, crop plant, crop seed, and/or crop plant propagule comprise, are at least partially coated, imbibed, and/or are mixed with the engineered bacterium or a composition comprising the engineered bacterium and an agriculturally acceptable carrier.

141. The system of embodiment 140, wherein the crop plant, seed, or vegetative propagule is an alfalfa, apple, banana, barley, bean, buckwheat, cabbage, cassava, chili, clover, coffee, corn, cotton, cowpea, cucumber, fonio, garlic, herb, lettuce, maize, melon, millet, nut, oat, oilseed rape, olive, onion, orange, sunflower, pea, *Phaseolus* bean, plantain, potato, *quinoa*, rice, rye, safflower, sorghum, soybean, sugar beet, sugar cane, sunflower, tangerine, tobacco, tomato, triticale, turnip, wheat, or yam plant, seed, or vegetative propagule.

142. The system of embodiment 140 or 141, wherein the plant growth medium comprises soil and/or water, optionally wherein the soil and/or water is non-axenic.

143. The system of any one of embodiments 140 to 142, wherein the vegetative propagule comprises a cutting, tuber, or stolon.

144. A treated plant seed or plant propagule system comprising: (i) at least one crop plant seed or crop plant vegetative propagule; and (ii) at least one engineered bacterium of any one of embodiments 120 to 131, wherein the crop plant seed or crop plant propagule are at least partially coated, imbibed, and/or mixed with the engineered bacterium or a composition comprising the engineered bacterium and an agriculturally acceptable carrier.

145. The system of embodiment 144, wherein the crop plant, seed, or vegetative propagule is an alfalfa, apple, banana, barley, bean, buckwheat, cabbage, cassava, chili, clover, coffee, corn, cotton, cowpea, cucumber, fonio, garlic, herb, lettuce, maize, melon, millet, nut, oat, oilseed rape, olive, onion, orange, sunflower, pea, *Phaseolus* bean, plantain, potato, *quinoa*, rice, rye, safflower, sorghum, soybean, sugar beet, sugar cane, sunflower, tangerine, tobacco, tomato, triticale, turnip, wheat, or yam plant, seed, or vegetative propagule.

In the description, tables, and numbered embodiments 1-145 set forth herein, genes and the proteins they encode which are referred to solely by name include genes and proteins identified in Table 5 and the sequence listing, include genes having at least 70%, 75%, 76%, 80%, 85%, 90%, 95%, 98%, or 99% identity to the genes identified in Table 5 and the sequence listing, and include proteins having at least 70%, 75%, 80%, 85%, 90%, 95%, 98%, or 99% identity to the proteins identified in Table 5 and the sequence listing. GlnE proteins lacking an adenylyl removing domain which exhibit unidirectional adenylyltransferase (uAT) activity referred to solely by name in the preceding description, tables, and numbered embodiments include proteins comprising a protein sequence having at least 70%, 80%, 85%, 90%, 95%, 98%, or 99% identity to SEQ ID NO: 16-24, or 25. Genes encoding GlnE proteins lacking an adenylyl removing domain which exhibit unidirectional adenylyltransferase (uAT) activity referred to solely by name in the preceding description, tables, and numbered embodiments include genes comprising a DNA sequence having at least 70%, 80%, 85%, 90%, 95%, 98%, or 99% identity to SEQ ID NO: 1-14, or 15. Wild-type GlnA proteins (glutamine synthetase or GS proteins) referred to solely by name in the preceding description, tables, and numbered embodiments include proteins having a protein sequence having at least 70%, 80%, 85%, 90%, 95%, 98%, or 99% identity to SEQ ID NO: 229, 230, 460-512, 519-521, 530-532, or 533. Wild-type glnA genes encoding wild-type GlnA proteins referred to solely by name in the preceding description, tables, and numbered embodiments include glnA genes encoding proteins having a protein sequence having at least 70%, 80%, 85%, 90%, 95%, 98%, or 99% identity to SEQ ID NO: 229, 230, 460-512, 519-521, 530-532, or 533. Phytases referred to solely by name in the preceding description, tables, and numbered embodiments include phytases comprising a protein sequence having at least 70%, 75%, 80%, 85%, 90%, 95%, 98%, or 99% sequence identity to SEQ ID NO: 58-138, or 139. Phytase or phy genes referred to solely by name in the preceding description, tables, and numbered embodiments include phytase genes encoding phytase proteins comprising a protein sequence having at least 70%, 75%, 80%, 85%, 90%, 95%, 98%, or 99% sequence identity to SEQ ID NO: 58-138, or 139.

TABLE 5

| Description | SEQ ID NO | Type | Organism name |
| --- | --- | --- | --- |
| *E. coli* uAT10 gene (glnE 423-946) | 1 | DNA | synthetic construct |
| uAT10r2 gene (Codon refactored uAT10 for *A. brasilense*) | 2 | DNA | synthetic construct |
| uAT10r3 gene (Codon refactored uAT10 for *A. brasilense*) | 3 | DNA | synthetic construct |
| uAT10r4 gene (Codon refactored uAT10 for *A. brasilense*) | 4 | DNA | synthetic construct |
| uAT10r5 gene (Codon refactored uAT10 for *A. brasilense*) | 5 | DNA | synthetic construct |
| *E. coli* uAT11 gene (glnE 609-946) | 6 | DNA | synthetic construct |

TABLE 5-continued

| Summary of Biological Sequences in Sequence Listing | | | |
| --- | --- | --- | --- |
| Description | SEQ ID NO | Type | Organism name |
| *A. brasilense* uAT21 gene (glnE 449-1003) | 7 | DNA | synthetic construct |
| *A. brasilense* uAT22 gene (glnE 481-1003) | 8 | DNA | synthetic construct |
| *A. brasilense* uAT23 gene (glnE 506-1003) | 9 | DNA | synthetic construct |
| *A. brasilense* uAT24 gene (glnE 529-1003) | 10 | DNA | synthetic construct |
| *A. brasilense* uAT25 gene (glnE 625-1003) | 11 | DNA | synthetic construct |
| uAT23r2 gene (Codon refactored uAT23 gene) | 12 | DNA | synthetic construct |
| *A. caulinodans* uAT-Ac1 gene (glnE 528-996) | 13 | DNA | synthetic construct |
| *A. caulinodans* uAT-Ac2 gene (glnE 538-996) | 14 | DNA | synthetic construct |
| *A. caulinodans* uAT-Ac3 gene (glnE 548-996) | 15 | DNA | synthetic construct |
| *E. coli* uAT10 protein (GlnE 423-946) | 16 | PRT | synthetic construct |
| *E. coli* uAT11 protein (GlnE 609-946) | 17 | PRT | synthetic construct |
| *A. brasilense* uAT21 protein (GlnE 449-1003) | 18 | PRT | synthetic construct |
| *A. brasilense* uAT22 protein (GlnE 481-1003) | 19 | PRT | synthetic construct |
| *A. brasilense* uAT23 protein (GlnE 506-1003) | 20 | PRT | synthetic construct |
| *A. brasilense* uAT24 protein (GlnE 529-1003) | 21 | PRT | synthetic construct |
| *A. brasilense* uAT25 protein (GlnE 625-1003) | 22 | PRT | synthetic construct |
| *A. caulinodans* uAT-Ac1 protein (GlnE 528-996) | 23 | PRT | synthetic construct |
| *A. caulinodans* uAT-Ac2 protein (GlnE 538-996) | 24 | PRT | synthetic construct |
| *A. caulinodans* uAT-Ac3 protein (GlnE 548-996) | 25 | PRT | synthetic construct |
| Lambda repressor protein (cI) | 26 | PRT | synthetic construct |
| Tet repressor protein (TetR) | 27 | PRT | synthetic construct |
| Reverse tet repressor protein (rTetR) | 28 | PRT | synthetic construct |
| Lac repressor protein (LacI) | 29 | PRT | synthetic construct |
| PhlF repressor protein (PhlF) | 30 | PRT | synthetic construct |
| pR promoter (binds cl repressor) | 31 | DNA | synthetic construct |
| Ptet promoter (binds TetR repressors) | 32 | DNA | synthetic construct |
| Plac promoter (binds lac repressor) | 33 | DNA | synthetic construct |
| PphlA promoter (binds PhIF repressor) | 34 | DNA | synthetic construct |
| PhiC31 integrase protein | 35 | PRT | synthetic construct |
| IntM integrase protein | 36 | PRT | synthetic construct |
| IntS integrase protein | 37 | PRT | synthetic construct |
| IntG integrase protein | 38 | PRT | synthetic construct |
| YdcL integrase protein | 39 | PRT | synthetic construct |
| Sxt/R391 integrase protein | 40 | PRT | synthetic construct |
| PhiC31 integrase gene | 41 | DNA | synthetic construct |
| PhiC31 integrase attP recombinase recognition site | 42 | DNA | synthetic construct |
| PhiC31 integrase attB recombinase recognition site | 43 | DNA | synthetic construct |
| J23104 constitutive promoter | 44 | DNA | synthetic construct |

TABLE 5-continued

Summary of Biological Sequences in Sequence Listing

| Description | SEQ ID NO | Type | Organism name |
|---|---|---|---|
| Tobacco etch virus (TEV) protease (P04517) | 45 | PRT | synthetic construct |
| Tobacco vein mottling virus (TVMV) protease (P09814) | 46 | PRT | synthetic construct |
| Sunflower mild mosaic virus (SMMV) protease | 47 | PRT | synthetic construct |
| Turnip mosaic virus (TuMV) protease (Q02597) | 48 | PRT | synthetic construct |
| Soybean mosaic virus (SMV) protease (Q90069) | 49 | PRT | synthetic construct |
| Plum pox potyvirus (PPV) protease (P17767) | 50 | PRT | synthetic construct |
| Hepatitis C virus (HCV) protease (P27958) | 51 | PRT | synthetic construct |
| Coagulation factor Xa (P00742) | 52 | PRT | *Homo sapiens* |
| Furin (P09958) | 53 | PRT | *Homo sapiens* |
| TEV protease coding sequence optimized for *A. brasilense* | 54 | DNA | synthetic construct |
| TVMV protease coding sequence optimized for *A. brasilense* | 55 | DNA | synthetic construct |
| SMMV protease coding sequence optimized for *A. brasilense* | 56 | DNA | synthetic construct |
| *B. subtilis* phytase protein (PhyC) | 57 | PRT | *Bacillus subtilis* |
| Phytase protein (HAP) | 58 | PRT | unidentified |
| Phytase protein (BPP) | 59 | PRT | unidentified |
| Phytase protein (CPhy) | 60 | PRT | *Clostridium colicanis* |
| Phytase protein (BPP) | 61 | PRT | *Chlorobaculum limnaeum* |
| Phytase protein (BPP) | 62 | PRT | *Bacillus amyloliquefaciens* |
| Phytase protein (CPhy) | 63 | PRT | *Cystobacter fuscus* |
| Phytase protein (HAP) | 64 | PRT | *Acinetobacter baumannii* |
| Phytase protein (CPhy) | 65 | PRT | unidentified |
| Phytase protein (CPhy) | 66 | PRT | *Clostridium ihumii* |
| Phytase protein (CPhy) | 67 | PRT | *Desulfovibrio fructosovorans* |
| Phytase protein (CPhy) | 68 | PRT | *Clostridium novyi* |
| Phytase protein (CPhy) | 69 | PRT | *Clostridium bornimense* |
| Phytase protein (HAP) | 70 | PRT | *Bacteroides stercorirosoris* |
| Phytase protein (CPhy) | 71 | PRT | *Clostridium paraputrificum* |
| Phytase protein (CPhy) | 72 | PRT | *Clostridium pasteurianum* |
| Phytase protein (CPhy) | 73 | PRT | *Clostridium perfringens* |
| Phytase protein (CPhy) | 74 | PRT | *Clostridium botulinum* |
| Phytase protein (CPhy) | 75 | PRT | unidentified |
| Phytase protein (CPhy) | 76 | PRT | *Acidovorax avenae* |

TABLE 5-continued

| | SEQ | | |
|---|---|---|---|
| Description | ID NO | Type | Organism name |
| Phytase protein (CPhy) | 77 | PRT | *Clostridium* sp. |
| Phytase protein (CPhy) | 78 | PRT | *Clostridium* sp. |
| Phytase protein (CPhy) | 79 | PRT | *Acidaminococcus* sp. |
| Phytase protein (CPhy) | 80 | PRT | *Anaerovibrio lipolyticus* |
| Phytase protein (BPP) | 81 | PRT | *Cellulophaga* sp. |
| Phytase protein (HAP) | 82 | PRT | *Bifidobacterium dentium* |
| Phytase protein (BPP) | 83 | PRT | *Chryseobacterium* sp. |
| Phytase protein (BPP) | 84 | PRT | *Erythrobacter litoralis* |
| Phytase protein (BPP) | 85 | PRT | unidentified |
| Phytase protein (BPP) | 86 | PRT | *Devosia riboflavina* |
| Phytase protein (CPhy) | 87 | PRT | *Bradyrhizobium* sp. |
| Phytase protein (BPP) | 88 | PRT | *Algoriphagus marincola* |
| Phytase protein (HAP) | 89 | PRT | *Bryobacter aggregatus* |
| Phytase protein (BPP) | 90 | PRT | *Asticcacaulis* sp. |
| Phytase protein (BPP) | 91 | PRT | unidentified |
| Phytase protein (BPP) | 92 | PRT | *Bacillus licheniformis* |
| Phytase protein (BPP) | 93 | PRT | *Deinococcus proteolyticus* |
| Phytase protein (HAP) | 94 | PRT | unidentified |
| Phytase protein (BPP) | 95 | PRT | *Bacillus* sp. |
| Phytase protein (BPP) | 96 | PRT | *Saccharicrinis fermentans* |
| Phytase protein (HAP) | 97 | PRT | *Asticcacaulis benevestitus* |
| Phytase protein (BPP) | 98 | PRT | *Amycolatopsis orientalis* |
| Phytase protein (HAP) | 99 | PRT | *Asticcacaulis benevestitus* |
| Phytase protein (HAP) | 100 | PRT | *Acidobacteriaceae* sp. |
| Phytase protein (HAP) | 101 | PRT | *Bacteroides* sp. |
| Phytase protein (HAP) | 102 | PRT | *Barnesiella intestinihominis* |
| Phytase protein (HAP) | 103 | PRT | *Endozoicomonas elysicola* |
| Phytase protein (HAP) | 104 | PRT | *Asaia astilbes* |
| Phytase protein (HAP) | 105 | PRT | *Alistipes timonensis* |
| Phytase protein (HAP) | 106 | PRT | unidentified |
| Phytase protein (HAP) | 107 | PRT | unidentified |
| Phytase protein (HAP) | 108 | PRT | *Desulfovibrio piger* |
| Phytase protein (BPP) | 109 | PRT | *Chitinibacter* sp. |
| Phytase protein (BPP) | 110 | PRT | *Caulobacter* sp. |
| Phytase protein (HAP) | 111 | PRT | *Butyrivibrio* sp. |

TABLE 5-continued

| Description | SEQ ID NO | Type | Organism name |
|---|---|---|---|
| Phytase protein (HAP) | 112 | PRT | *Desulfatirhabdium butyrativorans* |
| Phytase protein (BPP) | 113 | PRT | *Cystobacter fuscus* |
| Phytase protein (BPP) | 114 | PRT | unidentified |
| Phytase protein (BPP) | 115 | PRT | *Microbulbifer agarilyticus* |
| Phytase protein (BPP) | 116 | PRT | *Acinetobacter nectaris* |
| Phytase protein (BPP) | 117 | PRT | *Catenovulum agarivorans* |
| Phytase protein (HAP) | 118 | PRT | *Corynebacterium timonense* |
| Phytase protein (BPP) | 119 | PRT | *Alteromonas macleodii* |
| Phytase protein (CPhy) | 120 | PRT | *Clostridium* sp. |
| Phytase protein (CPhy) | 121 | PRT | *Clostridium beijerinckii* |
| Phytase protein (CPhy) | 122 | PRT | *Bdellovibrio bacteriovorus* |
| Phytase protein (CPhy) | 123 | PRT | *Clostridium tyrobutyricum* |
| Phytase protein (CPhy) | 124 | PRT | *Acidaminococcus fermentans* |
| Phytase protein (CPhy) | 125 | PRT | *Desulfovibrio alcoholivorans* |
| Phytase protein (CPhy) | 126 | PRT | *Desulfovibrio frigidus* |
| Phytase protein (CPhy) | 127 | PRT | *Clostridium acetobutylicum* |
| Phytase protein (CPhy) | 128 | PRT | *Allisonella histaminiformans* |
| Phytase protein (CPhy) | 129 | PRT | *Centipeda periodontii* |
| Phytase protein (CPhy) | 130 | PRT | *Desulfovibrio magneticus* |
| Phytase protein (HAP) | 131 | PRT | *Burkholderiales bacterium* |
| Phytase protein (HAP) | 132 | PRT | *Acinetobacter nectaris* |
| Phytase protein (HAP) | 133 | PRT | *Dyella marensis* |
| Phytase protein (HAP) | 134 | PRT | *Escherichia coli* |
| Phytase protein (HAP) | 135 | PRT | *Anaerovibrio* sp. |
| Phytase protein (HAP) | 136 | PRT | *Avibacterium paragallinarum* |
| Phytase protein (HAP) | 137 | PRT | *Cronobacter sakazakii* |
| Phytase protein (HAP) | 138 | PRT | unidentified |
| Phytase protein (HAP) | 139 | PRT | *Corynebacterium singulare* |
| *B. subtilis* phytase coding sequence (phyC) | 140 | DNA | *Bacillus subtilis* |
| Phytase coding sequence (HAP) | 141 | DNA | unidentified |

TABLE 5-continued

Summary of Biological Sequences in Sequence Listing

| Description | SEQ ID NO | Type | Organism name |
|---|---|---|---|
| Phytase coding sequence (BPP) | 142 | DNA | unidentified |
| Phytase coding sequence (CPhy) | 143 | DNA | *Clostridium colicanis* |
| Phytase coding sequence (BPP) | 144 | DNA | *Chlorobaculum limnaeum* |
| Phytase coding sequence (BPP) | 145 | DNA | *Bacillus amyloliquefaciens* |
| Phytase coding sequence (CPhy) | 146 | DNA | *Cystobacter fuscus* |
| Phytase coding sequence (HAP) | 147 | DNA | *Acinetobacter baumannii* |
| Phytase coding sequence (CPhy) | 148 | DNA | unidentified |
| Phytase coding sequence (CPhy) | 149 | DNA | *Clostridium ihumii* |
| Phytase coding sequence (CPhy) | 150 | DNA | *Desulfovibrio fructosovorans* |
| Phytase coding sequence (CPhy) | 151 | DNA | *Clostridium novyi* |
| Phytase coding sequence (CPhy) | 152 | DNA | *Clostridium bornimense* |
| Phytase coding sequence (HAP) | 153 | DNA | *Bacteroides stercorirosoris* |
| Phytase coding sequence (CPhy) | 154 | DNA | *Clostridium paraputrificum* |
| Phytase coding sequence (CPhy) | 155 | DNA | *Clostridium pasteurianum* |
| Phytase coding sequence (CPhy) | 156 | DNA | *Clostridium perfringens* |
| Phytase coding sequence (CPhy) | 157 | DNA | *Clostridium botulinum* |
| Phytase coding sequence (CPhy) | 158 | DNA | unidentified |
| Phytase coding sequence (CPhy) | 159 | DNA | *Acidovorax avenae* |
| Phytase coding sequence (CPhy) | 160 | DNA | *Clostridium* sp. |
| Phytase coding sequence (CPhy) | 161 | DNA | *Clostridium* sp. |
| Phytase coding sequence (CPhy) | 162 | DNA | *Acidaminococcus* sp. |
| Phytase coding sequence (CPhy) | 163 | DNA | *Anaerovibrio lipolyticus* |
| Phytase coding sequence (BPP) | 164 | DNA | *Cellulophaga* sp. |
| Phytase coding sequence (HAP) | 165 | DNA | *Bifidobacterium dentium* |
| Phytase coding sequence (BPP) | 166 | DNA | *Chryseobacterium* sp. |
| Phytase coding sequence (BPP) | 167 | DNA | *Erythrobacter litoralis* |
| Phytase coding sequence (BPP) | 168 | DNA | unidentified |
| Phytase coding sequence (BPP) | 169 | DNA | *Devosia riboflavina* |
| Phytase coding sequence (CPhy) | 170 | DNA | *Bradyrhizobium* sp. |
| Phytase coding sequence (BPP) | 171 | DNA | *Algoriphagus marincola* |
| Phytase coding sequence (HAP) | 172 | DNA | *Bryobacter aggregatus* |
| Phytase coding sequence (BPP) | 173 | DNA | *Asticcacaulis* sp. |
| Phytase coding sequence (BPP) | 174 | DNA | unidentified |
| Phytase coding sequence (BPP) | 175 | DNA | *Bacillus licheniformis* |

TABLE 5-continued

Summary of Biological Sequences in Sequence Listing

| Description | SEQ ID NO | Type | Organism name |
|---|---|---|---|
| Phytase coding sequence (BPP) | 176 | DNA | *Deinococcus proteolyticus* |
| Phytase coding sequence (HAP) | 177 | DNA | unidentified |
| Phytase coding sequence (BPP) | 178 | DNA | *Bacillus* sp. |
| Phytase coding sequence (BPP) | 179 | DNA | *Saccharicrinis fermentans* |
| Phytase coding sequence (HAP) | 180 | DNA | *Asticcacaulis benevestitus* |
| Phytase coding sequence (BPP) | 181 | DNA | *Amycolatopsis orientalis* |
| Phytase coding sequence (HAP) | 182 | DNA | *Asticcacaulis benevestitus* |
| Phytase coding sequence (HAP) | 183 | DNA | *Acidobacteriaceae* sp. |
| Phytase coding sequence (HAP) | 184 | DNA | *Bacteroides* sp. |
| Phytase coding sequence (HAP) | 185 | DNA | *Barnesiella intestinihominis* |
| Phytase coding sequence (HAP) | 186 | DNA | *Endozoicomonas elysicola* |
| Phytase coding sequence (HAP) | 187 | DNA | *Asaia astilbes* |
| Phytase coding sequence (HAP) | 188 | DNA | *Alistipes timonensis* |
| Phytase coding sequence (HAP) | 189 | DNA | unidentified |
| Phytase coding sequence (HAP) | 190 | DNA | unidentified |
| Phytase coding sequence (HAP) | 191 | DNA | *Desulfovibrio piger* |
| Phytase coding sequence (BPP) | 192 | DNA | *Chitinibacter* sp. |
| Phytase coding sequence (BPP) | 193 | DNA | *Caulobacter* sp. |
| Phytase coding sequence (HAP) | 194 | DNA | *Butyrivibrio* sp. |
| Phytase coding sequence (HAP) | 195 | DNA | *Desulfatirhabdium butyrativorans* |
| Phytase coding sequence (BPP) | 196 | DNA | *Cystobacter fuscus* |
| Phytase coding sequence (BPP) | 197 | DNA | unidentified |
| Phytase coding sequence (BPP) | 198 | DNA | *Microbulbifer agarilyticus* |
| Phytase coding sequence (BPP) | 199 | DNA | *Acinetobacter nectaris* |
| Phytase coding sequence (BPP) | 200 | DNA | *Catenovulum agarivorans* |
| Phytase coding sequence (HAP) | 201 | DNA | *Corynebacterium timonense* |
| Phytase coding sequence (BPP) | 202 | DNA | *Alteromonas macleodii* |
| Phytase coding sequence (CPhy) | 203 | DNA | *Clostridium* sp. |
| Phytase coding sequence (CPhy) | 204 | DNA | *Clostridium beijerinckii* |
| Phytase coding sequence (CPhy) | 205 | DNA | *Bdellovibrio bacteriovorus* |
| Phytase coding sequence (CPhy) | 206 | DNA | *Clostridium tyrobutyricum* |

TABLE 5-continued

Summary of Biological Sequences in Sequence Listing

| Description | SEQ ID NO | Type | Organism name |
|---|---|---|---|
| Phytase coding sequence (CPhy) | 207 | DNA | *Acidaminococcus fermentans* |
| Phytase coding sequence (CPhy) | 208 | DNA | *Desulfovibrio alcoholivorans* |
| Phytase coding sequence (CPhy) | 209 | DNA | *Desulfovibrio frigidus* |
| Phytase coding sequence (CPhy) | 210 | DNA | *Clostridium acetobutylicum* |
| Phytase coding sequence (CPhy) | 211 | DNA | *Allisonella histaminiformans* |
| Phytase coding sequence (CPhy) | 212 | DNA | *Centipeda periodontii* |
| Phytase coding sequence (CPhy) | 213 | DNA | *Desulfovibrio magneticus* |
| Phytase coding sequence (HAP) | 214 | DNA | *Burkholderiales bacterium* |
| Phytase coding sequence (HAP) | 215 | DNA | *Acinetobacter nectaris* |
| Phytase coding sequence (HAP) | 216 | DNA | *Dyella marensis* |
| Phytase coding sequence (HAP) | 217 | DNA | *Escherichia coli* |
| Phytase coding sequence (HAP) | 218 | DNA | *Anaerovibrio* sp. |
| Phytase coding sequence (HAP) | 219 | DNA | *Avibacterium para gallinarum* |
| Phytase coding sequence (HAP) | 220 | DNA | *Cronobacter sakazakii* |
| Phytase coding sequence (HAP) | 221 | DNA | unidentified |
| Phytase coding sequence (HAP) | 222 | DNA | *Corynebacterium singulare* |
| Gluconate 2-dehydrogenase cytochrome c subunit | 223 | PRT | *Pseudomonas putida* |
| Gluconate 2-dehydrogenase flavoprotein subunit | 224 | PRT | *Pseudomonas putida* |
| Gluconate 2-dehydrogenase gamma subunit | 225 | PRT | *Pseudomonas putida* |
| Acid phosphatase AcpA | 226 | PRT | *Burkholderia pseudomallei* |
| Acid Phosphatase (Pho C) | 227 | PRT | *Acetobacter pomorum* |
| Acid Phosphatase Morganella morganii aphA | 228 | PRT | *Morganella morganii* |
| *A. brasilense* glutamine synthetase protein (GlnA) | 229 | PRT | *Azospirillum brasilense* |
| *P. stutzeri* glutamine synthetase protein (GlnA) | 230 | PRT | *Pseudomonas stutzeri* |
| *A. brasilense* GS adenylyltransferase protein (GlnE) | 231 | PRT | *Azospirillum brasilense* |
| *A. caulinodans* GS adenylyltransferase protein (GlnE) | 232 | PRT | *Azorhizobium caulinodans* |
| *E. coli* GS adenylyltransferase protein (GlnE) | 233 | PRT | *Escherichia coli* |
| *E. coli* PhoB box 1 | 234 | DNA | *Escherichia coli* |
| *E. coli* PhoB box 2 | 235 | DNA | *Escherichia coli* |
| *E. coli* PhoB box 3 | 236 | DNA | *Escherichia coli* |
| *E. coli* PhoB box 4 | 237 | DNA | *Escherichia coli* |
| *E. coli* PhoB box 5 | 238 | DNA | *Escherichia coli* |

TABLE 5-continued

| | SEQ | | |
|---|---|---|---|
| Description | ID NO | Type | Organism name |
| *E. coli* PhoB box 6 | 239 | DNA | *Escherichia coli* |
| *E. coli* PhoB box 7 | 240 | DNA | *Escherichia coli* |
| *E. coli* PhoB box 8 | 241 | DNA | *Escherichia coli* |
| *E. coli* PhoB box 9 | 242 | DNA | *Escherichia coli* |
| *E. coli* PhoB box 10 | 243 | DNA | *Escherichia coli* |
| *E. coli* PhoB box 11 | 244 | DNA | *Escherichia coli* |
| *E. coli* PhoB box 12 | 245 | DNA | *Escherichia coli* |
| *E. coli* PhoB box 13 | 246 | DNA | *Escherichia coli* |
| *E. coli* PhoB box 14 | 247 | DNA | *Escherichia coli* |
| *E. coli* PhoB box 15 | 248 | DNA | *Escherichia coli* |
| *E. coli* PhoB box 16 | 249 | DNA | *Escherichia coli* |
| *E. coli* PhoB box 17 | 250 | DNA | *Escherichia coli* |
| *E. coli* PhoB box 18 | 251 | DNA | *Escherichia coli* |
| *E. coli* PhoB box 19 | 252 | DNA | *Escherichia coli* |
| *E. coli* PhoB box 20 | 253 | DNA | *Escherichia coli* |
| *E. coli* PhoB box 21 | 254 | DNA | *Escherichia coli* |
| *E. coli* PhoB box 22 | 255 | DNA | *Escherichia coli* |
| *E. coli* PhoB box 23 | 256 | DNA | *Escherichia coli* |
| *E. coli* PhoB box 24 | 257 | DNA | *Escherichia coli* |
| *E. coli* PhoB box 25 | 258 | DNA | *Escherichia coli* |
| *E. coli* PhoB box 26 | 259 | DNA | *Escherichia coli* |
| *E. coli* PhoB box 27 | 260 | DNA | *Escherichia coli* |
| *E. coli* PhoB box 28 | 261 | DNA | *Escherichia coli* |
| *E. coli* PhoB box 29 | 262 | DNA | *Escherichia coli* |
| *E. coli* PhoB box 30 | 263 | DNA | *Escherichia coli* |
| *E. coli* PhoB box 31 | 264 | DNA | *Escherichia coli* |
| *E. coli* PhoB box 32 | 265 | DNA | *Escherichia coli* |
| *E. coli* PhoB box 33 | 266 | DNA | *Escherichia coli* |
| *E. coli* PhoB box 34 | 267 | DNA | *Escherichia coli* |
| *E. coli* PhoB box 35 | 268 | DNA | *Escherichia coli* |
| *E. coli* PhoB box 36 | 269 | DNA | *Escherichia coli* |
| *E. coli* PhoB box 37 | 270 | DNA | *Escherichia coli* |
| *E. coli* PhoB box 38 | 271 | DNA | *Escherichia coli* |
| *E. coli* PhoB box 39 | 272 | DNA | *Escherichia coli* |
| *E. coli* PhoB box 40 | 273 | DNA | *Escherichia coli* |
| *E. coli* PhoB box 41 | 274 | DNA | *Escherichia coli* |
| *E. coli* PhoB box 42 | 275 | DNA | *Escherichia coli* |
| *E. coli* PhoB box 43 | 276 | DNA | *Escherichia coli* |

TABLE 5-continued

| Summary of Biological Sequences in Sequence Listing | | | |
| --- | --- | --- | --- |
| Description | SEQ ID NO | Type | Organism name |
| *E. coli* PhoB box 44 | 277 | DNA | *Escherichia coli* |
| *E. coli* PhoB box 45 | 278 | DNA | *Escherichia coli* |
| *E. coli* PhoB box 46 | 279 | DNA | *Escherichia coli* |
| *E. coli* PhoB box 47 | 280 | DNA | *Escherichia coli* |
| E. coli PhoB box 48 | 281 | DNA | *Escherichia coli* |
| *E. coli* PhoB box 49 | 282 | DNA | *Escherichia coli* |
| *E. coli* PhoB box 50 | 283 | DNA | *Escherichia coli* |
| *E. coli* PhoB box 51 | 284 | DNA | *Escherichia coli* |
| *E. coli* PhoB box 52 | 285 | DNA | *Escherichia coli* |
| *E. coli* PhoB box 53 | 286 | DNA | *Escherichia coli* |
| *E. coli* PhoB box 54 | 287 | DNA | *Escherichia coli* |
| *E. coli* PhoB box 55 | 288 | DNA | *Escherichia coli* |
| *E. coli* PhoB box 56 | 289 | DNA | *Escherichia coli* |
| *E. coli* PhoB box 57 | 290 | DNA | *Escherichia coli* |
| *E. coli* PhoB box 58 | 291 | DNA | *Escherichia coli* |
| *E. coli* PhoB box 59 | 292 | DNA | *Escherichia coli* |
| *E. coli* PhoB box 60 | 293 | DNA | *Escherichia coli* |
| *E. coli* PhoB box 61 | 294 | DNA | *Escherichia coli* |
| *E. coli* PhoB box 62 | 295 | DNA | *Escherichia coli* |
| *E. coli* PhoB box 63 | 296 | DNA | *Escherichia coli* |
| *E. coli* PhoB box 64 | 297 | DNA | *Escherichia coli* |
| *E. coli* PhoB box 65 | 298 | DNA | *Escherichia coli* |
| *E. coli* PhoB box 66 | 299 | DNA | *Escherichia coli* |
| *E. coli* PhoB box 67 | 300 | DNA | *Escherichia coli* |
| *E. coli* PhoB box 68 | 301 | DNA | *Escherichia coli* |
| *E. coli* PhoB box 69 | 302 | DNA | *Escherichia coli* |
| *E. coli* PhoB box 70 | 303 | DNA | *Escherichia coli* |
| *E. coli* PhoB box 71 | 304 | DNA | *Escherichia coli* |
| *E. coli* PhoB box 72 | 305 | DNA | *Escherichia coli* |
| *E. coli* PhoB box 73 | 306 | DNA | *Escherichia coli* |
| *E. coli* PhoB box 74 | 307 | DNA | *Escherichia coli* |
| *E. coli* PhoB box 75 | 308 | DNA | *Escherichia coli* |
| *E. coli* PhoB box 76 | 309 | DNA | *Escherichia coli* |
| *E. coli* PhoB box 77 | 310 | DNA | *Escherichia coli* |
| *E. coli* PhoB box 78 | 311 | DNA | *Escherichia coli* |
| *E. coli* PhoB box 79 | 312 | DNA | *Escherichia coli* |
| *E. coli* PhoB box 80 | 313 | DNA | *Escherichia coli* |

TABLE 5-continued

Summary of Biological Sequences in Sequence Listing

| Description | SEQ ID NO | Type | Organism name |
|---|---|---|---|
| *E. coli* PhoB box 81 | 314 | DNA | *Escherichia coli* |
| *E. coli* PhoB box 82 | 315 | DNA | *Escherichia coli* |
| *E. coli* PhoB box 83 | 316 | DNA | *Escherichia coli* |
| *E. coli* PhoB box 84 | 317 | DNA | *Escherichia coli* |
| *E. coli* PhoB box 85 | 318 | DNA | *Escherichia coli* |
| *E. coli* PhoB box 86 | 319 | DNA | *Escherichia coli* |
| *E. coli* PhoB box 87 | 320 | DNA | *Escherichia coli* |
| *E. coli* PhoB box 88 | 321 | DNA | *Escherichia coli* |
| *E. coli* PhoB box 89 | 322 | DNA | *Escherichia coli* |
| *E. coli* PhoB box 90 | 323 | DNA | *Escherichia coli* |
| *E. coli* PhoB box 91 | 324 | DNA | *Escherichia coli* |
| *E. coli* PhoB box 92 | 325 | DNA | *Escherichia coli* |
| *E. coli* PhoB box 93 | 326 | DNA | *Escherichia coli* |
| *E. coli* PhoB box 94 | 327 | DNA | *Escherichia coli* |
| *E. coli* PhoB box 95 | 328 | DNA | *Escherichia coli* |
| *E. coli* PhoB box 96 | 329 | DNA | *Escherichia coli* |
| *E. coli* PhoB box 97 | 330 | DNA | *Escherichia coli* |
| *E. coli* PhoB box 98 | 331 | DNA | *Escherichia coli* |
| *E. coli* PhoB box 99 | 332 | DNA | *Escherichia coli* |
| *E. coli* PhoB box 100 | 333 | DNA | *Escherichia coli* |
| *E. coli* PhoB box 101 | 334 | DNA | *Escherichia coli* |
| *E. coli* PhoB box 102 | 335 | DNA | *Escherichia coli* |
| *E. coli* PhoB box 103 | 336 | DNA | *Escherichia coli* |
| *E. coli* PhoB box 104 | 337 | DNA | *Escherichia coli* |
| *E. coli* PhoB box 105 | 338 | DNA | *Escherichia coli* |
| *E. coli* PhoB box 106 | 339 | DNA | *Escherichia coli* |
| *E. coli* PhoB box 107 | 340 | DNA | *Escherichia coli* |
| *E. coli* PhoB box 108 | 341 | DNA | *Escherichia coli* |
| *E. coli* PhoB box 109 | 342 | DNA | *Escherichia coli* |
| *E. coli* PhoB box 110 | 343 | DNA | *Escherichia coli* |
| *E. coli* PhoB box 111 | 344 | DNA | *Escherichia coli* |
| *E. coli* PhoB box 112 | 345 | DNA | *Escherichia coli* |
| *S. coelicolor* PhoP box 1 | 346 | DNA | *Streptomyces coelicolor* |
| *S. coelicolor* PhoP box 2 | 347 | DNA | *Streptomyces coelicolor* |
| *S. coelicolor* PhoP box 3 | 348 | DNA | *Streptomyces coelicolor* |
| *S. coelicolor* PhoP box 4 | 349 | DNA | *Streptomyces coelicolor* |
| *S. coelicolor* PhoP box 5 | 350 | DNA | *Streptomyces coelicolor* |
| *S. coelicolor* PhoP box 6 | 351 | DNA | *Streptomyces coelicolor* |

TABLE 5-continued

Summary of Biological Sequences in Sequence Listing

| Description | SEQ ID NO | Type | Organism name |
|---|---|---|---|
| S. coelicolor PhoP box 7 | 352 | DNA | Streptomyces coelicolor |
| S. coelicolor PhoP box 8 | 353 | DNA | Streptomyces coelicolor |
| S. coelicolor PhoP box 9 | 354 | DNA | Streptomyces coelicolor |
| S. coelicolor PhoP box 10 | 355 | DNA | Streptomyces coelicolor |
| S. coelicolor PhoP box 11 | 356 | DNA | Streptomyces coelicolor |
| S. coelicolor PhoP box 12 | 357 | DNA | Streptomyces coelicolor |
| S. coelicolor PhoP box 13 | 358 | DNA | Streptomyces coelicolor |
| S. coelicolor PhoP box 14 | 359 | DNA | Streptomyces coelicolor |
| S. coelicolor PhoP box 15 | 360 | DNA | Streptomyces coelicolor |
| S. coelicolor PhoP box 16 | 361 | DNA | Streptomyces coelicolor |
| S. coelicolor PhoP box 17 | 362 | DNA | Streptomyces coelicolor |
| S. coelicolor PhoP box 18 | 363 | DNA | Streptomyces coelicolor |
| S. coelicolor PhoP box 19 | 364 | DNA | Streptomyces coelicolor |
| S. coelicolor PhoP box 20 | 365 | DNA | Streptomyces coelicolor |
| S. coelicolor PhoP box 21 | 366 | DNA | Streptomyces coelicolor |
| S. coelicolor PhoP box 22 | 367 | DNA | Streptomyces coelicolor |
| S. coelicolor PhoP box 23 | 368 | DNA | Streptomyces coelicolor |
| S. coelicolor PhoP box 24 | 369 | DNA | Streptomyces coelicolor |
| S. coelicolor PhoP box 25 | 370 | DNA | Streptomyces coelicolor |
| S. coelicolor PhoP box 26 | 371 | DNA | Streptomyces coelicolor |
| S. coelicolor PhoP box 27 | 372 | DNA | Streptomyces coelicolor |
| S. coelicolor PhoP box 28 | 373 | DNA | Streptomyces coelicolor |
| S. coelicolor PhoP box 29 | 374 | DNA | Streptomyces coelicolor |
| S. coelicolor PhoP box 30 | 375 | DNA | Streptomyces coelicolor |
| A. caulinodans PstS box 1 | 376 | DNA | Azorhizobium caulinodans |
| A. brasilense PstS box 1 | 377 | DNA | Azospirillum brasilense |
| E. coli PhoA box 1 | 378 | DNA | Escherichia coli |
| E. coli PstS box 1 | 379 | DNA | Escherichia coli |
| E. coli PstS box 2 | 380 | DNA | Escherichia coli |
| E. coli PstS box 3 | 381 | DNA | Escherichia coli |
| E. coli PstS box 4 | 382 | DNA | Escherichia coli |
| G. diazotrophicus PstS box 1 | 383 | DNA | Gluconacetobacter diazotrophicus |
| G. diazotrophicus PstS box 2 | 384 | DNA | Gluconacetobacter diazotrophicus |
| H. seropedicae PstS box 1 | 385 | DNA | Herbaspirillum seropedicae |
| K. radicincitans PstS box 1 | 386 | DNA | Kosakonia radicincitans |

TABLE 5-continued

| Description | SEQ ID NO | Type | Organism name |
|---|---|---|---|
| _K. radicincitans_ PstS box 2 | 387 | DNA | _Kosakonia radicincitans_ |
| _K. radicincitans_ PstS box 3 | 388 | DNA | _Kosakonia radicincitans_ |
| _K. radicincitans_ PstS box 4 | 389 | DNA | _Kosakonia radicincitans_ |
| _K. radicincitans_ PstS box 5 | 390 | DNA | _Kosakonia radicincitans_ |
| _P. azotofixans_ PstS box 1 | 391 | DNA | _Paenibacillus azotofixans_ |
| _P. stutzeri_ PhoX box 1 | 392 | DNA | _Pseudomonas stutzeri_ |
| _P. stutzeri_ PhoX box 2 | 393 | DNA | _Pseudomonas stutzeri_ |
| _P. stutzeri_ PhoX box 3 | 394 | DNA | _Pseudomonas stutzeri_ |
| _P. stutzeri_ PhoX box 4 | 395 | DNA | _Pseudomonas stutzeri_ |
| _P. stutzeri_ Phy box 1 | 396 | DNA | _Pseudomonas stutzeri_ |
| _P. stutzeri_ PstS box 1 | 397 | DNA | _Pseudomonas stutzeri_ |
| _K. radicincitans_ PhoA alkaline phosphatase | 398 | PRT | _Kosakonia radicincitans_ |
| _K. radicincitans_ PstS phosphate transporter ABC | 399 | PRT | _Kosakonia radicincitans_ |
| _P. durus_ PhoA alkaline phosphatase | 400 | PRT | _Paenibacillus durus_ |
| _P. durus_ PstS phosphate ABC transporter | 401 | PRT | _Paenibacillus durus_ |
| _A. caulinodans_ PhoA alkaline phosphatase | 402 | PRT | _Azorhizobium caulinodans_ |
| _A. caulinodans_ PstS phosphate ABC transporter | 403 | PRT | _Azorhizobium caulinodans_ |
| _E. coli_ PhoA alkaline phosphatase | 404 | PRT | _Escherichia coli_ |
| _E. coli_ PstS phosphate ABC transporter | 405 | PRT | _Escherichia coli_ |
| _A. olearius_ PhoA alkaline phosphatase | 406 | PRT | _Azoarcus olearius_ |
| _A. olearius_ PstS phosphate ABC transporter | 407 | PRT | _Azoarcus olearius_ |
| _S. stutzeri_ PhoX family phosphatase | 408 | PRT | _Stutzerimonas stutzeri_ |
| _S. stutzeri_ PstS phosphate ABC transporter | 409 | PRT | _Stutzerimonas stutzeri_ |
| _P. aeruginosa_ PhoX family phosphatase | 410 | PRT | _Pseudomonas aeruginosa_ |
| _A. aromaticum_ PhoX family phosphatase | 411 | PRT | _Aromatoleum aromaticum_ |
| _Y. vestfoldensis_ PhoX family phosphatase | 412 | PRT | _Yoonia vestfoldensis_ |
| _M. alkaliphilus_ PhoX family phosphatase | 413 | PRT | _Maritimibacter alkaliphilus_ |
| _B. subtilis_ phytase | 414 | PRT | _Bacillus subtilis_ |
| _H. seropedicae_ PstS phosphate ABC transporter | 415 | PRT | _Herbaspirillum seropedicae_ |
| _G. diazotrophicus_ PstS phosphate ABC transporter | 416 | PRT | _Gluconacetobacter diazotrophicus_ |
| _A. caulinodans_ pstS promoter | 417 | DNA | _Azorhizobium caulinodans_ |
| _A. brasilense_ pstS promoter | 418 | DNA | _Azospirillum brasilense_ |
| _E. coli_ phoA promoter | 419 | DNA | _Escherichia coli_ |
| _E. coli_ pstS promoter | 420 | DNA | _Escherichia coli_ |

TABLE 5-continued

Summary of Biological Sequences in Sequence Listing

| Description | SEQ ID NO | Type | Organism name |
|---|---|---|---|
| *G. diazotrophicus* pstS promoter | 421 | DNA | *Gluconacetobacter diazotrophicus* |
| *H. seropedicae* pstS promoter | 422 | DNA | *Herbaspirillum seropedicae* |
| *K. radicincitans* pstS promoter 1 | 423 | DNA | *Kosakonia radicincitans* |
| *K. radicincitans* pstS promoter 2 | 424 | DNA | *Kosakonia radicincitans* |
| *P. azotofixans* pstS promoter | 425 | DNA | *Paenibacillus azotofixans* |
| *P. stutzeri* phoX promoter | 426 | DNA | *Pseudomonas stutzeri* |
| *P. stutzeri* phy promoter | 427 | DNA | *Pseudomonas stutzeri* |
| *P. stutzeri* pstS promoter | 428 | DNA | *Pseudomonas stutzeri* |
| BCD 1 ribosome binding site | 429 | DNA | synthetic construct |
| BCD 2 vL ribosome binding site | 430 | DNA | synthetic construct |
| BCD 2 vS ribosome binding site | 431 | DNA | synthetic construct |
| BCD 5 ribosome binding site | 432 | DNA | synthetic construct |
| BCD 6 ribosome binding site | 433 | DNA | synthetic construct |
| BCD 7 ribosome binding site | 434 | DNA | synthetic construct |
| BCD 8 ribosome binding site | 435 | DNA | synthetic construct |
| BCD 9 ribosome binding site | 436 | DNA | synthetic construct |
| BCD 10 ribosome binding site | 437 | DNA | synthetic construct |
| BCD 11 ribosome binding site | 438 | DNA | synthetic construct |
| BCD 12 ribosome binding site | 439 | DNA | synthetic construct |
| BCD 13 ribosome binding site | 440 | DNA | synthetic construct |
| BCD 14 ribosome binding site | 441 | DNA | synthetic construct |
| BCD 15 ribosome binding site | 442 | DNA | synthetic construct |
| BCD 16 ribosome binding site | 443 | DNA | synthetic construct |
| BCD 17 ribosome binding site | 444 | DNA | synthetic construct |
| BCD 18 ribosome binding site | 445 | DNA | synthetic construct |
| BCD 19 ribosome binding site | 446 | DNA | synthetic construct |
| BCD 20 ribosome binding site | 447 | DNA | synthetic construct |
| BCD 21 ribosome binding site | 448 | DNA | synthetic construct |
| BCD 22 vL ribosome binding site | 449 | DNA | synthetic construct |
| BCD 22 vS ribosome binding site | 450 | DNA | synthetic construct |
| BCD 23 ribosome binding site | 451 | DNA | synthetic construct |
| BCD 24 ribosome binding site | 452 | DNA | synthetic construct |
| BBa B0029 ribosome binding site | 453 | DNA | synthetic construct |
| BBa B0030 ribosome binding site | 454 | DNA | synthetic construct |
| BBa B0034 ribosome binding site | 455 | DNA | synthetic construct |
| BBa_B1002 terminator | 456 | DNA | synthetic construct |
| BBa_B1006 terminator | 457 | DNA | synthetic construct |

TABLE 5-continued

| Description | SEQ ID NO | Type | Organism name |
|---|---|---|---|
| BBa_B1015 terminator | 458 | DNA | synthetic construct |
| Pliar53 promoter | 459 | DNA | synthetic construct |
| *Acetobacter malorum* GlnA protein sequence | 460 | PRT | *Acetobacter malorum* |
| *Acetobacter tropicalis* GlnA protein sequence | 461 | PRT | *Acetobacter tropicalis* |
| *Acetobacter pasteurianus* GlnA protein sequence | 462 | PRT | *Acetobacter pasteurianus* |
| *Acidothermus cellulolyticus* GlnA protein sequence | 463 | PRT | *Acidothermus cellulolyticus* |
| *Acinetobacter baumannii* GlnA protein sequence | 464 | PRT | *Acinetobacter baumannii* |
| *Acinetobacter calcoaceticus* GlnA protein sequence | 465 | PRT | *Acinetobacter calcoaceticus* |
| *Agrobacterium deltaense* GlnA protein sequence | 466 | PRT | *Agrobacterium deltaense* |
| *Aromatoleum aromaticum* GlnA protein sequence | 467 | PRT | *Aromatoleum aromaticum* |
| *Arthrobacer* sp. GlnA protein sequence | 468 | PRT | *Arthrobacer* sp. |
| *Azoarcus* sp. GlnA protein sequence | 469 | PRT | *Azoarcus* sp. |
| *Azorhizobium caulinodans* GlnA protein sequence | 470 | PRT | *Azorhizobium caulinodans* |
| *Azotobacter vinelandii* GlnA protein sequence | 471 | PRT | *Azotobacter vinelandii* |
| *Bacillus subtilis* GlnA protein sequence | 472 | PRT | *Bacillus subtilis* |
| *Bifidobacterium adolescentis* GlnA protein sequence | 473 | PRT | *Bifidobacterium adolescentis* |
| *Bifidobacterium asteroides* GlnA protein sequence | 474 | PRT | *Bifidobacterium asteroides* |
| *Bradyrhizobium diazoefficiens* GlnA protein sequence | 475 | PRT | *Bradyrhizobium diazoefficiens* |
| *Bradyrhizobium frederickii* GlnA protein sequence | 476 | PRT | *Bradyrhizobium frederickii* |
| *Burkholderia cenocepacia* GlnA protein sequence | 477 | PRT | *Burkholderia cenocepacia* |
| *Burkholderia stagnalis* GlnA protein sequence | 478 | PRT | *Burkholderia stagnalis* |
| *Conexibacter* sp. GlnA protein sequence | 479 | PRT | *Conexibacter* sp. |
| *Curtobacterium albidum* GlnA protein sequence | 480 | PRT | *Curtobacterium albidum* |
| *Ensifer adhaerens* GlnA protein sequence | 481 | PRT | *Ensifer adhaerens* |
| *Enterobacter agglomerans* GlnA protein sequence | 482 | PRT | *Enterobacter agglomerans* |
| *Erwinia amylovora* GlnA protein sequence | 483 | PRT | *Erwinia amylovora* |
| *Escherichia coli* GlnA protein sequence | 484 | PRT | *Escherichia coli* |
| *Flavobacterium glycines* GlnA protein sequence | 485 | PRT | *Flavobacterium glycines* |
| *Frankia canadensis* GlnA protein sequence | 486 | PRT | *Frankia canadensis* |
| *Gluconacetobacter diazotrophicus* GlnA protein sequence | 487 | PRT | *Gluconacetobacter diazotrophicus* |
| *Gluconobacter oxydans* GlnA protein sequence | 488 | PRT | *Gluconobacter oxydans* |

TABLE 5-continued

Summary of Biological Sequences in Sequence Listing

| Description | SEQ ID NO | Type | Organism name |
|---|---|---|---|
| *Herbaspirillum seropedicae* GlnA protein sequence | 489 | PRT | *Herbaspirillum seropedicae* |
| *Klebsiella oxytoca* GlnA protein sequence | 490 | PRT | *Klebsiella oxytoca* |
| *Klebsiella variicola* GlnA protein sequence | 491 | PRT | *Klebsiella variicola* |
| *Kosakonia* sp. GlnA protein sequence | 492 | PRT | *Kosakonia* sp. |
| *Lactobacillus helveticus* GlnA protein sequence | 493 | PRT | *Lactobacillus helveticus* |
| *Lactococcus laudensis* GlnA protein sequence | 494 | PRT | *Lactococcus laudensis* |
| *Lysinibacillus halotolerans* GlnA protein sequence | 495 | PRT | *Lysinibacillus halotolerans* |
| *Maritimibacter harenae* GlnA protein sequence | 496 | PRT | *Maritimibacter harenae* |
| *Methylobacterium aquaticum* GlnA protein sequence | 497 | PRT | *Methylobacterium aquaticum* |
| *Paenibacillus polymyxa* GlnA protein sequence | 498 | PRT | *Paenibacillus polymyxa* |
| *Priestia megaterium* GlnA protein sequence | 499 | PRT | *Priestia megaterium* |
| *Pseudarthrobacter siccitolerans* GlnA protein sequence | 500 | PRT | *Pseudarthrobacter siccitolerans* |
| *Pseudomonas azotoformans* GlnA protein sequence | 501 | PRT | *Pseudomonas azotoformans* |
| *Pseudomonas putida* GlnA protein sequence | 502 | PRT | *Pseudomonas putida* |
| *Pseudomonas syringae* GlnA protein sequence | 503 | PRT | *Pseudomonas syringae* |
| *Rahnella contaminans* GlnA protein sequence | 504 | PRT | *Rahnella contaminans* |
| *Rahnella* sp. GlnA protein sequence | 505 | PRT | *Rahnella* sp. |
| *Rhizobium leguminosarum* GlnA protein sequence | 506 | PRT | *Rhizobium leguminosarum* |
| *Rhodococcus oryzae* GlnA protein sequence | 507 | PRT | *Rhodococcus oryzae* |
| *Sphingomonas glacialis* GlnA protein sequence | 508 | PRT | *Sphingomonas glacialis* |
| *Stenotrophomonas maltophilia* GlnA protein sequence | 509 | PRT | *Stenotrophomonas maltophilia* |
| *Stutzerimonas stutzeri* GlnA protein sequence | 510 | PRT | *Stutzerimonas stutzeri* |
| *Variovorax paradoxus* GlnA protein sequence | 511 | PRT | *Variovorax paradoxus* |
| *Yoonia vestfoldensis* GlnA protein sequence | 512 | PRT | *Yoonia vestfoldensis* |
| *R. aceris* PstS phosphate ABC transporter | 513 | PRT | *Rahnella aceris* |
| PstS phosphate ABC transporter consensus motif (GSTVNWP[T/V\|GLGGKGNDG\|V/I]AAFVQR LPGSIGYVEYAYAKQNNL[A/T][Y/W]TKL [V/F][D/S]ADGK; SEQ ID NO: 514) | 514 | PRT | synthetic construct |
| *K. variicola* pstS promoter | 515 | DNA | *Klebsiella variicola* |
| Optimized TetR | 516 | PRT | synthetic construct |
| *K. sacchari* pstS promoter | 517 | DNA | *Kosakonia sacchari* |
| *R. aceris* pstS promoter | 518 | DNA | *Rahnella aceris* |
| *K. sacchari* glutamine synthetase | 519 | PRT | *Kosakonia sacchari* |
| *K. variicola* glutamine synthetase | 520 | PRT | *Klebsiella variicola* |

TABLE 5-continued

| Description | SEQ ID NO | Type | Organism name |
|---|---|---|---|
| Summary of Biological Sequences in Sequence Listing | | | |
| *R. aceris* glutamine synthetase | 521 | PRT | *Rahnella aceris* |
| Control GFP reporter gene expression cassette | 522 | DNA | synthetic construct |
| *K. variicola* PstS phosphate transporter ABC | 523 | PRT | *Klebsiella variicola* |
| *K. sacchari* PstS phosphate transporter ABC | 524 | PRT | *Kosakonia sacchari* |
| *K. variicola* pstS promoter PHO BOX 1 | 525 | DNA | *Klebsiella variicola* |
| *K. variicola* pstS promoter PHO BOX 2 | 526 | DNA | *Klebsiella variicola* |
| *K. variicola* pstS promoter PHO BOX 3 | 527 | DNA | *Klebsiella variicola* |
| *K. variicola* pstS promoter PHO BOX 4 | 528 | DNA | *Klebsiella variicola* |
| *K. variicola* pstS promoter PHO BOX 5 | 529 | DNA | *Klebsiella variicola* |
| *P. graminis* glutamine synthetase | 530 | PRT | *Paenibacillus graminis* |
| *Enterobacter* sp. glutamine synthetase | 531 | PRT | *Enterobacter* sp |
| *P. diazotrophicus* glutamine synthetase | 532 | PRT | *Phytobacter diazotrophicus* |
| *E. dykesii* glutamine synthetase | 533 | PRT | *Enterobacter dykesii* |

TABLE 6

Non-limiting examples of
protease-specific recognition sequence (PSRS)
insertion sites in glnA and glnE target genes for ammonia release.

| Strain | Target Gene Name | SEQ ID NO | Name of Cut Site for insertion of PSRS | N-terminal AA | N-terminal AA # | C-terminal AA | C-terminal AA # |
|---|---|---|---|---|---|---|---|
| *A. brasilense* Sp245 | glnA | 229 | 1 | T | 98 | G | 99 |
| *A. brasilense* Sp245 | glnA | 229 | 2 | G | 121 | I | 122 |
| *A. brasilense* Sp245 | glnA | 229 | 3 | G | 279 | Q | 280 |
| *A. brasilense* Sp245 | glnA | 229 | 4 | G | 285 | N | 286 |
| *P. stutzeri* DSM 4166 | glnA | 230 | 1 | Q | 98 | G | 99 |
| *P. stutzeri* DSM 4166 | glnA | 230 | 2 | G | 119 | I | 120 |
| *P. stutzeri* DSM 4166 | glnA | 230 | 3 | A | 283 | G | 284 |
| *P. stutzeri* DSM 4166 | glnA | 230 | 4 | I | 298 | G | 299 |
| *A. brasilense* Sp245 | glnE | 231 | 1 | Q | 448 | L | 449 |
| *A. brasilense* Sp245 | glnE | 231 | 2 | D | 480 | P | 481 |
| *A. brasilense* Sp245 | glnE | 231 | 3 | W | 505 | H | 506 |
| *A. brasilense* Sp245 | glnE | 231 | 4 | A | 528 | M | 529 |
| *A. brasilense* Sp245 | glnE | 231 | 5 | H | 624 | N | 625 |
| *A. caulinodans* ORS 571 | glnE | 232 | 1 | P | 527 | R | 528 |
| *A. caulinodans* ORS 571 | glnE | 232 | 2 | E | 537 | H | 538 |

TABLE 6-continued

Non-limiting examples of
protease-specific recognition sequence (PSRS)
insertion sites in glnA and glnE target genes for ammonia release.

| Strain | Target Gene Name | SEQ ID NO | Name of Cut Site for insertion of PSRS | N-terminal AA | N-terminal AA # | C-terminal AA | C-terminal AA # |
|---|---|---|---|---|---|---|---|
| *A. caulinodans* ORS 571 | glnE | 232 | 3 | I | 547 | E | 548 |
| *E. coli* | glnE | 233 | 1 | T | 422 | A | 423 |
| *E. coli* | glnE | 233 | 2 | D | 608 | D | 609 |

Corresponding insertion sites in other glnA and glnE genes including those set forth in Table 3, Table 5, and the sequence listing are also provided.

EXAMPLES

Example 1. Identification and Selection of Phosphate-Sensitive Promoters and Pho Boxes The phosphate (Pho) regulon is a bacterial regulatory mechanism that senses and responds to changing availability and concentration of inorganic phosphate (Pi). The Pho regulon activates the expression of extracellular enzymes, phosphate-specific carriers, and enzymes involved in phosphate storage and preservation. The most conserved member of the Pho regulon in bacteria is the high affinity Pi transporter (Pst), and the most common enzymes induced in response to inorganic phosphate starvation in bacteria are alkaline phosphatases (PhoA, PhoX), phospholipases (PhoD), glycerophosphodiester phosphodiesterases, phytases (Phy), 5'-nucleotidase, and the Pst itself.

The Pho regulon is controlled by a two-component regulatory system that includes an inner membrane histidine kinase sensor protein and a regulator of the cytoplasmic transcriptional response. These proteins are named differently in some bacteria, for example, PhoR-PhoB in *Escherichia coli*, PhoR-PhoP in *Bacillus subtilis*, PnpR-PnpS in *Streptococcus pneumoniae*. In all cases of inorganic phosphate deficiency, the response regulator is phosphorylated at an aspartic acid residue by the sensor kinase. The phosphorylated response regulator binds to specific DNA sequences and activates or inhibits gene transcription.

These specific regulator-binding DNA sequences that facilitate the activation or inhibition of gene expression in a phosphate-sensitive manner are termed Pho boxes. Pho boxes have been identified using ChIP-Seq, sequence similarity, and RNA-Seq in *Escherichia coli* and *Streptomyces coelicolor* (Allenby et al. (doi:10.1093/nar/gks766) and Fitzgerald et al. (doi: 10.1128/mbio.02535-22), respectively; SEQ ID NO: 234-375).

Beyond the two-component PhoR-PhoB system, phosphate-sensitive bacterial responses involve additional proteins. By way of example, the *E. coli* inorganic phosphate uptake pathway requires five more proteins, four of them being the components of the Pst and one a component of the PhoU metal-binding protein.

Depleting inorganic phosphate in a growth medium activates the Pho regulon in bacteria in the medium. When the concentration of inorganic phosphate decreases, PhoB is activated by PhoR acting as a kinase, but under conditions of excess free phosphate, PhoB activation is interrupted by PhoR acting as a phosphatase. PhoU is required for PhoB dephosphorylation under phosphate-rich conditions. Although PhoU is found in many bacterial genomes, this gene is absent in *B. subtilis*. The inorganic phosphate-signaling network in this bacterium includes a positive feedback loop between the PhoP-PhoR and ResD-ResE two-component systems. ResD does not bind to the phoPR operon and appears to transfer its control through the expression of terminal oxidases.

To express an RNA sequence or protein of interest in a phosphate-sensitive manner in agriculturally relevant bacteria, promoters were constructed that are activated by decreasing phosphate concentration. Initially, sequence alignments were calculated for published Pho boxes to identify a consensus sequence so that additional phosphate-sensitive promoters could be identified simply by searching for sequences similar to the consensus sequence in agriculturally relevant bacteria. However, poor homology among published Pho boxes in bacteria of the same species made this approach unsuccessful. As a result, two distinct approaches were pursued to determine lists of Pho boxes that could be searched to find phosphate-sensitive promoters in agriculturally relevant bacteria.

In the first approach adapted from Torres-Bacete et al. (doi:10.1111/1751-7915.13808), a DNA motif WebLogo and position-by-position DNA base probability were calculated from known Pho boxes. Based on these statistics, degenerate primers were synthesized to create a library of alternative Pho boxes via polymerase chain reaction (PCR) amplification of a DNA template comprising the sequences based on the aforementioned WebLogo. To construct a library of phosphate-sensitive reporter circuits, the DNA library of alternative Pho boxes above was integrated into the −35 region of a constitutive promoter (BG42), which was operably linked to a strong ribosome binding site (BCD2) and a green fluorescent protein (GFP) gene. The library of phosphate-sensitive GFP reporter circuits was then screened in *Pseudomonas* and *Escherichia* strains at varying phosphate concentrations to determine the Pho box and phosphate-sensitive promoter with the greatest response to changes in extracellular phosphate concentration. The Pho box from the maximally responding promoter was subsequently searched using the US National Center for Biotechnology Information (NCBI) Basic Local Alignment Search Tool (BLAST) to identify naturally occurring Pho boxes with high sequence similarity to the Pho box of the maximally responding phosphate-sensitive promoter identified above. Those promoters were screened for ability to induce phosphate-sensitive changes in gene expression as in EXAMPLE 2.

In the second approach, phosphate-sensitive promoter sequences were bioinformatically extracted from agriculturally relevant bacteria. Bacterial species across a range of agriculturally relevant and model taxa were selected, similar to those described by Santos-Beneit (doi: 10.3389/ fmicb.2015.00402), Grillo-Puertas et al. (doi:10.3389/fmicb.2021.666277), and Torres-Bacete et al. (doi:10.1111/1751-7915.13808). Taxa searched for phosphate-sensitive promoters included both gram-positive bacteria such as *Bacillus subtilis, Paenibacillus azotofixans*, and *Paenibacillus durus* as well as gram-negative bacteria. Among gram-negative bacteria, several classes of soil bacteria were searched for phosphate-sensitive promoters, including: alphaproteobacteria like *Azospirillum brasilense, Azorhizobium caulinodans, Gluconacetobacter diazotrophicus, Maritimibacter alkaliphilus*, and *Yoonia vestfoldensis*; betaproteobacteria like *Aromatoleum aromaticum, Azoarcus olearius*, and *Herbaspirillum seropedicae*; and gammaproteobacteria like *Escherichia coli, Kosakonia radicincitans, Pseudomonas aeruginosa*, and *Pseudomonas stutzeri*. Genes of each bacterial Pho regulon were identified because these genes are known to have phosphate-sensitive expression. The presence of Pho boxes in each of the identified Pho regulon genes was confirmed by sequence similarity to Pho boxes described in Allenby et al. (doi:10.1093/nar/gks766). Pho boxes present in agriculturally relevant bacteria are included as SEQ ID NO: 376-397. CLUSTAL alignment performed using Mview with default parameters showed that no consensus sequence could be easily constructed for these Pho boxes.

Since no consensus sequence emerged using the second approach, phosphate-sensitive promoters were identified by determining the DNA regions immediately upstream of the protein-coding regions of Pho regulon genes in the agriculturally relevant bacterial taxa. The protein-coding sequences of certain Pho regulon genes (given by SEQ ID NO: 398-416, TABLE 7) were determined by querying the US National Center for Biotechnology Information (NCBI) Protein database. The sequence similarity among homologous Pho regulon genes was determined by CLUSTAL alignment using the M-Coffee multiple sequence aligner with default parameters, and multiple sequence alignment statistics were calculated using Mview (SEQ ID NO: 398-416, TABLE 7). Subsequently, promoter DNA sequences were extracted by locating regions immediately upstream of the start codon of the phoA, phoX, phy, and pstS genes associated with SEQ ID NO: 398-416, TABLE 7. DNA regions selected as promoters can comprise about 100 bp upstream of a relevant start codon but at least 50 bp upstream of the start codon and frequently about 50 to about 250 bp upstream of the relevant start codon (SEQ ID NO: 417-428, TABLE 8).

Subsequently, phosphate-sensitive promoter sequences were identified in agricultural soil isolates of *Klebsiella variicola, Kosakonia sacchari*, and *Rahnella aceris* using a method adapted from the method above. The phosphate ABC transporter substrate-binding protein PstS amino acid sequences of these soil isolates each has more than 76% homology to the *Rahnella aceris* PstS amino acid sequence (SEQ ID NO: 513), as well as a consensus motif shown in SEQ ID NO: 514. Additionally, the protein-coding sequences of the pstS genes in these *Klebsiella variicola* and *Kosakonia sacchari* isolates were determined to be SEQ ID NO: 523 and 524 respectively, with promoter DNA sequences for the three species given by SEQ ID NO: 515, 517, and 518.

Rows are organized by different bacterial species or strains. Columns are organized by different Pho regulon proteins. Cells contain the SEQ ID NO of each protein's amino acid sequence. "Absent" indicates that the bacterial species or strain does not have a gene encoding a specific Pho regulon protein. "Not tested" indicates that a specific species was not searched for a gene encoding a specific Pho regulon protein.

TABLE 7

| Protein-coding sequences of Pho regulon genes in agriculturally relevant and model bacteria. | | | | |
| --- | --- | --- | --- | --- |
| Bacterial Species/ Strain | PhoA | PhoX | Phytase* | PstS |
| *Kosakonia radicincitans* DSM 16656 | SEQ ID NO: 398 | Absent | Absent | SEQ ID NO: 399 |
| *Paenibacillus durus* ATCC 35681 | SEQ ID NO: 400 | Absent | Absent | SEQ ID NO: 401 |
| *Azorhizobium caulinodans* ORS 571 | SEQ ID NO: 402 | Absent | Absent | SEQ ID NO: 403 |
| *Escherichia coli* K12-MG1655 | SEQ ID NO: 404 | Absent | Absent | SEQ ID NO: 405 |
| *Azoarcus olearius* DQS4 | SEQ ID NO: 406 | Absent | Absent | SEQ ID NO: 407 |
| *Stutzerimonas stutzeri* CMT.A.9 | Absent | SEQ ID NO: 408 | Absent | SEQ ID NO: 409 |
| *Pseudomonas aeruginosa* | Not tested | SEQ ID NO: 410 | Not tested | Not tested |
| *Aromatoleum aromaticum* | Not tested | SEQ ID NO: 411 | Not tested | Not tested |
| *Yoonia vestfoldensis* | Not tested | SEQ ID NO: 412 | Not tested | Not tested |
| *Maritimibacter alkaliphilus* | Not tested | SEQ ID NO: 413 | Not tested | Not tested |
| *Bacillus subtilis* | Not tested | Not tested | SEQ ID NO: 414 | Not tested |
| *Herbaspirillum seropedicae* Z67 | Absent | Absent | Absent | SEQ ID NO: 415 |
| *Gluconacetobacter diazotrophicus* PA15 | Absent | Absent | Absent | SEQ ID NO: 416 |

TABLE 8

DNA regions upstream of Pho regulon coding sequences identified as phosphate-sensitive promoters.

| Bacterial Species/Strain | phoA | phoX | phy | pstS |
|---|---|---|---|---|
| *Azorhizobium caulinodans* | Not tested | Not tested | Not tested | Promoter: SEQ ID NO: 417 Pho boxes: SEQ ID NO: 376 |
| *Azospirillum brasilense* | Not tested | Not tested | Not tested | Promoter: SEQ ID NO: 418 Pho boxes: SEQ ID NO: 377 |
| *Escherichia coli* | Promoter: SEQ ID NO: 419 Pho boxes: SEQ ID NO: 378 | Not tested | Not tested | Promoter: SEQ ID NO: 420 Pho boxes: SEQ ID NO: 379-382 |
| *Gluconacetobacter diazotrophicus* | Not tested | Not tested | Not tested | Promoter: SEQ ID NO: 421 Pho boxes: SEQ ID NO: 383-384 |
| *Herbaspirillum seropedicae* | Not tested | Not tested | Not tested | Promoter: SEQ ID NO: 422 Pho boxes: SEQ ID NO: 385 |
| *Kosakonia radicincitans* | Not tested | Not tested | Not tested | Promoters: SEQ ID NO: 423-424 Pho boxes: SEQ ID NO: 386-390 |
| *Paenibacillus azotofixans* | Not tested | Not tested | Not tested | Promoter: SEQ ID NO: 425 Pho boxes: SEQ ID NO: 391 |
| *Pseudomonas stutzeri* | Not tested | Promoter: SEQ ID NO: 426 Pho boxes: SEQ ID NO: 392-395 | Promoter: SEQ ID NO: 427 Pho boxes: SEQ ID NO: 396 | Promoter: SEQ ID NO: 428 Pho boxes: SEQ ID NO: 397 |

Rows are organized by different bacterial species or strains.
Columns are organized by Pho regulon genes.
Cells contain promoter SEQ ID NO and any relevant Pho box SEQ ID NO.
"Not tested" indicates that a specific species was not searched for a specific Pho regulon gene promoter.

Example 2. Engineering Bacteria to Express a Reporter Gene in Response to Decreasing Phosphate Concentration To generate strains that express a GFP reporter gene in response to phosphate depletion, the pstS promoter regions of *Azospirillum brasilense* Sp245 (SEQ ID NO: 418), *Herbaspirillum seropedicae* Z67 (SEQ ID NO: 422), *Pseudomonas stutzeri* DSM 4166 (SEQ ID NO: 428), and *Kosakonia radicincitans* DSM16656 (SEQ ID NO: 423-424) were PCR amplified from genomic DNA, and the synthetic promoter Pliar53 (SEQ ID NO: 459) was synthesized, each with HiFi adapters for cloning into an entry plasmid digested with NotI. The cloning site was designed such that the Pi-dependent promoters were positioned upstream of GFP. Plasmids were confirmed by next generation sequencing and conjugated with aid of the helper strain pRK2013 from the *E. coli* DH5a donor strains into the strains listed above. Plasmid recipients were confirmed by antibiotic selection and by presence of constitutive LSSmScarlett fluorescence which was additionally conveyed by the cloning plasmid.

To confirm that pstS and Pliar53 promoters carried by *Azospirillum brasilense* Sp245, *Herbaspirillum seropedicae* Z67, *Pseudomonas stutzeri* DSM 4166, and *Kosakonia radicincitans* DSM16656 were specifically activated under Pi depleted conditions, expression from these promoters was measured in cultures (n=3) incubated for 15 hours in nitrogen-free basal high phosphate (NFbHP) media with or without addition of 500 uM potassium phosphate. In these experiments, each pstS and Pliar53 promoter was fused to the reporter gene GFP on a plasmid also carrying a constitutively expressed LSSmScarlett reporter gene such that LSSmScarlett fluorescence could be used to track cell density and internally standardize GFP fluorescence as relative expression units (REU), calculated as GFP fluorescence/

Figure 1:
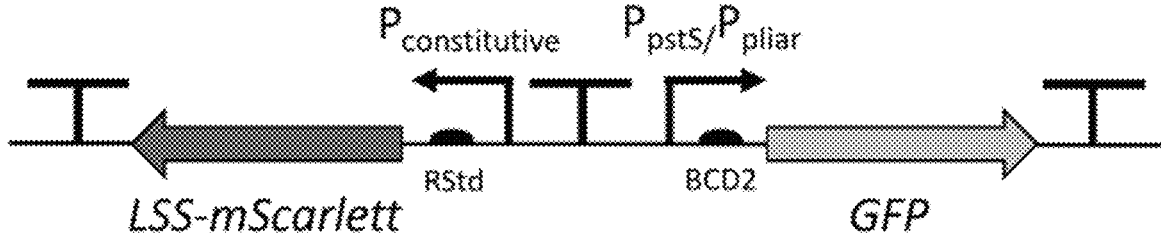
FIG. 1 shows a genetic reporter circuit for measuring expression of a green fluorescent protein reporter under control of the phosphate-sensitive pstS and Pliar53 promoters when there is a decrease in phosphate concentration in a bacterial growth medium.
Figure 2:
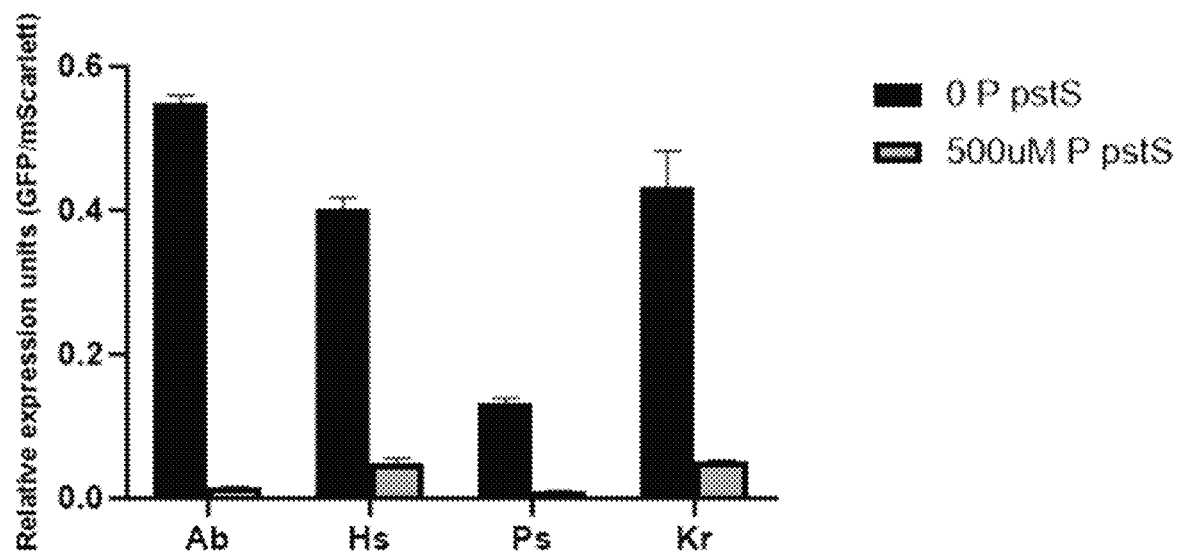
FIG. 2 shows low-Pi dependent induction of expression (defined as GFP/constitutive LSS mScarlett fluorescence) from the pstS reporters in model bacterial strains incubated for 15 h in minimal media with or without supplementation of 500 uM potassium phosphate. Error bars represent one standard deviation from mean calculated from 3 biological replicates.
Figure 3:
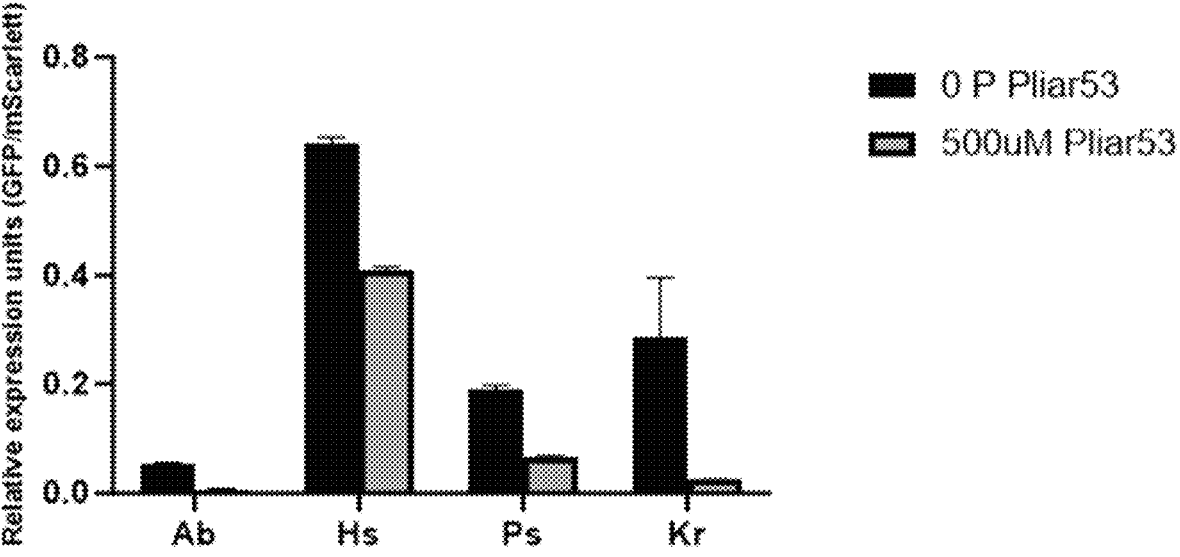
FIG. 3 shows low-Pi dependent induction of expression (defined as GFP/constitutive LSS mScarlett fluorescence) from the Pliar53 reporters in model bacterial strains incubated for 15 h in minimal media with or without supplementation of 500 uM potassium phosphate. Error bars represent one standard deviation from mean calculated from 3 biological replicates.

LSSmScarlett fluorescence (FIG. 1). In all strains tested, expression was activated from the pstS and Pliar53 promoters greater than 10-fold in the absence of Pi compared to where Pi was added into the media (FIGS. 2-3).

Figure 4A:
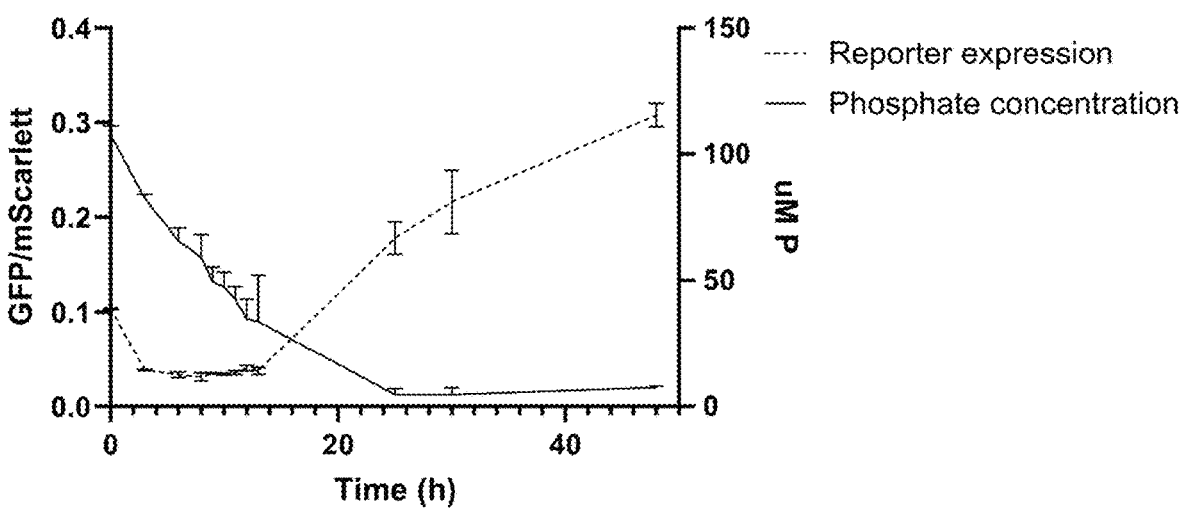
FIGS. 4A, B, C, D show decreasing phosphate concentration led to expression of a GFP reporter protein of interest operably linked to control elements comprising the phosphate-sensitive Pliar53 promoter and promoters of the indicated pstS gene. Model soil bacterial strains are shown. The solid black line data series shows phosphate concentration over time while the dotted line data series shows per-cell GFP fluorescence over time. Error bars represent one standard deviation from mean calculated from 3 biological replicates.
Figure 4A:
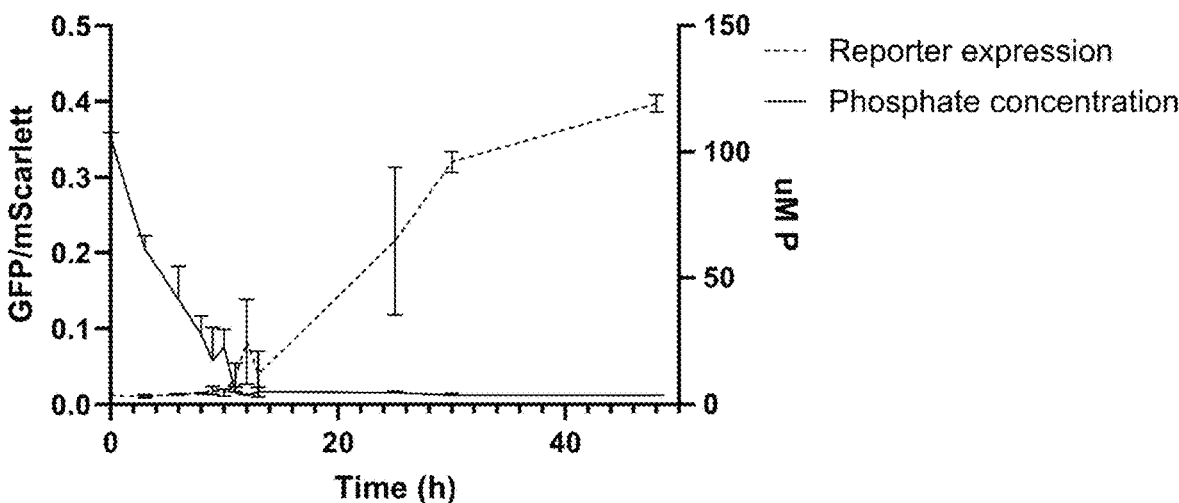
Figure 4B:
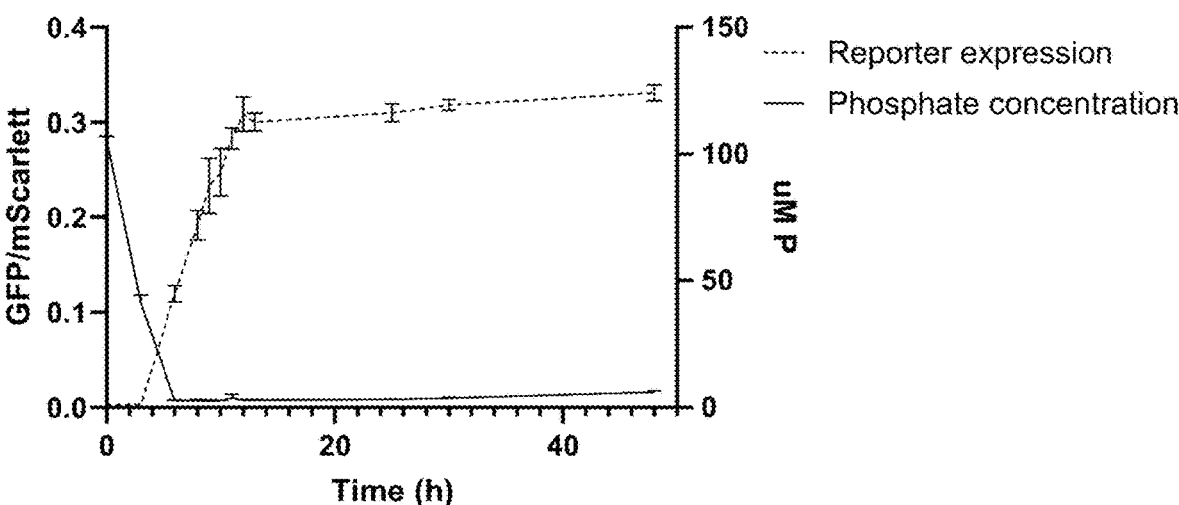
Figure 4B:
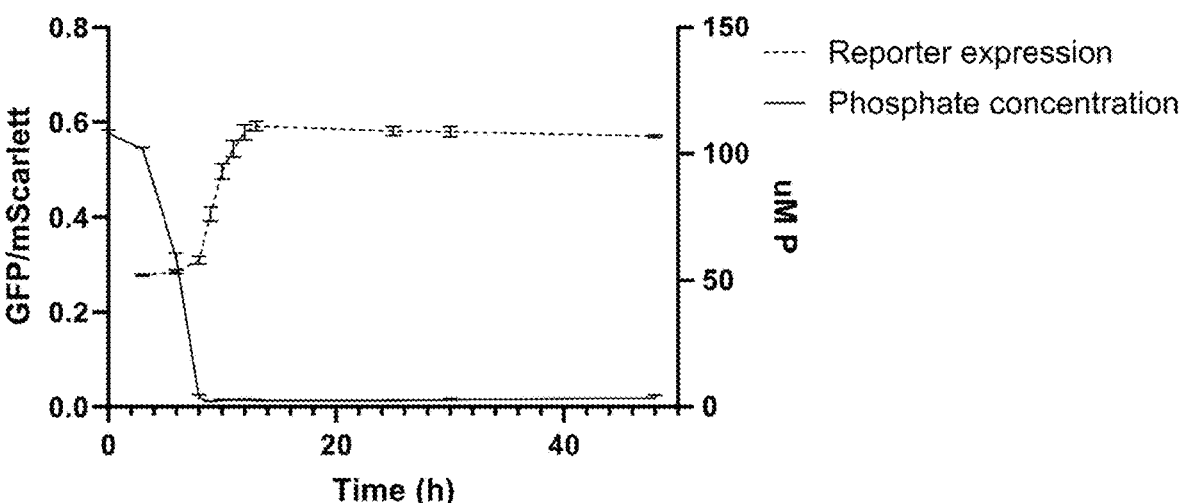
Figure 4C:
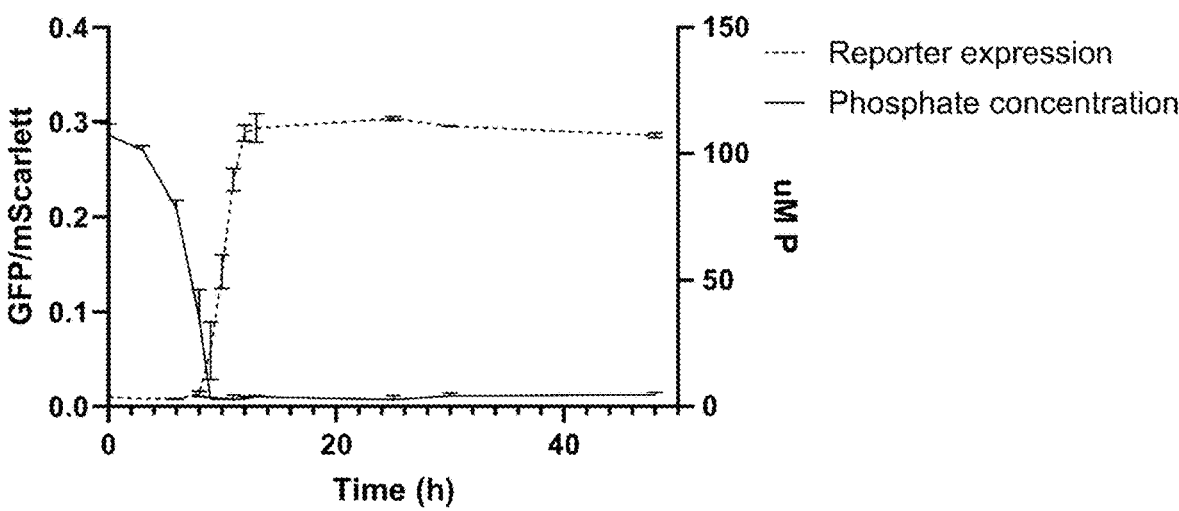
Figure 4C:
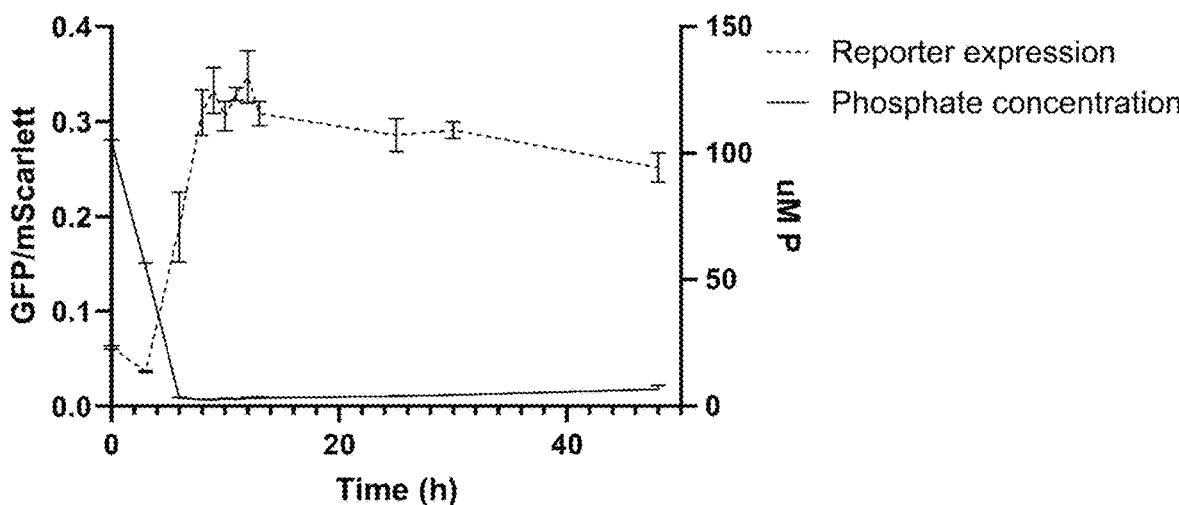
Figure 4D:
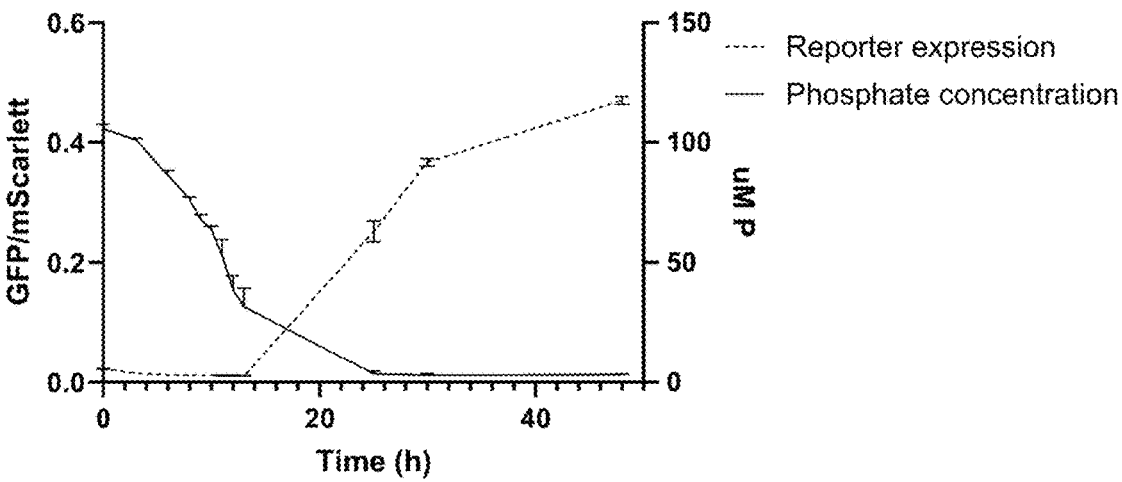
Figure 4D:
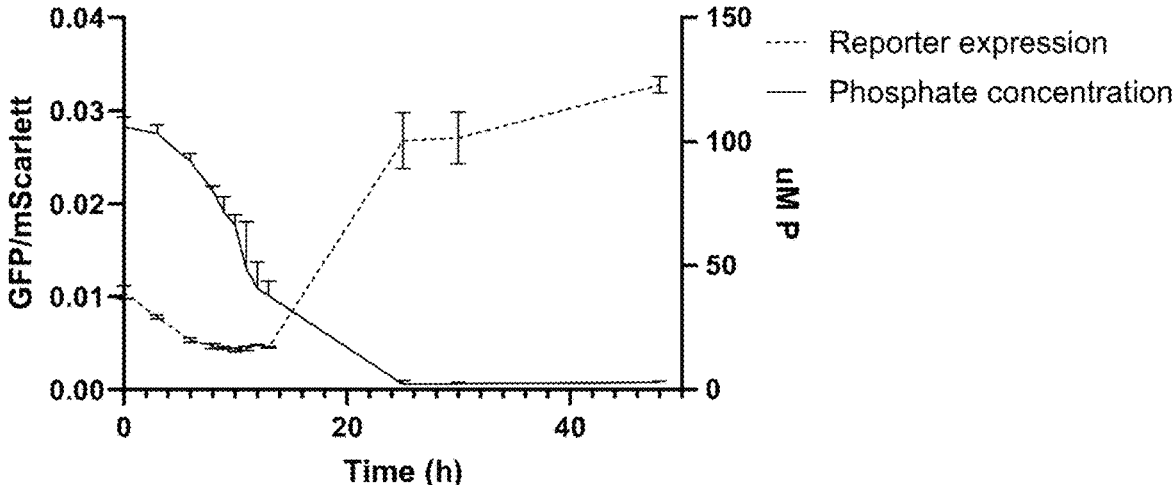

To test whether depletion of Pi in the growth media over time would result in activation of pstS and Pliar53 promoters in *Azospirillum brasilense* Sp245, *Herbaspirillum seropedicae* Z67, *Pseudomonas stutzeri* DSM 4166, and *Kosakonia radicincitans* DSM16656, cultures (n=3) were thrice washed and inoculated into flat bottomed 96-well plates containing 100 uL of NFbHP supplemented with 100 uM starter potassium phosphate. Cultures were incubated with shaking and GFP/LSSmScarlett fluorescence was read at defined time intervals. In these experiments, each pstS and Pliar53 promoter was fused to the reporter gene GFP on a plasmid also carrying a constitutively expressed LSSmScarlett reporter gene such that LSSmScarlett fluorescence could be used to track cell density and internally standardize GFP fluorescence as relative expression units (REU), calculated as GFP fluorescence/LSSmScarlett fluorescence (FIG. 1). At each interval, cultures were pelleted by centrifugation after and Pi concentration was measured in the cleared supernatant using a Sigma Aldrich Phosphate Assay Kit (Cat MAK308), as per the manufacturer recommendations. In all strains tested, Pi was completely depleted in the media between 0-24 h, whereas, expression was induced in all cases only once the Pi concentration dropped below 50 uM (FIGS. 4A, B, C, and D). Greatest phosphate-sensitive activation of the GFP reporter gene occurred when native pstS promoters derived from each tested strain were used as the control element in the heterologous gene expression cassette, and the heterologous gene expression cassette was integrated at a chromosomal locus distinct from the locus of the endogenous phosphate-sensitive promoter.

Example 3. Inducing Reporter Gene Expression in Model Soil Bacteria in Response to Decreasing Phosphate Concentration in a Plant Growth Medium Promoters induced by low Pi concentration activated GFP expression on plant roots following Pi depletion in a sterile sand plant growth medium. Surface sterilized corn seeds were sowed into sterilized 250 mL Schott bottles filled with 200 g of washed sand and 30 mL of Pi-free Hoagland solution. Seeds were germinated in the Schott bottles for 3 days in a growth room set with the following parameters: light intensity 250 $\mu$mol/m$^2$/s at 7 inches from the floor; 16:8 light cycles with 30 minute sunrise/sunset dimming; 50-55% humidity. Plants were then inoculated with 1×10$^5$ cells of *A. brasilense* Sp245 carrying a PstS::GFP reporter plasmid (EXAMPLE 2, FIG. 1) with constitutive LSSmScarlett reporter, as confirmed by viable CFU counts. The inoculant cells were prepared by sub-culturing single colonies into NFbHP media with 50 mM potassium phosphate to repress PstS::GFP, 20 mM ammonium chloride, and relevant antibiotics, then incubating overnight at 30° C. with shaking. The following day, cells were harvested by centrifugation and washed twice in NFbHP and resuspended in NFbHP containing 500 uM potassium phosphate to repress the PstS::GFP reporter and provide starter Pi for the plant experiment. After inoculation, plants were incubated in the growth room and sampled at 1, 3, 6, 20, and 40 days post inoculation (dpi). For each sampling point, three plant replicates were destructively uprooted and loose sand was discarded. The roots were then excised from the shoot at the cotyledon and vortexed in water to create a bacterial cell suspension. This fraction was defined in these experiments as the rhizosphere. To measure Pi concentration in the samples, aliquots of the cell suspensions were centrifuged at high speed to remove all solids, and the cleared supernatant was assayed using a Sigma Aldrich Phosphate Assay Kit (Cat MAK308). To isolate bacterial cells for analysis of the PstS::GFP reporter, plant and sand debris remaining in the rhizosphere suspension were selectively cleared by centrifugation at low speed, and one hundred microlitre aliquots of the supernatant containing the bacterial cells were analyzed by flow cytometry.

Because the PstS::GFP reporter plasmid carried a constitutively expressed LSSmScarlett reporter protein, flow cytometry events corresponding to bacterial cells could be gated based on LSSmScarlett fluorescence above the background (here defined as LSSmScarlett+), as validated by Haskett et al. (doi: 10.3389/fmicb.2021.690439). The percentage of the LSSmScarlett+ population activated for PstS::GFP expression at each time point was quantified by establishing PstS::GFP "−" and "+" threshold fluorescence values for the bacteria. This was done by supplementing one experimental treatment with 50 mM potassium phosphate at the time of inoculation to repress expression from PstS::GFP reporter, then generating the GFP−/+ threshold value as the upper 99th percentile of GFP fluorescence in this repressed state, as validated by Haskett et al. (doi:10.1073/pnas.2117465119).

Figure 5:
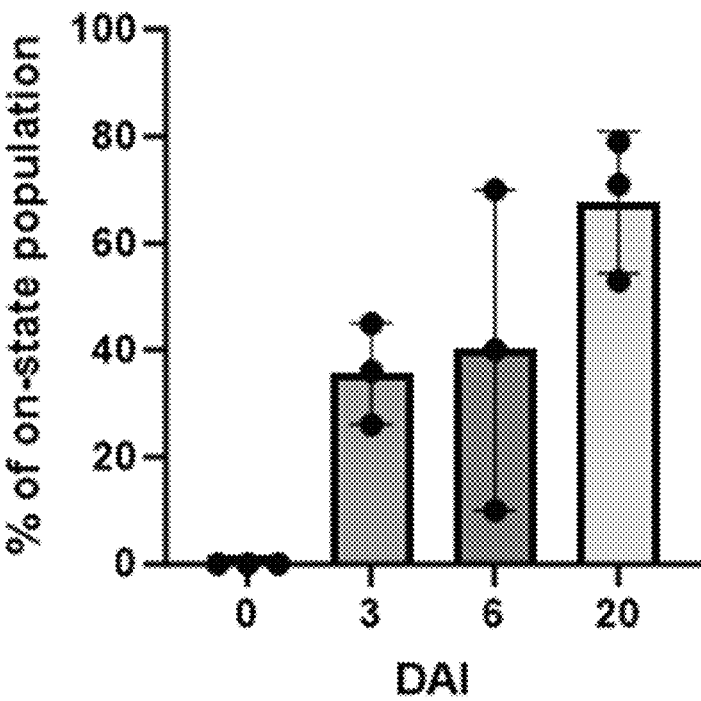
FIG. 5 shows phosphate switch activation in the rhizosphere of corn inoculated with *Azospirillum brasilense* (pstS promoter controlling GFP expression) in a sterile system containing sand.
Figure 6:
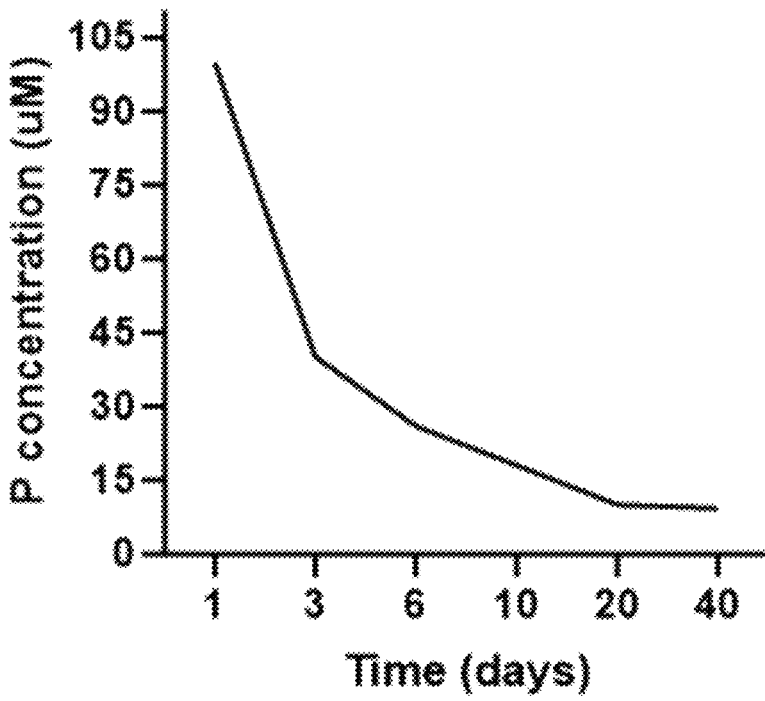
FIG. 6 shows phosphate concentration in sand in the rhizosphere of corn plants inoculated with *Azospirillum brasilense* (strain containing pstS promoter controlling GFP expression) in sterile conditions.

As shown in FIG. 5 and FIG. 6, after 1-dpi, the phosphate concentration in the rhizosphere was determined to be approximately 100 uM, however, the bacterial cell density at this time point was below the detection range for analysis by flow cytometry. After 3-dpi, the phosphate concentration in the rhizosphere fell to 40 uM, triggering a fraction of about 35% of the bacterial population to activate PstS::GFP and enter the GFP+ state. The concentration of Pi continued to decline to about 10 uM by 20-dpi, at which point approximately 70% of the bacterial population were expressing the PstS::GFP reporter fusion, entering the GFP+ state. By 40-dpi, the Pi concentration remained at about 10 uM, and LSSmScarlett+ events were no longer detected in the sample.

Example 4. Engineering Bacteria to Produce Ammonia with Unidirectional Glutamine Synthetase Adenylyltransferase in Response to Decreasing Phosphate Concentration Diazotrophic bacteria encode the nitrogenase enzyme capable of reducing inert atmospheric di-nitrogen gas into ammonia under micro-aerobic conditions, providing an autonomous source of nitrogen to the cell. In natural diazotrophs, ammonia derived from nitrogen fixation is assimilated rapidly through the biosynthetic action of glutamine synthetase (GS), which catalyzes the reaction of ammonia and glutamate to form glutamine. Glutamine acts as an indicator of intracellular nitrogen status and blocks expression and activity of nitrogenase on multiple genetic levels. This negative feedback repression prevents diazotrophs from producing more ammonia than is needed for assimilation and prevents release of ammonia for use by plants.

Blocking the activity of GS drives ammonia release in diazotrophs, because a) inability to produce glutamine alleviates negative feedback repression on nitrogenase, and b) inability to assimilate ammonia results in diffusion from the cell. GS activity is modulated through post-translational modification, specifically adenylylation. GS biosynthetic activity can be inhibited by manipulating the adenylylation state. Fully adenylated GS is inactive but can be de-adenylated to restore function. In bacteria, adenylylation and deadenylation of GS is controlled by the bidirectional adenylyltransferase GlnE. Replacement of the glnE gene with a truncated form that carries only the domain required for adenylylation can be used to inactivate GS and drive ammonia release. Ammonia production in response to decreasing phosphate concentration can be caused by operably linking a control element comprising an inducible promoter triggered by low Pi concentration to such a truncated GlnE protein lacking an adenylyl removing domain which exhibits unidirectional adenylyltransferase (uAT) activity.

Figure 7:
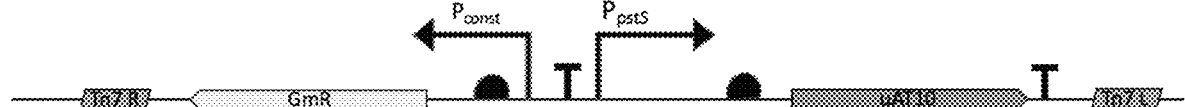
FIG. 7 shows a schematic of a gene expression cassette comprising a phosphate-sensitive pstS promoter operably linked to a gene encoding a GlnE protein lacking an adenylyl removing domain (uAT10). Constitutive expression of a gentamicin resistance gene (GmR) permits selection of bacterial strains comprising the cassette.

To generate strains able to release ammonia with uATs in response to decreasing phosphate concentration, the pstS promoter regions of *Azospirillum brasilense* Sp245 (SEQ ID NO: 418), *Herbaspirillum seropedicae* Z67 (SEQ ID NO: 422), *Pseudomonas stutzeri* DSM 4166 (SEQ ID NO: 428), and *Kosakonia radicincitans* DSM16656 (SEQ ID NO: 423-424) were PCR amplified. Plasmids were designed to encode a uAT (SEQ ID NO: 1) protein of interest operably linked to three different ribosome binding sites (BCD2: strong (SEQ ID NO: 430); BCD22: weak (SEQ ID NO: 449); BCD17: medium strength (SEQ ID NO: 444)) with no promoter, facilitating incorporation of different control elements upstream of the uAT gene. The plasmids were digested with NotI and ligated to the amplified pstS promoters. Assembled plasmids containing complete heterologous gene expression cassettes (FIG. 7) were introduced into *Azospirillum brasilense* Sp245, *Herbaspirillum seropedicae* Z67, *Pseudomonas stutzeri* DSM 4166, and *Kosakonia radicincitans* DSM16656 host strains with a deletion of the endogenous glnE gene. The expression cassettes were integrated into the chromosome in single copy downstream of each host strain's glmS gene via site-specific Tn7 transposon-mediated recombination. Strains comprising successfully integrated gene expression cassettes were selected via gentamicin resistance, and chromosomal cassette integration was validated by PCR using primers that anneal to junction of the chromosomal DNA and the inserted heterologous gene expression cassettes.

Genetic circuits containing ribosome binding sites of varying strength were tested because uAT expression can reduce glutamine synthetase (GS) activity to a level that is not compatible with cell survival. The level of uAT expression in each strain sufficient to cause ammonia release without impairing cell viability was ascertained.

Figure 8:
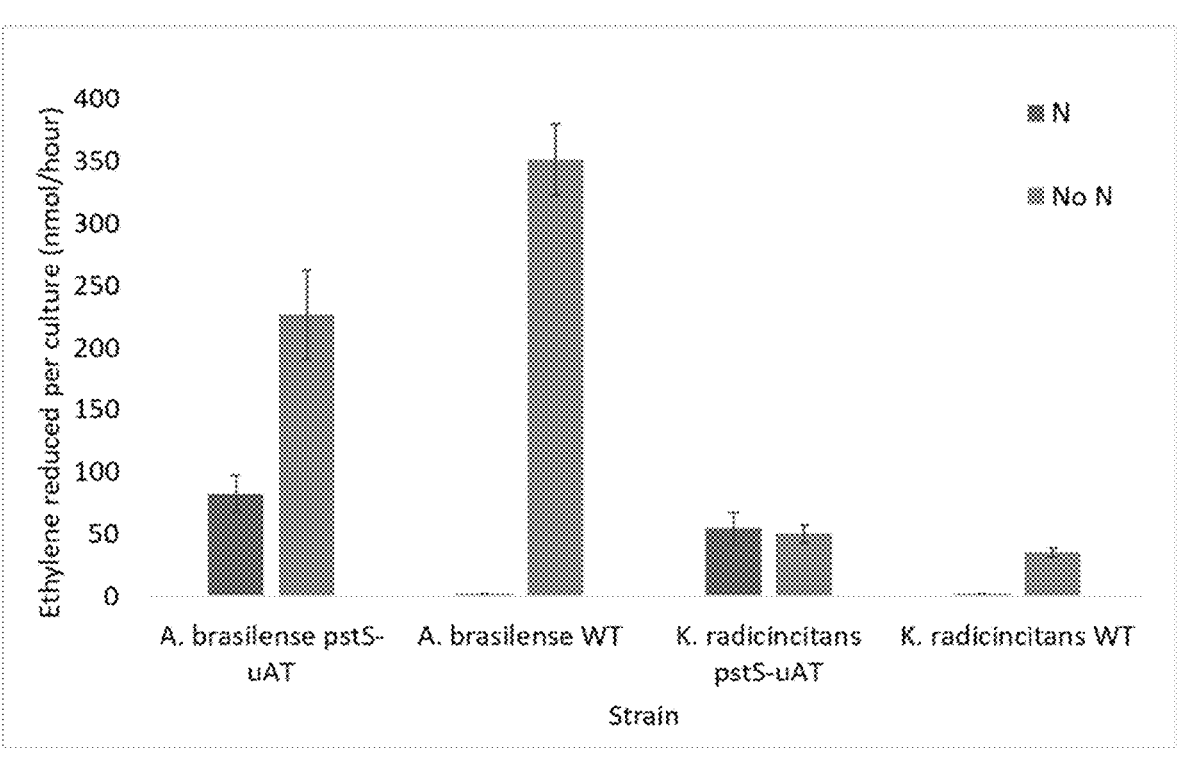
FIG. 8 shows de-repression of nitrogenase activity in engineered diazotrophs where glnE is replaced with a low Pi-inducible uAT.

The genetically engineered *Azospirillum, Herbaspirillum, Kosakonia,* and *Pseudomonas* strains with the PstS::uAT10 gene expression cassettes (described above) were assayed for de-repression of nitrogenase activity under low phosphate conditions using an acetylene reduction assay. The acetylene reduction assay measures conversion of acetylene to ethylene by nitrogenase as a proxy for conversion of di-nitrogen gas into ammonia. In this experiment, engineered and wild-type bacteria were grown on LB agar plates. Cells were scraped from each plate and resuspended in 22 mL gas chromatography vials at OD600 0.3 in 3 mL of Pi-free semi-solid NFbHP media with either 10 mM ammonium chloride or no added nitrogen. Cultures were sealed by crimping with septum caps and incubated at 30° C. for 24 h prior to starting the assay. The assay was initiated by replacing 10% of the headspace with acetylene gas using a fine gauge needle. Cultures were incubated for an additional 24 h, and ethylene production was quantified in the headspace of each vial using an Agilent 8860 Gas Chromatograph fitted with autosampler (FIG. 8). Wild-type bacteria reduced acetylene into ethylene when cultured in nitrogen-free conditions, but they did not reduce acetylene into ethylene in the presence of 10 mM ammonium chloride. This phenotype was expected because wild-type diazotrophs expressing glutamine synthetase rapidly convert ammonia into glutamine, which represses transcription and activity of nitrogenase. In contrast, glnE mutant bacteria carrying PstS::uAT10 gene expression cassettes reduced acetylene into ethylene both in the absence and presence of ammonium chloride, indicating that GS was inactivated, ammonia was not converted to glutamine, and cells escaped negative feedback repression of nitrogenase.

Figure 9:
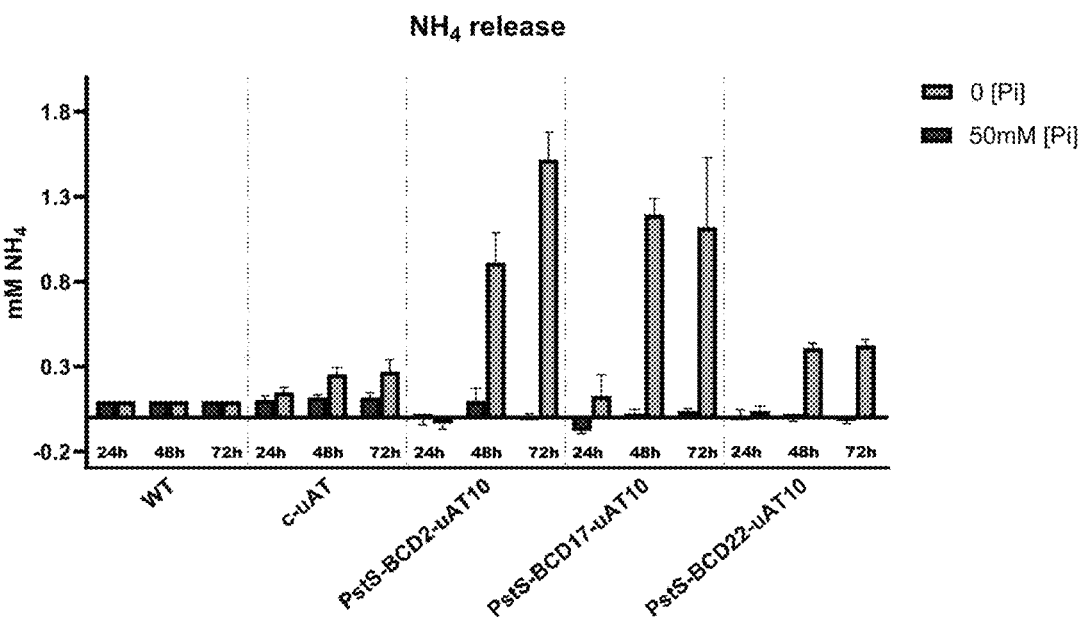
FIG. 9 shows Pi-dependent ammonia release by *Azospirillum brasilense* Sp245 glnE mutants carrying chromosomally integrated pstS::uAT cassettes.

The three genetically engineered *Azospirillum brasilense* Sp245 strains with the PstS::uAT10 gene expression cassettes containing ribosome binding sites of varying strength were assayed for production of ammonia in the setting of low phosphate concentration. Cells were inoculated in culture tubes at OD600 0.3 into 3 mL semi-solid NFbHP media with or without 50 mM potassium phosphate, and incubated for 72 h at 30° C. 100 μL aliquots of media were sampled from below the pellicle at 24 h time points, centrifuged to pellet agar and cells, and measured for ammonia concentration in the cleared supernatant using an indophenol assay adapted from Schnabel and Sattely (doi:10.1128/AEM.00582-21). Engineered strains comprising PstS: uAT10 gene expression cassettes were compared to *Azospirillum brasilense* constitutively expressing uAT10 (c-uAT strain in Schnabel and Sattely (doi:10.1021/acssynbio.1c00287)) and wild-type *A. brasilense* Sp245 (FIG. 9).

As expected, wild-type *A. brasilense* Sp245 did not release ammonia in any condition, and *Azospirillum brasilense* constitutively expressing uAT10 released a small amount of ammonia at 48 h. All three genetically engineered *Azospirillum brasilense* Sp245 strains with the PstS::uAT10 gene expression cassettes released ammonia after 48 h in the absence of Pi, but did not release ammonia in the presence of Pi. Strains where the uAT10 gene expressed from the pstS promoter was operably linked to a strong- (BCD 2) or medium-strength (BCD 17) ribosome binding site released approximately two-fold the amount of ammonia compared to the strain where a weak ribosome binding site (BCD 22) was utilized, showing that stronger uAT expression increased ammonia release.

Example 5. Producing Ammonia from Engineered Bacteria by Overexpressing a GlnE Protein Lacking an Adenylyl Removing Domain Intracellular glutamine concentration is the dominant indicator of nitrogen status in many nitrogen-fixing bacteria. Decreasing intracellular glutamine concentration prevents cells from sensing high ammonia levels in the environment. Intracellular glutamine concentration can be decreased by increasing expression or activity of glutaminase, an enzyme that converts glutamine into glutamate. Separately, intracellular glutamine concentration can be lowered by decreasing expression or activity of glutamine synthase (GS), an enzyme encoded by the gene glnA that converts ammonia into glutamine. In nitrogen-fixing bacteria, fixed ammonia is quickly assimilated into glutamine and glutamate shunted into cellular metabolism. Blocking ammonia assimilation causes fixed nitrogen to be released into the environment.

Most ammonia is assimilated into glutamine by glutamine synthetase (GS), and subsequently into glutamate by glutamine oxoglutarate aminotransferase (GOGAT). GS is regulated post-translationally by GS adenylyltransferase (GlnE), a bidirectional enzyme encoded by the glnE gene that catalyzes both the adenylylation and de-adenylylation of GS through activity of its adenylyltransferase (AT) and adenylyl-removing (AR) domains, respectively. When nitrogen is abundant, GS is not expressed, and the GlnE AT domain adenylates and deactivates GS. When nitrogen is scarce, GS is expressed, and the GlnE AR domain de-adenylylates and activates GS.

GS adenylyltransferase can be engineered such that it only adenylates and deactivates GS, lacking the ability to reactivate the enzyme. This change in function is achieved by expressing a truncated variant of the GlnE enzyme that lacks the AR domain and regulatory region of the enzyme. Such a truncated GlnE is termed a unidirectional adenylyltransferase (uAT). When a uAT is overexpressed in nitrogen-fixing bacteria, uAT activity deactivates GS independently of the concentration of ammonia, glutamine, and other regulators of nitrogen assimilation. Reduced GS activity in the cells causes a decrease in intracellular glutamine concentration and increase in intracellular ammonia concentration. Cells interpret decreased intracellular glutamine concentration as a need for additional nitrogen fixation, further increasing the intracellular concentration of ammonia through increased fixation of $N_2$ to $NH_3$ by nitrogenase. The excess intracellular ammonia is then secreted into the surrounding environment for uptake and assimilation by nearby plants and microbes.

Unidirectional ATases (uATs) are engineered as follows. Where present, the glnE gene encoding glutamine synthetase adenylyltransferase (ATase) is identified in soil bacteria such as those of the genera *Acetobacter, Acidothermus, Acinetobacter, Agrobacterium, Aromatoleum, Arthrobacter, Azoarcus, Azorhizobium, Azospirillum, Azotobacter, Bacillus, Bifidobacterium, Bradyrhizobium, Burkholderia, Conexibacter, Curtobacterium, Ensifer, Enterobacter,*

US 12,649,699 B2

*Erwinia, Escherichia, Flavobacterium, Frankia, Gaiella, Gluconacetobacter, Gluconobacter, Herbaspirillum, Klebsiella, Kosakonia, Lactobacillus, Lactococcus, Lysinibacillus, Maritimibacter, Methylobacterium, Nitrosocosmicus, Nitrososphaera, Paenarthrobacter, Paenibacillus, Pantoea, Pediococcus, Peribacillus, Phytobacter, Priestia, Pseudarthrobacter, Pseudomonas, Rahnella, Rhizobium, Rhodococcus, Rhodoplanes, Rhodopseudomonas, Rhodospirillum, Serratia, Solirubrobacter, Sphingobacterium, Sphingomonas, Stenotrophomonas, Streptomyces, Stutzerimonas, Variovorax, Xanthobacter,* and *Yoonia.* Next, the locations of the adenylyl-transferring (AT) and adenylyl-removing (AR) domains within each ATase are predicted. By one method, since the adenylyl-transferring (AT) and adenylyl-removing (AR) domains within ATase are homologous to each other, their locations are predicted through alignment of the N- and C-terminal halves of ATase to each other before designing uAT variants based on this intraprotein homology. By way of a second distinct method, the ATase amino acid sequence in one organism is aligned to that of another to identify the AT and AR domains. After AT and AR domains are identified, a series of uAT candidates is created based on each ATase where each uAT candidate in the series is obtained by selecting a different truncation site in the region between the AR and AT domain (SEQ ID NO: 1-25). The native glnE gene in each organism is then scarlessly deleted by double homologous recombination or other methods, and candidate uATs are expressed. Ammonia release is measured by growing strains in nitrogen-free liquid minimal media with an atmosphere of less than 3% oxygen, or by growing them in nitrogen-free semi-solid agar where bacteria form a pellicle at an oxygen concentration that permits nitrogenase activity. After incubation under these conditions, ammonia is then quantified in samples of cleared supernatant using an ammonium probe or a colorimetric assay such as the indophenol assay described by Schnabel and Sattely (doi:10.1128/ AEM.00582-21).

Figure 10:
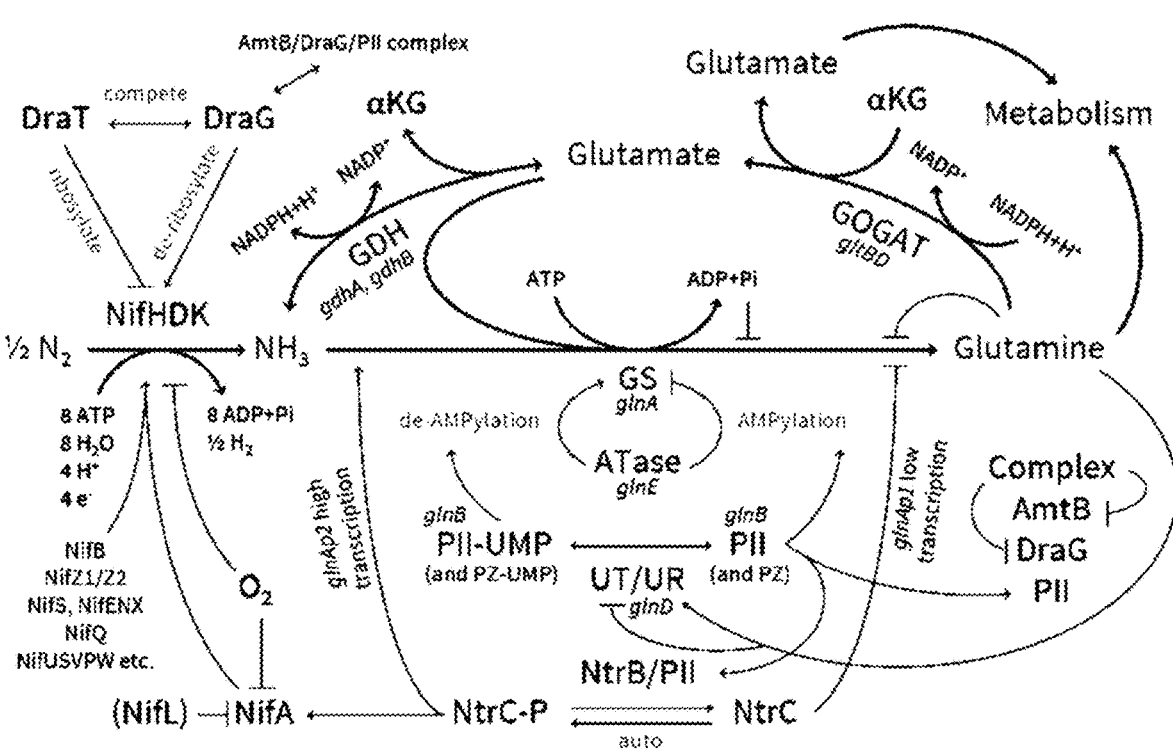
FIG. 10 shows metabolism and regulation of bacterial nitrogen fixation.

Example 6—Producing Ammonia from Engineered Bacteria by Overexpressing Proteins from Nitrogen Fixation and Assimilation Pathways Since nitrogen fixation consumes at least 16 mol of adenosine triphosphate (ATP) per mol $N_2$ fixed, diazotrophic bacteria have evolved complex regulatory networks to control this energy-intensive metabolic process. To conserve energy, the $N_2$-fixing catalyst nitrogenase is expressed only under conditions of nitrogen starvation, and the same conditions stimulate upregulation of high-affinity ammonia assimilation by the enzyme glutamine synthetase (GlnA, GS), preventing release of excess ammonia for plants (FIG. 10). Diazotrophs can be engineered to produce and release ammonia by decoupling their ability to repress nitrogenase under nitrogen replete conditions. De-repression of nitrogenase can be achieved by a number of genetic strategies, and in many bacteria, results in more ammonia produced than can be assimilated, causing diffusion of ammonia from the cell.

A distinct method to stimulate ammonia production and release is to prevent bacteria from assimilating fixed nitrogen derived from $N_2$ into glutamine, the intracellular signal for nitrogen status. This can be accomplished by chemically or genetically inactivating glutamine synthetase by a number of strategies. In addition to preventing assimilation of ammonia derived from nitrogen fixation, low glutamine levels force the cell to engage a nitrogen starvation response, driving de-repression of nitrogenase. High levels of ammonia production paired with inability to assimilate it causes diffusion of ammonia from the cell in high concentrations.

Whether a) nitrogenase feedback repression is alleviated, b) ammonia assimilation and glutamine production is inhibited or c) both processes are engineered, bacteria that produce and release large quantities of ammonia suffer a marked fitness defect that renders them non-competitive and unable to persist in the environment. Thus, inducible ammonia production releases a greater amount of ammonia from an initial bacterial inoculum than constitutive ammonia production because bacterial growth before ammonia production increases bacterial biomass and overall ammonia generated.

The NifA protein, encoded by the nifA gene, is the master transcriptional regulator of genes involved in nitrogenase assembly, function and maintenance, which are encoded by nif cluster and fix cluster genes. Specifically, NifA acts in association with the sigma factor 654 to drive expression of nif cluster and fix cluster genes. The nifA gene in bacteria can be regulated at the transcriptional and posttranslational level by nitrogen, oxygen, and carbon. In *Azotobacter vinelandii*, overexpression of nifA from a heterologous promoter drives constitutive nitrogenase activity and stimulates ammonia release.

In nature, intracellular levels of active NifA protein are controlled by two key factors: transcription of the nifLA operon and inhibition of NifA protein activity by protein-protein interaction with the NifL protein. Increasing the transcription level of the nifLA operon leads to a higher intracellular concentration of NifA proteins, which increases expression of nitrogenase, the rate of ammonia production, and resulting ammonia release.

The nifL gene is common amongst gamma-proteobacteria and acts as an anti-activator of the nitrogenase master regulator NifA. In conditions of low oxygen and low glutamine, NifL represses activity of NifA, preventing nitrogenase expression and nitrogen fixation. However, deletions in nifL stop NifA inhibition and stop nitrogenase activity from repression by glutamine. Removal of nitrogenase feedback inhibition leads to ammonia release. A nifL gene deletion therefore will stop production of NifL protein, free NifA from inhibition by protein-protein interaction, and permit ammonia release.

glnR acts as a regulator of nitrogen metabolism genes in gram-positive bacteria. In *P. polymyxa* WLY78, overexpression of glnR drives nitrogenase activity even in the presence of added nitrogen. As such, overexpression of glnR can drive ammonia release in this strain.

Example 7—Producing Ammonia from Engineered Bacteria by Reducing Expression of Proteins from Nitrogen Fixation and Assimilation Pathways Ammonia uptake from the environment can be reduced by decreasing the expression level of AmtB ammonia transporter protein (FIG. 10). In *Pseudomonas stutzeri* A1501, *Azotobacter vinlandii* DJ, and *Gluconobacter diazotrophicus*, deletion of the ammonium uptake system encoded by one or more copies of the amtB gene prevents uptake of ammonium from the extracellular environment, and also results in excretion of ammonia from the cells under diazotrophic growth conditions.

Separately, the PII proteins are global nitrogen response regulators, acting on a suite of nitrogen metabolism proteins. In *Rhodobacter capsulatus* and *Azorhizobium caulinodans* ORS 571, deletion of both PII proteins forces the adenylyl transferase (AT) to adenylate the GS protein, leading to de-repressed nitrogenase activity in the presence of ammonia. When both PII genes are deleted, ORS 571 releases ammonia into the growth media when grown under nitrogen fixing conditions.

Separately, nitrogenase is regulated by feedback repression at the transcriptional and post translational level by ADP-ribosylation via the DraT-DraG system. DraT catalyzes the ADP-ribosylation of the nitrogenase Fe protein and shuts off of nitrogenase under nitrogen excessive conditions, whereas DraG catalyzes the removal of ADP ribose and reactivation of nitrogenase under nitrogen starvation. Deletion of DraT in a cell where nitrogenase is not regulated by feedback repression at the transcriptional level results in nitrogenase activity that escapes feedback repression.

Example 8—Producing Ammonia from Engineered Bacteria by Inducibly Repressing Glutamine Synthetase Expression As described in EXAMPLE 5, down-regulating glutamine synthetase (GS) activity blocks bacteria from assimilating fixed nitrogen and results in ammonia release into the environment. Transcriptionally repressing glnA in response to depletion of phosphate can down-regulate GS and lead to conditional ammonia release under phosphate-limited conditions.

To transcriptionally repress the native glutamine synthetase gene, the native glnA in soil bacteria such as those of the genera *Acetobacter, Acidothermus, Acinetobacter, Agrobacterium, Aromatoleum, Arthrobacter, Azoarcus, Azorhizobium, Azospirillum, Azotobacter, Bacillus, Bifidobacterium, Bradyrhizobium, Burkholderia, Conexibacter, Curtobacterium, Ensifer, Enterobacter, Erwinia, Escherichia, Flavobacterium, Frankia, Gaiella, Gluconacetobacter, Gluconobacter, Herbaspirillum, Klebsiella, Kosakonia, Lactobacillus, Lactococcus, Lysinibacillus, Maritimibacter, Methylobacterium, Nitrosocosmicus, Nitrososphaera, Paenarthrobacter, Paenibacillus, Pantoea, Pediococcus, Peribacillus, Phytobacter, Priestia, Pseudarthrobacter, Pseudomonas, Rahnella, Rhizobium, Rhodococcus, Rhodoplanes, Rhodopseudomonas, Rhodospirillum, Serratia, Solirubrobacter, Sphingobacterium, Sphingomonas, Stenotrophomonas, Streptomyces, Stutzerimonas, Variovorax, Xanthobacter,* and/or *Yoonia* (SEQ ID NO: 229, 230, 460-511, and 512) is operably linked to a repressible promoter, such as the Ptet promoter (SEQ ID NO: 32), the Plac promoter (SEQ ID NO: 33), or the PphlA promoter (SEQ ID NO: 34). A protein-coding sequence encoding a repressor protein paired with the repressible promoter, TetR (SEQ ID NO: 27), LacI (SEQ ID NO: 29), or PhlF (SEQ ID NO: 30) respectively, is operably linked to a phosphate-sensitive promoter (SEQ ID NO: 417-428) in a heterologous gene expression cassette, which is introduced into a soil bacterium to create a genetically engineered bacterium. The genetically engineered bacterium (GEB) is fermented in high-phosphate media such that the bacteria grow to high cell density. The GEB are then introduced into a plant growth medium in an agricultural context. Once the phosphate concentration in the plant growth medium falls below a threshold level (e.g. about 50 µM, 40 µM, 30 µM, 20 µM, or 10 µM to about 1 µM to about 1 µM), the repressor protein is expressed from the phosphate sensitive promoter, binds to the repressible promoter, and down-regulates expression of glnA, leading to ammonia release.

Example 9—Producing Ammonia from Engineered Bacteria by Inducibly Cleaving an Engineered Glutamine Synthetase to Abrogate Enzymatic Activity Glutamine synthetase (GS) is catalytically inactivated by disrupting the structure of its active site through cleavage of the GS peptide backbone. Hydrolysis of the GS peptide backbone can be catalyzed by proteases, a class of enzymes that recognize specific short amino acid sequences and cleave a protein's peptide backbone a consistent distance from said amino acid recognition sequences, herein referred to as protease-specific recognition sequences (PSRS). A GS protein variant that is controllably cleaved by a protease is engineered by encoding one or more PSRS within the coding sequence of the glnA gene. By engineering a nitrogen-fixing bacterial strain to contain (i) a GS protein comprising one or more PSRS and (ii) the cognate protease under inducible control, GS is catalytically inactivated in response to environmental changes. In this system, introduction of an environmental stimulus induces expression of a protease. The protease then binds the one or more PSRS in the engineered GS and cleaves the GS backbone, causing a structural change in GS that inactivates it catalytically and causes ammonia accumulation due to GS down-regulation.

To engineer an organism with a GS protein that is inactivated by an inducible protease, the GS protein is engineered to comprise one or more PSRS. Proteases capable of cleaving the engineered GS protein peptide backbone include the tobacco etch virus (TEV) protease (SEQ ID NO: 45), tobacco vein mottling virus (TVMV) protease (SEQ ID NO: 46), sunflower mild mosaic virus (SMMV) protease (SEQ ID NO: 47), turnip mosaic virus (TuMV) protease (SEQ ID NO: 48), soybean mosaic virus (SMV) protease (SEQ ID NO: 49), plum pox potyvirus (PPV) protease (SEQ ID NO: 50), Hepatitis C virus (HCV) NS3 protease (SEQ ID NO: 51), Coagulation factor Xa (SEQ ID NO: 52), and Furin (SEQ ID NO: 53). The proteases above recognize the following PSRS sequences, respectively: EXXYXQ-(S/G) or ENLYFQ-(S/G/A/M/C/H), wherein X is any amino acid and the TEV protease cleaves between the Q and the S, G, A, M, C, or H residues; ETVRFQ-(G/S), wherein the TVMV protease cleaves between the Q and S or G residues; EEIHLQ-(S/G), wherein the SMMV protease cleaves between the Q and S or G residues; VXHQ or VRHQ-S, wherein X is any amino acid and the TuMV protease cleaves C-terminal to the Q residue; XVXXQ-(G/S), wherein X is any amino acid and the SMV protease cleaves between Q and S or G residues; NVVVHQ-A, wherein the PPV protease cleaves between the Q and the A residue; (D/E)XXXXC(A/S), wherein X is any amino acid and the HCV NS3 protease cleaves between the C and the A or S residues; I(D/E)GR, wherein the Factor Xa protease cleaves C-terminal to the R residue; or RX(K/R)R, wherein the furin protease cleaves C-terminal to the C-terminal R residue.

The one or more PSRS are incorporated into the GS coding sequence in a number of locations. To ensure that the one or more PSRS will be efficiently bound by a protease, the PSRS is/are located at the solvent-facing surface of the GS protein to increase the probability that the protease molecule will collide with the PSRS in the GS protein variant and bind to it/them. Multiple methods are used to identify the solvent-facing surface of the GS protein, including visualization of external amino acid residues using crystal structure data, alignment of the amino acid sequence of GS variants without a crystal structure to those with one in order to identify homologous regions of the protein, in silico structure prediction for GS variants without a crystal structure and identification of solvent-facing regions of the protein, and mass-spectrometry based protein labeling methods that identify solvent-facing regions of a protein. Additionally, catalytic deactivation of GS is more complete if protease cleavage compromises the structure of the GS enzyme active site. Compromising the structure of the active site is achieved by rationally positioning the PSRS such that cleavage will create multiple protein fragments that each contain a portion of the incomplete active site, rationally positioning the one or more PSRS near or within the active site so that the break in the peptide backbone alters the sterics of the active site, or screening the enzymatic activity of a library of GS variants with the PSRS positioned at random locations.

In the *Azospirillum brasilense* Sp245 GS polypeptide (SEQ ID NO: 229), locations to incorporate one or more PSRS that meet the above criteria include between amino acid residues 98 and 99, 121 and 122, 279 and 280, and/or 285 and 286. In the *Pseudomonas stutzeri* GS polypeptide (SEQ ID NO: 230), locations to incorporate one or more PSRS that meet the above criteria include between amino acid residues 98 and 99, 119 and 120, 283 and 284, and/or 298 and 299. These insertion sites are depicted in Table 6.

To achieve inducible deactivation of GS, GS must function normally until an environmental stimulus triggers protease expression, at which point enzymatic activity is minimized. To achieve normal function of GS until the protease is expressed, the native glnA gene in a bacterial strain is replaced with an engineered copy of glnA encoding the one or more PSRS so that the engineered GS is expressed by way of the native glnA genetic context of the host strain. To minimize GS activity after protease cleavage, the engineered copy of glnA encoding the one or more PSRS is the only glnA allele in the host strain. The gene encoding GS, glnA, is an essential gene for many bacterial strains. However, replacing a single native allele with a single engineered allele is accomplished by inserting certain site-specific recombinase recognition sites (SSRRS) flanking a bacterium's native glnA allele in the bacterium's chromosome (including FRT sites and/or loxP sites), encoding the corresponding site-specific recombinase (a yeast flippase (FLP) recombinase if FRT SSRRS or a Cre-recombinase if loxP SSRRS) under inducible control on a plasmid with the glnA allele encoding a GS variant comprising the one or more PSRS, and inducing recombination to swap the engineered glnA allele into the chromosome while excising the native allele. Such a process achieves exchange of the wild-type glnA allele for the engineered glnA allele encoding the GS that comprises the one or more PSRS without ever requiring deletion of the essential glnA gene.

Once a bacterial strain is obtained where the native gene encoding GS has been replaced by a GS gene encoding a GS variant comprising the one or more PSRS, a heterologous gene expression cassette comprising a protease-encoding gene (e.g. SEQ ID NO: 54, 55, or 56) operably linked to a phosphate sensitive promoter (SEQ ID NO: 417-428) is introduced. Since the protease gene is expressed by a phosphate-sensitive promoter, (SEQ ID NO: 417-428), expression of the protease is prevented before the phosphate-sensitive promoter is activated.

A genetically engineered bacterium (GEB) comprising, (i) a gene encoding a GS variant comprising one or more PSRS and (ii) a heterologous gene expression cassette comprising a protease gene of interest operably linked to a phosphate-sensitive promoter, is obtained. Enzymatic activity of a GS variant comprising one or more PSRS within a GEB is compared to activity of wildtype GS in a strain-matched bacterium containing a wild-type GS variant to confirm enzymatic function of the PSRS-containing GS variant, using a biochemical assay. Subsequently the GEB comprising the PSRS-containing GS variant is evaluated for ammonia release via an indophenol assay.

In *Azospirillum brasilense* Sp245, introducing two PSRS into the natively controlled glnA gene followed by inducing TEV protease expression under control of a tetracycline-responsive promoter via anhydrotetracycline yields a significant decrease in GS activity compared to the wild-type. Placing the engineered glnA alleles under control of constitutive promoters at the native locus (instead of the natively regulated promoter) additionally abolishes up-regulation of glnA expression when GS is cleaved by the proteases.

In its agricultural application, the genetically engineered bacterium (GEB) is fermented in high-phosphate media such that the bacteria grow to high cell density. The GEB are then introduced into a plant growth medium in an agricultural context. Once the phosphate concentration in the plant growth medium falls below a threshold level (e.g. about 50 μM, 40 μM, 30 μM, 20 μM, or 10 μM to about 1 μM to about 1 μM), the protease is expressed from the phosphate sensitive promoter, cleaves the GS variant expressed by the GEB, and down-regulates expression of glnA, leading to ammonia release.

Example 10. Engineering Bacteria Isolated from Agricultural Fields to Express a Reporter Gene in Response to Decreasing Phosphate Concentration To generate strains from agricultural soil isolates that express a chromosomally integrated GFP reporter gene in response to phosphate depletion, the pstS promoter regions of soil isolates of *Klebsiella variicola* (SEQ ID NO: 515), *Kosakonia sacchari* (SEQ ID NO: 517), and *Rahnella aceris* (SEQ ID NO: 518) were PCR amplified from genomic DNA, each with HiFi adapters for cloning into an entry plasmid digested with NotI. The cloning site was designed such that the Pi-dependent promoters were positioned upstream of GFP. Plasmids were confirmed by next generation sequencing. Assembled plasmids containing complete heterologous gene expression cassettes (FIG. 1) were introduced into *Klebsiella variicola*, *Kosakonia sacchari*, and *Rahnella aceris* strains isolated from agricultural corn fields. The expression cassettes were integrated into the chromosome in single copy downstream of each host strain's glmS gene via site-specific Tn7 transposon-mediated recombination. Strains comprising successfully integrated gene expression cassettes were selected via gentamicin resistance, and chromosomal cassette integration was validated by PCR using primers that anneal to junction of the chromosomal DNA and the inserted heterologous gene expression cassettes.

Example 11. Inducing Reporter Gene Expression in Bacteria Isolated from an Agricultural Field in Response to Decreasing Phosphate Concentration in an Agricultural Field Soil Substrate Promoters induced by low Pi concentration activated GFP expression on corn roots following Pi depletion in agricultural field soils used as a growth medium. Topsoil was collected from within 10 inches of the surface from American commercial maize fields in the states of Illinois (two sites), North Dakota, and Oklahoma ("Field Soil") and underwent soil chemistry analysis. 2×10" Deepot cells (Stu-ewe & Sons, Inc.) were each filled with 300 g of Field Soil from a single location that had been titrated to 100 ppm potassium and 100 ppm nitrate. In one experimental group ("Illinois B+P solution"), 226 µL of Anderson's 10-34-0 in furrow fertilizer was also added to each Deepot cell. After 24 hours, surface sterilized corn seeds were sown at a depth of 2 inches and inoculated with either (i) 6.2×10$^7$ cells of *K. sacchari* carrying a GFP reporter expression cassette driven by the *K. sacchari* pstS promoter (SEQ ID NO: 517) or (ii) 8.7×10$^7$ cells of *K. variicola* carrying a GFP reporter expression cassette driven by the *K. variicola* pstS promoter (SEQ ID NO: 515), as confirmed by viable CFU counts. After inoculation, plants were incubated in a growth room set with the following parameters: light intensity 250 gmol/m$^2$/s at 7 inches from the floor; 16:8 light cycles with 30 minute sunrise/sunset dimming; 50-55% humidity. Plants were sampled at 7 days ("1 week") and 14 days ("2 weeks") post inoculation. For each sampling point, five plant replicates were destructively uprooted and loose field soil was discarded. The roots were then excised from the shoot at the cotyledon and vortexed in phosphate-buffered saline with 10 mM ammonium chloride for 1 hour to create a bacterial cell suspension. This fraction was defined in these experiments as the rhizosphere. To isolate bacterial cells for analysis of the GFP reporter, plant and soil debris remaining in the rhizosphere suspension were selectively cleared by centrifugation at low speed, and one hundred microlitre aliquots of the supernatant containing the bacterial cells were analyzed by flow cytometry.

Because the GFP reporter cassette carried a constitutively expressed LSSmScarlett reporter protein, flow cytometry events corresponding to bacterial cells could be gated based on LSSmScarlett fluorescence above the background (here defined as LSSmScarlett+), as validated by Haskett et al.

Figure 11:
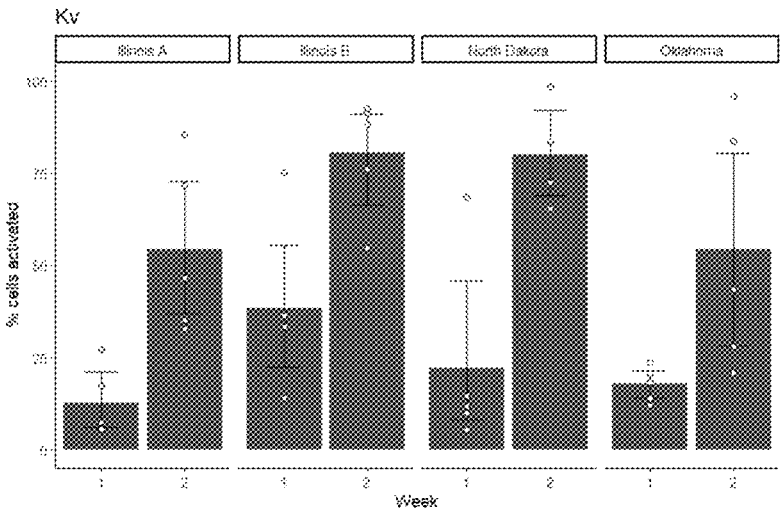
FIG. 11 shows low P concentration activated GFP expression in *Kosakonia sacchari* (Ks) and *Klebsiella variicola* (Kv) soil isolates engineered with a chromosomally integrated PpstS-GFP construct under simulated Midwestern United States field conditions (Illinois A, Illinois B, North Dakota, Oklahoma) in a plant growth room with controlled lighting, temperature, and humidity.
Figure 11:
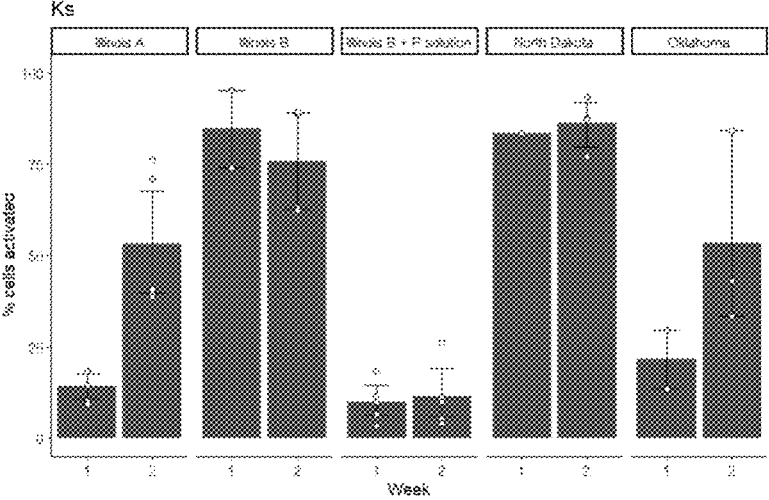

(doi: 10.3389/fmicb.2021.690439). The percentage of the LSSmScarlett+ population activated for GFP expression at each time point was quantified by establishing GFP "−" and "+" threshold fluorescence values for the bacteria. This was done by supplementing one experimental treatment with 50 mM potassium phosphate at the time of inoculation to repress expression from GFP reporter, then generating the GFP−/+ threshold value as the upper 99th percentile of GFP fluorescence in this repressed state, as validated by Haskett et al. (doi:10.1073/pnas.2117465119). As shown in FIG. 11, engineered *K. sacchari* demonstrated over 25% activation with a 2 week delay in 2 out of 4 field soil types while engineered *K. variicola* demonstrated from over 25% to over 50% activation with a 2 week delay in 4 out of 4 field soil types. In the group where each sample was treated with extra phosphate by way of an additional 226 µL of Anderson's 10-34-0 in furrow fertilizer, the GFP reporter was not expressed above background, even after 2 weeks.

Example 12. Further Description of Ammonia Production from Engineered Bacteria by Inducibly Repressing Glutamine Synthetase Expression As described in EXAMPLE 8, down-regulating glutamine synthetase (GS) activity blocks bacteria from assimilating fixed nitrogen and results in ammonia release into the environment. Transcriptionally repressing glnA in response to depletion of phosphate can down-regulate GS and lead to conditional ammonia release under phosphate-limited conditions.

Figure 12:
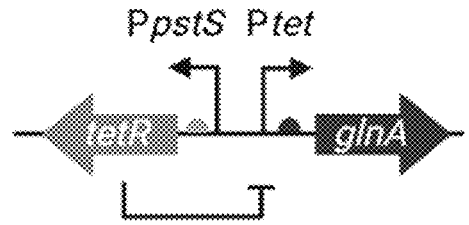
FIG. 12 shows the construct with a phosphate PpstS promoter driving expression of TetR repressor and Ptet driving expression of glnA where TetR represses expression of glnA (upper panel). The position of various RBS which were tested (BCD2, BCD13, and BCD22 for glnA; BCD2, BCD17, and BCD22 for TetR) in each transcription unit are shown as half circles (upper panel).
Figure 12:
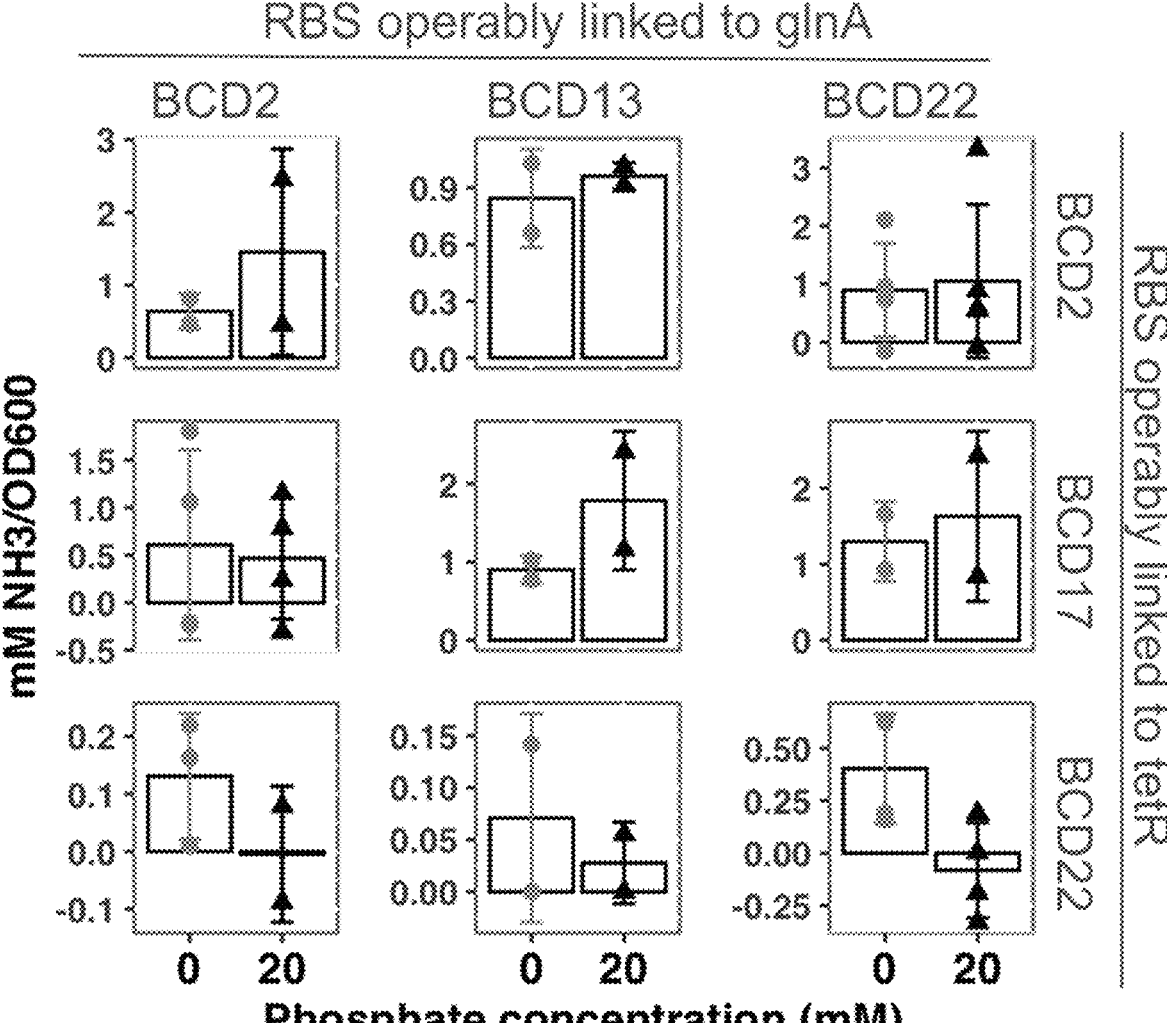

In this example, the native (endogenous) glnA gene encoding GS is deleted, and a cassette is integrated into the chromosome in single copy with the design in the schematic shown in FIG. 12 with one sequence element for each of sites 1-6 as described in Table 9.

TABLE 9

| Non-limiting Examples of glnA Cassettes with Sequence Elements Depicted in FIG. 12: | | | | | |
|---|---|---|---|---|---|
| Site # | Part Type | Description | SEQ ID NO | Type | Organism name |
| 1 | Phosphate-sensitive promoter | *A. brasilense* pstS promoter | 418 | DNA | *Azospirillum brasilense* |
| | | *H. seropedicae* pstS promoter | 422 | DNA | *Herbaspirillum seropedicae* |
| | | *K. radicincitans* pstS promoter 1 | 423 | DNA | *Kosakonia radicincitans* |
| | | *P. stutzeri* pstS promoter | 428 | DNA | *Pseudomonas stutzeri* |
| | | *K. sacchari* pstS promoter | 517 | DNA | *Kosakonia sacchari* |
| | | *K. variicola* pstS promoter | 515 | DNA | *Klebsiella variicola* |
| | | *R. aceris* pstS promoter | 518 | DNA | *Rahnella aquatilis* |
| 2, 5 | Ribosome binding site | BCD 2 vL ribosome binding site | 430 | DNA | synthetic construct |
| | | BCD 13 ribosome binding site | 440 | DNA | synthetic construct |
| | | BCD 17 ribosome binding site | 444 | DNA | synthetic construct |
| | | BCD 22 vL ribosome binding site | 449 | DNA | synthetic construct |
| 3 | Repressor protein encoded | Optimized TetR | 516 | PRT | synthetic construct |
| 4 | Repressor-bound promoter | Ptet promoter (binds TetR repressors) | 32 | DNA | synthetic construct |
| 6 | Glutamine synthetase encoded | *A. brasilense* glutamine synthetase protein (GlnA) | 229 | PRT | *Azospirillum brasilense* |
| | | *K. sacchari* glutamine synthetase | 519 | PRT | *Kosakonia sacchari* |

TABLE 9-continued

Non-limiting Examples of glnA Cassettes
with Sequence Elements Depicted in FIG. 12:

| Site # | Part Type | Description | SEQ ID NO | Type | Organism name |
|---|---|---|---|---|---|
| | | K. variicola glutamine synthetase | 520 | PRT | Klebsiella variicola |
| | | R. aceris glutamine synthetase | 521 | PRT | Rahnella aceris |

Site 1 (Phosphate-sensitive promoters);
Sites 2 and 5 (Ribosome Binding sites);
Site 3 (Encoded Repressor proteins);
Site 4 (Repressor-bound promoters); and
Site 6 (encoded glutamine synthase).

In certain embodiments, other TetR proteins and Ptet promoters or TetR binding sites in those promoters that can be used include those described in Ramos et al., 2005, doi.org/10.1128/mmbr.69.2.326-356.2005.

Example 13. Ammonia Release is Activated Under Low Pi Conditions for Constructs Made with Heterologous Parts Systems as described in Example 12 were constructed essentially as described in Example 10 with TetR as a repressor expressed from a K. variicola pstS promoter (SEQ ID NO: 515) and Azospirillum glnA expressed from Ptet promoter and tested for ammonia production in the presence and absence of Pi.

To test for ammonia production, cell mass of each genetically engineered strain of interest was grown on solid Luria-Bertani agar and resuspended in 1% potassium chloride to $OD_{600}$ 3.0. Cells were inoculated at a final $OD_{600}$ of 0.3 into gas chromatography (GC) vials containing liquid HEPES-buffered NFbHP medium supplemented with glucose, with or without 20 mM Pi. To generate microaerobic culture conditions amendable to nitrogen fixation, cultures were incubated shaking for 30 minutes at room temperature in a 2% oxygen atmosphere in a custom-built anaerobic chamber. GC vials were sealed and verified to be air-tight prior to transfer out of the anaerobic chamber. GC vials were subsequently incubated for 24 hours at 30° C. shaking at 200 rpm. A separate 200 µL of each culture was sampled for (i) quantification of ammonia production using a Sigma-Aldrich MAK310 kit according to manufacturer instructions and (ii) quantification of $OD_{600}$ using a spectrophotometric 96-well plate reader.

Constructs (FIG. 12, upper panel) carrying each combination of RBSs (FIG. 12, lower panel) were integrated into the Kosakonia sacchari (Ks) soil isolate and the endogenous glnA gene was deleted from the chromosome. Ammonia release+/−added Pi was measured in vitro as described above (FIG. 12, lower panel). While all combinations display the desirable phenotype of ammonia release in absence of Pi, strains comprising a strong- (BCD2) or medium-strength (BCD17) ribosome binding site operably linked to the tetR gene also display the undesirable phenotype of ammonia release in presence of Pi. Transformed strains exhibiting desirable inducible ammonia release phenotype are displayed in the bottom row of panels of the 3×3 FIG. 12. The relative strength of the RBS used in the various constructs is BCD22<BCD13~BCD17<BCD2. The results of these experiments show that constructs where the tetR gene encoding the TetR is operably linked to a weak RBS (BCD22) provide the best induction of ammonia release under low Pi conditions.

Figure 13:
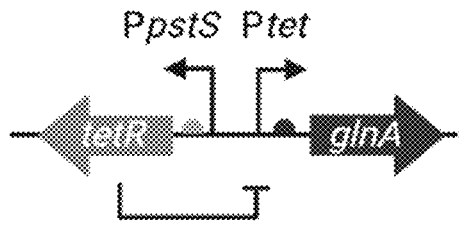
FIG. 13 shows the construct with a phosphate PpstS promoter driving expression of TetR repressor and Ptet driving expression of glnA where TetR represses expression of glnA (upper panel). The position of various RBS which were tested (BCD2, BCD13, and BCD22 for glnA; BCD2, BCD17, and BCD22 for TetR) in each transcription unit are shown as half circles (upper panel).
Figure 13:
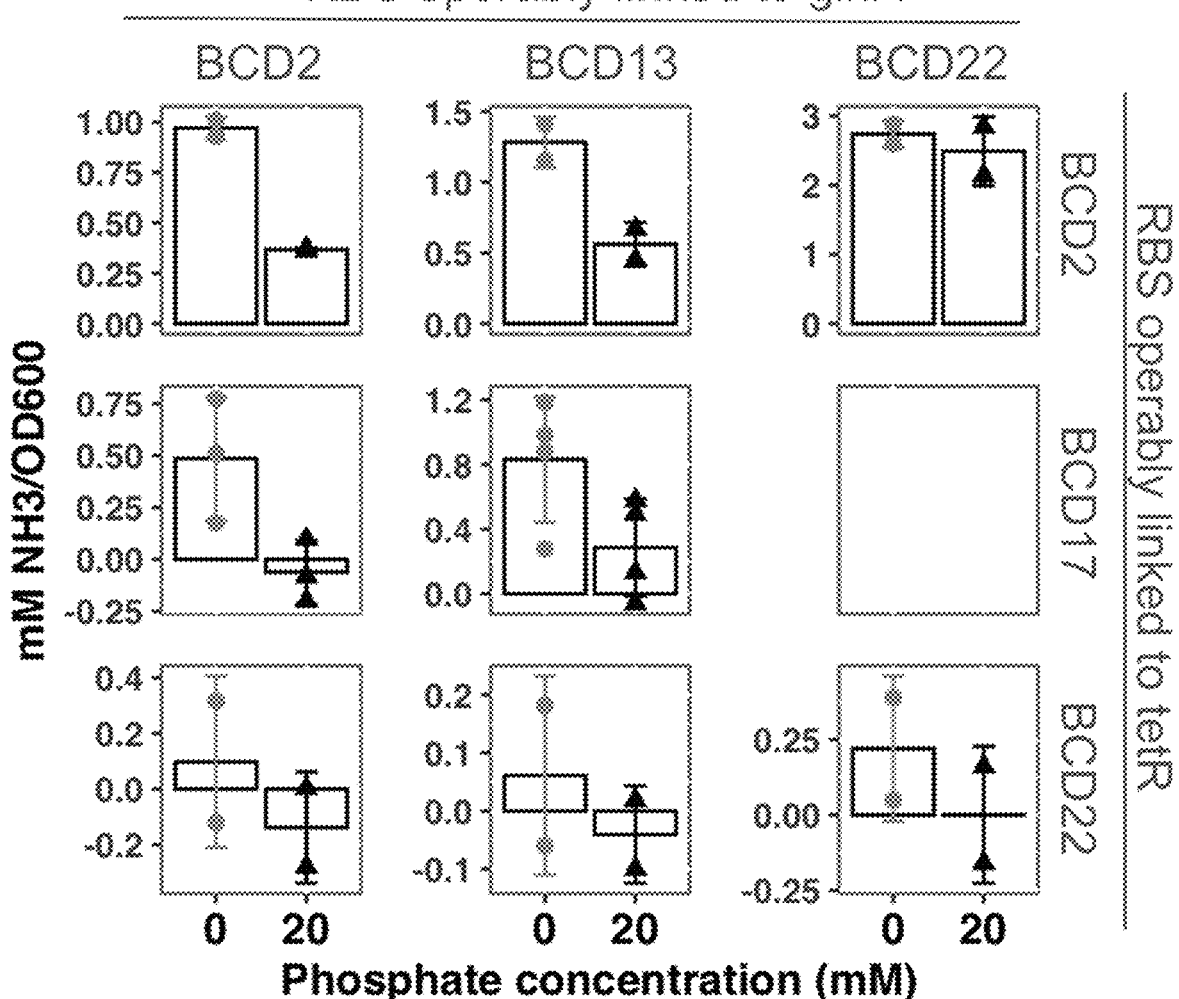

Constructs (FIG. 13, upper panel) carrying each combination of RBSs (FIG. 13, lower panel) were integrated into the Rahnella aceris (Ra) soil isolate, and the endogenous glnA gene was deleted from the chromosome. Ammonia release+/−added Pi was measured in vitro as described above (FIG. 13, lower panel). While all combinations display the desirable phenotype of ammonia release in absence of Pi, strains comprising a strong- (BCD2) ribosome binding site operably linked to the tetR gene also display the undesirable phenotype of leaky ammonia release in presence of Pi. The relative strength of the RBS used in the various constructs is BCD22<BCD13~BCD17<BCD2. The results of these experiments show that constructs where the tetR gene encoding the TetR is operably linked to a weak RBS (BCD22) or medium-strength RBS (BCD17) provide the best induction of ammonia release under low Pi conditions.

Figure 14:
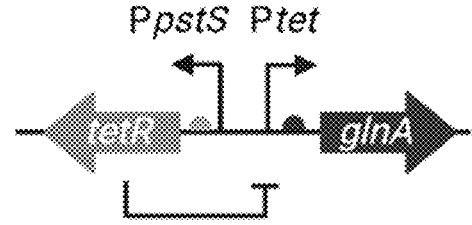
FIG. 14 shows the construct with a phosphate PpstS promoter driving expression of TetR repressor and Ptet driving expression of glnA where TetR represses expression of glnA (upper panel). The position of various RBS which were tested in each transcription unit are shown as half circles (upper panel).
Figure 14:
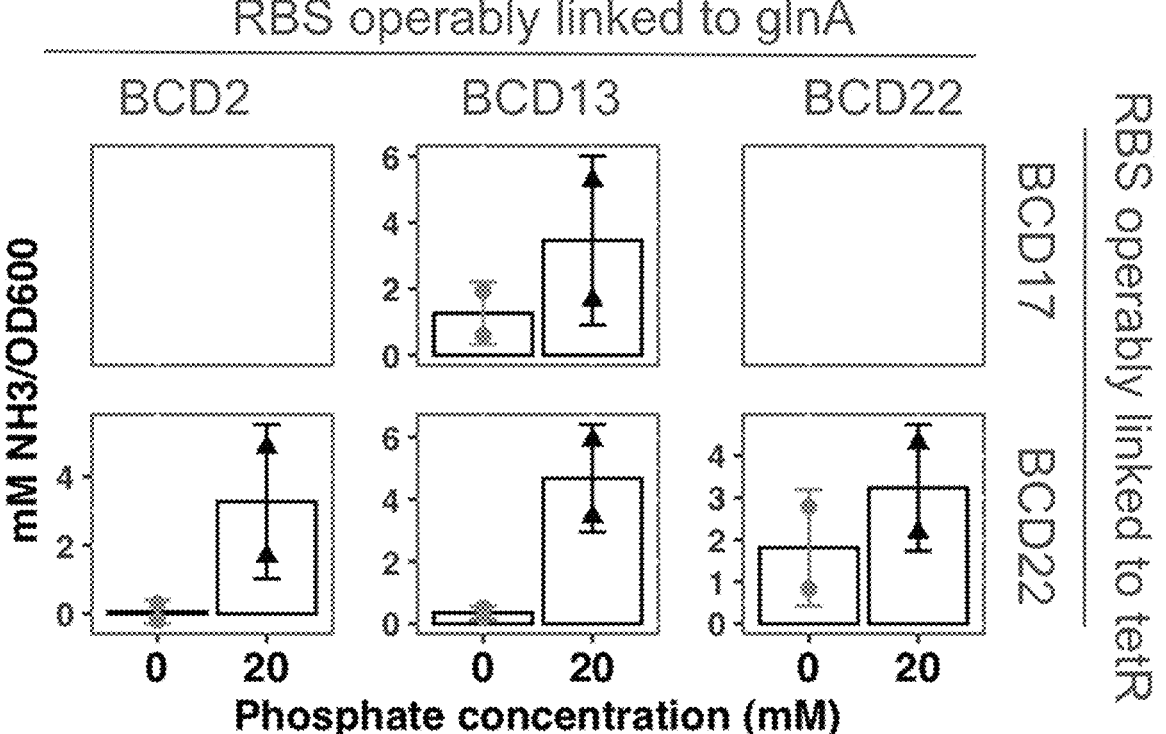

Constructs (FIG. 14, upper panel) carrying each combination of RBSs (FIG. 14, lower panel) were integrated into the Klebsiella variicola (Kv) soil isolate, and the endogenous glnA gene was deleted from the chromosome. Ammonia release+/−added Pi was measured in vitro as described above (FIG. 14, lower panel). None of these strains achieved ammonia production inducible by a reduction in Pi concentration.

Figure 15:
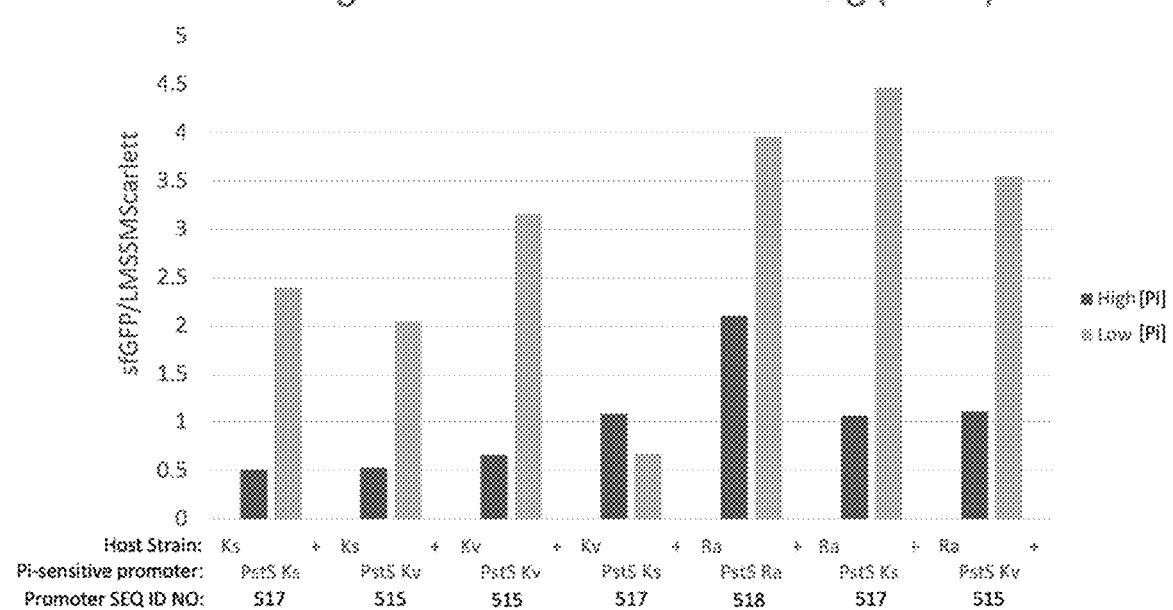
FIG. 15 shows low-Pi inducible expression of GFP by PstS promoters in gamma-proteobacterial soil isolates (culture data). *Rahnella aceris, Klebsiella variicola,* and *Kosa-*

Example 14. PpstS Promoters Activate GFP in Response to Low-Pi in Sterile Cultures of Gram-Negative Gamma-Proteobacteria and Gram-Positive Paenibacillus Activation of GFP reporter expression driven by various PpstS promoters in response to low Pi in the genetically engineered bacterial strains of Example 10 was tested in sterile culture essentially as described in Example 2. The promoters that were tested are disclosed in Table 9. Promoters comprising ~300-bp upstream of the endogenous pstS gene in a Kosakonia sacchari soil isolate, a Klebsiella varicella soil isolate, and a Rahnella aceris soil isolate activated GFP expression in response to low Pi in response to Pi depletion as shown in FIG. 15. Phosphate sensitive promoters were also tested in Paenibacillus graminis. The PstSI and PstsII promoters for a Paenibacillus graminis soil isolate activate GFP expression in liquid media in response to Pi depletion (Ppst 1, Ppst2.1, and Ppst 2.2 in FIG. 16).

Example 15. Low Phosphate Control of a
Unidirectional Adenylyl Transferase Fused to the
PstS Promoter Drives Ammonia Release in
*Kosakonia sacchari*

A *Kosakonia sacchari* soil isolate was transformed with a
vector containing a PstS promoter (SEQ ID NO: 423) fused
to DNA encoding a unidirectional adenylyl transferase (SEQ
ID NO: 16). Ammonia was released at 0 mM Pi but not at
20 mM Pi as shown in FIG. 17.

What is claimed is:

1. A genetically engineered bacterium comprising:

(i) a first gene expression cassette comprising a recombinant DNA molecule comprising a phosphate-sensitive promoter of a bacterial pstS phosphate ABC transporter gene operably linked to DNA encoding a transcript comprising a ribosome binding site (RBS) operably linked to a transcriptional repressor protein coding region, wherein the phosphate-sensitive promoter comprises a sequence having at least 95% sequence identity to SEQ ID NO: 515 and comprising the sequences of SEQ ID NO: 525, 526, 527, 528, and 529, wherein the RBS comprises SEQ ID NO: 449, and wherein the transcriptional repressor protein coding region encodes a bacterial TetR repressor protein; and (ii) a second gene expression cassette comprising a recombinant DNA molecule comprising a promoter which is repressed by the transcriptional repressor protein and which is operably linked to a DNA sequence encoding a bacterial glutamine synthetase wherein the promoter in the second gene expression cassette comprises a Ptet promoter;

wherein the genetically engineered bacterium is of the genus *Kosakonia* and releases a greater amount of ammonia when grown in liquid culture under microaerobic conditions when inoculated in the presence of 0 mM inorganic phosphate than when grown in liquid culture under microaerobic conditions when inoculated in the presence of 20 mM inorganic phosphate.

2. The bacterium of claim 1, wherein the transcriptional repressor protein coding region encodes a bacterial TetR transcriptional repressor protein having at least 95% sequence identity to SEQ ID NO: 516.

3. The bacterium of claim 1, wherein the transcriptional repressor protein coding region encodes a bacterial TetR transcriptional repressor protein comprising the amino acid sequence of SEQ ID NO: 516.

4. The bacterium of claim 1, wherein the bacterial glutamine synthetase is an *Azospirillum* glutamine synthetase and the endogenous gene encoding the *Kosakonia* glutamine synthetase protein contains a null mutation or is deleted.

5. The bacterium of claim 1, wherein the bacterial glutamine synthetase comprises a *Kosakonia* glutamine synthetase.

6. The bacterium of claim 5, wherein the *Kosakonia* glutamine synthetase is encoded by an endogenous *Kosakonia* gene.

7. The bacterium of claim 1, wherein:

(i) the phosphate-sensitive promoter in the first gene expression cassette comprises a *Klebsiella variicola* pstS phosphate-sensitive promoter having at least 95% sequence identity to SEQ ID NO: 515, the RBS in the first gene expression cassette comprises a BCD22vL RBS encoded by SEQ ID NO: 449, and the transcriptional repressor protein coding region encodes a protein comprising an amino acid sequence having at least 95% sequence identity to SEQ ID NO: 516; and (ii) the promoter in the second gene expression cassette comprises a Ptet promoter having at least 95% sequence identity to SEQ ID NO: 32, and the bacterial glutamine synthetase is a glutamine synthetase having at least 95% sequence identity to SEQ ID NO: 229.

8. A composition comprising the genetically engineered bacterium of claim 1 and an agriculturally acceptable carrier.

9. The composition of claim 8, wherein the composition further comprises:

(i) an agriculturally acceptable adjuvant, optionally wherein the adjuvant comprises an adhesive agent, a desiccant, and/or a dispersant;

(ii) a fungicide, an insecticide, a nematicide, a rodenticide, and/or a bacteriocide; and/or (iii) a fertilizer, optionally wherein the fertilizer comprises nitrogen, phosphorous, potassium, calcium, sulfur, magnesium, boron, chloride, manganese, iron, zinc, copper, molybdenum, and/or selenium.

10. A plant part or plant propagule which is at least partially coated, imbibed, or mixed with the composition of claim 8.

11. An agricultural system comprising:

(i) at least one engineered bacterium of claim 1;

(ii) at least one plant growth medium; and (iii) at least one crop plant, crop plant seed, or crop plant vegetative propagule; wherein the plant growth medium, crop plant, crop seed, and/or crop plant propagule comprise, are at least partially coated, imbibed, and/or are mixed with the engineered bacterium or a composition comprising the engineered bacterium and an agriculturally acceptable carrier.

12. The system of claim 11, wherein the crop plant, seed, or vegetative propagule is an alfalfa, apple, banana, barley, bean, buckwheat, cabbage, cassava, chili, clover, coffee, corn, cotton, cowpea, cucumber, fonio, garlic, herb, lettuce, maize, melon, millet, nut, oat, oilseed rape, olive, onion, orange, sunflower, pea, *Phaseolus* bean, plantain, potato, *quinoa*, rice, rye, safflower, sorghum, soybean, sugar beet, sugar cane, sunflower, tangerine, tobacco, tomato, triticale, turnip, wheat, or yam plant, seed, or vegetative propagule.

13. The system of claim 11, wherein the plant growth medium comprises soil and/or water, optionally wherein the soil and/or water is non-axenic.

14. The system of claim 11, wherein the vegetative propagule comprises a cutting, tuber, or stolon.

15. A treated plant seed or plant propagule system comprising:

(i) at least one crop plant seed or crop plant vegetative propagule; and (ii) at least one engineered bacterium of claim 1, wherein the crop plant seed or crop plant propagule are at least partially coated, imbibed, and/or mixed with the engineered bacterium or a composition comprising the engineered bacterium and an agriculturally acceptable carrier.

16. The system of claim 15, wherein the crop plant, seed, or vegetative propagule is an alfalfa, apple, banana, barley, bean, buckwheat, cabbage, cassava, chili, clover, coffee, corn, cotton, cowpea, cucumber, fonio, garlic, herb, lettuce, maize, melon, millet, nut, oat, oilseed rape, olive, onion, orange, sunflower, pea, *Phaseolus* bean, plantain, potato, *quinoa*, rice, rye, safflower, sorghum, soybean, sugar beet, sugar cane, sunflower, tangerine, tobacco, tomato, triticale, turnip, wheat, or yam plant, seed, or vegetative propagule.

\* \* \* \* \*